United States Patent
Gong et al.

(10) Patent No.: US 8,481,536 B2
(45) Date of Patent: Jul. 9, 2013

(54) BENZOTRIAZINE INHIBITORS OF KINASES

(75) Inventors: Xianchang Gong, La Jolla, CA (US);
Kathy Barrett, La Jolla, CA (US);
Jianguo Cao, San Diego, CA (US);
Colleen Gritzen, Vista, CA (US); Glenn Noronha, Seattle, WA (US); John D. Hood, San Diego, CA (US); Chi Ching Mak, San Diego, CA (US); Andrew McPherson, San Diego, CA (US); Ved Prakash Pathak, San Diego, CA (US); Joel Renick, San Diego, CA (US);
Richard M. Soll, San Diego, CA (US);
Ute Splittgerber, South San Francisco, CA (US); Wolfgang Wrasidlo, La Jolla, CA (US); Binqi Zeng, San Diego, CA (US); Ningning Zhao, San Diego, CA (US); Elena Dneprovskaia, San Diego, CA (US)

(73) Assignee: TargeGen, Inc., Bridgewater, NJ (US)

( * ) Notice: Subject to any disclaimer, the term of this patent is extended or adjusted under 35 U.S.C. 154(b) by 0 days.

(21) Appl. No.: 12/980,235

(22) Filed: Dec. 28, 2010

(65) Prior Publication Data
US 2011/0294796 A1 Dec. 1, 2011

Related U.S. Application Data

(63) Continuation of application No. 12/207,019, filed on Sep. 9, 2008, now abandoned, which is a continuation of application No. 11/102,405, filed on Apr. 7, 2005, now Pat. No. 7,456,176.

(60) Provisional application No. 60/561,237, filed on Apr. 8, 2004, provisional application No. 60/643,439, filed on Jan. 12, 2005.

(51) Int. Cl.
*A61K 31/53* (2006.01)
*A61P 35/00* (2006.01)
*C07D 401/12* (2006.01)
*C07D 401/14* (2006.01)
*C07D 403/04* (2006.01)
*C07D 403/12* (2006.01)
*C07D 403/14* (2006.01)
*C07D 413/12* (2006.01)
*C07D 413/14* (2006.01)
*C07D 417/12* (2006.01)
*C07D 417/14* (2006.01)

(52) U.S. Cl.
USPC .......................................... 514/243; 544/183

(58) Field of Classification Search
USPC ......................................... 544/183; 514/243
See application file for complete search history.

(56) References Cited

U.S. PATENT DOCUMENTS

| | | | |
|---|---|---|---|
| 2,001,051 A | 5/1935 | Bruno |
| 2,002,165 A | 5/1935 | Winslow |
| 2,003,060 A | 5/1935 | Thomas |
| 2,003,065 A | 5/1935 | Boyce |
| 2,003,149 A | 5/1935 | Johnson |
| 2,003,166 A | 5/1935 | Zancan |
| 2,003,187 A | 5/1935 | Good |
| 2,003,199 A | 5/1935 | Johnson et al. |
| 2,004,092 A | 6/1935 | Chaney |
| 2,004,102 A | 6/1935 | Dickey |
| 2,004,138 A | 6/1935 | Story et al. |
| 2,667,486 A | 1/1954 | Cain |
| 4,057,530 A | 11/1977 | Pigerol et al. |
| 4,160,833 A | 7/1979 | Diel et al. |
| 4,309,211 A | 1/1982 | Serban et al. |
| 5,062,685 A | 11/1991 | Cain et al. |
| 5,214,059 A | 5/1993 | Tegeler et al. |
| 5,231,097 A | 7/1993 | Klausener et al. |
| 5,332,745 A | 7/1994 | Carter et al. |
| 5,482,951 A | 1/1996 | Ozaki et al. |
| 5,527,763 A | 6/1996 | Miyazaki et al. |

(Continued)

FOREIGN PATENT DOCUMENTS

| | | |
|---|---|---|
| AU | 38554/93 A1 | 11/1993 |
| CA | 2375982 A1 | 2/2001 |

(Continued)

OTHER PUBLICATIONS

Allgayer, H. et al. (Jan. 15, 2002). "Activation of Src Kinase in Primary Colorectal Carcinoma: An Indicator of Poor Clinical Prognosis," *Cancer* 94(2):344-351.
Arbiser, J. L. (Oct. 2007). "Why Targeted Therapy Hasn't Worked in Advanced Cancer," *J. Clin. Invest.* 117(10):2762-2765.
Assmus, B. et al. (May 16, 2003). "HMG-CoA Reductase Inhibitors Reduce Senescence and Increase Proliferation of Endothelial Progenitor Cells Via Regulation of Cell Cycle Regulatory Genes," *Circ. Res.* 92(9):1049-1055.
Bailey, W. C. et al. (2007). "Pharmacologic Therapy: Novel Approaches for Chronic Obstructive Pulmonary Disease," *Proc. Am. Thorac. Soc.* 4:543-548.

(Continued)

*Primary Examiner* — Venkataraman Balasubramanian
(74) *Attorney, Agent, or Firm* — Morrison & Foerster LLP

(57) ABSTRACT

The invention provides benzotriazine compounds having formula (I). The benzotriazine compounds of the invention are capable of inhibiting kinases, such members of the Src kinase family, and various other specific receptor and non-receptor kinases.

(I)

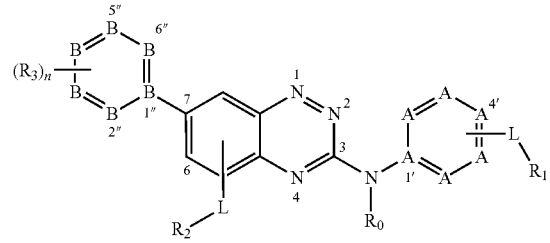

5 Claims, No Drawings

U.S. PATENT DOCUMENTS

| | | | |
|---|---|---|---|
| 5,530,000 A | 6/1996 | Sanfilippo et al. |
| 5,597,826 A | 1/1997 | Howard et al. |
| 5,597,901 A | 1/1997 | Stern |
| 5,665,724 A | 9/1997 | Sanfilippo et al. |
| 5,763,441 A | 6/1998 | App et al. |
| 5,776,502 A | 7/1998 | Foulkes et al. |
| 5,827,850 A | 10/1998 | Brown et al. |
| 5,830,880 A | 11/1998 | Sedlacek et al. |
| 5,849,738 A | 12/1998 | Lee et al. |
| 5,935,383 A | 8/1999 | Sun et al. |
| 5,965,761 A | 10/1999 | Buchecker et al. |
| 5,972,580 A | 10/1999 | Fukui et al. |
| 6,048,675 A | 4/2000 | Hirano et al. |
| 6,070,126 A | 5/2000 | Kokolus et al. |
| 6,093,838 A | 7/2000 | Vasudevan et al. |
| 6,121,434 A | 9/2000 | Peyman et al. |
| 6,127,382 A | 10/2000 | Beard et al. |
| 6,136,779 A | 10/2000 | Foulkes et al. |
| 6,136,971 A | 10/2000 | Harrington et al. |
| 6,153,752 A | 11/2000 | Bauer et al. |
| 6,194,191 B1 | 2/2001 | Zhang et al. |
| 6,204,260 B1 | 3/2001 | Bruns, Jr. et al. |
| 6,235,736 B1 | 5/2001 | Ina et al. |
| 6,245,916 B1 | 6/2001 | Fauchere et al. |
| 6,277,502 B1 | 8/2001 | Buchecker et al. |
| 6,288,230 B1 | 9/2001 | Wissner et al. |
| 6,297,258 B1 | 10/2001 | Wissner et al. |
| 6,326,487 B1 | 12/2001 | Peyman et al. |
| 6,348,312 B1 | 2/2002 | Peyman et al. |
| 6,378,526 B1 | 4/2002 | Bowman et al. |
| 6,399,773 B1 | 6/2002 | Liu et al. |
| 6,471,968 B1 | 10/2002 | Baker, Jr. et al. |
| 6,489,328 B2 | 12/2002 | Snow et al. |
| 6,506,769 B2 | 1/2003 | Snow et al. |
| 6,531,491 B1 | 3/2003 | Kania et al. |
| 6,596,749 B2 | 7/2003 | Fauchere et al. |
| 6,605,615 B2 | 8/2003 | Medina et al. |
| 6,613,773 B2 | 9/2003 | Clough et al. |
| 6,635,626 B1 | 10/2003 | Barrish et al. |
| 6,685,938 B1 | 2/2004 | Cheresh et al. |
| 6,689,778 B2 | 2/2004 | Bemis et al. |
| 6,777,412 B2 | 8/2004 | Clough et al. |
| 6,794,378 B2 | 9/2004 | Iino et al. |
| 6,838,464 B2 | 1/2005 | Pease et al. |
| 7,008,954 B1 | 3/2006 | Arimura et al. |
| 7,067,522 B2 | 6/2006 | Pease et al. |
| 7,087,597 B1 | 8/2006 | Miwa et al. |
| 7,087,625 B2 | 8/2006 | Schumacher et al. |
| 7,115,597 B2 | 10/2006 | Bilodeau et al. |
| 7,208,493 B2 | 4/2007 | Wrasidlo et al. |
| 7,230,101 B1 | 6/2007 | Murthi et al. |
| 7,402,696 B2 | 7/2008 | Suzuki et al. |
| 7,435,823 B2 | 10/2008 | Potashman et al. |
| 7,456,176 B2 * | 11/2008 | Noronha et al. ............... 514/243 |
| 7,528,143 B2 | 5/2009 | Noronha et al. |
| 7,652,051 B2 | 1/2010 | Wrasidlo et al. |
| 7,691,858 B2 | 4/2010 | Doukas et al. |
| 7,700,631 B2 | 4/2010 | Schumacher et al. |
| 7,816,365 B2 | 10/2010 | Schiemann et al. |
| 7,825,246 B2 | 11/2010 | Noronha et al. |
| 8,030,487 B2 | 10/2011 | Noronha et al. |
| 8,084,618 B2 | 12/2011 | Wrasidlo et al. |
| 8,133,900 B2 | 3/2012 | Hood et al. |
| 8,138,199 B2 | 3/2012 | Noronha et al. |
| 2001/0051620 A1 | 12/2001 | Berger et al. |
| 2002/0165244 A1 | 11/2002 | Zhou et al. |
| 2003/0060626 A1 | 3/2003 | Clough et al. |
| 2003/0065180 A1 | 4/2003 | Tsou et al. |
| 2003/0134838 A1 | 7/2003 | Bornemann et al. |
| 2003/0149061 A1 | 8/2003 | Nishihara et al. |
| 2003/0166932 A1 | 9/2003 | Beard et al. |
| 2003/0199511 A1 | 10/2003 | Li et al. |
| 2004/0092746 A1 | 5/2004 | Clough et al. |
| 2004/0102630 A1 | 5/2004 | Brumby et al. |
| 2004/0106615 A1 | 6/2004 | Cochran et al. |
| 2004/0138257 A1 | 7/2004 | Bouchard et al. |
| 2005/0234083 A1 | 10/2005 | Chamberlain et al. |
| 2005/0239852 A1 | 10/2005 | Ciufolini et al. |
| 2005/0282814 A1 | 12/2005 | Wrasidlo et al. |
| 2006/0131762 A1 | 6/2006 | Meudt et al. |
| 2006/0131835 A1 | 6/2006 | Simpson |
| 2006/0247250 A1 | 11/2006 | Cao et al. |
| 2006/0292203 A1 | 12/2006 | Dellamary et al. |
| 2007/0032493 A1 | 2/2007 | Foley et al. |
| 2007/0072682 A1 | 3/2007 | Crawford et al. |
| 2007/0149508 A1 | 6/2007 | Noronha et al. |
| 2007/0161645 A1 | 7/2007 | Noronha et al. |
| 2007/0208019 A1 | 9/2007 | Wrasidlo et al. |
| 2007/0259876 A1 | 11/2007 | Doukas et al. |
| 2009/0275569 A1 | 11/2009 | Noronha et al. |
| 2010/0278811 A1 | 11/2010 | Wrasidlo et al. |
| 2010/0330030 A1 | 12/2010 | Wrasidlo et al. |
| 2011/0166149 A1 | 7/2011 | Dellamary et al. |
| 2011/0212077 A1 | 9/2011 | Noronha et al. |
| 2011/0243999 A1 | 10/2011 | Dellamary et al. |
| 2011/0269721 A1 | 11/2011 | Hood et al. |
| 2011/0294796 A1 | 12/2011 | Gong et al. |

FOREIGN PATENT DOCUMENTS

| | | |
|---|---|---|
| CN | 1202827 A | 12/1998 |
| DE | 3205638 A | 8/1983 |
| DE | 10024622 A1 | 11/2001 |
| EP | 0 059 524 A1 | 9/1982 |
| EP | 0 444 769 A1 | 9/1991 |
| EP | 1 282 628 B1 | 2/2004 |
| EP | 1 170 353 B1 | 11/2005 |
| FR | 2 275 461 A1 | 1/1976 |
| GB | 1 149 640 A | 4/1969 |
| GB | 1 423 585 A | 2/1976 |
| JP | 02-064553 A | 3/1990 |
| JP | 03-127790 A | 5/1991 |
| JP | 03-240066 A | 10/1991 |
| JP | 07-041461 A | 2/1995 |
| JP | 07-082183 A | 3/1995 |
| JP | 09-508642 A | 9/1997 |
| JP | 09-274290 A | 10/1997 |
| JP | 10-153838 A | 6/1998 |
| JP | 10-207019 A | 8/1998 |
| JP | 10-213820 A | 8/1998 |
| JP | 10-260512 A | 9/1998 |
| JP | 10-310583 A | 11/1998 |
| JP | 2001-089412 A | 4/2001 |
| JP | 2001-247411 A | 9/2001 |
| JP | 2002-221770 A | 8/2002 |
| WF | WO-02/12227 A3 | 2/2002 |
| WO | WO-91/18887 A1 | 12/1991 |
| WO | WO-92/01675 A2 | 2/1992 |
| WO | WO-92/01675 A3 | 2/1992 |
| WO | WO-94/15622 A1 | 7/1994 |
| WO | WO-95/21613 A1 | 8/1995 |
| WO | WO-97/09315 A1 | 3/1997 |
| WO | WO 97/11699 A1 | 4/1997 |
| WO | WO-97/21711 A1 | 6/1997 |
| WO | WO-97/24122 A1 | 7/1997 |
| WO | WO-98/24974 A1 | 6/1998 |
| WO | WO-98/28282 A2 | 7/1998 |
| WO | WO-98/28282 A3 | 7/1998 |
| WO | WO-99/09016 A1 | 2/1999 |
| WO | WO-99/24404 A1 | 5/1999 |
| WO | WO-99/32454 A1 | 7/1999 |
| WO | WO-99/41253 A1 | 8/1999 |
| WO | WO-00/18740 A1 | 4/2000 |
| WO | WO-00/18761 A1 | 4/2000 |
| WO | WO-00/39101 A1 | 7/2000 |
| WO | WO-00/39108 A1 | 7/2000 |
| WO | WO-00/39129 A1 | 7/2000 |
| WO | WO-00/46203 A2 | 8/2000 |
| WO | WO-00/46203 A3 | 8/2000 |
| WO | WO-00/62778 A1 | 10/2000 |
| WO | WO-00/66583 A1 | 11/2000 |
| WO | WO-00/71536 A1 | 11/2000 |
| WO | WO-01/00213 A1 | 1/2001 |
| WO | WO-01/07027 A2 | 2/2001 |
| WO | WO-01/07027 A3 | 2/2001 |
| WO | WO-01/07401 A1 | 2/2001 |
| WO | WO-01/12227 A1 | 2/2001 |
| WO | WO-01/17995 A1 | 3/2001 |

| | | |
|---|---|---|
| WO | WO-01/19825 A1 | 3/2001 |
| WO | WO-01/21597 A1 | 3/2001 |
| WO | WO-01/27105 A1 | 4/2001 |
| WO | WO-01/32628 A1 | 5/2001 |
| WO | WO-01/44194 A2 | 6/2001 |
| WO | WO-01/44194 A3 | 6/2001 |
| WO | WO-01/47892 A1 | 7/2001 |
| WO | WO-01/53266 A1 | 7/2001 |
| WO | WO-01/55116 A2 | 8/2001 |
| WO | WO-01/55116 A3 | 8/2001 |
| WO | WO-01/62233 A2 | 8/2001 |
| WO | WO-01/62233 A3 | 8/2001 |
| WO | WO-01/64646 A2 | 9/2001 |
| WO | WO-01/64646 A3 | 9/2001 |
| WO | WO-01/64655 A1 | 9/2001 |
| WO | WO-01/64674 A1 | 9/2001 |
| WO | WO-01/68186 A2 | 9/2001 |
| WO | WO-01/68186 A3 | 9/2001 |
| WO | WO-01/70668 A2 | 9/2001 |
| WO | WO-01/70668 A3 | 9/2001 |
| WO | WO-01/72758 A1 | 10/2001 |
| WO | WO-01/76582 A1 | 10/2001 |
| WO | WO-02/12227 A2 | 2/2002 |
| WO | WO-02/22608 A1 | 3/2002 |
| WO | WO-02/30358 A2 | 4/2002 |
| WO | WO-02/30358 A3 | 4/2002 |
| WO | WO-02/36570 A1 | 5/2002 |
| WO | WO-02/42272 A2 | 5/2002 |
| WO | WO-02/42272 A3 | 5/2002 |
| WO | WO-02/44166 A1 | 6/2002 |
| WO | WO-02/053101 A2 | 7/2002 |
| WO | WO-02/053101 A3 | 7/2002 |
| WO | WO-02/053160 A1 | 7/2002 |
| WO | WO-02/064096 A2 | 8/2002 |
| WO | WO-02/064096 A3 | 8/2002 |
| WO | WO-02/064211 A1 | 8/2002 |
| WO | WO-02/068409 A1 | 9/2002 |
| WO | WO-02/076438 A2 | 10/2002 |
| WO | WO-02/076438 A3 | 10/2002 |
| WO | WO-02/079197 A1 | 10/2002 |
| WO | WO-02/090347 A1 | 11/2002 |
| WO | WO-02/092087 A1 | 11/2002 |
| WO | WO-02/094766 A1 | 11/2002 |
| WO | WO-02/096905 A1 | 12/2002 |
| WO | WO-02/097116 A2 | 12/2002 |
| WO | WO-02/097116 A3 | 12/2002 |
| WO | WO-03/004018 A1 | 1/2003 |
| WO | WO-03/016306 A1 | 2/2003 |
| WO | WO-03/024448 A2 | 3/2003 |
| WO | WO-03/024448 A3 | 3/2003 |
| WO | WO-03/030909 A1 | 4/2003 |
| WO | WO-03/032994 A2 | 4/2003 |
| WO | WO-03/032994 A3 | 4/2003 |
| WO | WO-03/032997 A1 | 4/2003 |
| WO | WO-03/033503 A2 | 4/2003 |
| WO | WO-03/033503 A3 | 4/2003 |
| WO | WO-03/033504 A1 | 4/2003 |
| WO | WO-03/033505 A1 | 4/2003 |
| WO | WO-03/037869 A1 | 5/2003 |
| WO | WO-03/037891 A1 | 5/2003 |
| WO | WO-03/045921 A1 | 6/2003 |
| WO | WO-03/050090 A1 | 6/2003 |
| WO | WO-03/051366 A2 | 6/2003 |
| WO | WO-03/051366 A3 | 6/2003 |
| WO | WO-03/057165 A2 | 7/2003 |
| WO | WO-03/057165 A3 | 7/2003 |
| WO | WO-03/066575 A1 | 8/2003 |
| WO | WO-03/066601 A1 | 8/2003 |
| WO | WO-03/074515 A1 | 9/2003 |
| WO | WO-03/078404 A1 | 9/2003 |
| WO | WO-03/082272 A1 | 10/2003 |
| WO | WO-03/099771 A2 | 12/2003 |
| WO | WO-03/099771 A3 | 12/2003 |
| WO | WO-2004/000833 A1 | 12/2003 |
| WO | WO-2004/005283 A1 | 1/2004 |
| WO | WO-2004/014382 A1 | 2/2004 |
| WO | WO-2004/018433 A1 | 3/2004 |
| WO | WO-2004/024663 A1 | 3/2004 |
| WO | WO-2004/030635 A2 | 4/2004 |
| WO | WO-2004/030635 A3 | 4/2004 |
| WO | WO-2004/032709 A2 | 4/2004 |
| WO | WO-2004/032709 A3 | 4/2004 |
| WO | WO-2004/032882 A2 | 4/2004 |
| WO | WO-2004/032882 A3 | 4/2004 |
| WO | WO-2004/037176 A2 | 5/2004 |
| WO | WO-2004/037176 A3 | 5/2004 |
| WO | WO-2004/037814 A1 | 5/2004 |
| WO | WO-2004/039780 A1 | 5/2004 |
| WO | WO-2004/052373 A1 | 6/2004 |
| WO | WO-2004/054186 A1 | 6/2004 |
| WO | WO-2004/056786 A2 | 7/2004 |
| WO | WO-2004/056786 A3 | 7/2004 |
| WO | WO-2004/058254 A1 | 7/2004 |
| WO | WO-2004/058782 A1 | 7/2004 |
| WO | WO-2004/060305 A2 | 7/2004 |
| WO | WO-2004/060305 A3 | 7/2004 |
| WO | WO-2004/060376 A1 | 7/2004 |
| WO | WO-2004/069812 A1 | 8/2004 |
| WO | WO-2004/071426 A2 | 8/2004 |
| WO | WO-2004/071426 A3 | 8/2004 |
| WO | WO-2004/074261 A1 | 9/2004 |
| WO | WO-2004/074262 A1 | 9/2004 |
| WO | WO-2004/074266 A1 | 9/2004 |
| WO | WO-2004/097504 A1 | 11/2004 |
| WO | WO-2005/016894 A1 | 2/2005 |
| WO | WO-2005/026130 A1 | 3/2005 |
| WO | WO-2005/030140 A2 | 4/2005 |
| WO | WO-2005/030140 A3 | 4/2005 |
| WO | WO-2005/035541 A1 | 4/2005 |
| WO | WO-2005/054246 A2 | 6/2005 |
| WO | WO-2005/054246 A3 | 6/2005 |
| WO | WO 2005/070891 A2 | 8/2005 |
| WO | WO 2005/070891 A3 | 8/2005 |
| WO | WO-2005/096784 A2 | 10/2005 |
| WO | WO-2005/096784 A3 | 10/2005 |
| WO | WO-2005/108370 A1 | 11/2005 |
| WO | WO-2006/024034 A1 | 3/2006 |
| WO | WO-2006/081172 A2 | 8/2006 |
| WO | WO-2006/081172 A3 | 8/2006 |
| WO | WO-2006/101977 A2 | 9/2006 |
| WO | WO-2006/101977 A3 | 9/2006 |
| WO | WO-2006/128129 A2 | 11/2006 |
| WO | WO-2006/128129 A3 | 11/2006 |
| WO | WO-2006/131835 A2 | 12/2006 |
| WO | WO-2006/131835 A3 | 12/2006 |
| WO | WO-2006/133411 A1 | 12/2006 |
| WO | WO-2007/008541 A2 | 1/2007 |
| WO | WO-2007/008541 A3 | 1/2007 |
| WO | WO-2007/021937 A2 | 2/2007 |
| WO | WO-2007/021937 A3 | 2/2007 |
| WO | WO-2007/032028 A1 | 3/2007 |
| WO | WO-2007/053452 A1 | 5/2007 |
| WO | WO-2007/056023 A2 | 5/2007 |
| WO | WO-2007/056023 A3 | 5/2007 |
| WO | WO-2007/056075 A2 | 5/2007 |
| WO | WO-2007/056075 A3 | 5/2007 |
| WO | WO-2007/127366 A2 | 11/2007 |
| WO | WO-2007/127366 A3 | 11/2007 |
| WO | WO-2008/008234 A1 | 1/2008 |
| WO | WO-2009/026345 A1 | 2/2009 |
| WO | WO-2009/026346 A1 | 2/2009 |
| WO | WO-2009/046416 A1 | 4/2009 |
| WO | WO-2009/049028 A1 | 4/2009 |
| WO | WO-2009/055674 A1 | 4/2009 |
| WO | WO-2009/100305 A1 | 8/2009 |
| WO | WO-2010/017122 A2 | 2/2010 |
| WO | WO-2010/017122 A3 | 2/2010 |

OTHER PUBLICATIONS

Banker, G. S. et al. (1996). *Modern Pharmaceutics*, 3rd edition, Marcel Dekker Inc., New York, pp. 451, 596.

Barber, D. F. et al. (Sep. 2005, e-pub: Aug. 28, 2005). "PI3Kγ Inhibition Blocks Glomerulonephritis and Extends Lifespan in a Mouse Model of Systemic Lupus," *Nat. Med.* 11(9):933-935.

Bell, R. M. et al. (Feb. 2003). "Bradykinin Limits Infarction When Administered as an Adjunct to Reperfusion in Mouse Heart: the Role of PI3K, Akt and eNOS," *J. Mol. & Cellul. Cardiol.* 35(2):185-193.

Bénistant, C. et al. (Jul. 5, 2000). "Deregulation of Cytoplasmic

Tyrosine Kinase cSRC in the Absence of a Truncating Mutation at Codon 531 in Human Bladder Carcinoma," *Biochem. Biophys. Res. Commun.* 273(2):425-430.
Berti, F. et al. (Nov. 1990). "Production and Biologic Interactions of Prostacyclin and Platelet-Activating Factor in Acute Myocardial Ischemia in the Perfused Rabbit Heart," *J. Cardiovasc. Pharmacol.* 16(5):727-732.
Bolen, J. B. et al. (1991). "Expression and Interactions of the Src Family of Tyrosine Protein Kinases in T Lymphocytes," *Adv. Cancer Res.* 57:103-149.
Bolli, R. et al. (Jul. 23, 2004). "Myocardial Protection at a Crossroads: The Need for Translation Into Clinical Therapy," *Cir. Res.* 95:125-134.
Bonniaud, P. et al. (2005). "Progressive Transforming Growth Factor β1-Induced Lung Fibrosis is Blocked by an Orally Active ALK5 Kinase Inhibitor," *Am. J. Respir. Crit. Care Med.* 171:889-898.
Boyer, B. et al. (Oct. 15, 2000). "Induction and Regulation of Epithelial-Mesenchymal Transitions," *Biochem. Pharmacol.* 60(8):1091-1099.
Boyer, B. et al. (Apr. 4, 2002). "Src Kinase Contributes to the Metastatic Spread of Carcinoma Cells," *Oncogene* 21(15):2347-2356.
Brugge, J. S. et al. (Sep. 22, 1977). "Identification of a Transformation-Specific Antigen Induced by Avian Sarcoma Virus," *Nature* 269(5626):346-348.
Bussolino, F. et al. (Oct. 1, 1987). "Human Endothelial Cells Are Target for Platelet-Activating Factor, I. Platelet-Activating Factor Induces Changes in Cytoskeleton Structures," *J. Immunol.* 139(7):2439-2446.
Cain, C. K. et al. (Mar. 1949). "Pteridines. IV. Derivatives of 2,4-Diamino-6,7-Diphenylpteridine," *J. Am. Chem. Soc.* 71(3):892-896.
Camps, M. et al. (Sep. 2005, e-pub. Aug. 28, 2005). "Blockade of PI3Kγ Suppresses Joint Inflammation and Damage in Mouse Models of Rheumatoid Arthritis," *Nat. Med.* 11(9):936-943.
Cartwright, C. A. et al. (Jan. 1990). "Activation of pp60$^{c-src}$ Protein Kinase is an Early Event in Colonic Carcinogenesis," *Proc. Natl. Acad. Sci. USA* 87(2):558-562.
Chawla, G. et al. (Jan.-Mar. 2004). "Challenges in Polymorphism of Pharmaceuticals", *CRIPS* 5(1)12-15.
Cohen, P. et al. (Aug. 1999). "The Development and Therapeutic Potential of Protein Kinase Inhibitors," *Curr. Opin.Chem. Bio.* 3(4):459-465.
Collett, M. S. et al. (Apr. 1978). "Protein Kinase Activity Associated With the Avian Sarcoma Virus src Gene Product," *Proc. Natl. Acad. Sci. USA* 75(4):2021-2024.
Condliffe, A. M. et al. (Aug. 15, 2005, e-pub. May 5, 2005). "Sequential Activation of Class IB and Class IA PI3K is Important for the Primed Respiratory Burst of Human But Not Murine Neutrophils," *Blood* 106(4):1432-1440.
De La Peña, L. et al. (Jun. 2006). "Inhibition of Akt by the Alkylphospholipid Perifosine Does Not Enhance the Radiosensitivity of Human Glioma Cells," *Mol. Cancer Ther.* 5(6):1504-1510.
Dermer, G. B. (Mar. 12, 1994). "Another Anniversary on the War of Cancer," *Bio/Technology* 12:320.
Dörwald, F. Z. (2005). "Organic Synthesis: General Remarks," *Side Reactions in Organic Synthesis*, A Guide to Successful Synthesis Design, Wiley-VCH, Weinheim, p. IX of preface pp. 1-16.
Doukas, J. et al. (Dec. 26, 2006, e-pub. Dec. 15, 2006). "Phosphoinositide 3-Kinase γ/δ Inhibition Limits Infarct Size After Myocardial Ischemia/Reperfusion Injury," *Proc. Natl. Acad. Sci. USA* 103(52):19866-19871.
Doukas, J. et al. (Mar. 2009, e-pub. Dec. 4, 2008). "Aerosolized Phosphoinositide 3-Kinase γ/δ Inhibitor TG100-115 [3-[2,4-Diamino-6-(3-Hydroxyphenyl)Pteridin-7-yl]Phenol] as a Therapeutic Candidate for Asthma and Chronic Obstructive Pulmonary Disease," *J. Pharmacol. Exp. Ther.* 328(3):758-765.
Doukas, J. et al. (2009). "Aerosolized Phosphoinositide 3-Kinase Gamma/Delta Inhibitor TG100-115 [3-[2,4-Diamino-6-(3-Hydroxyphenyl)Pteridin-7-yl]Phenol] as a Therapeutic Candidate for Asthma and Chronic Obstructive Pulmonary Disease," *J. Pharmacol. Exp. Ther.* 328(3):758-765, ACS on STN, caplus 2009:272611, 2 pages.

Duncan, R. L. et al. (Feb. 1973). "Synthesis of Indolo and Benzimidazoquinazolines and Benzodiazepines," *J. Heterocycl. Chem.* 10(1):65-70.
Ebrahim, S. et al. (Mar.-Apr. 2005). "Applications of Liposomes in Ophthalmology," *Surv. Ophthalmol.* 50(2):167-182.
Emedicinehealth, (Nov. 19, 2007). "Acute Respiratory Distress Syndrome," located at <http://www.emedicinehealth.com/acute_respiratory_distress_syndrome/page2_em.htm>, last visited on Nov. 19, 2007, 2 pages.
Fabbro, D. et al. (Feb.-Mar. 2002). "Protein Kinases as Targets for Anticancer Agents: From Inhibitors to Useful Drugs," *Pharmacol. Ther.* 93(2-3):79-98.
Fincham, V. J. et al. (Jan. 2, 1998). "The Catalytic Activity of Src is Dispensable for Translocation to Focal Adhesions But Controls the Turnover of These Structures During Cell Motility," *EMBO J.* 17(1):81-92.
Freshney, R. I. et al. (1983). "Chapter 1: Introduction," in *Culture of Animal Cells*, A Manual of Basic Technique, Alan R. Liss, Inc., New York, pp. 1-6.
Fröhlich, L. G. et al. (1999, E-pub Sep. 18, 1999). "Inhibition of Neuronal Nitric Oxide Synthase by 4-Amino Pteridine Derivatives: Structures-Activity Relationship of Antagonists of 6R)-5,6,7,8,-Tetrahydrobiopterin Cofactor," *J. Med. Chem.* 42(20):4108-4121.
Gazit, A. et al. (May 24, 1996). "Tyrphostins. 5. Potent Inhibitors of Platelet-Derived Growth Factor Receptor Tyrosine Kinase: Structure-Activity Relationships in Quinoxalines, Quinolines, and Indole Tyrphostins," *J. Med. Chem.* 39(11):2170-2177.
Golub, T. R. et al. (Oct. 15, 1999). "Molecular Classification of Cancer: Class Directory and Class Prediction by Gene Expression Monitoring," *Science* 286(5439):531-537.
Granelli-Piperno, A. (Apr. 1992). "SRC-Related Proto-Oncogenes and Transcription Factors in Primary Human T Cells: Modulation by Cyclosporine A and FK506," *J. Autoimmun.* 5(Suppl. A):145-158.
Hanke, J. H. et al. (Jan. 12, 1996). "Discovery of a Novel, Potent, and Src Family-Selective Tyrosine Kinase Inhibitor: Study of Lck- and FynT-Dependent T Cell Activation," *J. Bio. Chem.* 271(2):695-701.
Innovaro Pharmalicensing (2012). "Treatment of Vascular Leakage and Related Syndromes by Administering Metalloproteinase Inhibitors," article located at http://pharmalicensing.com/public/outlicensing/view/8022/treatment-of-vascular-leakage-and-related-symdromes-by-administering-metalloproteinase-inhibitors, last visited Mar. 9, 2012, 2 pages.
Ito, K. et al. (Apr. 2007, e-pub.: Oct. 4, 2006). "Therapeutic Potential of Phosphatidylinositol 3-Kinase Inhibitors in Inflammatory Respiratory Disease," *J. Pharm. Exp. Ther.* 321(1):1-8.
Jacobson, J. R. et al. (Jun. 2005, e-pub.: Jan. 21, 2005). "Simvastatin Attenuates Vascular Leak and Inflammation in Murine Inflammatory Lung Injury," *Am. J. Physiol. Lung. Cell. Mol. Physiol.* 288(6):L1026-L1032.
Jacquet, R. et al. (2004). "Liquid Chromatography Analysis of Monosubstituted Sulfobutyl Ether-β-Cyclodextrin Isomers on Porous Graphitic Carbon," *J. Sep. Sci.* 27:1221-1228.
Kiang, A. K. et al. (1956). "The Action of Acyl Cyanides on 2- and 1, 2-Substituted Indoles. Part II. Derivatives of 2-o-Aminophenylindole," *J. Am. Chem. Soc.* 2(14):1319-1324.
Kijlstra, a. et al. (Feb. 2005). "Immunological Factors in the Pathogenesis and Treatment of Age-Related Macular Degeneration," *Ocul. Immunol. Inflamm.* 13(1):3-11.
Klein, R. J. et al. (Apr. 15, 2005, e-pub. Mar. 20, 2010). "Complement Factor H Polymorphism in Age-Related Macular Degeneration," *Science* 308(5720):385-389.
Klutchko, S. R. et al. (Aug. 13, 1998, e-pub. Jul. 24, 1998). "2-Substituted Aminopyrido [2,3-*d*] pyrimidin-7 (8*H*)—ones. Structure-Activity Relationships Against Selected Tyrosine Kinases and in Vitro and in Vivo Anticancer Activity," *J. Med. Chem.* 41(17):3276-3292.
Kobayashi, N. et al. (May 1, 1993). "Functional Coupling of the src-Family Protein Tyrosine Kinases p59$^{fyn}$ and p53/56$^{lyn}$ with the Interleukin 2 Receptor: Implications for Redundancy and Pleiotropism in Cytokine Signal Transduction," *Proc. Natl. Acad. Sci. USA* 90(9):4201-4205.
Laffargue, M. et al. (Mar. 2002). "Phosphoinositide 3-Kinase γ is an Essential Amplifier of Mast Cell Function," *Immunity* 16(3):441-451.

Lee, C.-H. et al. (2001). "Discovery of 4-Amino-5-(3-Bromophenyl)-7-(6-Morpholino-Pyridin-3-yl)Pyrido[2,3-d]Pyrimidine, an Orally Active, Non-Nucleoside Adenosine Kinase Inhibitor," *J. Med. Chem.* 44(13):2133-2138.

Liu, K. et al. (Apr. 11, 2008). "Epidermal Growth Factor Receptor Signaling to Erk1/2 and STATs Control the Intensity of the Epithelial Inflammatory Responses to Rhinovirus Infection," *J. Biol. Chem.* 283(15):9977-9985.

Lowe, C. et al. (May 15, 1993). "Osteopetrosis in Src-Deficient Mice is Due to an Autonomous Defect of Osteoclasts," *Proc. Natl. Acad. Sci. USA* 90(10):4485-4489.

Madhusudan, S. et al. (2004). "Tyrosine Kinase Inhibitors in Cancer Therapy," *Clin. Biochem.* 37:618-635.

Mainardes, R. M. et al. (2005). "Colloidal Carriers for Ophthalmic Drug Delivery," *Curr. Drug. Targets* 6(3):363-371.

Mass, R. D. (Mar. 1, 2004). "The HER Receptor Family: A Rich Target for Therapeutic Development," *Int. J. Radiat Oncol. Bio. Phys.* 58(3):932-940.

Mayoclinic, (Jul. 5, 2006). "Stroke," article located at <http://www.mayoclinic.com/health/stroke/DS00150/dsection=7>, last visited on Nov. 19, 2007, 4 pages.

Medscape, (Sep. 5, 2006). "VEGF Manipulation Ameliorates Murine Asthma Symptoms," by David Douglas, located at <http://www.medscape.com/viewarticle/544205_print>, last visited on Nov. 19, 2007, one page.

Milhoan, K. A. et al. (Sep. 1992). "Hypoxia Induces Endothelial Cells to Increase Their Adherence for Neutrophils: Role of PAF," *Am. J. Physiol* 263(3 Pt 2):H956-H962.

Montrucchio, G. et al. (Oct. 2000). "Role of Platelet-Activating Factor in Cardiovascular Pathophysiology," *Physiol Rev.* 80(4):1669-1699.

Mullins, R. F. et al. (May 2000). "Drusen Associated with Aging and Age-Related Macular Degeneration Contain Proteins Common to Extracellular Deposits Associated with Atherosclerosis, Elastosis, Amyloidosis, and Dense Deposit Disease," *FASEB J.* 14:835-846.

New Mexico Department of Health, (Apr. 30, 2002). "Interleukin-2," located at <http://www.aidsinfonet.org> Project of the New Mexico Aids Education and Training Center, Fact Sheet No. 622, one page.

Newman, A. W. et al. (Oct. 19, 2003). "Solid-State Analysis of the Active Pharmaceutical Ingredient in Drug Products," *Drug Discovery Today* 8(19):898-905.

Nienaber, J. J. et al. (Oct. 2003). "Inhibition of Receptor-Localized PI3K Preserves Cardiac β-Adrenergic Receptor Function and Ameliorates Pressure Overload Heart Failure," *J. Clin. Invest.* 112(7):1067-1079.

O'Shea, J. J. et al. (Mar. 1, 1991). "Expression of v-*src* in a Murine T-Cell Hybridoma Results in Constitutive of T-Cell Receptor Phosphorylation and Interleukin 2 Production," *Proc. Natl. Acad. Sci. USA* 88(5):1741-1745.

Palanki, M. S. S. et al. (2007). "Discovery of 3,3'-(2,4-Diaminopteridine-6,7-diyl) diphenol as an Isozyme-Selective Inhibitor of PI3K for the Treatment of Ischemia Reperfusion Injury Associated With Myocardial Infarction," *J. Med. Chem.* 50(18):4279-4294, corresponding to caplus 2007:866646, one page.

Palanki, M. S. S. et al. (2007). "Discovery of 3,3'-(2,4-Diaminopteridine-6,7-diyl) diphenol as an Isozyme-Selective Inhibitor of PI3K for the Treatment of Ischemia Reperfusion Injury Associated With Myocardial Infarction," *J. Med. Chem.* 50(18):4279-4294.

Patrucco, E. et al. (Aug. 6, 2004). "PI3Kγ Modulates the Cardiac Response to Chronic Pressure Overload by Distinct Kinase-Dependent and -Independent Effects," *Cell* 118(3):375-387.

Plé, P. A. et al. (Feb. 12, 2004). "Discovery of a New Class of Anilinoquinazoline Inhibitors With High Affinity and Specificity for the Tyrosine Kinase Domain of c-Src," *J. Med. Chem.* 47(4):871-887.

Powell, T. J. et al. (Nov. 1999). "Growth Inhibition of Psoriatic Keratinocytes by Quinazoline Tyrosine Kinase Inhibitors," *Br. J. Dermatol.* 141(5):802-810.

Purchio, A. F. et al. (Mar. 1978). "Identification of a Polypeptide Encoded by the Avian Sarcoma Virus *src* Gene," *Proc. Natl. Acad. Sci. USA* 75(3):1567-1571.

Puri, K. D. et al. (May 1, 2004, e-pub. Jan. 29, 2004). "Mechanisms and Implications of Phosphoinositide 3-Kinase δ in Promoting Neutrophil Trafficking Into Inflamed Tissue," *Blood* 103(9):3448-3456.

Reissig, D. et al. (Apr. 2001). "Elevated Activity and Expression of Src Family Kinases in Human Breast Carcinoma Tissue Versus Matched Non-Tumor Tissue," *J. Cancer Res. Clin. Oncol.* 127(4):226-230.

Rosen, N. et al. (Oct. 15, 1986). "Analysis of pp60$^{c-src}$ Protein Kinase Activity in Human Tumor Cell Lines and Tissues," *J. Biol. Chem.* 261(29):13754-13759.

Sakurai, Y. et al. (1952). "367. Studies on Cancerocidal Substances. I. Effect of Pterins on the Yoshida Sarcoma," *Yakugaku Zasshi* 72(10):1294-1296.

Schoenwald, R. D. et al. (Nov. 1983). "Corneal Penetration Behavior of β-Blocking Agents I: Physicochemical Factors," *J. Pharm. Sci.* 72(11):1266-1272.

Schroeder, M. C. et al. (Jun. 7, 2001). "Soluble 2-Substituted Aminopyrido [2,3-*d*] pyrimidin-7-yl Ureas. Structure-Activity Relationships against Selected Tyrosine Kinases and Exploration of in Vitro and in Vivo Anticancer Activity," *J. Med. Chem.* 44(12):1915-1926.

Simone, J. V. (1996). "Introduction," in Chapter 154, in *Cecil Textbook of Medicine*, Philadelphia, W.B. Saunders Co., J. C. Bennett, eds., 20$^{th}$ edition, vol. 1, Part XIV entitled "Oncology," pp. 1004-1010.

Summy, J. M. et al. (Dec. 2003). "Src Family Kinases in Tumor Progression and Metastasis," *Cancer Metastasis Rev.* 22(4):337-358.

Taghavi-Moghadam, S. et al. (Sep. 29, 1997). "A New, General and Regioselective Method for the Synthesis of 2,6-Disubstituted 4-Aminopteridines," *Tetrahedron Letters* 38(39):6835-6836.

Talamonti, M. S. et al. (Jan. 1993). "Increase in Activity and Level of pp60$^{c-src}$ in Progressive Stages of Human Colorectal Cancer," *J. Clin. Investig.* 91(1):53-60.

Tanaka, N. et al. (Jun. 7, 1993). "A Novel Human Tyrosine Kinase Gene Inducible in T Cells by Interleukin 2," *FEBS Lett.* 324(1):1-5.

Torigoe, T. et al. (1992). "Regulation of SRC-Family Protein Tyrosine Kinases by Interleukins, IL-2, and IL-3," *Leukemia* 6(Suppl. 3):94S-97S.

Ulrich, J. (2004). "Crystal Engineering," in *Kirk-Othmer Encyclopedia of Chemical Technology*, 5$^{th}$ Edition, Wiley-Interscience, A John Wiley & Sons, Inc. Publication, vol. 8, definition of "Pseudopolymorphs," pp. 68-70.

Vippagunta, S. R. et al. (May 16, 2001). "Crystalline Solids," *Adv. Drug Deliv. Rev.* 48(1):3-26.

Weber, T. (Nov. 11, 2002). "Molecular Approaches to Study Cellular Roadblocks to Transfection and Transduction (Non-Viral Vectors and AAV-Based Vectors for Gene Therapy," located at <http://www.mssm.edu/genetherapy/weber.htm>, pp. 1-8.

Weis, S. et al. (Mar. 2004). "Src Blockade Stabilizes a Flk/Cadherin Complex, Reducing Edema and Tissue Injury Following Myocardial Infarction," *J. Clin. Investig.* 113(6):885-894.

Wermuth, C. G. (1996). "Molecular Variations Based on Isosteric Replacements," in *The Practice of Medicinal Chemistry*, Chapter 13, Publisher Technomiucs, Inc., U.S. Edition published by Academic Press Limited, vol. 1, p. vi, pp. 203-204, 210-215.

West, A. R. (1988). "Chapter 10—Solid Solutions," *Solid State Chemistry and Its Applications*, John Wiley & Sons, New York, pp. 358 & 365.

Wikipedia, (Nov. 14, 2007). "Acute Respiratory Distress Syndrome," located at <http://en.wikipedia.org/wiki/Acute_respiratory_distress_syndrome>, last visited on Nov. 19, 2007, 11 pages.

Wikipedia, (Apr. 30, 2008). "Myocardial Infarction," located at <http://en.wikipedia.org/wiki/Myocardial_Infarction>, last visited on May 1, 2008, 49 pages.

Wikipedia (Oct. 31, 2010). "Wortmannin" located at <http://en.wikipedia.org/wiki/Wortmannin>, last modified on Oct. 31, 2010, last visited on Mar. 16, 2011, 2 pages.

Wills, B. A. et al. (Sep. 1, 2005). "Comparison of Three Fluid Solutions for Resuscitation in Dengue Shock Syndrome," *The New England Journal of Medicine* 353(9):877-889.

Yamamoto, T. et al. (1991). "Role of *src*-Like Protooncogenes in Lymphocyte Proliferation," in *Multistage Carcinogenesis, Proceed-* ings of the 22<sup>nd</sup> *International Symposium of the Princess Takamatsu Cancer Research Fund*, Tokyo, C. C. Harris et al. (eds), Japan Scientific Societies Press, Tokyo, CRC Press, vol. 22, pp. 293-305.

Yum, H. K. et al. (Dec. 1, 2001). "Involvement of Phosphoinositide 3-Kinases in Neutrophil Activation and the Development of Acute Lung Injury," *J. Immunol.* 167(11):6601-6608.

Non Final Office Action mailed on Jun. 5, 2006, for U.S. Appl. No. 10/679,209, filed on Oct. 2, 2003, for Wrasidlo et al., 7 pages.

Notice of Allowance mailed on Oct. 4, 2006, for U.S. Appl. No. 10/679,209, filed on Oct. 2, 2003, for Wrasidlo et al., with PTO Form 892, 9 pages.

Non Final Office Action mailed on Jun. 1, 2009, for U.S. Appl. No. 11/653,190, filed on Jan. 11, 2007, for Wrasidlo et al., 14 pages.

Non Final Office Action mailed on Nov. 26, 2007, for U.S. Appl. No. 11/105,845, filed on Apr. 13, 2005, for Wrasidlo et al., 15 pages.

Final Office Action mailed on May 5, 2008, for U.S. Appl. No. 11/105,845, filed on Apr. 13, 2005, for Wrasidlo et al., 8 pages.

Final Office Action mailed on Nov. 7, 2008, for U.S. Appl. No. 11/105,845, filed on Apr. 13, 2005, for Wrasidlo et al., 9 pages.

Final Office Action mailed on Apr. 30, 2009, for U.S. Appl. No. 11/105,845, filed on Apr. 13, 2005, for Wrasidlo et al., 5 pages.

Non Final Office Action mailed on Jul. 28, 2011, for U.S. Appl. No. 12/780,401, filed on May 14, 2010, 11 pages.

Final Office Action mailed on Mar. 7, 2012, for U.S. Appl. No. 12/780,401, filed on May 14, 2010, 7 pages.

Non Final Office Action mailed on Sep. 20, 2007, for U.S. Appl. No. 11/102,405, filed on Apr. 7, 2005, 20 pages.

Non Final Office Action mailed on Mar. 24, 2008, for U.S. Appl. No. 11/102,405, filed on Apr. 7, 2005, 12 pages.

Non Final Office Action mailed on Jun. 28, 2010, for U.S. Appl. No. 12/207,019, filed on Sep. 9, 2008, 22 pages.

Non Final Office Action mailed on Jan. 6, 2009, for U.S. Appl. No. 11/212,064, filed on Aug. 24, 2005, 26 pages.

Non Final Office Action mailed on Jul. 23, 2008, for U.S. Appl. No. 11/377,234, filed on Mar. 15, 2006, 23 pages.

Non Final Office Action mailed on Jan. 12, 2009, for U.S. Appl. No. 11/377,234, filed on Mar. 15, 2006, 6 pages.

International Search Report mailed on Jul. 2, 2004, for PCT Patent Application No. PCT/US2003/031721, filed on Oct. 2, 2003, published on Apr. 15, 2004, as WO 2004/30635, 2 pages.

International Preliminary Report mailed on Patentability mailed on Dec. 3, 2004, for PCT Patent Application No. PCT/US2003/031721, filed on Oct. 2, 2003, published on Apr. 15, 2004, as WO 2004/30635, 3 pages.

Supplementary European Search Report mailed on Mar. 17, 2008, for European Patent Application No. 03774610.4, filed on Oct. 2, 2003, published on Jul. 6, 2005, as EP 1 549 614, 5 pages.

European Examination Report mailed on Nov. 24, 2009, for European Patent Application No. 03774610.4, filed on Oct. 2, 2003, published on Jul. 6, 2005, as EP 1 549 614, 8 pages.

Supplementary European Search Report mailed on Jun. 18, 2009, for European Patent Application No. 08014818.2, filed on Oct. 2, 2003, published on Mar. 25, 2009, as EP 2 039 683, 3 pages.

European Written Opinion mailed on Jun. 18, 2009, for European Patent Application No. 08014818.2, filed on Oct. 2, 2003, published on Mar. 25, 2009, as EP 2 039 683, 2 pages.

European Office Action mailed on Oct. 4, 2010, for European patent Application No. 08014818.2, filed on Oct. 2, 2003, published on Mar. 25, 2009, as EP 2 039 683, 7 pages.

International Search Report mailed on Sep. 2, 2008, for PCT Patent Application No. PCT/US2005/012057, filed on Apr. 7, 2005, published on Oct. 20, 2005, as PCT Publication No. WO 2005/096784, 2 pages.

Written Opinion mailed on Sep. 2, 2008, for PCT Patent Application No. PCT/US2005/012057, filed on Apr. 7, 2005, published on Oct. 20, 2005, as PCT Publication No. WO 2005/096784, 4 pages.

Supplementary European Search Report mailed on Jan. 18, 2010, for European Patent Application No. 07562774.7, filed on Apr. 7, 2005, published on Jul. 25, 2007, as European Publication No. 1 809 614, 3 pages.

European Examination Report mailed on May 3, 2010, for European Patent Application No. 07562774.7, filed on Apr. 7, 2005, published on Jul. 25, 2007, as European Publication No. 1 809 614, 4 pages.

International Search Report mailed on Jan. 27, 2006, for PCT Patent Application No. PCT/US2005/030614, filed on Aug. 24, 2005, published on Mar. 2, 2006, as PCT Publication No. WO 2006/024034, one page.

Written Opinion mailed on Jan. 27, 2006, for PCT Patent Application No. PCT/US2005/030614, filed on Aug. 24, 2005, published on Mar. 2, 2006, as PCT Publication No. WO 2006/024034, 5 pages.

European Search Report and European Written Opinion mailed on Aug. 5, 2009, for European Patent Application No. 05792421.9, filed on Aug. 24, 2005, published on Jun. 27, 2007 as European Publication No. 1 799 656, 5 pages.

International Search Report mailed on Sep. 21, 2006, for PCT Patent Application No. PCT/US2006/009518, filed on Mar. 15, 2006, published on Sep. 28, 2006, as WO 2006/101977, 2 pages.

Written Opinion mailed on Sep. 21, 2006, for PCT Patent Application No. PCT/US2006/009518, filed on Mar. 15, 2006, published on Sep. 28, 2006, as WO 2006/101977, 4 pages.

International Search Report mailed on Sep. 18, 2006, for PCT Patent Application No. PCT/US2006/022480, filed on Jun. 7, 2006, published on Dec. 14, 2006, as WO 2006/133411, one page.

Written Opinion mailed on Sep. 18, 2006, for PCT Patent Application No. PCT/US2006/022480, filed on Jun. 7, 2006, published on Dec. 14, 2006, as WO 2006/133411, 3 pages.

International Search Report mailed on Jul. 8, 2009, for PCT Patent Application No. PCT/US2009/033353, filed on Feb. 6, 2009, published on Aug. 13, 2009, as WO 2009/100305, 2 pages.

Written Opinion mailed on Jul. 8, 2009, for PCT Patent Application No. PCT/US2009/033353, filed on Feb. 6, 2009, published on Aug. 13, 2009, as WO 2009/100305, 5 pages.

U.S. Appl. No. 12/846,702, filed on Jul. 29, 2010, for Noronha et al.
U.S. Appl. No. 13/220,394, filed on Aug. 29, 2011, for Noronha et al.
U.S. Appl. No. 13/243,924, filed on Sep. 23, 2011, for Wrasidlo et al.
U.S. Appl. No. 13/357,500, filed on Jan. 24, 2012, for Noronha et al.

Extended European Search Report mailed on Nov. 12, 2012 for European Patent Application No. 1118890.5, filed on Mar. 19, 2007, 5 pages.

Extended European Search Report mailed on Dec. 6, 2012, for European Patent Application No. 12167912.0, filed on Apr. 4, 2005, 6 pages.

* cited by examiner

BENZOTRIAZINE INHIBITORS OF KINASES

CROSS REFERENCE TO RELATED APPLICATIONS

This application is a continuation of U.S. Ser. No. 12/207,019, filed Sep. 9, 2008, which is a continuation of U.S. Ser. No. 11/102,405 (now U.S. Pat. No. 7,456,176), filed Apr. 7, 2005, which claims the benefit of priority under 35 U.S.C. §119(e) of patent applications U.S. Ser. No. 60/561,237 filed Apr. 8, 2004, and 60/643,439 filed Jan. 12, 2005, and which the entire content of each is incorporated herein by reference.

FIELD OF THE INVENTION

The present invention relates generally to the use of compounds to treat a variety of disorders, diseases and pathologic conditions and more specifically to the use of benzotriazine compounds to treat disorders.

BACKGROUND c-Src plays a major role in the growth, progression and metastasis of a large number of cancers. c-Src can be the transforming element of the oncogenic Rous sarcoma retrovirus. Subsequently, it has been demonstrated that c-Src kinase can have the oncogenic potential. Gene knockout experiments suggest that inhibition of some members of the Src family might have potential therapeutic benefit.

Tyrosine kinases (TKs) phosphorylate tyrosine residues in peptides and proteins. These enzymes are key elements in the regulation of cell signaling including cell proliferation and cell differentiation. Protein TKs comprise the receptor TKs, including the epidermal growth family members (HER1 and HER2 for example), platelet derived growth factor (PDGF) and kinases that play a role in angiogenesis (Tie-2 and KDR for example), and the cellular or non-receptor kinases, which include members of the Src family.

c-Src TK is one of three members of the Src family expressed ubiquitously. c-Src is expressed at low levels in most cell types and, in the absence of the appropriate extracellular stimuli, maintained in an inactive conformation through phosphorylation of a regulatory tyrosine domain at Tyr530. Activation of c-Src occurs through dephosphorylation of the Tyr530 site and phosphorylation of a second tyrosine, Tyr419, present in the kinase domain of the enzyme.

Src kinase modulates signal transduction through multiple oncogenic pathways, including EGFR, HER2, PDGFR, FGFR and VEGFR. Thus, blocking signaling through the inhibition of the kinase activity of Src can be an effective means of modulating aberrant pathways that drive the oncogenic transformation of cells.

There exists a body of evidence of misregulated increased kinase activity of c-Src in several human tumor types, most notably colon and breast tumors. Misregulated c-Src TK activity has also been associated with adhesion and cytoskeletal changes both in tumor cells and otherwise, ultimately resulting in an invasive phenotype that may be motile. c-Src TK activity has been shown to be an important component in the epithelial to mesenchymal transition that occurs in the early stages of invasion of carcinoma cells. c-Src activity is also known to be essential in the turnover of local adhesions, a critical cell-motility component. In in vivo models of metastasis, c-Src inhibition markedly reduces the rate of lymph and liver metastases. Clinical data supports the link between misregulated Src activity and the increased invasive potential of tumor cells. In colon tumors, increased c-Src TK activity has been shown to correlate to tumor progression, with the highest activity found in metastatic tissue. Increased Src activity in colon tumors might be an indicator of poor prognosis. In breast and ovarian cancers, enhancement of Src kinase activity has been reported, and in transitional cell carcinoma of the bladder, c-Src activity peaked as superficial tumors became muscle invasive.

Biochemically, cellular stimuli that lead to Src activation result in increased association between Src and the cytoskeleton. As a result, Src mediates the phosphorylation of many intracellular substrates such as EGFR, FAK, PYK2, paxillin, Stat3, and cyclin D. The biological effects of these interactions affect cell motility, adhesion, cell cycle progression, and apoptosis and might have some connection to the disease related effects stated above. Thus, Src plays a role in responses to regional hypoxia, limited nutrients, and internal cellular effects to self-destruct.

Increased c-Src TK activity results in breakdown of the E-cadherin-mediated epithelial cell-cell adhesion, which can be restored by Src inhibition. Intimate connections between increased VEGF activity, Src activity, and cellular barrier function related to vascular leak have been also demonstrated. Inhibition of Src results in decrease in vascular leak when exogenous VEGF is administered in in vivo studies. Examples where excessive vascular permeability leads to particularly deleterious effects include pulmonary edema, cerebral edema, and cardiac edema.

The cascade of events leading to loss of endothelial barrier function is complex and incompletely understood. Data support some role for kinases in this process. For example, VEGF-mediated edema has been shown to involve intracellular signaling by Src family kinases, protein kinase C, and Akt kinase. Rho-associated kinases have been linked to thrombin-mediated vascular leakage, and protein kinase C to TNF-induced leakage. Kinases are believed to mediate the phosphorylation of junctional proteins such as beta-catenin and vascular endothelial VE-cadherin, leading to the dissolution of adherens junctions and the dissociation of cadherin-catenin complexes from their cytoskeletal anchors. Proteins which regulate the intercellular contractile machinery such as myosin light chain kinase (MLCK) and myosin light chain (MLC) are also activated, resulting in cellular contraction, and therefore an opening of intercellular junctions.

A general approach to the inhibition of vascular leakage can be to interfere with any of the underlying mechanistic pathways, whether by inhibition of kinase signaling or the intercellular contractile apparatus or other cellular processes. This can then lead to potential treatments for edema and its associated pathologies. For example, inhibiting edema formation should be beneficial to overall patient outcome in situations such as inflammation, allergic diseases, cancer, cerebral stroke, myocardial infarction, pulmonary and cardiac insufficiency, renal failure, and retinopathies, to name a few. Furthermore, as edema is a general consequence of tissue hypoxia, it can also be concluded that inhibition of vascular leakage represents a potential approach to the treatment of tissue hypoxia. For example, interruption of blood flow by pathologic conditions (such as thrombus formation) or medical intervention (such as cardioplegia, organ transplantation, and angioplasty) could be treated both acutely and prophylactically using inhibitors of vascular leakage, especially as in the case of Src inhibitors.

Accordingly, a small molecule inhibitor of c-Src can be beneficial for the treatment of several disease states.

SUMMARY

The present invention provides methods of use for certain chemical compounds such as kinase inhibitors for treatment of various diseases, disorders, and pathologies, for example, cancer, and vascular disorders, such as myocardial infarction (MI), stroke, or ischemia.

The benzotriazine compounds described in this invention may block the enzymatic activity of some or many of the members of the Src family, in addition to blocking the activity of other receptor and non-receptor kinases. Such compounds may be beneficial for treatment of the diseases where disorders affect cell motility, adhesion, and cell cycle progression, and in addition, diseases with related hypoxic conditions, osteoporosis and conditions, which result from or are related to increases in vascular permeability, inflammation or respiratory distress, tumor growth, invasion, angiogenesis, metastases and apoptosis.

According to the embodiments of the invention, some examples of kinase inhibitors that can be used to bring about beneficial therapeutic results include inhibitors of Src kinase.

According to one embodiment of the invention, there are provided compounds having the structure (I), and pharmaceutically acceptable salts, hydrates, solvates, crystal forms, N-oxides, and individuals diastereoners thereof:

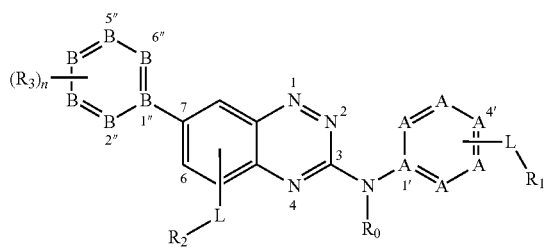

(I)

wherein each of A can be $(CH)_{0-1}$, N, NH, O, S, or a part of a ring fusion to form a second ring, where the second ring can be an aromatic, a heteroaromatic, a bicyclic aromatic, a bicyclic aromatic heterocyclic ring, or a bicyclic with only the first ring being aromatic or heteroaromatic;

each of B can be $(CH)_{0-1}$, N, NH, O, S, or a part of a ring fusion to form a second ring, where the second ring can be an aromatic, a heteroaromatic, a bicyclic aromatic, a bicyclic aromatic heterocyclic ring, or a bicyclic with only the first ring being aromatic or heteroaromatic, with the further proviso that if each B is $(CH)_0$, $R_3$ can be any substitutent described below, other than hydrogen, bonded directly to the position 7 of the adjacent ring;

$R_0$ can be H or lower alkyl;

L can be a bond, or a substituted or unsubstituted alkyl, alkenyl, or alkynyl linking moiety;

$R_1$ can be $C(R')_3$, OR', $N(R')_2$, NR'C(O)R', NR'C(O)O(R'), NR'C(O)N(R')_2$, SR', C(O)(O)R', C(O), C(O)N(R')_2$, $SO_3R'$, $OSO_2R'$, $SO_2R'$, SOR', $S(O)N(R')_2$, $OS(O)(O)N(R')_2$, S(O)(O)N(R')_2$, $S(O)N(R')_2$, $PO_4R'$, $OPO_2R'$, $PO_3R'$, $PO_2R'$, or a 3-6 membered heterocycle with one or more heterocyclic atoms, with each heteroatom being capable of carrying any R' group on it, wherein R' can be hydrogen, lower alkyl, alkyl-hydroxyl, thiol-alkyl, alkyl-thiol, aminoalkyl, alkylamino, branched alkyl, branched alkyl hydroxyl, branched thio-alkyl, branched alkyl-thiol, branched aminoalkyl, branched alkylamino, or a closed 3-6 membered carbocycle or heterocycle, with each heteroatom in the 3-6 membered heterocycle being capable of carrying any R' group on it, and wherein each R' can be independent in case there is more than one R';

$R_2$ is a substitutent situated at position 5, 6 or 8 of the ring, wherein $R_2$ can be methyl, ethyl, n-propyl, iso-propyl, n-butyl, iso-butyl, tert-butyl, iso-pentyl, phenyl, substituted phenyl, halogen, branched or unbranched alkylamino, branched or unbranched aminoalkyl, branched or unbranched alkyloxo, branched or unbranched oxyalkyl, branched or unbranched thioalkyl, branched or unbranched alkylthiol, $CF_3$, sulfonamido, substituted sulfonamido, sulfonate, sulfonate ester, phosphate, phosphate ester, phosphonate, phosphonate ester, carboxo, amido, ureido, substituted carboxo, substituted amido, substituted ureido, or a 3-6 membered carbocycle or heterocycle attached to positions 5, 6 or 8 directly or through group L, each heteroatom being capable of carrying any group $R_2$, with the further proviso that either one, two or three substituents $R_2$ can be present in the ring, and each of the substituents $R_2$ can be the same or different;

$R_3$ can be hydrogen, alkyl, alkoxy, halogen, $CF_3$, cyano, substituted alkyl, or hydroxyl, aryl, substituted aryl, heteroaryl, substituted heteroaryl, heterocycle, $C(R'')_3$, OR'', $N(R'')_2$, NR''C(O)R'', NR''C(O)NR'', R'', C(O)(O)R'', OC(O)R'', C(O)N(R'')_2$, C(O), OC(O)N(R'')_2$, $SO_3R''$, $OSO_2R''$, $SO_2R''$, SOR'', $PO_4R''$, $OPO_2R''$, $PO_3R''$, $PO_2R''$, wherein R'' can be hydrogen, aryl, substituted aryl, heteroaryl, substituted heteroaryl, lower alkyl, branched lower alkyl, alkyl-hydroxyl, branched alkyl-hydroxyl, amino-alkyl, branched amino-alkyl, alkyl-amino, branched alkyl-amino, thiol-alkyl, branched thiol-alkyl, alkyl-thiol, branched thiol-alkyl, or may form a closed 3-6 membered heterocycle with one or more heterocyclic atoms, branched alkyl, branched alkyl hydroxyl, where each R'' can be independent in case there is more than one R'';

n is an integer that can have value between 1 and 5, with the further proviso that if n≧2, then each group $R_3$ is independent of the other groups $R_3$, with the further proviso that if each A is $(CH)_0$, L is a bond.

In yet another embodiment, there are provided articles of manufacture including packaging material and a pharmaceutical composition contained within the packaging material, wherein the packaging material includes a label which indicates that the pharmaceutical composition can be used for treatment of disorders associated with compromised vasculostasis, and wherein the pharmaceutical composition includes at least one compound of structure (I).

In another embodiment, there are provided articles of manufacture including packaging material and a pharmaceutical composition contained within the packaging material, wherein the packaging material includes a label which indicates that the pharmaceutical composition can be used for treatment of disorders associated with vascular permeability leakage or compromised vasculostasis, such as myocardial infarction, stroke, congestive heart failure, an ischemia or reperfusion injury, cancer, arthritis or other arthropathy, retinopathy or vitreoretinal disease, macular degeneration, autoimmune disease, vascular leakage syndrome, inflammatory disease, edema, transplant rejection, burn, or acute or adult respiratory distress syndrome (ARDS) and wherein the pharmaceutical composition includes at least one compound of structure (I).

In another embodiment, there are provided methods of treating a disorder associated with compromised vasculostasis, including the administration of a therapeutically effective amount of at least one compound of structure (I) or pharmaceutically acceptable salts, hydrates, solvates, crystal forms and individual diastereomers thereof, to a subject in need of such treatment.

In yet another embodiment, there are provided methods of treating a disorder associated with compromised vasculostasis including the administration of a therapeutically effective amount of at least one compound of structure (I), or pharmaceutically acceptable salts, hydrates, solvates, crystal forms and individual diastereomers thereof, in combination with an anti-inflammatory, chemotherapeutic agent, immunomodulatory agent, therapeutic antibody or a protein kinase inhibitor, to a subject in need of such treatment.

In others embodiment, there are provided methods of treating a subject having or at risk of having a disorder selected from myocardial infarction, vascular leakage syndrome (VLS), cancer, stroke, ARDS, burns, arthritis, edema, retinopathy or vitreoretinal disease, ischemic or reperfusion related tissue injury or damage, autoimmune disease, transplant rejection, inflammatory disease, including administering to the subject a therapeutically effective amount of at least one compound of structure (I), thereby treating the subject.

In another embodiment, there are provided processes for making a pharmaceutical composition including combining a combination of at least one compound of structure (I) or its pharmaceutically acceptable salts, hydrates, solvates, crystal forms salts and individual diastereomers thereof and a pharmaceutically acceptable carrier.

DETAILED DESCRIPTION

A. Terms and Definitions

The following terminology and definitions apply as used in the present application, generally in conformity with the terminology recommended by the International Union of Pure and Applied Chemistry (IUPAC):

The term "heterocyclic," when used to describe an aromatic ring, refer to the aromatic ring containing at least one heteroatom.

The term "heteroatom" refers to any atom other than carbon, for example, N, O, or S.

The term "aromatic" refers to a cyclically conjugated molecular entity with a stability, due to delocalization, significantly greater than that of a hypothetical localized structure, such as the Kekulé structure.

The term "heterocyclic," when not used to describe an aromatic ring, refers to cyclic (i.e., ring-containing) groups other than aromatic groups, the cyclic group being formed by between 3 and about 14 carbon atoms and at least one heteroatom described above.

The term "substituted heterocyclic" refers, for both aromatic and non-aromatic structures, to heterocyclic groups further bearing one or more substituents described above.

The term "alkyl" refers to a monovalent straight or branched chain hydrocarbon group having from one to about 12 carbon atoms, for example, methyl, ethyl, n-propyl, isopropyl, n-butyl, iso-butyl, tert-butyl, n-pentyl (also known as n-amyl), n-hexyl, and the like.

The term "substituted alkyl" refers to alkyl groups further bearing one or more substituents such as hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, aldehyde, acyl, oxyacyl, carboxyl, sulfonyl, sulfonamide, sulfuryl, and the like.

The term "lower alkyl" refers to alkyl groups having from 1 to about 6 carbon atoms.

The term "alkenyl" refers to straight-chained or branched hydrocarbyl groups having at least one carbon-carbon double bond, and having between about 2 and about 12 carbon atoms, and the term "substituted alkenyl" refers to alkenyl groups further bearing one or more substituents described above.

The term "alkynyl" refers to straight-chained or branched hydrocarbyl groups having at least one carbon-carbon triple bond, and having between about 2 and about 12 carbon atoms, and the term "substituted alkynyl" refers to alkynyl groups further bearing one or more substituents described above.

The term "aryl" refers to aromatic groups having between about 5 and about 14 carbon atoms and the term "substituted aryl" refers to aryl groups further bearing one or more substituents described above.

The term "heteroaryl" refers to aromatic rings, where the ring structure is formed by between 3 and about 14 carbon atoms and by at least one heteroatom described above, and the term "substituted heteroaryl" refers to heteroaryl groups further bearing one or more substituents described above.

The term "alkoxy" refers to the moiety —O-alkyl, wherein alkyl is as defined above, and the term "substituted alkoxy" refers to alkoxy groups further bearing one or more substituents described above.

The term "cycloalkyl" refers to alkyl groups having between 3 and about 8 carbon atoms arranged as a ring, and the term "substituted cycloalkyl" refers to cycloalkyl groups further bearing one or more substituents described above.

The term "alkylaryl" refers to alkyl-substituted aryl groups and the term "substituted alkylaryl" refers to alkylaryl groups further bearing one or more substituents described above.

The term "arylalkyl" refers to aryl-substituted alkyl groups and the term "substituted arylalkyl" refers to arylalkyl groups further bearing one or more substituents described above.

The term "arylalkenyl" refers to aryl-substituted alkenyl groups and the term "substituted arylalkenyl" refers to arylalkenyl groups further bearing one or more substituents described above.

The term "arylalkynyl" refers to aryl-substituted alkynyl groups and the term "substituted arylalkynyl" refers to arylalkynyl groups further bearing one or more substituents described above.

The term "arylene" refers to divalent aromatic groups having between 5 and about 14 carbon atoms and the term "substituted arylene" refers to arylene groups further bearing one or more substituents described above.

The term "kinase" refers to any enzyme that catalyzes the addition of phosphate groups to a protein residue; for example, serine and threonine kinases catalyze the addition of phosphate groups to serine and threonine residues.

The terms "Src kinase," "Src kinase family," and "Src family" refer to the related homologs or analogs belonging to the mammalian family of Src kinases, including, for example, c-Src, Fyn, Yes and Lyn kinases and the hematopoietic-restricted kinases Hck, Fgr, Lck and Blk.

The terms "Src kinase signaling pathway," and "Src cascade" refer to both the upstream and downstream components of the Src signaling cascade.

The term "therapeutically effective amount" refers to the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

The term "pharmaceutically acceptable" refers to the fact that the carrier, diluent or excipient must be compatible with the other ingredients of the formulation and not deleterious to the recipient thereof.

The terms "administration of a compound" or "administering a compound" refer to the act of providing a compound of the invention or pharmaceutical composition to the subject in need of treatment.

The term "antibody" refers to intact molecules of polyclonal or monoclonal antibodies, as well as fragments thereof, such as Fab and F(ab')$_2$, Fv and SCA fragments which are capable of binding an epitopic determinant.

The term "vasculostasis" refers to the maintenance of the homeostatic vascular functioning leading to the normal physiologic functioning. The term "vasculostatic agents" refers to agents that seek to address conditions in which vasculostasis is compromised by preventing the loss of or restoring or maintaining vasculostasis.

B. Embodiments of the Invention

According to an embodiment of the invention, compounds having the structure (I) are provided for treatment of various diseases, disorders, and pathologies, as well as pharmaceutically acceptable salts, hydrates, solvates, crystal forms, N-oxides, and individuals diastereomers of compounds having the structure (I):

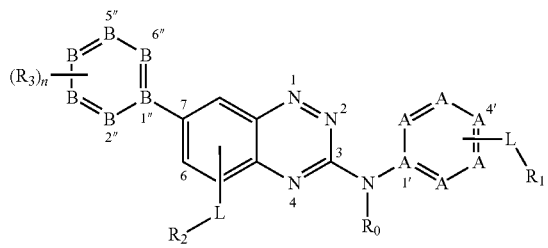

(I)

wherein each of A can be (CH)$_{0-1}$, N, NH, O, S, or a part of a ring fusion to form a second ring, where the second ring can be an aromatic, a heteroaromatic, a bicyclic aromatic, a bicyclic aromatic heterocyclic ring, or a bicyclic with only the first ring being aromatic or heteroaromatic;

each of B can be (CH)$_{0-1}$, N, NH, O, S, or a part of a ring fusion to form a second ring, where the second ring can be an aromatic, a heteroaromatic, a bicyclic aromatic, a bicyclic aromatic heterocyclic ring, or a bicyclic with only the first ring being aromatic or heteroaromatic, with the further proviso that if each B is (CH)$_0$, R$_3$ can be any substituent described below, other than hydrogen, bonded directly to the position 7 of the adjacent ring;

R$_0$ can be H or lower alkyl;

L can be a bond, or a substituted or unsubstituted alkyl, alkenyl, or alkynyl linking moiety;

R$_1$ can be C(R')$_3$, OR', N(R')$_2$, NR'C(O)R', NR'C(O)O(R'), NR'C(O)N(R')$_2$, SR', C(O)(O)R', C(O), C(O)N(R')$_2$, SO$_3$R', OSO$_2$R', SO$_2$R', SOR', S(O)N(R')$_2$, OS(O)(O)N(R')$_2$, S(O)(O)N(R')$_2$, S(O)N(R')$_2$, PO$_4$R', OPO$_2$R', PO$_3$R', PO$_2$R', or a 3-6 membered heterocycle with one or more heterocyclic atoms, with each heteroatom being capable of carrying any R' group on it, wherein R' can be hydrogen, lower alkyl, alkyl-hydroxyl, thiol-alkyl, alkyl-thiol, aminoalkyl, alkylamino, branched alkyl, branched alkyl hydroxyl, branched thio-alkyl, branched alkyl-thiol, branched aminoalkyl, branched alkylamino, or a closed 3-6 membered carbocycle or heterocycle, with each heteroatom in the 3-6 membered heterocycle being capable of carrying any R' group on it, and wherein each R' can be independent in case there is more than one R';

R$_2$ is a substituent situated at position 5, 6 or 8 of the ring, wherein R$_2$ can be methyl, ethyl, n-propyl, iso-propyl, n-butyl, iso-butyl, tert-butyl, iso-pentyl, phenyl, substituted phenyl, halogen, branched or unbranched alkylamino, branched or unbranched aminoalkyl, branched or unbranched alkyloxo, branched or unbranched oxyalkyl, branched or unbranched thioalkyl, branched or unbranched alkylthiol, CF$_3$, sulfonamido, substituted sulfonamido, sulfonate, sulfonate ester, phosphate, phosphate ester, phosphonate, phosphonate ester, carboxo, amido, ureido, substituted carboxo, substituted amido, substituted ureido, or a 3-6 membered carbocycle or heterocycle attached to positions 5, 6 or 8 directly or through group L, each heteroatom being capable of carrying any group R$_2$, with the further proviso that either one, two or three substituents R$_2$ can be present in the ring, and each of the substituents R$_2$ can be the same or different;

R$_3$ can be hydrogen, alkyl, alkoxy, halogen, CF$_3$, cyano, substituted alkyl, or hydroxyl, aryl, substituted aryl, heteroaryl, substituted heteroaryl, heterocycle, C(R")$_3$, OR", N(R")$_2$, NR"C(O)R", NR"C(O)NR", R", C(O)(O)R", OC(O)R", C(O)N(R")$_2$, C(O), OC(O)N(R")$_2$, SO$_3$R", OSO$_2$R", SO$_2$R", SOR", PO$_4$R", OPO$_2$R", PO$_3$R", PO$_2$R", wherein R" can be hydrogen, aryl, substituted aryl, heteroaryl, substituted heteroaryl, lower alkyl, branched lower alkyl, alkyl-hydroxyl, branched alkyl-hydroxyl, amino-alkyl, branched amino-alkyl, alkyl-amino, branched alkyl-amino, thiol-alkyl, branched thiol-alkyl, alkyl-thiol, branched thiol-alkyl, or may form a closed 3-6 membered heterocycle with one or more heterocyclic atoms, branched alkyl, branched alkyl hydroxyl, where each R" can be independent in case there is more than one R";

n is an integer that can have value between 1 and 5, with the further proviso that if n≧2, then each group R$_3$ is independent of the other groups R$_3$, with the further proviso that if each A is (CH)$_0$, L is a bond.

Some exemplary compounds described by formula (I) that can be used include the following compounds:

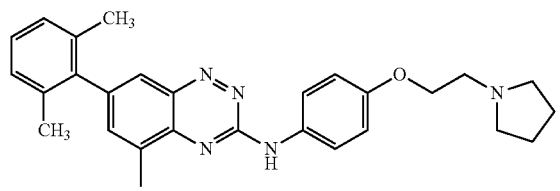

(IX)                                      (XI)

-continued
(XLVIII)
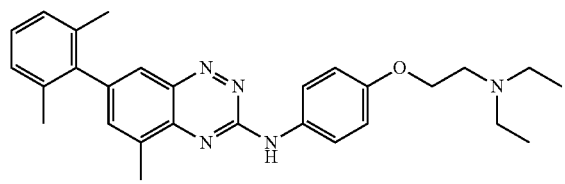
(XLIX)
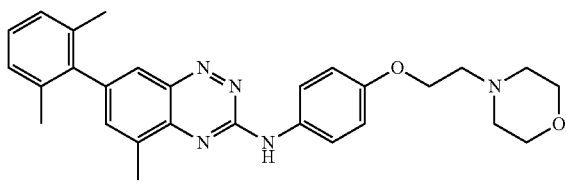
(L)
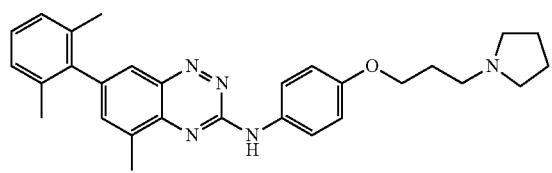
(LII)
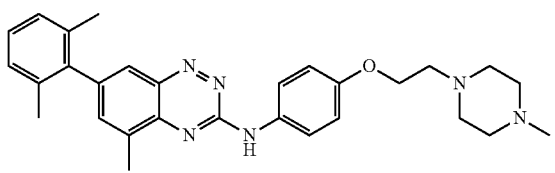
(LIII)
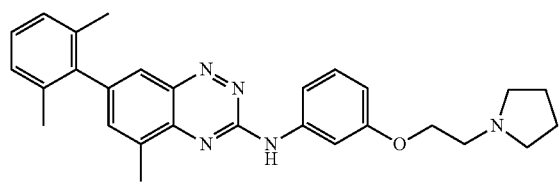
(LIV)
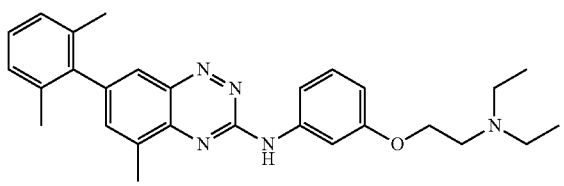
(CXXXII)
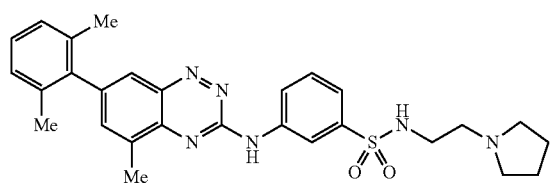
(CXXXIV)
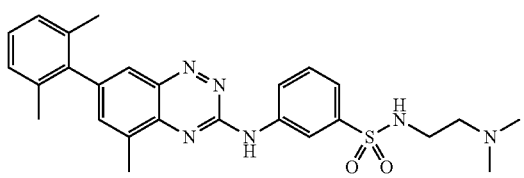
(CXXXVIII)
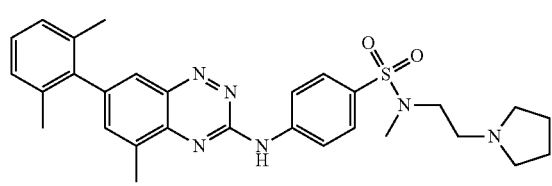
(CCXLIII)
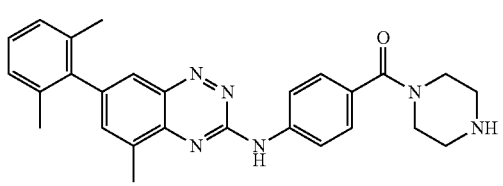
(CCLV)
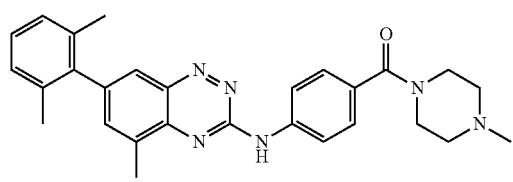
(CCLVIII)
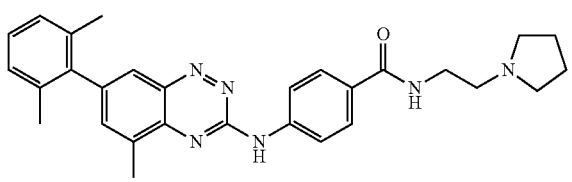
(CCLX)
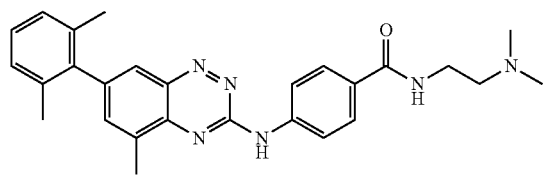
(CCLXI)
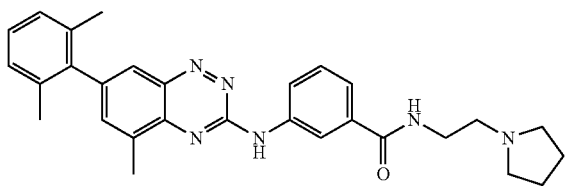

-continued
(CCLXII)
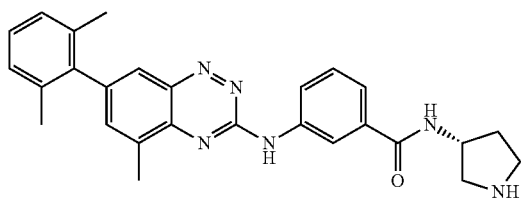
(CCLXIII)
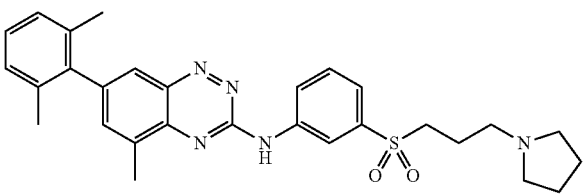
(CCLXV)
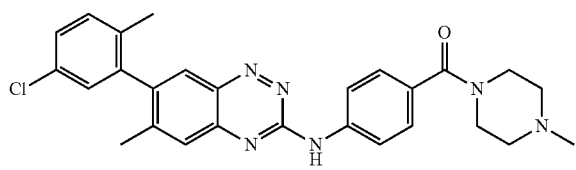
(CCLXVI)
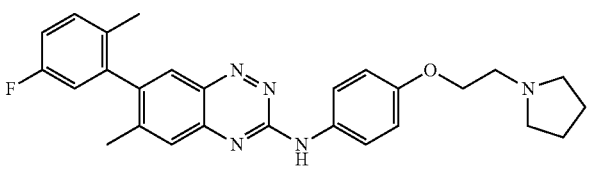
(CCLXXII)
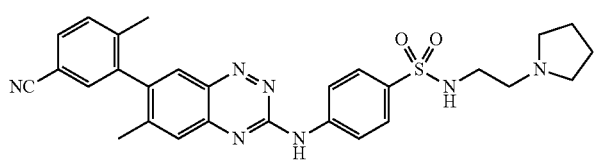
(CCLXXVII)
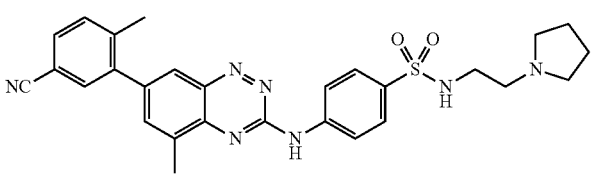
(LI)
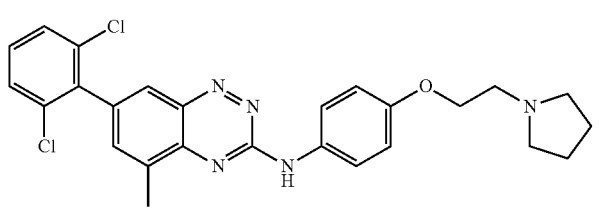
(LXX)
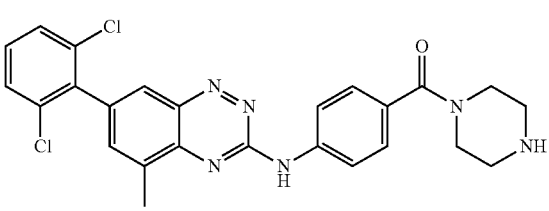
(LXXI)
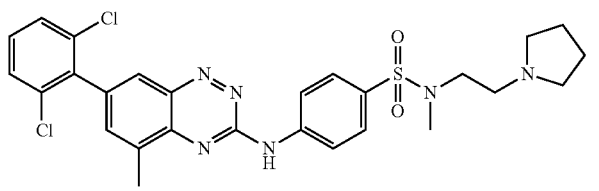
(CXII)
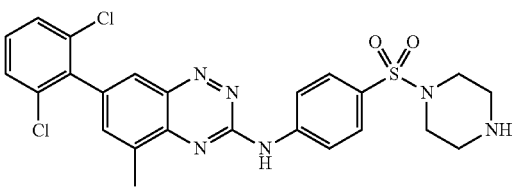
(CXIV)
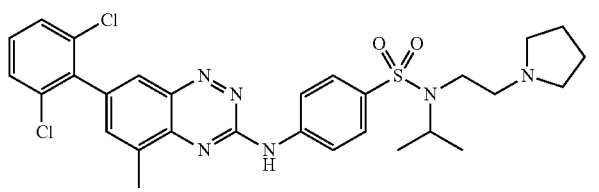
(CXV)
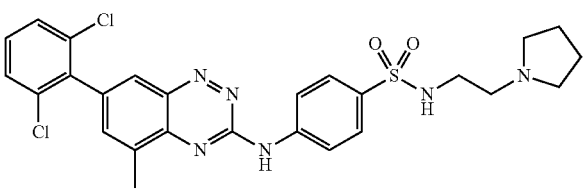
(CCLXXIX)
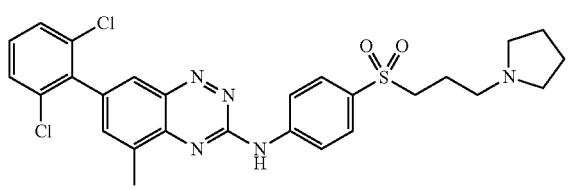
(LVIII)
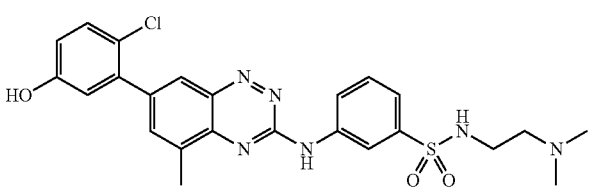

-continued
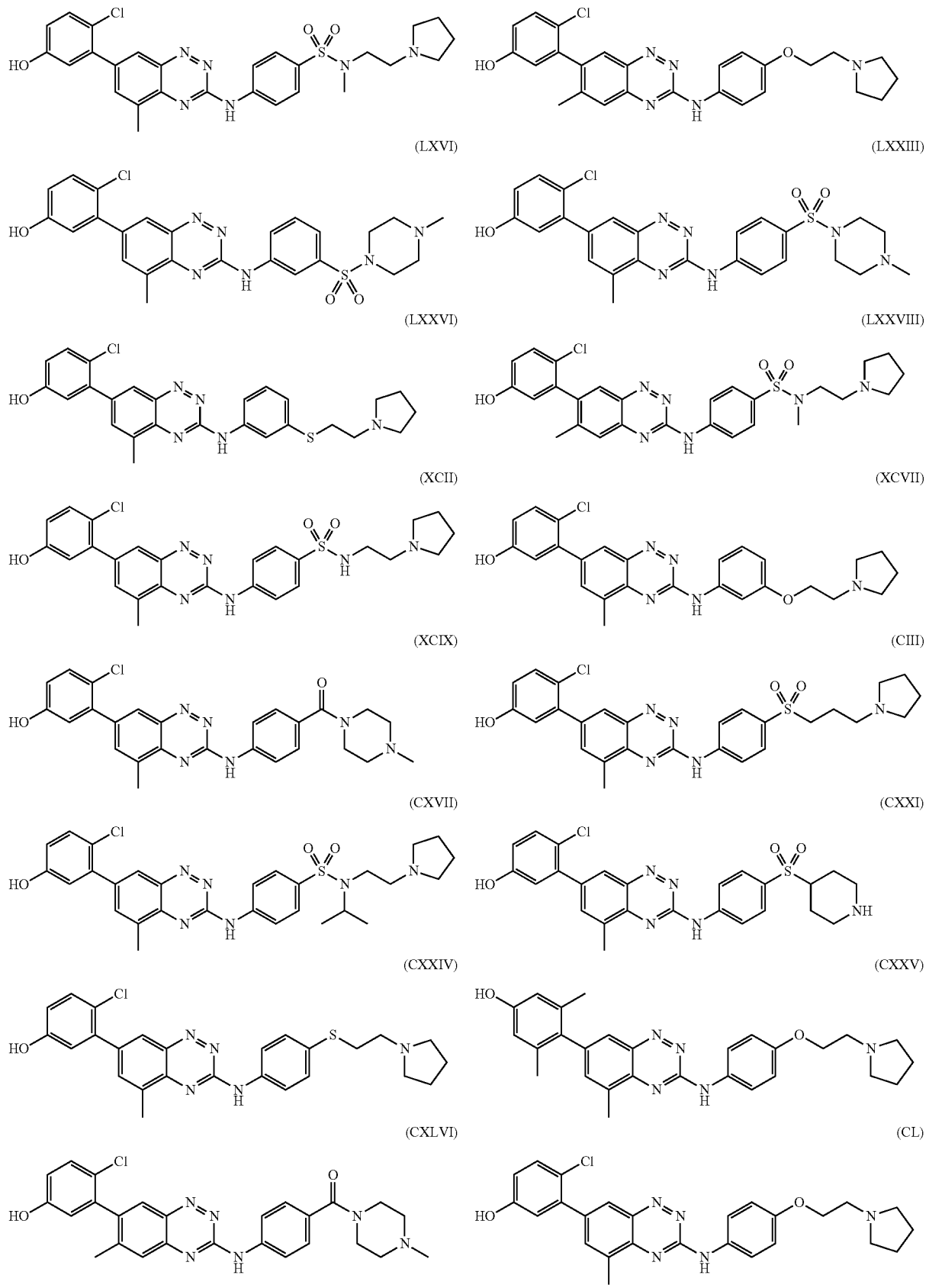

-continued
(CLI)
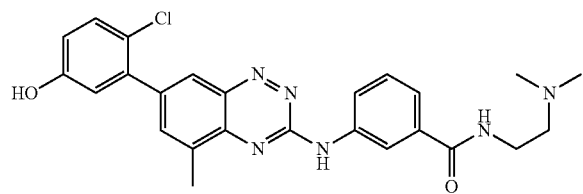
(CLVII)
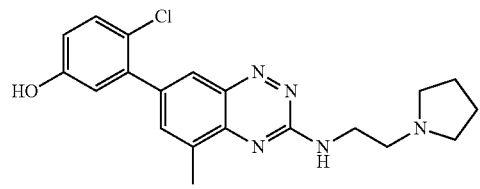
(CLXIV)
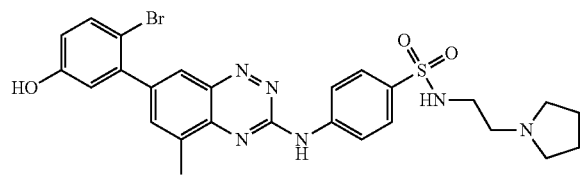
(CLXVI)
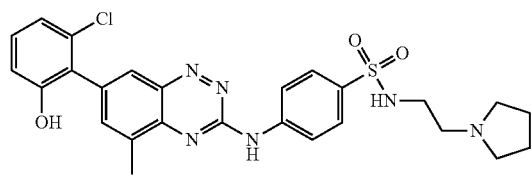
(CLXXI)
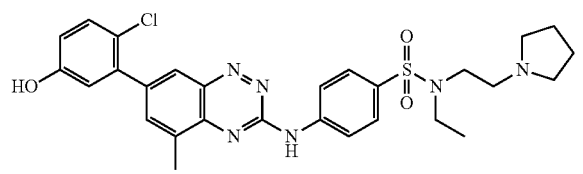
(CLXXII)
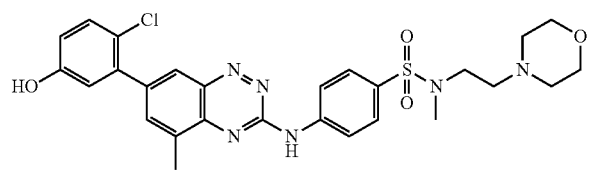
(CLXXIII)
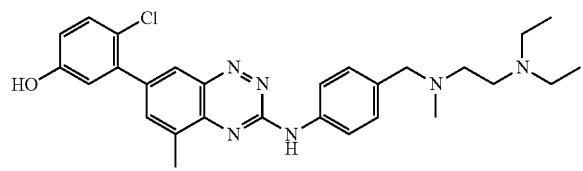
(CLXXIV)
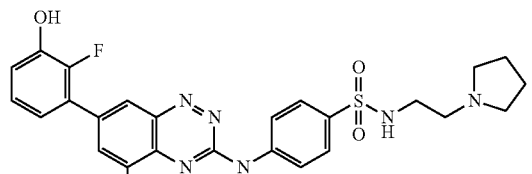
(CLXXV)
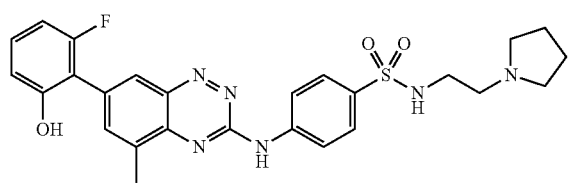
(CLXXXIV)
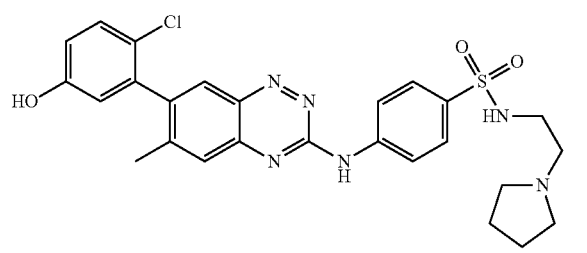
(CLXXXVI)
(CXC)
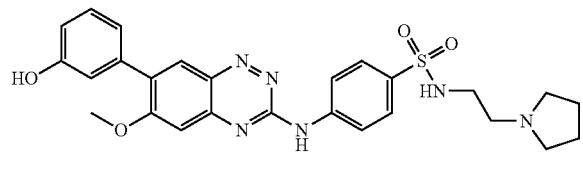
(CCXII)
(CCXXVI)
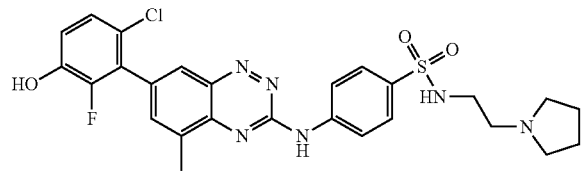

-continued
(CCXXXI)
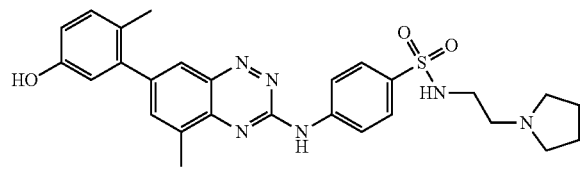
(CCXLVII)
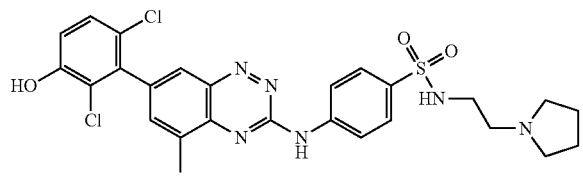
(CCXLVIII)
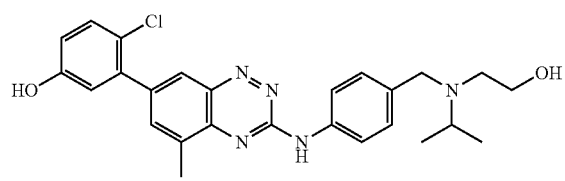
(CCL)
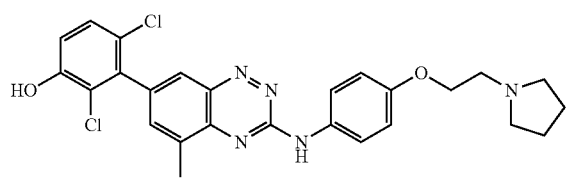
(CCLII)
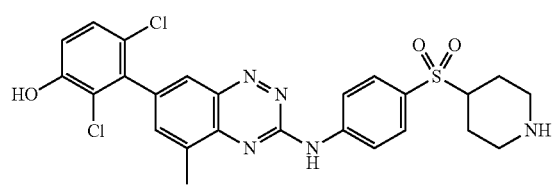
(CCLXVII)
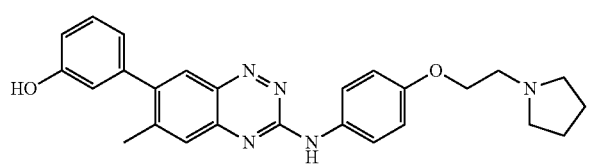
(CCLXXIII)
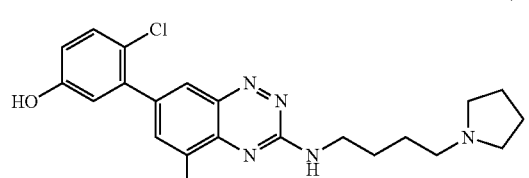
(CCLXXV)
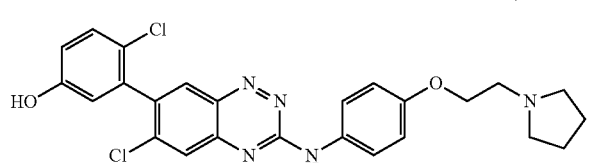
(CCLXXX)
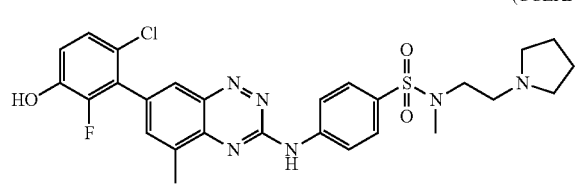
(X)
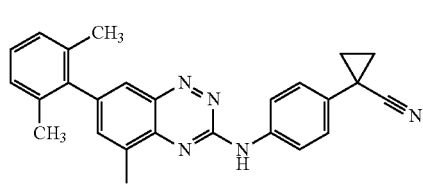
(XII)
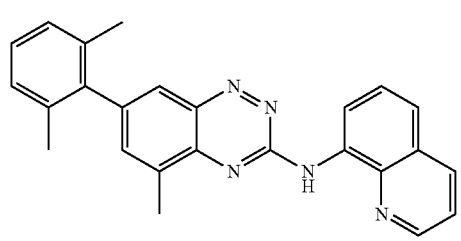
(XIII)
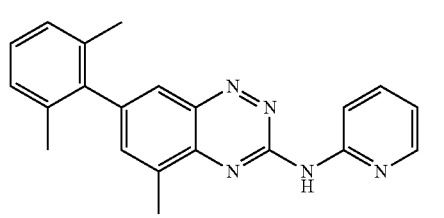
(XIV)
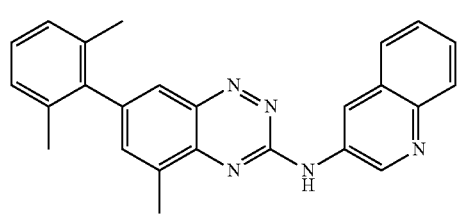
(XV)

-continued
(XVI)
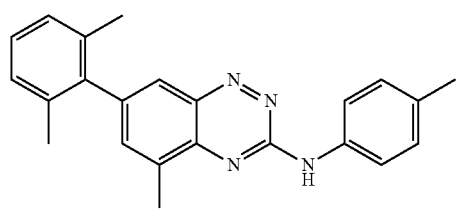
(XVII)
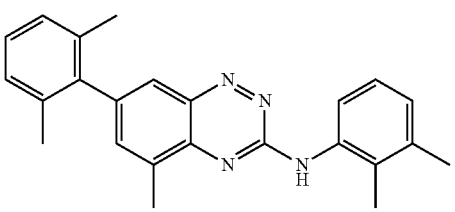
(XVIII)
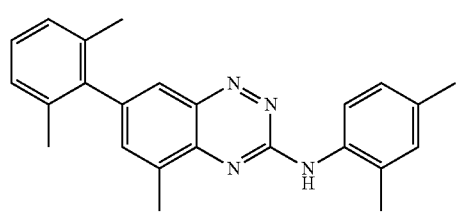
(XIX)
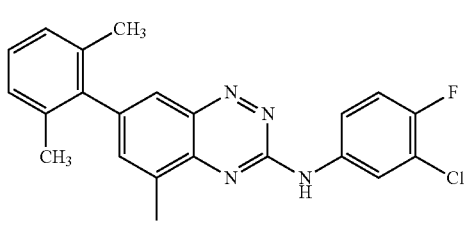
(XX)
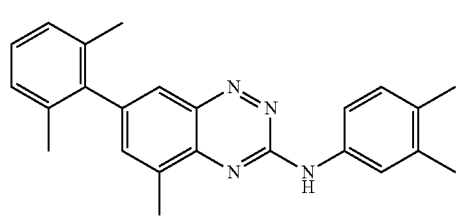
(XXI)
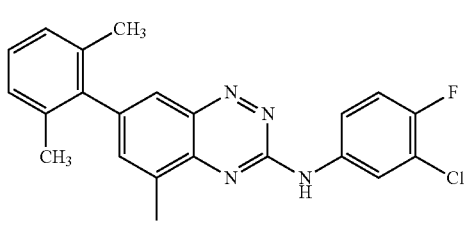
(XXIV)
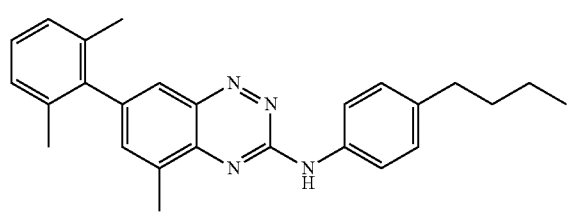
(XXV)
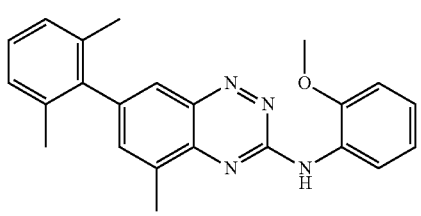
(XXVI)
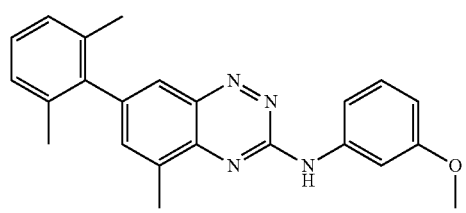
(XXVIII)
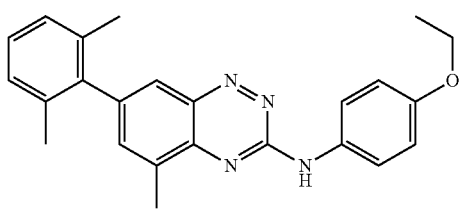
(XXIX)
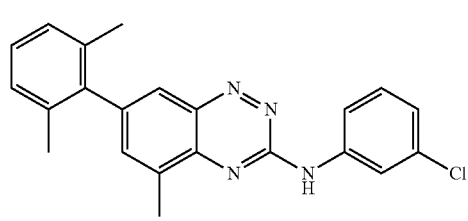
(XXX)
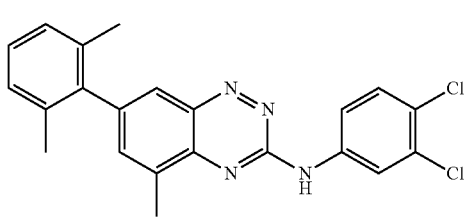
(XLII)
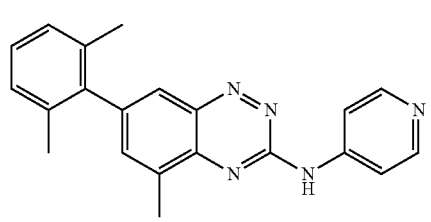
(CXXX)
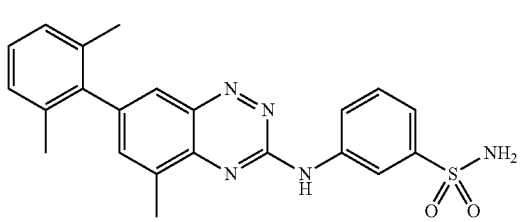

-continued
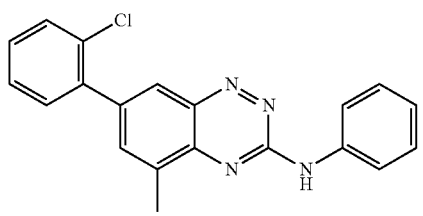
(XXII)
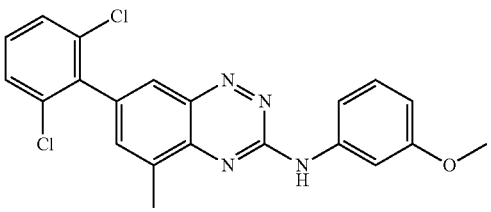
(XLIII)
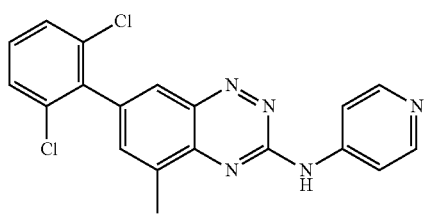
(XLV)
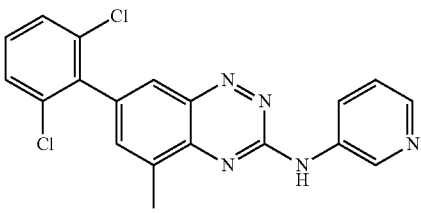
(XLVI)
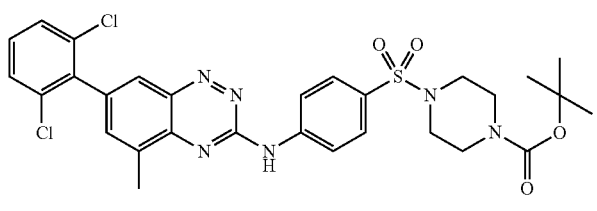
(CXI)
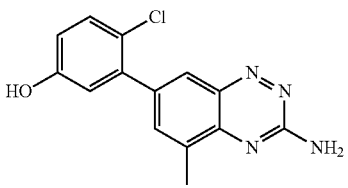
(XCIII)
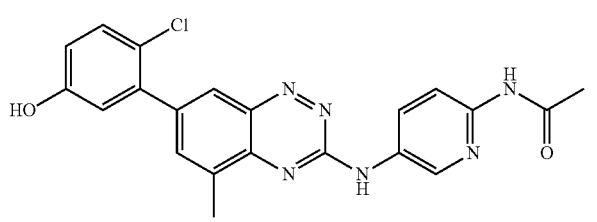
(XCIV)
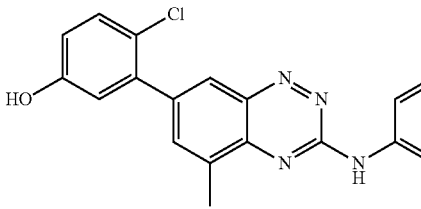
(CLIII)
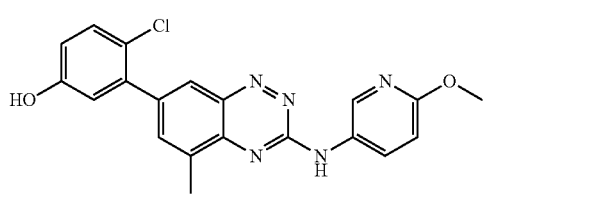
(CLV)
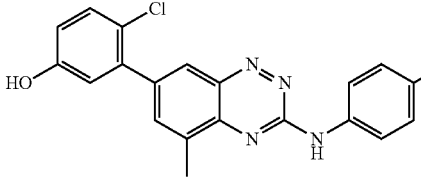
(CCLXXVIII)
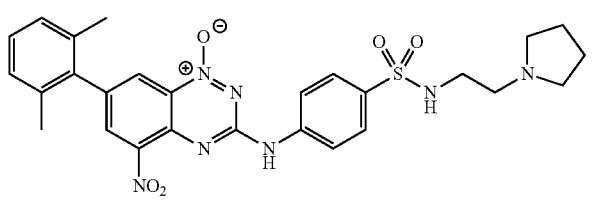
(LXXXVII)
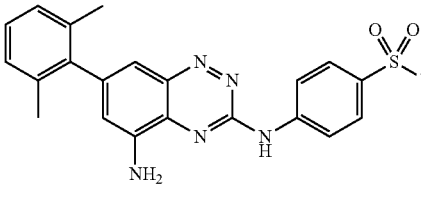
(LXXXVIII)
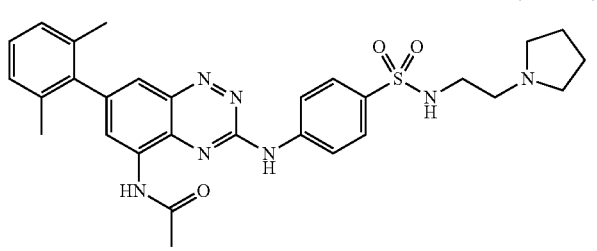
(LXXXIX)
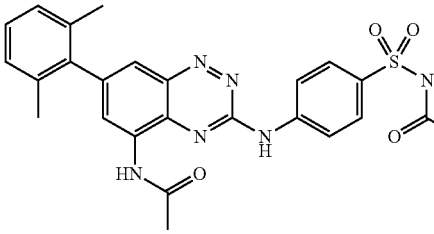
(XC)

-continued
(CXL)
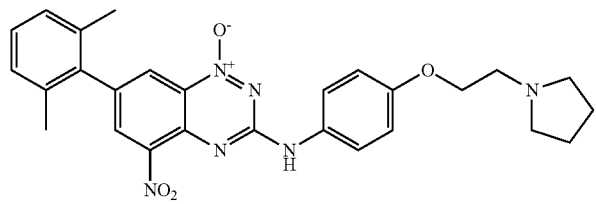
(CXLII)
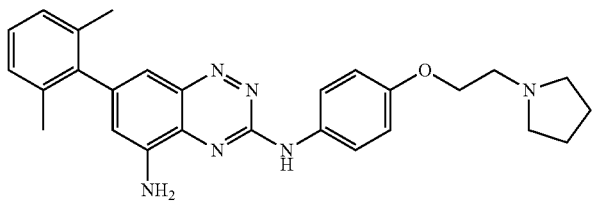
(CXLIII)
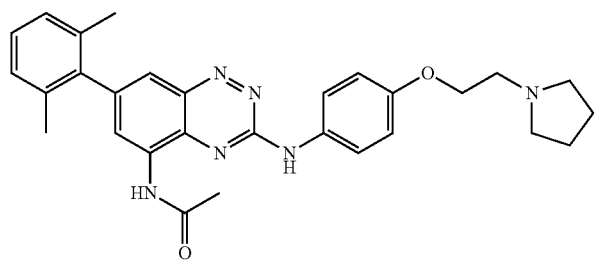
(CXLIV)
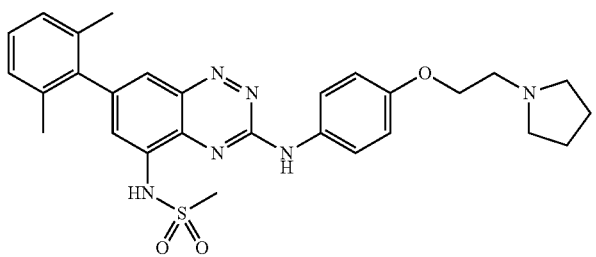
(CXCVIII)
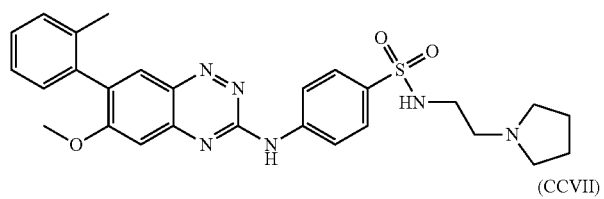
(CCV)
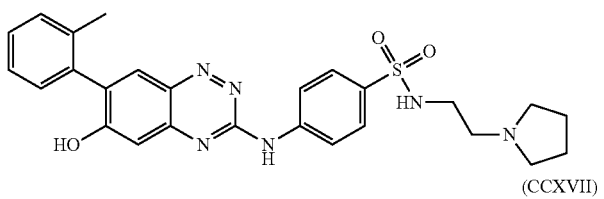
(CCVII)
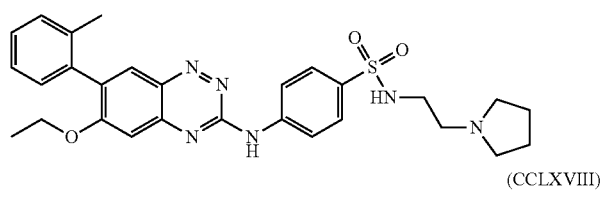
(CCXVII)
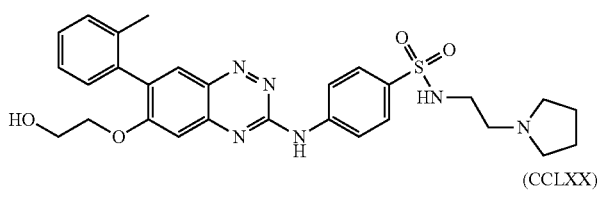
(CCLXVIII)
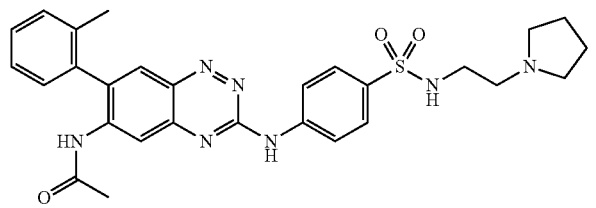
(CCLXX)
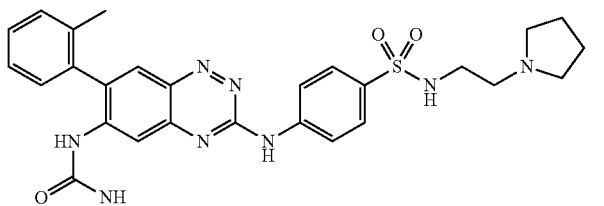
(LXXXVI)
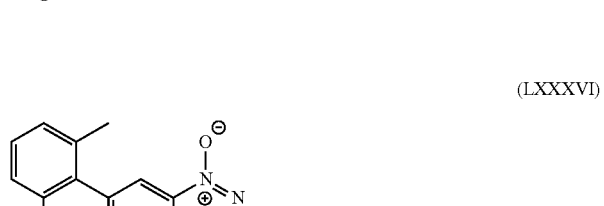
(CXXXVI)
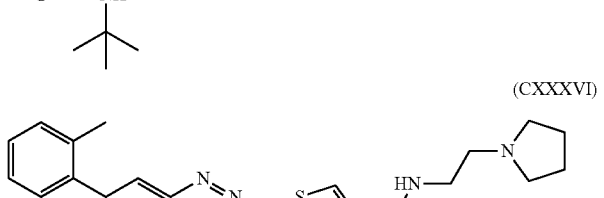
(CLXXX)
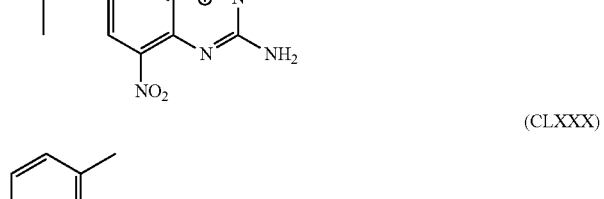
(CCXLIV)
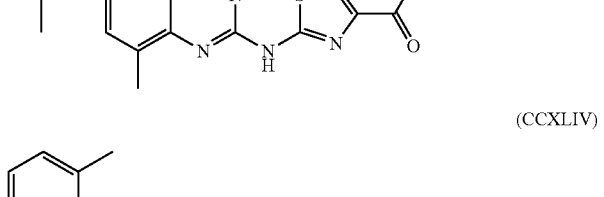
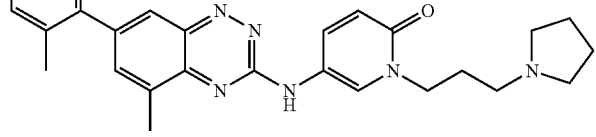
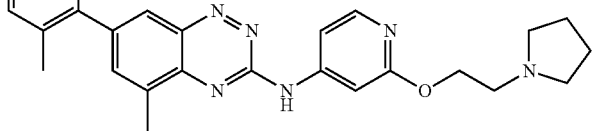

-continued
(CLXIX)
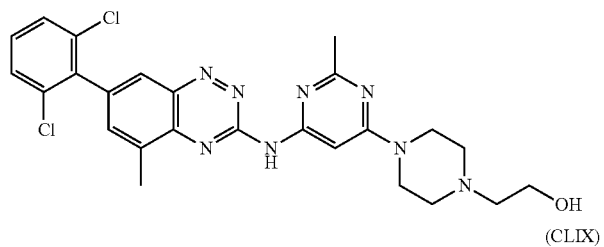
(CCXX)
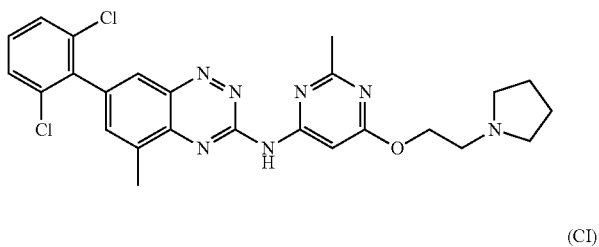
(CLIX)
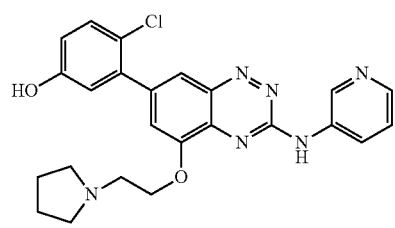
(CI)
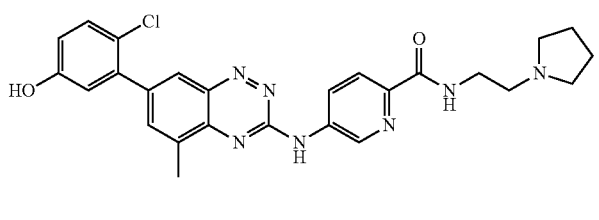
(CLXX)
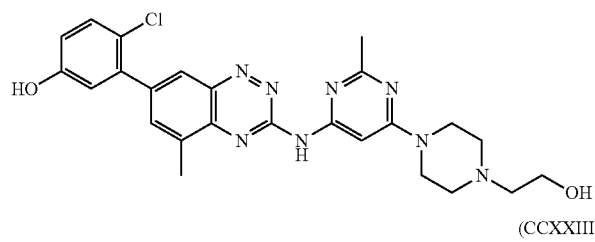
(CLXXXII)
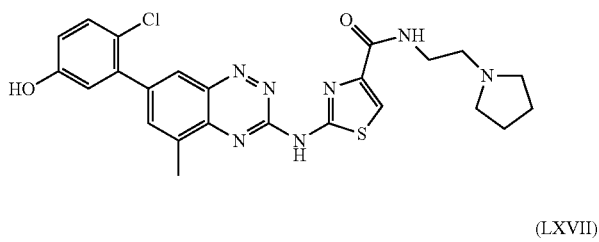
(CCXXIII)
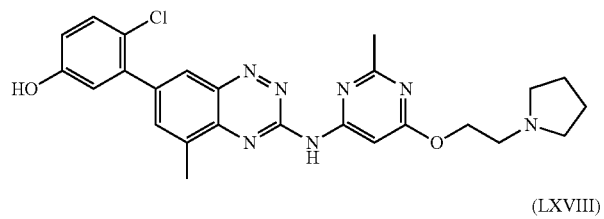
(LXVII)
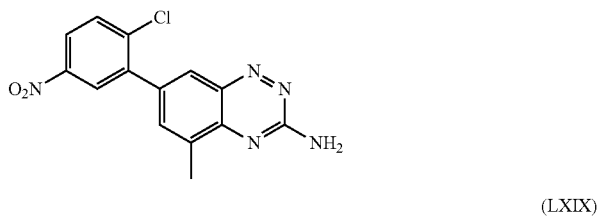
(LXVIII)
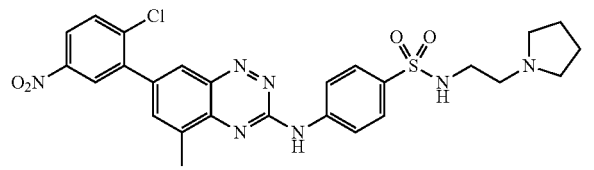
(LXIX)
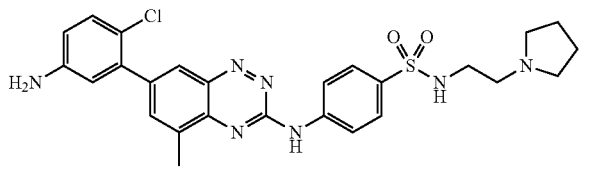
(CIV)
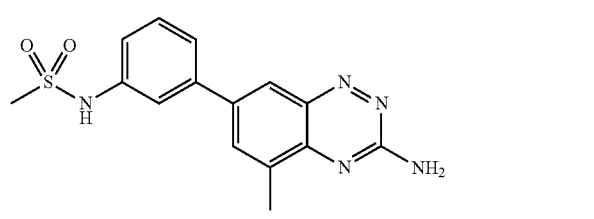
(CV)

-continued
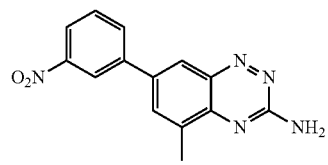
(CVI)
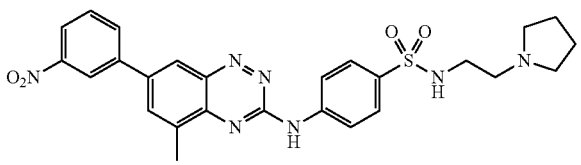
(CVII)
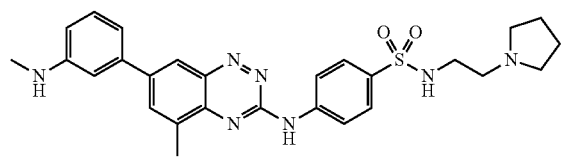
(CVIII)
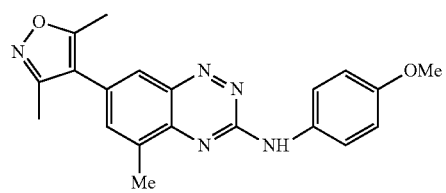
(CIX)
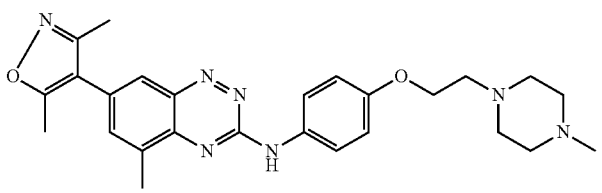
(CXXVII)
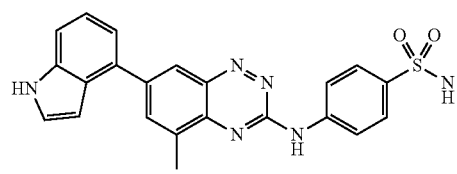
(CXXVIII)
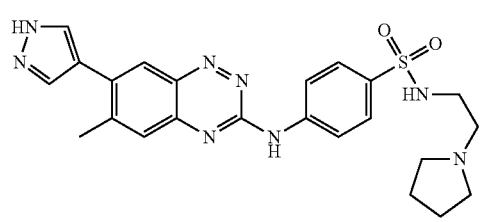
(CLXIII)
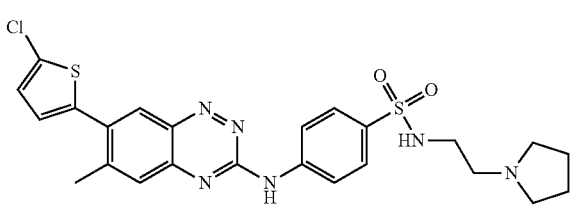
(CLXXVIII)
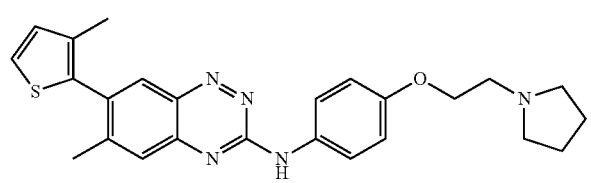
(CLXXXVIII)
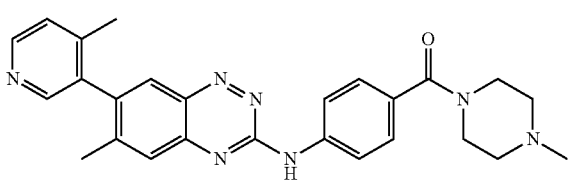
(CXCV)
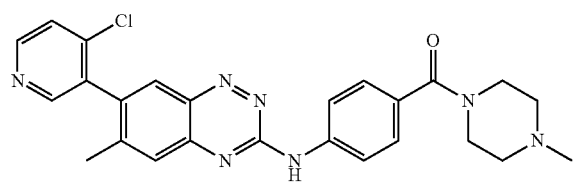
(CCXL)
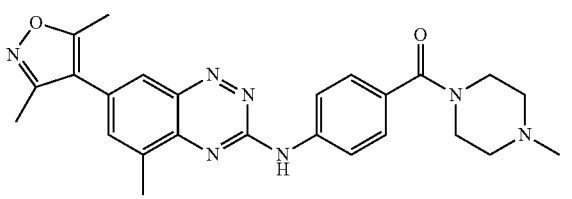
(CCXLI)
(CCXLII)
(CCLIII)

-continued
(CCLVI)
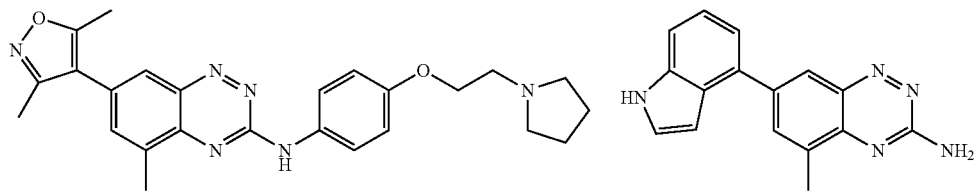
(CLXI)
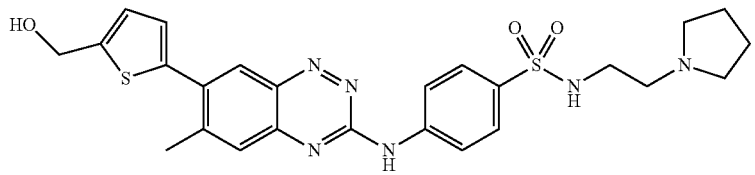
(CCLXXI)
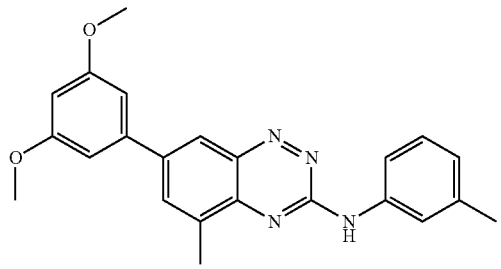
(XXXI)
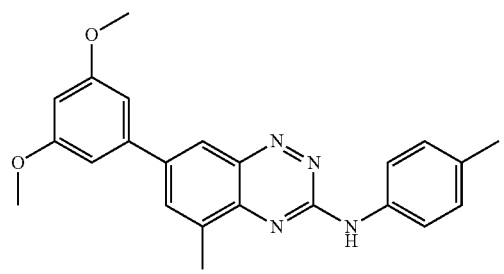
(XXXII)
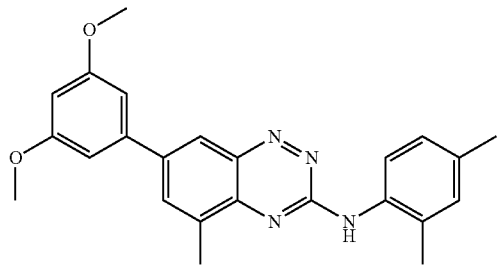
(XXXIII)
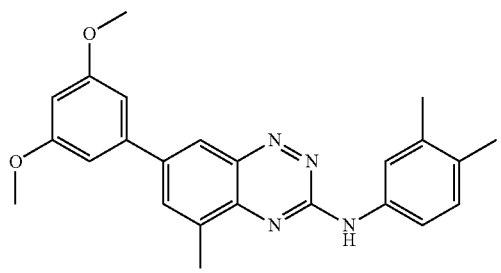
(XXXIV)
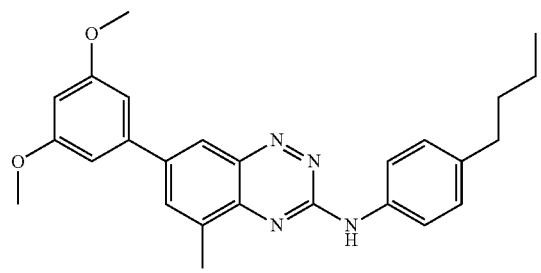
(XXXV)
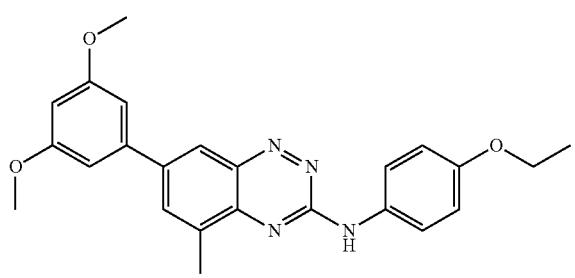
(XXXVI)
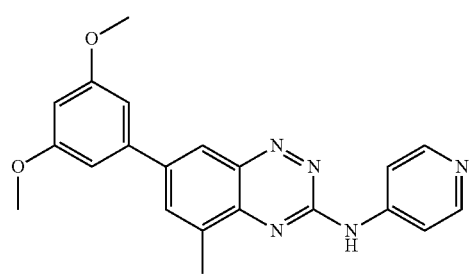
(XXXVII)
(XXXVIII)

-continued
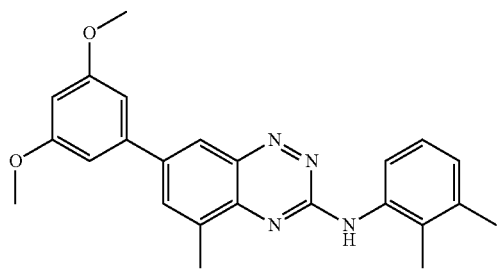
(XXXIX)
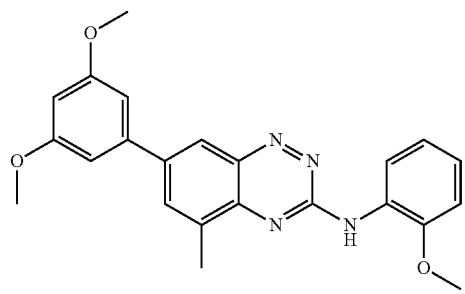
(XL)
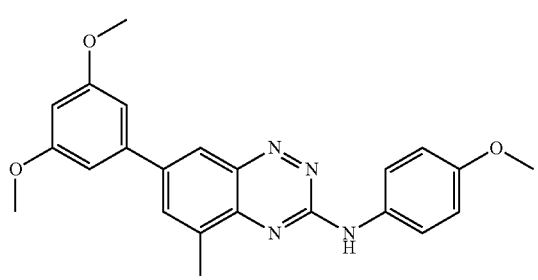
(XLI)
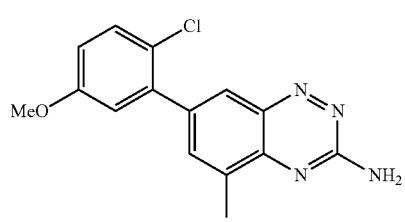
(LV)
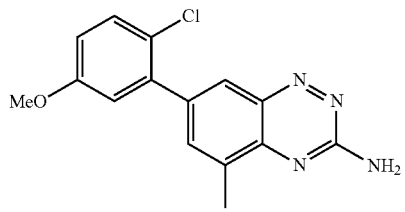
(LXIII)
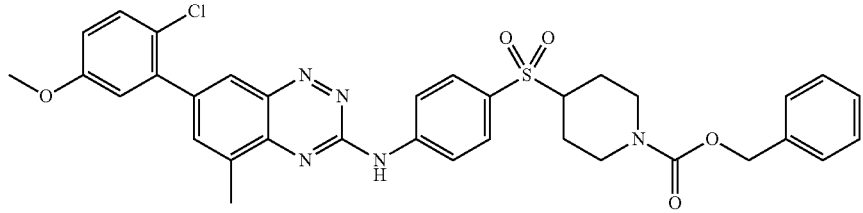
(CXX)
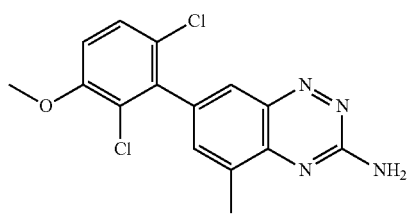
(CCXLV)
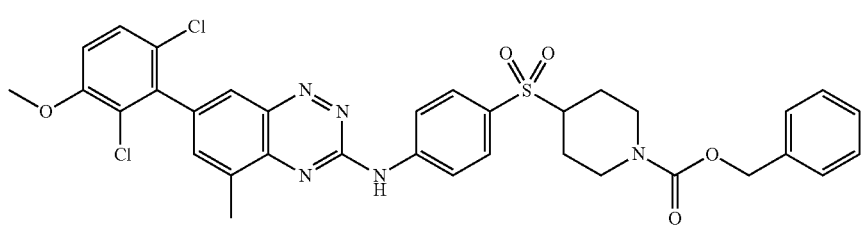
(CCLI)

-continued
(LVII)
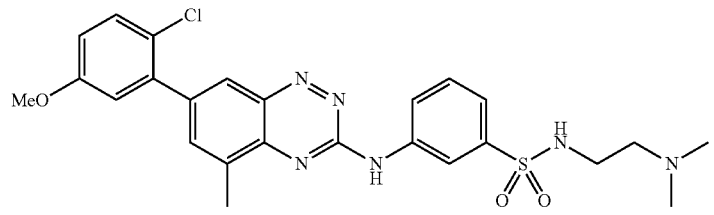
(LIX)
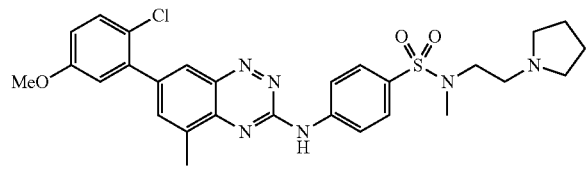
(LXI)
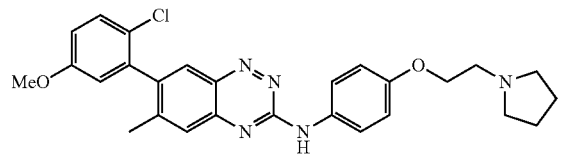
(LXV)
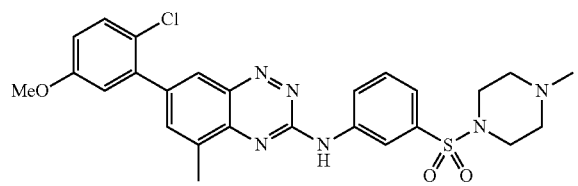
(LXXII)
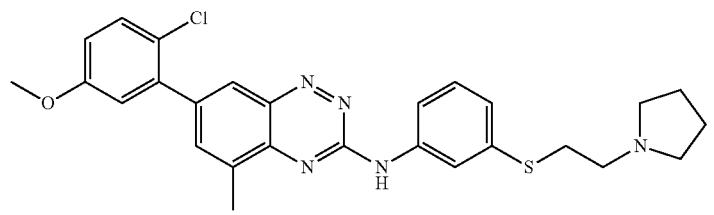
(LXXV)
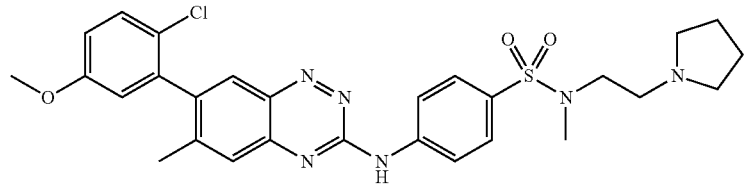
(XCI)
(XCVI)
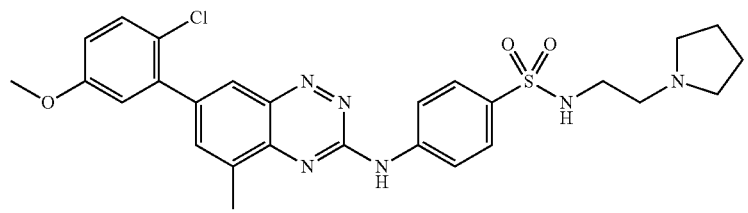

-continued
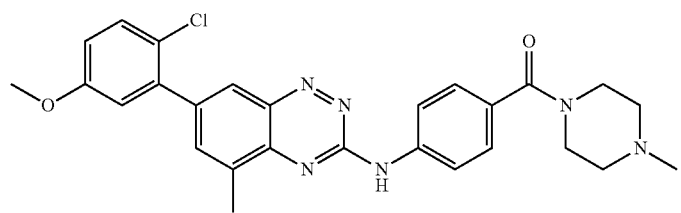
(XCVIII)
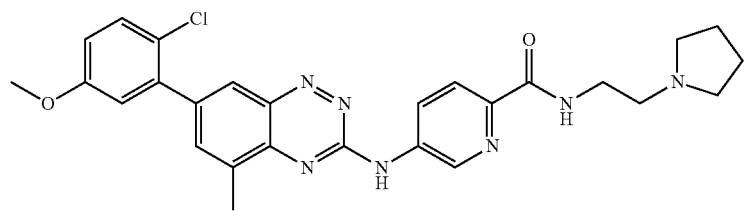
(C)
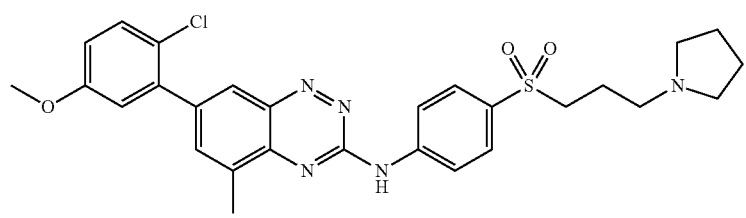
(CII)
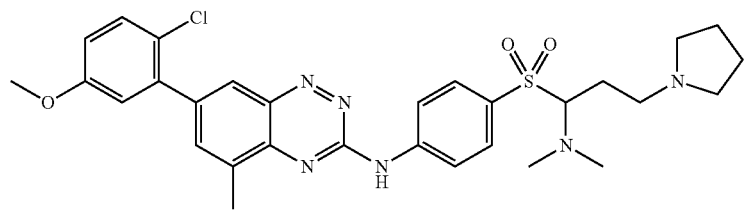
(CXVI)
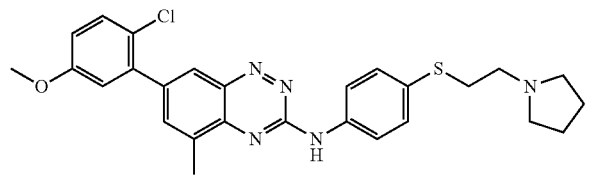
(CXXIII)
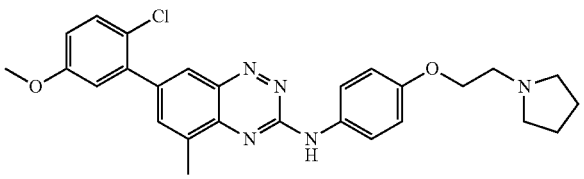
(CXLVIII)
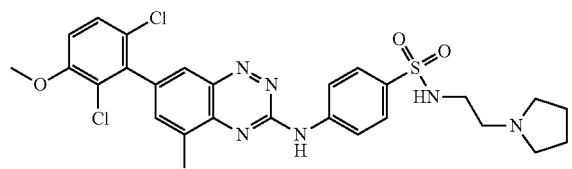
(CCXLVI)
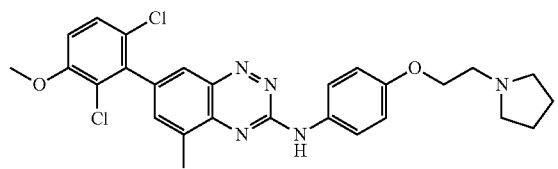
(CCXLIX)
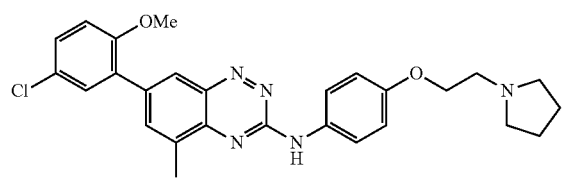
(CCLIV)
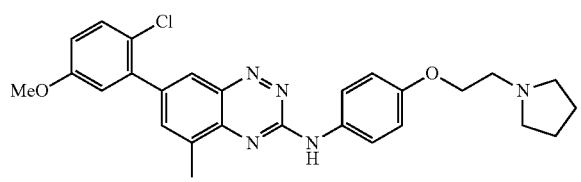
(CCLIX)

-continued
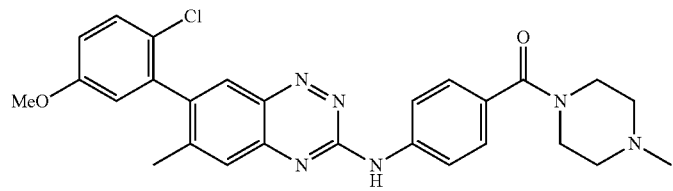
(CCLXIV)
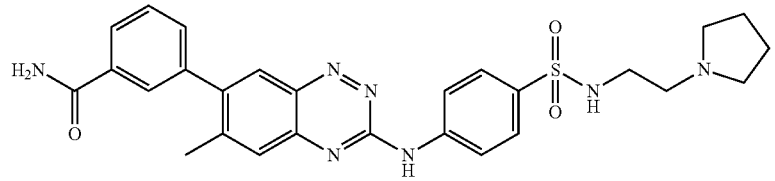
(CLXVIII)
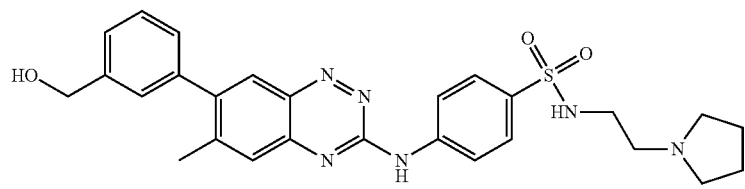
(CXCII)
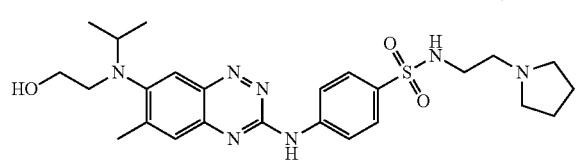
(CCXXXVII)
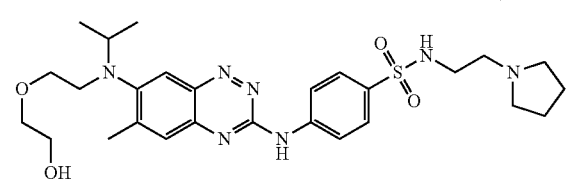
(CCXXXVIII)
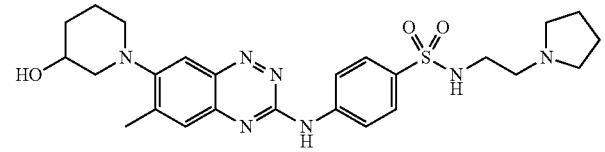
(CCLXXIV)
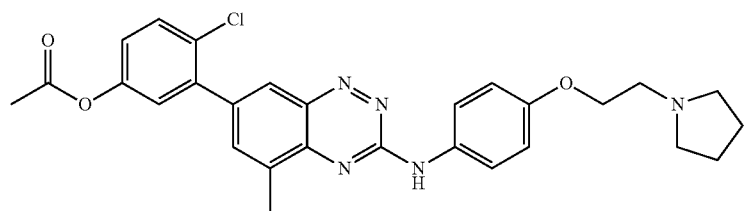
(LXXIX)
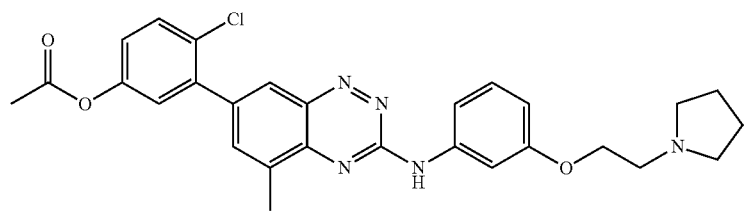
(LXXX)

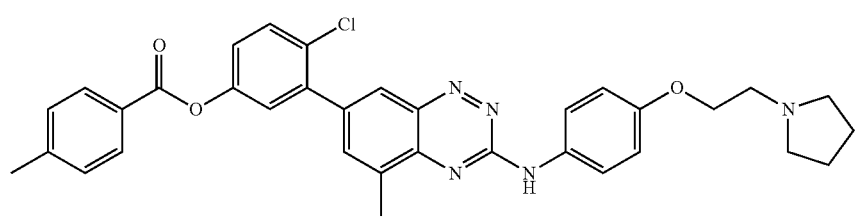

(LXXXI)

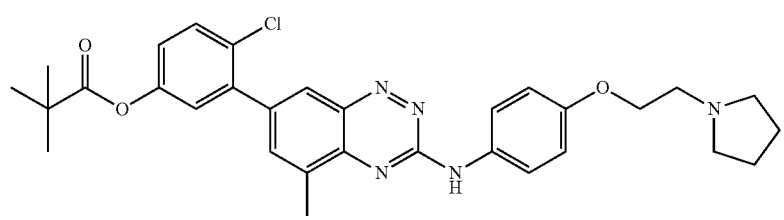

(LXXXII)

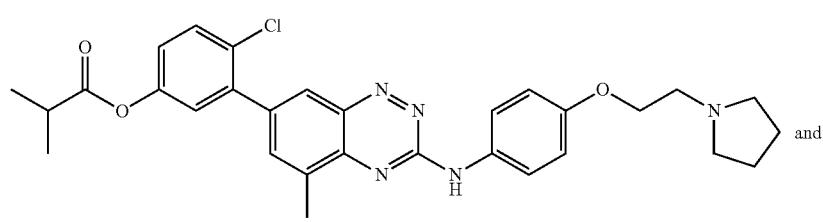

and (LXXXIII)

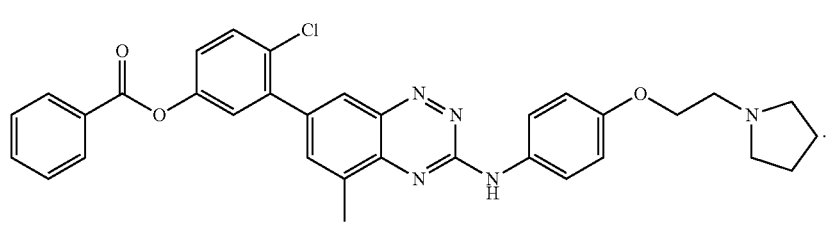

(CLXXVI)

The compounds and methods of the present invention, either when administered alone or in combination with other agents (e.g., chemotherapeutic agents or protein therapeutic agents described below) are useful in treating a variety of disorders associated with compromised vasculostasis and other disorders, including but not limited to, for example: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), cancer, pleural effusions, rheumatoid arthritis, diabetic retinopathy, retinitis pigmentosa, and retinopathies, including diabetic retinopathy and retinopathy of prematurity, inflammatory diseases, restenosis, edema (including edema associated with pathologic situations such as cancers and edema induced by medical interventions such as chemotherapy), asthma, acute or adult respiratory distress syndrome (ARDS), lupus, vascular leakage, transplant (such as organ transplant, acute transplant or heterograft or homograft (such as is employed in burn treatment)) rejection; protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituitarism; Guillain-Barre syndrome; other autoimmune diseases; cancers, including those where kinases such as Src-family kinases are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic sclerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener's granulomatosis, and Behcet's disease; scleroderma; preeclampsia; thalassemia; Kaposi's sarcoma; von Hippel Lindau disease; and the like.

Src-family tyrosine kinases other than Lck, such as Hck and Fgr, are important in the Fc gamma receptor induced respiratory burst of neutrophils as well as the Fc gamma receptor responses of monocytes and macrophages. The compositions and methods of the present invention may be useful in inhibiting the Fc gamma induced respiratory burst response in neutrophils, and may also be useful in inhibiting the Fc gamma dependent production of TNF alpha. The ability to inhibit Fc gamma receptor dependent neutrophil, monocyte and macrophage responses would result in additional anti-inflammatory activity for the compounds employed in invention methods. This activity would be especially of value, for example, in the treatment of inflammatory diseases, such as arthritis or inflammatory bowel disease. The compositions and methods of the present invention may also be useful in the treatment of autoimmune glomerulonephritis and other instances of glomerulonephritis induced by deposition of immune complexes in the kidney that trigger Fc gamma receptor responses and which can lead to kidney damage.

In addition, certain Src-family tyrosine kinases, such as Lyn and Src, may be important in the Fc epsilon receptor induced degranulation of mast cells and basophils that plays an important role in asthma, allergic rhinitis, and other allergic disease. Fc epsilon receptors are stimulated by IgE-antigen complexes. Compounds employed in the methods of the present invention may inhibit the Fc epsilon induced degranulation responses. The ability to inhibit Fc epsilon receptor dependent mast cell and basophil responses may result in additional anti-inflammatory activity for the present compounds beyond their effect on T cells.

The present invention also provides articles of manufacture comprising packaging material and a pharmaceutical composition contained within the packaging material, wherein the packaging material comprises a label which indicates that the pharmaceutical composition can be used for treatment of disorders and wherein the pharmaceutical composition comprises a compound according to the present invention. Thus, in one aspect, the invention provides a pharmaceutical composition including a therapeutic agent and a compound of the invention, wherein the compound is present in a concentration effective to reduce vascular leakage associated with indications or therapeutic agents which have vascular leak as a side effect. For example, administration of a compound of the invention can be in conjunction with IL-2, immunotoxins, antibodies or chemotherapeutics. In these cases, IL-2, immunotoxin, antibody or chemotherapeutic concentration can be determined by one having ordinary skill in the art according to standard treatment regimen or, for example, as determined by an in vivo animal assay.

The present invention also provides pharmaceutical compositions comprising IL-2, immunotoxin, antibody or chemotherapeutic and at least one invention compound in an amount effective for inhibiting vascular permeability, and a pharmaceutically acceptable vehicle or diluent. The compositions of the present invention may contain other therapeutic agents, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques known in the art of pharmaceutical formulation.

The compounds of the invention may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the invention include amine salts formed by the protonation of an amino group with inorganic acids such as hydrochloric acid, hydrobromic acid, hydroiodic acid, sulfuric acid, phosphoric acid, and the like. Salts of the invention also include amine salts formed by the protonation of an amino group with suitable organic acids, such as p-toluenesulfonic acid, acetic acid, and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs of the invention compounds are included in the present invention.

Pharmaceutical compositions of the invention may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The pharmaceutical compositions for the administration of the compounds of this embodiment either alone or in combination with IL-2, immunotoxin, antibody or chemotherapeutic may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butanediol, polyethylene glycols, polypropylene glycols, ethanol or other alcohols, povidones, various brands of TWEEN surfactant, sodium dodecyl sulfate, sodium deoxycholate, dimethylacetamide, polysorbates, poloxamers, cyclodextrins, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles).

In one aspect, the invention compounds are administered in combination with an anti-inflammatory agent, antihistamines, chemotherapeutic agent, immunomodulator, therapeutic antibody or a protein kinase inhibitor, e.g., a tyrosine kinase inhibitor, to a subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-dimethoxydaunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topotecan, oxaliplatin, chlorambucil, methotrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, anti folates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase, and hydroxyurea, etc.; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

The pharmaceutical composition and method of the present invention may further comprise other therapeutically active compounds as noted herein which are usually applied in the treatment of the above mentioned pathological conditions. Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

Other agents that may be administered in combination with invention compounds include protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay.

The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

When other therapeutic agents are employed in combination with the compounds of the present invention they may be used for example in amounts as noted in the Physician Desk Reference (PDR) or as otherwise determined by one having ordinary skill in the art.

In the treatment or prevention of conditions which involve compromised vasculostasis an appropriate dosage level can generally be between about 0.01 and about 500 mg per 1 kg of patient body weight per day which can be administered in single or multiple doses. For example, the dosage level can be between about 0.01 and about 250 mg/kg per day; more narrowly, between about 0.5 and about 100 mg/kg per day. A suitable dosage level can be between about 0.01 and about 250 mg/kg per day, between about 0.05 and about 100 mg/kg per day, or between about 0.1 and about 50 mg/kg per day, or about 1.0 mg/kg per day. For example, within this range the dosage can be between about 0.05 and about 0.5 mg/kg per day, or between about 0.5 and about 5 mg/kg per day, or between about 5 and about 50 mg/kg per day. For oral administration, the compositions can be provided in the form of tablets containing between about 1.0 and about 1,000 mg of the active ingredient, for example, about 1.0, about 5.0, about 10.0, about 15.0, about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, and about 1,000.0 mg of the active ingredient for the symptomatic adjustment of the dosage to the patient to be treated. The compounds can be administered on a regimen of 1 to 4 times per day, such as once or twice per day. There may be a period of no administration followed by another regimen of administration. Preferably, administration of the compound is closely associated with the schedule of IL-2 administration. For example, administration can be prior to, simultaneously with or immediately following IL-2 administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compounds of the present invention can be used, alone or in combination with an effective amount of a therapeutic antibody (or therapeutic fragment thereof), a chemotherapeutic or an immunotoxic agent, for treatment of tumors. While doxorubicin, docetaxel, or taxol are described in the present application as illustrative examples of chemotherapeutic agents, it should be understood that the invention includes combination therapy including a compound of the invention, including but not limited to vasculostatic agents, such as tyrosine, serine or threonine kinase inhibitors, for example, Src-family inhibitors, and any chemotherapeutic agent or therapeutic antibody.

C. EXAMPLES

The following examples are provided to further illustrate the advantages and features of the present invention, but are not intended to limit the scope of the invention.

1. General Methodology

All experiments were performed under anhydrous conditions (i.e. dry solvents) in an atmosphere of argon, except where stated, using oven-dried apparatus and employing standard techniques in handling air-sensitive materials. Aqueous solutions of sodium bicarbonate ($NaHCO_3$) and sodium chloride (brine) were saturated.

Analytical thin layer chromatography (TLC) was carried out on Merck Kieselgel 60 $F_{254}$ plates with visualization by ultraviolet and/or anisaldehyde, potassium permanganate or phosphomolybdic acid dips.

Reverse-phase HPLC chromatography was carried out on Gilson 215 liquid handler equipped with Waters Symmetry-Shield™ RP18 7 μm (40×100 mm) Prep-Pak cartridge. Mobile phase consisted of standard acetonitrile (ACN) and DI Water, each with 0.1% TFA added. Purification was carried out at a flow rate of 40 mL/min, and a gradient such that the peak of interest was eluted between 12-15 min in a 30 min run.

NMR spectra: 1H Nuclear magnetic resonance spectra were recorded at 500 MHz. Data are presented as follows: chemical shift, multiplicity (s=singlet, d=doublet, t=triplet, q=quartet, qn=quintet, dd=doublet of doublets, m=multiplet, bs=broad singlet), coupling constant (J/Hz) and integration. Coupling constants were taken directly from the spectra and are uncorrected.

Low resolution mass spectra: Electrospray (ES+) ionization was used. The protonated parent ion (M+H) or fragment of highest mass is quoted. Analytical gradient consisted of 10% ACN in water ramping up to 100% ACN over 5 minutes unless otherwise stated.

2. General Synthetic Procedures.

Wherever Suzuki coupling was used, the following general procedure was employed. To a mixture of boronic acid, aryl bromide, and palladium tetrakis(triphenylphosphine)palladium(0) ($Pd(Ph_3)_4$) in 4:1 DME/EtOH was added a 2 M aqueous solution of sodium carbonate. The mixture was flushed with argon for 5 min and a condenser was added under argon flow. The reaction was heated to reflux (ca. 100° C.) for 2-18 h. The crude mixture was filtered and the solid filter cake was rinsed thoroughly with MeOH and DCM. The filtrate was concentrated in vacuo and purified by column chromatography.

Wherever Buchwald coupling was used, the following general procedure was employed. A mixture of amine, bromide, $Cs_2CO_3$, Xantphos, and $Pd_2(dba)_3$ in dioxane was purged with argon for 5 min after which a condenser was added under argon flow. The reaction was heated to reflux (ca 110° C.) for 4-18 h. The crude mixture was filtered and the solid filter cake was rinsed thoroughly with MeOH and DCM. The filtrate was concentrated in vacuo and purified by column chromatography.

Wherever deprotection of aryl methoxy was necessary, the following general procedure was employed. To a solution of the aryl methoxy compound in DCM was added $BBr_3$ (either 1 M in DCM or neat). The reaction was checked for completion and additional $BBr_3$ was added if needed. The reaction was quenched with $NaHCO_3$ and basified to ca. pH 10-11. The biphasic mixture was filtered and the collected solid was rinsed with water. Trace solvents were removed in vacuo.

In general, one of three methods A, B, or C, can be used for synthesizing some of the compounds of the present invention. Those having ordinary skill in the art can determine, depending on variety of factors, including the particular compound that is sought to be made, whether to selected the method A, B or C.

Method A

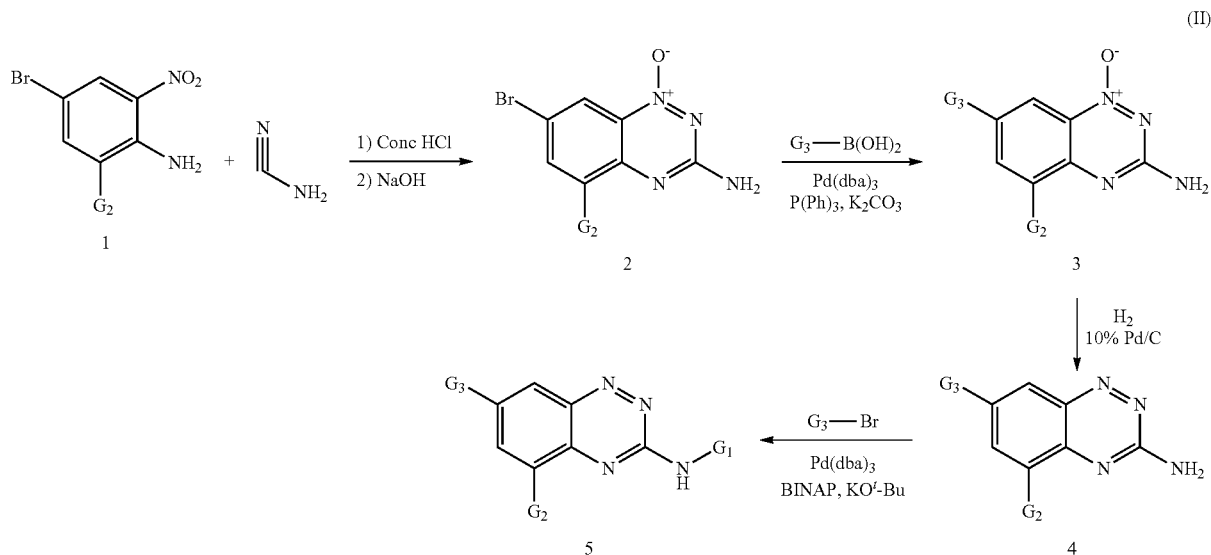

The synthetic method A is shown by the reaction scheme (II). About 1 equivalent of compound 1 was mixed with 2 equivalent of cyanamide in a vial. The mixture was heated to about 100° C. until the mixture was completely melted. The mixture was cooled down to room temperature and concentrated HCl was added. The mixture was then again heated at about 100° C. for about 40 minutes and cooled down in ice water. About 14 moles of NaOH were carefully added to the above reaction mixture followed by heating the mixture at about 100° C. for about 2 hours, and by cooling down to room temperature.

Compound 2, shown by the reaction scheme (II), was isolated by filtration and washed several times with water, methanol and diethyl ether. About 1 equivalent of compound 2 was dissolved in N,N-dimethylacetamide, and ethanol solution containing about 4 equivalent of boronic acid and the aqueous solution containing about 0.15 equivalent of potassium carbonate were added. About 0.1 equivalent of triphenylphosphine and about 0.0246 equivalent of tris(dibenzylideneatone) dipalladium (0) were added to the mixture. The mixture was reflux overnight. The crude product was poured into saturated $NaHCO_3$ solution, and $CH_2Cl_2$ was used to extract the product.

Compound 3, shown by the reaction scheme (II), was isolated by removing solvent in the organic phase. Compound 3 was dissolved in N,N-dimethylacetamide in a vial with a septum. Catalytic amount of 10% palladium on carbon was added to the mixture. A balloon filled with hydrogen was placed on the top of the vial. The mixture was stirred at room temperature for about 2 hours. Celite was used to remove the palladium and carbon. Solvent was removed under vacuum and compound 4, shown by the reaction scheme (II), was isolated. About 1 equivalent of compound 4 was dissolved in anhydrous toluene solution containing about 1.2 equivalent of bromide $R_3Br$, about 0.025 equivalent of $Pd(dba)_3$, about 0.07 equivalent of BINAP, and about 0.6 equivalent of KOt-Bu. The mixture was kept at about 100° C. for 24 hours under argon. Compound 5, shown by the reaction scheme (II), was then isolated by high pressure liquid chromatography (HPLC).

Method B

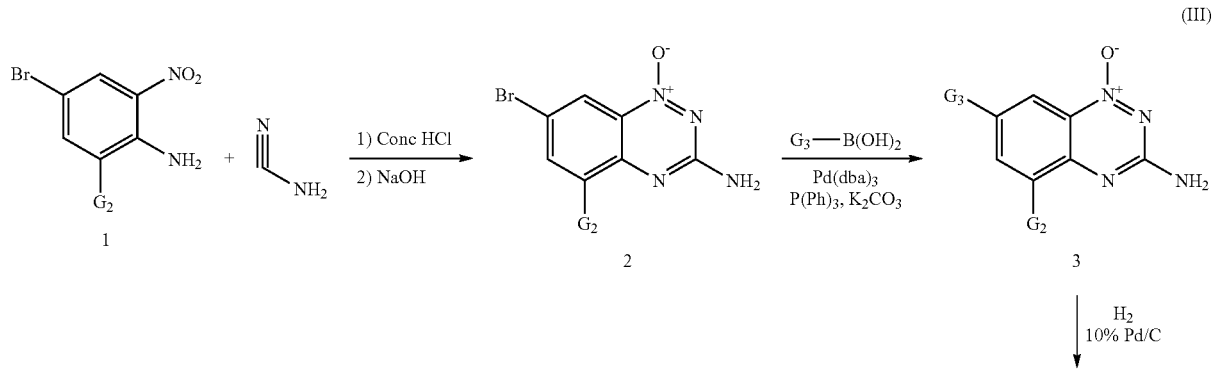

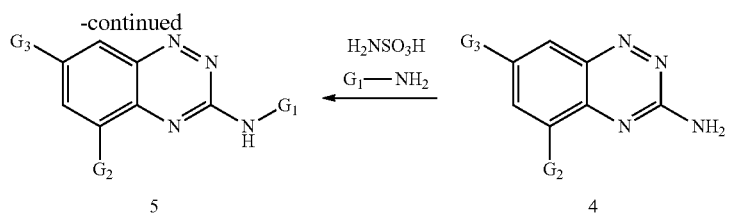

The synthetic method B is shown by the reaction scheme (III). Compounds 1, 2, 3, and 4 were consecutively prepared and isolated as described in Method A. About 1 equivalent of compound 4 was dissolved in an aniline followed by adding about 2 equivalents of sulfamic acid. The mixture was heated at about 200° C. overnight. Compound 5 was isolated by HPLC.

Method C lowed by adding about 2 equivalent of sulfamic acid. The mixture was heated at about 200° C. overnight. Compound 5 was isolated by HPLC and was dissolved in dry $CH_2Cl_2$. The mixture was cooled to about −78° C. using a dry ice-acetone bath. About 2 equivalents of $BBr_3$ (1M solution in $CH_2Cl_2$) was added dropwise to the mixture at about −78° C. under nitrogen atmosphere. The mixture was then allowed to warm to about 0° C. and stirred overnight at about 0° C., followed by adding saturated aqueous solution of $NaHCO_3$ at about 0° C. and by separating the mixture in a separator funnel. The water

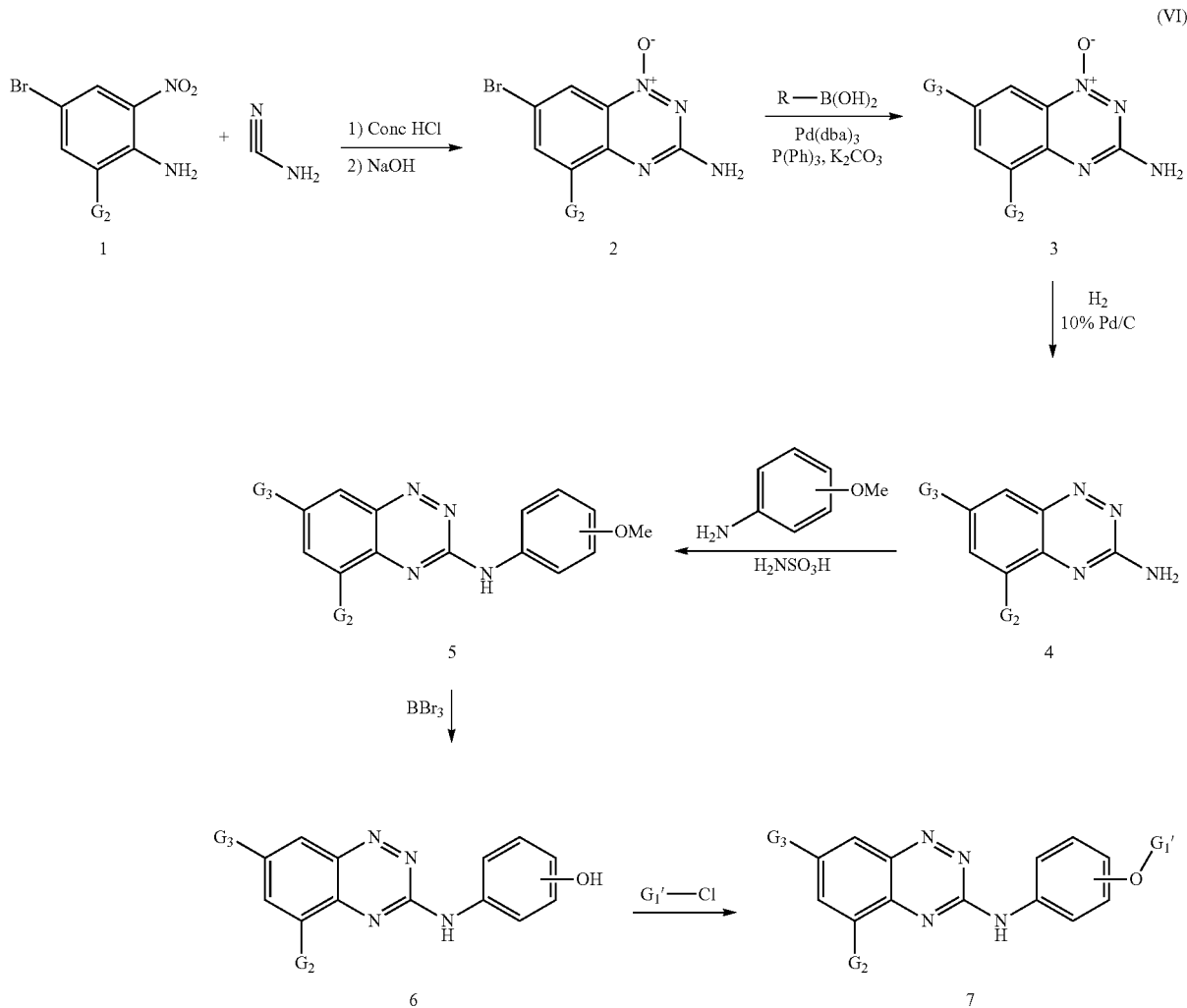

The synthetic method C is shown by the reaction scheme (IV). Compounds 1, 2, 3, and 4 were consecutively prepared and isolated as described in Method A. About 1 equivalent of compound 4 was dissolved in substituted phenylamine follayer was extracted twice with $CH_2Cl_2$, and the combined organic layer was washed with brine and dried over $Na_2SO_4$. Compound 6 was isolated by removing solvent under vacuum. Compound 6 was dissolved in acetone, and about 6 equivalent of K$_2$CO$_3$ and about 2 equivalent of R$_3$Cl were added to the mixture. The mixture was heated to reflux and stirred overnight, cooled and water was added. Compound 7 was isolated by prep HPLC.

Example 1

Synthesis of 7-bromo-benzo[1,2,4]triazin-3-ylamine-1-oxide

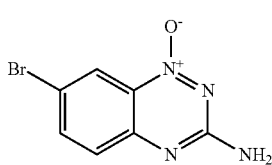
(V)

About 2.48 g (11.4 mmol) of 4-bromo-2-nitro-phenylamine was mixed with about 1.51 g (about 36 mmol) of cyanamide in a 20 ml vial. The mixture was heated to about 100° C. till the mixture was totally melted. The mixture was cooled down to room temperature and about 6.5 ml of concentrated HCl was added. The mixture was heated at about 100° C. for about 40 minutes and cooled down in ice water. About 6.5 ml of 14M NaOH was carefully added to the above reaction mixture. The resulted mixture was heated at about 100° C. for about 2 hours, then cooled down to room temperature, and filtrated. After filtration, the precipitate was washed several times with water, methanol and diethylether to remove the starting material. About 0.739 g of the product having formula (V) was obtained. Yield: about 27%. ESI-MS: [M+H]$^+$, 241, 243; $^1$H NMR (DMSO-d$_6$): δ 7.48 (d, J=9.0 Hz, 1 H), 7.89 (dd, J$_1$=9.0 Hz, J$_2$=2.1 Hz, 1 H), 8.26 (d, J=2.1 Hz, 1 H).

Example 2

Synthesis of 7-bromo-5-methyl-benzo[1,2,4]triazin-3-ylamine-1-oxide

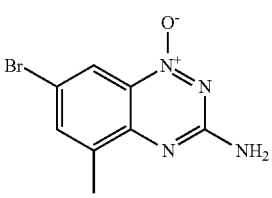
(VI)

About 1 g (4.33 mmol) of 4-bromo-2-methyl-6-nitro-phenylamine was mixed with about 0.5 g (12 mmol) of cynamide and about 5 g pyridine hydrochloride in a 20 ml vial. The mixture was heated to reflux overnight. The mixture was cooled down to room temperature and 10% NaOH was carefully added. The resulted mixture was heated at about 100° C. for about 2 hours, then cooled down to room temperature, and filtrated. After, filtration, the precipitate was washed several times with water, acetone and diethyl ether to remove the starting material. About 0.4 g of the product having the formula (VI) was obtained. Yield: about 36%. ESI-MS: [M+H]$^+$, 255, 257; $^1$H NMR (DMSO-d$_6$): δ 2.45 (s, 3 H), 7.81 (s, 1 H), 8.26 (s, 1 H).

Example 3

Synthesis of 7-bromo-5-methyl-benzo[1,2,4]triazin-3-ylamine

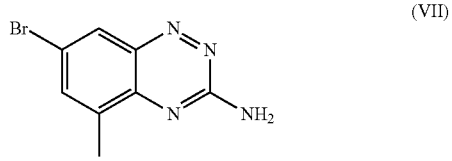
(VII)

About 4.26 g of 7-bromo-5-methyl-benzo[1,2,4]triazin-3-ylamine-1-oxide (VI) prepared as described in Example 2, was dissolved in about 100 ml of acetic acid, and about 1 g of iron powder was added to the solution. The mixture was refluxing for about 10 minutes. The iron was removed by filtration. The solvent in the filtrate was removed under vacuum. Water was added to remove the salt from the product. About 3.9 g of the pure product having formula (VII) was obtained.

Example 4

Synthesis of 1-(3-chloropropanyl)pyrrolidine

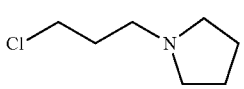
(VIII)

To the solution of about 186 g (1.18 mol) of 1-bromo-3-chloropropane in about 200 ml of ether was added about 2 equivalent of pyrrolidine at about 0° C. After addition, the mixture was allowed to warm to room temperature and stirred overnight. The resulting white solid residue was removed and to the clear solution was added ice-cold 10% hydrochloric acid. The ether layer was discarded and the acid layer was basified with ice-cold 20% NaOH, extracted with ether and dried over Na$_2$SO$_4$. Ether was removed and the residue was distilled under vacuum (95° C./30 mmHg). About 91 g of product having formula (VIII) was obtained in a form of a pale yellow liquid. The yield was about 53%.

Example 5

Synthesis of [7-(2,6-dimethyl-phenyl)-5-methyl-benzo[1,2,4]triazin-3-yl]-[4-(2-pyrrolidin-1-yl-ethoxy)-phenyl]-amine

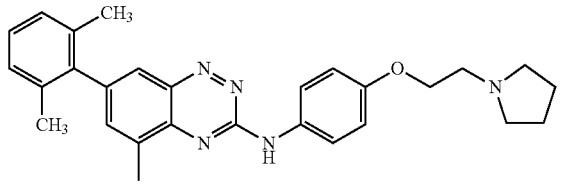

(IX)

About 1 g (3.78 mmol) of 7-bromo-5-methyl-benzo[1,2,4]triazin-3-ylamine and about 2.04 g (7.56 mmol) of 1-[2-(4-bromo-phenoxy)-ethyl]-pyrrolidine were dissolved in about 500 ml of toluene. About 174 mg (0.19 mmol) of Pd(dba)$_3$, about 340 mg (0.54 mmol) of BINAP, and about 500 mg (4.46 mmol) KU-Bu were added to the solution. The mixture was kept at about 100° C. for about 24 hours under argon. The crude product was purified by preparative HPLC. About 90 mg of [7-(2,6-dimethyl-phenyl)-5-methyl-benzo[1,2,4]triazin-3-yl]-[4-(2-pyrrolidin-1-yl-ethoxy)-phenyl]-amine (product having formula (IX)) was isolated. Yield: about 5.2%. ESI-MS: [M+H]$^+$, 454.6; $^1$H NMR (DMSO-d$_6$): δ 1.90-2.05 (m, 10 H), 2.64 (s, 3H), 3.15 (m, 2 H), 3.59-3.64 (m, 4 H), 4.31 (t, J=5.2 Hz, 2 H), 7.09 (d, J=9.2 Hz, 2 H), 7.18 (d, J=7.4 Hz, 2 H), 7.23 (m, 1H), 7.60 (s, 1 H), 7.91 (s, 1 H), 7.98 (d, J=9.2 Hz, 2 H).

Example 6

Synthesis of 1-{4-[7-(2,6-dimethyl-phenyl)-5-methyl-benzo[1,2,4]triazin-3-ylamino]-phenyl}-cyclopropanecarbonitrile

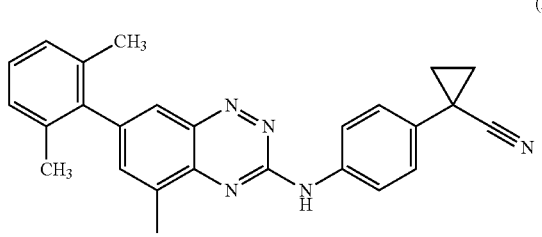

(X)

About 50 mg (0.2 mmol) of 7-bromo-5-methyl-benzo[1,2,4]triazin-3-ylamine and about 84 mg (0.38 mmol) of 1-(4-bromo-phenyl)-cyclopropanecarbonitrile were dissolved in about 10 ml of toluene. About 8 mg (0.009 mmol) of Pd(dba)$_3$, about 17 mg (0.027 mmol) of BINAP, and about 50 mg (0.226 mmol) of KO$^t$-Bu were added to the solution. The mixture was kept at about 100° C. for about 24 hours under argon. The crude product was purified by preparative HPLC. About 5 mg of 1-{4-[7-(2,6-dimethyl-phenyl)-5-methyl-benzo[1,2,4]triazin-3-ylamino]-phenyl}-cyclopropanecarbonitrile (product having formula (X)) was isolated. ESI-MS: [M+H]$^+$, 406.5; $^1$H NMR (DMSO-d$_6$): δ 1.49 (q, 2 H, J=5.3 Hz), 1.72 (q, 2 H, J=5.3 Hz), 2.05 (s, 6 H), 2.67 (s, 3H), 7.18 (d, J=7.4 Hz, 2 H), 7.23 (m, 1 H), 7.38 (d, J=6.85 Hz, 2 H), 7.63 (s, 1 H), 7.91 (s, 1 H), 8.06 (d, J=6.85 Hz, 2 H).

Example 7

Synthesis of [7-(2,6-dimethyl-phenyl)-benzo[1,2,4]triazin-3-yl]-[4-(2-pyrrolidin-1-yl-ethoxy)-phenyl]-amine

(XI)

To a solution of about 100 mg (0.42 mmol) of 7-bromo-benzo[1,2,4]triazin-3-ylamine-1-oxide dissolved in about 6 ml of N,N-dimethylacetamide in a 20 ml vial, were added about 240 mg (1.6 mmol) of 2,6-dimethylphenylboronic acid dissolved in about 1 ml of ethanol and about 64 mg (0.6 mmol) of potassium carbonate dissolved in about 1 ml of water. About 9 mg (0.034 mmol) of triphenylphosphine and about 9 mg (9.83 mmol) of tris(dibenzylideneacetone) dipalladium (0) were added to the mixture. The mixture was reflux overnight. The crude product was poured into about 50 ml of saturated aqueous solution of NaHCO$_3$, and CH$_2$Cl$_2$ was used to extract the product. Solvent in the organic phase was removed under vacuum. The residue was dissolved in a mixture of about 2 ml of N,N-dimethylacetamide and about 1 ml of ethyl alcohol in a 20 ml vial with a septum. Catalytic amount of 10% palladium on carbon was added to the mixture. A balloon filled with hydrogen was placed on the top of the vial. The mixture was stirred at room temperature for about 2 hours. Celite was used to remove the palladium and carbon. The crude product and about 200 mg (0.74 mmol) of 1-[2-(4-bromo-phenoxy)-ethyl]-pyrrolidine were dissolved in 10 ml of toluene. About 17 mg (0.018 mmol) of Pd(dba)$_3$, about 34 mg (0.054 mmol) of BINAP, and about 50 mg (0.226 mmol) of KOt-Bu were added to the solution. The mixture was kept at about 100° C. for about 24 hours under argon. The crude product was purified by preparative HPLC. About 2 mg of [7-(2,6-dimethyl-phenyl)-benzo[1,2,4]triazin-3-yl]-[4-(2-pyrrolidin-1-yl-ethoxy)-phenyl]-amine (product having formula (XI)) was isolated. Yield: about 1.6%; ESI-MS: [M+H]$^+$, 440.6; $^1$H NMR (DMSO-d$_6$): δ 1.90-2.05 (m, 10 H), 3.15 (m, 2 H), 3.59-3.64 (m, 4 H), 4.31 (t, J=5.15 Hz, 2 H), 7.09 (d, J=9.06 Hz, 2 H), 7.18 (d, J=7.4 Hz, 2 H), 7.23 (m, 1

H), 7.70 (d, J=8.7 Hz, 1 H), 7.78 (d, J=8.7 Hz, 1 H), 7.90 (d, J=9.06 Hz, 2 H), 8.08 (s, 1 H).

Example 8

Synthesis of [7-(2,6-dimethyl-phenyl)-5-methyl-benzo[1,2,4]triazin-3-yl]-quinolin-8-yl-amine by Method A

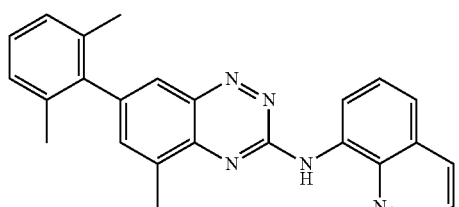

(XII)

About 100 mg (0.4 mmol) of 7-bromo-5-methyl-benzo[1,2,4]triazin-3-ylamine and about 158 mg (0.8 mmol) of 8-bromo-quinoline were dissolved in about 10 ml toluene. About 17 mg (0.018 mmol) of Pd(dba)$_3$, about 17 mg (0.027 mmol) of BINAP, and about 50 mg (0.226 mmol) of KOt-Bu were added to the solution. The mixture was kept at about 100° C. for about 24 hours under argon. The crude product was purified by preparative HPLC. About 50 mg [7-(2,6-dimethyl-phenyl)-5-methyl-benzo[1,2,4]triazin-3-yl]-quinolin-8-yl-amine (product having formula (XII)) was isolated. Yield: about 33.8%; ESI-MS: [M+H]$^+$, 392; $^1$H NMR (DMSO-d$_6$): δ 2.07 (s, 6 H), 2.79 (s, 3H), 7.19 (d, J=7.4 Hz, 2 H), 7.25 (m, 1 H), 7.71-7.79 (m, 4 H), 8.04 (s, 1 H), 8.50 (d, J=8.3 Hz, 1 H), 9.05 (m, 2 H).

Example 9

Synthesis of [7-(2,6-dimethyl-phenyl)-5-methyl-benzo[1,2,4]triazin-3-yl]-pyridin-2-yl-amine by Method A

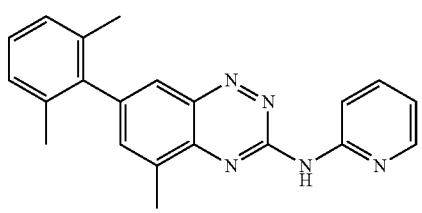

(XIII)

Title product having formula (XIII) was synthesized using Method A described above. ESI-MS: [M+H]$^+$, 342; $^1$H NMR (500 MHz, DMSO-d$_6$): δ 2.05 (s, 6H), 2.71 (s, 3H), 7.18-7.26 (m, 4 H), 7.71 (s, 1 H), 8.00 (m, 2 H), 8.44 (m, 2 H), 11.42 (s, 1H, NH).

Example 10

Synthesis of [7-(2,6-dimethyl-phenyl)-5-methyl-benzo[1,2,4]triazin-3-yl]-quinolin-3-yl-amine by Method A

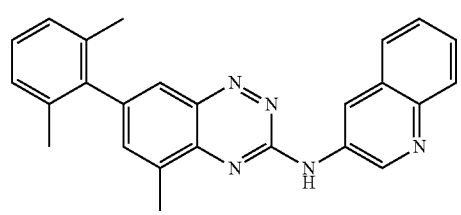

(XIV)

Title product having formula (XIII) was synthesized using Method A described above. ESI-MS: [M+H]$^+$, 392; $^1$H NMR (500 MHz, DMSO-d$_6$): δ 2.07 (s, 6H), 2.77 (s, 3H), 7.18 (d, J=7.4 Hz, 2 H), 7.23 (m, 1 H), 7.62 (m, 2H), 7.70 (s, 1H), 7.94 (dd, J$_1$=8.14 Hz, J$_2$=1.48 Hz, 1H), 8.01 (m, 2H), 9.16 (s, 1H), 9.30 (s, 1H), 11.44 (s, 1H, NH).

Example 11

Synthesis of [7-(2,6-dimethyl-phenyl)-5-methyl-benzo[1,2,4]triazin-3-yl]-m-tolyl-amine by Method B

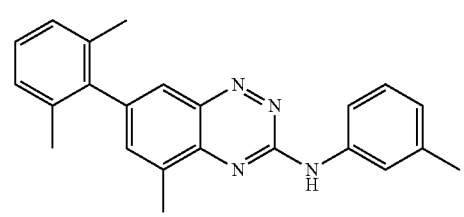

(XV)

Title product having formula (XV) was synthesized using Method B described above. ESI-MS: [M+H]$^+$, 355; $^1$H NMR (CDCl$_3$): δ 2.10 (s, 6 H), 2.44 (s, 3 H), 2.74 (s, 3 H), 6.97 (d, J=7.6 Hz, 1 H), 7.17 (d, J=7.6 Hz, 2 H), 7.22 (m, 1 H), 7.33 (m, 1 H), 7.49 (s, 1 H), 7.74 (d, J=7.6 Hz, 1 H), 7.96 (s, 1 H), 7.99 (s, 1 H).

Example 12

Synthesis of [7-(2,6-dimethyl-phenyl)-5-methyl-benzo[1,2,4]triazin-3-yl]-p-tolyl-amine by Method B

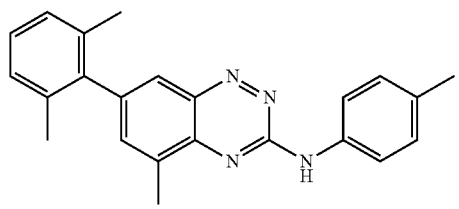

(XVI)

Title product having formula (XVI) was synthesized using Method B described above. ESI-MS: [M+H]$^+$, 355; $^1$H NMR (CDCl$_3$): δ 2.09 (s, 6 H), 2.38 (s, 3 H), 2.72 (s, 3 H), 7.16 (d, J=7.6 Hz, 2 H), 7.22 (m, 2 H), 7.47 (s, 1 H), 7.80 (d, J=8.4 Hz, 2 H), 7.96 (s, 1 H).

Example 13

Synthesis of (2,3-dimethyl-phenyl)-[7-(2,6-dimethyl-phenyl)-5-methyl-benzo[1,2,4]triazin-3-yl]-amine by Method B

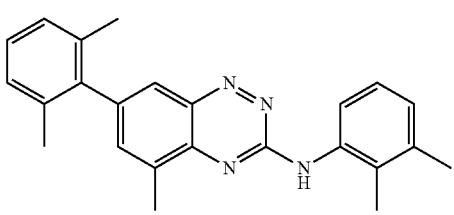

(XVII)

Title product having formula (XVII) was synthesized using Method B described above. ESI-MS: [M+H]$^+$, 369; $^1$H NMR (CDCl$_3$): δ 2.09 (s, 6 H), 2.35 (s, 3 H), 2.40 (s, 3 H), 2.72 (s, 3 H), 7.03 (d, J=7.6 Hz, 1 H), 7.16 (d, J=7.2 Hz, 2 H), 7.20-7.24 (m, 2 H), 7.45 (s, 1 H), 7.95 (s, 1 H), 8.20 (d, J=7.6 Hz, 1 H).

Example 14

Synthesis of (2,4-dimethyl-phenyl)-[7-(2,6-dimethyl-phenyl)-5-methyl-benzo[1,2,4]triazin-3-yl]-amine by Method B

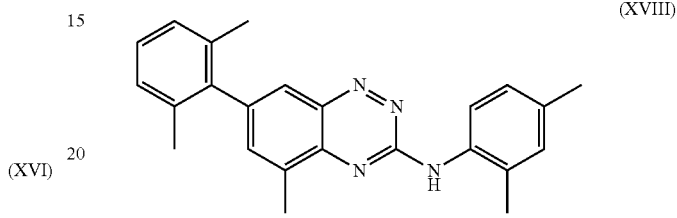

(XVIII)

Title product having formula (XVIII) was synthesized using Method B described above. ESI-MS: [M+H]$^+$, 369; $^1$H NMR (CDCl$_3$): δ 2.09 (s, 6 H), 2.36 (s, 3 H), 2.44 (s, 3 H), 2.66 (s, 3 H), 7.11-7.20 (m, 5 H), 7.45 (s, 1 H), 7.95 (s, 1 H), 8.20 (d, J=8.4 Hz, 1 H).

Example 15

Synthesis of (2,5-dimethyl-phenyl)-[7-(2,6-dimethyl-phenyl)-5-methyl-benzo[1,2,4]triazin-3-yl]-amine by Method B

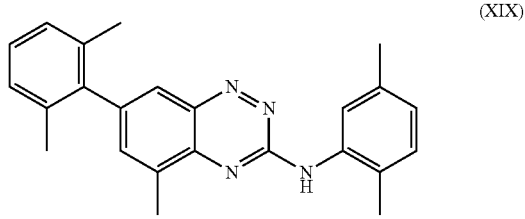 [SMILES: Cc1ccc(C)c(Nc2nnc3cc(-c4c(C)cccc4C)cc(C)c3n2)c1]

(XIX)

Title product having formula (XIX) was synthesized using Method B described above. ESI-MS: [M+H]$^+$, 369; $^1$H NMR (CDCl$_3$): δ 2.09 (s, 6 H), 2.42 (s, 3 H), 2.43 (s, 3 H), 2.69 (s, 3 H), 6.90 (d, J=7.6 Hz, 1 H), 7.16 (d, J=7.6 Hz, 2 H), 7.26 (m, 2 H), 7.47 (s, 1 H), 7.95 (s, 1 H), 8.40 (s, 1 H).

Example 16

Synthesis of (3,4-dimethyl-phenyl)-[7-(2,6-dimethyl-phenyl)-5-methyl-benzo[1,2,4]triazin-3-yl]-amine by Method B

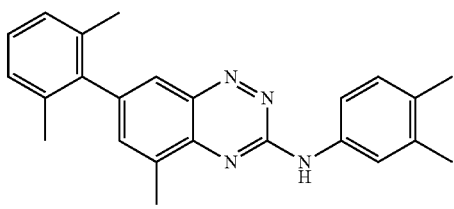

(XX)

Title product having formula (XX) was synthesized using Method B described above. ESI-MS: [M+H]$^+$, 369; $^1$H NMR (CDCl$_3$): δ 2.09 (s, 6 H), 2.29 (s, 3 H), 2.34 (s, 3 H), 2.72 (s, 3 H), 7.17-7.23 (m, 4 H), 7.47 (s, 1 H), 7.68 (d, J=8.0 Hz, 1 H), 7.92 (s, 1 H), 7.95 (s, 1 H).

Example 17

Synthesis of (3-chloro-4-fluoro-phenyl)-[7-(2,6-dimethyl-phenyl)-5-methyl-benzo[1,2,4]triazin-3-yl]-amine by Method B

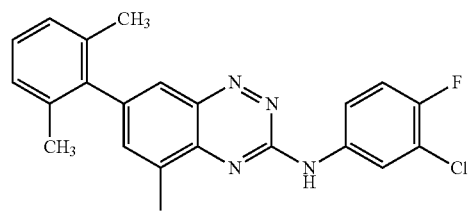

(XXI)

Title product having formula (XXI) was synthesized using Method B described above. ESI-MS: [M+H]$^+$, 393; $^1$H NMR (CDCl$_3$): δ 2.09 (s, 6 H), 2.74 (s, 3 H), 7.17 (d, J=7.6 Hz, 2 H), 7.24 (m, 1 H), 7.54 (s, 1 H), 7.65 (m, 1 H), 8.06 (s, 1 H), 8.30 (s, 1 H), 8.32 (dd, J$_1$=6.8 Hz, J$_2$=3.2 Hz, 1 H).

Example 18

Synthesis of [7-(2-chloro-phenyl)-5-methyl-benzo[1,2,4]triazin-3-yl]-phenyl-amine by Method B

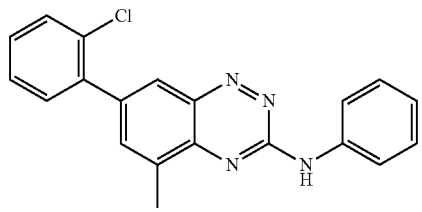

(XXII)

Title product having formula (XXII) was synthesized using Method B described above. ESI-MS: [M+H]$^+$, 347; $^1$H NMR (CDCl$_3$): δ 2.75 (s, 3 H), 7.15 (t, J=7.6 Hz, 1 H), 7.37-7.39 (m, 2 H), 7.44-7.48 (m, 3 H), 7.53 (d, J=7.6 Hz, 1 H), 7.81 (s, 1 H), 7.92 (d, J=7.6 Hz, 2 H), 8.24 (s, 1 H).

Example 19

Synthesis of (4-methoxy-phenyl)-[7-(2-methoxy-phenyl)-5-methyl-benzo[1,2,4]triazin-3-yl]-amine by Method B

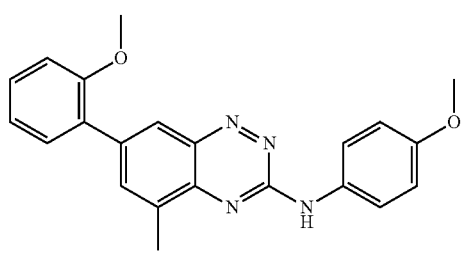

(XXIII)

Title product having formula (XXIII) was synthesized using Method B described above. ESI-MS: [M+H]$^+$, 373; $^1$H NMR (CDCl$_3$): δ 2.70 (s, 3 H), 3.83 (s, 3 H), 3.87 (s, 3 H), 6.99 (d, J=8.8 Hz, 2 H), 7.05 (d, J=8 Hz, 1 H), 7.09 (m, 1 H), 7.38 (m, 1 H), 7.45 (d, J=8 Hz, 1 H), 7.81 (d, J=8.8 Hz, 2 H), 7.88 (s, 1 H), 8.29 (s, 1 H).

Example 20

Synthesis of (4-butyl-phenyl)-[7-(2,6-dimethyl-phenyl)-5-methyl-benzo[1,2,4]triazin-3-yl]-amine by Method B

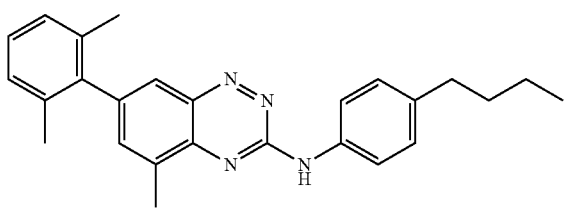

(XXIV)

Title product having formula (XXIV) was synthesized using Method B described above. ESI-MS: [M+H]$^+$, 397.3; $^1$H NMR (CDCl$_3$): δ 0.95 (t, J=7.6 Hz, 3 H), 1.32 (m, 2 H), 1.64 (m, 2 H), 2.10 (s, 6 H), 2.64 (t, J=7.6 Hz, 2 H), 2.66 (s, 3 H), 7.16 (d, J=8.4 Hz, 2 H), 7.16 (d, J=7.6 Hz, 2 H), 7.22 (m, 1 H), 7.47 (s, 1 H), 7.82 (d, J=8.4 Hz, 2 H), 7.95 (s, 1 H).

Example 21

Synthesis of [7-(2,6-dimethyl-phenyl), 5-methyl-benzo[1,2,4]triazin-3-yl]-(2-methoxy-phenyl)-amine by Method B

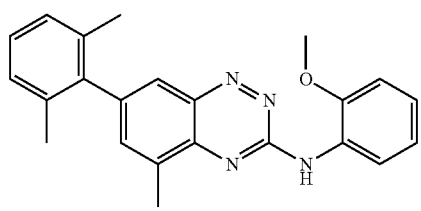

(XXV)

Title product having formula (XXV) was synthesized using Method B described above. ESI-MS: [M+H]$^+$, 371.2; $^1$H NMR (CDCl$_3$): δ 2.10 (s, 6 H), 2.75 (s, 3 H), 4.01 (s, 3 H), 6.98 (dd, J$_1$=7.6 Hz, J$_2$=2 Hz, 1 H), 7.10 (m, 2 H), 7.16 (d, J=7.6 Hz, 2 H), 7.22 (m, 1 H), 7.49 (s, 1 H), 7.97 (s, 1 H), 8.84 (dd, J$_1$=7.6 Hz, J$_2$=2.4 Hz, 1H).

Example 22

Synthesis of [7-(2,6-dimethyl-phenyl)-5-methyl-benzo[1,2,4]triazin-3-yl]-(3-methoxy-phenyl)-amine by Method B

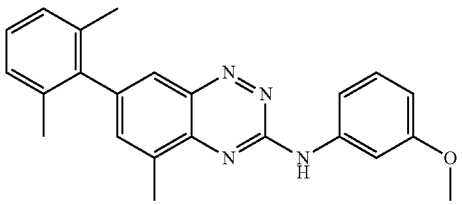

(XXVI)

Title product having formula (XXVI) was synthesized using Method B described above. ESI-MS: [M+H]$^+$, 371.2; $^1$H NMR (CDCl$_3$): δ 2.10 (s, 6 H), 2.75 (s, 3 H), 3.92 (s, 3 H), 6.70 (d, J=7.6 Hz, 1 H), 7.16 (d, J=7.6 Hz, 2 H), 7.22 (m, 1 H), 7.26-7.35 (m, 2 H), 7.49 (s, 1 H), 7.88 (s, 1 H), 7.98 (s, 1 H).

Example 23

Synthesis of [7-(2,6-dimethyl-phenyl)-5-methyl-benzo[1,2,4]triazin-3-yl]-(4-methoxy-phenyl)-amine by Method B (product TG100-412-1)

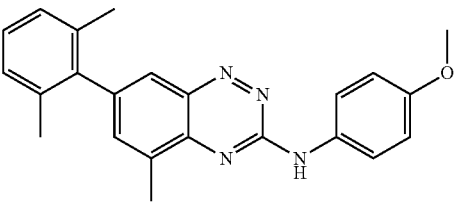

(XXVII)

Title product having formula (XXVII) was synthesized using Method B described above. ESI-MS: [M+H]$^+$, 371.2; $^1$H NMR (CDCl$_3$): δ 2.10 (s, 6 H), 2.70 (s, 3 H), 3.86 (s, 3 H), 7.0 (d, J=9.2 Hz, 2 H), 7.16 (d, J=7.6 Hz, 2 H), 7.22 (m, 1 H), 7.46 (s, 1 H), 7.80 (d, J=9.2 Hz, 2 H), 7.94 (s, 1 H).

Example 24

Synthesis of [7-(2,6-dimethyl-phenyl)-5-methyl-benzo[1,2,4]triazin-3-yl]-(4-ethoxy-phenyl)-amine by Method B

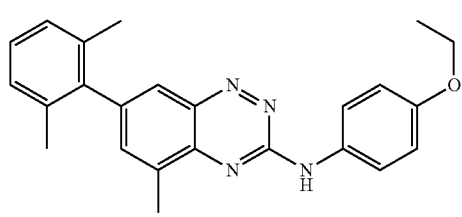

(XXVIII)

Title product having formula (XXVIII) was synthesized using Method B described above. ESI-MS: [M+H]⁺, 385.3; ¹H NMR (CDCl₃): δ 1.44 (t, J=7.2 Hz, 3 H), 2.10 (s, 6 H), 2.70 (s, 3 H), 4.08 (q, J=7.2 Hz, 2 H), 6.98 (d, J=9.2 Hz, 2 H), 7.16 (d, J=7.2 Hz, 2 H), 7.22 (m, 1 H), 7.46 (s, 1 H), 7.80 (d, J=9.2 Hz, 2 H), 7.94 (s, 1 H).

Example 25

Synthesis of (3-chloro-phenyl)-[7-(2,6-dimethyl-phenyl)-5-methyl-benzo[1,2,4]triazin-3-yl]-amine by Method B

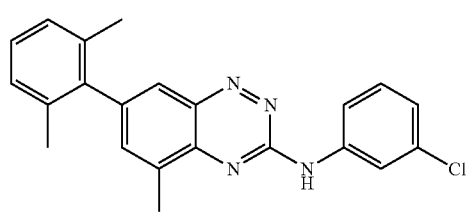

(XXIX)

Title product having formula (XXIX) was synthesized using Method B described above. ESI-MS: [M+H]⁺, 375.3; ¹H NMR (CDCl₃): δ 2.10 (s, 6 H), 2.76 (s, 3 H), 7.10 (d, J=9.2

Hz, 1 H), 7.17 (d, J=7.6 Hz, 2 H), 7.22 (m, 1 H), 7.37 (m, 1 H), 7.49 (s, 1 H), 7.64 (d, J=9.2 Hz, 1 H), 8.00 (s, 1 H), 8.25 (s, 1 H).

Example 26

Synthesis of (3,4-dichloro-phenyl)-[7-(2,6-dimethyl-phenyl)-5-methyl-benzo[1,2,4]triazin-3-yl]-amine by Method B

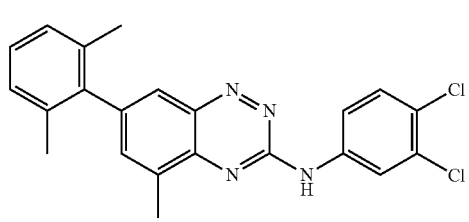

(XXX)

Title product having formula (XXX) was synthesized using Method B described above: ESI-MS: [M+H]⁺, 409.3; ¹H NMR (CDCl₃): δ 2.09 (s, 6 H), 2.75 (s, 3H), 7.17 (d, J=7.6 Hz, 2 H), 7.24 (m, 1 H), 7.47 (d, J=8.8 Hz, 1 H), 7.54 (s, 1 H), 7.62 (d, J=8.8 Hz, 1 H), 8.01 (s, 1 H), 8.38 (s, 1 H).

Example 27

Synthesis of [7-(3,5-dimethoxy-phenyl)-5-methyl-benzo[1,2,4]triazin-3-yl]-m-tolyl-amine by Method B

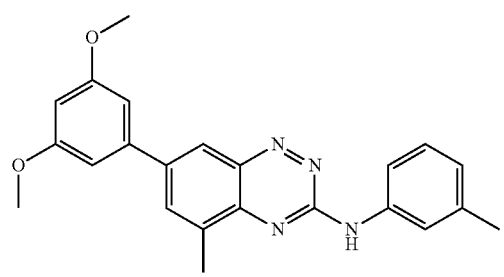

(XXXI)

Title product having formula (XXXI) was synthesized using Method B described above. ESI-MS: [M+H]⁺, 387.4; ¹H NMR (CDCl₃): δ 2.43 (s, 3 H), 2.76 (s, 3 H), 3.89 (s, 6 H), 6.53 (s, 1 H), 6.85 (s, 2 H), 6.96 (d, J=7.2 Hz, 1 H), 7.33 (m, 1 H), 7.72 (m, 2 H), 7.94 (s, 1 H), 8.36 (s, 1 H).

Example 28

Synthesis of [7-(3,5-dimethoxy-phenyl)-5-methyl-benzo[1,2,4]triazin-3-yl]-p-tolyl-amine by Method B

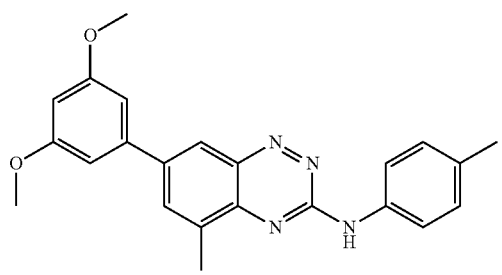

(XXXII)

Title product having formula (XXXII) was synthesized using Method B described above. ESI-MS: [M+H]+, 387.4; $^1$H NMR (CDCl$_3$): δ 2.38 (s, 3 H), 2.74 (s, 3 H), 3.89 (s, 6 H), 6.53 (s, 1 H), 6.85 (s, 2 H), 7.23 (d, J=8.0 Hz, 2 H), 7.78 (d, J=8.0 Hz, 2 H), 7.92 (s, 1 H), 8.35 (s, 1 H).

Example 29

Synthesis of [7-(3,5-dimethoxy-phenyl)-5-methyl-benzo[1,2,4]triazin-3-yl]-(2,4-dimethyl-phenyl)-amine by Method B

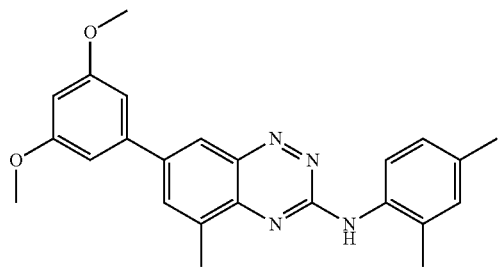

(XXXIII)

Title product having formula (XXXIII) was synthesized using Method B described above. ESI-MS: [M+H]+, 401.4; $^1$H NMR (CDCl$_3$): δ 2.36 (s, 3 H), 2.43 (s, 3 H), 2.69 (s, 3 H), 3.89 (s, 6 H), 6.53 (s, 1 H), 6.85 (s, 2 H), 7.11 (s, 1 H), 7.14 (d, J=8.8 Hz, 1 H), 7.90 (s, 1 H), 8.30 (d, J=8.8 Hz, 1 H), 8.35 (s, 1 H).

Example 30

Synthesis of [7-(3,5-dimethoxy-phenyl)-5-methyl-benzo[1,2,4]triazin-3-yl]-(2,5-dimethyl-phenyl)-amine by Method B

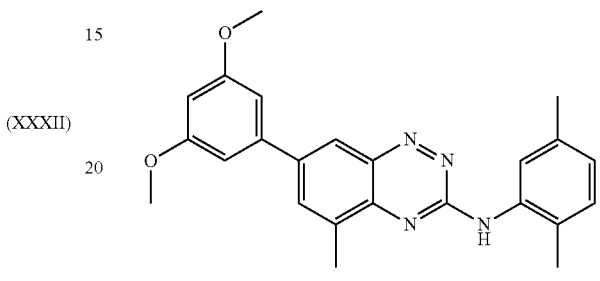

(XXXIV)

Title product having formula (XXXIV) was synthesized using Method B described above. ESI-MS: [M+H]+, 401.4; $^1$H NMR (CDCl$_3$): δ 2.43 (s, 6 H), 2.72 (s, 3 H), 3.89 (s, 6 H), 6.53 (s, 1 H), 6.86 (s, 2 H), 6.91 (d, J=7.2 Hz, 1 H), 7.16 (d, J=7.2 Hz, 1 H), 7.93 (s, 1 H), 8.36 (s, 1 H), 8.40 (s, 1 H).

Example 31

Synthesis of [7-(3,5-dimethoxy-phenyl)-5-methyl-benzo[1,2,4]triazin-3-yl]-(3,4-dimethyl-phenyl)-amine by Method B

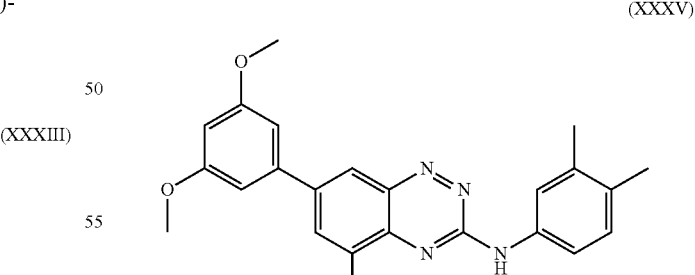

(XXXV)

Title product having formula (XXXV) was synthesized using Method B described above. ESI-MS: [M+H]+, 401.4; $^1$H NMR (CDCl$_3$): δ 2.29 (s, 3 H), 2.34 (s, 3 H), 2.75 (s, 3 H), 3.89 (s, 6 H), 6.53 (s, 1 H), 6.86 (s, 2 H), 7.20 (d, J=7.6 Hz, 1 H), 7.65 (d, J=7.6 Hz, 1 H), 7.68 (s, 1 H), 7.92 (s, 1 H), 8.36 (s, 1 H).

Example 32

Synthesis of (4-butyl-phenyl)-[7-(3,5-dimethoxy-phenyl)-5-methyl-benzo[1,2,4]triazin-3-yl]-amine by Method B

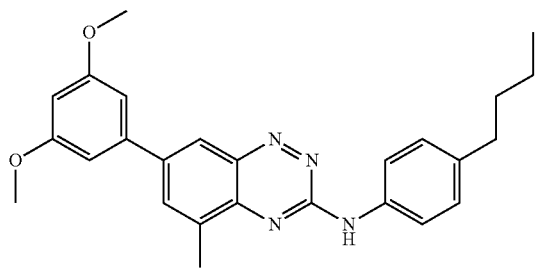

(XXXVI)

Title product having formula (XXXVI) was synthesized using Method B described above. ESI-MS: [M+H]+, 429.4; 1H NMR (CDCl3): δ 0.95 (t, J=7.2 Hz, 3 H), 1.40 (m, 2 H), 1.64 (m, 2 H), 2.64 (t, J=8 Hz, 2 H), 2.75 (s, 3 H), 3.89 (s, 6 H), 6.53 (s, 1H), 6.86 (s, 2 H), 7.24 (d, J=8.4 Hz, 2 H), 7.80 (d, J=8.4 Hz, 2 H), 7.92 (s, 1 H), 8.35 (s, 1 H).

Example 33

Synthesis of [7-(3,5-dimethoxy-phenyl)-5-methyl-benzo[1,2,4]triazin-3-yl]-(4-ethoxy-phenyl)-amine by Method B

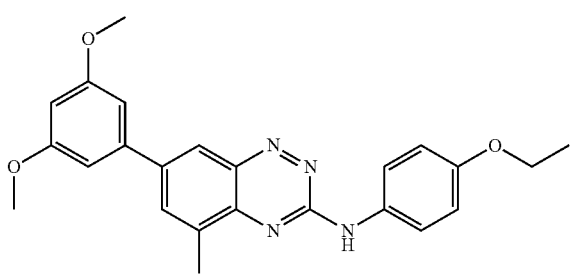

(XXXVII)

Title product having formula (XXXVII) was synthesized using Method B described above. ESI-MS: [M+H]+, 417.3; 1H NMR (CDCl3): δ 1.44 (t, J=6.8 Hz, 3 H), 2.73 (s, 3 H), 3.89 (s, 6 H), 4.07 (q, J=6.8 Hz, 2 H), 6.53 (s, 1 H), 6.86 (s, 2 H), 6.98 (d, J=8.8 Hz, 2 H), 7.80 (d, J=8.8 Hz, 2 H), 7.91 (s, 1 H), 8.34 (s, 1 H).

Example 34

Synthesis of [7-(3,5-dimethoxy-phenyl)-5-methyl-benzo[1,2,4]triazin-3-yl]-pyridin-4-yl-amine by Method B

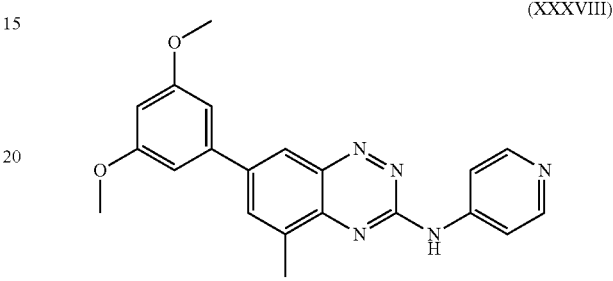

(XXXVIII)

Title product having formula (XXXVIII) was synthesized using Method B described above. ESI-MS: [M+H]+, 374.4; 1H NMR (CDCl3): δ 2.82 (s, 3 H), 3.89 (s, 6H), 6.53 (s, 1 H), 6.87 (s, 2 H), 7.87 (d, J=5.2 Hz, 2 H), 8.02 (s, 1 H), 8.43 (s, 1 H), 8.60 (d, J=5.2 Hz, 2 H).

Example 35

Synthesis of [7-(3,5-dimethoxy-phenyl)-5-methyl-benzo[1,2,4]triazin-3-yl]-(2,3-dimethyl-phenyl)-amine by Method B

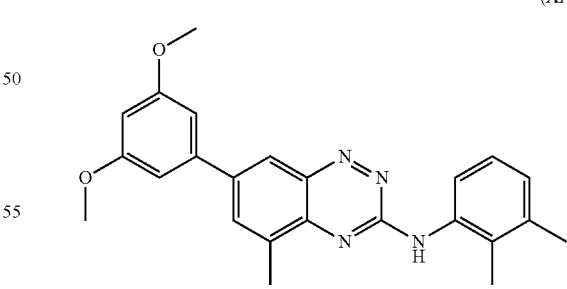

(XXXIX)

Title product having formula (XXXIX) was synthesized using Method B described above. ESI-MS: [M+H]+, 401.4; 1H NMR (CDCl3): δ 2.36 (s, 3 H), 2.39 (s, 3 H), 2.68 (s, 3 H), 3.89 (s, 6 H), 6.53 (s, 1 H), 6.86 (s, 2 H), 7.04 (d, J=7.6 Hz, 1 H), 7.22 (m, 1 H), 7.90 (s, 1 H), 8.18 (d, J=7.6 Hz, 1 H), 8.35 (s, 1 H).

Example 36

Synthesis of [7-(3,5-dimethoxy-phenyl)-5-methyl-benzo[1,2,4]triazin-3-yl]-(2-methoxy-phenyl)-amine by Method B

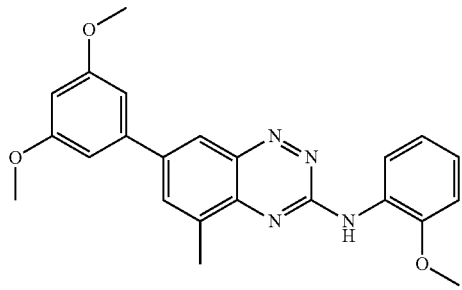
(XL)

Title product having formula (XL) was synthesized using Method B described above. ESI-MS: [M+H]+, 403.4; $^1$H NMR (CDCl$_3$): δ 2.77 (s, 3 H), 3.89 (s, 6 H), 3.99 (s, 3 H), 6.53 (s, 1 H), 6.86 (s, 2 H), 7.00 (d, J=7.6 Hz, 1 H), 7.08 (m, 2 H), 7.93 (s, 1 H), 8.36 (s, 1 H), 8.80 (d, J=7.6 Hz, 1 H).

Example 37

Synthesis of [7-(3,5-dimethoxy-phenyl)-5-methyl-benzo[1,2,4]triazin-3-yl]-(4-methoxy-phenyl)-amine by Method B

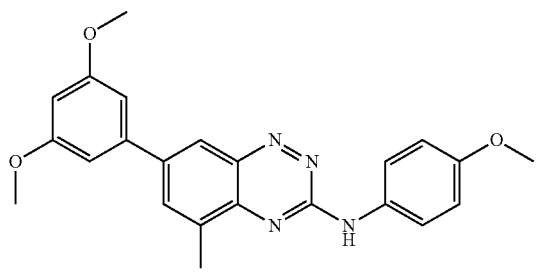
(XLI)

Title product having formula (XLI) was synthesized using Method B described above. ESI-MS: [M+H]+, 403.4; $^1$H NMR (CDCl$_3$): δ 2.73 (s, 3 H), 3.86 (s, 3 H), 3.89 (s, 6 H),
6.53 (s, 1 H), 6.86 (s, 2 H), 7.00 (d, J=9.2 Hz, 2 H), 7.82 (d, J=9.2 Hz, 2 H), 7.91 (s, 1 H), 8.35 (s, 1 H).

Example 38

Synthesis of [7-(2,6-dimethyl-phenyl)-5-methyl-benzo[1,2,4]triazin-3-yl]-pyridin-4-yl-amine by Method A

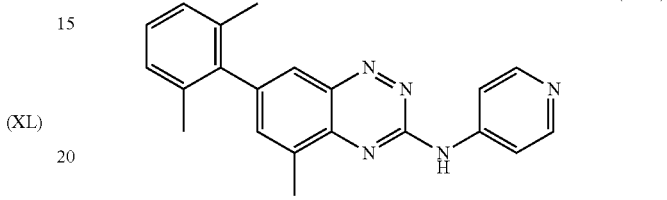
(XLII)

Title product having formula (XLII) was synthesized using Method A described above. ESI-MS: [M+H]+, 442.4; $^1$H NMR (DMSO-d$_6$): δ 2.04 (s, 6 H), 2.75 (s, 3 H), 7.18 (d, 2 H), 7.25 (m, 1 H), 7.84 (s, 1 H), 8.15 (s, 1 H), 8.40 (d, 2 H), 8.75 (d, 2H).

Example 39

Synthesis of [7-(2,6-dichloro-phenyl)-5-methyl-benzo[1,2,4]triazin-3-yl]-(3-methoxy-phenyl)-amine by Method B

(XLIII)

Title product having formula (XXLIII) was synthesized using Method B described above. ESI-MS: [M+H]+, 411.3; $^1$H NMR (DMSO-d$_6$): δ 2.68 (s, 3 H), 3.83 (s, 3 H), 6.67 (d, J=7.7 Hz, 1 H), 7.30 (t, J=8.2 Hz, 1 H), 7.46 (d, J=7.7 Hz, 1 H), 7.52 (m, 1 H), 7.66 (d, J=8.2 Hz, 2 H), 7.73 (s, 1 H), 7.96 (s, 1 H), 8.12 (s, 1 H).

Example 40

Synthesis of [7-(2,6-dichloro-phenyl)-5-methyl-benzo[1,2,4]triazin-3-yl]-(4-methoxy-phenyl)-amine by Method B

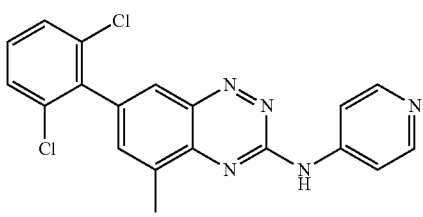

(XLIV)

Title product having formula (XLIV) was synthesized using Method B described above. ESI-MS: [M+H]+, 411.3; $^1$H NMR (CDCl$_3$): δ 2.72 (s, 3 H), 3.86 (s, 3 H), 7.0 (d, J=8.8 Hz, 2 H), 7.30 (m, 1 H), 7.46 (d, J=8.4 Hz, 2 H), 7.54 (s, 1 H), 7.81 (d, J=8.8 Hz, 2 H), 8.09 (s, 1 H).

Example 41

Synthesis of [7-(2,6-dichloro-phenyl)-5-methyl-benzo[1,2,4]triazin-3-yl]-pyridin-4-yl-amine by Method A (XLV)

Title product having formula (XLV) was synthesized using Method A described above. ESI-MS: [M+H]+, 382.4; $^1$H NMR (DMSO-d$_6$): δ 2.77 (s, 3 H), 7.5 (t, 1 H), 7.70 (d, 2 H), 7.90 (s, 1 H), 8.30 (s, 1 H), 8.40 (d, 2 H), 8.70 (d, 2 H).

Example 42

Synthesis of [7-(2,6-dichloro-phenyl)-5-methyl-benzo[1,2,4]triazin-3-yl]-pyridin-3-yl-amine by Method A

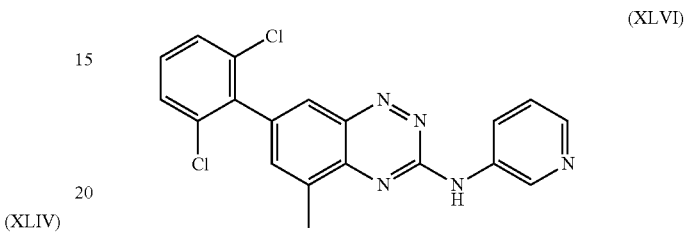

(XLVI)

Title product having formula (XLVI) was synthesized using Method A described above. ESI-MS: [M+H]+, 382.4; $^1$H NMR (DMSO-d$_6$): δ 2.68 (s, 3 H), 7.5 (t, 1H), 7.70 (m, 3 H), 7.80 (s, 1 H), 8.20 (s, 1 H), 8.40 (m, 1 H), 8.60 (d, 1 H), 9.35 (s, 1 H).

Example 43

Synthesis of [4-(2-diethylamino-ethoxy)-phenyl]-[7-(2,6-dimethyl-phenyl)-5-methyl-benzo[1,2,4]triazin-3-yl]-amine by Method C

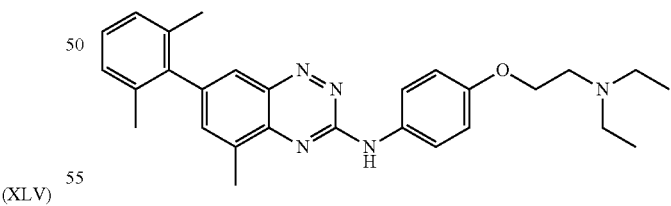

(XLVIII)

Title product having formula (XLVIII) was synthesized using Method C described above. ESI-MS: [M+H]+, 456.3; $^1$H NMR (DMSO-d$_6$): δ 1.25 (t, J=7.2 Hz, 6H), 2.05 (s, 6 H), 2.63 (s, 3 H), 3.23 (m, 4 H), 3.59 (t, J=5.0 Hz, 2 H), 4.44 (t, J=5.0 Hz, 2 H), 7.10 (d, J=9.2 Hz, 2 H), 7.16 (d, J=7.4 Hz, 2 H), 7.21 (m, 1 H), 7.60 (s, 1 H), 7.91 (s, 1 H), 8.0 (d, J=9.2 Hz, 2 H).

Example 44

Synthesis of [7-(2,6-dimethyl-phenyl)-5-methyl-benzo[1,2,4]triazin-3-yl]-[4-(2-morpholin-4-yl-ethoxy)-phenyl]-amine by Method C

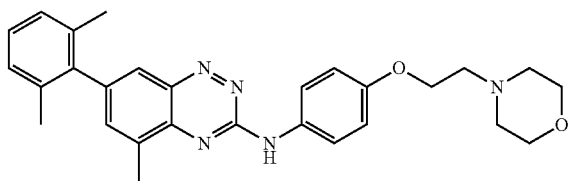

(XLIX)

Title product having formula (XLIX) was synthesized using Method C described above. ESI-MS: [M+H]$^+$, 470.3; $^1$H NMR (DMSO-d$_6$): δ 2.06 (s, 6 H), 2.64 (s, 3 H), 3.20 (br, 2 H), 3.52-3.58 (b, 4 H), 3.75 (b, t, 2 H), 3.99 (b, 2 H), 4.38 (b, 2 H), 7.06 (d, J=8.4 Hz, 2 H), 7.16 (d, J=7.6 Hz, 2 H), 7.21 (m, 1 H), 7.58 (s, 1 H), 7.89 (s, 1 H), 7.96 (d, J=8.4 Hz, 2 H).

Example 45

Synthesis of [7-(2,6-dimethyl-phenyl)-5-methyl-benzo[1,2,4]triazin-3-yl]-[4-(3-pyrrolidin-1-yl-propoxy)-phenyl]-amine by Method C

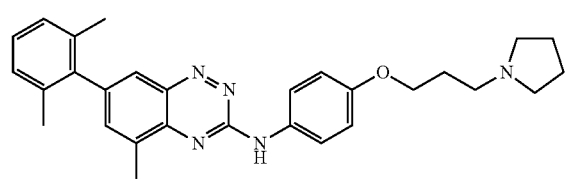

(L)

Title product having formula (L) was synthesized using Method C described above. ESI-MS: [M+H]$^+$, 468.3; $^1$H NMR (CDCl$_3$): δ 2.09-2.21 (m, 10 H), 2.32 (m, 2 H), 2.70 (s, 3H), 2.84 (m, 2 H), 3.33 (b, 2 H), 3.91 (m, 2 H), 4.10 (t, J=5.6 Hz, 2 H), 6.95 (d, J=9.2 Hz, 2 H), 7.16 (d, J=7.6 Hz, 2 H), 7.21 (m, 1 H), 7.48 (s, 1 H), 7.82 (d, J=9.2 Hz, 2 H), 7.94 (s, 1 H), 8.04 (s, 1 H, NH).

Example 46

Synthesis of [7-(2,6-dichloro-phenyl)-5-methyl-benzo[1,2,4]triazin-3-yl]-[4-(2-pyrrolidin-1-yl-ethoxy)-phenyl]-amine by Method C

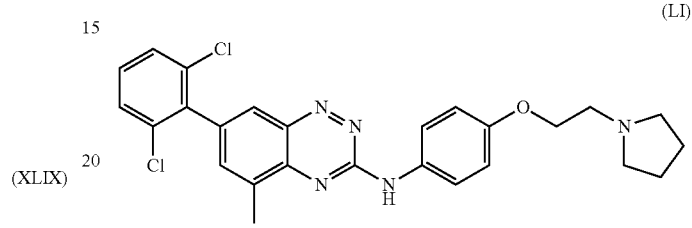

(LI)

Title product having formula (LI) was synthesized using Method C described above. ESI-MS: [M+H]$^+$, 494.3; $^1$H NMR (DMSO-d$_6$): δ 1.90 (m, 2 H), 2.04 (m, 2 H), 2.63 (s, 3H), 3.15 (m, 2 H), 3.60 (m, 4 H), 3.98 (m, b, 2 H), 4.32 (t, J=4.8 Hz, 2 H), 7.10 (d, J=9.2 Hz, 2 H), 7.51 (t, J=8.2 Hz, 1 H), 7.67 (d, J=8.2 Hz, 2 H), 7.69 (s, 1 H), 7.98 (d, J=9.2 Hz, 2 H), 8.08 (s, 1 H).

Example 47

Synthesis of [7-(2,6-dimethyl-phenyl)-5-methyl-benzo[1,2,4]triazin-3-yl]-{4-[2-(4-methyl-piperazin-1-yl)-ethoxy]-phenyl}-amine by Method C

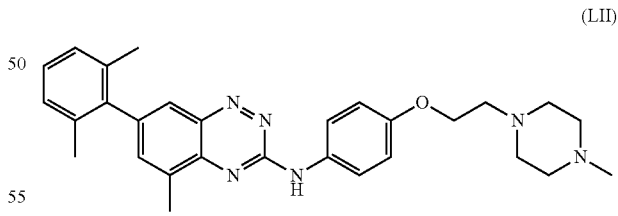

(LII)

Title product having formula (LII) was synthesized using Method C described above. ESI-MS: [M+H]$^+$, 483.3; $^1$H NMR (CDCl$_3$): δ 2.10 (s, 6 H), 2.69 (s, 3 H), 2.81 (s, 3 H), 3.10-3.50 (b, 10 H), 4.29 (b, 2 H), 6.98 (d, J=8.8 Hz, 2 H), 7.16

(d, J=7.6 Hz, 2 H), 7.21 (m, 1 H), 7.47 (s, 1 H), 7.84 (d, J=8.8 Hz, 2 H), 7.94 (s, 1 H), 8.05 (s, 1 H, NH).

Example 48

Synthesis of [7-(2,6-dimethyl-phenyl)-5-methyl-benzo[1,2,4]triazin-3-yl]-[3-(2-pyrrolidin-1-yl-ethoxy)-phenyl]-amine by Method C

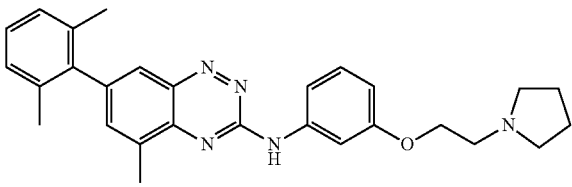

(LIII)

Title product having formula (LIII) was synthesized using Method C described above. ESI-MS: [M+H]$^+$, 454.3; $^1$H NMR (DMSO-d$_6$): δ 1.85-2.06 (br, m, 10 H), 2.68 (s, 3 H), 3.15 (br, 2 H), 3.60 (br, 4 H), 4.37 (br, 2 H), 6.73 (d, J=8.2 Hz, 1 H), 7.18 (d, J=7.4 Hz, 2 H), 7.22 (m, 1 H), 7.34 (m, 1 H), 7.55 (d, J=8.2 Hz, 1 H), 7.65 (s, 1 H), 7.95 (s, 1 H), 7.98 (s, 1 H)

Example 49

Synthesis of [3-(2-diethylamino-ethoxy)-phenyl]-[7-(2,6-dimethyl-phenyl)-5-methyl-benzo[1,2,4]triazin-3-yl]-amine by Method C

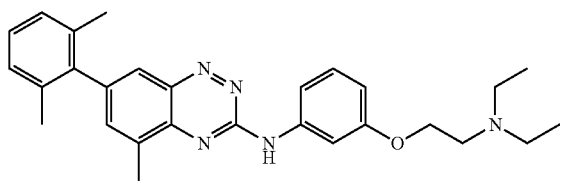

(LIV)

Title product having formula (LIV) was synthesized using Method C described above. ESI-MS: [M+H]$^+$, 456.3; $^1$H NMR (DMSO-d$_6$): δ 1.27 (t, J=7.2 Hz, 6 H), 2.05 (s, 6 H), 2.68 (s, 3 H), 3.25 (br, 4 H), 3.58 (br, 2 H), 4.38 (br, 2 H), 6.72 (d, J=8.8 Hz, 1H), 7.19 (d, J=7.3 Hz, 2 H), 7.24 (m, 1 H), 7.33 (m, 1 H), 7.51 (d, J=8.8 Hz, 1 H), 7.66 (s, 1 H), 7.96 (s, 1 H), 8.02 (s, 1 H).

Example 50

Synthesis of 7-(2-chloro-5-methoxy-phenyl)-5-methyl-benzo[1,2,4]triazin-3-ylamine

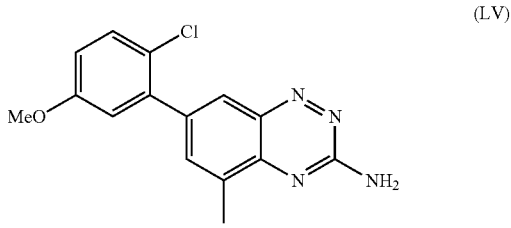 [SMILES: COc1ccc(Cl)c(-c2cc(C)c3nc(N)nnc3c2)c1]

(LV)

7-bromo-5-methyl-benzo[1,2,4]triazin-3-ylamine (33.47 mmol, 1.0 equiv), 1-chloro-4-methoxy-2-boronic acid (50.21 mmol, 1.5 equiv), Pd(PPH$_3$)$_4$ (3.347 mmol, 0.1 equiv), and Na$_2$CO$_3$ (133.9 mmol, 4.0 equiv) dissolved in DME/EtOH/water 6:1:1 and refluxed at 100° C. under an argon blanket for 4 h. The reaction was cooled to room temperature and diluted with 100 mL DCM and filtered. Precipitate recovered was suspended in water, filtered and rinsed with ether. Precipitate afforded product: 7-(2-chloro-5-methoxy-phenyl)-5-methyl-benzo[1,2,4]triazin-3-ylamine, a green solid (8.37 g, 84% yield). R$_f$=0.85 (9:1 DCM/MeOH). $^1$H NMR (DMSO-d$_6$): δ 3.35 (s, 6H), 7.01 (dd, J=8.8 Hz, J=3.0, 1H), 7.09 (d, J=3.0 Hz, 1H), 7.48 (d, J=8.8 Hz, 1H), 7.75 (bm, 2H). MS (ES+) m/z=303. LC retention time 3.03 min.

Example 51

Synthesis of 3-bromo-N-(2-dimethylamino-ethyl)-benzenesulfonamide

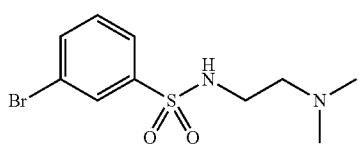

(LVI)

3-bromobenzoyl chloride (4.56 mmol, 1.0 equiv) and N,N-dimethylethylenediamine (9.11 mmol, 2.0 equiv) dissolved in 20 mL of anhydrous DCM and placed under an argon atmosphere. Et$_3$N (22.8 mmol, 5.0 equiv) added to solution mixture via syringe and stirred at room temperature for 18 h. EtOAc added to mixture and the organics were washed with saturated NaHCO$_3$ and brine, dried (Na$_2$SO$_4$) and concentrated under reduced pressure to give 3-bromo-N-(2-dimethylamino-ethyl)-benzenesulfonamide, a pale yellow oil (1.20 g, 86% yield). Material used as was in the next reaction. $^1$H NMR (DMSO-d$_6$): δ 2.17 (s, 6H), 2.40 (t, J=6.8 Hz, 2H), 3.35 (q, J=6.7 Hz, 2H), 7.42 (t, J=7.9 Hz, 1H), 7.70 (d, J=7.9

Hz, 1H), 7.84 (d, J=7.8 Hz, 1H), 8.01 (s, 1H), 8.53 (t, J=2.3 Hz, 1H). MS (ES+): m/z=227 (m-Br) LC retention time 1.54 min.

Example 52

Synthesis of 3-[7-(2-chloro-5-methoxy-phenyl)-5-methyl-benzo[1,2,4]triazin-3-ylamino]-N-(2-dimethylamino-ethyl)-benzenesulfonamide

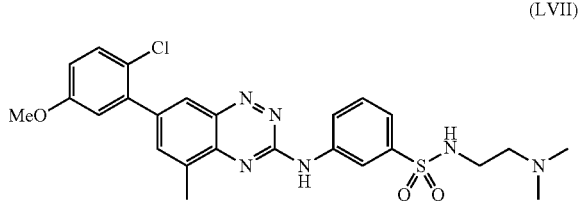 [SMILES: COc1ccc(Cl)c(-c2cc(C)c3nc(Nc4cccc(S(=O)(=O)NCCN(C)C)c4)nnc3c2)c1]

(LVII)

7-(2-chloro-5-methoxy-phenyl)-5-methyl-benzo[1,2,4]triazin-3-ylamine (0.333 mmol, 1.0 equiv), 3-bromo-N-(2-dimethylamino-ethyl)-benzenesulfonamide (0.499 mmol, 1.5 equiv), $Cs_2CO_3$ (0.999 mmol, 3.0 equiv), $Pd_2(dba)_3$ (0.0333 mmol, 0.1 equiv), and Xantphos (0.0666 mmol, 0.2 equiv) were dissolved in 7 mL dioxane. The reaction was placed under an argon atmosphere and refluxed at 100° C. for 18 h. The organics were filtered to remove excess inorganics, dissolved in EtOAc, washed with saturated $NaHCO_3$ and brine, dried over $Na_2SO_4$ and concentrated under reduced pressure to give 3-[7-(2-chloro-5-methoxy-phenyl)-5-methyl-benzo[1,2,4]triazin-3-ylamino]-N-(2-dimethylamino-ethyl)-benzenesulfonamide, which was precipitated using EtOAc/hexanes (1:5 v/v) to give a dark orange solid (168.4 mg, 96% yield). $R_f$=0.50 MS (ES+) m/z=527.

Example 53

Synthesis of 3-[7-(2-chloro-5-hydroxy-phenyl)-5-methyl-benzo[1,2,4]triazin-3-ylamino]-N-(2-dimethylamino-ethyl)-benzenesulfonamide

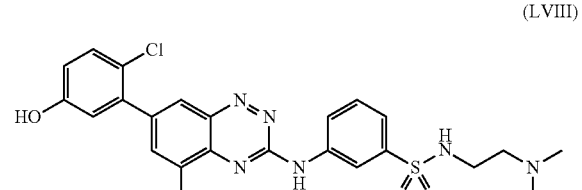

(LVIII)

3-[7-(2-chloro-5-methoxy-phenyl)-5-methyl-benzo[1,2,4]triazin-3-ylamino]-N-(2-dimethylamino-ethyl)-benzenesulfonamide (0.32 mmol, 1.0 equiv) was dissolved in 10 mL of anhydrous DCM and placed under an argon atmosphere. 4 mL of $BBr_3$ (0.1 M) added via syringe and the reaction stirred at room temperature for 2 h. $BBr_3$ was quenched with saturated $NaHCO_3$ until pH=7. The mixture was filtered and washed with water and $Et_2O$ to give 3-[7-(2-chloro-5-hydroxy-phenyl)-5-methyl-benzo[1,2,4]triazin-3-ylamino]-N-(2-dimethylamino-ethyl)-benzenesulfonamide, as an orange solid (132.2 mg, 81% yield). $^1$H NMR (DMSO-$d_6$): δ 2.71 (s, 2H), 3.01 (bs, 2H), 6.87 (dd, J=8.8 Hz, J=2.9 Hz, 1H), 6.94 (d, J=3.0 Hz, 1H), 7.41 (d, J=8.8 Hz, 1H), 7.51 (d, J=7.9 Hz, 1H), 7.64 (t, J=8.1 Hz, 2H), 7.90 (s, 1H), 8.06 (d, J=6.7 Hz, 1H), 8.20 (s, 1H), 8.89 (s, 1H), 9.93 (s, 1H), 11.34 (s, 1H). MS (ES+) m/z=513. LC retention time 2.24 min.

Example 54

Synthesis of 4-[7-(2-chloro-5-methoxy-phenyl)-5-methyl-benzo[1,2,4]triazin-3-ylamino]-N-methyl-N-(2-pyrrolidin-1-yl-ethyl)-benzenesulfonamide

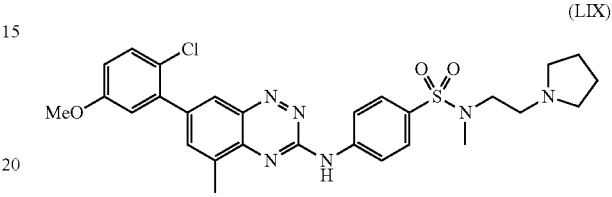

(LIX)

7-(2-chloro-5-methoxy-phenyl)-5-methyl-benzo[1,2,4]triazin-3-ylamine (0.33 mmol, 1.0 equiv), 4-bromo-N-methyl-N-(2-pyrrolidin-1-yl-ethyl)-benzenesulfonamide (0.5 mmol, 1.5 equiv), $Cs_2CO_3$ (0.99 mmol, 3.0 equiv), $Pd_2(dba)_3$ (0.033 mmol, 0.10 equiv.), and Xantphos (0.066 mmol, 0.2 equiv) were dissolved in 10 mL dioxane and refluxed at 100° C. under an argon atmosphere for 18 h. The reaction was cooled to room temperature and filtered. The filtrate was dissolved in EtOAc and washed with saturated $NaHCO_3$ and brine, and the organic phase was dried ($Na_2SO_4$). The organics were concentrated under reduced pressure to afford residue that was purified by reverse phase HPLC using a 10-50-75 gradient over 30 minutes, and again concentrated under reduced pressure to afford 4-[7-(2-chloro-5-methoxy-phenyl)-5-methyl-benzo[1,2,4]triazin-3-ylamino]-N-methyl-N-(2-pyrrolidin-1-yl-ethyl)-benzenesulfonamide, as a tan residue (168 mg, 90% yield). $R_f$=0.50 (9:1 DCM/MeOH) MS (ES+) m/z=567. LC retention time 2.82 min.

Example 55

Synthesis of 4-[7-(2-chloro-5-hydroxy-phenyl)-5-methyl-benzo[1,2,4]triazin-3-ylamino]-N-methyl-N-(2-pyrrolidin-1-yl-ethyl)-benzenesulfonamide

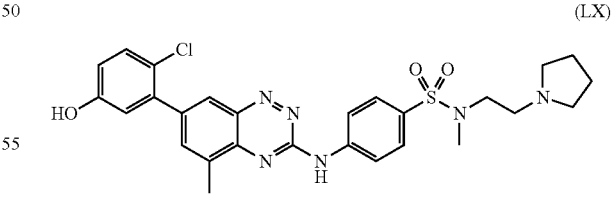

(LX)

4-[7-(2-chloro-5-methoxy-phenyl)-5-methyl-benzo[1,2,4]triazin-3-ylamino]-N-methyl-N-(2-pyrrolidin-1-yl-ethyl)-benzenesulfonamide (0.297 mmol, 1.0 equiv) was dissolved in 10 mL anhydrous DCM and placed under an argon atmosphere. 4 mL of $BBr_3$ (0.1 M) was added via syringe and the reaction was stirred at room temperature for 2 h. $BBr_3$ was quenched with saturated $NaHCO_3$ until pH=7. The mixture was filtered and washed with water and $Et_2O$ to give 4-[7-(2-chloro-5-hydroxy-phenyl)-5-methyl-benzo[1,2,4]triazin-3- ylamino]-N-methyl-N-(2-pyrrolidin-1-yl-ethyl)-benzene-sulfonamide, as a dark green solid (120.5 mg, 74% yield). $R_f$=0.61 $^1$H NMR (DMSO-d$_6$): δ 1.90 (m, 2H), 2.01 (m, 2H), 2.72 (s, 6H), 3.06 (m, 2H), 3.30 (t, J=5.6 Hz, 2H), 3.38 (t, J=6.0 Hz, 2H), 3.59 (m, 2H), 6.89 (dd, J=8.8 Hz, J=2.9 Hz, 1H), 6.96 (d, J=2.9 Hz, 1H), 7.40 (d, J=8.6 Hz, 1H), 7.87 (d, J=8.9 Hz, 2H), 7.92 (d, J=0.9 Hz, 1H), 8.21 (d, J=1.7 Hz, 1H), 8.30 (d, J=9.0 Hz, H), 11.50 (s, 1H). MS (ES+) m/z=553 LC retention time 2.41 min. Elemental for $C_{27}H_{30}Cl_2N_6O_3S$ 5H$_2$O Calculated: C, 47.72; H, 5.93; N, 11.37. Found: C, 46.59; H, 5.67; N, 11.42.

Example 56

Synthesis of [7-(2-chloro-5-methoxy-phenyl)-6-methyl-benzo[1,2,4]triazin-3-yl]-[4-(2-pyrrolidin-1-yl-ethoxy)-phenyl]-amine

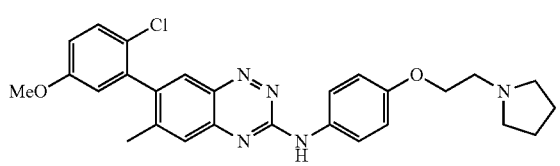

(LXI)

7-(2-chloro-5-methoxy-phenyl)-6-methyl-benzo[1,2,4]triazin-3-ylamine (0.67 mmol, 1.0 equiv), 1-[2-(4-bromophenoxy)-ethyl]pyrrolidine (0.005 mmol, 1.5 equiv), Cs$_2$CO$_3$ (2.01 mmol, 3.0 equiv), Pd$_2$(dba)$_3$ (0.067 mmol, 0.1 equiv), and Xantphos (0.134 mmol, 0.2 equiv) were dissolved in 20 mL dioxane, placed under an argon atmosphere and refluxed at 100° C. for 18 h. The reaction was cooled to room temperature and filtered. The filtrate was dissolved in EtOAc, washed with saturated NaHCO$_3$ and brine and organic phase was dried (Na$_2$SO$_4$). The organics were concentrated under reduced pressure to afford residue that was precipitated out using EtOAc/hexanes (1:5 v/v) to give [7-(2-chloro-5-methoxy-phenyl)-6-methyl-benzo[1,2,4]triazin-3-yl]-[4-(2-pyrrolidin-1-yl-ethoxy)-phenyl]-amine, as an orange solid (271.2 mg, 83% yield). $R_f$=0.56 (9:1 DCM/MeOH). MS (ES+) m/z=491. LC retention time 2.72 min.

Example 57

Synthesis of 4-chloro-3-{6-methyl-3-[4-(2-pyrrolidin-1-yl-ethoxy)-phenylamino]-benzo[1,2,4]triazin-7-yl}-phenol

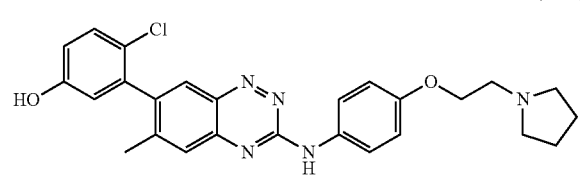

(LXII)

[7-(2-chloro-5-methoxy-phenyl)-6-methyl-benzo[1,2,4]triazin-3-yl]-[4-(2-pyrrolidin-1-yl-ethoxy)-phenyl]-amine (0.553 mmol, 1.0 equiv) was dissolved in 10 mL anhydrous DCM and stirred under an argon atmosphere. 6 mL of BBr$_3$ (0.1 M) was added via syringe and the reaction was stirred at room temperature for 2 h. BBr$_3$ was quenched with saturated NaHCO$_3$ until pH=7. The mixture was filtered and washed with water and Et$_2$O to give 4-chloro-3-{6-methyl-3-[4-(2-pyrrolidin-1-yl-ethoxy)-phenylamino]-benzo[1,2,4]triazin-7-yl}-phenol, as a dark green solid (245.2 mg 93% yield). $R_f$=0.65 (9:1 DCM/MeOH) $^1$H NMR (DMSO-d$_6$): δ 1.69 (m, 4H), 2.24 (s, 3H), 2.54 (m, 4H), 2.79 (t, J=5.9 Hz, 2H), 4.07 (t, J=5.9 Hz, 2H), 6.78 (d, J=2.9 Hz, 1H), 6.87 (dd, J=8.8 Hz, J=2.9 Hz, 1H), 6.95 (d, J=11.9 Hz, 2H), 7.38 (dd, J=8.8 Hz, J=3.6 Hz, 1H), 7.65 (s, 1H), 7.85 (s, J=9.1 Hz, 2H), 7.98 (s, 1H), 9.93 (s, 1H), 10.67 (s, 1H). MS (ES+): m/z=476. LC retention time 2.32 min.

Example 58

Synthesis of 7-(2-chloro-5-methoxy-phenyl)-5-methyl-benzo[1,2,4]triazin-3-ylamine

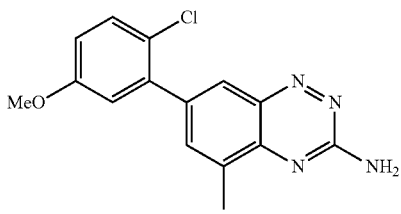

(LXIII)

7-bromo-5-methyl-benzo[1,2,4]triazin-3-ylamine (33.47 mmol, 1.0 equiv), 1-chloro-4-methoxy-2-boronic acid (50.21 mmol, 1.5 equiv), Pd(PPH$_3$)$_4$ (3.347 mmol, 0.1 equiv), and Na$_2$CO$_3$ (133.9 mmol, 4.0 equiv) were dissolved in DME/EtOH/water 6:1:1 and refluxed at 100° C. under an argon blanket for 4 h. The reaction was cooled to room temperature, diluted with 100 mL DCM and filtered. The precipitate that was recovered was suspended in water, filtered and rinsed with ether. The precipitate afforded 7-(2-chloro-5-methoxy-phenyl)-5-methyl-benzo[1,2,4]triazin-3-ylamine, as a green solid (8.37 g, 84% yield). $R_f$=0.85 (9:1 DCM/MeOH). $^1$H NMR (DMSO-d$_6$): δ 3.35 (s, 6H), 7.01 (dd, J=8.8 Hz, J=3.0, 1H), 7.09 (d, J=3.0 Hz, 1H), 7.48 (d, J=8.8 Hz, 1H), 7.75 (bm, 2H). MS (ES+) m/z=303. LC retention time 3.03 min.

Example 59

Synthesis of 1-(3-bromo-benzenesulfonyl)-4-methyl-piperazine

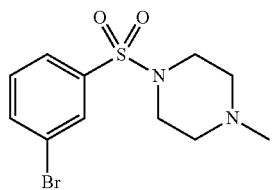

(LXIV)

3-bromo-benzenesulfonyl chloride (3.914 mmol, 1.0 equiv) and 1-methyl-piperazine (7.83 mmol, 2.0 equiv) were dissolved in 15 mL DCM. Et$_3$N (15.66 mmol, 4.0 equiv) was added via syringe to the reaction and stirred at room temperature for 2 h. The reaction was diluted with DCM, the organic phase was extracted with saturated NaHCO$_3$ and brine and dried (Na$_2$SO$_4$). The organics were removed under reduced pressure to give 1-(3-bromo-benzenesulfonyl)-4-methyl-piperazine, as a white solid (1.1 g. 88% yield). $^1$H NMR (DMSO-d$_6$): δ 2.14 (s, 3H), 2.35 (m, 4H), 2.92 (m, 4H), 7.62 (t, J=7.9 Hz, 2H0, 7.55 (dd, J=7.9 Hz, J=0.8 Hz, 1H), 7.85 (t, J=1.8 Hz, 1H), 7.95 (dd, J=9.1 Hz, J=0.9 Hz, 1H) MS (ES+) m/z=321 LC retention time 1.74 min.

Example 60

Synthesis of [7-(2-chloro-5-methoxy-phenyl)-5-methyl-benzo[1,2,4]triazin-3-yl]-[3-(4-methyl-piperazine-1-sulfonyl)-phenyl]-amine

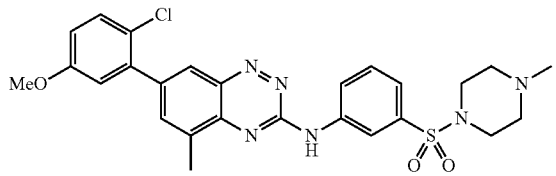

(LXV)

7-(2-chloro-5-methoxy-phenyl)-5-methyl-benzo[1,2,4]triazin-3-ylamine (0.315 mmol, 1.0 equiv), 1-(3-bromo-benzenesulfonyl)-4-methyl-piperazine (0.472 mmol, 1.5 equiv), Pd$_2$(dba)$_3$ (0.0315 mmol, 0.1 equiv), Cs$_2$CO$_3$ (0.945 mmol, 3.0 equiv), and Xantphos (0.063 mmol, 0.2 equiv) were dissolved in 10 mL of dioxane, purged of air and placed under an argon atmosphere to reflux at 100° C. for 18 h. The reaction was cooled to room temperature and filtered to remove excess Cs$_2$CO$_3$. The filtrate was extracted with EtOAc and washed with saturated NaHCO$_3$ and brine, and the organics were dried (Na$_2$SO$_4$). The organics were removed under reduced pressure to afford brown residue which was precipitated using DCM/Et$_2$O (1:5 v/v) to give [7-(2-chloro-5-methoxy-phenyl)-5-methyl-benzo[1,2,4]triazin-3-yl]-[3-(4-methyl-piperazine-1-sulfonyl)-phenyl]-amine, as a yellow solid (45 mg, 27% yield). $^1$H NMR (DMSO-d$_6$): δ 2.12 (s, 3H), 2.37 (m, 4H), 2.71 (s, 3H), 2.95 (m, 4H), 3.83 (s, 3H), 7.06 (dd, J=8.9 Hz, J=3.1 Hz, 1H), 7.14 (d, J=3.1 Hz, 1H), 7.41 (dd, J=6.3 Hz, J=1.1 Hz, 1H), 7.54 (d, J=8.7 Hz, 1H), 7.67 (t, J=8.1 Hz, 2H), 8.06 (dd, J=7.6 Hz, J=1.6 Hz, 1H), 8.27 (d, J=1.9 Hz, 1H), 8.9 (bs, 1H). MS (ES+): m/z=540 LC retention time 2.70 min.

Example 61

Synthesis of 4-chloro-3-{5-methyl-3-[3-(4-methyl-piperazine-1-sulfonyl)-phenylamino]-benzo[1,2,4]triazin-7-yl}-phenol

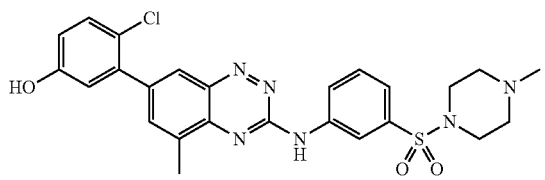

(LXVI)

[7-(2-chloro-5-methoxy-phenyl)-5-methyl-benzo[1,2,4]triazin-3-yl]-[3-(4-methyl-piperazine-1-sulfonyl)-phenyl]-amine (0.0742 mmol, 1.0 equiv) was dissolved in 5 ml, anhydrous DCM and placed under an argon atmosphere. 200 mL of BBr$_3$ (0.1 M) was added via syringe to the amine solution and stirred at room temperature for 2 h. BBr$_3$ was quenched with saturated NaHCO$_3$ until pH was adjusted to 7. The mixture was filtered and rinsed with water and Et$_2$O to give 4-chloro-3-{5-methyl-3-[3-(4-methyl-piperazine-1-sulfonyl)-phenylamino]-benzo[1,2,4]triazin-7-yl}-phenol, as a tan solid (24.3 mg, 62% yield). $^1$H NMR (DMSO-d$_6$): δ 2.71 (s, 6H), 2.72 (bs, 2H), 3.16 (m, 2H), 3.46 (m, 2H), 3.78 (m, 2H), 6.88 (dd, J=8.8 Hz, J=2.9 Hz, 1H), 6.95 (d, J=2.9 Hz, 1H), 7.41 (d, J=8.7 Hz, 1H), 7.45 (dd, J=7.9 Hz, J=1.7 Hz, 1H), 7.72 (t, J=8.1 Hz, 2H), 7.91 (d, J=1.7 Hz, 1H), 8.12 (dd, J=8.3 Hz, J=1.7 Hz, 1H), 8.21 (d, J=1.9 Hz, 1H), 8.93 (d, J=1.9 Hz, 1H), 9.99 (s, 1H), 11.46 (s, 1H). MS (ES+): m/z=526. Elemental for C$_{25}$H$_{36}$Cl$_2$N$_6$O$_8$S 5H$_2$O Calculated: C, 46.08; H, 5.57; N, 12.90. Found: C, 46.84; H, 5.04; N, 12.66.

Example 62

Synthesis of 7-(2-chloro-5-nitro-phenyl)-5-methyl-benzo[1,2,4]triazin-3-ylamine

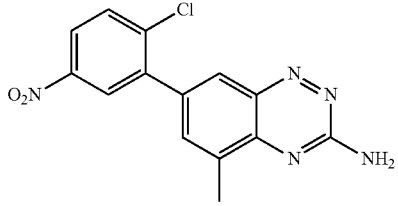

(LXVII)

7-bromo-5-methyl-benzo[1,2,4]triazin-3-ylamine (3.35 mmol, 1.0 equiv), 2-chloro-5-nitrophenyl-boronic acid (5.02 mmol, 1.5 equiv), Pd(PPh$_3$)$_4$ (0.335 mmol, 0.1 equiv), and Na$_2$CO$_3$ (13.4 mmol, 4.0 equiv) were dissolved in a mixture of DME/EtOH/H2O (4:1:1 v/v/v) and refluxed at 100° C. for 18 h. The reaction was diluted with 50 mL DCM and filtered. The precipitate was suspended in water to remove excess Na$_2$CO$_3$ and filtered again with a final Et$_2$O wash to remove water. The crude precipitate gave 7-(2-chloro-5-nitro-phenyl)-5-methyl-benzo[1,2,4]triazin-3-ylamine, as a dark green solid (1.0 g, 94% yield). R$_f$=0.55 MS (ES+) m/z=316 LC retention time 2.96 min.

Example 63

Synthesis of 4-[7-(2-chloro-5-nitro-phenyl)-5-methyl-benzo[1,2,4]triazin-3-ylamino]-N-(2-pyrrolidin-1-yl-ethyl)-benzenesulfonamide

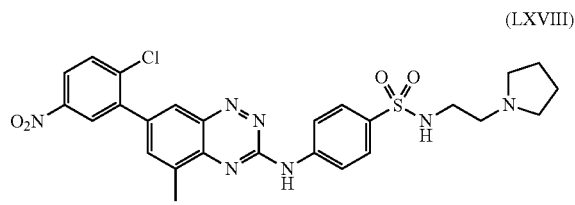 [SMILES: Cc1cc(-c2cc([N+](=O)[O-])ccc2Cl)cc2nnc(Nc3ccc(S(=O)(=O)NCCN4CCCC4)cc3)nc12]

(LXVIII)

7-(2-chloro-5-nitro-phenyl)-5-methyl-benzo[1,2,4]triazin-3-ylamine (0.65 mmol, 1.0 equiv), 4-bromo-N-(2-pyrrolidin-1-yl-ethyl)-benzenesulfonamide (0.95 mmol, 1.5 equiv), Xantphos (0.065 mmol, 0.10 equiv), Pd(OAc)$_2$ (0.033 mmol, 0.05 equiv), and potassium-t-butoxide (1.3 mmol, 2.0 equiv) were dissolved in 45 mL of dioxane and placed under an argon atmosphere. The reaction mixture was refluxed at 100° C. for 18 h and then cooled to room temperature. Inorganic salts were filtered out of solution and the organics were concentrated under reduced pressure. The residue was precipitated using EtOAC/hexanes (1:5 v/v) to afford 4-[7-(2-chloro-5-nitro-phenyl)-5-methyl-benzo[1,2,4]triazin-3-ylamino]-N-(2-pyrrolidin-1-yl-ethyl)-benzenesulfonamide, as a red solid (232 mg, 63% yield). R$_f$=0.42 MS (ES+) m/z=570. LC retention time 2.56 min.

Example 64

Synthesis of 4-[7-(5-amino-2-chloro-phenyl)-5-methyl-benzo[1,2,4]triazin-3-ylamino]-N-(2-pyrrolidin-1-yl-ethyl)-benzenesulfonamide

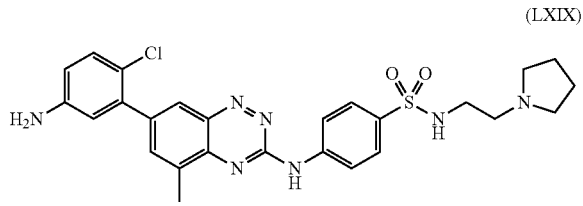 [SMILES: Cc1cc(-c2cc(N)ccc2Cl)cc2nnc(Nc3ccc(S(=O)(=O)NCCN4CCCC4)cc3)nc12]

(LXIX)

4-[7-(2-chloro-5-nitro-phenyl)-5-methyl-benzo[1,2,4]triazin-3-ylamino]-N-(2-pyrrolidin-1-yl-ethyl)-benzenesulfonamide (0.41 mmol, 1.0 equiv) was dissolved in 20 mL of MeOH, and the reaction was evacuated of air by vacuum and placed under a blanket of argon. Pd/C (10% by wt) was added to the reaction, followed by another evacuation of argon, and by blanketing with hydrogen. The reaction was stirred under hydrogen blanket for 4 h, filtered through Celite, and concentrated by reduced pressure to give a crude residue, which was precipitated using EtOAc/hexanes (1:5 v/v) to give 4-[7-(5-amino-2-chloro-phenyl)-5-methyl-benzo[1,2,4]triazin-3-ylamino]-N-(2-pyrrolidin-1-yl-ethyl)-benzenesulfonamide, as a dark green solid (89.4 mg, 41% yield). $^1$H NMR (DMSO-d$_6$): δ 1.61 (m, 4H), 2.34 (m, 4H), 2.42 (t, J=6.9 Hz, 2H), 2.71 (s, 3H), 2.85 (t, J=7.1 Hz, 2H), 5.43 (s, 1H), 6.65 (dd, J=8.7 Hz, J=2.8 Hz, 1H), 6.73 (d, J=2.7 Hz, 1H), 7.21 (d, J=8.7 Hz, 1H), 7.83 (d, J=8.9 Hz, 2H), 7.89 (s, 1H), 8.15 (s, 1H), 8.21 (d, J=8.8 Hz, 2H). MS (ES+) m/z=538, LC retention time 2.13 min.

Example 65

Synthesis of {4-[7-(2,6-dichloro-phenyl)-5-methyl-benzo[1,2,4]triazin-3-ylamino]-phenyl}-piperazin-1-yl-methanone

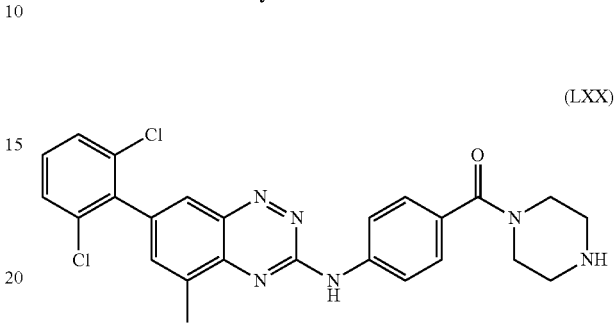

(LXX)

4-(4-bromo-benzoyl)-piperazine-1-carboxylic acid tert-butyl ester (1.5 equiv, 0.49 mmol), 7-(2,6-dichloro-phenyl)-5-methyl-benzo[1,2,4]triazin-3-ylamine (1.0 equiv, 0.33 mmol), Xantphos (0.1 equiv, 0.123 mmol), palladium acetate (0.05 equiv, 0.0165 mmol), and Potassium-t-butoxide (2.0 equiv, 0.66 mmol) were dissolved in 10 mL of dioxane, purged of air and placed under an argon blanket before refluxing at 100° C. for 18 h. The reaction was cooled to room temperature and filtered before extracting with EtOAc and washing with saturated bicarbonate and brine, followed by drying over Na$_2$SO$_4$. The organics were condensed under reduced pressure to give brown oil that was precipitated out using EtOAc/hexanes (1:5 v/v) to afford brown/tan precipitate. BOC protecting group was removed with 30% TFA/DCM (v/v) stirring at room temperature for 1 h.

The product was concentrated, then suspended in DCM, extracted with saturated bicarbonate and brine, dried over Na$_2$SO$_4$, and condensed again to afford {4-[7-(2,6-dichloro-phenyl)-5-methyl-benzo[1,2,4]triazin-3-ylamino]-phenyl}-piperazin-1-yl-methanone, as an orange solid (26.7 mg, 34% yield). $^1$H NMR (DMSO-d$_6$): δ 2.69 (s, 3H), 3.19 (bt, J=4.85 Hz, 4H), 3.74 (bs, 4H), 7.52 (d, J=8.05 Hz, 2H), 7.56 (d, J=8.75 Hz, 1H), 7.67 (d, J=8.2 Hz, 2H), 7.76 (s, 1H), 8.13 (d, J=14.4 Hz, 2H), 8.15 (s, 1H), 11.25 (s, 1H). MS (ES+) m/z=492, LC retention time 2.45 minutes.

Example 66

Synthesis of 4-[7-(2,6-dichloro-phenyl)-5-methyl-benzo[1,2,4]triazin-3-ylamino]-N-methyl-N-(2-pyrrolidin-1-yl-ethyl)-benzenesulfonamide

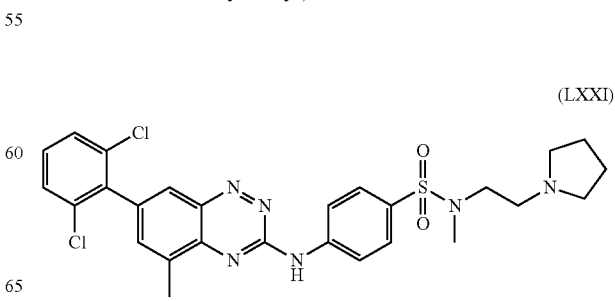

(LXXI)

4-bromo-N-methyl-N-(2-pyrrolidin-1-yl-ethyl)-benzene-sulfonamide (1.0 equiv, 0.82 mmol), 7-(2,6-dichloro-phenyl)-5-methyl-benzo[1,2,4]triazin-3-ylamine (1.5 equiv, 1.23 mmol), Cs$_2$CO$_3$ (3.0 equiv, 2.46 mmol), Pd$_2$(dba)$_3$ (0.1 equiv, 0.082 mmol), and Xantphos (0.2 equiv, 0.1634 mmol) were dissolved in 15 mL dioxane and purged of air, then placed under an argon blanket and refluxed for 18 h at 100° C. The reaction was cooled to room temperature and filtered and condensed under reduced pressure. The residue that was recovered was dissolved in EtOAc and extracted with saturated bicarbonate and brine; the organics were then dried (Na$_2$SO$_4$) and concentrated to afford brown oil. Using EtOAc/hexanes (1:5 v/v) the residue was precipitated out to afford 4-[7-(2,6-dichloro-phenyl)-5-methyl-benzo[1,2,4]triazin-3-ylamino]-N-methyl-N-(2-pyrrolidin-1-yl-ethyl)-benzenesulfonamide, as a tan solid, (297.2 mg, 76% yield). $^1$H NMR (DMSO-d$_6$): δ 1.95 (dm, 4H), 2.72 (s, 3H), 2.73 (s, 3H), 3.04 (q, J=7.5 Hz, 2H), 3.35 (dt, J=5.3 Hz, J=5.4 Hz, 4H), 3.58 (q, J=5.2 Hz, 2H), 7.52 (t, J=7.6 Hz, 1H), 7.67 (d, J=3.2 Hz, 2H), 7.79 (s, 1H), 7.87 (d, J=3.2 Hz, 2H), 8.18 (s, 1H), 8.31 (s, J=9.0 Hz, 2H), 10.51 (bs, 1H), 11.55 (s, 1H). MS (ES+) m/z=574, LC retention time 2.80 minutes.

Example 67

Synthesis of [7-(2-chloro-5-methoxy-phenyl)-5-methyl-benzo[1,2,4]triazin-3-yl]-[4-(4-methyl-piperazine-1-sulfonyl)-phenyl]-amine

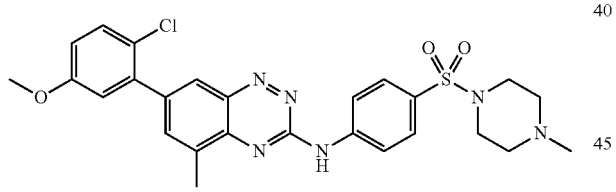

(LXXII)

7-(2-chloro-5-methoxy-phenyl)-5-methyl-benzo[1,2,4]triazin-3-ylamine (1.0 equiv., 0.75 mmol), 1-(4-bromo-benzenesulfonyl)-4-methyl-piperazine (1.5 equiv., 1.125 mmol), Xantphos (0.1 equiv., 0.074 mmol), palladium acetate (0.05 equiv., 0.0375 mmol), and potassium-tert-butoxide (2.0 equiv, 1.5 mmol) were dissolved in 20 mL of dioxane and bubbled with argon. The reaction was stirred in an oil bath at 100° C. for 18 h under an argon blanket. The reaction was cooled to room temperature and filtered to remove inorganics, concentrated under reduced pressure, then brought up in EtOAc and extracted using saturated NaHCO$_3$ and brine. The organics were dried over Na$_2$SO$_4$ and concentrated under reduced pressure then precipitated using EtOAc/Hexanes (1:5 v/v) to afford brown solid (182.3 mg, 45% yield). MS (ES+): m/z=540 LC retention time: 2.67 min.

Example 68

Synthesis of 4-chloro-3-{5-methyl-3-[4-(4-methyl-piperazine-1-sulfonyl)-phenylamino]-benzo[1,2,4]triazin-7-yl}-phenol

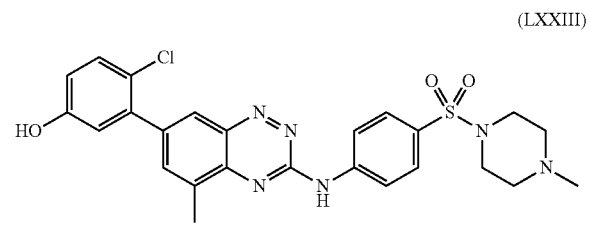 [SMILES: Cc1cc(-c2cc(O)ccc2Cl)cc2nnc(Nc3ccc(S(=O)(=O)N4CCN(C)CC4)cc3)nc12]

(LXXIII)

[7-(2-chloro-5-methoxy-phenyl)-5-methyl-benzo[1,2,4]triazin-3-yl]-[4-(4-methyl-piperazine-1-sulfonyl)-phenyl]-amine (1.0 equiv., 0.339 mmol) was dissolved in 10 mL anhydrous DCM, purged of air via house vacuum, then blanketed with argon. Neat BBr$_3$ (4.0 equiv., 1.355 mmol) was added via syringe dropwise and allowed to stir at room temperature for 2 h. The reaction was quenched with saturated NaHCO$_3$; the precipitate was filtered and rinsed with Et$_2$O to afford crude orange solid. The compound was purified by prep. HPLC using 10-50-75 gradient, collecting peaks for 9-14 minutes. A yellow solid was recovered (70.5 mg, 40% yield). $^1$H NMR (DMSO-d$_6$): δ 1.98 (s, 3H), 2.37 (bs, 4H), 2.72 (s, 3H), 2.90 (bs, 4H), 6.88 (dd, J=2.94 Hz, 8.81 Hz, 1H), 6.95 (d, J=2.92 Hz, 1H), 7.41 (d, J=8.79 Hz, 1H), 7.78 (d, J=8.89 Hz, 2H), 7.92 (m, 1H), 8.21 (d, J=1.35 Hz, 1H), 8.28 (d, J=8.88 Hz, 2H), 11.47 (s, 1H). MS (ES+): m/z=526 LC retention time: 2.30 minutes.

Example 69

Synthesis of 1-[2-(3-bromo-phenylsulfanyl)-ethyl]-pyrrolidine

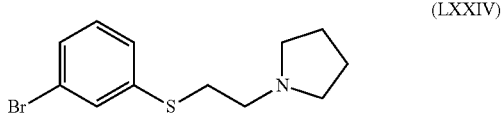 [SMILES: Brc1cccc(SCCN2CCCC2)c1]

(LXXIV)

1-(2-chloroethyl)pyrrolidine hydrochloride (1.0 equiv., 8.82 mmol) and 3-bromothiophenol (1.5 equiv., 13.23 mmol) were dissolved in acetonitrile (100 mL). Potassium carbonate (10.0 equiv., 88.2 mmol) was added to the reaction while stirring. The reaction was kept in oil bath at 80° C. to reflux for 18 h. The reaction was then cooled to room temperature and filtered to remove excess inorganics, and the organics were extracted with saturated NaHCO$_3$ and brine. The organics were dried over Na$_2$SO$_4$ then concentrated under reduced pressure. The resulting crude oil was purified by flash chromatography using 4:6 EtOAc/hexanes. The fractions were concentrated to afford product as a yellow oil (792.3 mg, 32% yield). $R_f$=0.75 MS (ES+): m/z=287 LC retention time: 1.81 min.

Example 70

Synthesis of [7-(2-chloro-5-methoxy-phenyl)-5-methyl-benzo[1,2,4]triazin-3-yl]-[3-(2-pyrrolidin-1-yl-ethylsulfanyl)-phenyl]-amine

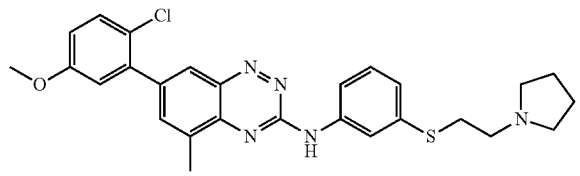

(LXXV)

7-(2-chloro-5-methoxy-phenyl)-5-methyl-benzo[1,2,4] triazin-3-ylamine (1.0 equiv., 083 mmol), 1-[2-(3-bromo-phenylsulfanyl)-ethyl]-pyrrolidine (1.5 equiv., 1.25 mmol), Xantphos (0.1 equiv., 0.084 mmol), palladium acetate (0.05 equiv., 0.042 mmol), and potassium-tert-butoxide (2.0 equiv., 1.66 mmol) were dissolved in 10 mL of dioxane, and argon was bubbled through the solution. The reaction was run under an argon blanket while refluxing at 100° C. for 18 h. The reaction was then cooled to room temperature, filtered to remove inorganics, extracted using EtOAc with saturated NaHCO$_3$ and brine, dried over Na$_2$SO$_4$, and concentrated under reduced pressure. A crude material was precipitated using 1:5 (v/v) EtOAc/hexanes to afford a bright orange solid (311.8 mg, 74% yield). $R_f$=0.48.

Example 71

Synthesis of 4-chloro-3-{5-methyl-3-[3-(2-pyrrolidin-1-yl-ethylsulfanyl)-phenylamino]-benzo[1,2,4]triazin-7-yl}-phenol

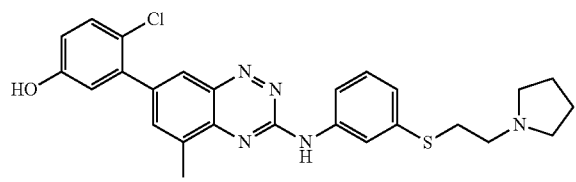

(LXXVI)

[7-(2-chloro-5-methoxy-phenyl)-5-methyl-benzo[1,2,4] triazin-3-yl]-[3-(2-pyrrolidin-1-yl-ethylsulfanyl)-phenyl]-amine (1.0 equiv., 0.62 mmol) was dissolved in anhydrous DCM, purged of air using house vacuum, and placed under an argon blanket. Neat BBr$_3$ (4.0 equiv., 2.5 mmol) was then added via syringe and allowed to stir at room temperature for 2 h. The reaction was quenched using saturated NaHCO$_3$; the precipitate was filtered and washed with water and Et$_2$O to afford a dark orange/brown solid. The compound was purified by flash chromatography using 90:10 DCM/MeOH to recover a burnt orange solid (64.6 mg, 22% yield). $R_f$=0.32 $^1$H NMR (DMSO-d$_6$): δ 1.68 (bs, 4H), 2.68 (s, 3H), 2.73 (bs, 2H), 3.14 (t, J=6.87 Hz, 2H), 6.87 (d, J=8.10 Hz, 1H), 6.93 (s, 1H), 3.03 (d, J=7.42 Hz, 1H), 7.34 (t, J=7.58 Hz, 1H), 7.40 (d, J=8.65 Hz, 1H), 7.77 (d, J=7.95 Hz, 1H), 8.16 (s, 2H), 9.93 (s, 1H), 11.01 (s, 1H). MS (ES+): m/z=493

Example 72

Synthesis of 4-[7-(2-chloro-5-methoxy-phenyl)-6-methyl-benzo[1,2,4]triazin-3-ylamino]-N-methyl-N-(2-pyrrolidin-1-yl-ethyl)-benzenesulfonamide

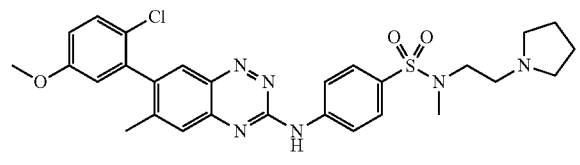

(LXXVII)

7-(2-chloro-5-methoxy-phenyl)-6-methyl-benzo[1,2,4] triazin-3-ylamine (1.0 equiv., 0.28 mmol), 4-bromo-N-methyl-N-(2-pyrrolidin-1-yl-ethyl)-benzenesulfonamide (1.5 equiv., 0.42 mmol), Cs$_2$CO$_3$ (3.0 equiv., 0.84 mmol), Pd$_2$(dba)$_3$ (0.1 equiv., 0.028 mmol), and Xantphos (0.2 equiv., 0.056 mmol) were dissolved in 20 mL of dioxane and argon was bubbled through the reaction mixture. The reaction was kept in oil bath to reflux at 100° C. for 18 h. The reaction was then cooled to room temperature, filtered to remove inorganics, extracted with EtOAc, saturated NaHCO$_3$ and brine, and the organics were dried over Na$_2$SO$_4$, then concentrated under reduced pressure to give an orange solid (147.2 mg, 93% yield). The resulting crude material was used as is to prepare 4-[7-(2-chloro-5-hydroxy-phenyl)-6-methyl-benzo[1,2,4]triazin-3-ylamino]-N-methyl-N-(2-pyrrolidin-1-yl-ethyl)-benzenesulfonamide as described in the next example.

Example 73

Synthesis of 4-[7-(2-chloro-5-hydroxy-phenyl)-6-methyl-benzo[1,2,4]triazin-3-ylamino]-N-methyl-N-(2-pyrrolidin-1-yl-ethyl)-benzenesulfonamide

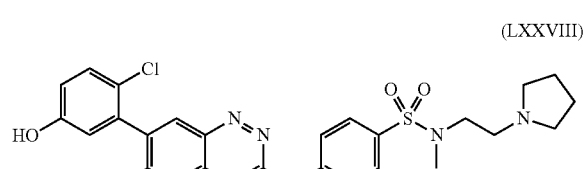

(LXXVIII)

4-[7-(2-chloro-5-methoxy-phenyl)-6-methyl-benzo[1,2,4]triazin-3-ylamino]-N-methyl-N-(2-pyrrolidin-1-yl-ethyl)-benzenesulfonamide (1.0 equiv., 0.26 mmol) obtained as described in Example 72, was dissolved in anhydrous DCM, purged of air using house vacuum, and placed under an argon blanket. Neat BBr$_3$ (4.0 equiv., 1.04 mmol) was then added via syringe and allowed to stir at room temperature for 2 h. The reaction was quenched using saturated NaHCO$_3$, and the resulting precipitate was filtered and washed with water and Et$_2$O to afford an olive green solid. The compound was purified by flash chromatography using 90:10 DCM/MeOH to recover a yellow/orange solid (88.2 mg, 62% yield). $R_f$=0.19

¹H NMR (DMSO-d₆): δ 1.19 (t, J=7.32 Hz, 2H), 1.89 (m, 2H), 2.01 (m, 2H), 2.29 (s, 3H), 2.73 (s, 3H), 3.06 (m, 4H), 6.82 (d, J=2.85 Hz, 1H), 6.91 (dd, J=2.91 Hz, 8.61 Hz, 1H), 7.40 (d, J=8.81 Hz, 1H), 7.79 (s, 1H), 7.83 (d, J=8.95 Hz, 2H), 8.11 (s, 1H), 8.26 (d, J=8.90 Hz, 2H). MS (ES+): m/z=555 LC retention time: 2.28 min.

Example 74

Synthesis of Acetic acid 4-chloro-3-{5-methyl-3-[4-(2-pyrrolidin-1-yl-ethoxy)-phenylamino]-benzo[1,2,4]triazin-7-yl}-phenyl ester

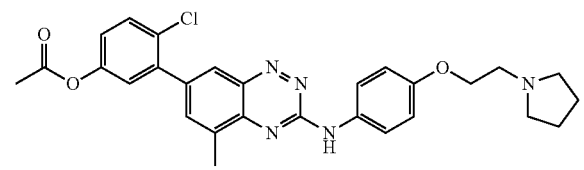

(LXXIX)

To a solution of 4-chloro-3-{5-methyl-3-[4-(2-pyrrolidin-1-yl-ethoxy)-phenylamino]-benzo[1,2,4]triazin-7-yl}-phenol hydrochloride (1.0 equiv., 0.978 mmol) in DCM (30 mL) was added neat Et₃N (10 equiv., 4.89 mmol) under an argon rich atmosphere and stirred for 10 minutes. Neat Acetyl chloride (1.2 equiv., 1.17 mmol) was added dropwise via syringe to the reaction mixture and allowed to stir at room temperature for 24 h. The reaction was quenched using saturated NaHCO₃; the organics were dried over Na₂SO₄ and then concentrated down under reduced pressure. The resulting crude solid was then brought up in DCM and purified by flash chromatography using a solvent system of 85:10:5 (v/v/v) DCM/MeOH/Et₃N. The fractions were concentrated under reduced pressure and precipitated out using 1:5 (v/v) DCM/hexanes to afford an orange solid (409.1 mg, 75% yield). ¹H NMR (DMSO-d₆): δ 1.68 (m, 4H), 2.29 (s, 3H), 2.51 (m, 4H), 2.63 (s, 3H), 2.78 (t, J=5.94 Hz, 2H), 4.07 (t, J=5.99 Hz, 2H), 6.99 (dd, J=7.05 Hz, 12.55 Hz, 2H), 7.27 (dd, J=5.90 Hz, 8.75 Hz, 1H), 7.41 (d, J=2.80 Hz, 1H), 7.67 (d, J=8.75 Hz, 1H), 7.85 (m, 1H), 7.93 (d, J=9.05 Hz, 2H), 8.17 (m, 1H), 10.83 (s, 1H). R_f=0.29 MS (ES+) m/z=520, LC retention time 2.57 minutes.

Example 75

Synthesis of Acetic acid 4-chloro-3-{5-methyl-3-[3-(2-pyrrolidin-1-yl-ethoxy)-phenylamino]-benzo[1,2,4]triazin-7-yl}-phenyl ester

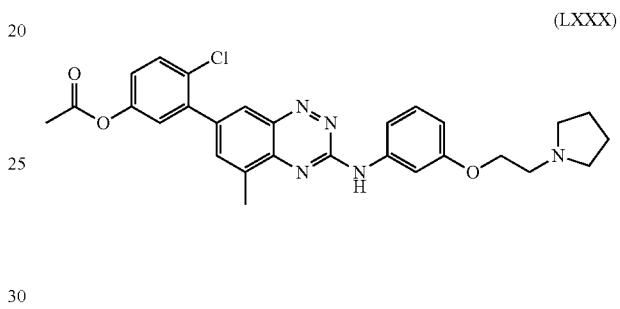

(LXXX)

The title product was synthesized and had the following characteristics. ¹H NMR (DMSO-d₆): δ 1.73 (m, 4H), 2.30 (s, 3H), 2.65 (m, 4H), 2.68 (s, 3H), 2.92 (m, 2H), 4.16 (t, J=5.85 Hz, 2H), 6.67 (dd, J=2.49 Hz, 8.24 Hz, 1H), 7.29 (t, J=8.45 Hz, 2H), 7.43 (d, J=2.74 Hz, 1H), 7.48 (d, J=9.58 Hz, 1H), 7.68 (d, J=8.69 Hz, 1H), 7.92 (d, J=11.72 Hz, 2H), 8.23 (s, 1H). MS (ES+) m/z=519, LC retention time: 2.61 minutes.

Example 76

Synthesis of 4-methyl-benzoic acid 4-chloro-3-{5-methyl-3-[4-(2-pyrrolidin-1-yl-ethoxy)-phenylamino]-benzo[1,2,4]triazin-7-yl}-phenyl ester

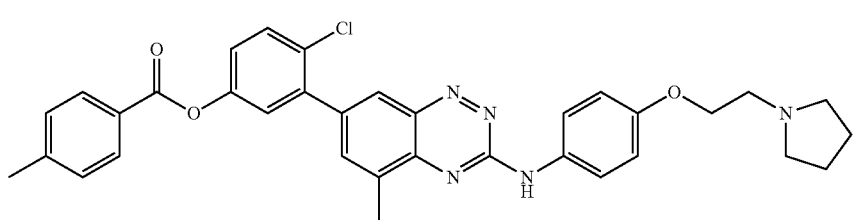

(LXXXI)

The title product was synthesized and had the following characteristics. ¹H NMR (DMSO-d₆): δ 1.69 (m, 4H), 2.42 (s, 3H), 2.52 (m, 4H), 2.64 (s, 3H), 2.78 (t, J=5.96 Hz, 2H), 4.06 (t, J=5.97 Hz, 2H), 6.99 (d, J=5.0 Hz, 2H), 7.42 (d, J=7.5 Hz, 2H), 7.44 (d, J=2.8 Hz, 1H), 7.58 (d, J=2.8 Hz, 1H), 7.72 (d, J=8.7 Hz, 1H), 7.88 (d, J=0.85 Hz, 1H), 7.92 (d, J=9.15 Hz, 2H), 8.05 (d, J=6.55 Hz, 2H), 8.21 (d, J=1.75 Hz, 1H), 10.83 (s, 1H). MS (ES+) m/z=594.5, LC retention time: 3.08 minutes.

Example 77

Synthesis of 2,2-dimethyl-propionic acid 4-chloro-3-{5-methyl-3-[4-(2-pyrrolidin-1-yl-ethoxy)-phenylamino]-benzo[1,2,4]triazin-7-yl}-phenyl ester

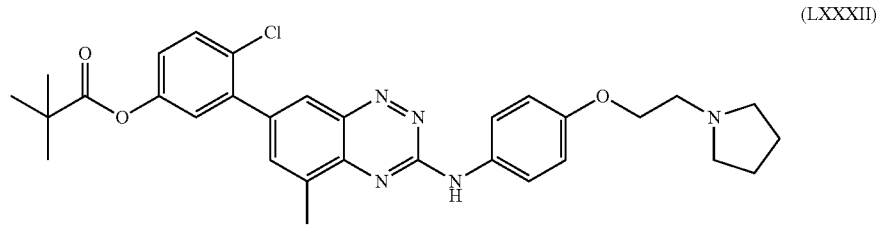 [SMILES: Cc1cc(-c2cc(OC(=O)C(C)(C)C)ccc2Cl)cc2nnc(Nc3ccc(OCCN4CCCC4)cc3)nc12]

(LXXXII)

The title product was synthesized and had the following characteristics. $^1$H NMR (DMSO-$d_6$): δ 1.31 (s, 9H), 1.69 (m, 4H), 2.54 (m, 4H), 2.64 (s, 3H), 2.80 (t, J=5.67 Hz, 2H), 4.07 (t, J=5.95 Hz, 2H), 7.0 (d, J=2.2 Hz, 2H), 7.25 (dd, J=2.55 Hz, 8.45 Hz, 1H), 7.39 (d, J=2.7 Hz, 1H), 7.67 (d, J=8.75 Hz, 1H), 7.85 (d, J=0.9 Hz, 1H), 7.93 (d, J=9.15 Hz, 2H), 8.19 (d, J=1.65 Hz, 1H), 10.84 (s, 1H). MS (ES+) m/z=560.4, LC retention time: 2.98 minutes.

Example 78

Synthesis of Isobutyric acid 4-chloro-3-{5-methyl-3-[4-(2-pyrrolidin-1-yl-ethoxy)-phenylamino]-benzo[1,2,4]triazin-7-yl}-phenyl ester

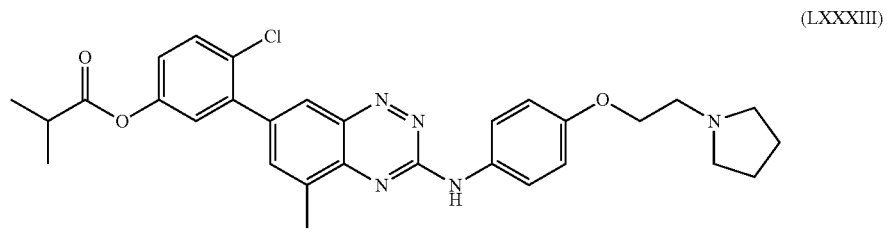 [SMILES: Cc1cc(-c2cc(OC(=O)C(C)C)ccc2Cl)cc2nnc(Nc3ccc(OCCN4CCCC4)cc3)nc12]

(LXXXIII)

The title product was synthesized and had the following characteristics. $^1$H NMR (DMSO-$d_6$): δ 1.23 (s, 3H), 1.25 (s, 3H), 1.69 (m, 4H), 2.53 (m, 4H), 2.64 (s, 3H), 2.79 (t, J=5.88 Hz, 2H), 4.07 (t, J=5.94 Hz, 2H), 6.99 (d, J=7.05 Hz, 2H), 7.25 (dd, J=2.85 Hz, 8.8 Hz, 1H), 7.41 (d, J=2.85 Hz, 1H), 7.67 (d, J=8.8 Hz, 1H), 7.85 (d, J=1.1 Hz, 1H), 7.93 (d, J=9.05 Hz, 2H), 8.18 (d, J=1.85 Hz, 1H), 10.84 (s, 1H). MS (ES+) m/z=548.7, LC retention time: 2.80 minutes.

Example 79

Synthesis of 7-bromo-1-oxy-benzo[1,2,4]triazin-3-ylamine

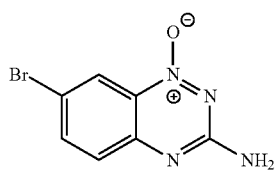

(LXXXIV)

4-bromo-2-nitro-phenylamine (11.0 g) and cyanamide (11.0 g) were weighed out into a 1000 mL round bottom flask and heated to 100° C. until melted. Heating was removed and concentrated HCl (35 mL) was added slowly in multiple small portions as this addition was extremely exothermic. Upon complete addition of HCl, reaction heating was resumed at 110° C. for 4 hours. Reaction heating was then removed and 30% NaOH was added slowly in sufficient quantity so as to bring the reaction pH to about 13-14. This resulted in copious yellow precipitate. Reaction heating was resumed for 1 hour. The reaction mixture was cooled, diluted with water (400 mL) and filtered. Isolated solids were dried, taken up in DCM and filtered again to provide the pure material. Yellow solids (9.56 g, 80% yield). MS (ESI+): m/z=243.0, $^1$H NMR (DMSO-$d_6$): δ 7.46 (d, J=9.1 Hz, 1H), 7.88 (dd, J=9.0 Hz, J=2.4 Hz, 1H), 8.25 (d, J=2.3 Hz, 1H).

Example 80

Synthesis of 7-bromo-5-nitro-1-oxy-benzo[1,2,4]triazin-3-ylamine

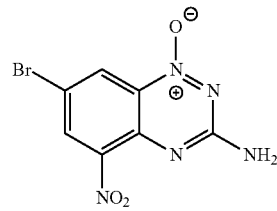

(LXXXV)

In a 1000 mL round bottom flask, 7-bromo-1-oxy-benzo[1,2,4]triazin-3-ylamine (9.5 g, 39.4 mmol, 1 equiv) was dissolved completely in sulfuric acid (24 mL) and chilled to 0° C. using an ice bath. Fuming nitric acid (24 mL) was added in 3 portions over several minutes while the solution was stirred. The reaction was then allowed to come to ambient temperature and the stirring was continued for 16 hours. The contents were then poured carefully onto ice and the resulting solids yellow were collected and dried (10.75 g, 95% yield). MS (ESI+): m/z=288.0, LC retention time: 2.39 min. $R_f$=0.65, 30% EtOAc/hexanes. $^1$H NMR (DMSO-$d_6$): δ 7.99 (bs, 2H), 8.49 (d, f=2.4 Hz, 1H), 8.59 (d, J=2.4 Hz, 1H).

Example 81

Synthesis of 7-(2,6-dimethyl-phenyl)-5-nitro-1-oxy-benzo[1,2,4]triazin-3-ylamine

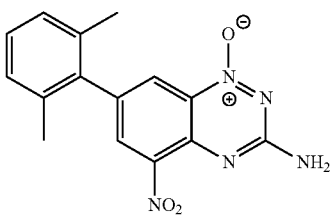

(LXXXVI)

An oven dried 25 mL round bottom flask was charged with 7-bromo-5-nitro-1-oxy-benzo[1,2,4]triazin-3-ylamine (0.1 g, 0.35 mmol, 1 equiv), 2,6-dimethyl phenyl boronic acid (0.105 g, 0.69 mmol, 2 equiv), sodium carbonate (0.15 g, 1.39 mmol, 4 equiv) and tetrakis(triphenylphosphine) palladium (0) (0.04 g, 0.035 mmol, 0.1 equiv). The reactants were flushed with argon and diluted with ethylene glycol dimethyl ether (6 mL), ethanol (1 mL) and DI water (1 mL). The reaction vessel was outfitted with condenser and refluxed for 18 hours. The reaction was cooled to ambient temperature and the crude product was filtered, diluted with ethyl acetate, and washed with brine. The brine layer was back extracted once with fresh ethyl acetate. The organic phases were combined and dried over sodium sulfate ($Na_2SO_4$). Filtration was followed by evaporation and silica gel chromatography (2:3 EtOAc/hexanes) provided the desired product as a yellow powder (0.08 g, 74% yield). MS (ESI+): m/z=312.4, LC retention time: 2.96 min. $R_f$=0.42, 30% EtOAc/hexanes.

Example 82

Synthesis of 4-[7-(2,6-dimethyl-phenyl)-5-nitro-1-oxy-benzo[1,2,4]triazin-3-ylamino]-N-(2-pyrrolidin-1-yl-ethyl)-benzenesulfonamide

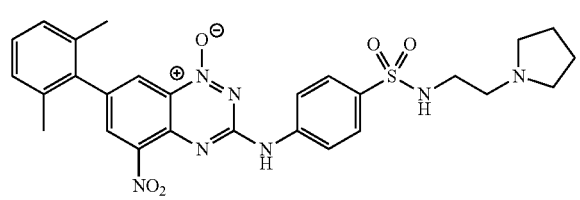

(LXXXVII)

In a dry 25 mL round bottom flask, 7-(2,6-dimethyl-phenyl)-5-nitro-1-oxy-benzo[1,2,4]triazin-3-ylamine (0.069 g, 0.22 mmol, 1 equiv), 4-bromo-N-(2-pyrrolidin-1-yl-ethyl)-benzenesulfonamide (0.11 g, 0.33 mmol, 1.5 equiv), cesium carbonate (0.22 g, 0.67 mmol, 3 equiv), 4,5-bis(diphenylphosphino)-9,9-dimethyl xanthene (0.026 g, 0.044 mmol, 0.2 equiv) and tris(dibenzylideneacetone) dipalladium (0.021 g, 0.022 mmol, 0.1 equiv) were combined. The reactants were flushed with argon, diluted with dioxane (8 mL) and outfitted with reflux condenser. The reaction was heated to reflux for 6 hours, then filtered hot, and the solvents were diluted with ethyl acetate and washed with brine. The brine layer was back extracted once with fresh ethyl acetate. The organic phases were combined and dried over sodium sulfate ($Na_2SO_4$). Filtration followed by evaporation and silica gel chromatography (6:1 DCM/MeOH) provided desired product as a yellow powder (0.079 g, 63% yield). MS (ESI+): m/z=564.4, LC retention time: 2.73 min.

Example 83

Synthesis of 4-[5-amino-7-(2,6-dimethyl-phenyl)-benzo[1,2,4]triazin-3-ylamino]-N-(2-pyrrolidin-1-yl-ethyl)-benzenesulfonamide

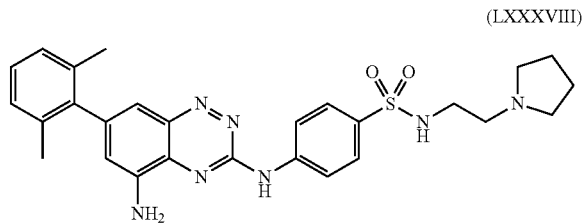 [SMILES: Cc1cccc(C)c1-c1cc(N)c2nc(Nc3ccc(S(=O)(=O)NCCN4CCCC4)cc3)nnc2c1]

(LXXXVIII)

4-[7-(2,6-dimethyl-phenyl)-5-nitro-1-oxy-benzo[1,2,4]triazin-3-ylamino]-N-(2-pyrrolidin-1-yl-ethyl)-benzenesulfonamide (0.079 g, 0.14 mmol, 1 equiv) was combined with 10% palladium on carbon (0.029 g) and flushed with argon. The reactants were then diluted with methanol (5 mL) and the reaction atmosphere was evacuated and replaced with hydrogen. A hydrogen balloon was affixed and the reaction was allowed to stir for 3 hours. Argon was then bubbled through the reaction mixture and contents were filtered though a pad of Celite. Solvents were evaporated to provide a green solid product (0.045 g, 62% yield). MS (ESI+): 518.4 (M+H), r.t.=2.56 min.

Example 84

Synthesis of N-{7-(2,6-dimethyl-phenyl)-3-[4-(2-pyrrolidin-1-yl-ethylsulfamoyl)-phenylamino]-benzo[1,2,4]triazin-5-yl}-acetamide TFA salt

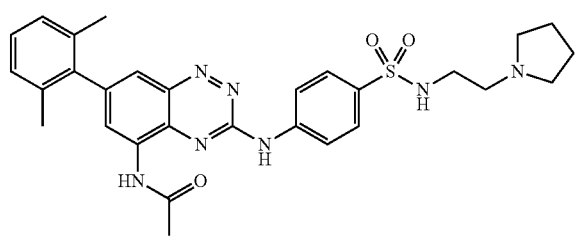

(LXXXIX)

A 0° C. solution of 4-[5-amino-7-(2,6-dimethyl-phenyl)-benzo[1,2,4]triazin-3-ylamino]-N-(2-pyrrolidin-1-yl-ethyl)-benzenesulfonamide (0.045 g, 0.087 mmol, 1 equiv) in DCM (3 mL) was treated with acetyl chloride (0.011 g, 0.14 mmol, 1.6 equiv) and allowed to warm to ambient temperature. After 18 hours, the reaction solvents were evaporated to provide crude residue. HPLC purification provided the TFA salt of desired product as a yellow powder (0.011 g, 23% yield). MS (ESI+): m/z=560.4, LC retention time: 2.67 min. $^1$H NMR (DMSO-$d_6$): δ 1.85-1.88 (m, 2H), 1.99-2.01 (m, 2H), 2.07 (s, 6H), 2.28 (s, 3H), 3.02-3.08 (m, 4H), 3.23-3.27 (m, 2H), 3.54-3.57 (m, 2H), 7.20 (d, J=7.6 Hz, 2H), 7.24-7.27 (m, 1H), 7.87 (d, J=8.9 Hz, 2H), 7.89 (t, J=6.1 Hz, 1H), 7.94 (d, J=1.8 Hz, 1H), 8.26 (d, J=8.9 Hz, 3H), 9.56 (bs, 1H), 9.84 (s, 1H) 11.48 (s, 1H).

Example 85

Synthesis of N-[3-{4-[acetyl-(2-pyrrolidin-1-yl-ethyl)-sulfamoyl]-phenylamino}-7-(2,6-dimethyl-phenyl)-benzo[1,2,4]triazin-5-yl]-acetamide

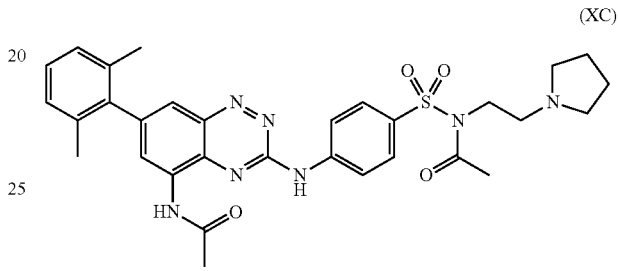

(XC)

A 0° C. degree solution of 4-[5-amino-7-(2,6-dimethyl-phenyl)-benzo[1,2,4]triazin-3-ylamino]-N-(2-pyrrolidin-1-yl-ethyl)-benzenesulfonamide (0.045 g, 0.087 mmol, 1 equiv) in DCM (3 mL) was treated with acetyl chloride (0.011 g, 0.14 mmol, 1.6 equiv) and allowed to warm to ambient temperature. After 18 hours, the reaction solvents were evaporated to provide crude residue. HPLC purification provided the TFA salt of the desired product as a yellow powder (0.004 g, 8% yield). MS (ESI+): m/z=602.4, LC retention time: 2.83 min. $^1$H NMR (DMSO-$d_6$): δ 1.87-1.89 (m, 2H), 2.04-2.08 (m, 8H), 2.29 (s, 3H), 2.36 (s, 3H), 3.09-3.11 (m, 2H), 3.64-3.66 (m, 2H), 4.08 (t, J=7.0 Hz, 2H), 7.20 (d, J=7.6 Hz, 2H), 7.24-7.27 (m, 1H), 7.96 (d, J=1.6 Hz, 1H), 8.04 (d, J=9.0 Hz, 2H), 8.26-8.30 (m, 3H), 9.73 (bs, 1H), 9.85 (s, 1H) 11.60 (s, 1H).

Example 86

Synthesis of 4-[7-(2-chloro-5-methoxy-phenyl)-5-methyl-benzo[1,2,4]triazin-3-ylamino]-N-(2-pyrrolidin-1-yl-ethyl)-benzenesulfonamide

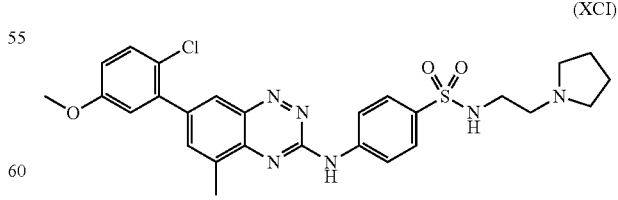

(XCI)

In a dry 25 mL round bottom flask, 7-(2-chloro-5-methoxy-phenyl)-5-methyl-benzo[1,2,4]triazin-3-ylamine (0.157 g, 0.523 mmol, 1 equiv), 4-bromo-N-(2-pyrrolidin-1-yl-ethyl)-benzenesulfonamide (0.261 g, 0.785 mmol, 1.5 equiv), cesium carbonate (0.512 g, 1.57 mmol, 3 equiv), 4,5-bis (diphenylphosphino)-9,9-dimethyl xanthene (0.061 g, 0.10 mmol, 0.2 equiv) and tris(dibenzylideneacetone) dipalladium (0.048 g, 0.052 mmol, 0.1 equiv) were combined. The reactants were flushed with argon, diluted with dioxane (5 mL) and outfitted with reflux condenser. The reaction was heated to reflux for 18 hours, then filtered hot, and the solvents were diluted with ethyl acetate and washed with brine. The brine layer was back extracted once with fresh ethyl acetate. The organic phases were combined and dried over sodium sulfate ($Na_2SO_4$). Filtration followed by evaporation provided slightly impure product. Solids were diluted in minimum amount of DCM and precipitated out using excess hexanes. The resulting solids were filtered off and dried to yield a yellow powder (0.276 g, 95% yield). MS (ESI+): m/z=553.3, LC retention time: 2.77 min.

Example 87

Synthesis of 4-[7-(2-chloro-5-hydroxy-phenyl)-5-methyl-benzo[1,2,4]triazin-3-ylamino]-N-(2-pyrrolidin-1-yl-ethyl)-benzenesulfonamide TFA salt

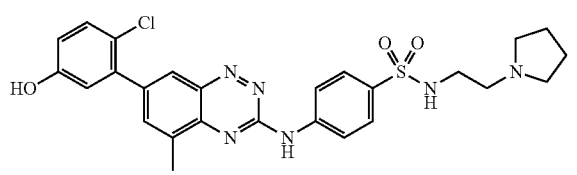

(XCII)

4-[7-(2-chloro-5-methoxy-phenyl)-5-methyl-benzo[1,2,4]triazin-3-ylamino]-N-(2-pyrrolidin-1-yl-ethyl)-benzenesulfonamide (0.055 g, 0.099 mmol, 1 equiv) was diluted with 15 mL DCM and chilled to 0° C. using an ice bath. A 1.0 M solution of $BBr_3$ in DCM (0.25 mL, 0.25 mmol, 2.5 equiv) was then added in one portion resulting in a dark reaction mixture. The reaction was allowed to come to ambient temperature and stirred for 15 hours, then quenched by carefully pouring onto a saturated solution of sodium bicarbonate followed by sonication for 3-5 minutes. Additional DCM was added and this mixture was washed with sodium bicarbonate followed by brine. The organic phase was separated, dried over sodium sulfate ($Na_2SO_4$), filtered and evaporated to dryness. HPLC purification provided the TFA salt of desired product as a yellow solid (0.013 g, 25% yield). MS (ESI+): m/z=539.3, LC retention time: 2.50 min. $^1$H NMR (DMSO-$d_6$): δ 1.86 (bs, 2H), 1.99 (bs, 2H), 2.71 (s, 3H), 2.28 (s, 3H), 3.04-3.07 (m, 4H), 3.23 (bs, 2H), 3.55 (s, 2H), 6.53 (s, 1H), 6.89 (dd, J=8.7 Hz, J=2.9 Hz, 1H), 6.94 (d, J=2.9 Hz, 1H), 7.41 (d, J=8.7 Hz, 1H), 7.83 (bs, 1H), 7.87 (d, J=8.8 Hz, 2H), 7.92 (s, 1H), 8.22 (d, J=1.7 Hz, 1H), 8.26 (d, J=8.8 Hz, 2H), 9.55 (bs, 1H), 9.96 (s, 1H) 11.44 (s, 1H).

Example 88

Synthesis of 3-(3-amino-5-methyl-benzo[1,2,4]triazin-7-yl)-4-chloro-phenol

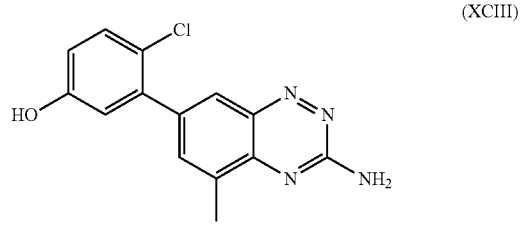 [SMILES: Cc1cc(-c2cc(O)ccc2Cl)cc2nnc(N)nc12]

(XCIII)

7-(2-chloro-5-methoxy-phenyl)-5-methyl-benzo[1,2,4]triazin-3-ylamine (0.158 g, 0.527 mmol, 1 equiv) was diluted with 10 mL DCM and chilled to 0° C. using an ice bath. A 1.0 M solution of $BBr_3$ in DCM (3.16 mL, 3.16 mmol, 6.0 equiv) was then added in one portion resulting in a dark reaction mixture. The reaction was allowed to come to ambient temperature and stirred for 3.5 hours, then quenched by carefully pouring onto a saturated solution of sodium bicarbonate followed by sonication for 3-5 minutes. Additional DCM was added and this mixture was washed with sodium bicarbonate followed by brine. The organic phase was separated, dried over sodium sulfate ($Na_2SO_4$), filtered and evaporated to dryness. Solids were then diluted with minimum amount of ethyl acetate and precipitated out with hexanes. Product was filtered off and dried to yield a yellow solid (0.110 g, 73% yield). MS (ESI+): m/z=287.1, LC retention time: 2.46 min.

Example 89

Synthesis of N-{5-[7-(2-chloro-5-hydroxy-phenyl)-5-methyl-benzo[1,2,4]triazin-3-ylamino]-pyridin-2-yl}-acetamide TFA salt

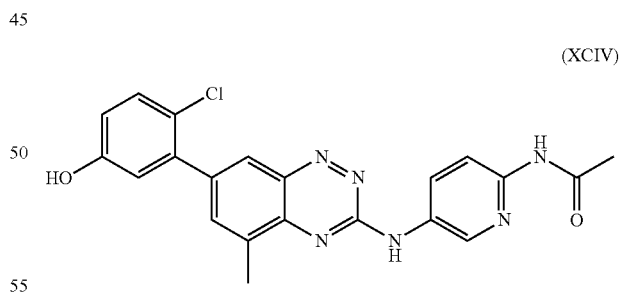

(XCIV)

In a dry 25 mL round bottom flask, 3-(3-amino-5-methyl-benzo[1,2,4]triazin-7-yl)-4-chloro-phenol (0.0641 g, 0.224 mmol, 1 equiv), N-(5-bromo-pyridin-2-yl)-acetamide (0.0723 g, 0.336 mmol, 1.5 equiv), cesium carbonate (0.220 g, 0.672 mmol, 3 equiv), 4,5-bis(diphenylphosphino)-9,9-dimethyl xanthene (0.026 g, 0.0448 mmol, 0.2 equiv) and tris(dibenzylideneacetone) dipalladium (0.0205 g, 0.0224 mmol, 0.1 equiv) were combined. The reactants were flushed with argon, diluted with dioxane (8 mL) and outfitted with reflux condenser. The reaction was heated to reflux for 18 hours, then filtered hot and solvents were diluted with ethyl acetate and washed with brine. The brine layer was back extracted once with fresh ethyl acetate. The organic phases were combined and dried over sodium sulfate (Na$_2$SO$_4$). Filtration followed by evaporation and HPLC purification provided the TFA salt of desired product as a yellow powder (0.004 g, 4% yield). MS (ESI+): m/z=421.1, LC retention time: 2.44 min. $^1$H NMR (DMSO-d$_6$): δ 2.09 (s, 3H), 2.65 (s, 3H), 6.87 (dd, J=8.7 Hz, J=2.9 Hz, 1H), 6.93 (d, J=2.9 Hz, 1H), 7.40 (d, J=8.7 Hz, 1H), 7.86 (s, 1H), 8.11 (d, J=8.9 Hz, 1H), 8.16 (d, J=1.7 Hz, 1H), 8.39 (dd, J=9.0 Hz, J=2.7 Hz, 1H), 8.93 (d, J=2.5 Hz, 1H), 9.92 (bs, 1H), 10.47 (s, 1H), 11.05 (s, 1H).

Example 90

Synthesis of 1-[2-(3-bromo-phenoxy)-ethyl]-pyrrolidine

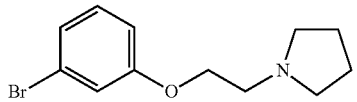

(XCV)

3-bromo-phenol (5.34 g, 30.9 mmol, 1 equiv), 1-(2-chloro-ethyl)-pyrrolidine (5.24 g, 30.9 mmol, 1 equiv) and potassium carbonate (K$_2$CO$_3$) (34 g, 24.7 mmol, 8 equiv) were weighed out into a 500 mL round bottom flask, were diluted with 150 mL DMF and stirred for 2 days. The contents were poured onto ethyl acetate water mixture and extracted once. The organic layer was separated, washed with brine and dried over sodium sulfate (Na$_2$SO$_4$). Filtration followed by concentration provided crude product as a pale yellow oil. Column chromatography (1:9 ethyl acetate/hexanes) provided desired product as a yellow oil (3.6 g, 43% yield). $^1$H NMR (DMSO-d$_6$): δ 1.65-1.69 (m, 4H), 2.72 (s, 1H), 2.75 (t, J=5.8 Hz, 2H), 2.88 (s, 1H), 4.06 (t, J=5.8 Hz, 2H), 6.95 (dd, J=8.35 Hz, 1H), 7.11 (d, J=7.7, 1H), 7.13-7.14 (m, 1H), 7.22 (t, J=8.1 Hz, 1H).

Example 91

Synthesis of [7-(2-chloro-5-methoxy-phenyl)-5-methyl-benzo[1,2,4]triazin-3-yl]-[3-(2-pyrrolidin-1-yl-ethoxy)-phenyl]-amine

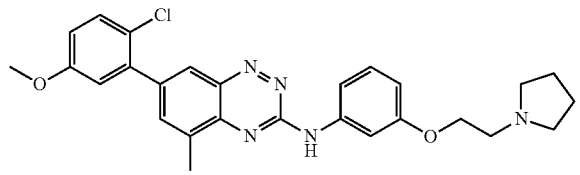

(XCVI)

In a dry 25 mL round bottom flask, 7-(2-chloro-5-methoxy-phenyl)-5-methyl-benzo[1,2,4]triazin-3-ylamine (0.113 g, 0.377 mmol, 1 equiv), 1-[2-(3-bromo-phenoxy)-ethyl]pyrrolidine (0.153 g, 0.565 mmol, 1.5 equiv), cesium carbonate (0.368 g, 1.13 mmol, 3 equiv), 4,5-bis(diphenylphosphino)-9,9-dimethyl xanthene (0.044 g, 0.0753 mmol, 0.2 equiv) and tris(dibenzylideneacetone) dipalladium (0.034 g, 0.0376 mmol, 0.1 equiv) were combined. The reactants were flushed with argon, diluted with dioxane (8 mL) and outfitted with reflux condenser. The reaction was heated to reflux for 18 hours, then filtered hot and the solvents were diluted with ethyl acetate and washed with brine. The brine layer was back extracted once with fresh ethyl acetate. The organic phases were combined and dried over sodium sulfate (Na$_2$SO$_4$). Filtration followed by evaporation and column chromatography (1:5 MeOH/DCM) provided desired product as a yellow powder (0.12 g, 65% yield). MS (ESI+): m/z=491.1, LC retention time: 2.94 min.

Example 92

Synthesis of 4-chloro-3-{5-methyl-3-[3-(2-pyrrolidin-1-yl-ethoxy)-phenylamino]-benzo[1,2,4]triazin-7-yl}-phenol TFA salt

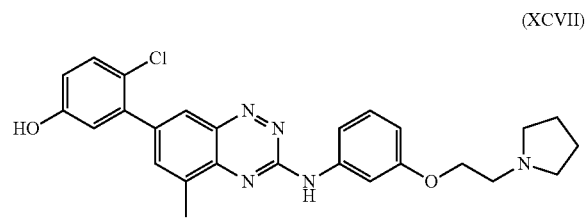 [SMILES: Cc1cc(-c2cc(O)ccc2Cl)cc2nnc(Nc3cccc(OCCN4CCCC4)c3)nc12]

(XCVII)

[7-(2-chloro-5-methoxy-phenyl)-5-methyl-benzo[1,2,4] triazin-3-yl]-[3-(2-pyrrolidin-1-yl-ethoxy)-phenyl]-amine (0.120 g, 0.245 mmol, 1 equiv) was diluted with 8 mL DCM and chilled to 0° C. using an ice bath. A 1.0 M solution of BBr$_3$ in DCM (2 mL, 1.96 mmol, 8.0 equiv) was then added in one portion resulting in a dark reaction mixture. The reaction was allowed to come to ambient temperature and stirred for 3.5 hours, then quenched by carefully pouring onto a saturated solution of sodium bicarbonate, followed by sonication for 5 minutes. Additional DCM was added and this mixture was washed with sodium bicarbonate followed by brine. The organic phase was separated, dried over sodium sulfate (Na$_2$SO$_4$), filtered and evaporated to dryness. Solids were then diluted with minimum amount of ethyl acetate and precipitated out with hexanes. Product was filtered off and dried. HPLC purification provided TFA salt of desired product as a yellow solid (0.008 g, 7% yield). MS (ESI+): m/z=476.1, LC retention time: 2.64 min. $^1$H NMR (DMSO-d$_6$): δ 1.88-1.91 (m, 2H), 2.04-2.07 (m, 2H), 2.68 (s, 3H), 3.17-3.20 (m, 2H), 3.64-3.66 (m, 4H), 4.36 (t, J=4.7 Hz, 2H), 6.74 (dd, J=8.1 Hz, J=2.3 Hz, 1H), 6.88 (dd, J=8.5 Hz, J=2.8 Hz, 1H), 6.93 (d, J=2.9 Hz, 1H), 7.35 (t, J=8.2 Hz, 1H), 7.41

(d, J=8.7 Hz, 1H), 7.55 (d, J=8.7 Hz, 1H), 7.88 (s, 1H), 7.95-7.96 (m, 1H), 8.17 (d, J=1.7 Hz, 1H), 9.79 (bs, 1H), 9.95 (s, 1H), 11.04 (s, 1H).

Example 93

Synthesis of {4-[7-(2-chloro-5-methoxy-phenyl)-5-methyl-benzo[1,2,4]triazin-3-ylamino]-phenyl}-(4-methyl-piperazin-1-yl)-methanone

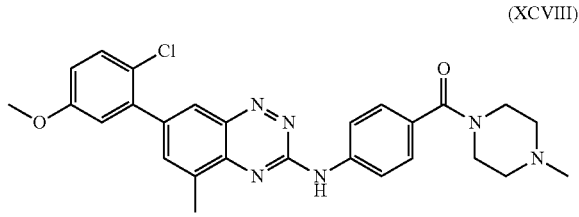

(XCVIII)

In a dry 25 mL round bottom flask, 7-(2-chloro-5-methoxy-phenyl)-5-methyl-benzo[1,2,4]triazin-3-ylamine (0.282 g, 0.94 mmol, 1 equiv), (4-bromo-phenyl)-(4-methyl-piperazin-1-yl)-methanone (0.399 g, 1.41 mmol, 1.5 equiv), cesium carbonate (0.919 g, 2.82 mmol, 3 equiv), 4,5-bis(diphenylphosphino)-9,9-dimethyl xanthene (0.109 g, 0.188 mmol, 0.2 equiv) and tris(dibenzylideneacetone) dipalladium (0.086 g, 0.094 mmol, 0.1 equiv) were combined. The reactants were flushed with argon, diluted with dioxane (12 mL) and outfitted with reflux condenser. The reaction was heated to reflux for 18 hours, then filtered hot and solvents were evaporated. The residue was diluted with toluene and water (approx. 2:1), and the mixture was heated to 70° C. and stirred for 20 min. The contents were then poured into 250 mL separatory funnel and shaken. The resulting precipitate was filtered off, washed with water and dried to yield a yellow powder (0.275 g, 58% yield). MS (ESI+): m/z=504.1, LC retention time: 1.75 min.

Example 94

Synthesis of {4-[7-(2-chloro-5-hydroxy-phenyl)-5-methyl-benzo[1,2,4]triazin-3-ylamino]-phenyl}-(4-methyl-piperazin-1-yl)-methanone TFA salt

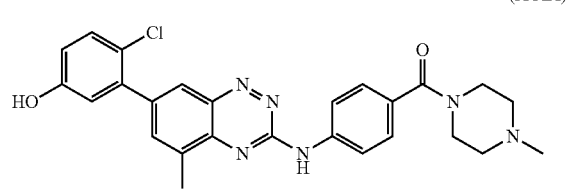

(XCIX)

{4-[7-(2-chloro-5-methoxy-phenyl)-5-methyl-benzo[1,2,4]triazin-3-ylamino]-phenyl}-(4-methyl-piperazin-1-yl)-methanone (0.139 g, 0.276 mmol, 1 equiv) was diluted with 10 mL DCM and chilled to 0° C. using an ice bath. A 1.0 M solution of BBr$_3$ in DCM (1.66 mL, 1.66 mmol, 6.0 equiv) was then added in one portion resulting in a dark reaction mixture. The reaction was allowed to come to ambient temperature and stirred for 1 hour, then quenched by carefully pouring onto a saturated solution of sodium bicarbonate followed by sonication for 5 minutes. The resulting solids were filtered off and dried. HPLC purification provided desired product as TFA salt to yield a yellow solid (0.024 g, 18% yield). MS (ESI+): m/z=489.1, LC retention time: 2.11 min. $^1$H NMR (DMSO-d$_6$): δ 2.69 (s, 3H), 2.84 (s, 3H), 3.22 (bs, 2H), 6.88 (dd, J=8.8 Hz, J=2.9 Hz, 1H), 6.93 (d, J=2.9 Hz, 1H), 7.41 (d, J=8.7 Hz, 1H), 7.55 (d, J=8.7 Hz, 2H), 7.89 (s, 1H), 8.14 (d, J=8.7 Hz, 2H), 8.19 (d, J=1.3 Hz, 1H), 9.88 (bs, 1H), 9.95 (bs, 1H), 11.24 (s, 1H).

Example 95

Synthesis of 5-[7-(2-chloro-5-methoxy-phenyl)-5-methyl-benzo[1,2,4]triazin-3-ylamino]-pyridine-2-carboxylic acid (2-pyrrolidin-1-yl-ethyl)-amide

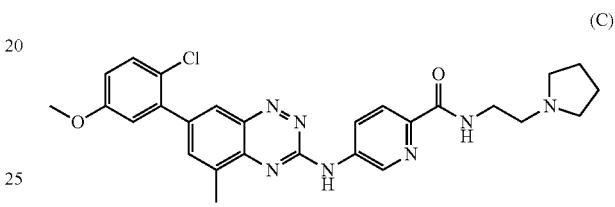

(C)

In a dry 25 mL round bottom flask, 7-(2-chloro-5-methoxy-phenyl)-5-methyl-benzo[1,2,4]triazin-3-ylamine (0.090 g, 0.299 mmol, 1 equiv), 5-bromo-pyridine-2-carboxylic acid (2-pyrrolidin-1-yl-ethyl)-amide (0.134 g, 0.449 mmol, 1.5 equiv), cesium carbonate (0.293 g, 0.899 mmol, 3 equiv), 4,5-bis(diphenylphosphino)-9,9-dimethyl xanthene (0.035 g, 0:059 mmol, 0.2 equiv) and tris(dibenzylideneacetone) dipalladium (0.027 g, 0.0299 mmol, 0.1 equiv) were combined. The reactants were flushed with argon, diluted with dioxane (8 mL) and outfitted with reflux condenser. The reaction was heated to reflux for 24 hours, then sonicated and slowly diluted with water. The resulting orange precipitate was filtered and dried. Column chromatography (1:5 MeOH/DCM) provided desired product as a yellow solid (0.085 g, 55% yield).

Example 96

Synthesis of 5-[7-(2-chloro-5-hydroxy-phenyl)-5-methyl-benzo[1,2,4]triazin-3-ylamino]-pyridine-2-carboxylic acid (2-pyrrolidin-1-yl-ethyl)-amide HCl salt

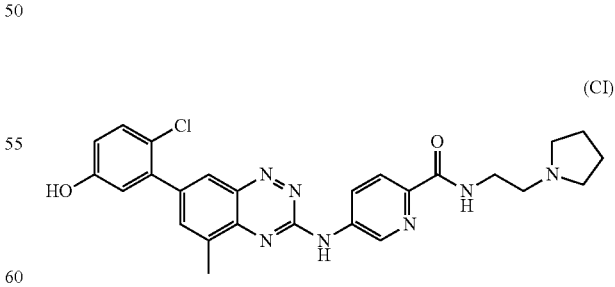

(CI)

5-[7-(2-chloro-5-methoxy-phenyl)-5-methyl-benzo[1,2,4]triazin-3-ylamino]-pyridine-2-carboxylic acid (2-pyrrolidin-1-yl-ethyl)-amide (0.085 g, 0.164 mmol, 1 equiv) was diluted with 20 mL DCM and chilled to 0° C. using an ice bath. A 1.0 M solution of BBr$_3$ in DCM (1 mL, 0.984 mmol, 6.0 equiv) was then added in one portion resulting in a dark reaction mixture. The reaction was allowed to come to ambient temperature and stirred for 6 hours, then quenched by carefully pouring onto a saturated solution of sodium bicarbonate followed by sonication for 5 minutes. The resulting solids were filtered off, dried, and dissolved in DCM (10 mL) and MeOH (20 mL) mixture and treated with 2.0 M solution of HCl in diethyl ether (0.16 mL, 0.317 mmol, 2 equiv). The solvents were evaporated leaving desired product as HCl salt in a form of a yellow solid (0.084 g, 95% yield). MS (ESI+): m/z=504.1, LC retention time: 2.23 min. $^1$H NMR (DMSO-$d_6$): δ 1.86-1.88 (m, 2H), 1.99-2.02 (m, 2H), 2.70 (s, 3H), 3.01-3.05 (m, 2H), 3.33-3.37 (m, 2H), 6.90 (dd, J=8.7 Hz, J=2.9 Hz, 1H), 6.97 (d, J=2.9 Hz, 1H), 7.41 (d, J=8.8 Hz, 1H), 7.92-7.93 (m, 1H), 8.12 (d, J=8.7 Hz, 1H), 8.22 (d, J=1.5 Hz, 1H), 8.51 (dd, J=8.6 Hz, J=2.5 Hz, 1H), 9.06 (t, J=5.9 Hz, 1H), 9.43 (d, J=2.4 Hz, 1H), 10.17 (bs, 1H), 11.50 (s, 1H).

Example 97

Synthesis of [7-(2-chloro-5-methoxy-phenyl)-5-methyl-benzo[1,2,4]triazin-3-yl]-[4-(3-pyrrolidin-1-yl-propane-1-sulfonyl)-phenyl]-amine

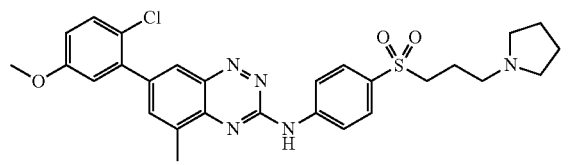

(CII)

In a dry 25 mL round bottom flask, 7-(2-chloro-5-methoxy-phenyl)-5-methyl-benzo[1,2,4]triazin-3-ylamine (0.0361 g, 0.122 mmol, 1 equiv), 1-[3-(4-bromo-benzenesulfonyl)-propyl]-pyrrolidine (0.061 g, 0.184 mmol, 1.5 equiv), cesium carbonate (0.120 g, 0.367 mmol, 3 equiv), 4,5-bis(diphenylphosphino)-9,9-dimethyl xanthene (0.014 g, 0.0244 mmol, 0.2 equiv) and tris(dibenzylideneacetone) dipalladium (0.012 g, 0.0122 mmol, 0.1 equiv) were combined. The reactants were flushed with argon, diluted with dioxane (6 mL) and outfitted with reflux condenser. The reaction was heated to reflux for 18 hours, filtered hot, diluted with ethyl acetate and washed with brine. The brine layer was back extracted once with fresh ethyl acetate. The organic phases were combined and dried over sodium sulfate ($Na_2SO_4$). Filtration followed by evaporation provided crude product, which was dissolved in minimum amount of DCM and precipitated out with excess hexanes. Solids were filtered off and dried to yield a yellow powder (0.06 g, 91% yield).

Example 98

Synthesis of 4-chloro-3-{5-methyl-3-[4-(3-pyrrolidin-1-yl-propane-1-sulfonyl)-phenylamino]-benzo[1,2,4]triazin-7-yl}-phenol TFA salt

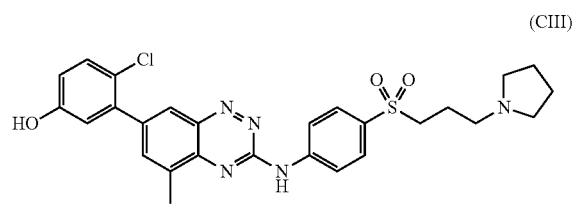 [SMILES: Cc1cc(-c2cc(O)ccc2Cl)cc2nnc(Nc3ccc(S(=O)(=O)CCCN4CCCC4)cc3)nc12]

(CIII)

[7-(2-chloro-5-methoxy-phenyl)-5-methyl-benzo[1,2,4]triazin-3-yl]-[4-(3-pyrrolidin-1-yl-propane-1-sulfonyl)-phenyl]-amine (0.080 g, 0.145 mmol, 1 equiv) was diluted with 10 mL DCM and chilled to 0° C. using an ice bath. A 1.0 M solution of $BBr_3$ in DCM (0.87 mL, 0.87 mmol, 6.0 equiv) was then added in one portion resulting in a dark reaction mixture. The reaction was allowed to come to ambient temperature and stirred for 6 hours, then quenched by carefully pouring onto a saturated solution of sodium bicarbonate followed by sonication for 3-5 minutes. The resulting solids were filtered off and dried. HPLC purification provided desired product as TFA salt in a form of a yellow solid (0.013 g, 17% yield). MS (ESI+): m/z=538.1, LC retention time: 2.35 min. $^1$H NMR (DMSO-$d_6$): δ 1.81-1.84 (m, 2H), 1.93-2.00 (m, 4H), 2.72 (s, 3H), 2.95-2.99 (m, 2H), 3.20-3.24 (m, 2H), 3.53-3.54 (m, 2H), 6.89 (dd, J=8.7 Hz, J=2.9 Hz, 1H), 6.94 (d, J=2.8 Hz, 1H), 7.41 (d, J=8.7 Hz, 1H), 7.95 (d, J=9.0 Hz, 1H), 8.23 (d, J=1.6 Hz, 1H), 8.31 (d, J=8.9 Hz, 2H), 9.61 (bs, 1H), 9.98 (s, 1H), 11.52 (s, 1H).

Example 99

Synthesis of N-[3-(3-amino-5-methyl-benzo[1,2,4]triazin-7-yl)-phenyl]-methanesulfonamide

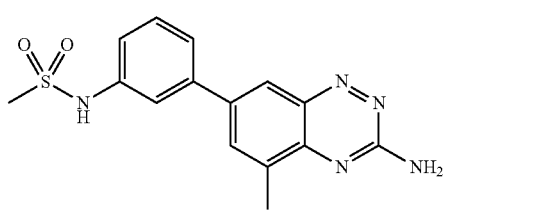

(CIV)

An oven dried 25 mL round bottom flask was charged with 7-bromo-5-methyl-benzo[1,2,4]triazin-3-ylamine (0.889 g, 3.72 mmol, 1 equiv), 3-(methylsulfonylamino) phenyl boronic acid (1.12 g, 5.21 mmol, 1.4 equiv), sodium carbonate (1.57 g, 14.9 mmol, 4 equiv) and tetrakis(triphenylphosphine) palladium(0) (0.43 g, 0.372 mmol, 0.1 equiv). The reactants were flushed with argon and diluted with ethylene glycol dimethyl ether (20 mL), ethanol (5 mL) and DI water (5 mL). The reaction vessel was outfitted with condenser and refluxed for 4 hours. The reaction was filtered hot and diluted with ethyl acetate. The Organic layer was isolated and concentrated to a dark residue. This was dissolved in DMF (6 mL) and slowly diluted with water so as to precipitate out the product. Solids were filtered off and dried to yield an orange solid (1 g, 82% yield).

Example 100

Synthesis of 4-[7-(3-methanesulfonylamino-phenyl)-5-methyl-benzo[1,2,4]triazin-3-ylamino]-N-(2-pyrrolidin-1-yl-ethyl)-benzenesulfonamide TFA salt

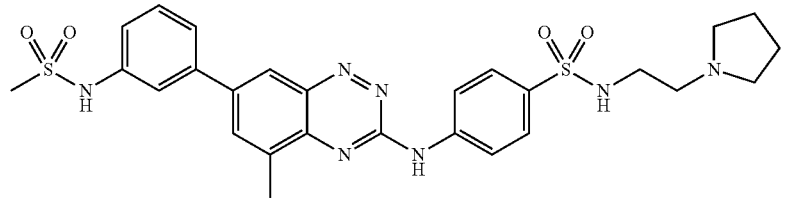

(CV)

In a dry 25 mL round bottom flask, N-[3-(3-amino-5-methyl-benzo[1,2,4]triazin-7-yl)-phenyl]-methanesulfonamide (0.12 g, 0.365 mmol, 1 equiv), 4-bromo-N-(2-pyrrolidin-1-yl-ethyl)-benzenesulfonamide (0.182 g, 0.55 mmol, 1.5 equiv), cesium carbonate (0.357 g, 1.09 mmol, 3 equiv), 4,5-bis(diphenylphosphino)-9,9-dimethyl xanthene (0.0422 g, 0.073 mmol, 0.2 equiv) and tris(dibenzylideneacetone) dipalladium (0.033 g, 0.036 mmol, 0.1 equiv) were combined. The reactants were flushed with argon, diluted with dioxane (10 mL) and outfitted with reflux condenser. The reaction was heated to reflux for 2 hours, then filtered hot and the solvents were evaporated. HPLC purification provided desired product as TFA salt, in a form of a yellow powder (0.02 g, 9% yield). MS (ESI+): m/z=582.1, LC retention time: 2.21 min. $^1$H NMR (DMSO-$d_6$): δ 1.85-1.87 (m, 2H), 1.99-2.01 (m, 2H), 2.74 (s, 3H), 3.04-3.08 (m, 3H), 3.04-3.07 (m, 7H), 3.23-3.25 (m, 2H), 3.56 (bs, 2H), 7.29 (dd, J=8.0 Hz, J=1.6 Hz, 1H), 7.52 (t, J=7.9 Hz, 1H), 7.63 (d, J=8.0 Hz, 2H), 7.66 (bs, 1H), 7.83-7.88 (m, 3H), 8.18 (bs, 1H), 8.25 (d, J=8.9 Hz, 2H), 8.43 (d, J=1.7 Hz, 1H), 9.57 (bs, 1H), 9.92 (s, 1H) 11.43 (s, 1H).

Example 101

Synthesis of 5-methyl-7-(3-nitro-phenyl)-benzo[1,2,4]triazin-3-ylamine

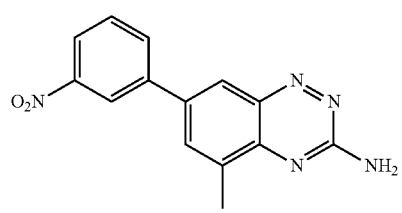

(CVI)

An oven dried 25 mL round bottom flask was charged with 7-bromo-5-methyl-benzo[1,2,4]triazin-3-ylamine (1.05 g, 4.49 mmol, 1 equiv), 3-Nitro phenyl boronic acid (1.05 g, 6.29 mmol, 1.4 equiv), sodium carbonate (1.9 g, 18 mmol, 4 equiv) and tetrakis(triphenylphosphine) palladium(0) (0.519 g, 0.449 mmol, 0.1 equiv). The reactants were flushed with argon and diluted with ethylene glycol dimethyl ether (6 mL), ethanol (1 mL) and DI water (1 mL). The reaction vessel was outfitted with condenser and refluxed for 2.5 hours. The reaction was cooled to ambient temperature and diluted with water. The resulting precipitate was filtered off, washed thoroughly with water and dried. Brown solids (0.9 g, 73% yield). MS (ESI+): m/z=282.4, LC retention time: 2.77 min.

Example 102

Synthesis of 4-[5-methyl-7-(3-nitro-phenyl)-benzo[1,2,4]triazin-3-ylamino]-N-(2-pyrrolidin-1-yl-ethyl)-benzenesulfonamide

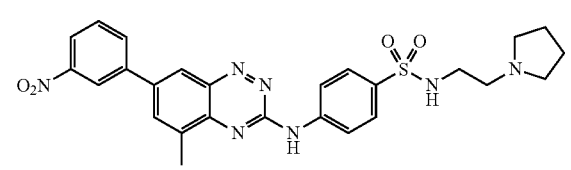

(CVII)

In a dry 25 mL round bottom flask, 5-methyl-7-(3-nitrophenyl)-benzo[1,2,4]triazin-3-ylamine (0.223 g, 0.7935 mmol, 1 equiv), 4-bromo-N-(2-pyrrolidin-1-yl-ethyl)-benzenesulfonamide (0.396 g, 1.19 mmol, 1.5 equiv), cesium carbonate (0.776 g, 2.38 mmol, 3 equiv), 4,5-bis(diphenylphosphino)-9,9-dimethyl xanthene (0.092 g, 0.159 mmol, 0.2 equiv) and tris(dibenzylideneacetone) dipalladium (0.073 g, 0.079 mmol, 0.1 equiv) were combined. The reactants were flushed with argon, diluted with dioxane (10 mL) and outfitted with a reflux condenser. The reaction was heated to reflux for 5 hours, then filtered hot and the solvents were evaporated.

Example 103

Synthesis of 4-[5-methyl-7-(3-methylamino-phenyl)-benzo[1,2,4]triazin-3-ylamino]-N-(2-pyrrolidin-1-yl-ethyl)-benzenesulfonamide TFA salt

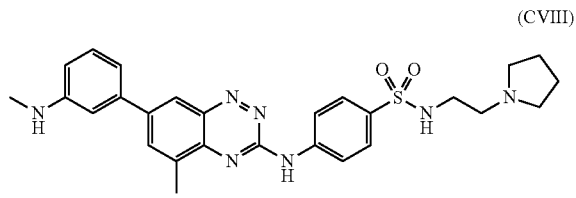 [SMILES: CNc1cccc(-c2cc(C)c3nc(Nc4ccc(S(=O)(=O)NCCN5CCCC5)cc4)nnc3c2)c1]

(CVIII)

4-[7-(3-amino-phenyl)-5-methyl-benzo[1,2,4]triazin-3-ylamino]-N-(2-pyrrolidin-1-yl-ethyl)-benzenesulfonamide (0.031 g, 0.062 mmol, 1 equiv) and cesium carbonate (0.012 g, 0.037 mmol, 0.6 equiv) were combined and diluted with dioxane (5 mL). The mixture was then treated with methyl iodide (0.013 g, 0.092 mmol, 1.5 equiv) and stirred at ambient temperature. After initial 5-10 minutes of stirring, DMF (1 mL) was added to improve solubility, followed by stirring for 16 hours, after which the solvents were evaporated and the resulting residue purified by HPLC chromatography to yield a yellow solid, the TFA salt (0.07 g, 22% yield). MS (ESI+): m/z=518.7, LC retention time: 1.86 min. $^1$H NMR (DMSO-$d_6$): δ 2.08 (bs, 4H), 2.74 (s, 3H), 3.02 (s, 3H), 3.24 (m, 2H), 3.46-3.49 (m, 5H), 3.52-3.56 (m, 3H), 6.8 (d, J=8.2 Hz, 1H), 7.19 (m, 2H), 7.26-7.29 (m, 1H), 7.88 (d, J=8.8 Hz, 1H), 7.94 (t, J=7.7 Hz, 1H), 8.16 (d, J=1.7 Hz, 1H), 8.25 (d, J=8.8 Hz, 2H), 8.36 (d, J=1.7 Hz, 1H), 11.44 (s, 1H).

Example 104

Synthesis of 4-[7-(3-amino-phenyl)-5-methyl-benzo[1,2,4]triazin-3-ylamino]-N-(2-pyrrolidin-1-yl-ethyl)-benzenesulfonamide

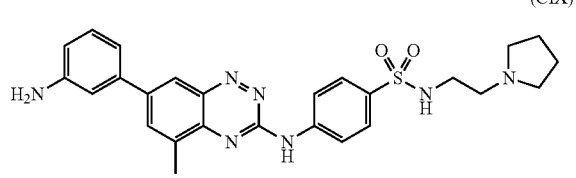

(CIX)

4-[5-methyl-7-(3-nitro-phenyl)-benzo[1,2,4]triazin-3-ylamino]-N-(2-pyrrolidin-1-yl-ethyl)-benzenesulfonamide (0.16 g, 0.3 mmol, 1 equiv) was combined with 10% palladium on carbon (0.135 g) and flushed with argon. The reactants were then diluted with methanol (15 mL), and the reaction atmosphere was evacuated and replaced with hydrogen. A hydrogen balloon was affixed and the reaction was allowed to stir for 3 hours. Argon was then bubbled through the reaction mixture and the contents were filtered though a pad of Celite. The solvents were evaporated to provide the product as an orange solid (0.15 g, 98% yield). MS (ESI+): m/z=504.6, LC retention time: 1.84 min. $^1$H NMR (DMSO-$d_6$): δ 1.64 (bs, 4H), 2.72 (s, 3H), 2.87 (bs, 2H), 5.26 (s, 2H), 6.65 (d, J=7.8 Hz, 1H), 7.00 (d, J=8.1 Hz, 1H), 7.05 (m, 1H), 7.18 (t, J=7.8 Hz, 1H), 7.83 (d, J=8.8 Hz, 2H), 8.12 (s, 1H), 8.21 (d, J=8.8 Hz, 2H), 8.27 (d, J=1.7 Hz, 1H), 11.44 (s, 1H).

Example 105

Synthesis of 4-(4-bromo-benzenesulfonyl)-piperazine-1-carboxylic acid tert-butyl ester

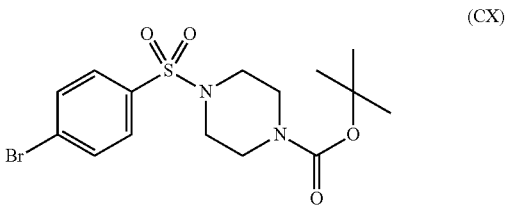 [SMILES: CC(C)(C)OC(=O)N1CCN(S(=O)(=O)c2ccc(Br)cc2)CC1]

(CX)

To a stirring, 0° C. solution of piperazine-1-carboxylic acid tert-butyl ester (1.17 g, 6.29 mmol, 1.05 equiv) and TEA (1.67 mL, 11.98 mmol, 2.0 equiv) in DCM (10 mL) was added 4-bromo-benzenesulfonyl chloride (1.53 g, 5.99 mmol, 1 equiv). The reaction was allowed to warm to ambient temperature and stir for 3 h. The reaction solvents were evaporated and the resulting solids were dried, washed with water and filtered, yielding a white powder (2.24 g, 92% yield). MS (ESI+): m/z=306.9, LC retention time: 3.17 min. $R_f$=0.56 (30% EtOAc/hexanes).

Example 106

Synthesis of 4-{4-[7-(2,6-dichloro-phenyl)-5-methyl-benzo[1,2,4]triazin-3-ylamino]-benzenesulfonyl}-piperazine-1-carboxylic acid tert-butyl ester

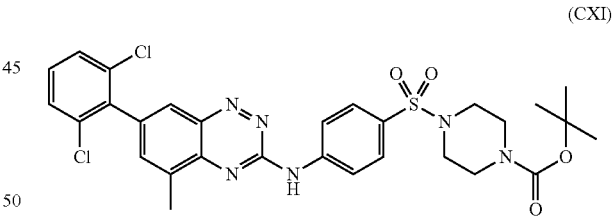

(CXI)

In a dry 25 mL round bottom flask, 7-(2,6-dichloro-phenyl)-5-methyl-benzo[1,2,4]triazin-3-ylamine (0.205 g, 0.672 mmol, 1 equiv), 4-(4-bromo-benzenesulfonyl)-piperazine-1-carboxylic acid tert-butyl ester (0.408 g, 1.01 mmol, 1.5 equiv), cesium carbonate (0.657 g, 2.02 mmol, 3 equiv); 4,5-bis(diphenylphosphino)-9,9-dimethyl xanthene (0.078 g, 0.134 mmol, 0.2 equiv) and tris(dibenzylideneacetone) dipalladium (0.0615 g, 0.067 mmol, 0.1 equiv) were combined. The reactants were flushed with argon, diluted with dioxane (20 mL) and outfitted with a reflux condenser. The reaction was heated to reflux for 2 hours, then filtered hot, and the solvents were evaporated. Purification on silica gel flash column provided desired product as a yellow solid (0.185 g, 44% yield). MS (ESI+): m/z=529.0 (M−100), LC retention time: 3.51 min. $^1$H NMR (DMSO-$d_6$): δ 1.33 (s, 9H), 2.72 (s, 3H), 2.87 (m, 4H), 3.4 (m, 7.5 (m, 1H), 7.67 (d, J=8.7 Hz, 2H), 7.78 (m, 3H), 8.18 (d, J=1.7 Hz, 1H), 8.30 (d, J=8.8 Hz, 2H), 11.53 (s, 1H).

Example 107

Synthesis of [7-(2,6-dichloro-phenyl)-5-methyl-benzo[1,2,4]triazin-3-yl]-[4-(piperazine-1-sulfonyl)-phenyl]-amine TFA salt

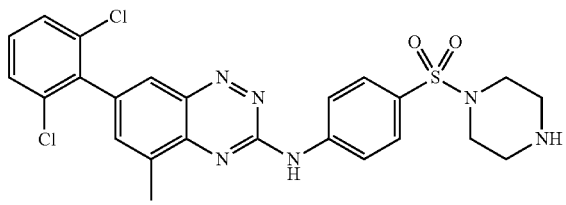

(CXII)

4-{4-[7-(2,6-dichloro-phenyl)-5-methyl-benzo[1,2,4]triazin-3-ylamino]-benzenesulfonyl}-piperazine-1-carboxylic acid tert-butyl ester (0.0696 g, 0.111 mmol, 1 equiv) was diluted with DCM (5 mL) and treated with TFA (0.051 mL, 0.664 mmol, 6 equiv). The resulting red solution was stirred at ambient temperature for 6 hours. Additional 6 equivalents of TFA were then added and the reaction was stirred for 12 hours. The solvents were then evaporated and the resulting solids collected and dried to yield a yellow powder (0.062 g, 99% yield). MS (ESI+): m/z=528.9, LC retention time: 2.70 min. $^1$H NMR (DMSO-$d_6$): δ 2.72 (s, 3H), 3.13 (m, 4H), 3.22 (m, 4H), 7.53 (m, 1H), 7.68 (d, J=8.2 Hz, 2H), 7.81 (d, J=1.6 Hz, 1H), 7.84 (d, J=8.7 Hz, 2H), 8.20 (d, J=1.7 Hz, 1H), 8.32 (d, J=8.8 Hz, 2H), 8.62 (bs, 2H), 11.53 (s, 1H).

Example 108

Synthesis of 4-bromo-N-isopropyl-N-(2-pyrrolidin-1-yl-ethyl)-benzenesulfonamide

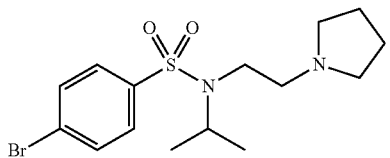

(CXIII)

4-bromo-N-isopropyl-N-(2-pyrrolidin-1-yl-ethyl)-benzenesulfonamide (1.03 g, 3.09 mmol, 1 equiv), 2-bromo-propane (3.8 g, 31 mmol, 10 equiv) and cesium carbonate (2 g, 6.2 mmol, 2.0 equiv) were refluxed in acetone for 24 h. The solvents were then removed and the resulting residue was dissolved in ethyl acetate and washed with water. The organic phase was then washed again with brine, dried over sodium sulfate, filtered and evaporated to yield the oily residue (0.86 g, 74% yield). MS (ESI+): m/z=377.5, LC retention time: 2.16 min. $R_f$=0.48 (10% MeOH:DCM).

Example 109

Synthesis of [7-(2,6-dichloro-phenyl)-5-methyl-benzo[1,2,4]triazin-3-yl]-[4-(piperazine-1-sulfonyl)-phenyl]-amine HCl salt

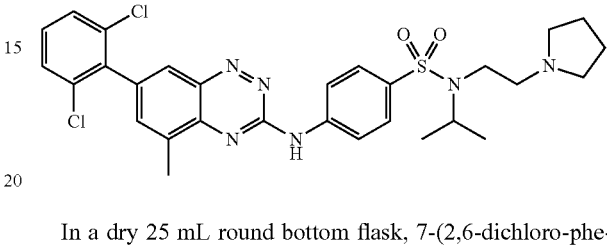

(CXIV)

In a dry 25 mL round bottom flask, 7-(2,6-dichloro-phenyl)-5-methyl-benzo[1,2,4]triazin-3-ylamine (0.162 g, 0.533 mmol, 1 equiv), 4-bromo-N-isopropyl-N-(2-pyrrolidin-1-yl-ethyl)-benzenesulfonamide (0.3 g, 0.8 mmol, 1.5 equiv), cesium carbonate (0.522 g, 1.59 mmol, 3 equiv), 4,5-bis(diphenylphosphino)-9,9-dimethyl xanthene (0.062 g, 0.106 mmol, 0.2 equiv) and tris(dibenzylideneacetone) dipalladium (0.049 g, 0.0533 mmol, 0.1 equiv) were combined. The reactants were flushed with argon, diluted with dioxane (20 mL), and outfitted with a reflux condenser. The reaction was heated to reflux for 2 hours, then filtered hot and the solvents were evaporated. Purification on silica gel flash column provided desired product, 0.144 g yellow solids, which were taken up in 5 mL DCM and treated with 2 mL 2M HCl in ether solution. The solvents were then evaporated and the resulting solids were collected and dried to yield a yellow solid (0.16 g, 50% yield). MS (ESI+): m/z=599.2, LC retention time: 2.99 min. $^1$H NMR (DMSO-$d_6$): δ 0.98 (d, 6H), 1.88 (m, 2 H), 2.01 (m, 2H), 2.72 (s, 3H), 3.02-108 (m, 2H), 3.37 (m, 2H), 3.46 (m, 2H), 3.62 (m, 2H), 4.02 (m, 1H), 7.53 (m, 1H), 7.67 (d, J=8.1 Hz, 2H), 7.79 (s, 1H), 7.92 (d, J=8.7 Hz, 2H), 8.18 (d, J=1.6 Hz, 1H), 8.27 (d, J=8.7 Hz, 2H), 10.7 (m, 1H), 11.51 (s, 1H).

Example 110

Synthesis of 4-[7-(2,6-dichloro-phenyl)-5-methyl-benzo[1,2,4]triazin-3-ylamino]-N-(2-pyrrolidin-1-yl-ethyl)-benzenesulfonamide HCl salt

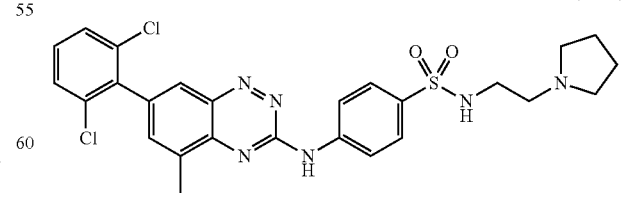

(CXV)

In a dry 25 mL round bottom flask, 7-(2,6-dichloro-phenyl)-5-methyl-benzo[1,2,4]triazin-3-ylamine (0.193 g, 0.633 mmol, 1 equiv), 4-bromo-N-(2-pyrrolidin-1-yl-ethyl)-benzenesulfonamide (0.316 g, 0.95 mmol, 1.5 equiv), cesium carbonate (0.62 g, 1.89 mmol, 3 equiv), 4,5-bis(diphenylphosphino)-9,9-dimethyl xanthene (0.073 g, 0.127 mmol, 0.2 equiv) and tris(dibenzylideneacetone) dipalladium (0.058 g, 0.0533 mmol, 0.1 equiv) were combined. The reactants were flushed with argon, diluted with dioxane (20 mL), and outfitted with a reflux condenser. The reaction was heated to reflux for 16 hours, then filtered hot and the solvents were evaporated. HPLC purification provided desired product. Pure HPLC fractions were combined, diluted with ethyl acetate and washed with saturated sodium bicarbonate solution. The organic phase was evaporated to dryness, diluted with DCM (10 mL) and treated with 2 mL 2M HCl in ether solution. The solvents were then evaporated and the resulting solids were collected and dried to yield a yellow solid (0.091 g, 26% yield). MS (ESI+): m/z=559.6, LC retention time: 2.71 min. $^1$H NMR (DMSO-d$_6$): δ 1.86 (bs, 2H), 1.98 (bs, 2H), 2.71 (s, 3H), 2.98-3.01 (m, 2H), 3.09-3.13 (m, 2H), 3.21-3.25 (m, 2H), 3.51-3.53 (m, 2H), 7.52 (m, 1H), 7.67 (d, J=8.7 Hz, 2H), 7.79 (m, 1H), 7.89 (dd, J=8.7 Hz, J=2.9 Hz, 1H), 7.95 (t, J=6.1 Hz, 1H), 8.18 (d, J=1.7 Hz, 1H), 8.26 (d, J=8.8 Hz, 2H), 10.37 (bs, 1H), 11.44 (s, 1H).

Example 111

Synthesis of 7-(2-chloro-5-methoxy-phenyl)-5-methyl-benzo[1,2,4]triazin-3-ylamine

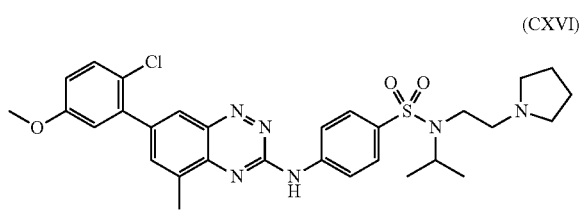 [SMILES: COc1ccc(Cl)c(-c2cc(C)c3nc(Nc4ccc(S(=O)(=O)N(CCN5CCCC5)C(C)C)cc4)nnc3c2)c1]

(CXVI)

In a dry 25 mL round bottom flask, 7-(2-chloro-5-methoxy-phenyl)-5-methyl-benzo[1,2,4]triazin-3-ylamine (0.214 g, 0.713 mmol, 1 equiv), 4-bromo-N-isopropyl-N-(2-pyrrolidin-1-yl-ethyl)-benzenesulfonamide (0.321 g, 0.856 mmol, 1.2 equiv), Cesium carbonate (0.698 g, 2.14 mmol, 3 equiv), 4,5-bis(diphenylphosphino)-9,9-dimethyl xanthene (0.083 g, 0.143 mmol, 0.2 equiv) and tris(dibenzylideneacetone) dipalladium (0.065 g, 0.071 mmol, 0.1 equiv) were combined. The reactants were flushed with argon, diluted with dioxane (20 mL), and outfitted with a reflux condenser. The reaction was heated to reflux for 18 hours, then cooled to room temperature and the solvents were removed. The residue was diluted with DCM and purified via ISCO silica gel column chromatography (0% to 6% methanol in chloroform as solvent system), yielding a yellow powder (0.265 g, 62% yield). MS (ESI+): m/z=597.7, LC retention time: 2.94 min. R$_f$=0.45 (10% MeOH: DCM).

Example 112

Synthesis of 4-[7-(2-chloro-5-hydroxy-phenyl)-5-methyl-benzo[1,2,4]triazin-3-ylamino]-N-isopropyl-N-(2-pyrrolidin-1-yl-ethyl)-benzenesulfonamide HCl salt

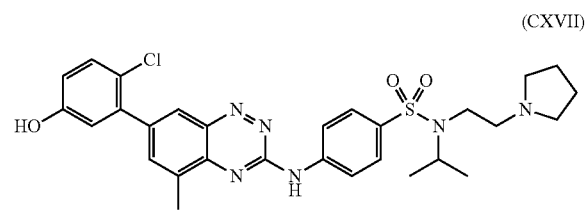 [SMILES: Cc1cc(-c2cc(O)ccc2Cl)cc2nnc(Nc3ccc(S(=O)(=O)N(CCN4CCCC4)C(C)C)cc3)nc12]

(CXVII)

7-(2-chloro-5-methoxy-phenyl)-5-methyl-benzo[1,2,4]triazin-3-ylamine (0.158 g, 0.527 mmol, 1 equiv) was diluted with 10 mL DCM and chilled to 0° C. using an ice bath. A 1.0 M solution of BBr$_3$ in DCM (3.16 mL, 3.16 mmol, 6.0 equiv) was then added in one portion resulting in a dark reaction mixture. The reaction was allowed to come to ambient temperature and stirred for 3.5 hours, then quenched by carefully pouring onto a saturated solution of sodium bicarbonate, followed by sonication for 3-5 minutes. Additional DCM was added and this mixture was washed with sodium bicarbonate followed by brine. The organic phase was separated, dried over sodium sulfate (Na$_2$SO$_4$), filtered and evaporated to dryness. The resulting solids were then diluted with minimum amount of ethyl acetate and precipitated out with hexanes. The product was filtered off and dried yielding a yellow solid (0.110 g, 73% yield). MS (ESI+): m/z=582.0, LC retention time: 2.57 min. $^1$H NMR (DMSO-d$_6$): δ 0.97 (d, J=6.7 Hz, 6H), 1.87 (m, 2H), 2.02 (m, 2H), 2.71 (s, 3H), 3.04 (m, 2H), 3.29-3.37 (m, 2H), 3.49 (m, 2H), 3.61 (m, 2H), 4.00 (m, 1H), 6.89 (dd, J=8.7 Hz, J=2.8 Hz, 1H), 6.96 (d, J=2.8 Hz, 1H), 7.40 (d, J=8.7 Hz, 1H), 7.91-7.94 (m, 3H), 8.21 (d, J=1.5 Hz, 1H), 8.26 (d, J=8.9 Hz, 2H), 10.0 (s, 1H), 11.17 (bs, 1H) 11.47 (s, 1H).

Example 113

Synthesis of 4-(4-bromo-benzenesulfonyl)-piperidine-1-carboxylic acid benzyl ester

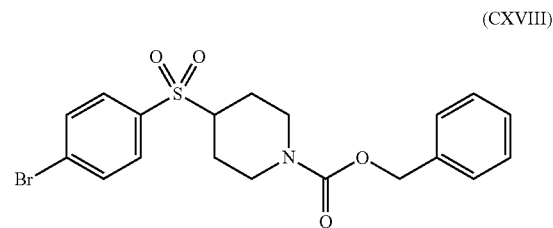 [SMILES: O=C(OCc1ccccc1)N1CCC(S(=O)(=O)c2ccc(Br)cc2)CC1]

(CXVIII)

4-(4-bromo-phenylsulfanyl)-piperidine-1-carboxylic acid benzyl ester (1.2 g, 2.96 mmol, 1 equiv) and sodium perborate tetrahydrate (NaBO$_3$.4H$_2$O) (1.36 g, 8.87 mmol, 3 equiv) were heated to 55° C. in HOAc and stirred for 18 h. The reaction was cooled to room temperature and poured onto water. The aqueous phase was extracted with EtOAc (3×100 mL). The organic phases were combined and washed carefully with saturated sodium bicarbonate solution (CAUTION: copious gas evolution), dried over sodium sulfate, filtered and evaporated to yield a white solid (1.2 g, 93% yield). $R_f$=0.16 (20% EtOAc/hexanes).

Example 114

Synthesis of 4-(4-bromo-phenylsulfanyl)-piperidine-1-carboxylic acid benzyl ester

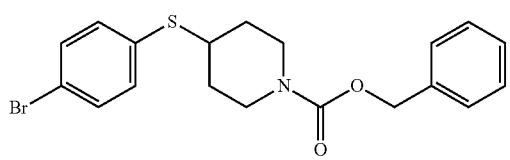
(CXIX)

4-bromo-benzenethiol (0.634 g, 3.36 mmol, 1 equiv), 4-bromo-piperidine-1-carboxylic acid benzyl ester (1 g, 3.36 mmol, 1 equiv) and cesium carbonate (2.18 g, 6.7 mmol, 2 equiv) were refluxed in acetone for 2 h. The reaction solvents were then removed and the resulting white solids were taken up in EtOAc and washed with water, then with brine. The organic phase was then dried over sodium sulfate, filtered and evaporated to yield clear oil (1.2 g, 88% yield). $R_f$=0.45 (20% EtOAc: Hexanes).

Example 115

Synthesis of 4-{4-[7-(2-chloro-5-methoxy-phenyl)-5-methyl-benzo[1,2,4]triazin-3-ylamino]-benzenesulfonyl}-piperidine-1-carboxylic acid benzyl ester

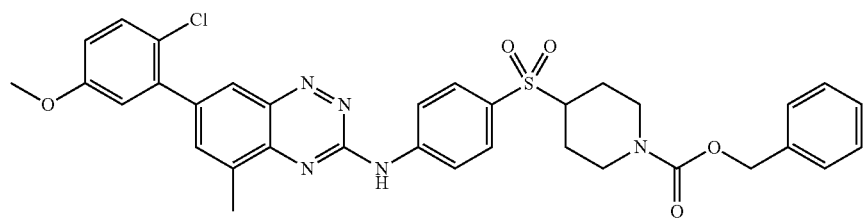
(CXX)

In a dry 25 mL round bottom flask, 7-(2-chloro-5-methoxy-phenyl)-5-methyl-benzo[1,2,4]triazin-3-ylamine (0.132 g, 0.44 mmol, 1 equiv), 4-(4-bromo-benzenesulfonyl)-piperidine-1-carboxylic acid benzyl ester (0.232 g, 0.529 mmol, 1.2 equiv), Cesium carbonate (0.432 g, 1.33 mmol, 3 equiv), 4,5-bis(diphenylphosphino)-9,9-dimethyl xanthene (0.051 g, 0.088 mmol, 0.2 equiv) and tris(dibenzylideneacetone) dipalladium (0.040 g, 0.044 mmol, 0.1 equiv) were combined. The reactants were flushed with argon, diluted with dioxane (12 mL) and outfitted with a reflux condenser. The reaction was heated to reflux for 18 hours, then cooled to room temperature and slowly diluted with water. The resulting precipitate was collected and dried yielding a yellow powder (0.271 g, 93% yield). MS (ESI+): m/z=658.2, LC retention time: 3.41 min.

Example 116

Synthesis of 4-chloro-3-{5-methyl-3-[4-(piperidine-4-sulfonyl)-phenylamino]-benzo[1,2,4]triazin-7-yl}-phenol HCl salt

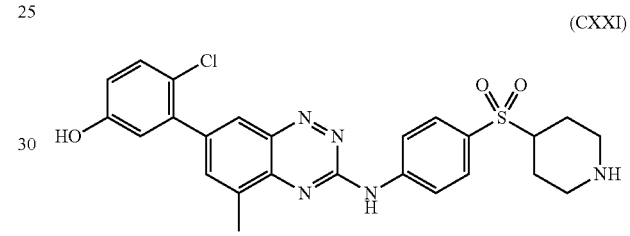
(CXXI)

4-{4-[7-(2-chloro-5-methoxy-phenyl)-5-methyl-benzo[1,2,4]triazin-3-ylamino]-benzenesulfonyl}-piperidine-1-carboxylic acid benzyl ester (0.165 g, 0.251 mmol, 1 equiv) was diluted with 15 mL DCM and chilled to 0° C. using an ice bath. A 1.0 M solution of BBr$_3$ in DCM (2.5 mL, 2.5 mmol, 10 equiv) was then added in one portion resulting in a dark reaction mixture. The reaction was allowed to come to ambient temperature and stirred for 3.5 hours, then quenched by carefully pouring onto a saturated solution of sodium bicarbonate followed by sonication for 3-5 minutes. The resulting solids were filtered off and dried. HPLC purification provided desired product as TFA salt in a form of a yellow solid (0.028 g, 22% yield). MS (ESI+): m/z=510.0, LC retention time: 2.27 min. $^1$H NMR (DMSO-d$_6$): δ 1.68-1.77 (m, 2H), 2.02-2.07 (m, 2H), 2.72 (s, 3H), 2.82-2.88 (m, 2H), 3.51-3.58 (m, 1H), 6.89 (dd, J=8.8 Hz, J=2.9 Hz, 1H), 6.95 (d, J=2.9 Hz, 1H), 7.41 (d, J=8.7 Hz, 1H), 7.88 (d, J=8.8 Hz, 2H), 7.93 (s, 1H), 8.22 (d, J=1.7 Hz, 1H), 8.33 (d, J=8.8 Hz, 2H), 10.01 (s, 1H), 11.56 (s, 1H).

Example 117

Synthesis of 1-[2-(4-bromo-phenylsulfanyl)-ethyl]-pyrrolidine

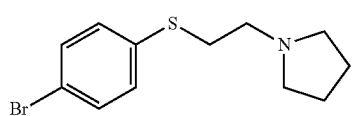

(CXXII)

4-bromo-benzenethiol (7.05 g, 37.3 mmol, 1 equiv), 1-(2-chloro-ethyl)-pyrrolidine hydrochloride (8.8 g, 52.2 mmol, 1.4 equiv) and cesium carbonate (26.8 g, 82.06 mmol, 2.2 equiv) were refluxed in acetone for 18 h. The reaction solvents were then evaporated, and the resulting residue was diluted with EtOAc and washed with water. The organic phase was then dried over sodium sulfate, filtered and evaporated to yield a pale brown oil (8 g, 75% yield). $R_f$=0.1 (40% EtOAc: Hexanes).

Example 118

Synthesis of [7-(2-chloro-5-methoxy-phenyl)-5-methyl-benzo[1,2,4]triazin-3-yl]-[4-(2-pyrrolidin-1-yl-ethylsulfanyl)-phenyl]-amine

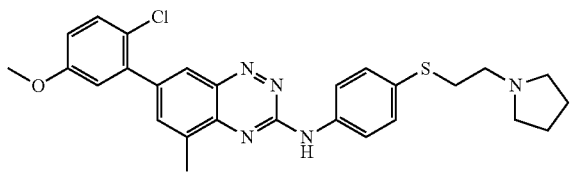

(CXXIII)

In a dry 25 mL round bottom flask, 7-(2-chloro-5-methoxy-phenyl)-5-methyl-benzo[1,2,4]triazin-3-ylamine (0.625 g, 2.08 mmol, 1 equiv), 1-[2-(4-bromo-phenylsulfanyl)-ethyl]-pyrrolidine (0.894 g, 3.12 mmol, 1.5 equiv), cesium carbonate (2.04 g, 6.25 mmol, 3 equiv), 4,5-bis(diphenylphosphino)-9,9-dimethyl xanthene (0.24 g, 0.417 mmol, 0.2 equiv) and tris(dibenzylideneacetone) dipalladium (0.19 g, 0.208 mmol, 0.1 equiv) were combined. The reactants were flushed with argon, diluted with dioxane (12 mL), outfitted with reflux condenser and heated to reflux for 16 hours. The reaction was then filtered and the solvents were removed. The residue was taken up in minimum amount of DCM (ca. 5 mL) and precipitated out with excess hexanes. The resulting precipitate was collected and dried. 0.5 g of this crude product was taken on and purified by ISCO silica gel chromatography to afford product as an orange solid (0.224 g, 22% yield). MS (ESI+): m/z=506.1, LC retention time: 2.91 min.

Example 119

Synthesis of 4-chloro-3-{5-methyl-3-[4-(2-pyrrolidin-1-yl-ethylsulfanyl)-phenylamino]-benzo[1,2,4]triazin-7-yl}-phenol TFA salt

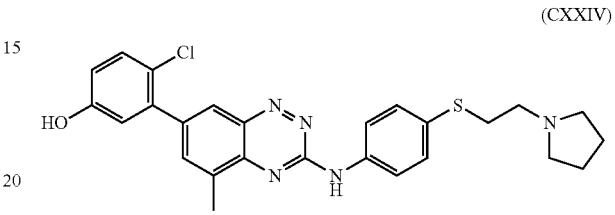

(CXXIV)

[7-(2-chloro-5-methoxy-phenyl)-5-methyl-benzo[1,2,4]triazin-3-yl]-[4-(2-pyrrolidin-1-yl-ethylsulfanyl)-phenyl]-amine (0.22 g, 0.435 mmol, 1 equiv) was diluted with 20 mL DCM and chilled to 0° C. using an ice bath. A 1.0 M solution of BBr$_3$ in DCM (3.4 mL, 3.5 mmol, 10 equiv) was then added in one portion resulting in a dark reaction mixture. The reaction was allowed to come to ambient temperature and stirred for 3.5 hours, then quenched by carefully pouring onto a saturated solution of sodium bicarbonate followed by sonication for 5 minutes. The resulting solids were filtered off and dried. HPLC purification provided desired product as TFA salt in a form of an orange solid (0.088 g, 41% yield). MS (ESI+): m/z=492.1, LC retention time: 2.52 min. $^1$H NMR (DMSO-d$_6$): δ 1.83-1.86 (m, 2H), 1.98-2.01 (m, 2H), 2.67 (s, 3H), 3.01-3.05 (m, 2H), 3.23-3.26 (m, 2H), 3.31-3.35 (m, 2H), 3.57-3.58 (m, 2H), 6.88 (dd, J=8.8 Hz, J=2.9 Hz, 1H), 6.93 (d, J=2.9 Hz, 1H), 7.41 (d, J=8.7 Hz, 1H), 7.51 (d, J=8.8 Hz, 2H), 7.87 (s, 1H), 8.07 (d, J=8.8 Hz, 2H), 8.17 (d, J=1.7 Hz, 1H), 9.64 (bs, 1H), 9.95 (bs, 1H), 11.11 (s, 1H).

Example 120

Synthesis of 4-(3-(4-(2-(pyrrolidin-1-yl)ethoxy)phenylamino)-5-methylbenzo[e][1,2,4]triazin-7-yl)-3,5-dimethylphenol

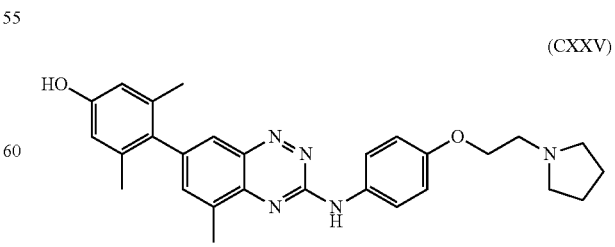

(CXXV)

The title compound was synthesized as shown by the reaction scheme (CXXVI).

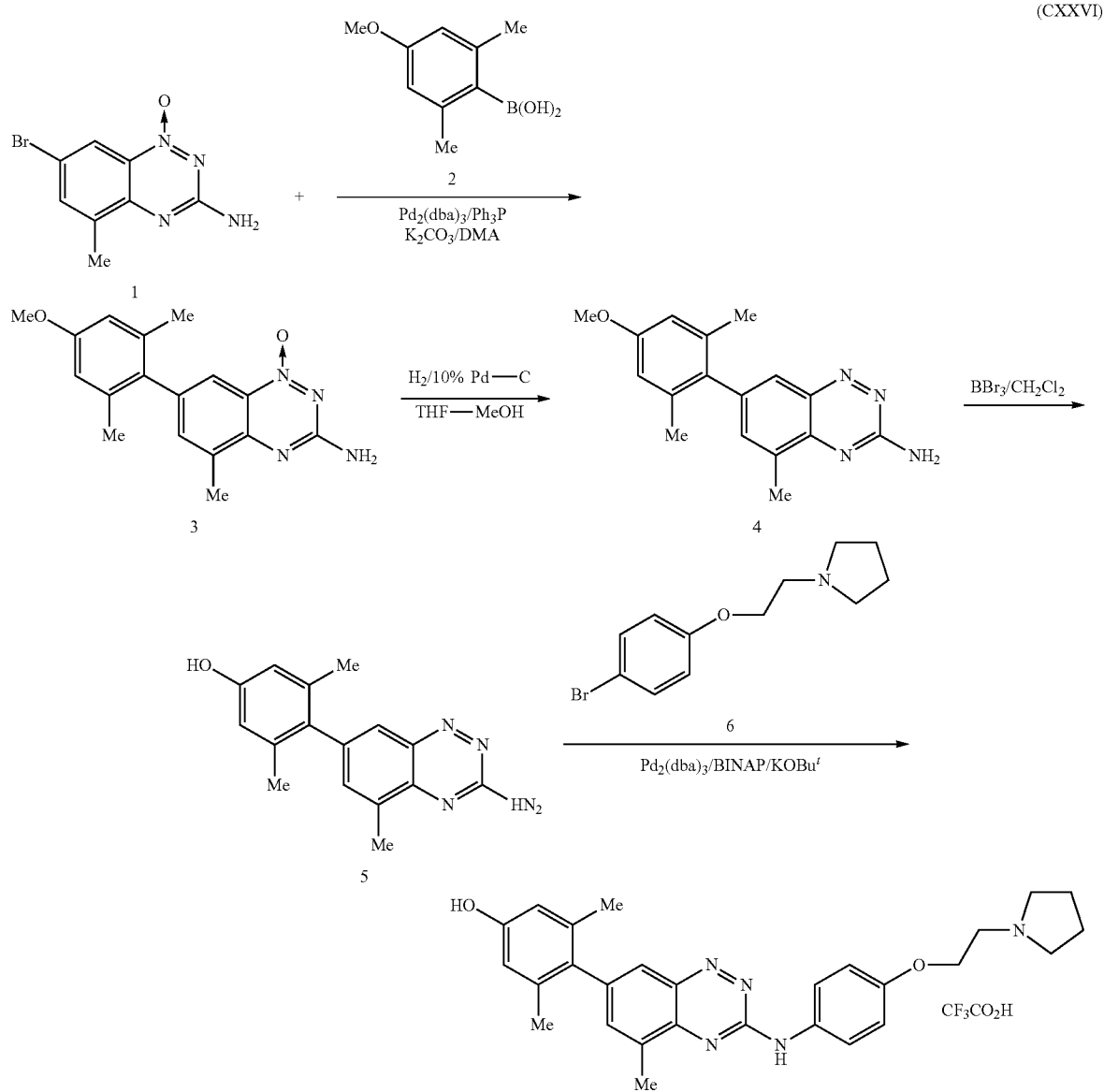

(CXXVI)

To a solution of the 7-bromo-5-methylbenzo[1,2,4]triazin-3-yl-amine-1-oxide 1 shown on scheme (CCXXVI) (100 mg, 0.39 mmol) in N,N-dimethylacetamide (6 mL) was added a solution of 4-methoxy-2,6-dimethylphenylboronic acid 2 (210 mg, 1.17 mmol) in EtOH (1 mL), a solution of $K_2CO_3$ (90 mg, 0.65 mmol) in $H_2O$ (1 mL), tris(dibenzylideneacetone)dipalladium [0] ($Pd_2(dba)_3$, 9 mg, 0.01 mmol), and $PPh_3$ (9 mg, 0.034 mmol). The suspension was heated under reflux for 18 h. The cold reaction mixture was poured into saturated $NaHCO_3$ and $CH_2Cl_2$ was used to extract the product. The crude product was purified by chromatography ($SiO_2$/Hexane:EtOAc=1:1) to afford 3 as yellow solid. The 3 was reduced to 4 by hydrogenation, as shown by scheme (CCXXVI). To a solution of 4 in $CH_2Cl_2$ was added 1.0 M $BBr_3$ in $CH_2Cl_2$ (1 mL, 1 mmol). The mixture was stirred overnight at room temperature. The saturated $NaHCO_3$ was added and the organic layer was separated. The aqueous layer was extracted with $CH_2Cl_2$ (3×10 mL). The combined organic solution was dried ($MgSO_4$) to afford 5.

As further shown by scheme (CCXXVI), to a suspension of 5 in dry PhMe (1 mL) was added 1-(2-(4-bromophenoxy)ethyl)pyrrolidine 6 (44.4 mg, 0.16 mmol), rac-2,2'-bis(diphenyl-phosphino)-1,1'-binaphthyl (BINAP, 8 mg, 0.012 mmol), $Pd_2(dba)_3$ (4 mg, 0.004 mmol), and KOBut (38 mg, 0.33 mmol). The mixture was heated under reflux for 48 h under argon. The solid was filtered off and washed with PhMe. The product was purified by preparative HPLC (Symmetry Shield-C18, 200×40 mm, 7 μm, starting from 30% solvent A (0.1% TFA in $H_2O$) to 100% solvent B (0.1% TFA in MeCN), flow rate 40 ml/min, λ=282 nm). Fractions containing the products were combined to yield the title product (CXXV) as its TFA salt (1.3 mg, 3%). $^1$H NMR ($CDCl_3$): δ 2.02-2.04 (m, 2H); 2.12-2.17 (m, 2H); 2.93 (s, 3H); 3.01 (s, 6H); 3.59-3.61 (m, 2H); 3.94-4.00 (m, 4H); 4.40 (t, J=4.9 Hz, 2H); 6.65 (s, 1H); 7.30 (s, 1H); 7.48 (d, J=7.9 Hz, 2H); 7.61 (s, 1H); 8.06 (s, 1H); 8.09 (d, J=7.9 Hz, 1H); 8.92 (br, 1H). MS (ESI+): m/z=470.3.

Example 121
Synthesis of [7-(3,5-dimethyl-isoxazol-4-yl)-5-methyl-benzo[1,2,4]triazin-3-yl]-(4-methoxy-phenyl)-amine
(CXXVII)
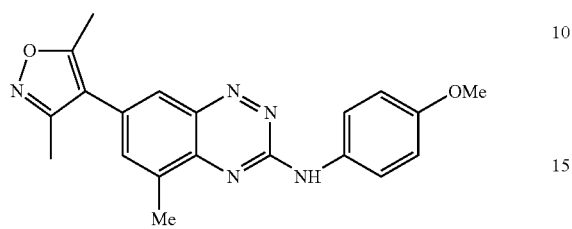
The reaction scheme (CXXVIII) includes an illustration of the synthesis of the title compound.
(CXXVIII)
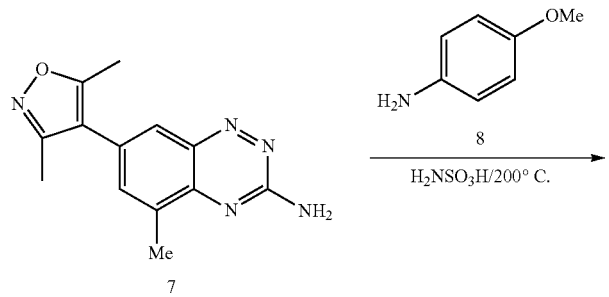
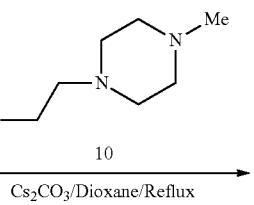

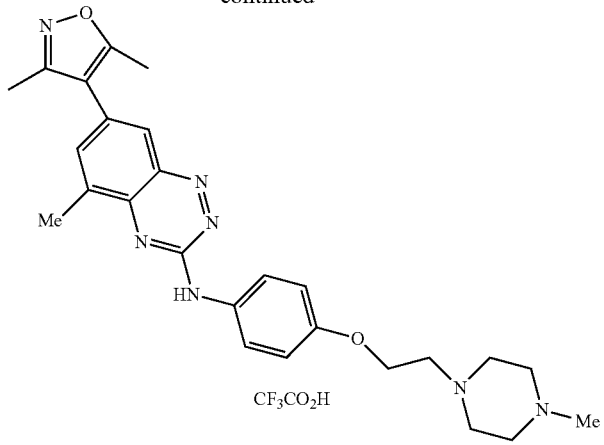

The mixture of 5-methyl-7-(3,5-dimethylisoxazol-4-yl)benzo[e][1,2,4]triazin-3-amine (compound 7 on scheme (CXXVIII)) (107 mg, 0.42 mmol), sulfamic acid (81.4 mg, 0.84 mmol), and 4-methoxybenzenamine 8 (774 mg, 6.3 mmol) was heated at 180° C. overnight. The product was purified by chromatography (SiO$_2$/CH$_2$Cl$_2$) and the title product (48.7 mg, 32%) was obtained as a yellow solid. $^1$H NMR (CD$_2$Cl$_2$): δ 2.34 (s, 3H); 2.49 (s, 3H); 2.70 (s, 3H); 3.84 (s, 3H); 6.99 (d, J=8.9 Hz, 2H); 7.57 (s, 1H); 7.83 (d, J=8.9 Hz, 2H); 8.03 (s, 1H); 8.10 (br, 1H). MS (ESI+): m/z=362.1.

Example 122

Synthesis of [7-(3,5-dimethyl-isoxazol-4-yl)-5-methyl-benzo[1,2,4]triazin-3-yl]-{4-[2-(4-methyl-piperazin-1-yl)-ethoxy]-phenyl}-amine (CXXIX)

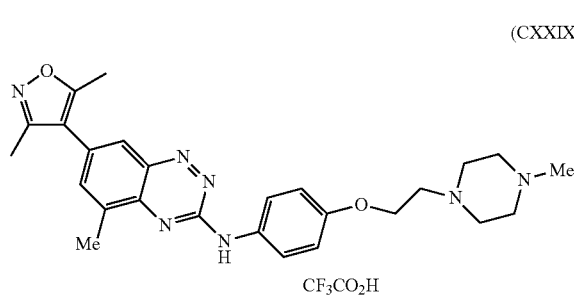 [SMILES: Cc1noc(C)c1-c1cc(C)c2nc(Nc3ccc(OCCN4CCN(C)CC4)cc3)nnc2c1 ; "CF3CO2H"]

The synthesis of the title compound is also illustrated by the reaction scheme (CXXVIII). Compound (CXXVII) obtained as described in Example 121 (48.7 mg, 0.13 mmol) was demethylated by using BBr$_3$/CH$_2$Cl$_2$ to obtain compound 9 shown by the scheme (CXXVIII) (46 mg, 99%). To a solution of 9 (18.8 mg, 0.054 mmol) in anhydrous 1,4-dioxane (10 mL) was added Cs$_2$CO$_3$ (176 mg, 0.54 mmol), and 1-(2-bromoethyl)-4-methylpiperazine 10 shown by the scheme (CXXVIII) (40 mg, 0.11 mmol). The mixture was heated under reflux overnight. The product was purified by preparative HPLC (Symmetry Shield-C18, 200×40 mm, 7 μm, starting from 30% solvent A (0.1% TFA in H$_2$O) to 100% solvent B (0.1% TFA in MeCN), flow rate 40 ml/min, λ=288 nm). Fractions containing the products were combined. The title compound was obtained (0.8 mg, 3%) as its TFA salt. $^1$H NMR (CD$_2$Cl$_2$): δ 2.24 (s, $^3$H); 2.39 (s, 3H); 2.61 (s, 3H); 2.73 (s, 3H); 3.17 (t, J=4.5 Hz, 2H); 3.25-3.40 (m, 8H); 4.20 (t, J=4.5 Hz, 2H); 6.91 (d, J=9.0 Hz, 2H); 7.48 (s, 1H); 7.75 (d, J=9.0 Hz, 2H); 7.94 (s, 1H). MS (ESI+): m/z=474.2.

Example 123

Synthesis of 3-(5-methyl-7-(2,6-dimethylphenyl)benzo[e][1,2,4]triazin-3-ylamino)benzene-sulfonamide (CXXX)

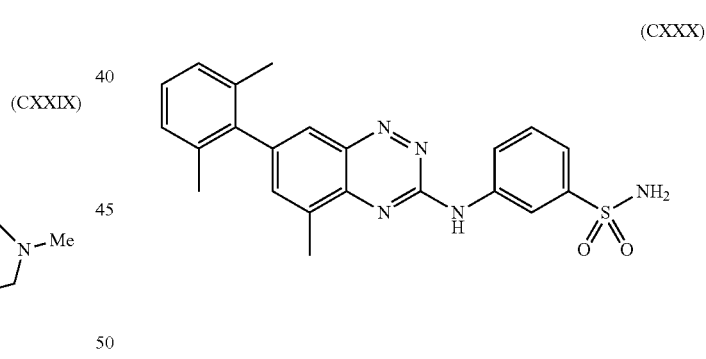

The title compound was synthesized as shown by the reaction scheme (CXXXI).

(CXXXI)

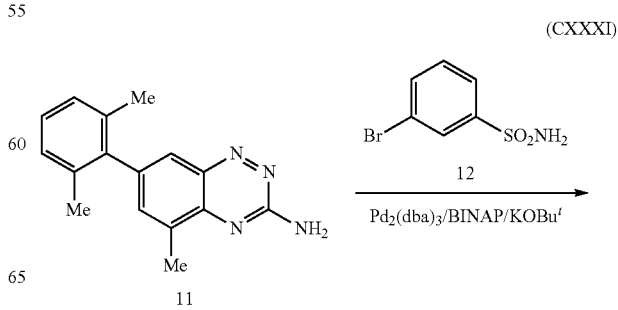

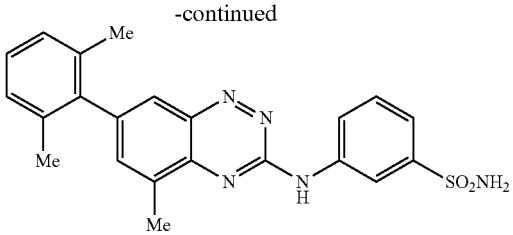

To a suspension of compound 11 shown on scheme (CXXXI) (200 mg, 0.75 mmol) in dry PhMe (5 mL) was added 3-bromobenzenesulfonamide 12 (268 mg, 1.13 mmol), rac-2,2'-bis(diphenylphosphino)-1,1'-binaphthyl (BINAP, 141 mg, 0.23 mmol), Pd$_2$(dba)$_3$ (69 mg, 0.075 mmol), and KOBut (170 mg, 1.51 mmol). The mixture was heated under reflux for 20 h. The solid was filtered off and washed with PhMe. The product was purified by preparative HPLC (Symmetry Shield-C18, 200×40 mm, 7 μm, starting from 30% solvent A (0.1% TFA in H$_2$O) to 100% solvent B (0.1% TFA in MeCN), flow rate 40 ml/min, λ=288 nm). Fractions containing the products were combined. The title compound was obtained (10.4 mg, 3%) as its TFA salt. $^1$H NMR (DMSO-d$^6$): δ 2.06 (s, 6H); 2.71 (s, 3H); 7.19 (d, J=7.3 Hz, 2H); 7.24 (m, 1H); 7.35 (br, 2H); 7.53 (d, J=7.9 Hz, 1H); 7.60 (t, J=7.9 Hz, 1H); 7.65 (s, 1H); 7.97 (s, 1H); 8.05 (d, J=7.9 Hz, 1H); 8.85 (s, 1H); 11.24 (s, 1H). MS (ESI+): m/z=420.1.

Example 124

Synthesis of 3-(5-methyl-7-(2,6-dimethylphenyl)benzo[e][1,2,4]triazin-3-ylamino)-N-(2-pyrrolidin-1-yl)ethyl)benzenesulfonamide hydrochloride (CXXXII)

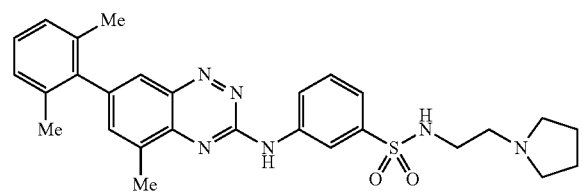

The title compound was synthesized as shown by the reaction scheme (CXXXIII).

(CXXXIII)

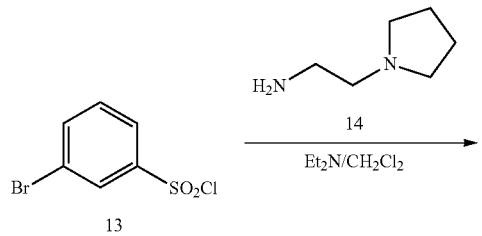

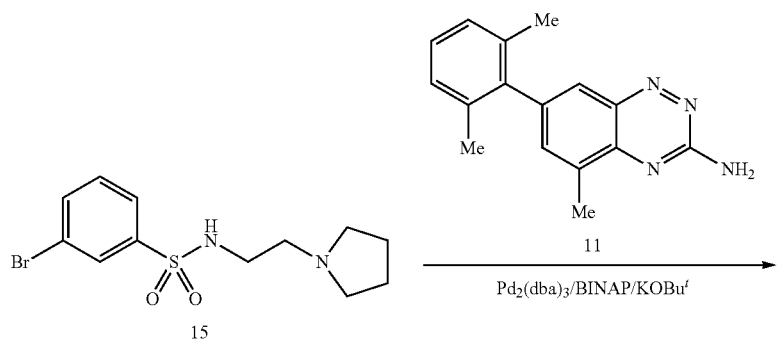

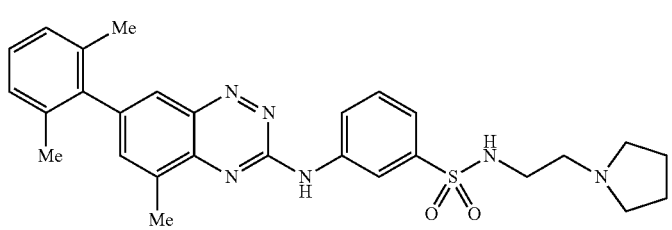

To a solution of 3-bromobenzenesulfonyl chloride 13 shown on scheme (CXXXIII) (930 mg, 3.7 mmol) in anhydrous $CH_2Cl_2$ (10 mL) was added 2-(pyrrolidin-1-yl)ethanamine 14 (840 mg, 7.32 mmol) and $Et_3N$ (1.85 g, 18.3 mmol). The mixture was stirred 24 h at room temperature. Saturated $NaHCO_3$ (50 mL) was added and organic layer was separated and washed with brine (3×20 mL), dried ($Na_2SO_4$). The solvent was removed and product 15 shown on scheme (CXXXIII) was obtained as a colorless oil.

The title compound was prepared by a method that was analogous to that used to synthesize compound (CXXX) (Example 123) using compounds 15 (780 mg, 2.54 mmol) and 11 (447 mg, 1.69 mmol) to give the title compound (260 mg, 31%) as a orange solid. $^1$H NMR ($CD_2Cl_2$): δ 1.57-163 (m, 4H); 2.10 (s, 6H); 2.29 (br, 4H); 2.50 (t, J=5.9 Hz, 2H); 2.80 (s, 3H); 3.04 (t, J=5.6 Hz, 2H); 7.17 (d, J=7.7 Hz, 2H); 7.21-7.24 (m, 1H); 7.57-7.60 (m, 3H); 8.03 (s, 2H); 8.87 (br, 1H); 8.97 (s, 1H). MS (ESI+): m/z=517.4.

Example 125

Synthesis of 3-(5-methyl-7-(2,6-dimethylphenyl)benzo[e][1,2,4]triazin-3-ylamino)-N-(2-(dimethylamino)ethyl)benzenesulfonamide hydrochloride (CXXXIV)

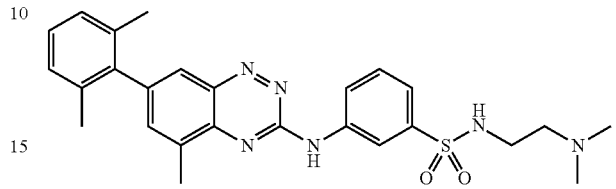

The title compound was synthesized as shown by the reaction scheme (CXXXV).

(CXXXV)

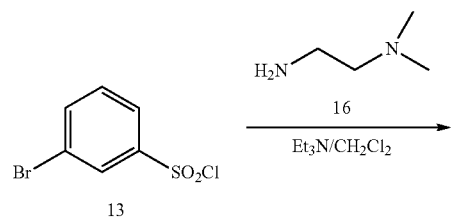

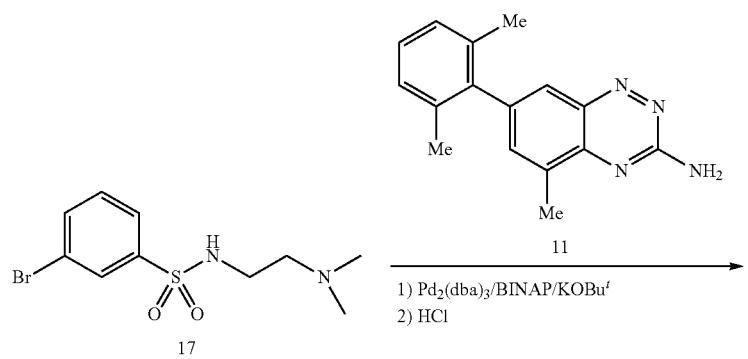

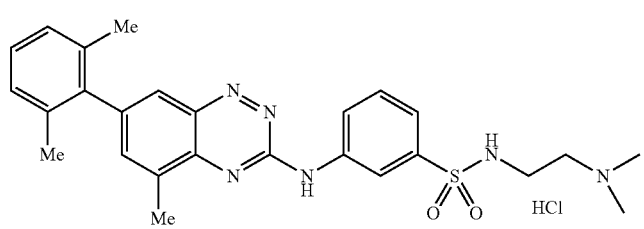

Compound 17 shown on scheme (CXXXV) was prepared by a method that was analogous to that used for preparation of compound 15 shown on scheme (CXXXIII), except compounds 16 (700 mg, 7.9 mmol) and 13 (1.2 g, 3.9 mmol) were used to yield the compound 17 (1.2 g, 99%) as a colorless oil. The title compound (CXXXIV) was prepared by a method that was analogous to that used to synthesize compound (CXXX) (Example 123), except compounds 17 (840 mg, 2.53 mmol) and 11 (450 mg, 1.69 mmol) were used, as shown by scheme (CXXXV), to give title compound (CXXXIV) (260 mg, 31%) as a orange solid. $^1$H NMR (CD$_2$Cl$_2$): δ 2.11 (s, 6H); 2.84 (s, 9H); 3.30 (br, 2H); 3.59 (br, 2H); 7.15-7.18 (m, 3H); 7.21-7.24 (m, 1H); 7.45 (d, J=7.6 Hz, 1H); 7.56 (s, 1H); 7.84-7.86 (m, 2H); 7.93 (s, 1H); 9.06 (s, 1H); 9.37 (s, 1H); 11.87 (br, 1H). MS (ESI+): m/z=491.3.

Example 126

Synthesis of 2-(5-methyl-7-(2,6-dimethylphenyl)benzo[e][1,2,4]triazin-3-ylamino)-N-(2-(pyrrolidin-1-yl)ethyl)thiazole-4-carboxamide (CXXXVI)

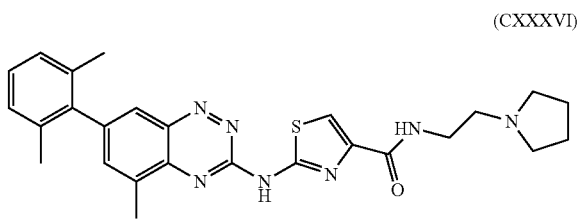 [SMILES: Cc1cccc(C)c1-c1cc(C)c2nc(Nc3nc(C(=O)NCCN4CCCC4)cs3)nnc2c1]

The title compound was synthesized as shown by the reaction scheme (CXXXVII).

(CXXXVII)

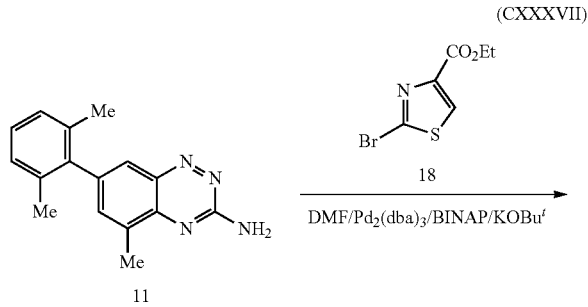

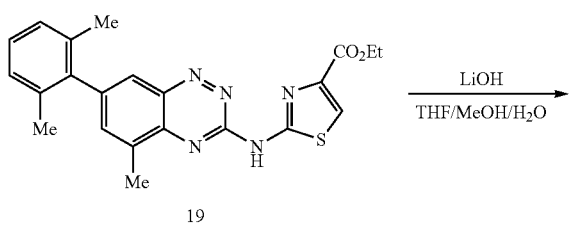

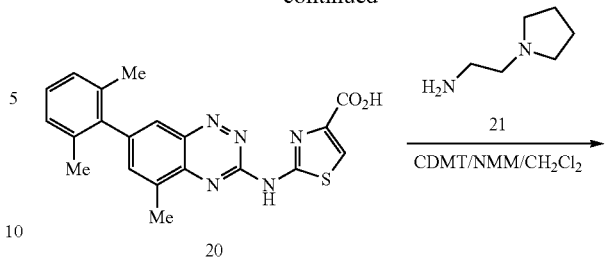

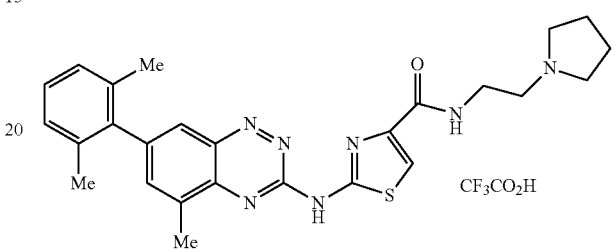

To a solution of 11 shown by scheme (CXXXVII) (646 mg, 2.44 mmol) in dry DMF (20 mL) was added ethyl 2-bromothiazole-4-carboxylate 18 (750 mg, 3.17 mmol), rac-2,2'-bis(diphenylphosphino)-1,1'-binaphthyl (BINAP, 304 mg, 0.48 mmol), Pd$_2$(dba)$_3$ (223 mg, 0.24 mmol), and Cs$_2$CO$_3$ (1.6 g, 4.88 mmol). The mixture was heated under reflux for 20 h. The solid was filtered off and washed with DMF. The filtrate was concentrated. The residue was dissolved in CH$_2$Cl$_2$ and washed with brine (3×100 mL). The crude product ethyl 2-(5-methyl-7-(2,6-dimethylphenyl)benzo[e][1,2,4]triazin-3-ylamino)thiazole-4-carboxylate 19 was dissolved in MeOH (10 mL) and THF (10 mL), followed by adding solution of LiOH (586 mg, 24.4 mmol) in H$_2$O (10 mL). The mixture was heated at 60° C. for 2 h. The solvent was removed in vacuo. The product was purified using chromatography (SiO$_2$/CH$_2$Cl$_2$:MeOH:NH$_3$.H$_2$O=100:10:2.5 and then 100:100:50). 2-(5-methyl-7-(2,6-dimethylphenyl)benzo[e][1,2,4]triazin-3-ylamino)thiazole-4-carboxylic acid (750 mg, 78%) (compound 20 shown by scheme (CXXXVII)) was obtained as an orange solid.

The synthesis was continued by dissolving compound 20 (400 mg, 1.02 mmol) in anhydrous CH$_2$Cl$_2$ (20 mL), followed by adding 2-chloro-4,6-dimethoxy-1,3,5-trizine (CDMT, 198 mg, 1.12 mmol) and 4-methylmorpholine (NMM, 0.23 mL, 2.04 mmol). The mixture was stirred at room temperature for 0.5 h, followed by adding 2-(pyrrolidin-1-yl)ethanamine 21 (198 mg, 1.12 mmol). The reaction was stirred at room temperature overnight. The solid was filtered off and washed with CH$_2$Cl$_2$. The filtrate was washed with saturated NaHCO$_3$ (1×50 mL) and then brine (2×50 mL). The organic solution was dried (Na$_2$SO$_4$).

The product was purified by preparative HPLC (Symmetry Shield-C18, 200×40 mm, 7 μm, starting from 30% solvent A (0.1% TFA in H$_2$O) to 100% solvent B (0.1% TFA in MeCN), flow rate 40 ml/min, λ=282 nm). Fractions containing the products were combined. The title product (CXXXVI) was obtained (110 mg, 20%) as its TFA salt. $^1$H NMR (DMSO-d$^6$): δ 1.86-1.89 (m, 2H); 2.02-2.05 (m, 2H); 2.05 (s, 6H); 2.80 (s, 3H); 3.05-3.09 (m, 2H); 3.35-3.38 (m, 2H); 3.64-3.67 (m, 4H); 7.20 (d, J=7.7 Hz, 2H); 7.24-7.27 (m, 1H); 7.78 (s, 1H);

7.97 (s, 1H); 8.10 (s, 1H); 8.25 (t, J=6.1 Hz, 1H); 9.42 (br, 1H); 12.56 (s, 1H). MS (ESI+): m/z=488.2.
Example 127
Synthesis of 3-(5-methyl-7-(2,6-dimethylphenyl)benzo[e][1,2,4]triazin-3-ylamino)-N-methyl-N-(2-(pyrrolidin-1-yl)ethyl)benzenesulfonamide hydrochloride
(CXXXVIII)
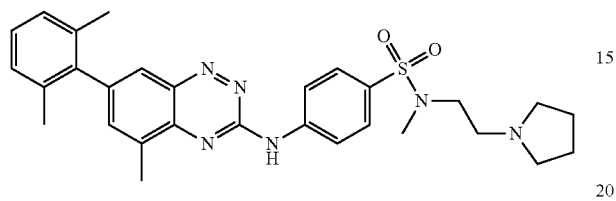
The title compound was synthesized as shown by the reaction scheme (CXXXIX).
(CXXXIX)
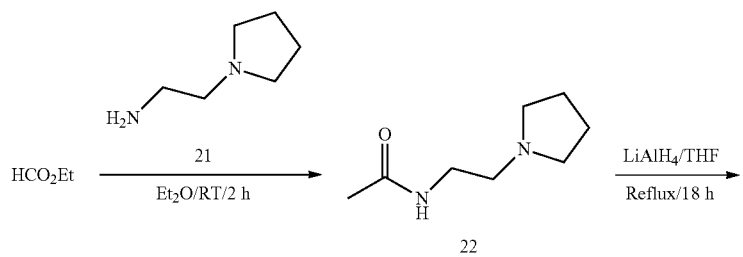
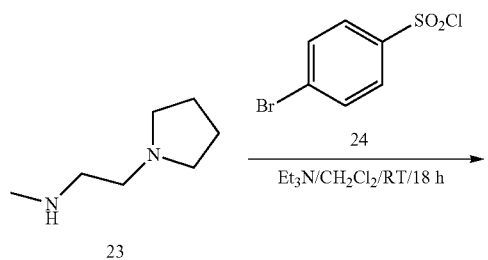
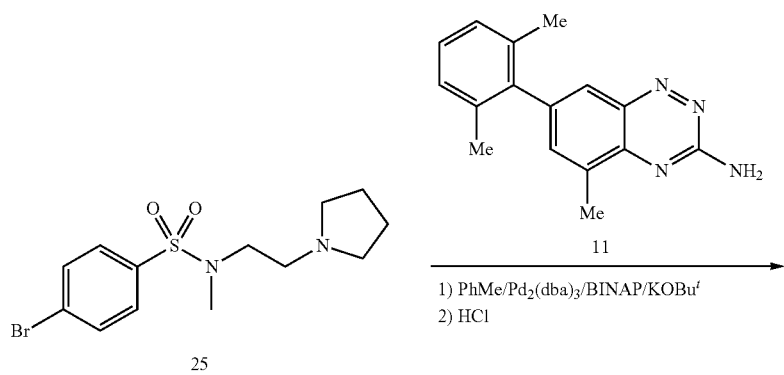

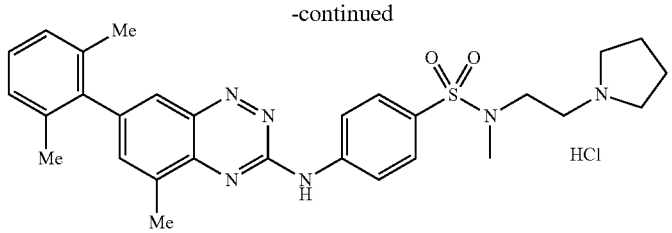

To a solution of ethyl formate (10 mL) in anhydrous Et$_2$O was added compound 21 as shown on scheme (CXXXIX) (2 mL). The solution was stirred at room temperature for 2 h. The solvent was removed in vacuo, followed by adding 1.0 M LiAlH$_4$ in THF (5 mL). The mixture was heated under reflux overnight and cooled. Water was then added slowly. The solid was filtered off and washed with THF. The filtrate was concentrated and remained aqueous, and was extracted with Et$_2$O (3×20 mL) and dried (Na$_2$SO$_4$). The solvent was removed and the residue was dissolved in CH$_2$Cl$_2$ (10 mL), followed by adding 4-bromobenzenesulfonyl chloride 24 (1.2 g, 4.72 mmol) and Et$_3$N (3 mL). The mixture was stirred at room temperature for 3 hours, then saturated NaHCO$_3$ (100 mL) was added. The organic layer was separated and the aqueous was extracted with CH$_2$Cl$_2$ (2×10 mL). Combined organic solution was dried (Na$_2$SO$_4$). The solvent was removed in vacuo and afforded compound 25 shown on scheme (CXXXIX) as a yellow oil.

The title compound (CXXXVIII) was prepared by using a method that was analogous to that used to synthesize compound (CXXX) (Example 123) except compounds 25 (600 mg, 1.72 mmol) and 11 (351 mg, 1.33 mmol) were used to give title compound (CXXXVIII) (276 mg, 37%) as its HCl salt. $^1$H NMR (DMSO-d$^6$): δ 1.88-1.91 (m, 2H); 2.02-2.05 (m, 2H); 2.06 (s, 6H); 2.72 (s, 3H); 2.74 (s, 3H); 3.05-3.09 (m, 2H); 3.30-3.38 (m, 4H); 3.58-3.61 (m, 2H); 7.19 (d, J=7.3 Hz, 2H); 7.23-7.26 (m, 1H); 7.70 (s, 1H); 7.86 (d, J=8.9 Hz, 2H); 8.01 (s, 1H); 8.31 (d, J=8.9 Hz, 2H); 10.18 (br, 1H); 11.47 (s, 1H). MS (ESI+): m/z=531.3.

Example 128

Synthesis of [7-(2,6-dimethyl-phenyl)-5-nitro-1-oxy-benzo[1,2,4]triazin-3-yl]-[4-(2-pyrrolidin-1-yl-ethoxy)-phenyl]-amine

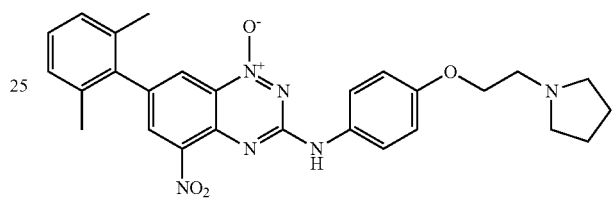

(CXL)

The title compound was synthesized as shown by the reaction scheme (CXLI). The intermediate compounds 27 and 28 shown on scheme (CXLI) had the following spectral characteristics:

Compound 27: $^1$H NMR (DMSO-d$^6$): δ 7.30 (d, J=8.8 Hz, 1H); 7.97 (dd, J=8.8 Hz, J=2.0 Hz, 1H); 8.25 (d, J=2.0 Hz, 1H). MS (ESI+): m/z=241. Compound 28: $^1$H NMR (DMSO-d$^6$): δ 8.22 (d, J=2.3 Hz, 1H); 8.27 (d, J=2.3 Hz, 1H). MS (ESI+): m/z=286.

(CXLI)

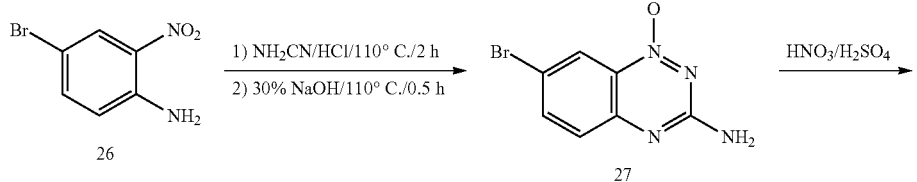

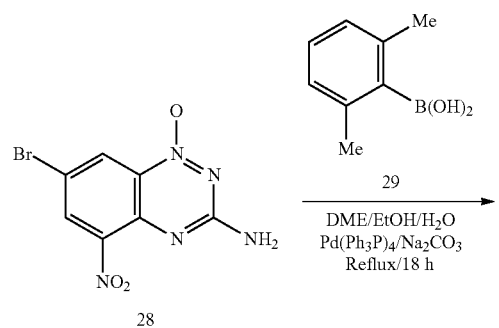

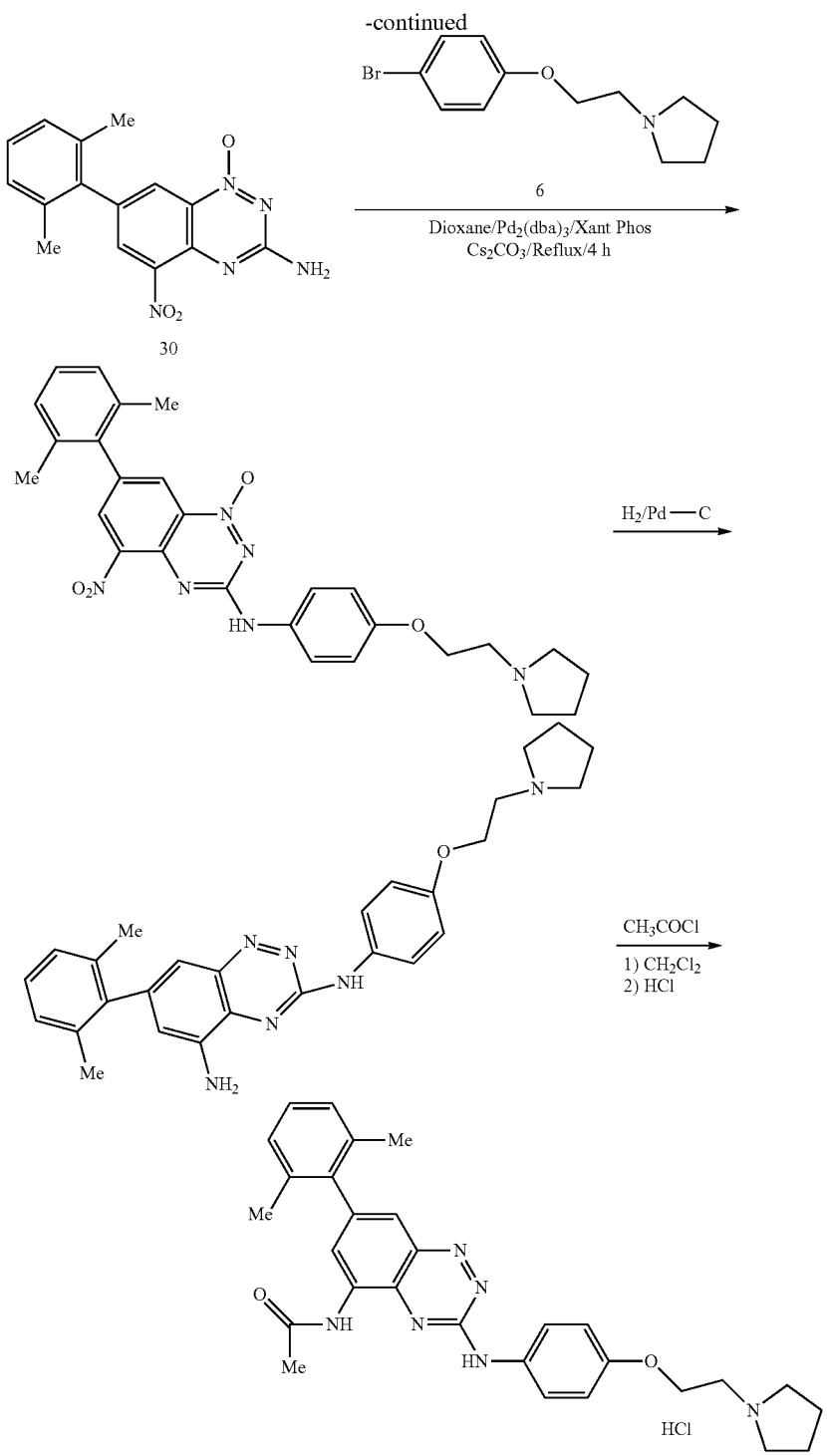

To a solution of compound 28 (500 mg, 1.75 mmol) in 1,2-dimethoxyethane (DME, 20 mL) was added solution of compound 29 (526 mg, 3.5 mmol) in EtOH (2 mL), solution of $Na_2CO_3$ (750 mg, 7.0 mmol) in $H_2O$ (2 mL), and $Pd(PPh_3)_4$ (202 mg, 0.2 mmol), as shown by scheme (CXLI). The mixture was heated under reflux overnight. The solid was filtered off and washed with EtOAc. The filtrate was washed with brine (1×100 mL). The organic solution was separated and dried ($Na_2SO_4$). The product was purified by chromatograph (($SiO_2$/Hexane:EtOAc=1:1) to yield compound 30 (450 mg, 82%) as a yellow solid.

To a solution of 30 (450 mg, 1.45 mmol) in 1,4-dioxane (20 mL) were added compound 6 (586 mg, 2.17 mmol), $Cs_2CO_3$ (1.90 g, 5.8 mmol), $Pd_2(dba)_3$ (133 mg, 0.14 mmol), and 4,5-bis(diphenylphosphino)-9,9-dimethyxanthene (Xant Phos, 251 mg, 0.43 mmol). The mixture was heated under reflux for 4 h under Ar. The solid was filtered off and washed with brine (1×100 mL). The organic solution was separated and dried ($Na_2SO_4$). The solvent was removed until 5 mL and hexane (50 mL) was added, the solid was collected by filtration. The crude product was purified by chromatograph (SiO$_2$/CH$_2$Cl$_2$, then CH$_2$Cl$_2$:MeOH:NH$_3$.H$_2$O=100:10:2.5) and afforded the title compound (CXL) (124 mg, 17%). $^1$H NMR (CD$_2$Cl$_2$): δ 1.82 (br, 4H); 2.08 (s, 6H); 2.69 (br, 4H); 2.95 (br, 2H); 4.16 (t, J=5.5 Hz, 2H); 6.99 (d, J=7.1 Hz, 2H); 7.17 (d, J=7.5 Hz, 2H); 7.24-7.27 (m, 1H); 7.52 (br, 1H); 7.72 (d, J=7.1 Hz, 2H); 8.13 (d, J=1.9 Hz, 1H); 8.35 (d, J=1.9 Hz, 1H). MS (ESI+): m/z=501.3.

Example 129

Synthesis of 7-(2,6-dimethyl-phenyl)-N3-[4-(2-pyrrolidin-1-yl-ethoxy)-phenyl]-benzo[1,2,4]triazine-3,5-diamine

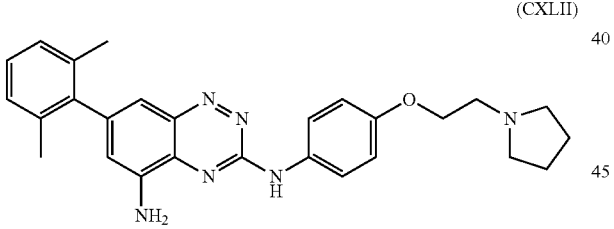

(CXLII)

Compound (CXL) synthesized as described in Example 128 was hydrogenated (scheme (CXLI)) to afford the title compound (CXLII) (yield, 73%). $^1$H NMR (CD$_2$Cl$_2$): δ 1.84 (br, 4H); 2.10 (s, 6H); 2.75 (br, 4H); 2.99 (br, 2H); 4.16 (t, J=4.25 Hz, 2H); 4.78 (br, 2H); 6.80 (d, J=1.6 Hz, 1H); 6.99 (d, J=6.9 Hz, 2H); 7.13 (d, J=7.6 Hz, 2H); 7.17-7.20 (m, 1H); 7.42 (d, J=1.6 Hz, 1H); 7.71 (d, J=6.9 Hz, 2H); 7.96 (br, 1H). MS (ESI+): m/z=455.4.

Example 130

Synthesis of N-(3-(4-(2-(pyrrolidin-1-yl)ethoxy) phenylamino)-7-(2,6-dimethylphenyl)benzo[e][1,2,4]triazin-5-yl)acetamide hydrochloride

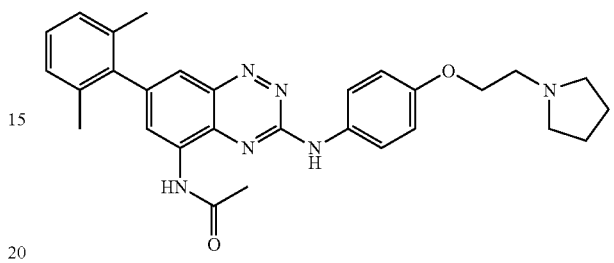

(CXLIII)

To a solution of compound (CXLII) obtained as described in Example 129 (122 mg, 0.27 mmol) in anhydrous CH$_2$Cl$_2$ (5 mL) was added acetyl chloride (25 mg, 0.32 mmol). The solution was stirred at RT for 0.5 h and solvent was removed in vacuo. The residue was dissolved in CH$_2$Cl$_2$ (2 mL) and Et$_2$O was added to precipitate product. The product was collected by filtration and dried. The title compound (CXLIII) (92 mg, 64%) was obtained as its HCl salt. $^1$H NMR (CD$_2$Cl$_2$): δ 2.06-2.12 (m, 2H); 2.10 (s, 6H); 2.18-2.21 (m, 2H); 2.28 (s, 3H); 2.97-3.02 (m, 2H); 3.48-3.51 (m, 2H); 3.83-3.85 (m, 2H); 4.57 (t, J=4.8 Hz, 2H); 7.06 (d, J=6.8 Hz, 2H); 7.14 (d, J=7.4 Hz, 2H); 7.19-7.22 (m, 1H); 7.73 (d, J=6.8 Hz, 2H); 7.77 (d, J=1.8 Hz, 1H); 8.48 (s, 1H); 8.57 (br, 1H); 8.94 (s, 1H); 12.4 (br, 1H). MS (ESI+): m/z=497.4.

Example 131

Synthesis of N-(3-(4-(2-(pyrrolidin-1-yl)ethoxy) phenylamino)-7-(2,6-dimethylphenyl)benzo[e][1,2,4]triazin-5-yl)methylsulfonyl amide hydrochloride

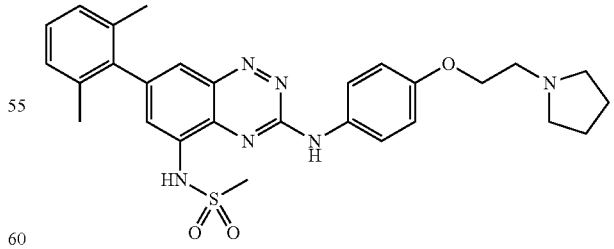

(CXLIV)

The title compound was synthesized as shown by the reaction scheme (CXLV).

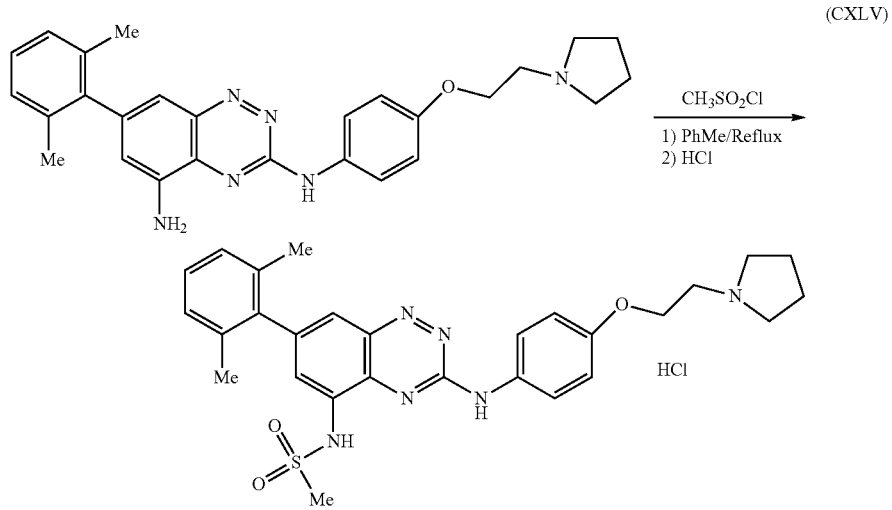

As shown by scheme (CXLV), to a solution of compound (CXLII) obtained as described in Example 129 (40 mg, 0.09 mmol) in anhydrous PhMe (5 mL) was added methylsulfonyl chloride (13 mg, 0.11 mmol). The solution was heated under reflux for 18 h and solvent was removed in vacuo. The residue was dissolved in $CH_2Cl_2$ (2 mL) and $Et_2O$ was added to precipitate product. The product was purified by HPLC. The title compound (CXLIV) (30 mg, 60%) was obtained as its HCl salt. $^1$H NMR ($CD_2Cl_2$): δ 2.00-2.02 (m, 2H); 2.12 (s, 6H); 2.08-2.12 (m, 2H); 3.14 (s, 3H); 3.18-3.21 (m, 2H); 3.61-3.64 (m, 2H); 3.73-3.76 (m, 2H); 4.62 (1, J=5.0 Hz, 2H); 7.13 (d, J=9.1 Hz, 2H); 7.19 (d, J=7.1 Hz, 2H); 7.20-7.25 (m, 1H); 7.69 (d, J=1.8 Hz, 1H); 7.88 (d, J=1.8 Hz, 1H); 7.95 (d, J=9.1 Hz, 1H); 8.49 (s, 1H); 9.92 (s, 1H); 12.4 (br, 1H). MS (ESI+): m/z=533.4.

Example 132

Synthesis of {4-[7-(2-chloro-5-hydroxy-phenyl)-6-methyl-benzo[1,2,4]triazin-3-ylamino]-phenyl}-(4-methyl-piperazin-1-yl)-methanone HCl salt

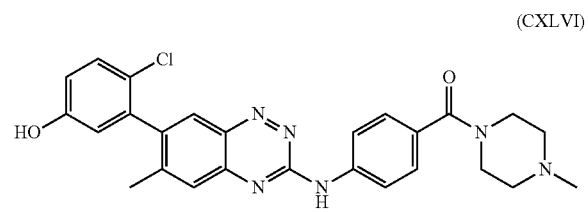 [SMILES: Cc1cc2nc(Nc3ccc(C(=O)N4CCN(C)CC4)cc3)nnc2cc1-c1cc(O)ccc1Cl]

The title compound was synthesized as shown by the reaction scheme (CXLVII).

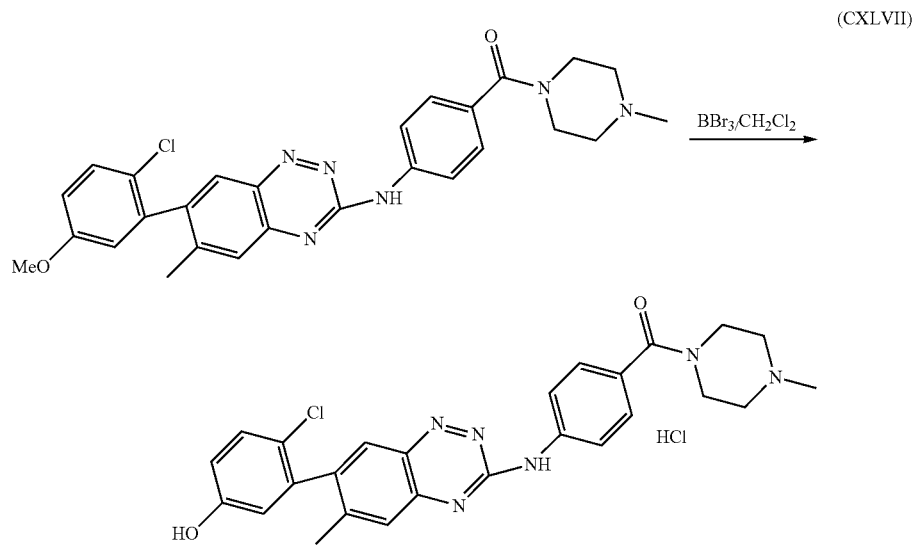

To a solution of a methoxylated product in MeSO₃H (50 mg, 0.083 mmol) in anhydrous CH₂Cl₂ (2 mL) was added 1.0 M BBr₃ (0.2 mL, 0.2 mmol) in CH₂Cl₂, as shown by scheme (CXLVII). The mixture was stirred at RT overnight. Sat. NaHCO₃ (10 mL) was added. The solid was collected and washed with H₂O and CHCl₃. The crude product was further purified by HPLC and transferred its HCl salt. The title product (CXLVI) (30 mg, 69%) was obtained as orange solid. $^1$H NMR (DMSO-d$^6$): δ 2.28 (s, 3H); 2.72 (s, 3H); 2.79 (s, 3H); 2.75-2.80 (m, 4H); 3.06-3.11 (m, 4H); 6.81 (d, J=2.9 Hz, 1H); 6.81 (dd, J=8.8 Hz, J=2.9 Hz, 1H); 7.40 (d, J=8.9 Hz, 1H); 7.52 (d, J=6.9 Hz, 1H); 7.76 (s, 1H); 8.07 (s, 1H); 8.09 (d, J=6.9 Hz, 2H); 9.98 (br, 1H); 10.78 (br, 1H); 11.13 (s, 1H). MS (ESI+): m/z=489.2.

Example 133

Synthesis of 7-(2-chloro-5-methoxy-phenyl)-5-methyl-benzo[1,2,4]triazin-3-yl]-[4-(2-pyrrolidin-1-yl-ethoxy)-phenyl]-amine

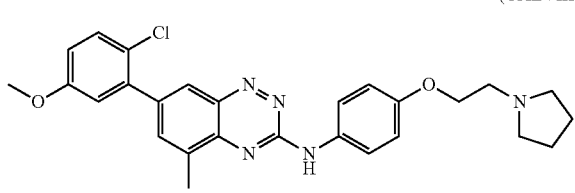

(CXLVIII)

The title compound was synthesized as shown by the reaction scheme (CXLIX).

(CXLIX)

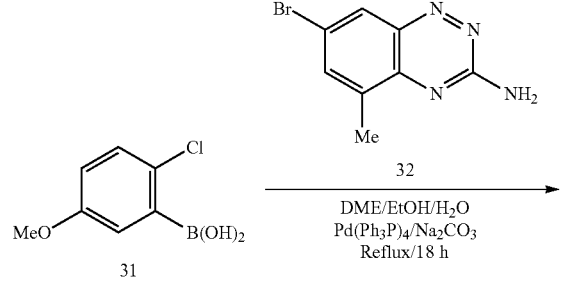

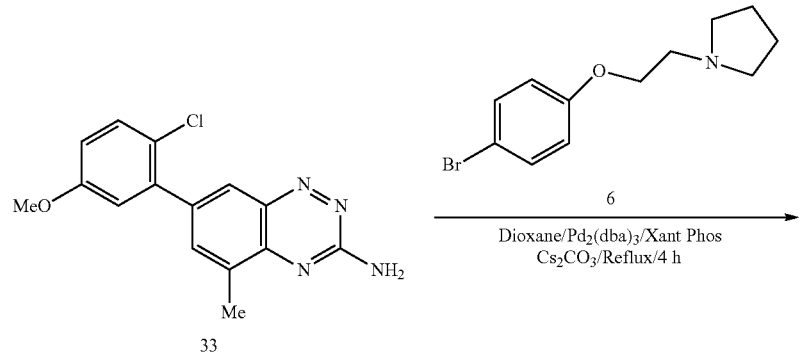

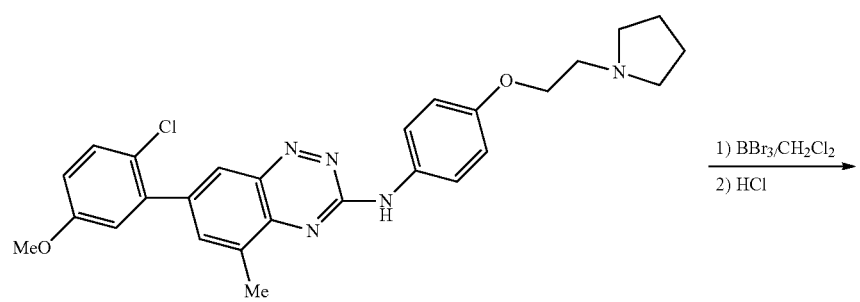

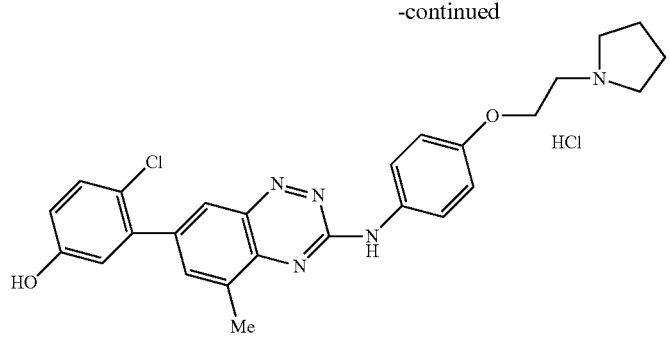

Compound 33 shown by scheme (CXLIX) was prepared by a method that was analogous to that used to make compound 30 as shown on scheme (CXLI), except 2-chloro-5-methoxyphenylboronic acid (compound 31) (510 mg, 2.73 mmol) and 7-bromo-5-methylbenzo[e][1,2,4]triazin-3-amine (compound 32) (503 mg, 2.10 mmol) were used to produce compound 33 (500 mg, 80%) as a yellow solid. The title compound (CXLVIII) was then prepared by a method that was analogous to that used to make compound (CXL) as described in Example 128, except compounds 33 (500 mg, 1.66 mmol) and 6 (674 mg, 2.49 mmol) were used as shown by scheme (CXLIX) to afford the title compound (CXLVIII) (440 mg, 54%) as a yellow solid.

Example 134

Synthesis of 3-(3-(4-(2-(pyrrolidin-1-yl)ethoxy)phenylamino)-5-methylbenzo[e][1,2,4]triazin-7-yl)-4-chlorophenol hydrochloride The title compound (CL) was prepared by a method that was analogous to that used to make compound (CXLVI) as described in Example 132, except compound (CXLVIII) as described in Example 133 (440 mg, 0.90 mmol) was use to produce the title compound (CL) (387 mg, 84%) as HCl salt and orange solid. $^1$H NMR (DMSO-d$^6$): δ 1.88-1.92 (m, 2H); 1.97-2.05 (m, 2H); 2.64 (s, 3H); 3.09-3.14 (m, 2H); 3.57-3.61 (m, 4H); 4.36 (t, J=4.9 Hz, 2H); 6.87 (dd, J=8.8 Hz, J=2.9 Hz, 1H); 6.94 (d, J=2.9 Hz, 1H); 7.09 (d, J=9.0 Hz, 2H); 7.39 (d, J=8.8 Hz, 1H); 7.83 (d, J=1.6 Hz, 1H); 7.98 (d, J=9.0 Hz, 2H); 8.12 (d, J=1.6 Hz, 1H); 9.97 (s, 1H); 10.55 (br, 1H); 10.87 (s, 1H). MS (ESI+): m/z=476.3.

Example 135

Synthesis of 3-(7-(2-chloro-5-hydroxyphenyl)-5-methylbenzo[e][1,2,4]triazin-3-ylamino)-N-(2-(pyrrolidin-1-yl)ethyl)benzamide hydrochloride

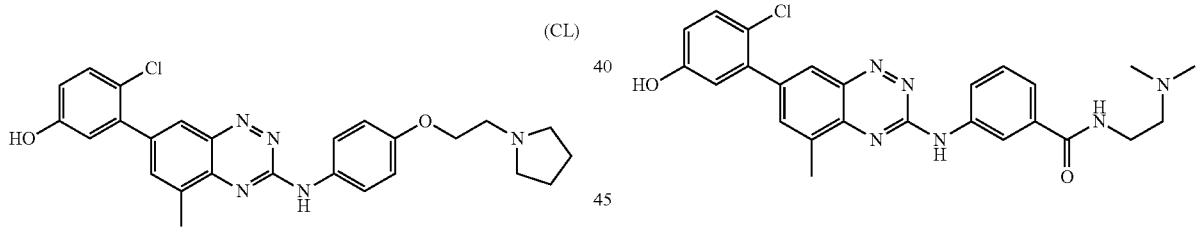

The title compound was synthesized as shown by the reaction scheme (CLII).

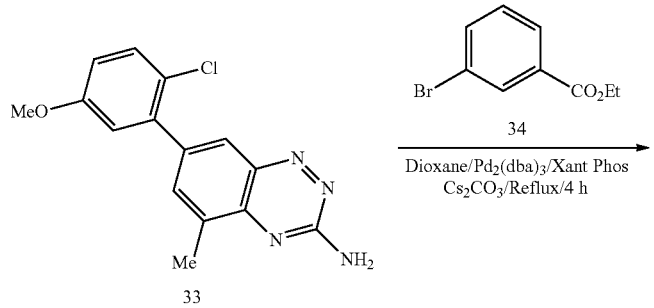

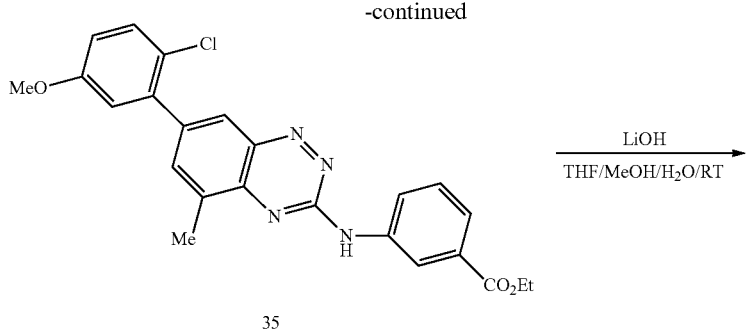

35

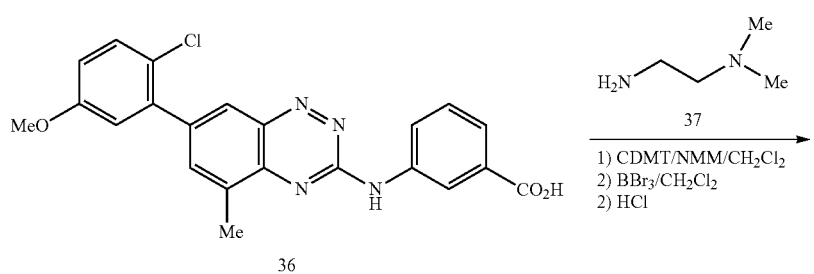

36

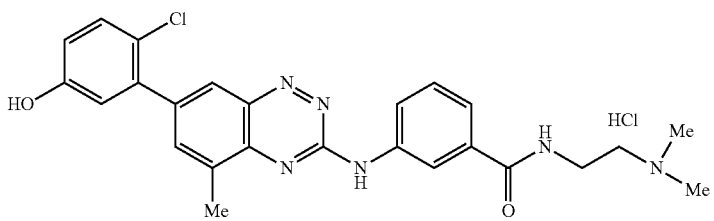

Compound 36 shown on scheme (CLII) was prepared by a method that was analogous to that used to make compound 20 shown on scheme (CXXXVII), except using compounds 34 (ethyl 3-bromobenzoate) (84 mg, 0.37 mmol) and 33 (74 mg, 0.24 mmol) were used to afford compound 36 (72 mg, 71%) as a yellow solid. The title compound (CLI) was prepared by a method that was analogous to that used to make compound (CXXXVI) as described in Example 126, except using compounds 36 (35 mg, 0.083 mmol) and 37 ($N^1,N^1$-dimethylethane-1,2-diamine) (15 mg, 0.17 mmol) were used to afford the title compound (CLI) (6.3 mg, 15%) as its HCl solid and yellow solid. $^1$H NMR (DMSO-d$^6$): δ 2.71 (s, 3H); 2.85 (s, 6H); 3.28 (t, J=5.3 Hz, 2H); 3.55-3.76 (m, 2H); 6.88 (dd, J=8.7 Hz, J=2.9 Hz, 1H); 6.95 (d, J=2.9 Hz, 1H); 7.40 (d, J=8.8 Hz, 1H); 7.52 (t, J=7.9 Hz, 1H); 7.61 (d, J=7.9 Hz, 1H); 7.87 (d, J=1.7 Hz, 1H); 8.10 (dd, J=8.1 Hz, J=1.8 Hz, 1H); 8.17 (d, J=1.8 Hz, 1H); 8.74 (s, 1H); 8.77 (t, J=5.6 Hz, 1H); 9.30 (br, 1H); 9.97 (s, 1H); 11.14 (s, 1H). MS (ESI+): m/z=477.1.

Example 136

Synthesis of 3-(3-(3-(dimethylamino)phenylamino)-5-methylbenzo[e][1,2,4]triazin-7-yl)-4-chlorophenol hydrochloride (CLIII)

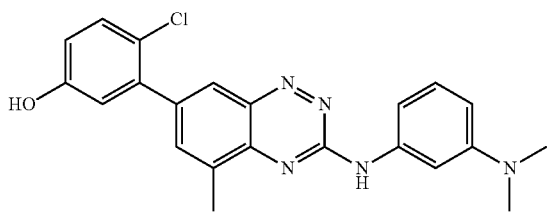

The title compound was synthesized as shown by the reaction scheme (CLIV).

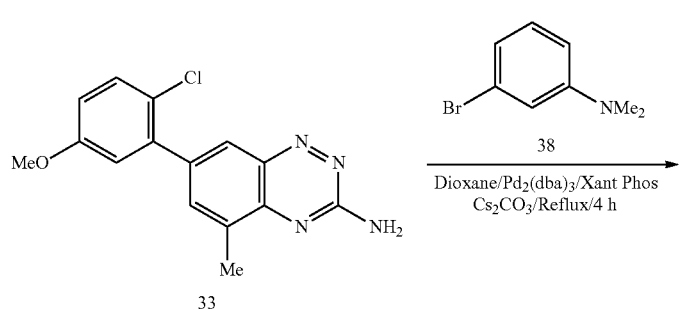

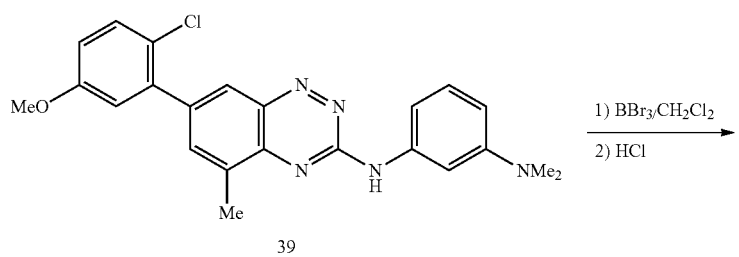

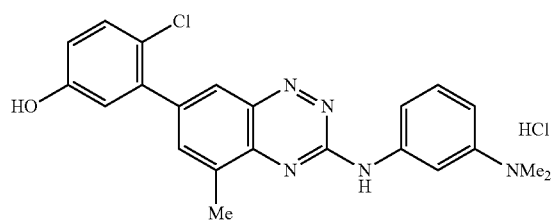

As shown by scheme (CLIV), to a solution of compound 33 (520 mg, 1.73 mmol) in anhydrous dioxane (20 mL) were added 3-bromo-N,N-dimethylbenzenamine (compound 38) (692 mg, 3.46 mmol), $Cs_2CO_3$ (2.3 g, 6.92 mmol), $Pd_2(dba)_3$ (158 mg, 0.17 mmol), and xantphos (300 mg, 0.52 mmol). The resulted mixture was heated under reflux for 2 h. The solid was filtered off and washed with EtOAc. The filtrate was washed with brine (1×100 mL). The organic layer was separated and dried ($Na_2SO_4$). The crude product was purified by chromatography ($SiO_2/CH_2Cl_2$, then 5% MeOH in $CH_2Cl_2$) and afforded compound 39 as shown by scheme (CLIV). Compound 39 was then demethylated by using $BBr_3/CH_2Cl_2$ to afford the title product (CLIII) (80 mg, 10%) as its HCl salt and yellow solid. $^1$H NMR (DMSO-$d^6$): δ 2.70 (s, 3H); 3.07 (s, 6H); 6.88 (dd, J=8.7 Hz, J=2.9 Hz, 1H); 6.94 (d, J=2.9 Hz, 1H); 7.36 (br, 2H); 7.40 (d, J=8.8 Hz, 1H); 7.48 (br, 1H); 7.86 (s, 1H); 8.10 (br, 1H); 8.16 (d, J=1.7 Hz, 1H); 9.98 (br, 1H); 11.02 (s, 1H). MS (ESI+): m/z=406.1.

Example 137

Synthesis of 3-(3-(6-methoxypyridin-3-ylamino)-5-methylbenzo[e][1,2,4]triazin-7-yl)-4-chlorophenol hydrochloride

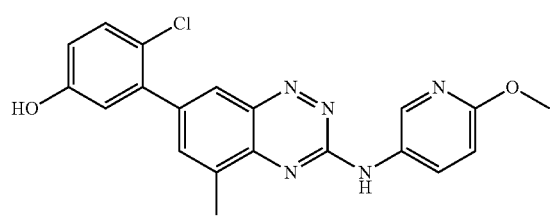

The title compound was synthesized as shown by the reaction scheme (CLVI).

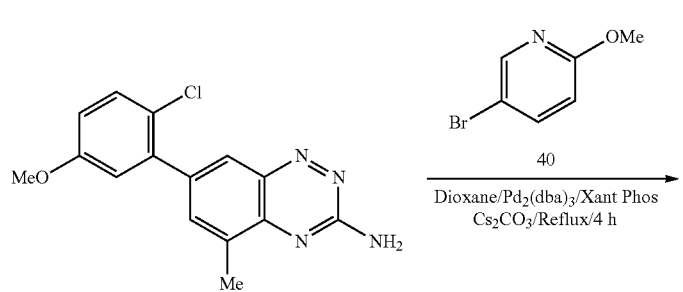

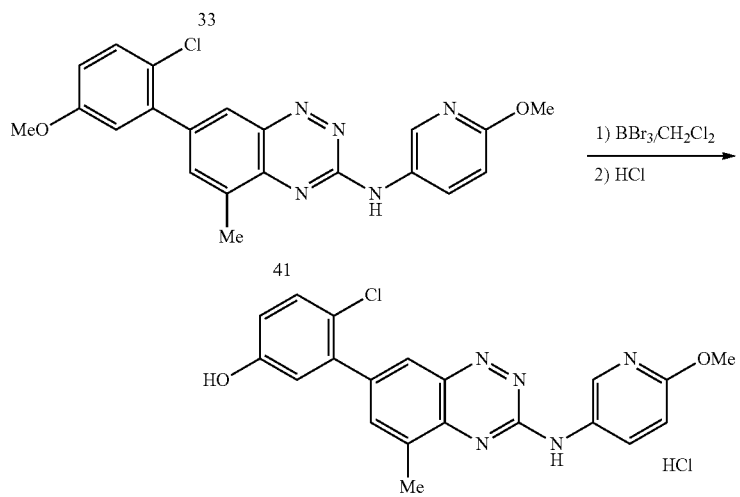

The title compound was prepared by a method that was analogous to that used to make compound (CLIII), as described in Example 136, except using compounds 33 (37 mg, 0.13 mmol) and 40 (5-bromo-2-methoxypyridine) (36.4 mg, 0.20 mmol) shown on scheme (CLVI) were used to afford the title compound (CLV) (13 mg, 23%) as its HCl salt in a form of a red solid. $^1$H NMR (DMSO-$d^6$): δ 64 (s, 3H); 3.87 (s, 3H); 6.88 (dd, J=8.7 Hz, J=2.9 Hz, 1H); 6.92 (d, J=8.9 Hz, 1H); 6.95 (d, J=2.9 Hz, 1H); 7.39 (d, J=8.8 Hz, 1H); 7.84 (dd, J=1.9 Hz, J=1.0 Hz, 1H); 8.14 (d, J=1.7 Hz, 1H); 8.24 (dd, J=8.9 Hz, J=2.9 Hz, 1H); 8.88 (d, J=2.6 Hz, 1H); 10.00 (br, 1H); 10.92 (s, 1H). MS (ESI+): m/z=394.0.

Example 138

Synthesis of 3-(3-(2-(pyrrolidin-1-yl)ethylamino)-5-methylbenzo[e][1,2,4]triazin-7-yl)-4-chlorophenol hydrochloride

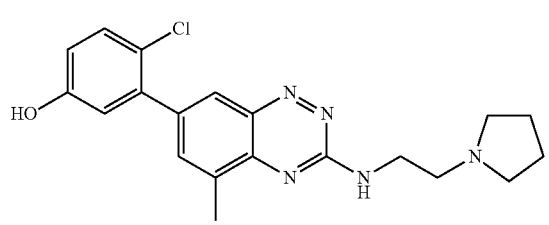

(CLVII)

The title compound was synthesized as shown by the reaction scheme (CLVIII).

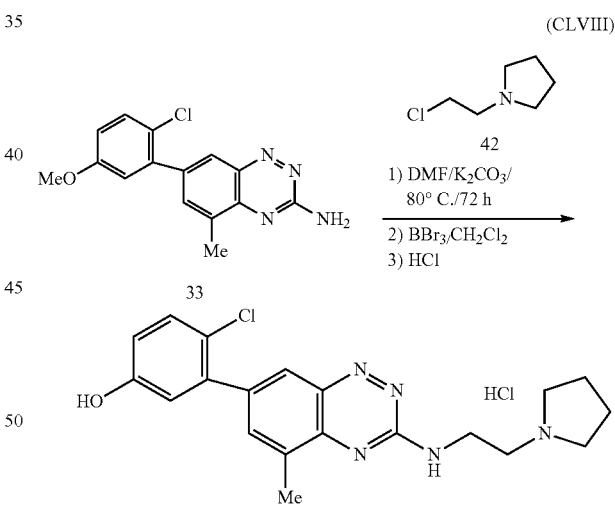

As shown by scheme (CLVIII), to a solution of compound 33 (320 mg, 1.06 mmol) in anhydrous DMF (20 mL) were added K$_2$CO$_3$ (1.2 g, 8.51 mmol), and 1-(2-chloroethyl)pyrrolidine 42 (217 mg, 1.27 mmol). The mixture was heated at 150° C. for 72 h. The solid was filtered off and washed with CH$_2$Cl$_2$. The filtrate was concentrated in vacuo. The residue was dissolved in CH$_2$Cl$_2$ and washed with brine (2×50 mL). The organic layer was separated and dried (Na$_2$SO$_4$). The solvent was removed and the residue was demethylated by using BBr$_3$/CH$_2$Cl$_2$. The product was purified by preparative HPLC. The title compound (CLVII) (90 mg, 21%) was obtained as HCl salt in a form of a yellow solid. $^1$H NMR (DMSO-$d^6$): δ 1.88-1.90 (m, 2H); 1.97-2.02 (m, 2H); 2.58 (s, 3H); 3.05-3.10 (m, 2H); 3.44-3.48 (m, 4H); 6.86 (dd, J=8.7 Hz, J=2.9 Hz, 1H); 6.94 (d, J=2.9 Hz, 1H); 7.37 (d, J=8.6 Hz, 1H); 7.76 (dd, J=1.8 Hz, J=1.0 Hz, 1H); 8.05 (d, J=1.8 Hz, 1H); 10.05 (br, 1H); 10.78 (br, 1H). MS (ESI+): m/z=384.1.

Example 139

Synthesis of 3-(5-(2-(pyrrolidin-1-yl)ethoxy)-3-(pyridin-3-ylamino)benzo[e][1,2,4]triazin-7-yl)-4-chlorophenol dihydrochloride The title compound was synthesized as shown by the reaction scheme (CLX).

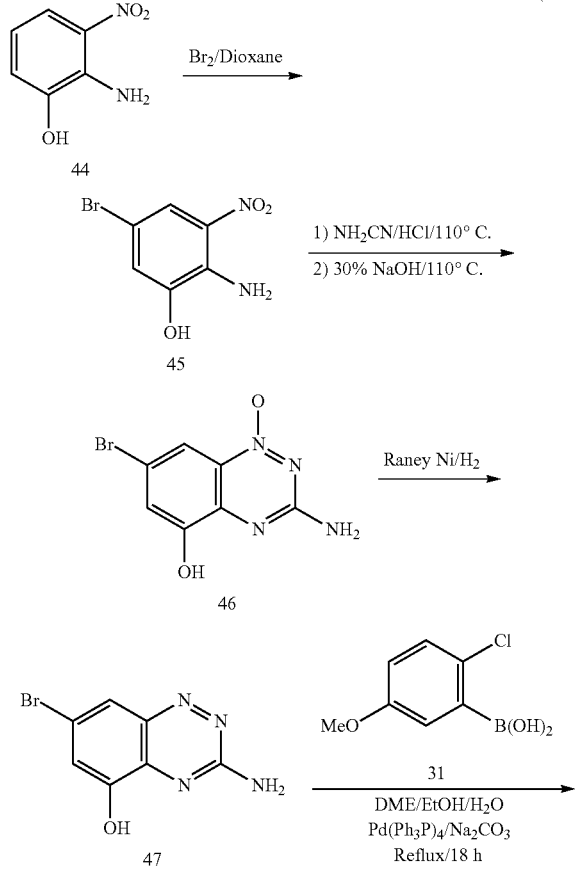

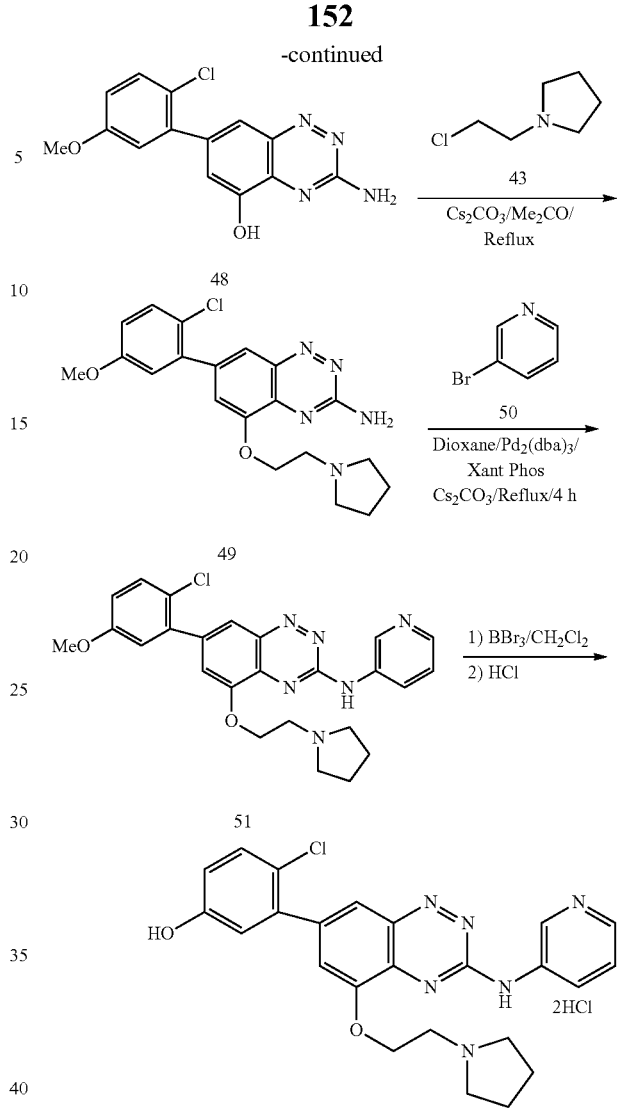

As shown by scheme (CLX), to a solution of 2-amino-3-nitrophenol 44 (10 g, 65 mmol) in anhydrous 1,4-dioxane (1 L) was added bromine (12.5 g, 78 mmol). The mixture was stirred at room temperature overnight. The solid was collected by filtration, washed with dioxane and dried. 2-amino-5-bromo-3-nitrophenol 45 (18 g, 90%) was obtained as its HBr salt in a form of a yellow solid. $^1$H NMR (DMSO-d$^6$): δ 6.28 (br, 2H); 6.99 (d, J=2.2 Hz, 1H); 7.57 (d, J=2.1 Hz, 1H). MS (ESI+): m/z=234. Compound 45 (6 g, 19.1 mmol) was converted into compound 46 by using a method that was analogous to that used to synthesize compound 27, as shown on scheme (CXLI). Hydrogenation of compound 46 affords compound 47 (3.1 g, 67%) as a red solid.

Compound 48 was then prepared by using a method that was analogous to that used to synthesize compound 33, as described in Example 133 (scheme (CXLIX)) except compounds 47 (870 mg, 3.6 mmol) and 31 (740 mg, 4.0 mmol) were used to afford compound 48 (108 mg, 10%) as yellow solid. $^1$H NMR (DMSO-d$^6$): δ 7.02 (dd, J=8.9 Hz, J=3.1 Hz, 1H); 7.07 (d, J=3.1 Hz, 1H); 7.16 (d, J=1.9 Hz, 1H); 7.49 (d, J=8.9 Hz, 1H); 7.60 (br, 2H); 7.69 (d, J=1.9 Hz, 1H). MS (ESI+): m/z=303.7.

To a solution of compound 48 (47 mg, 0.15) in Me$_2$CO (20 mL) were then added Cs$_2$CO$_3$ (202 mg, 0.62 mmol), 1-(2-chloroethyl)pyrrolidine 43 (26.4 mg, 0.15 mmol), and NaI (15 mg, 0.1 mmol). The mixture was heated under reflux overnight. The solid was filtered off and washed with Me$_2$CO. The filtrate was concentrated in vacuo. The residue was dissolved in CH$_2$Cl$_2$ and washed with brine (2×50 mL). The organic layer was separated and dried (Na$_2$SO$_4$). The solvent was removed in vacuo and compound 49 was obtained as a yellow solid. Compound 51 was then prepared by using a method that was analogous to that used to synthesize compounds 39 (scheme (CLIV), Example 136), except compound s 49 (62 mg, 0.15 mmol) and 50 (3-bromopyridine) (36.7 mg, 0.23 mmol) were used to afford compound 51 as a yellow solid.

Compound 51 was demethylated as shown by scheme (CLX), by using BBr$_3$/CH$_2$Cl$_2$ to afford the title compound (CLIX) (60 mg, 56%) as its HCl salt in a form of a yellow solid. $^1$H NMR (DMSO-d$^6$): δ 1.82-1.84 (m, 2H); 1.99-2.01 (m, 2H); 3.36-3.40 (m, 2H); 3.69-3.70 (m, 2H); 3.90-3.92 (m, 2H); 4.68 (t, J=4.2 Hz, 2H); 6.92 (dd, J=8.6 Hz, J=2.9 Hz, 1H); 7.00 (d, J=2.9 Hz, 1H); 7.43 (d, J=8.8 Hz, 2H); 7.58 (d, J=1.5 Hz, 1H); 8.01 (br, 1H); 8.06 (d, J=1.5 Hz, 1H); 8.62 (d, J=4.9 Hz, 1H); 8.69 (d, J=8.8 Hz, 1H); 9.77 (s, 1H); 10.06 (br, 1H); 10.79 (br, 1H); 11.90 (s, 1H). MS (ESI+): m/z=463.1.

Example 140

Synthesis of 7-(1H-indol-4-yl)-5-methyl-benzo[e][1,2,4]triazin-3-yl-amine

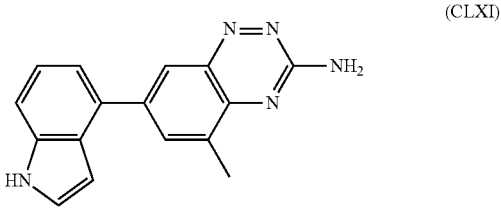 [SMILES: Cc1cc(-c2cccc3[nH]ccc23)cc2nnc(N)nc12]

(CLXI)

The title compound was synthesized as shown by the reaction scheme (CLXII).

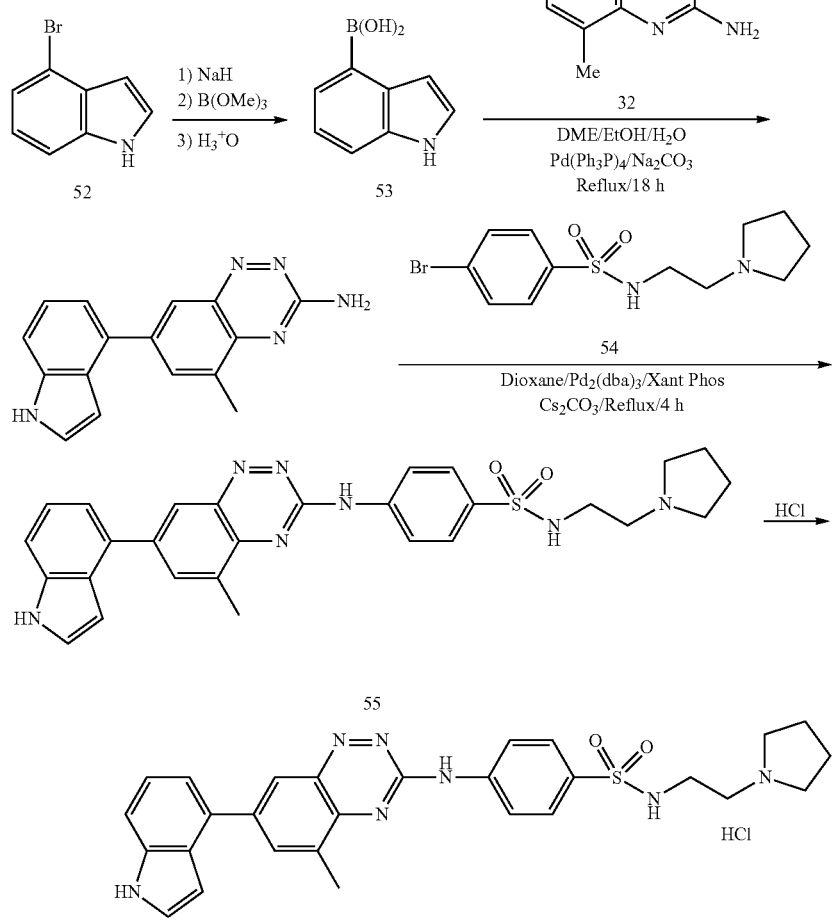

(CLXII)

As shown by scheme (CLXII), the solution of 4-bromo-1H-indole 52 (1.56 g, 7.96 mmol) in anhydrous Et$_2$O (20 mL) was cooled in ice-H$_2$O, followed by adding NaH (0.22 g, 9.6 mmol). The suspension was stirred at 0° C. for 30 min. The flask was further cooled in dry ice-acetone and 2.5 M BuLi in hexane (8 mL, 20 mmol) was dropped. After stirring for 30 min, the neat B(OMe)$_3$ was dropped and the mixture was stirred at room temperature overnight. The mixture was put into 1 M $H_3PO_4$ in portions and stirred for 30 min. The organic layer was separated and the aqueous layer was extracted with $Et_2O$ (2×20 mL). The combined organic layer was washed with 1 M NaOH (3×50 mL). The combined aqueous was actified with 1 M $H_3PO_4$ (pH<2) and extracted with $Et_2O$ (3×20 mL). The combined organic solution was dried ($Na_2SO_4$). The solvent was removed and compound 53 (1.16 g, 91%) was obtained, as demonstrated by scheme (CLXII), as a wax solid.

The title compound (CLXI) was prepared by using a method that was analogous to that used to synthesize compound 33, as described in Example 133 (scheme (CXLIX)), except compounds 53 (1.16 g, 7.2 mmol) and 31 (also described in Example 133 (scheme (CXLIX)) (1.15 g, 4.8 mmol) were used to afford the title compound (CLXI) (220 mg, 17%) as a yellow solid. $^1$H NMR (DMSO-d$^6$): δ 2.59 (s, 3H); 6.64 (t, J=1.1 Hz, 1H); 7.22-7.25 (m, 2H); 7.46-7.48 (m, 2H); 7.64 (br, 2H); 8.02 (d, J=1.9 Hz, 1H); 8.24 (d, J=1.9 Hz, 1H); 11.35 (s, 1H). MS (ESI+): m/z=276.2.

Example 141

Synthesis of 4-(7-(1H-indol-4-yl)-5-methylbenzo[e][1,2,4]triazin-3-ylamino)-N-(2-(pyrrolidin-1-yl)ethyl)benzenesulfonamide hydrochloride The title compound was prepared was prepared by using a method that was analogous to that used to synthesize compound (CXL), as described in Example 128, except compound (CLXI) (described in Example 140) (37 mg, 0.13 mmol) and compound 54 (shown on scheme (CLXII)) (53 mg, 0.16 mmol) were used to afford the title compound (CLXIII) (5.7 mg, 8%) as its HCl salt and orange solid. $^1$H NMR (DMSO-d$^6$): δ 1.85-1.88 (m, 2H); 1.98-2.01 (m, 2H); 2.78 (s, 3H); 2.98-3.04 (m, 2H); 3.08-3.12 (m, 2H); 3.22-3.26 (m, 2H); 3.53-3.56 (m, 2H); 6.69 (t, J=1.9 Hz, 1H); 7.25-7.31 (m, 2H); 7.51-7.52 (m, 2H); 7.88 (d, J=9.0 Hz, 2H); 8.23 (s, 1H); 8.27 (d, J=9.0 Hz, 1H); 8.43 (d, J=1.8 Hz, 1H); 10.04 (br, 1H); 11.40 (s, 1H); 11.42 (s, 1H). MS (ESI+): m/z=528.4.

Example 142

Synthesis of 4-(7-(2-bromo-5-hydroxyphenyl)-5-methylbenzo[e][1,2,4]triazin-3-ylamino)-N-(2-(pyrrolidin-1-yl)ethyl)benzenesulfonamide hydrochloride (CLXIII)

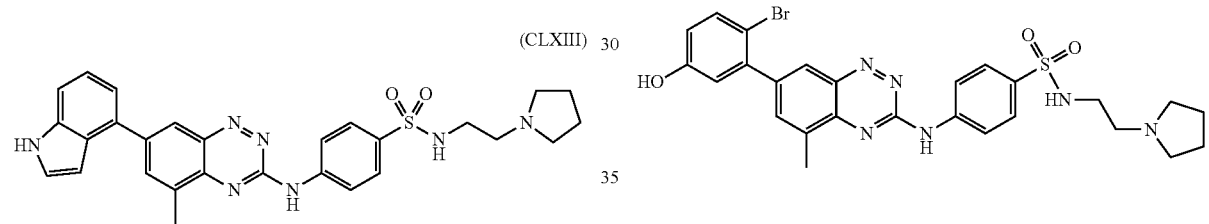

(CLXIV)

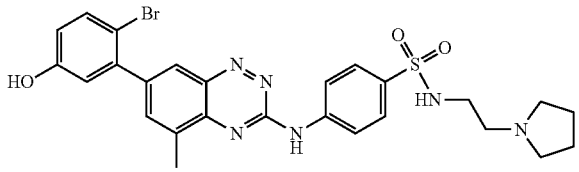

The title compound was synthesized as shown by the reaction scheme (CLXV).

(CLXV)

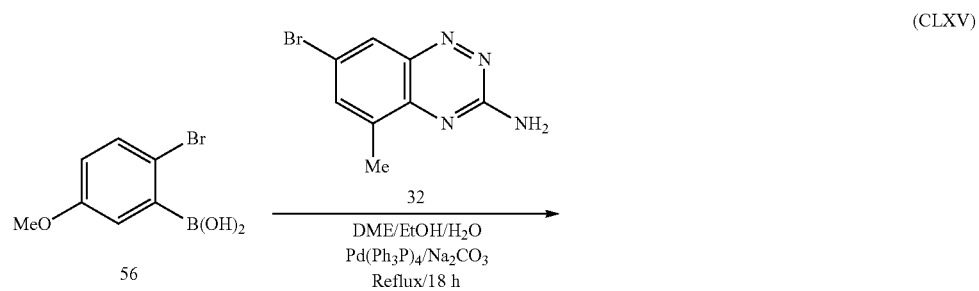

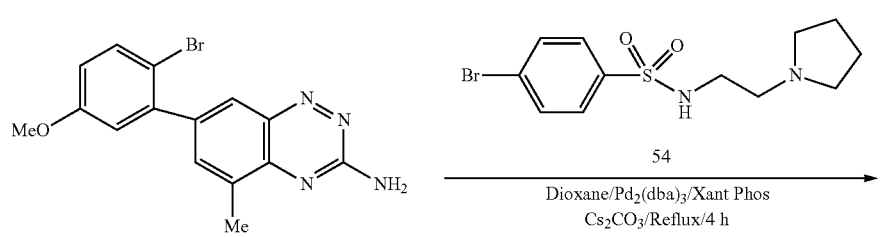

-continued

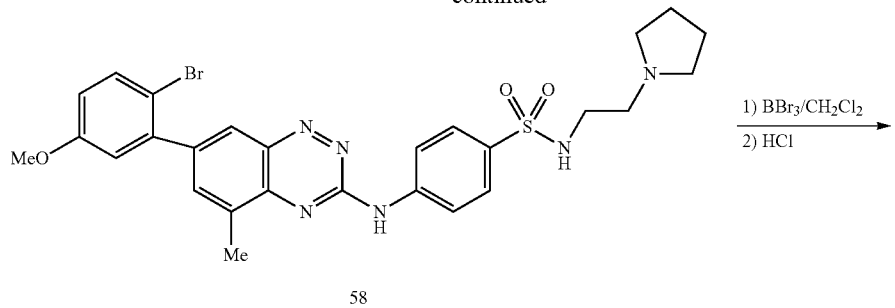

58

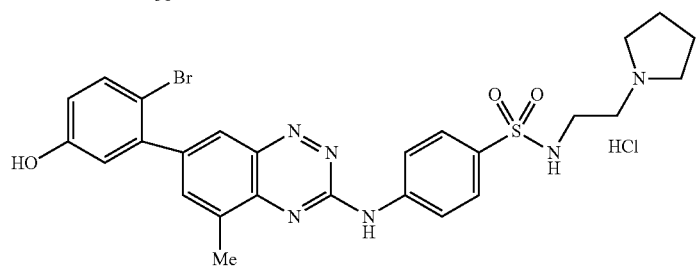

The intermediate compounds 57 and 58 shown on scheme (CLXV) were prepared as follows. Compound 57 was prepared by using a method that was analogous to that used to synthesize compound 30 shown on scheme (CXLI) and described in Example 128, except 2-bromo-5-methoxyphenylboronic acid (compound 56) (233 mg, 1.1 mmol) and 7-bromo-5-methylbenzo[e][1,2,4]triazin-3-amine (compound 32) (240 mg, 1.0 mmol) were used to afford compound 57 (300 mg, 87%) as a yellow solid. Compound 58 was prepared by using a method that was analogous to that used to synthesize compound (CXL), as described in Example 128, except compounds 57 (150 mg, 0.43 mmol) and 54 (174 mg, 0.52 mmol) were used, as shown on scheme (CLXV) to afford compound 58 as a yellow solid.

The title compound was prepared by using a method that was analogous to that used to synthesize compound (CXLVI), as described in Example 132, except compound 58 (0.90 mmol) was used to afford the title compound (CLXIV) (51 mg, 20% in two steps) as HCl salt and orange solid. $^1$H NMR (DMSO-d$^6$): δ 1.83-1.86 (m, 2H); 1.95-2.05 (m, 2H); 2.71 (s, 3H); 2.95-3.01 (m, 2H); 3.12-3.16 (m, 2H); 3.21-3.24 (m, 2H); 3.48-3.53 (m, 2H); 6.84 (dd, J=8.8 Hz, J=2.9 Hz, 1H); 6.97 (d, J=2.9 Hz, 1H); 7.55 (d, J=8.8 Hz, 1H); 7.88 (d, J=8.8 Hz, 2H); 7.87 (d, J=1.8 Hz, 1H); 8.04 (t, J=6.0 Hz, 1H); 8.17 (d, J=1.8 Hz, 1H); 8.25 (d, J=8.8 Hz, 2H); 10.12 (s, 1H); 10.85 (br, 1H); 11.44 (s, 1H). MS (ESI+): m/z=583.0.

Example 143

Synthesis of 4-(7-(2-chloro-6-hydroxyphenyl)-5-methylbenzo[e][1,2,4]triazin-3-ylamino)-N-(2-(pyrrolidin-1-yl)ethyl)benzensulfonamide hydrochloride (CLXVI)

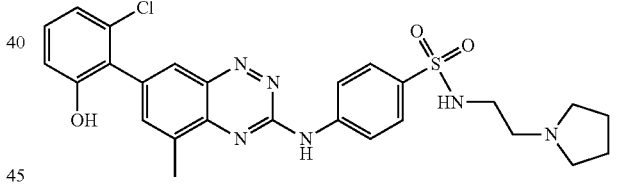

The title compound was synthesized as shown by the reaction scheme (CLXVII).

(CLXVII)

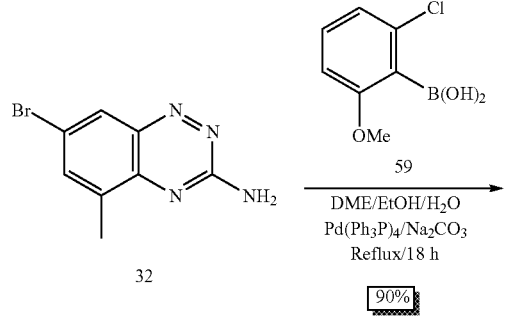

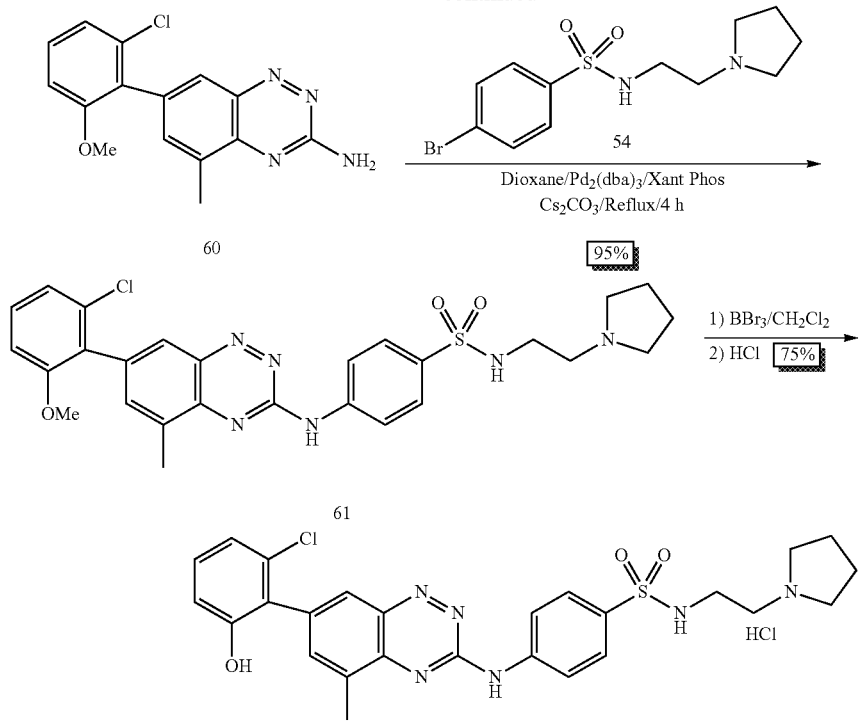

As shown by scheme (CLXVII), compound 60 was prepared by using a method that was analogous to that used to synthesize compound 30 shown on scheme (CXLI) and described in Example 128, except 2-chloro-6-methoxyphenylboronic acid 59 (1 g, 4.18 mmol) and 7-bromo-5-methyl-benzo[e][1,2,4]triazin-3-amine 32 (1.2 g, 6.28 mmol) were used to give compound 60 (7-(2-chloro-6-methoxyphenyl)-5-methylbenzo[e][1,2,4]triazin-3-amine) (1.12 g, 90%) as a yellow solid. Compound 61 was prepared was prepared by using a method that was analogous to that used to synthesize compound (CXL), as described in Example 128, except compounds 60 (390 mg, 1.30 mmol) and 54 (518 mg, 1.56 mmol) were used to afford compound 61 (4-(7-(2-chloro-6-methoxyphenyl)-5-methylbenzo[e][1,2,4]triazin-3-ylamino)-N-(2-(pyrrolidin-1-yl)ethyl)benzensulfonamide) (680 mg, 95%) as a yellow solid.

The title compound was prepared by using a method that was analogous to that used to synthesize compound (CXLVI), as described in Example 132, except compound 61 (680 mg, 1.23 mmol) was used to afford the title compound 4-(7-(2-chloro-6-hydroxyphenyl)-5-methylbenzo[e][1,2,4]triazin-3-ylamino)-N-(2-(pyrrolidin-1-yl)ethyl)benzensulfonamide (CLXVI) (529 mg, 75%) as HCl salt and yellow solid. $^1$H NMR (DMSO-d$^6$): δ 1.83-1.87 (m, 2H); 1.95-2.01 (m, 2H); 2.70 (s, 3H); 2.97-3.04 (m, 2H); 3.09-3.13 (m, 2H); 3.21-3.25 (m, 2H); 3.51-3.56 (m, 2H); 7.01 (d, J=8.3 Hz 1H); 7.06 (d, J=7.9 Hz, 1H); 7.27 (t, J=8.0 Hz, 1H); 7.77 (s, 1H); 7.88 (d, J=8.9 Hz, 2H); 7.92 (t, J=6.0 Hz, 1H); 8.09 (s, 1H); 8.26 (d, J=8.9 Hz, 2H); 10.09 (s, 1H); 10.22 (br, 1H); 11.40 (s, 1H). MS (ESI+): m/z=540.5.

Example 144

Synthesis of 3-{6-methyl-3-[4-(2-pyrrolidin-1-yl-ethylsulfamoyl)-phenylamino]-benzo[1,2,4]triazin-7-yl}-benzamide (CLXVIII)

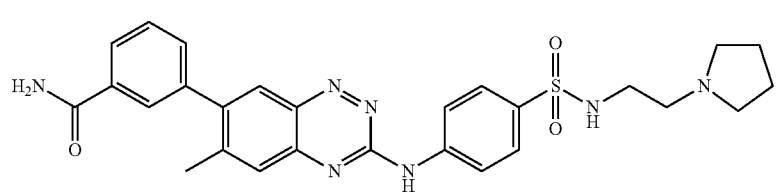

Compound 52 (scheme (CLXII), Example 140) (0.11 g, 0.22 mmol), 3-carbamoylphenylboronic acid (45 mg, 0.27 mmol), Pd(PPh$_3$)$_4$ (25 mg, 0.022 mmol), and 2 M Na$_2$CO$_3$ (0.5 mL, 1.0 mmol) were suspended in a mixture of DME/ethanol (4:1, 10 mL). The resulting mixture was heated at reflux for 6 h. The mixture was allowed to cool to room temperature, filtered and washed with DCM. The filtrate was concentrated and the residue was purified by HPLC. The corrected fractions were poured into saturated NaHCO$_3$ and extracted with EtOAc. The combined organic layers were washed with brine, dried over Na$_2$SO$_4$, and filtered. The filtrate was concentrated to afford the free base compound, which was converted to HCl salt according to method C and furnished the title compound as a yellow solid (40 mg, 32% overall). $^1$H NMR (DMSO-d$_6$): δ 1.78-1.90 (m, 2H), 1.90-2.03 (m, 2H), 2.45 (s, 3H), 2.95-3.10 (m, 2H), 3.12 (q, J=6.2 Hz, 2H), 3.23 (q, J=6.1 Hz, 2H), 3.48-3.55 (m, 2H), 7.47 (s, 1H), 7.61 (t, J=7.8 Hz, 1H), 7.68 (d, J=7.8 Hz, 1H), 7.83 (s, 1H), 7.86 (d, J=8.9 Hz, 1H), 7.95-8.05 (m, 3H), 8.12 (s, 1H), 8.20-8.24 (m, 3H), 10.55 (br s, 1H), 11.33 (s, 1H). MS (ESI+): m/z 533.

Example 145

Synthesis of 2-(4-{6-[7-(2,6-dichloro-phenyl)-5-methyl-benzo[1,2,4]triazin-3-ylamino]-2-methyl-pyrimidin-4-yl}-piperazin-1-yl)-ethanol (CLXIX)

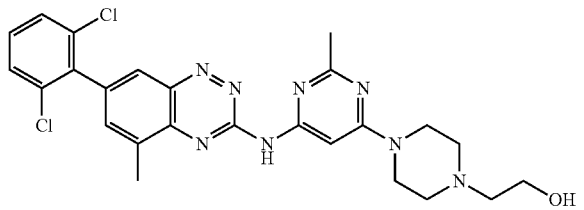

To synthesize the title compound (CLXIX), two intermediate compounds 62 (2-[4-(6-chloro-2-methyl-pyrimidin-4-yl)-piperazin-1-yl]-ethanol) and 63 (7-(2,6-dichloro-phenyl)-5-methyl-benzo[1,2,4]triazin-3-ylamine) shown below were used.

62

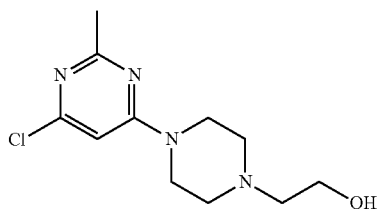

63

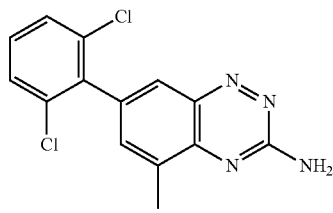

To synthesize compound 62, to a solution of 4,6-dichloro-2-methyl-pyrimidine (5.0 g, 31 mmol) and 2-piperazin-1-yl-ethanol (2.7 g, 21 mmol) in dioxane (25 mL) was added DIPEA (3.0 mL, 17 mmol). The mixture was heated at reflux for 16 h. The mixture was allowed to cool to room temperature and poured into water. The resulting aqueous layer was extracted with EtOAc and the combined organic layers washed with brine, dried over Na$_2$SO$_4$ and filtered. The filtrate was concentrated and the residue purified by flash chromatography on silica gel (5-10% MeOH/DCM) to afford compound 62 as a brown liquid (2.1 g, 39%). MS (ESI+): m/z 257.

To synthesize the title compound (CLXIX), a suspension of compound 62 (0.15 g, 0.49 mmol), compound 63 (0.16 g, 0.62 mmol), Pd(OAc)$_2$ (7 mg, 0.031 mmol), Xantphos (36 mg, 0.062 mmol) and potassium tert-butoxide (0.11 g, 0.98 mmol) in dioxane/DMF (4 mL, 3/1 v/v) was sealed in a microwave reaction tube and irradiated with microwave at 160° C. for 20 min. After cooling down to room temperature, the cap was removed and the resulting mixture filtered and the filtered solid washed with DCM. The filtrate was concentrated and the residue purified by flash chromatography on silica gel (5-10% MeOH/DCM) to afford the free base compound. The free base compound was converted to HCl salt according to method C and furnished the title compound as a yellow solid (0.18 g, 65% overall). $^1$H NMR (DMSO-d$_6$): δ 2.54 (s, 3H), 2.75 (s, 3H), 3.15-3.25 (m, 4H), 3.59-3.72 (m, 6H), 3.82 (t, J=4.6 Hz, 2H), 4.56 (br s, 1H), 7.55 (t, J=7.8 Hz, 1H), 7.67 (d, J=8.2 Hz, 2H), 7.91-7.93 (m, 1H), 8.31 (d, J=1.5 Hz, 1H), 10.93 (br s, 1H), 11.83 (br s, 1H). MS (ESI+): m/z 525.

Example 146

Synthesis of 4-chloro-3-(3-{6-[4-(2-hydroxy-ethyl)-piperazin-1-yl]-2-methyl-pyrimidin-4-ylamino}-5-methyl-benzo[1,2,4]triazin-7-yl)-phenol (CLXX)

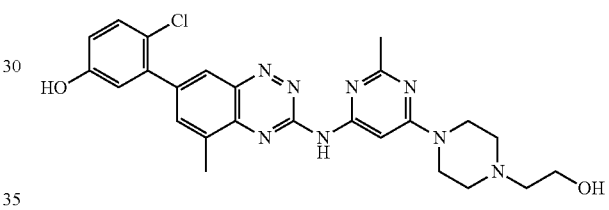

To synthesize the title compound (CLXX), an intermediate compound 64 (2-(4-{6-[7-(2-chloro-5-methoxy-phenyl)-5-methyl-benzo[1,2,4]triazin-3-ylamino]-2-methyl-pyrimidin-4-yl}-piperazin-1-yl)-ethanol) shown below was used.

64

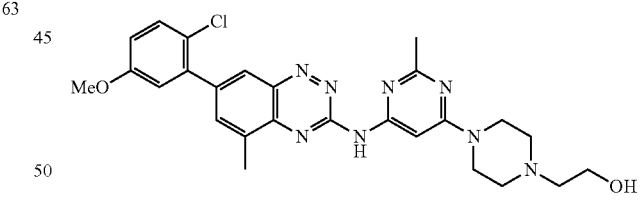

To synthesize compound 64, a suspension of compound 16 (scheme (CXXXV), Example 124) (0.10 g, 0.33 mmol), compound 53 (Example 145) (0.10 g, 0.39 mmol), Pd(OAc)$_2$ (5 mg, 0.022 mmol), Xantphos (26 mg, 0.045 mmol) and potassium tert-butoxide (80 mg, 0.71 mmol) in dioxane/DMF (2.5 mL, 4/1 v/v) was sealed in a microwave reaction tube and irradiated with microwave at 160° C. for 20 min. After cooling down to room temperature, the cap was removed and the resulting mixture filtered and the filtered solid washed with DCM. The filtrate was concentrated and the residue purified by flash chromatography on silica gel (5-10% MeOH/DCM) to yield compound 64 as a yellow solid (43 mg, 25%). MS (ESI+): m/z 521.

The title compound (CLXX) in the free base form was prepared from compound 64 according to method B and without further purification. The free base compound was then converted to HCl salt according to method C as a yellow solid (25 mg, 60% overall). ¹H NMR (DMSO-$d_6$): δ 2.74 (s, 3H), 3.15-3.25 (m, 4H), 3.55-3.75 (m, 6H), 3.82 (t, J=5.1 Hz, 2H), 4.54 (br s, 1H), 6.91 (dd, J=8.8 Hz, J=2.9 Hz, 1H), 6.98 (d, J=2.9 Hz, 1H), 7.42 (d, J=8.8 Hz, 1H), 7.75 (s, 1H), 8.03 (dd, J=1.8 Hz, J=0.9 Hz, 1H), 8.30 (d, J=1.8 Hz, 1H), 10.05 (br s, 1H), 10.78 (br s, 1H), 11.73 (br s, 1H). MS (ESI+): m/z 507.

Example 147

Synthesis of 4-[7-(2-chloro-5-hydroxy-phenyl)-5-methyl-benzo[1,2,4]triazin-3-ylamino]-N-ethyl-N-(2-pyrrolidin-1-yl-ethyl)-benzenesulfonamide

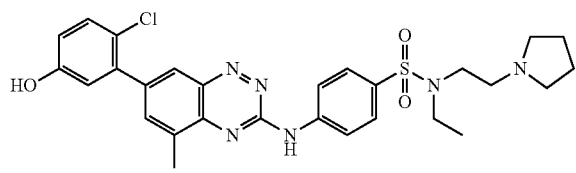
(CLXXI)

To synthesize the title compound (CLXXI), intermediate compounds 65 (4-bromo-N-ethyl-N-(2-pyrrolidin-1-yl-ethyl)-benzenesulfonamide) and 66 (4-[7-(2-chloro-5-methoxy-phenyl)-5-methyl-benzo[1,2,4]triazin-3-ylamino]-N-ethyl-N-(2-pyrrolidin-1-yl-ethyl)-benzenesulfonamide) shown below were used.

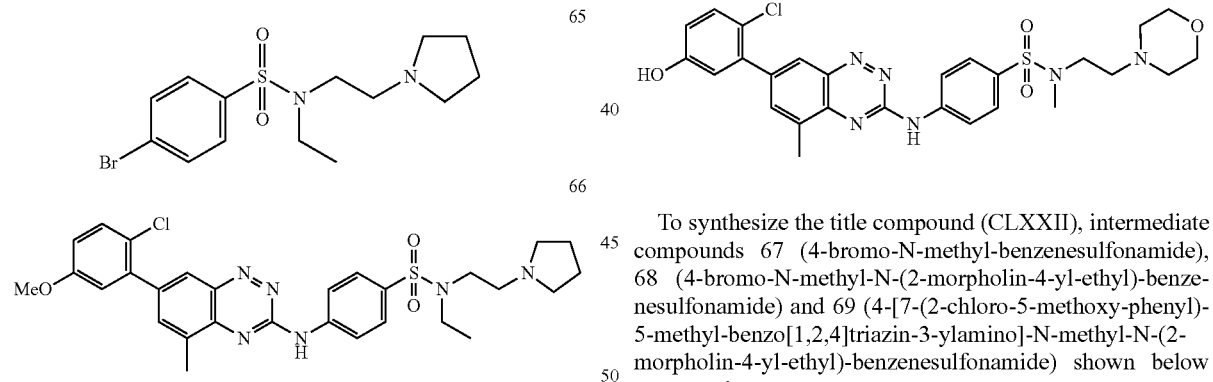

65

66

To synthesize compound 65, a solution of compound 38 (scheme (CLIV), Example 135) (1.0 g, 3.0 mmol), iodoethane (0.25 mL, 3.1 mmol) and cesium carbonate (1.5 g, 4.6 mmol) in acetonitrile (25 mL) was stirred at room temperature for 16 h. The mixture was poured into water and extracted with EtOAc. The combined organic layers were washed with brine, dried over $Na_2SO_4$ and filtered. The filtrate was concentrated and the residue purified by flash chromatography on silica gel (8% MeOH/DCM) to afford compound 65 as a white solid (0.80 g, 74%). ¹H NMR (DMSO-$d_6$): δ 1.03 (t, J=7.1 Hz, 3H), 1.55-1.75 (m, 4H), 2.35-2.75 (m, 4H), 3.15-3.25 (m, 4H), 3.32 (br s, 2H), 7.76 (d, J=8.8 Hz, 2H), 7.81 (d, J=8.6 Hz, 2H). MS (ESI+): m/z 363.

To synthesize compound 66, a suspension of compound 16 (scheme (CXXXV), Example 124) (0.10 g, 0.33 mmol), compound 65 (0.15 g, 0.42 mmol), Pd(OAc)$_2$ (5 mg, 0.022 mmol), Xantphos (26 mg, 0.045 mmol) and potassium tert-butoxide (80 mg, 0.71 mmol) in dioxane/DMF (3 mL, 2/1 v/v) was sealed in a microwave reaction tube and irradiated with microwave at 160° C. for 20 min. After cooling down to room temperature, the cap was removed, the resulting mixture was filtered and the filtered solid was washed with DCM. The filtrate was concentrated and the residue titrated in MeOH. Compound 66 was obtained as a yellow solid (0.17 g, 89%) after filtration and washed with MeOH. MS (ESI+): m/z 581.

The title compound (CLXXI) in the free base form was prepared from compound 66 according to method B and the crude product purified by flash chromatography on silica gel (10% MeOH/DCM). The free base compound was then converted to HCl salt according to method C to yield a yellow solid (0.13 g, 77% overall). ¹H NMR (DMSO-$d_6$): δ 1.04 (t, J=7.1 Hz, 3H), 1.80-1.92 (m, 2H), 1.95-2.10 (m, 2H), 2.72 (s, 3H), 3.00-3.15 (m, 2H), 3.23 (q, J=7.1 Hz, 2H), 3.28-3.38 (m, 2H), 3.40. (m, 2H), 3.53-3.63 (m, 2H), 6.89 (dd, J=8.7 Hz, J=2.8 Hz, 1H), 6.95 (d, J=2.9 Hz, 1H), 7.42 (d, J=8.8 Hz, 1H), 7.90 (d, J=8.8 Hz, 2H), 7.93 (dd, J=1.8 Hz, J=0.9 Hz, 1H), 8.23 (d, J=1.8 Hz, 1H), 8.28 (d, J=8.8 Hz, 2H), 9.97 (s, 1H), 10.01 (br s, 1H), 11.48 (s, 1H). MS (ESI+): m/z 567.

Example 148

Synthesis of 4-[7-(2-chloro-5-hydroxy-phenyl)-5-methyl-benzo[1,2,4]triazin-3-ylamino]-N-methyl-N-(2-morpholin-4-yl-ethyl)-benzenesulfonamide (CLXXII)

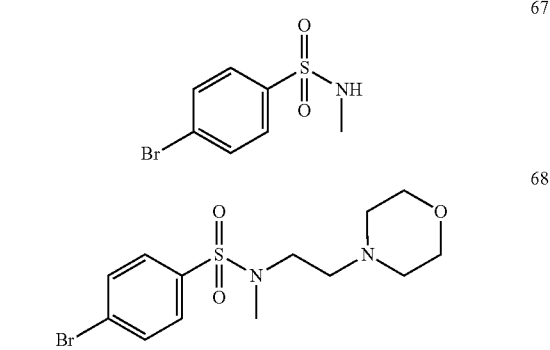

To synthesize the title compound (CLXXII), intermediate compounds 67 (4-bromo-N-methyl-benzenesulfonamide), 68 (4-bromo-N-methyl-N-(2-morpholin-4-yl-ethyl)-benzenesulfonamide) and 69 (4-[7-(2-chloro-5-methoxy-phenyl)-5-methyl-benzo[1,2,4]triazin-3-ylamino]-N-methyl-N-(2-morpholin-4-yl-ethyl)-benzenesulfonamide) shown below were used.

67

68

-continued

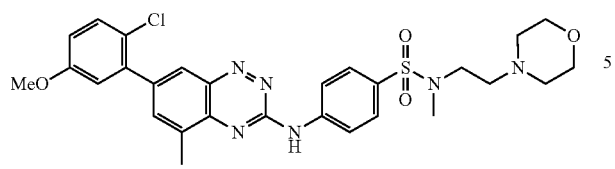

69

To synthesize compound 67, to a solution of 4-bromosulfonyl chloride (5.0 g, 20 mmol) in DCM (30 mL) was added methylamine (2 M in THF, 20 mL, 40 mmol). The mixture was stirred at room temperature for 1 h and then the solvent was removed. A saturated NaHCO$_3$ solution was added to the residue and then extracted with EtOAc. The combined organic layers were washed with water, brine, dried over anhydrous Na$_2$SO$_4$ and filtered. The filtrate was concentrated and the residue triturated in hexane., Compound 67 was obtained as a white solid after filtration (4.0 g, 82%). $^1$H NMR (DMSO-d$_6$): δ 2.41 (d, J=5.0 Hz, 3H), 7.56 (q, J=4.9 Hz, 1H), 7.70 (d, J=8.7 Hz, 2H), 7.83 (d, J=8.7 Hz, 2H).

To synthesize compound 68, a solution of compound 67 (1.0 g, 4.0 mmol), 4-(2-chloro-ethyl)-morpholine (0.85 g, 4.6 mmol) and cesium carbonate (3.3 g, 10 mmol) in acetonitrile (30 mL) was heated at reflux for 15 h. The mixture was cooled and poured into water. The aqueous layer was extracted with EtOAc and the combined organic layers washed with brine, dried over Na$_2$SO$_4$ and filtered. The filtrate was concentrated and the residue triturated in Et$_2$O/hexane (1/1) to afford compound 68 as an off-white solid (1.2 g, 83%) after filtration. MS (ESI+): m/z 363.

To synthesize compound 69 a suspension of compound 16 (scheme (CXXXV), Example 124) (0.10 g, 0.33 mmol), compound 68 (0.15 g, 0.41 mmol), Pd(OAc)$_2$ (5 mg, 0.022 mmol), Xantphos (26 mg, 0.045 mmol) and potassium tert-butoxide (80 mg, 0.71 mmol) in dioxane/DMF (3 mL, 2/1 v/v) was sealed in a microwave reaction tube and irradiated with microwave at 160° C. for 20 min. After cooling down to room temperature, the cap was removed and the resulting mixture filtered and the filtered solid washed with DCM. The filtrate was concentrated and the residue triturated in DCM/hexane (1/5). Compound 69 was obtained as a green solid (0.18 g, 93%) after filtration and washed with hexane. $^1$H NMR (DMSO-d$_6$): δ 2.35-2.42 (m, 4H), 2.46 (t, J=6.7 Hz, 2H), 2.72 (s, 3H), 2.73 (s, 3H), 3.10 (t, J=6.7 Hz, 2H), 3.55 (t, J=4.5 Hz, 2H), 3.84 (s, 3H), 7.07 (dd, J=8.9 Hz, J=3.0 Hz, 1H), 7.16 (d, J=3.1 Hz, 1H), 7.54 (d, J=8.9 Hz, 1H), 7.84 (d, J=8.9 Hz, 2H), 7.92 (s, 1H), 8.26 (d, J=8.9 Hz, 2H), 8.28 (d, J=1.8 Hz, 1H), 11.45 (s, 1H). MS (ESI+): m/z 583.

The title compound (CLXXII) in the free base form was prepared from compound 69 according to method B and the crude product purified by flash chromatography on silica gel (10% MeOH/DCM). The free base compound was then converted to HCl salt according to method C as a brown solid (0.10 g, 57% overall). $^1$H NMR (DMSO-d$_6$): δ 3.10-3.20 (m, 2H), 3.30-3.40 (m, 4H), 3.50 (br d, J=11.9 Hz, 2H), 3.78 (br t, J=11.8 Hz, 2H), 3.99 (br d, J=11.9 Hz, 2H), 6.89 (dd, J=8.8 Hz, J=2.9 Hz, 1H), 6.96 (d, J=2.9 Hz, 1H), 7.41 (d, J=8.8 Hz, 1H), 7.88 (d, J=8.9 Hz, 2H), 7.91-7.93 (m, 1H), 8.22 (d, J=1.8 Hz, 1H), 8.31 (d, J=8.9 Hz, 2H), 10.00 (s, 1H), 10.56 (br s, 1H), 11.50 (s, 1H). MS (ESI+): m/z 569 (M+H)$^+$.

Example 149

Synthesis of 4-chloro-3-[3-(4-{[(2-diethylamino-ethyl)-methyl-amino]-methyl}-phenylamino)-5-methyl-benzo[1,2,4]triazin-7-yl]-phenol

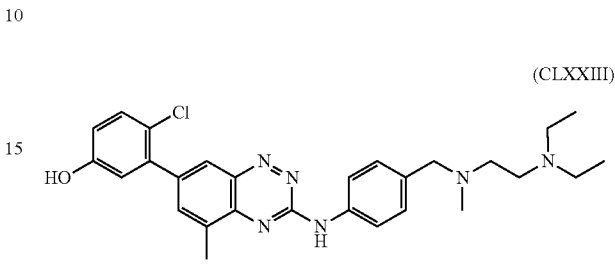

(CLXXIII)

To synthesize the title compound (CLXXIII), intermediate compounds 70 (N-(4-bromo-benzyl)-N',N'-diethyl-N-methyl-ethane-1,2-diamine) and 71 (N-{4-[7-(2-chloro-5-methoxy-phenyl)-5-methyl-benzo[1,2,4]triazin-3-ylamino]-benzyl}-N',N'-diethyl-N-methyl-ethane-1,2-diamine) shown below were used.

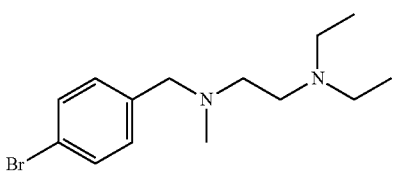

70

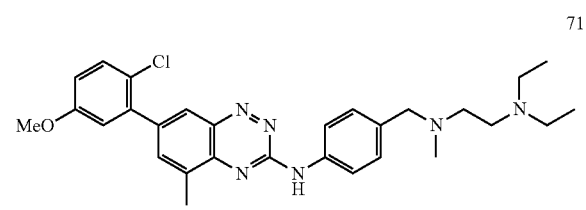 [SMILES: CCN(CC)CCN(C)Cc1ccc(Nc2nnc3cc(-c4cc(OC)ccc4Cl)cc(C)c3n2)cc1]

71

To synthesize compound 70, a solution of N,N-diethyl-N'-methyl-ethane-1,2-diamine (3.4 g, 26 mmol), 4-bromobenzyl bromide (5.0 g, 20 mmol) and cesium carbonate (13 g, 40 mmol) in acetonitrile (60 mL) was heated at reflux for 18 h. The mixture was cooled and poured into water. The aqueous layer was extracted with EtOAc and the combined organic layers washed with brine, dried over Na$_2$SO$_4$, and filtered. The filtrate was concentrated and the crude compound 70 was used in the next step without purification.

To synthesize compound 71 a suspension of compound 16 (scheme (CXXXV), Example 124) (0.10 g, 0.33 mmol), compound 70 (0.15 g, 0.50 mmol), Pd(OAc)$_2$ (5 mg, 0.022 mmol), Xantphos (26 mg, 0.045 mmol) and potassium tert-butoxide (80 mg, 0.71 mmol) in dioxane/DMF (3 mL, 2/1 v/v) was sealed in a microwave reaction tube and irradiated with microwave at 160° C. for 20 min. After cooling down to room temperature, the cap was removed, the resulting mixture was filtered, and the filtered solid was washed with DCM. The filtrate was concentrated and the residue was purified by flash chromatography on silica gel (10% MeOH/DCM to 20% MeOH, 2% TEA in DCM) to afford compound 71 as an orange solid (0.10 g, 59%). $^1$H NMR (DMSO-d$_o$): δ 0.93 (t, J=7.1 Hz, 6H), 2.15 (s, 3H), 2.35-2.46 (m, 8H), 2.66 (s, 3H), 3.47 (s, 2H), 3.83 (s, 3H), 7.05 (dd, J=8.9 Hz, J=3.1 Hz, 1H), 7.14 (d, J=3.2 Hz, 1H), 7.32 (d, J=8.5 Hz, 1H), 7.53 (d, J=8.9 Hz, 2H), 7.87-7.89 (m, 1H), 7.98 (d, J=8.6 Hz, 2H), 8.21 (d, J=1.8 Hz, 1H), 10.95 (s, 1H). MS (ESI+): m/z 519.

The title compound (CLXXIII) in the free base form was prepared from compound 71 according to method B and the crude product purified by HPLC. The corrected fractions were poured into saturated NaHCO$_3$ and extracted with EtOAc. The combined organic layers were washed with brine, dried over Na$_2$SO$_4$, and filtered. The filtrate was concentrated to afford the free base compound, which was converted to HCl salt according to method C and furnished the title compound as an orange solid (40 mg, 19% overall). $^1$H NMR (DMSO-d$_6$): δ 1.26 (t, J=7.2 Hz, 6H), 2.69 (s, 3H), 2.71 (br s, 3H), 3.10-3.25 (m, 4H), 3.45-3.62 (m, 4H), 4.20-4.30 (m, 1H), 4.51 (br d, J=11.3 Hz, 1H), 6.89 (dd, J=8.7 Hz, J=2.9 Hz, 1H), 6.95 (d, J=2.9 Hz, 1H), 7.41 (d, J=8.7 Hz, 1H), 7.67 (d, J=8.0 Hz, 2H), 7.89 (s, 1H), 8.13 (d, J=8.4 Hz, 2H), 8.18 (d, J=1.7 Hz, 1H), 10.00 (s, 1H), 10.81 (br s, 1H), 11.19 (s, 1H), 11.23 (br s, 1H). MS (ESI+): m/z 505.

Example 150

Synthesis of 4-[7-(2-fluoro-3-hydroxy-phenyl)-5-methyl-benzo[1,2,4]triazin-3-ylamino]-N-(2-pyrrolidin-1-yl-ethyl)-benzenesulfonamide (CLXXIV)

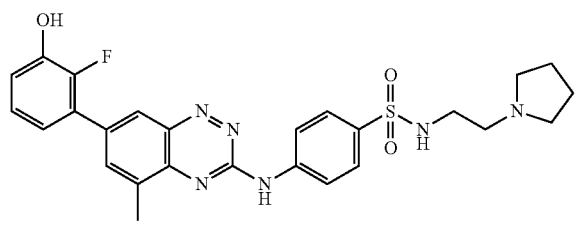

To synthesize the title compound (CLXXIV), intermediate compounds 72 (7-(2-fluoro-3-methoxy-phenyl)-5-methyl-benzo[1,2,4]triazin-3-ylamine) and 73 (4-[7-(2-fluoro-3-methoxy-phenyl)-5-methyl-benzo[1,2,4]triazin-3-ylamino]-N-(2-pyrrolidin-1-yl-ethyl)-benzenesulfonamide) shown below were used.

72

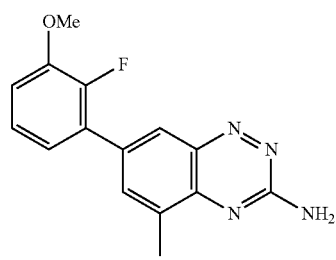

73

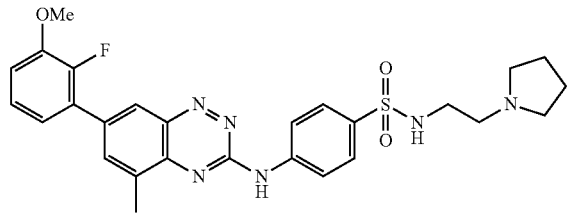

To synthesize compound 72, compound 2 (scheme (CXXVI), Example 120) (1.0 g, 4.2 mmol), 2-fluoro, 3-methoxybenzene boronic acid (0.87 g, 5.1 mmol), Pd(PPh$_3$)$_4$ (0.40 g, 0.35 mmol), 2 M Na$_2$CO$_3$ (5 mL, 10 mmol) were suspended in a mixture of DME/ethanol (4:1, 25 mL). The resulting mixture was heated at reflux for 1 h. The mixture was allowed to cool to room temperature, filtered and washed with DCM. The filtrate was concentrated and the residue triturated in MeOH. The resulting green solid was filtered and washed with MeOH. The resulting crude compound 72 was used in the next step without further purification. MS (ESI+): m/z 285.

To synthesize compound 73, a suspension of compound 72 (0.10 g, 0.35 mmol), compound 38 (scheme (CLIV), Example 135) (0.14 g, 0.42 mmol), Pd(OAc)$_2$ (5 mg, 0.022 mmol), Xantphos (26 mg, 0.045 mmol) and potassium tert-butoxide (80 mg, 0.71 mmol) in dioxane/DMF (3 mL, 2/1 v/v) was sealed in a microwave reaction tube and irradiated with microwave at 160° C. for 20 min. After cooling down to RT, the cap was removed and the resulting mixture filtered and the filtered solid washed with DCM. The filtrate was concentrated and the residue purified by flash chromatography on silica gel (10-20% MeOH/DCM) to afford compound 73 as a yellow solid (80 mg, 43%). $^1$H NMR (DMSO-d$_6$): δ 1.55-1.65 (m, 4H), 2.30-2.40 (m, 4H), 2.44 (t, J=7.0 Hz, 2H), 2.72 (s, 3H), 2.80-2.90 (m, 2H), 3.92 (s, 3H), 7.20-7.35 (m, 3H), 7.80 (d, J=8.5 Hz, 1H), 7.84 (d, J=8.9 Hz, 2H), 8.04 (s, 1H), 8.21 (d, J=8.9 Hz, 2H), 8.35 (s, 1H), 11.40 (s, 1H). MS (ESI+): m/z 537.

The title compound (CLXXIV) in the free base form was prepared from compound 73 (71 mg, 0.13 mmol) according to method B. The free base compound was then converted to HCl salt according to method C as an orange solid (48 mg, 66% overall). $^1$H NMR (DMSO-d$_6$): δ 1.80-1.90 (m, 2H), 1.95-2.03 (m, 2H), 2.73 (s, 3H), 2.95-3.05 (m, 2H), 3.10 (q, J=6.2 Hz, 2H), 3.24 (q, J=6.1 Hz, 2H), 3.48-3.58 (m, 2H), 7.00-7.20 (m, 3H), 7.88 (d, J=9.0 Hz, 2H), 7.91 (t, J=6.1 Hz, 1H), 8.05 (s, 1H), 8.25 (d, J=9.0 Hz, 2H), 8.34 (s, 1H), 10.05 (br s, 1H), 10.10 (s, 1H), 11.45 (s, 1H). MS (ESI+): m/z 523.

Example 151

Synthesis of 4-[7-(2-fluoro-6-hydroxy-phenyl)-5-methyl-benzo[1,2,4]triazin-3-ylamino]-N-(2-pyrrolidin-1-yl-ethyl)-benzenesulfonamide

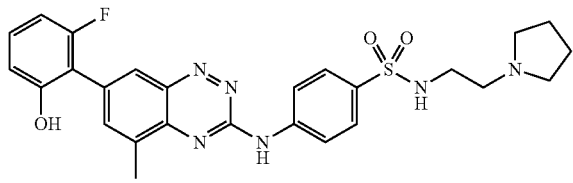
(CLXXV)

To synthesize the title compound (CLXXV), intermediate compounds 74 (7-(2-fluoro-6-methoxy-phenyl)-5-methyl-benzo[1,2,4]triazin-3-ylamine) and 75 (4-[7-(2-fluoro-6-methoxy-phenyl)-5-methyl-benzo[1,2,4]triazin-3-ylamino]-N-(2-pyrrolidin-1-yl-ethyl)-benzenesulfonamide) shown below were used.

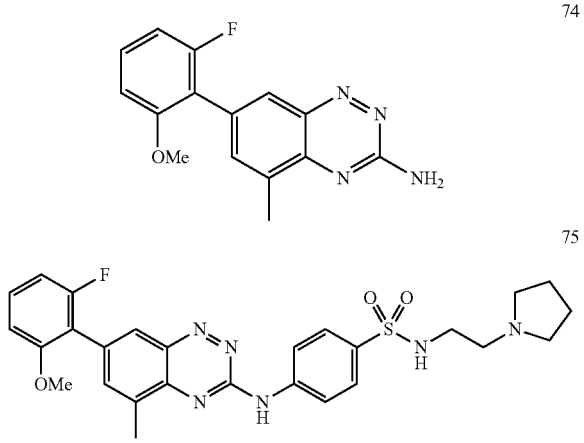

To synthesize compound 74, compound 2 (scheme (CXXVI), Example 120) (1.0 g, 4.2 mmol), 2-fluoro,6-methoxybenzene boronic acid (0.87 g, 5.1 mmol), Pd(PPh₃)₄ (0.40 g, 0.35 mmol), 2 M Na₂CO₃ (5 mL, 10 mmol) were suspended in a mixture of DME/ethanol (4:1, 25 mL). The resulting mixture was heated at reflux for 1 h. The mixture was allowed to cool to room temperature, filtered and washed with DCM. The filtrate was concentrated and the residue triturated in MeOH. The resulting green solid was filtered and washed with MeOH. The resulting crude compound 74 was used in the next step without further purification. MS (ESI+): m/z 285.

To synthesize compound 75, a suspension of compound 74 (0.10 g, 0.35 mmol), compound 38 (scheme (CLIV), Example 135) (0.14 g, 0.42 mmol), Pd(OAc)₂ (5 mg, 0.022 mmol), Xantphos (26 mg, 0.045 mmol) and potassium tert-butoxide (80 mg, 0.71 mmol) in dioxane/DMF (3 mL, 2/1 v/v) was sealed in a microwave reaction tube and irradiated with microwave at 160° C. for 20 min. After cooling down to room temperature, the cap was removed, the resulting mixture was filtered, and the filtered solid was washed with DCM. The filtrate was concentrated and the residue purified by flash chromatography on silica gel (10-20% MeOH/DCM) to afford compound 75 as a yellow solid (0.14 g, 74%). ¹H NMR (DMSO-d₆): δ 1.60-1.72 (m, 4H), 2.69 (s, 3H), 2.40-2.60 (m, 2H), 2.85-2.95 (m, 2H), 3.27-3.40 (m, 4H), 3.81 (s, 3H), 7.00 (t, J=8.8 Hz, 1H), 7.06 (d, J=8.5 Hz, 1H), 7.47 (dd, J=15.3 Hz, J=8.4 Hz, 1H), 7.83 (s, 1H), 7.84 (d, J=9.0 Hz, 2H), 8.18 (s, 1H), 8.22 (d, J=8.9 Hz, 2H), 11.37 (s, 1H). MS (ESI+): m/z 537.

The title compound (CLXXV) in the free base form was prepared from compound 75 (0.14 g, 0.26 mmol) according to method B. The free base compound was then converted to HCl salt according to method C as an orange solid (0.10 g, 69% overall). ¹H NMR (DMSO-d₆): δ 1.80-1.90 (m, 2H), 1.95-2.03 (m, 2H), 2.70 (s, 3H), 2.97-3.05 (m, 2H), 3.10 (q, J=6.3 Hz, 2H), 3.24 (q, J=6.1 Hz, 2H), 3.50-3.60 (m, 2H), 6.81 (t, J=9.1 Hz, 1H), 6.89 (d, J=8.3 Hz, 2H), 7.28 (dd, J=15.2 Hz, J=8.3 Hz, 1H), 7.88 (dd, J=8.8 Hz, 2H), 7.89 (s, 1H), 7.90 (t, J=6.1 Hz, 1H), 8.21 (s, 1H), 8.26 (d, J=9.0 Hz, 2H), 10.04 (br s, 1H), 10.20 (s, 1H), 11.40 (s, 1H). MS (ESI+): m/z 523.

Example 152

Synthesis of benzoic acid 4-chloro-3-{5-methyl-3-[4-(2-pyrrolidin-1-yl-ethoxy)-phenylamino]-benzo[1,2,4]triazin-7-yl}-phenyl ester

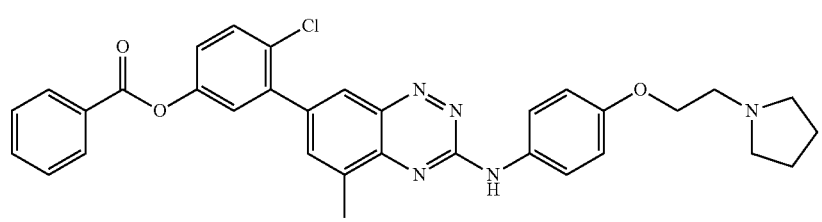
(CLXXVI)

The title compound was synthesized and had the following characteristics. ¹H NMR (DMSO-d₆): δ 1.65-1.72 (m, 4H), 2.50-2.56 (m, 4H), 2.63 (s, 3H), 2.79 (t, J=5.9 Hz, 2H), 4.07 (t, J=6.0 Hz, 2H), 7.00 (d, J=9.1 Hz, 2H), 7.46 (dd, J=8.7 Hz, J=2.8 Hz, 1H), 7.60-7.65 (m, 3H), 7.75 (d, J=8.6 Hz, 1H), 7.76 (t, J=7.4 Hz, 1H), 7.90 (dd, J=1.8 Hz, J=1.0 Hz, 1H), 7.93

(d, J=9.1 Hz, 2H), 8.16 (d, J=8.4 Hz, 2H), 8.22 (d, J=1.8 Hz, 1H), 10.84 (br s, 1H). MS (ESI+): m/z 581.

For all the Examples 153-159 that follow, the synthetic procedures that were used corresponded to the general synthetic scheme (CLXXVII).

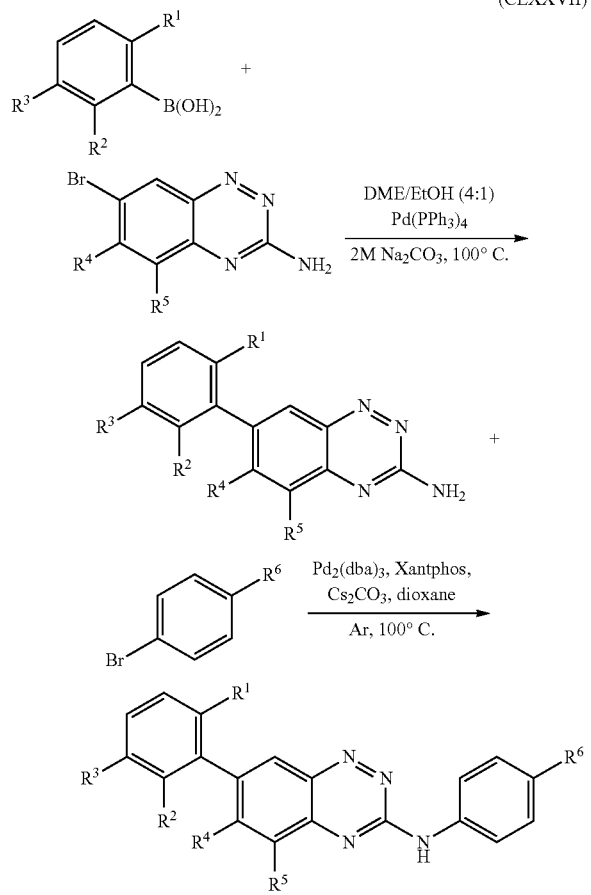

Example 153

Synthesis of N-(4-(2-(pyrrolidin-1-yl)ethoxy)phenyl)-6-methyl-7-(4-methylpyridin-3-yl)benzo[e][1,2,4]triazin-3-amine

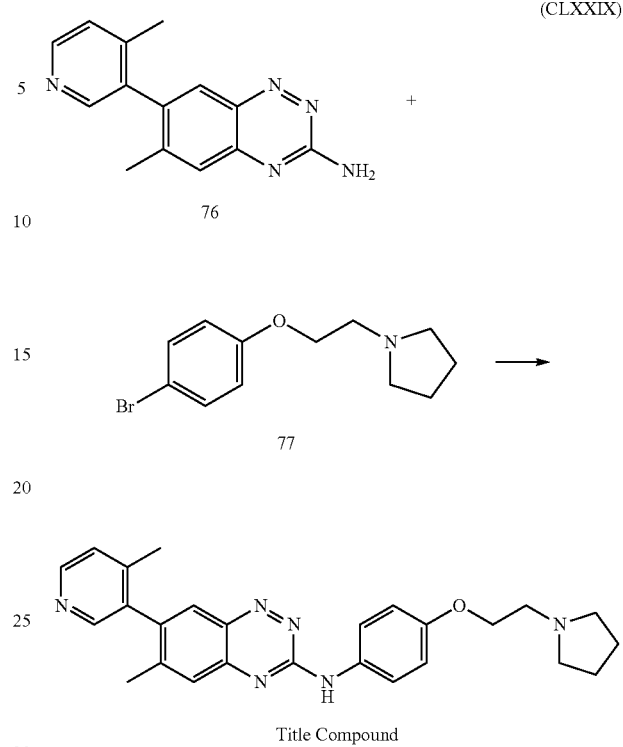

To synthesize the title compound, the general Buchwald procedure was employed using compounds 76 (124 mg, 0.5 mmol), 77 (171 mg, 0.6 mmol), Cs$_2$CO$_3$ (660 mg, 2.0 mmol), Xantphos (58 mg, 0.1 mmol), Pd$_2$(dba)$_3$ (47 mg, 0.05 mmol), 3 Å mol sieves (ca. 500 mg), and 10 mL dioxane for 18 h. The reaction mixture was concentrated in vacuo and purified using column chromatography (1:9 MeOH/CHCl$_3$) to afford the title compound as a red-orange solid (128 mg, 49%). R$_f$=0.24 (1:9 MeOH/CHCl$_3$); $^1$H NMR DMSO-d$_6$ 1.87-1.94 (m, 2H), 2.02-2.11 (m, 2H), 2.12 (s, 3H), 2.19 (s, 3H), 2.30 (s, 1.7H), 3.12-3.20 (m, 2H), 3.60-3.66 (m, 4H), 4.31 (t, J=5.0 Hz, 2H), 7.07 (d, J=9.1 Hz, 2H), 7.45 (d, J=5.0 Hz, 1H), 7.69 (s, 1H), 7.91 (d, J=9.0 Hz, 2H), 8.07 (s, 1H), 8.41 (s, 1H), 8.54 (d, J=5.1 Hz, 1H), 9.72 (br s, 1H), 10.75 (s, 1H).

Example 154

Synthesis of 5-(5-methyl-7-(2,6-dimethylphenyl)benzo[e][1,2,4]triazin-3-ylamino)-1-(3-(pyrrolidin-1-yl)propyl)pyridin-2(1H)-one

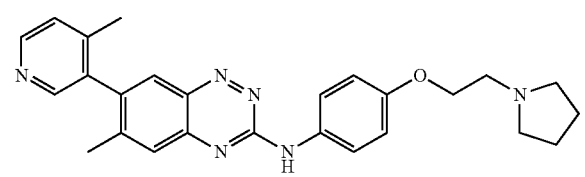

The synthesis of the title compound (CLXXVIII) can be generally described by the reaction scheme (CLXXIX).

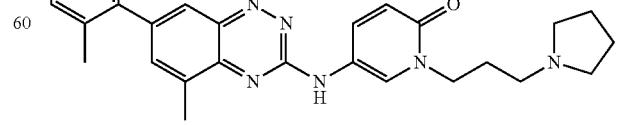

The synthesis of the title compound (CLXXX) can be generally described by the reaction scheme (CLXXXI).

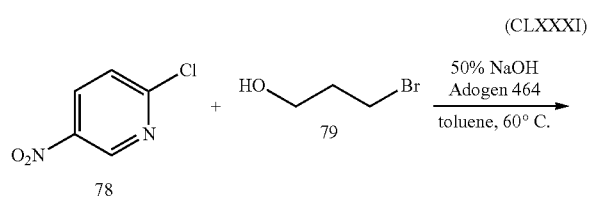

(CLXXXI)

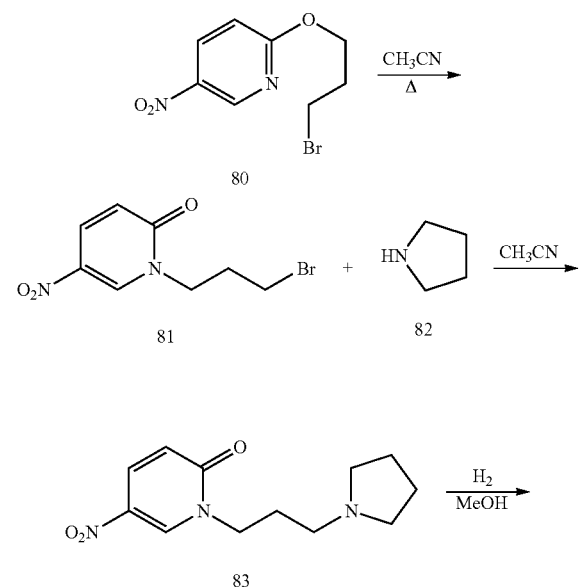

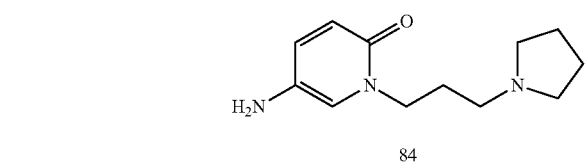

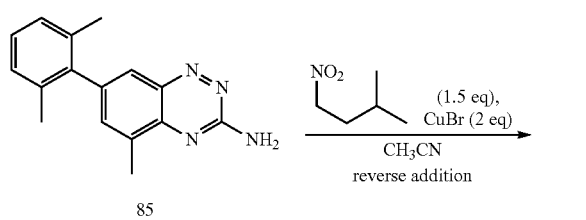

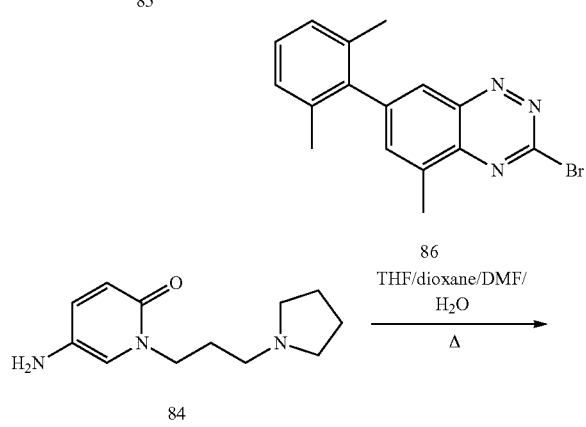

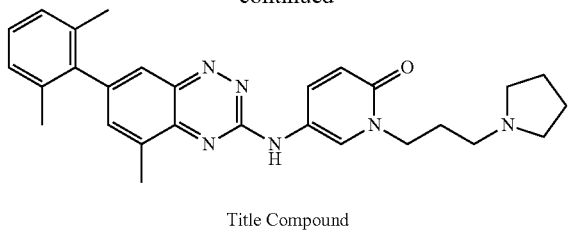

Title Compound

First, 2-(3-bromopropoxy)-5-nitropyridine (compound 80 on scheme (CLXXXI)) was synthesized. To synthesize, to a mixture of compounds 78 (5.0 g, 32 mmol) and 79 (4.1 mL, 47 mmol) in toluene (160 mL) was added 50% aqueous NaOH (1.9 mL, 49 mmol) followed by Adogen 464 (0.6 g, 1.6 mmol). The biphasic reaction mixture was stirred for 5 h. at 60° C., cooled, and concentrated in vacuo. The crude mixture was purified by column chromatography (3:7-4:7 EtoAc/hexanes) to afford compound 80 as an impure pale-yellow oil (3.7 g, 45%). $R_f$=0.5 (3:7 EtOAc/hexanes $^1$H NMR CDCl$_3$: δ 2.35 (quintet, J=6.4 Hz, 2H), 3.56 (t, J=6.7 Hz, 2H), 4.57 (t, J=5.9 Hz, 2H), 6.82 (d, J=9.6 Hz, 1H), 8.36 (dd, J=9.5, 3.0 Hz, 1H), 9.07 (d, J=2.6 Hz, 1H).

Next, compound 81 (1-(3-bromopropyl)-5-nitropyridin-2 (1H)-one) was synthesized by refluxing bromide 80 (3.7 g, 14 mmol) in acetonitrile (70 mL) for 5 h., cooling, and concentrating in vacuo. The crude mixture was purified by column chromatography (1:1 EtOAc/hexanes) to afford compound 81 as a pale-yellow oil (2.5 g, 68%, 90% yield corrected for starting impurity). $R_f$=0.2 (3:7 EtOAc/hexanes); $^1$H NMR CDCl$_3$: δ 2.38 (quintet, J=6.4 Hz, 2H), 3.43 (d, J=6.1 Hz, 2H), 4.20 (t, J=6.9 Hz, 2H), 6.57 (d, J=10.1 Hz, 1H), 8.11 (dd, J=10.1, 3.1 Hz, 1H), 8.67 (d, J=3.0 Hz, 1H).

Next, compound 83 (5-nitro-1-(3-(pyrrolidin-1-yl)propyl) pyridin-2(1H)-one) was synthesized by adding pyrrolidine (14 mL, 169 mmol) to compound 81 (2.5 g, 9.5 mmol) in acetonitrile (50 mL); solution immediately became yellow. The reaction sat for 14 h. to ensure completion, was concentrated in vacuo, and purified by column chromatography (1:10:189 NH$_4$OH/MeOH/CH$_3$Cl) to afford compound 83 as a pale-yellow oil (2.3 g, 95%). LC retention time: 1.09 min. MS (ESI+) m/z=252.1 NMR CDCl$_3$: δ 1.73-1.75 (m, 4H), 1.92 (quintet, J=6.5 Hz, 2H), 2.38-2.46 (m, 6H), 4.10 (t, J=6.5 Hz, 2H), 6.48 (d, J=10.0 Hz, 1H), 8.03 (dd, J=10.1, 3.1 Hz, 1H), 8.84 (d, J=3.0 Hz, 1H); $^{13}$C NMR CDCl$_3$: δ 23.7, 26.7, 49.2, 51.8, 53.8, 119.3, 130.2, 133.1, 141.2, 161.7.

To compound 83 (2.1 g, 8.3 mmol) in $_{MeOH}$ (65 mL) was added palladium acetate (178.4 mg, 0.8 mmol), and the suspension was bubbled with H$_2$ until the palladium turned black (ca. 10 min). The suspension was stirred under H$_2$ for 3 h., purged with argon, and filtered through celite using methanol to thoroughly wash the filter cake. The organic solution was concentrated in vacuo to afford compound 84 (5-amino-1-(3-(pyrrolidin-1-yl)propyl)pyridin-2(1H)-one) as a black oil (1.8 g, quant.). LC retention time=0.5 min MS (ESI+) m/z=222.2 $^1$H NMR CDCl$_3$: δ 1.91-2.00 (m, 4H), 2.15 (quintet, J=7.3 Hz, 2H), 2.82 (t, J=7.5 Hz, 2H), 2.88-2.95 (m, 4H), 3.63 (br s, 2H), 3.99 (t, J=7.0 Hz, 2H), 6.49 (d, J=9.5 Hz, 1H) 6.91 (d, J=3.0 Hz, 1H), 7.04 (dd, J=9.5, 3.0 Hz, 1H).

To copper (I) bromide (581 mg, 4.1 mmol) in CH$_3$CN (25 mL) was added 90% isoamyl nitrite (0.5 mL, 3.4 mmol) and the solution warmed to 65° C. A suspension of amine 85 in CH$_3$CN (10 mL) was added and the reaction was refluxed for 90 min. The black solution was filtered, diluted with 20% HCl (80 mL) and extracted with ether (2×80 mL). The combined organic layers were washed with 20% HCl (2×40 mL), dried (MgSO$_4$), filtered, and concentrated in vacuo to afford compound 86 (3-bromo-5-methyl-7-(2,6-dimethylphenyl)benzo[e][1,2,4]triazine) as an oily solid which was used immediately in the next reaction (717 mg, 54%). R$_f$=0.58 (3:7 EtOAc/hexanes).

To compound 86 (167 mg, 0.5 mmol) in THF (2 mL) was added a solution of 0.1 M (1:1:2:6 THF/dioxane/DMF/water) compound 84 (5.0 mL, 0.5 mmol) obtained as described above. After 22 h. under reflux with only minimal forward reaction, TEA (140 µL, 1.0 mmol) was added and continued reflux for 42 h. The reaction was diluted with water (10 mL) and extracted with EtOAc (3×15 mL). The organic layers were combined, dried (MgSO$_4$), filtered, and concentrated in vacuo. The crude mixture was purified by HPLC to afford the title product as an orange solid (3.7 mg, 1.3%). LC retention time=2.54 min, MS (ESI+) m/z=469.4 $^1$H NMR DMSO-d$_6$: δ 1.81-1.88 (m, 2H), 1.97-2.02 (m, 2H), 2.05 (s, 6H), 2.08-2.16 (m, 2H), 2.65 (s, 3H), 2.95-3.05 (m, 2H), 3.15-3.24 (m, 2H), 4.05 (t, J=6.8 Hz, 2H), 6.58 (d, J=9.7 Hz, 1H), 7.15-7.28 (m, 3H), 7.63 (s, 1H), 7.79 (dd, J=9.8, 2.9 Hz, 1H), 7.94 (d, J=1.6 Hz, 1H), 8.62 (br s, 1H), 9.51 (br s, 1H), 10.71 (br s, 1H).

Example 155

Synthesis of 2-(7-(2-chloro-5-hydroxyphenyl)-5-methylbenzo[e][1,2,4]triazin-3-ylamino)-N-(2-(pyrrolidin-1-yl)ethyl)thiazole-4-carboxamide

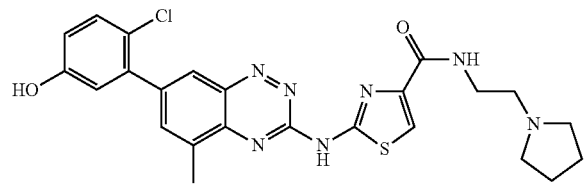

(CLXXXII)

The synthesis of the title compound (CLXXXII) can be generally described by the reaction scheme (CLXXXIII).

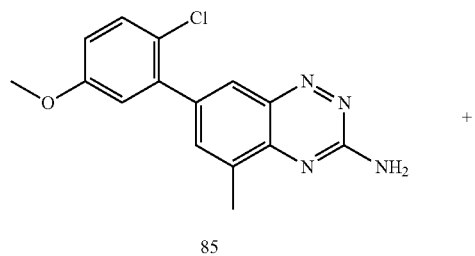

(CLXXXIII)

85

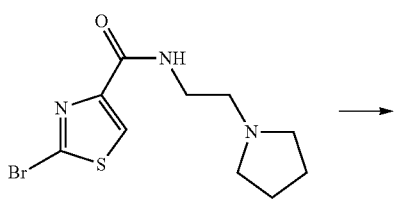

86

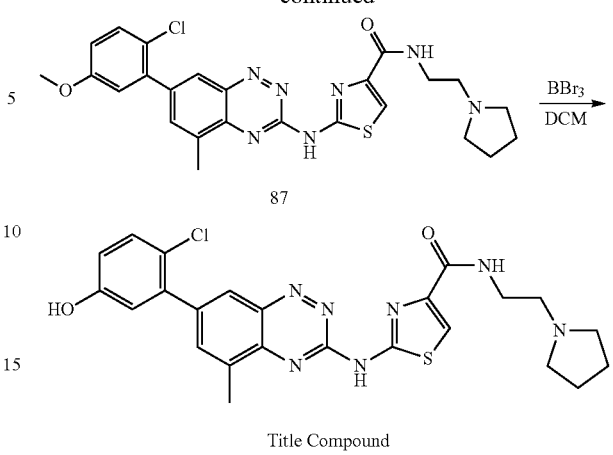

87

Title Compound

The general Buchwald procedure was employed using compounds 85 (254 mg, 0.84 mmol), 86 (214 mg, 0.70 mmol), Cs$_2$CO$_3$ (937 mg, 2.88 mmol), Xantphos (83 mg, 0.14 mmol), Pd$_2$(dba)$_3$ (66 mg, 0.07 mmol), and 15 mL dioxane for 22 h. The crude reaction mixture was diluted with 50 mL water and extracted with DCM (4×75 mL). The combined organic layers were concentrated in vacuo and purified using column chromatography (1:5:94 NH$_4$OH/MeOH/DCM) to afford compound 87 as a yellow solid (188 mg, 51%). R$_f$=0.06 (1:20:179% NH$_4$OH/MeOH/CHCl$_3$); LC retention time: 2.67 min, MS (ESI+) m/z=524.2/526.4.

The general aryl methoxy deprotection procedure was then employed using aryl methoxy compound 87 (188 mg, 0.36 mmol) and 1M BBr$_3$ in DCM (2.1 mL, 2.1 mmol), in 12 mL DCM for 1 h. The reaction was quenched and filtered to afford the title compound (CLXXXII) as a brown solid (132 mg, 72%). LC retention time: 2.20 min, MS (ESI+) m/z=510.5/512.3 $^1$H NMR DMSO-d$_6$: δ 1.72 (s, 4H), 2.52 (shoulder under DMSO), 2.62 (t, J=6.4 Hz, 2H), 2.76 (s, 3H), 3.43 (q, J=6.1 Hz, 2H), 6.88 (dd, J=8.8, 2.9 Hz, 1H), 6.95 (d, J=2.9 Hz, 1H), 7.41 (d, J=8.7 Hz, 1H), 7.83 (s, 1H), 7.86 (t, J=5.8 Hz, 1H), 7.94 (s, 1H), 8.23 (s, 1H), 9.94 (br s, 1H). Calcd for C$_{24}$H$_{24}$ClN$_7$O$_2$S.2.5H$_2$O.0.1Br: C, 51.14; H, 5.36; N, 17.39. Found: C, 50.74; H, 4.79; N, 17.03.

Example 156

Synthesis of 3-(3-(4-(2-(pyrrolidin-1-yl)ethoxy)phenylamino)-6-methylbenzo[e][1,2,4]triazin-7-yl)-4-fluorophenol

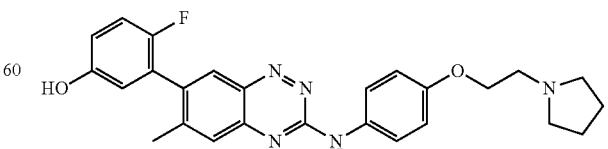

(CLXXXIV)

The synthesis of the title compound (CLXXXIV) can be generally described by the reaction scheme (CLXXXV).

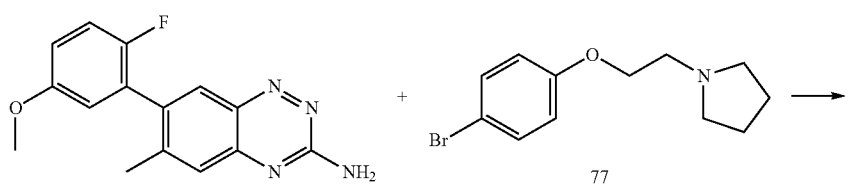

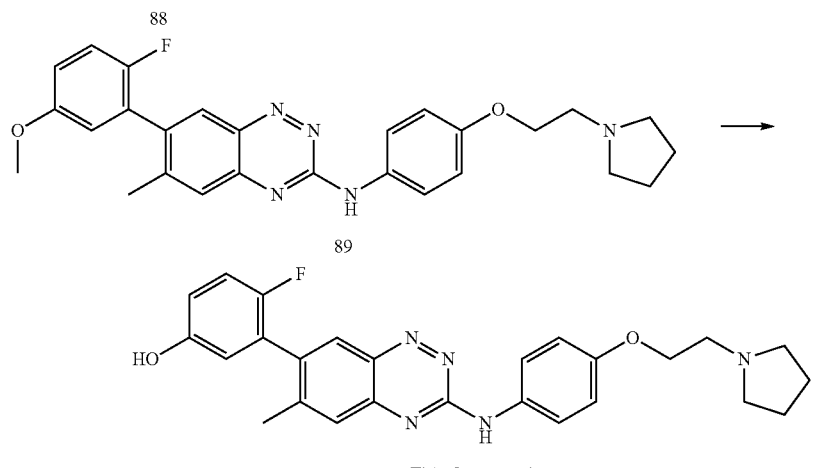

Title Compound

The general Buchwald procedure was employed using compounds 88 (2-(7-(2-chloro-5-methoxyphenyl)-5-methyl-benzo[e][1,2,4]triazin-3-ylamino)-N-(2-(pyrrolidin-1-yl)ethyl)thiazole-4-carboxamide) (254 mg, 0.94 mmol), 77 (described above) (177 μL, 0.85 mmol), Cs$_2$CO$_3$ (1.1 g, 3.42 mmol), Xantphos (102 mg, 0.18 mmol), Pd$_2$(dba)$_3$ (78 mg, 0.09 mmol), and 17 mL dioxane for 18 h, to obtain compound 89 (N-(4-(2-(pyrrolidin-1-yl)ethoxy)phenyl)-7-(2-fluoro-5-methoxyphenyl)-6-methylbenzo[e][1,2,4]triazin-3-amine). Chromatography was run at 1:10:189 NH$_4$OH/MeOH/CHCl$_3$ to afford the title compound as a red solid (181 mg, 45%). R$_f$=0.06 (1:20:179% NH$_4$OH/MeOH/CHCl$_3$); LC retention time: 2.65 min, MS (ESI+) m/z 474.2.

The general aryl methoxy deprotection procedure was then employed using aryl methoxy compound 89 (181 mg, 0.38 mmol) and 1M BBr$_3$ in DCM (2.3 mL, 2.3 mmol), in 10 mL DCM for 90 min. The reaction was quenched and filtered. The water soluble product was recovered by extraction with EtOAc (50 mL). The organic layer was combined with the filtered solid, concentrated in vacuo, and purified using HPLC to afford the title compound (CLXXXV) as a red solid (30 mg, 14%). LC retention time: 2.26 min, MS (ESI+) m/z=460.2 $^1$H NMR DMSO-d$_6$: δ 1.86-1.94 (m, 2H), 2.02-2.08 (m, 2H), 2.32 (s, 3H), 3.11-3.20 (m, 2H), 3.58-3.66 (m, 4H), 4.30 (t, J=5.0 Hz, 2H), 6.76 (dd, J=6.2, 3.1 Hz, 1H), 6.86 (dt, J=8.9, 3.6 Hz, 1H), 7.07 (d, J=9.1 Hz, 2H), 7.16 (t, J=9.2 Hz, 1H), 7.64 (s, 1H), 7.91 (d, J=9.1 Hz, 2H), 8.09 (s, 1H), 9.63 (s, 1H), 9.71 (br s, 1H), 10.75 (s, 1H).

Example 157

Synthesis of 4-[7-(2-fluoro-5-hydroxy-phenyl)-6-methyl-benzo[1,2,4]triazin-3-ylamino]-N-(2-pyrrolidin-1-yl-ethyl)-benzenesulfonamide

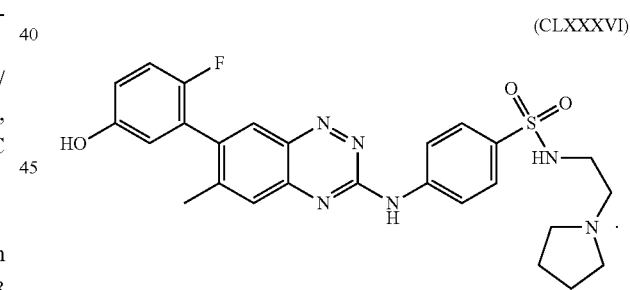

The synthesis of the title compound (CLXXXVI) can be generally described by the reaction scheme (CLXXXVII).

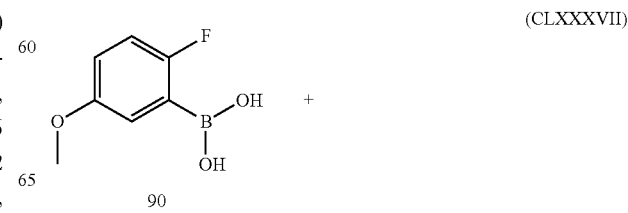

(d, J=8.9 Hz, 2H), 8.86 (t, J=6.2 Hz, 1H), 8.19 (s, 1H), 8.22 (d, J=8.9 Hz, 2H), 9.52 (br s, 1H), 9.66 (s, 1H).

Example 158

Synthesis of 4-[6-methyl-7-(1H-pyrazol-4-yl)-benzo[1,2,4]triazin-3-ylamino]-N-(2-pyrrolidin-1-yl-ethyl)-benzenesulfonamide

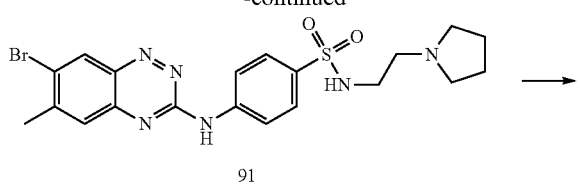

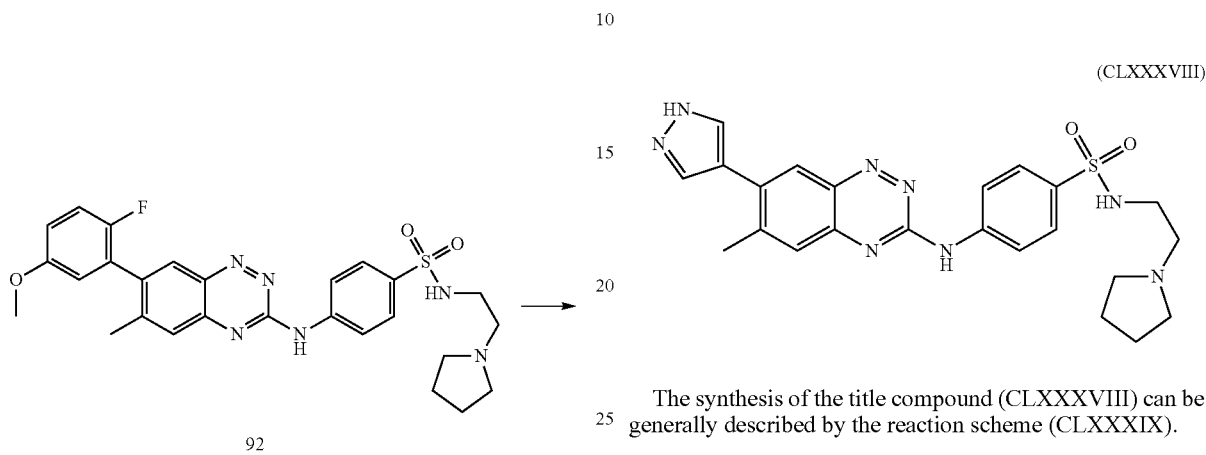

The synthesis of the title compound (CLXXXVIII) can be generally described by the reaction scheme (CLXXXIX).

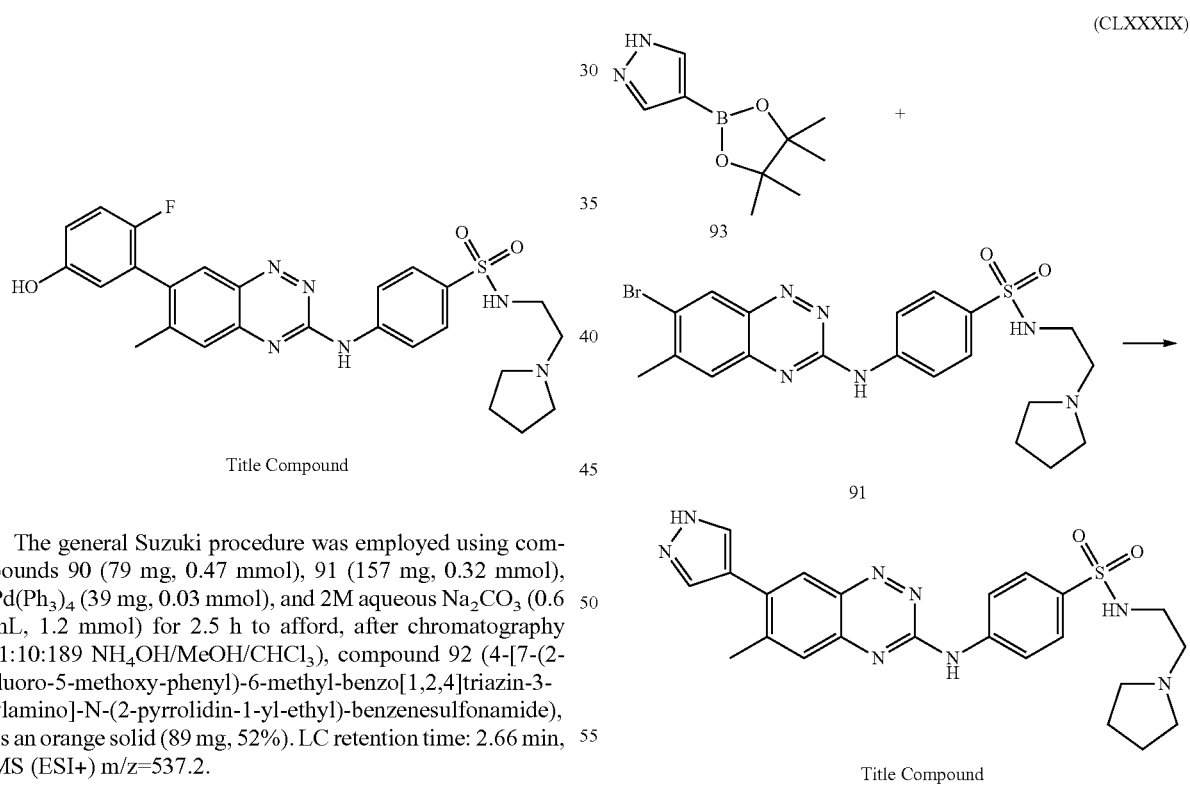

The general Suzuki procedure was employed using compounds 90 (79 mg, 0.47 mmol), 91 (157 mg, 0.32 mmol), Pd(Ph$_3$)$_4$ (39 mg, 0.03 mmol), and 2M aqueous Na$_2$CO$_3$ (0.6 mL, 1.2 mmol) for 2.5 h to afford, after chromatography (1:10:189 NH$_4$OH/MeOH/CHCl$_3$), compound 92 (4-[7-(2-fluoro-5-methoxy-phenyl)-6-methyl-benzo[1,2,4]triazin-3-ylamino]-N-(2-pyrrolidin-1-yl-ethyl)-benzenesulfonamide), as an orange solid (89 mg, 52%). LC retention time: 2.66 min, MS (ESI+) m/z=537.2.

The general aryl methoxy deprotection procedure was then employed using aryl methoxy compound 92 (89 mg, 0.17 mmol) and 1M BBr$_3$ in DCM (1 mL, 1.0 mmol), in 20 mL DCM for 90 min. The reaction was quenched, filtered, and purified using HPLC to afford the title compound (CLXXXVI), as an orange solid (19 mg, 22%). LC retention time: 2.24 min, MS (ESI+) m/z=523.2 $^1$H NMR DMSO-d$_6$: δ 1.83-1.91 (m, 2H), 1.96-2.04 (m, 2H), 2.36 (s, 3H), 2.99-3.08 (m, 4H), 3.21-3.27 (m, 2H), 3.52-3.60 (m, 2H), 6.78 (dd, J=6.2, 3.1 Hz, 1H), 6.88 (dt, J=9.2 Hz, 1H), 7.79 (s, 1H), 7.84

The general Suzuki procedure was employed using compounds 93 (117 mg, 2.2 mmol), 91 (206 mg, 0.42 mmol), Pd(Ph$_3$)$_4$ (53 mg, 0.05 mmol), and CsF (128 mg, 0.84 mmol) in 4:1 DME/MeOH (4 mL) and 2M aqueous Na$_2$CO$_3$ (0.8 mL, 1.2 mmol) for 16 h. Additional amounts of compound 93 (308 mg, 1.6 mmol), Pd(Ph$_3$)$_4$ (53 mg, 0.05 mmol), and CsF (178 mg, 1.2 mmol) were added and the reaction was refluxed for 7 h. to afford, after HPLC purification, the title compound (CLXXXVIII), as a yellow solid (62 mg, 31%). LC retention time: 1.94 min, MS (ESI+) m/z=479.2 NMR DMSO-$d_6$: δ 1.82-1.91 (m, 2H), 7.97-2.04 (m, 2H), 2.64 (s, 3H), 2.99-3.08 (m, 4H), 3.22-3.27 (m, 2H), 3.53-3.59 (m, 2H), 7.76 (s, 1H), 7.84 (d, J=7.1 Hz, 2H), 7.86 (t, J=6.2 Hz, 1H), 8.11 (br s, 1H), 8.20 (d, J=7.1 Hz, 2H), 8.35 (s, 1H), 9.57 (br s, 1H), 11.24 (s, 1H).

Example 159

Synthesis of 4-[7-(2-chloro-5-hydroxy-phenyl)-6-methyl-benzo[1,2,4]triazin-3-ylamino]-N-(2-pyrrolidin-1-yl-ethyl)-benzenesulfonamide

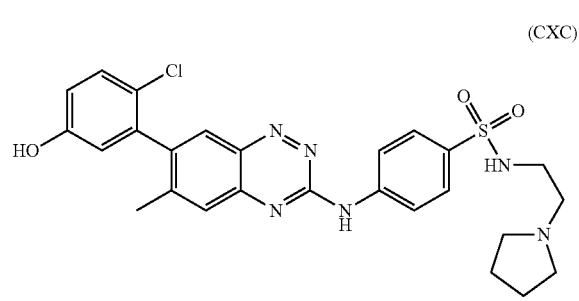 [SMILES: Cc1cc2nc(Nc3ccc(S(=O)(=O)NCCN4CCCC4)cc3)nnc2cc1-c1cc(O)ccc1Cl]
(CXC)

The synthesis of the title compound (CXC) can be generally described by the reaction scheme (CXCI).

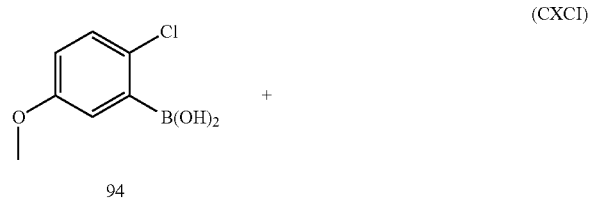
(CXCI)

94

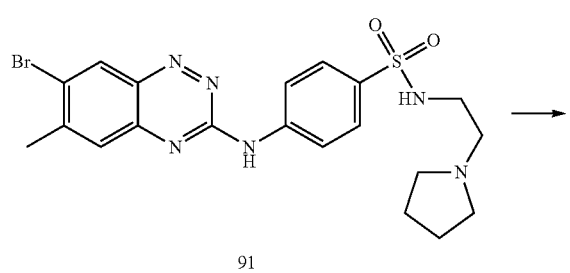

91

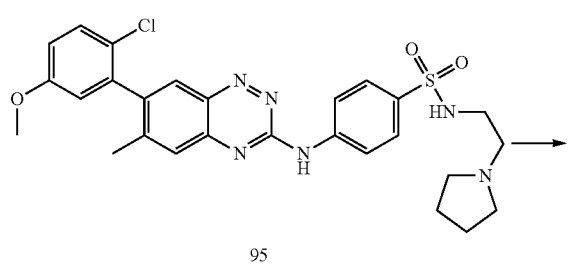

95

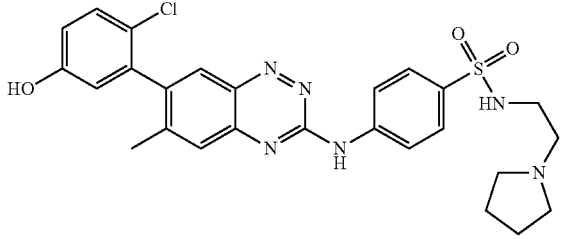

Title Compound

The general Suzuki procedure was employed using compounds 94 (194 mg, 1.0 mmol), 91 (252 mg, 0.5 mmol), Pd(Ph$_3$)$_4$ (59 mg, 0.05 mmol), and 2M aqueous Na$_2$CO$_3$ (1.0 mL, 2.0 mmol) for 15 h. The reaction was diluted with DCM (10 mL) and water (10 mL) and the biphasic mixture was filtered to afford compound 95 (4-[7-(2-chloro-5-methoxy-phenyl)-6-methyl-benzo[1,2,4]triazin-3-ylamino]-N-(2-pyrrolidin-1-yl-ethyl)-benzenesulfonamide), as an orange solid (85 mg, 15%). LC retention time: 2.75 min, MS (ESI+) m/z=553.2/555.4.

The general aryl methoxy deprotection procedure was then employed using aryl methoxy compound 95 (86 mg, 0.16 mmol) and 1M BBr$_3$ in DCM (0.93 mL, 0.93 mmol), in 5 mL DCM for 3 h. The reaction was quenched, filtered, and purified using HPLC to afford the title compound (CXC), as an orange solid (19 mg, 23%). LC retention time: 2.42 min, MS (ESI+) m/z=539.1/541.4 $^1$H NMR DMSO-$d_6$: δ 1.83-1.89 (m, 2H), 1.94-2.03 (m, 2H), 2.29 (s, 3H), 2.98-3.05 (m, 2H), 3.09 (q, J=6.2 Hz, 2H), 3.22-3.25 (m, 2H), 3.50-3.57 (m, 2H), 6.81 (d, J=2.9 Hz, 1H), 6.91 (dd, J=8.8, 2.9 Hz, 1H), 7.41 (d, J=8.8 Hz, 1H), 7.80 (s, 1H), 7.85 (d, J=8.9 Hz, 2H), 7.92 (t, J=4.5 Hz, 1H), 8.11 (s, 1H), 8.21 (d, J=8.9 Hz, 2H), 9.98 (s, 2H), 11.33 (s, 1H).

Example 160

Synthesis of 4-[7-(3-hydroxymethyl-phenyl)-6-methyl-benzo[1,2,4]triazin-3-ylamino]-N-(2-pyrrolidin-1-yl-ethyl)-benzenesulfonamide

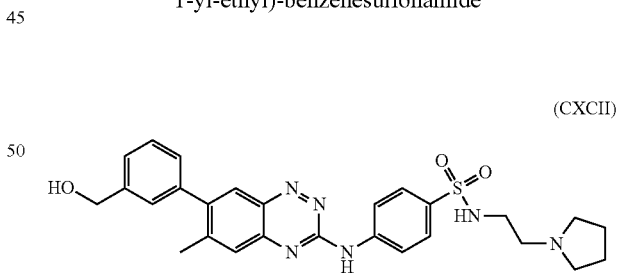
(CXCII)

The synthesis of the title compound (CXCII) can be generally described by the reaction schemes (CXCIII) and (CXCIV).

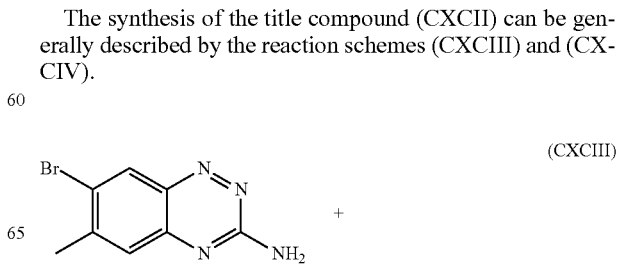
(CXCIII)

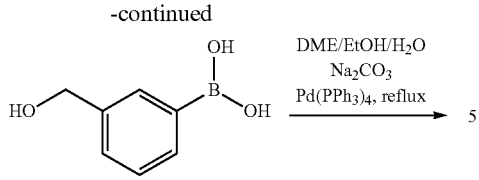

The mixture of 7-bromo-6-methylbenzo[e][1,2,4]triazin-3-amine (240 mg, 1.0 mmol), 3-(hydroxymethyl)phenylboronic acid (310 mg, 2.0 mmol), ethylene glycol dimethyl ether (10 mL), EtOH (1 mL), H₂O (1 mL), Pd(PPh₃)₄ (120 mg, 0.1 mmol) and Na₂CO₃ (1.1 g, 10 mmol) was degassed with argon for 5 minutes and refluxed for overnight under argon. The reaction mixture was brought to room temperature, and the solid was removed by filtration. After evaporation of the volatiles, the crude product was purified by silica gel column (3.5×16 cm) chromatography with 10% CH₃OH/CHCl₃ as an eluent to give a yellow solid product (200 mg, 75%).

The product of reaction shown by scheme (CXCIII) was further reacted as shown by scheme (CXCIV).

(CXCIV)

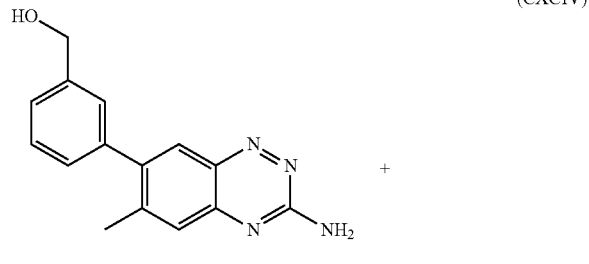

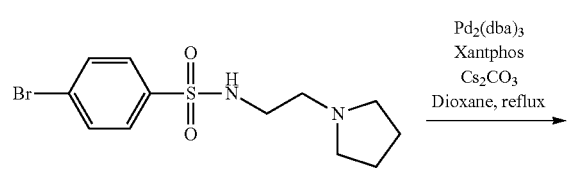

A mixture of (3-(3-amino-6-methylbenzo[e][1,2,4]triazin-7-yl)phenyl)methanol (200 mg, 0.75 mmol), 4-bromo-N-(2-pyrrolidin-1-yl-ethyl)-benzenesulfonamide (380 mg, 1.13 mmol), cesium carbonate (730 mg, 2.25 mmol), Xantphos (90 mg, 0.15 mmol), Pd₂(dba)₃ (70 mg, 0.075 mmol) in 15 mL of anhydrous dioxane was degassed with argon for 5 minutes and was refluxed for 4 h. The reaction mixture was brought to room temperature and the solvent was removed under reduced pressure. The crude product was purified by silica gel column (3.5×16 cm) chromatography using 30% CH₃OH in CHCl₃ as an eluent. The solid was washed with acetone to afford the title compound (CXCII), as a bright yellow solid (200 mg, 52%). ¹H NMR DMSO-d₆: δ 1.67 (br s, 4H), 2.44 (s, 3H), 2.50 (br s, 4H), 2.88 (br s, 2H), 4.60 (d, J=3.6 Hz, 2H), 5.28 (br s, 1H), 7.43 (m, 5H), 7.80 (m, 3H), 8.12 (s, 1H), 8.18 (d, J=8.7 Hz, 2H), 11.25 (s, 1H). MS (ESI+) m/z=519.

Example 161

Synthesis of 4-[7-(5-chloro-thiophen-2-yl)-6-methyl-benzo[1,2,4]triazin-3-ylamino]-N-(2-pyrrolidin-1-yl-ethyl)-benzenesulfonamide (CXCV)

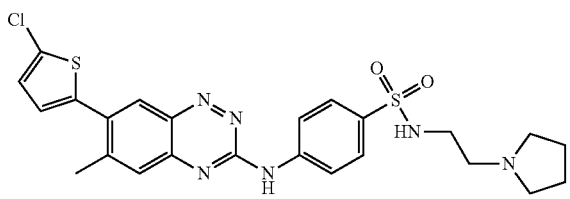

The synthesis of the title compound (CXCV) can be generally described by the reaction schemes (CXCVI) and (CXCVII).

(CXCVI)

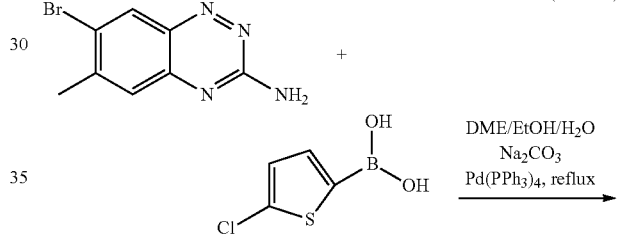

The mixture of 7-bromo-6-methylbenzo[e][1,2,4]triazin-3-amine (310 mg, 1.3 mmol), 5-chloro-2-thiopheneboronic acid (320 mg, 2.0 mmol), ethylene glycol dimethyl ether (10 mL), EtOH (1 mL), H₂O (1 mL), Pd(PPh₃)₄ (150 mg, 0.13 mmol) and Na₂CO₃ (1.38 g, 13 mmol) was degassed with argon for 5 minutes and refluxed for 16 h under argon. The reaction mixture was brought to room temperature, and the solid was removed by filtration. After evaporation of the volatiles, the crude product was purified by silica gel column (3.5×16 cm) chromatography using 10% CH₃OH/CHCl₃ as an eluent to give a yellow solid (220 mg, 61%).

The product of reaction shown by scheme (CXCVI) was further reacted as shown by scheme (CXCVII).

(CXCVII)

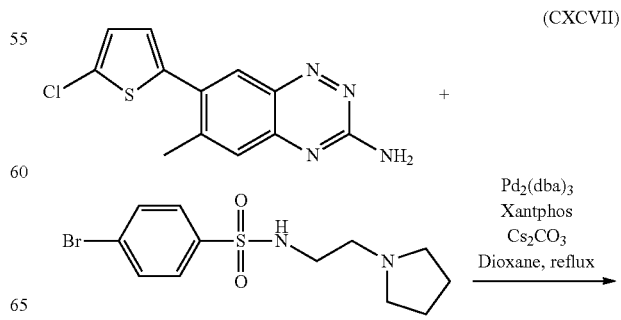

A mixture of 7-(5-chlorothiophen-2-yl)-6-methylbenzo[e][1,2,4]triazin-3-amine (110 mg, 0.4 mmol), 4-bromo-N-(2-pyrrolidin-1-yl-ethyl)benzenesulfonamide (260 mg, 0.78 mmol), cesium carbonate (390 mg, 1.2 mmol), Xantphos (46 mg, 0.08 mmol), Pd$_2$(dba)$_3$ (36 mg, 0.04 mmol) in anhydrous dioxane (15 mL) was degassed with argon for 5 minutes and the reaction mixture was refluxed for 16 h. The solvent was removed under reduced pressure and the crude product was purified by silica gel column (3.5×16 cm) chromatography using 30% CH$_3$OH in CHCl$_3$ as an eluent, to afford the title product (CXCV), as an orange solid (110 mg, 52%). $^1$H NMR DMSO-d$_6$: δ 1.65 (br s, 4H), 2.43 (br s, 4H), 2.60 (s, 3H), 2.86 (t, J=6.5 Hz, 2H), 7.26 (d, J=3.9 Hz, 1H), 7.31 (d, J=3.9 Hz, 1H), 7.45 (br s, 1H), 7.81 (m, 3H), 8.16 (d, J=9.3 Hz, 2), 8.32 (s, 1H), 11.33 (s, 1H). MS (ESI+) m/z=529.

Example 162

Synthesis of 4-(6-methoxy-7-o-tolyl-benzo[1,2,4]triazin-3-ylamino)-N-(2-pyrrolidin-1-yl-ethyl)-benzenesulfonamide (CXCVIII)

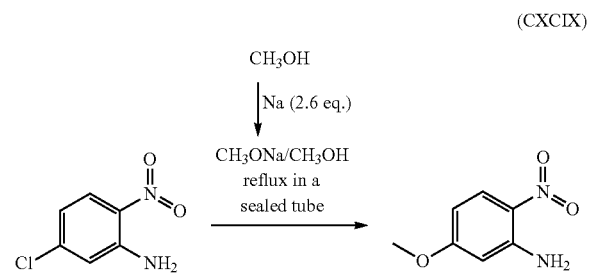

The synthesis of the title compound (CXCVIII) can be generally described by the sequence of reaction schemes (CXCIX), (CC), (CCI), (CCII), (CCIII), and (CCIV).

(CXCIX)

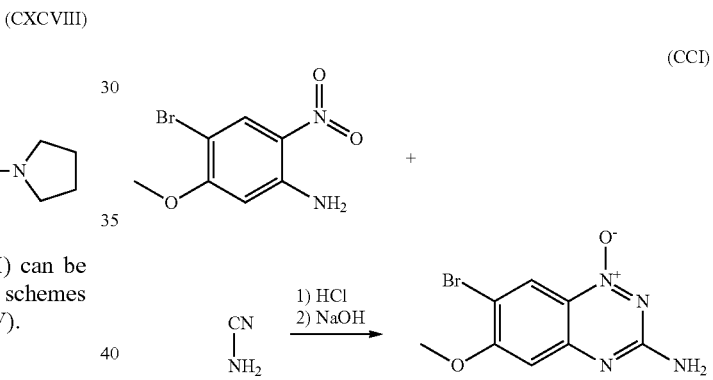

To freshly prepared sodium methoxide using sodium (900 mg, 39 mmol) and anhydrous methanol (20 mL) was added 3-chloro-6-nitroaniline (2.55 g, 15 mmol). The reaction mixture was heated in a sealed tube at 120° C. for 4 hours. The solvent was removed under reduced pressure and the crude solid was dissolved in water (50 mL) and extracted with ethyl acetate (3×50 mL). The combined ethyl acetate layer was dried over sodium sulfate. The sodium sulfate was removed by filtration and the solvent was removed. The crude was dried to yield a yellow solid (1.75 g, 69%).

The product of reaction shown by scheme (CXCIX) was further reacted as shown by scheme (CC).

(CC)

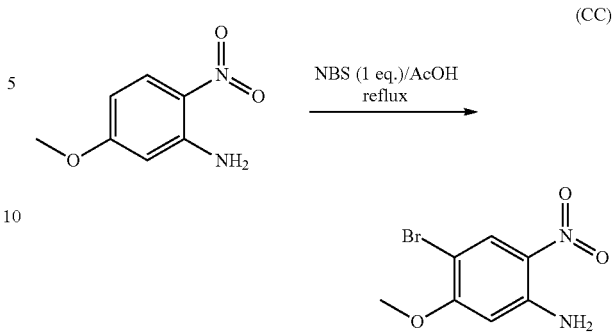

A mixture of 3-methoxy-6-nitroaniline (940 mg, 5.6 mmol) and NBS (1.1 g, 6.2 mmol) in glacial acetic acid (25 mL) was heated to reflux under argon for 3 h. The reaction mixture was brought to room temperature and the mixture was diluted with water (100 mL). The yellow precipitate was collected by filtration, washed with water to yield a yellow solid (1 g, 72%).

The product of reaction shown by scheme (CC) was further reacted as shown by scheme (CCI).

(CCI)

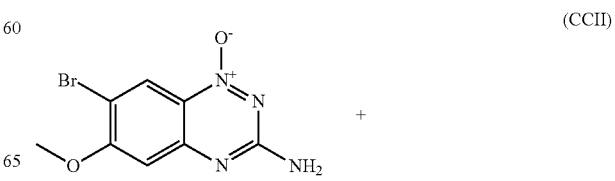

4-bromo-3-methoxy-6-nitroaniline (1 g, 4.05 mmol) was mixed with cyanamide (1.7 g, 40 mmol) and heated to melt at 90° C. Concentrated HCl (10 mL) was cautiously added dropwise within 20 minutes. The reaction mixture was heated to reflux until all starting material reacted (about 2 h). Another batch of cyanamide (1.7 g, 40 mmol) and hydrochloric acid (10 mL) was added and the reaction continued for another hour. The ice cooled reaction mixture was brought to pH 13 with 30% sodium hydroxide. The mixture was heated to reflux for 3 h. The precipitate was collected by filtration and washed with water to give a yellow solid (900 mg, 82%).

The product of reaction shown by scheme (CCI) was further reacted as shown by scheme (CCII).

(CCII)

-continued

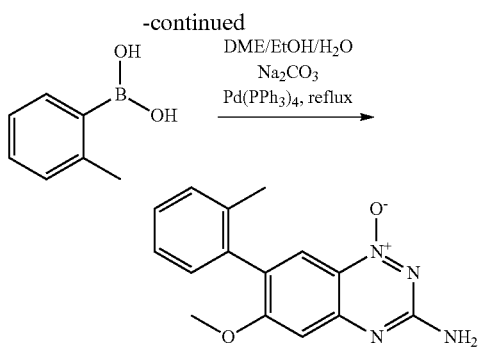

A mixture of 7-bromo-6-methoxybenzo[e][1,2,4]triazin-3-amine-1-N-oxide (350 mg, 1.3 mmol), 2-methyl phenylboronic acid (350 mg, 2.6 mmol), ethylene glycol dimethyl ether (30 mL), EtOH (3 mL), H₂O (3 mL), Pd(PPh₃)₄ (150 mg, 0.13 mmol) and Na₂CO₃ (1.38 g, 13 mmol) was degassed with argon for 5 minutes and refluxed for 16 h under argon. The reaction mixture was cooled to room temperature, and the solid was removed by filtration. After evaporation of the volatiles, the crude product was purified by silica gel column (3.5×16 cm) chromatography using 5% CH₃OH/CHCl₃ as an eluent to give a solid. The solid was washed with dichloromethane/hexanes (1:1) to give a yellow solid (220 mg, 61%).

The product of reaction shown by scheme (CCII) was further reacted as shown by scheme (CCIII).

(CCIII)

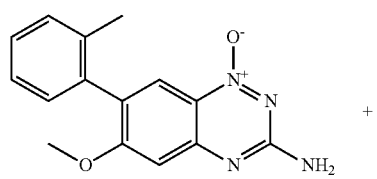

+

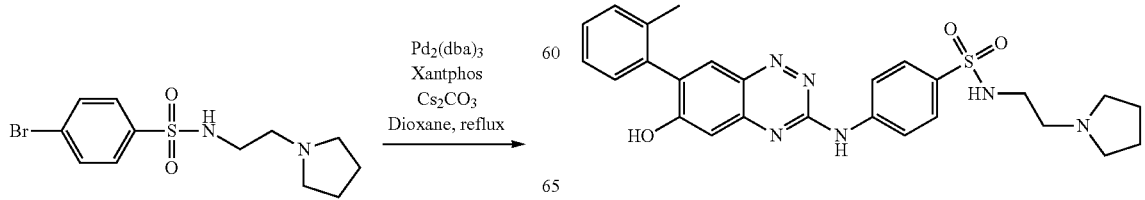

A mixture of 6-methoxy-7-o-tolylbenzo[e][1,2,4]triazin-3-amine-1-N-oxide (230 mg, 0.82 mmol), 4-bromo-N-(2-pyrrolidin-1-yl-ethyl)benzenesulfonamide (540 mg, 1.64 mmol), cesium carbonate (800 mg, 2.45 mmol), Xantphos (94 mg, 0.16 mmol), Pd₂(dba)₃ (75 mg, 0.08 mmol) in 15 mL of anhydrous dioxane was degassed with argon for 5 minutes and was refluxed for 4 h. The reaction mixture was cooled to room temperature and the solvent was removed under reduced pressure. The crude product was purified by silica gel column (3.5×16 cm) chromatography using 20% CH₃OH in CHCl₃ as an eluent. The solid was washed with minimum amount of methanol (about 5 mL) to give a orange solid (340 mg, 66%).

The product of reaction shown by scheme (CCIII) was further reacted as shown by scheme (CCIV).

(CCIV)

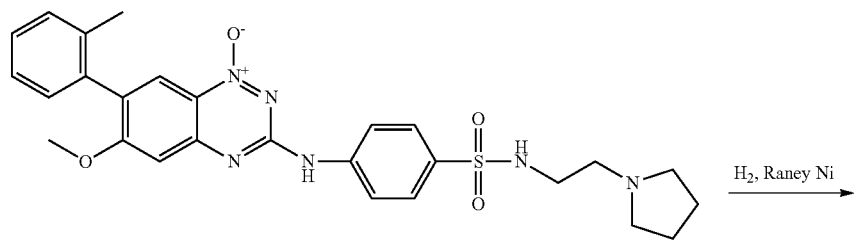

4-(6-methoxy-1-oxy-7-o-tolyl-benzo[1,2,4]triazin-3-ylamino)-N-(2-pyrrolidin-1-yl-ethyl)-benzenesulfonamide (140 mg, 0.26 mmol) was reduced in methanol (25 mL) and ethyl acetate (25 mL) mixture with catalytic amount of Raney Ni and hydrogen for 4 h. The catalyst was removed by filtration and the solvent was removed under reduced pressure to afford the title product (CXCVIII), as a yellow solid (60 mg, 44%). ¹H NMR DMSO-d₆: δ 1.63 (br s, 4H), 2.11 (s, 3H), 2.37 (br s, 4H), 2.44 (br s, 2H), 2.85 (t, J=6.8 Hz, 2H), 3.97 (s, 3H), 7.27 (m, 5H), 7.42 (br s, 1H), 7.79 (d, J=8.8 Hz, 2H), 8.02 (s, 1H), 8.18 (d, J=8.9 Hz, 2H), 11.12 (s, 1H). MS (ESI+) m/z=519.

Example 163

Synthesis of 4-(6-hydroxy-7-o-tolyl-benzo[1,2,4]triazin-3-ylamino)-N-(2-pyrrolidin-1-yl-ethyl)-benzenesulfonamide (CCV)

The synthesis of the title compound (CCV) can be generally described by the of reaction scheme (CCVI).

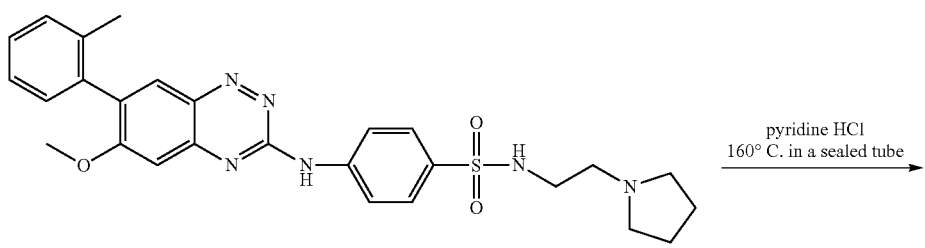

(CCVI)

4-(6-methoxy-7-o-tolyl-benzo[1,2,4]triazin-3-ylamino)-N-(2-pyrrolidin-1-yl-ethyl)-benzenesulfonamide (70 mg, 0.14 mmol) and pyridine hydrochloride (1.0 g, 8.6 mmol) was heated at 160° C. In a seal tube for 4 h. The crude was suspended in diluted HCl (30 mL), and the crude product was purified by silica gel column with 20% $CH_3OH$ in $CHCl_3$ as an eluent to afford the title compound (CCVI), as a yellow solid (15 mg, 22%). $^1H$ NMR DMSO-$d_6$: δ 1.65 (br s, 4H), 2.17 (s, 3H), 2.43 (br s, 4H), 2.86 (br s, 2H), 3.97 (s, 3H), 7.27 (m, 5H), 7.42 (br s, 1H), 7.79 (d, J=8.8 Hz, 2H), 8.02 (s, 1H), 8.18 (d, J=8.9 Hz, 2H), 11.12 (s, 1H). MS (ESI+) m/z=519.

Example 164

Synthesis of 4-(6-ethoxy-7-o-tolyl-benzo[1,2,4]triazin-3-ylamino)-N-(2-pyrrolidin-1-yl-ethyl)-benzenesulfonamide

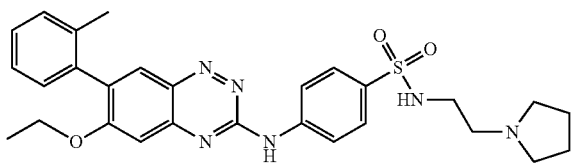

(CCVII)

The synthesis of the title compound (CCVII) can be generally described by the sequence of reaction schemes (CCVIII), (CCIX), (CCX), and (CCXI).

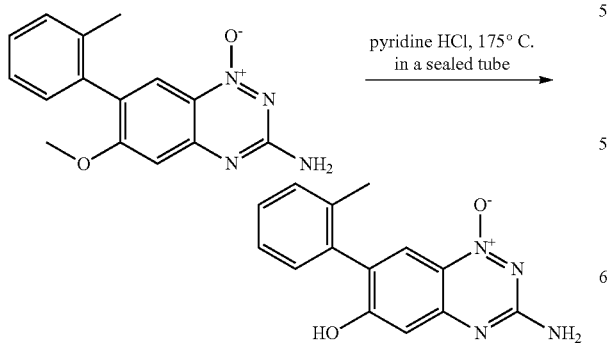

(CCVIII)

The mixture of 7-bromo-6-methoxybenzo[e][1,2,4]triazin-3-amine-1-N-oxide (170 mg, 0.6 mmol) and pyridine hydrochloride (1.0 g, 8.6 mmol) was heated at 170° C. in a seal tube for 2 h. The crude was triturated with dilute HCl (30 mL). The resulting yellow precipitate (100 mg, 62%) was isolated by filtration.

The product of reaction shown by scheme (CCVIII) was further reacted as shown by scheme (CCIX).

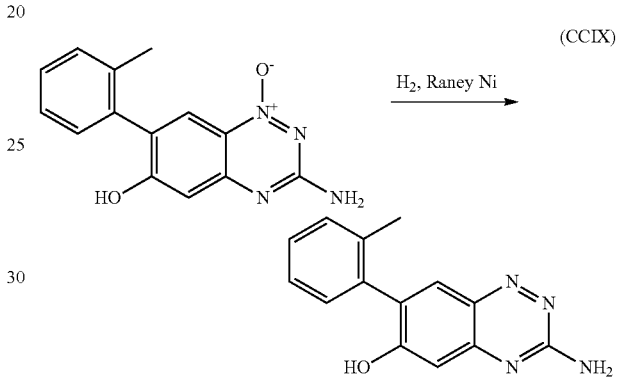

(CCIX)

3-amino-7-o-tolylbenzo[e][1,2,4]triazin-6-ol-1-N-oxide (60 mg, 0.2 mmol) was reduced in methanol (10 mL) and ethyl acetate (10 mL) with catalytic amount of Raney Ni and hydrogen at room temperature for 4 hours. The catalyst was removed by filtration and the solvent was removed. The solid was washed with acetone to give a yellow solid (50 mg, 89%).

The product of reaction shown by scheme (CCIX) was further reacted as shown by scheme (CCX).

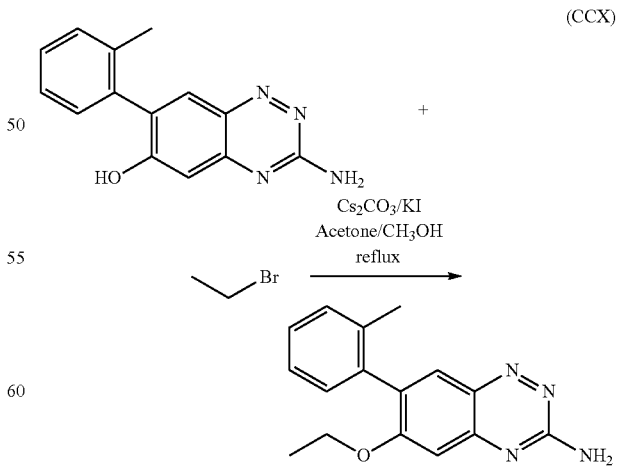

(CCX)

A mixture of 3-amino-7-o-tolylbenzo[e][1,2,4]triazin-6-ol (0.06 g, 0.22 mmol), ethyl bromide (0.24 g, 2.2 mmol), cesium carbonate (0.3 g, 0.92 mmol) and KI (0.1 g, 0.6 mmol)

in acetone/methanol (5:1, 20 mL) was refluxed for 3 hours. After removing the solvent, the crude product was purified by silica gel column with 5% methanol/chloroform as an eluent as an orange solid (0.046 g, 73%).

The product of reaction shown by scheme (CCX) was further reacted as shown by scheme (CCXI).

(CCXI)

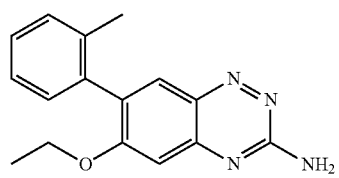
+

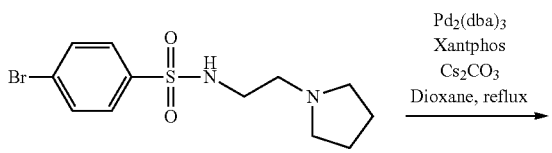

A mixture of 6-ethoxy-7-o-tolylbenzo[e][1,2,4]triazin-3-amine (0.046 g, 0.21 mmol), 4-bromo-N-(2-pyrrolidin-1-yl-ethyl)-benzenesulfonamide (0.14 g, 0.43 mmol), cesium carbonate (0.21 g, 0.63 mmol), Xantphos (25 mg, 0.15 mmol), Pd₂(dba)₃ (20 mg, 0.021 mmol) in 10 mL of anhydrous dioxane was degassed with argon for 5 minutes and was refluxed for 16 h. The solvent was removed and the crude product was purified by silica gel column (3.5×16 cm) chromatography using 20% CH₃OH in CHCl₃ as an eluent to afford the title compound (CCVII), as a yellow solid (61 mg, 52%). ¹H NMR DMSO-d₆: δ 1.27 (t, J=7 Hz, 3H), 1.62 (m, 4H), 2.13 (s, 3H), 2.35 (br s, 4H), 2.43 (t, J=7.3 Hz, 2H), 2.85 (t, J=6.9 Hz, 2H), 4.29 (m, 2H), 7.30 (m, 5H), 7.42 (br s, 1H), 7.79 (d, J=8.9 Hz), 8.02 (s, 1H), 8.18 (d, J=8.9 Hz, 2H). 11.09 (s, 1H). MS (ESI+) m/z=533.

Example 165

Synthesis of 4-[7-(3-hydroxy-phenyl)-6-methoxy-benzo[1,2,4]triazin-3-ylamino]-N-(2-pyrrolidin-1-yl-ethyl)-benzenesulfonamide (CCXII)

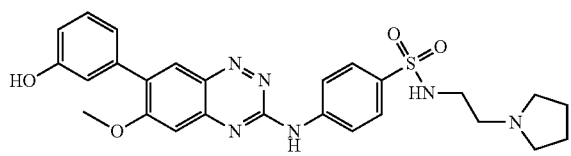

The synthesis of the title compound (CCXII) can be generally described by the sequence of reaction schemes (CCXIII), (CCXIV), (CCXV), and (CCXVI).

(CCXIII)

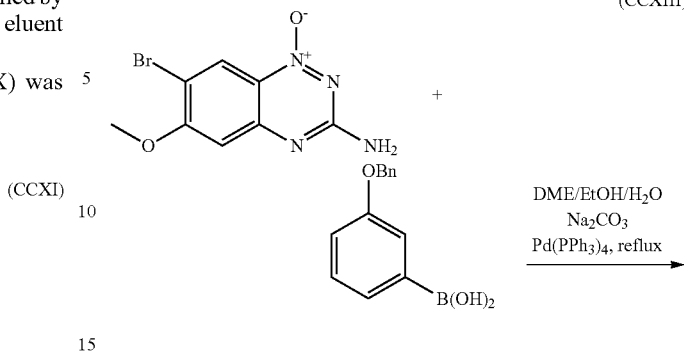

The mixture of 7-bromo-6-methoxybenzo[e][1,2,4]triazin-3-amine-1-N-oxide (0.14 g, 0.52 mmol), 3-benzyloxyphenylboronic acid (0.24 g, 0.10 mmol), ethylene glycol dimethyl ether (15 mL), EtOH (1.5 mL), H₂O (1.5 mL), Pd(PPh₃)₄ (60 mg, 0.05 mmol) and Na₂CO₃ (0.55 g, 5.2 mmol) was degassed with argon for 5 minutes and refluxed for 16 h under argon. The solid was filtered off, and the volatiles were evaporated. The crude product was purified by silica gel column (3.5×16 cm) chromatography using 10% CH₃OH/CHCl₃ as an eluent to give a yellow solid (0.14 g, 72%).

The product of reaction shown by scheme (CCXIII) was further reacted as shown by scheme (CCXIV).

(CCXIV)

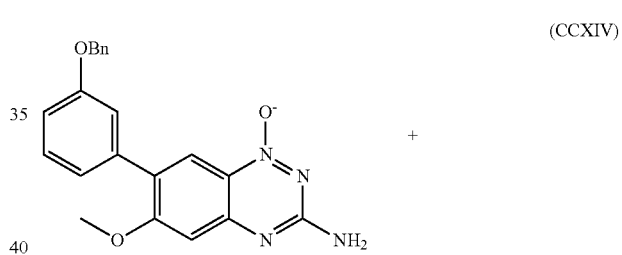

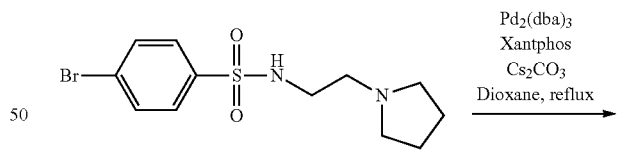

A mixture of 7-(3-(benzyloxy)phenyl)-6-methoxybenzo[e][1,2,4]triazin-3-amine-1-N-oxide (0.11 g, 0.29 mmol), 4-bromo-N-(2-pyrrolidin-1-yl-ethyl)-benzenesulfonamide (0.20 g, 0.6 mmol), cesium carbonate (0.29 g, 0.89 mmol), Xantphos (34 mg, 0.06 mmol), Pd₂(dba)₃ (27 mg, 0.029 mmol) in 15 mL of anhydrous dioxane was degassed with argon for 5 minutes and was refluxed overnight. The reaction mixture was brought to room temperature and the solvent was removed under reduced pressure. The crude product was purified by silica gel column (3.5×16 cm) chromatography using 30% CH₃OH in CHCl₃ as an eluent. The solid was washed with acetone to give a yellow solid (0.1 g, 54%).

The product of reaction shown by scheme (CCXIV) was further reacted as shown by scheme (CCXV).

(CCXV)

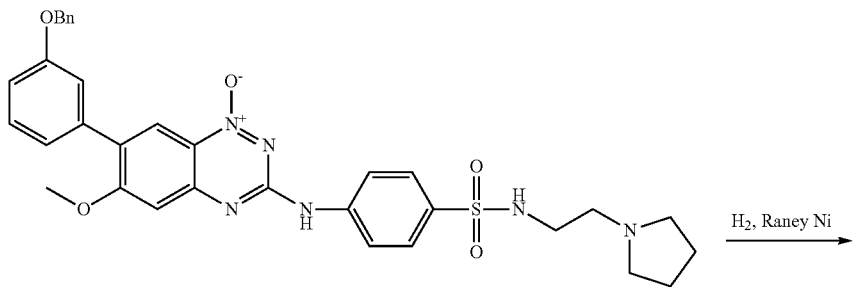

4-[7-(3-benzyloxy-phenyl)-6-methoxy-1-oxy-benzo[1,2,4]triazin-3-ylamino]-N-(2-pyrrolidin-1-yl-ethyl)-benzenesulfonamide (0.1 g, 0.16 mmol) was dissolved in methanol (10 mL) and ethyl acetate (10 mL) with catalytic amount of Raney Ni and atmosphere hydrogen at room temperature for 4 hours. The catalyst was removed by filtration. The solvent was removed by reduced pressure. The solid was used for the next reaction without further purification.

The product of reaction shown by scheme (CCXV) was further reacted as shown by scheme (CCXVI).

(CCXVI)

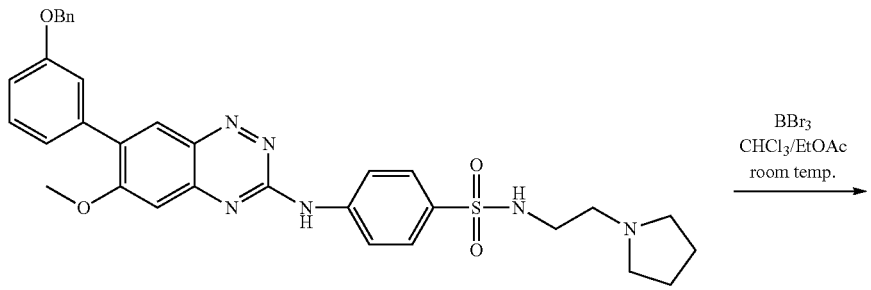

The above 4-[7-(3-benzyloxy-phenyl)-6-methoxy-benzo[1,2,4]triazin-3-ylamino]-N-(2-pyrrolidin-1-yl-ethyl)-benzenesulfonamide in chloroform (10 mL) and ethyl acetate (10 mL) was stirred with 1M BBr$_3$ in dichloromethane (10 mL, 10 mmol) at room temperature for 5 h. The reaction was quenched by methanol (1 mL). After removing the solvent, the crude product was purified by silica gel column chromatography with 20% % CH$_3$OH/CHCl$_3$ as an eluent to give a solid. The solid was washed with acetone to afford the title compound (CCXII), as a yellow solid (0.03 g, 36% in 2-steps). $^1$H NMR DMSO-d$_6$: δ 1.62 (br s, 4H), 2.36 (br s, 4H), 2.43 (t, J=7 Hz, 2H), 2.85 (t, J=6.9 Hz, 2H), 4.02 (s, 3H), 6.83 (d, J=8 Hz, 1H), 6.99 (m, 2H), 7.27 (t, J=8.7 Hz), 7.42 (br s, 1H), 7.80 (d, J=8.8 Hz, 2H), 8.12 (s, 1H), 8.17 (d, J=8.8 Hz, 2H), 9.55 (s, 1H), 11.10 (s, 1H). MS (ESI+) m/z=521.

Example 166

Synthesis of 4-[6-(2-hydroxy-ethoxy)-7-o-tolyl-benzo[1,2,4]triazin-3-ylamino]-N-(2-pyrrolidin-1-yl-ethyl)-benzenesulfonamide (CCXVII)

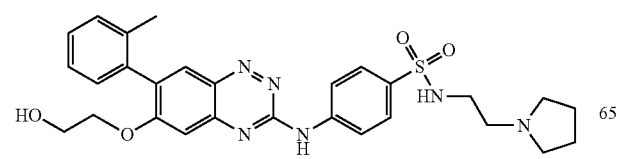

The synthesis of the title compound (CCXVII) can be generally described by the sequence of reaction schemes (CCXVIII) and (CCXIX).

(CCXVIII)

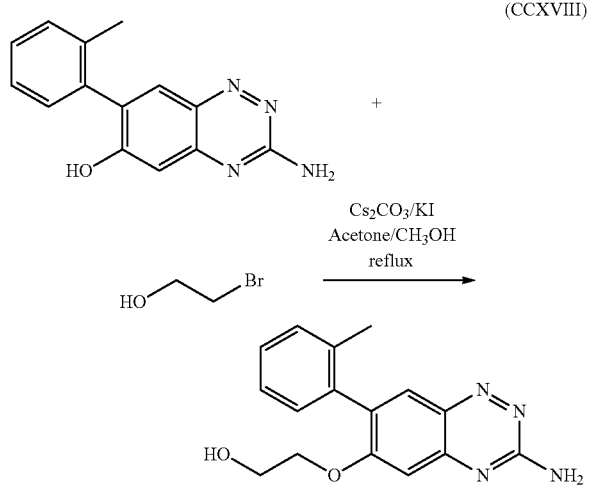

3-amino-7-o-tolylbenzo[e][1,2,4]triazin-6-ol (0.1 g, 0.4 mmol), 2-bromoethanol (0.5 g, 4 mmol), cesium carbonate (0.3 g, 0.92 mmol) and KI (0.1 g, 0.6 mmol) was stirred in acetone/methanol (5:1, 20 mL) at room temperature for overnight. After cooling down, the solvent was removed by reduced pressure. The crude was purified by silica gel column with 20% methanol/chloroform as an eluent to give an orange solid (0.04 g, 34%).

The product of reaction shown by scheme (CCXVIII) was further reacted as shown by scheme (CCXIX).

(CCXIX)

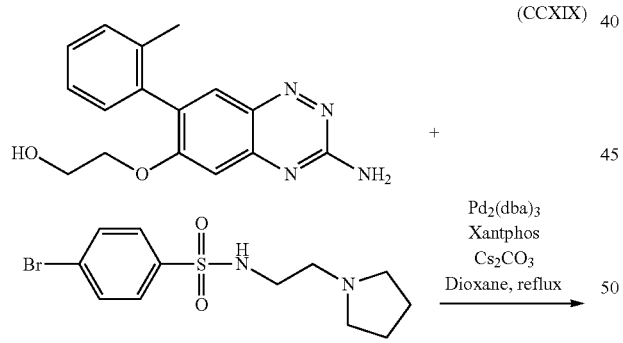

A mixture of 2-(3-amino-7-o-tolylbenzo[e][1,2,4]triazin-6-yloxy)ethanol (0.04 g, 0.13 mmol), 4-bromo-N-(2-pyrrolidin-1-yl-ethyl)-benzenesulfonamide (0.09 g, 0.27 mmol), cesium carbonate (0.13 g, 0.4 mmol), Xantphos (20 mg, 0.03 mmol), Pd$_2$(dba)$_3$ (10 mg, 0.01 mmol) in 10 mL of anhydrous dioxane was degassed with argon for 5 minutes and was refluxed for overnight. The reaction mixture was brought to room temperature and the solvent was removed under reduced pressure. The crude product was purified by silica gel column (3.5×10 cm) chromatography using 30% CH$_3$OH in CHCl$_3$ as an eluent to afford the title compound (CCXVII), as an orange solid (0.01 g, 14%). $^1$H NMR DMSO-d$_6$: δ 1.65 (br s, 4H), 2.10 (s, 3H), 2.41 (br s, 4H), 2.87 (t, J=6.9 Hz, 2H), 3.87 (t, J=5.0 Hz, 2H), 4.42 (t, J=4.9 Hz, 2H), 5.92 (s, 1H), 7.10 (d, J=7.3 Hz, 1H), 7.24 (m, 4H), 7.48 (br s, 1H), 7.76 (m, 4H). MS (ESI+) m/z=549.

Example 167

Synthesis of [7-(2,6-dichloro-phenyl)-5-methyl-benzo[1,2,4]triazin-3-yl]-[2-methyl-6-(2-pyrrolidin-1-yl-ethoxy)-pyrimidin-4-yl]-amine (CCXX)

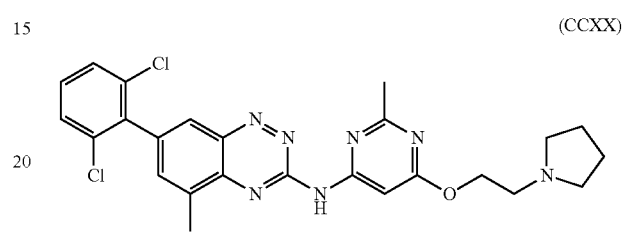

The synthesis of the title compound (CCXX) can be generally described by the sequence of reaction schemes (CCXXI) and (CCXXII).

(CCXXI)

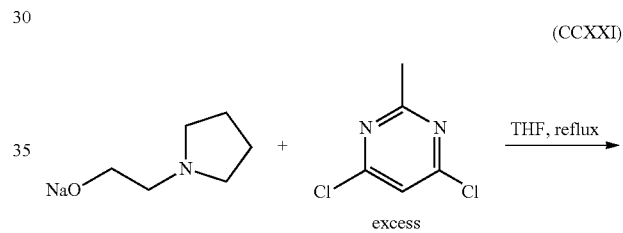

4,6-dichloro-2-methylpyrimidine (1 g, 6.1 mmol) was added into a freshly prepared sodium 2-(pyrrolidin-1-yl) ethoxide from 2-(pyrrolidin-1-yl)ethanol (0.35 g, 3.1 mmol) and sodium (0.08 g, 3.5 mmol) in anhydrous THF (10 mL) with stirring under argon. The mixture was refluxed under argon for 2 h. The reaction mixture was cooled to room temperature and the solvent was removed under reduced pressure. The crude product was purified by silica gel column (3.5×16 cm) chromatography with CHCl$_3$ as an eluent to give a pale yellow oil (540 mg, 73%). $^1$H NMR CDCl$_3$: δ 1.78 (m, 4H), 2.56 (s, 3H), 2.58 (m, 4H), 2.84 (t, J=5.8 Hz, 2H), 4.48 (t, J=5.8 Hz, 2H), 6.59 (s, 1H).

The product of reaction shown by scheme (CCXXI) was further reacted as shown by scheme (CCXXII).

(CCXXII)

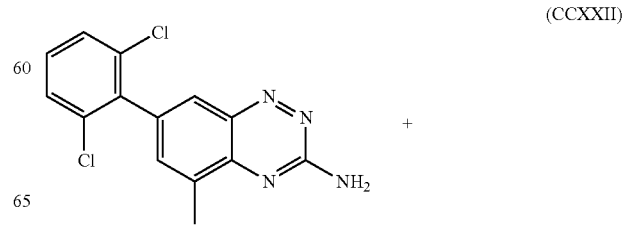

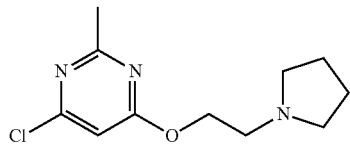
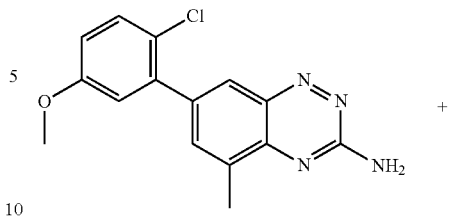

A mixture of 7-(2,6-dichlorophenyl)-5-methylbenzo[e][1,2,4]triazin-3-amine (170 mg, 0.56 mmol), 4-(2-(pyrrolidin-1-yl)ethoxy)-6-chloro-2-methylpyrimidine (270 mg, 1.12 mmol), cesium carbonate (550 mg, 1.7 mmol), Xantphos (65 mg, 0.11 mmol), $Pd_2(dba)_3$ (51 mg, 0.056 mmol) in anhydrous dioxane (25 mL) was degassed with argon for 5 minutes and was refluxed for 1 h. The reaction mixture was cooled to room temperature and the solvent was removed under reduced pressure. The crude product was purified by silica gel column (3.5×16 cm) chromatography with 10% $CH_3OH$ in $CHCl_3$ as an eluent to give the title compound (CCXX), as a yellow solid. (100 mg, 35%). $^1H$ NMR DMSO-$d_6$: δ 1.72 (br s, 4H), 2.6 (m, 7H), 2.92 (br s, 2H), 4.49 (br s, 2H), 7.53 (t, J=8.2 Hz, 1H), 7.67 (s, 1H), 7.69 (s, 1H), 7.79 (s, 1H), 7.83 (d, J=1.9 Hz, 1H), 8.23 8.23 (d, J=1.8 Hz, 1H), 11.59 (s, 1H). MS (ESI+) m/z=510.

Example 168

Synthesis of 4-chloro-3-{5-methyl-3-[2-methyl-6-(2-pyrrolidin-1-yl-ethoxy)-pyrimidin-4-ylamino]-benzo[1,2,4]triazin-7-yl}-phenol (CCXXIII)

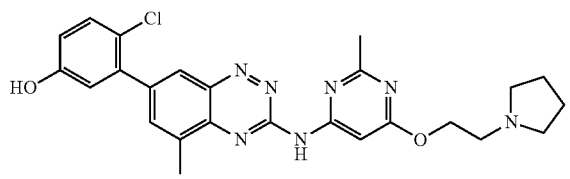

The synthesis of the title compound (CCXXIII) can be generally described by the sequence of reaction schemes (CCXXIV) and (CCXXV).

A mixture of 7-(2-chloro-5-methoxyphenyl)-5-methyl-benzo[e][1,2,4]triazin-3-amine (340 mg, 1.3 mmol), 4-(2-(pyrrolidin-1-yl)ethoxy)-6-chloro-2-methylpyrimidine (270 mg, 1.12 mmol), cesium carbonate (1.1 g, 3.37 mmol), Xantphos (130 mg, 0.22 mmol), $Pd_2(dba)_3$ (100 mg, 0.11 mmol) in anhydrous dioxane (25 mL) was degassed with argon for 5 minutes and was refluxed for 1 h. The reaction mixture was cooled to room temperature and the solvent was removed under reduced pressure. The crude product was purified by silica gel column (3.5×16 cm) chromatography with 10% $CH_3OH$ in $CHCl_3$. The solid was washed with acetone/hexanes (1:5) to yield a yellow solid (300 mg, 53%).

The product of reaction shown by scheme (CCXXIV) was further reacted as shown by scheme (CCXXV).

(CCXXV)

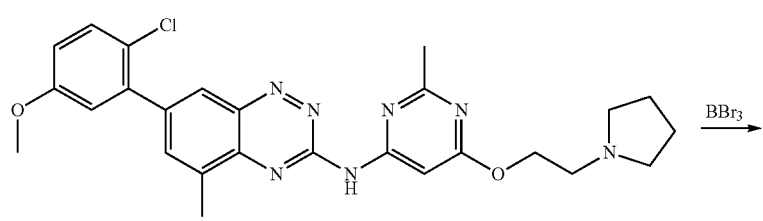

The N-(6-(2-(pyrrolidin-1-yl)ethoxy)-2-methylpyrimidin-4-yl)-7-(2-chloro-5-methoxyphenyl)-5-methylbenzo[e][1,2,4]triazin-3-amine (270 mg, 0.53 mmol) in chloroform (10 mL) was stirred with 1M BBr$_3$ in dichloromethane (5 mL, 5 mmol) at room temperature for 3 h. The reaction was quenched by methanol (1 mL). After removing the solvent, the crude product was neutralized with saturated sodium bicarbonate (1×25 mL). The crude product was extracted by ethyl acetate (2×50 mL). The combined ethyl acetate was dried over sodium sulfate. The salt was removed by filtration and the solvent was removed by vacuum. The crude product was purified by silica gel column chromatography with 20% CH$_3$OH/CHCl$_3$ as an eluent to afford the title compound (CCXXIII), as a yellow solid (100 mg, 38%). $^1$H NMR DMSO-d$_6$: δ 1.68 (m, 4H), 2.48 (s, 3H), 2.53 (m, 4H), 2.65 (s, 3H), 2.81 (t, J=6.0 Hz, 2H), 4.44 (t, J=5.8 Hz, 2H), 6.88 (dd, J=8.8 Hz, J=2.9 Hz, 1H), 6.94 (d, J=2.9 Hz, 1H), 7.40 (d, J=8.8 Hz, 1H), 7.73 (s, 1H), 7.93 (s, 1H), 8.24 (d, J=1.6 Hz, 1H), 9.95 (s, 1H), 11.55 (s, 1H). MS (ESI+) m/z=492.

Example 169

Synthesis of 4-[7-(6-chloro-2-fluoro-3-hydroxy-phenyl)-5-methyl-benzo[1,2,4]triazin-3-ylamino]-N-(2-pyrrolidin-1-yl-ethyl)-benzenesulfonamide (CCXXVI)

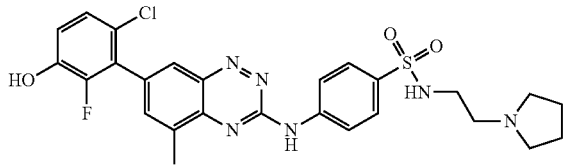

The synthesis of the title compound (CCXXVI) can be generally described by the sequence of reaction schemes (CCXXVII), (CCXXVIII), (CCXXIX), and (COM).

(CCXXVII)

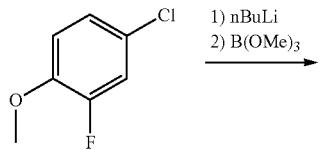

2.5M nBuLi (14.9 mL, 37.4 mmol) was added dropwise over 5 minutes into a mixture of 4-chloro-2-fluoro-1-methoxybenzene (5 g, 31.1 mmol) in anhydrous THF (30 mL) at −78° C. After the mixture was stirred at −78° C. for 20 minutes, anhydrous trimethyl borate (4.9 g, 46.6 mmol) was added into the solution at −78° C. The reaction mixture was brought to room temperature for over period of 2 h. The reaction was quenched by 2N HCl (1 mL). THF was removed by vacuum. The crude product was diluted with 2N HCl (100 mL). The acidic solution was extracted with ethyl acetate (2×50 mL). The combined ethyl acetate fraction was dried over sodium sulfate. The sodium sulfate was removed by filtration and the solvent was removed by vacuum. The oil was titrated with hexanes/chloroform (1:1) to yield a solid. The precipitate was collected by filtration and washed with hexanes to yield a white solid (2.5 g, 39%). $^1$H NMR DMSO-d$_6$: δ 3.81 (s, 3H), 7.12 (m, 2H), 8.66 (s, 2H)

The product of reaction shown by scheme (CCXXVII) was further reacted as shown by scheme (CCXXVIII).

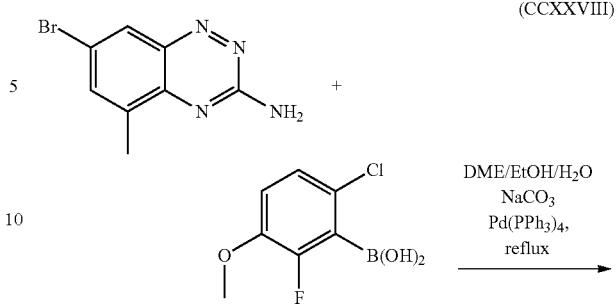

A mixture of 7-bromo-5-methylbenzo[e][1,2,4]triazin-3-amine (420 mg, 1.8 mmol), 6-chloro-2-fluoro-3-methoxyphenylboronic acid (350 mg, 5.4 mmol), ethylene glycol dimethyl ether (20 mL), EtOH (2 mL), H$_2$O (2 mL), Pd(PPh$_3$)$_4$ (200 mg, 0.17 mmol) and Na$_2$CO$_3$ (1.87 g, 18 mmol) was degassed with argon for 5 minutes and refluxed for 16 h under argon. The reaction mixture was cooled to room temperature, and the solid was removed by filtration. After evaporation of the volatiles, the crude product was purified by silica gel column (3.5×16 cm) chromatography with 5% CH$_3$OH/CHCl$_3$ as an eluent to give a solid. The solid was washed with chloroform to give a yellow solid (220 mg, 39%). $^1$H NMR DMSO-d$_6$: δ 2.52 (s, 3H), 3.90 (s, 3H), 7.29 (t, J=9 Hz, 1H), 7.43 (dd, J=9 Hz, J=1.7 Hz, 1H), 7.62 (s, 1H), 7.78 (br s, 2H), 8.02 (d, J=1.6 Hz, 1H). MS (ESI+) m/z=319.

The product of reaction shown by scheme (CCXXVIII) was further reacted as shown by scheme (CCXXIX).

(CCXXIX)

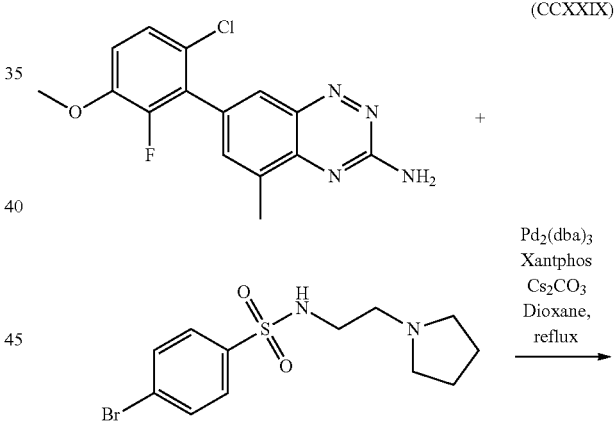

A mixture of 7-(6-chloro-2-fluoro-3-methoxyphenyl)-5-methylbenzo[e][1,2,4]triazin-3-amine (240 mg, 0.75 mmol), 4-bromo-N-(2-pyrrolidin-1-yl-ethyl)benzenesulfonamide (330 mg, 0.99 mmol), cesium carbonate (740 mg, 2.27 mmol), Xantphos (90 mg, 0.16 mmol), Pd$_2$(dba)$_3$ (70 mg, 0.08 mmol) in anhydrous dioxane (30 mL) was degassed with argon for 5 minutes and was refluxed for 2 h. The reaction mixture was cooled to room temperature and the solvent was removed under reduced pressure. The crude product was purified by silica gel column (3.5×16 cm) chromatography with 10% CH$_3$OH in CHCl$_3$. The solid was washed with acetone/hexanes (2:1) to yield a yellow solid. (250 mg, 58%). $^1$H NMR DMSO-d$_6$: δ 1.62 (m, 4H), 2.36 (br s, 4H), 2.43 (t, J=7 Hz, 3H), 2.70 (s, 3H), 2.86 (t, J=7 Hz, 2H), 3.92 (s, 3H), 7.32 (t, J=9 Hz, 1H), 7.42 (br s, 1H), 7.46 (dd, J=9 Hz, J=1.8 Hz, 1H), 7.84 (m, 3H), 8.21 (m, 3H), 11.43 (s, 1H). MS (ESI+) m/z=571.

The product of reaction shown by scheme (CCXXIX) was further reacted as shown by scheme (CCXXX).

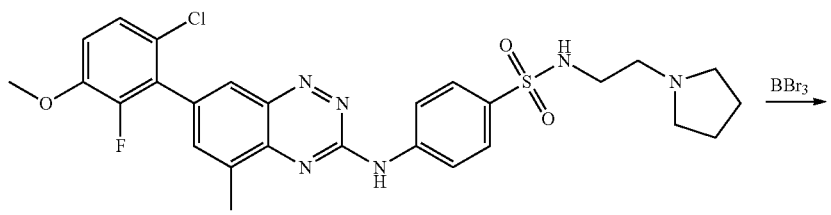

(CCXXX)

A mixture of 4-[7-(6-chloro-2-fluoro-3-methoxy-phenyl)-5-methyl-benzo[1,2,4]triazin-3-ylamino]-N-(2-pyrrolidin-1-yl-ethyl)-benzenesulfonamide (170 mg, 0.53 mmol) in chloroform (5 mL) was stirred with 1M BBr$_3$ in dichloromethane (5 mL, 5 mmol) at room temperature for overnight. The reaction was quenched by methanol (1 mL). After removing the solvent, the crude product was neutralized with saturated sodium bicarbonate (1×25 mL). The crude product was extracted by ethyl acetate (2×50 mL). The combined ethyl acetate fraction was dried over sodium sulfate. The salt was removed by filtration and the solvent was removed by vacuum. The crude product was purified by silica gel column chromatography with 20% CH$_3$OH/CHCl$_3$ as an eluent to afford the title compound ((CCXXVI), as a yellow solid (10 mg, 6%). $^1$H NMR DMSO-d$_6$: δ 1.62 (m, 4H), 2.36 (br s, 4H), 2.44 (t, J=7 Hz, 3H), 2.70 (s, 3H), 2.86 (t, J=7 Hz, 2H), 7.08 (t, J=9 Hz, 1H), 7.29 (dd, J=9 Hz, J=1.6 Hz, 1H), 7.42 (br s, 1H), 7.85 (m, 3H), 8.22 (m, 3H), 10.4 (br s, 1H), 11.42 (s, 1H). MS (ESI+) m/z=557.

Example 170

Synthesis of 4-[7-(5-hydroxy-2-methyl-phenyl)-5-methyl-benzo[1,2,4]triazin-3-ylamino]-N-(2-pyrrolidin-1-yl-ethyl)-benzenesulfonamide (CCXXXI)

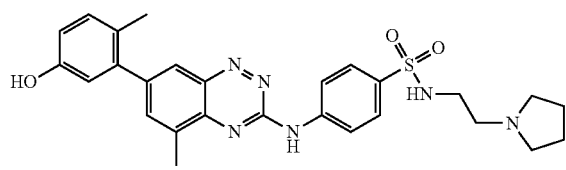

The synthesis of the title compound (CCXXXI) can be generally described by the sequence of reaction schemes (CCXXXII), (CCXXXIII), (CCXXXIV), (CCXXXV), and (CCXXXVI).

(CCXXXII)

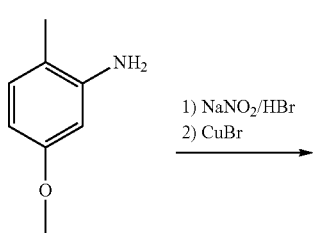

A solution of 5-methoxy-2-methylbenzenamine (1.3 g, 9.48 mmol) in 48% HBr (13 mL) and EtOH (10 mL) was cooled to 0° C. and NaNO$_2$ (0.78 g, 11.30 mmol) in water (5 mL) was added dropwise over 15 minutes while keeping the temperature of the reaction between 0-5° C. After the clear pale brown solution was kept at 0° C. with stirring for 1 h, this solution was transferred into the boiling solution of CuBr (6.8 g, 47.4 mmol) in 48% HBr (25 mL). The solution was refluxed for overnight. The reaction mixture was cooled to room temperature and the reaction was diluted with water (50 mL). The acidic solution was extracted with ethyl acetate (2×50 mL). The combined ethyl acetate was washed by saturated NaCl (1×50 mL) and was dried over sodium sulfate. The sodium sulfate was removed by filtration and the solvent was removed by vacuum. The crude product was purified by silica gel column (3.5×16 cm) chromatography with hexanes as an eluent to yield colorless oil (750 mg, 39%).

The product of reaction shown by scheme (CCXXXII) was further reacted as shown by scheme (CCXXXIII).

(CCXXXIII)

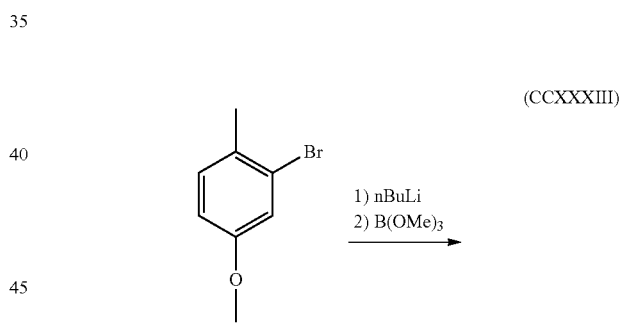

2.5M nBuLi (1.8 mL, 4.5 mmol) was added dropwise over 5 minutes into a mixture of 2-bromo-4-methoxy-1-methylbenzene (750 mg, 3.73 mmol) in anhydrous THF (30 mL) at −78° C. After the mixture was stirred at −78° C. for 20 minutes, anhydrous trimethyl borate (0.62 g, 6 mmol) was added into the solution at −78° C. The reaction mixture was brought to room temperature for over period of 2 h. The reaction was quenched by 2N HCl (1 mL). The THF was removed by vacuum. The crude product was diluted with 2N HCl (100 mL). The acidic solution was extracted with ethyl acetate (2×50 mL). The combined ethyl acetate fraction was dried over sodium sulfate. The sodium sulfate was removed by filtration and the solvent was removed by vacuum to yield a pale yellow solid (0.43 g, 69%).

The product of reaction shown by scheme (CCXXXIII) was further reacted as shown by scheme (CCXXXIV).

(CCXXXIV)

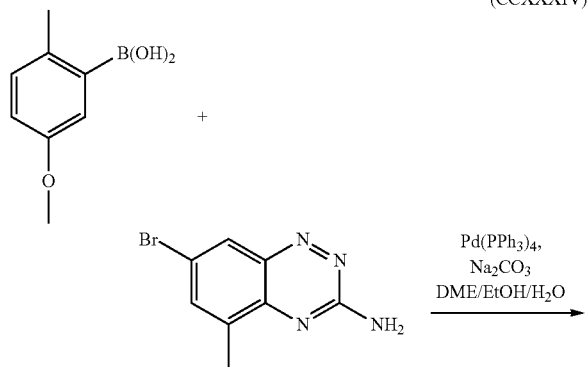

A mixture of 7-bromo-5-methylbenzo[e][1,2,4]triazin-3-amine (500 mg, 2.1 mmol), 5-methoxy-2-methylphenylboronic acid (430 mg, 2.6 mmol), ethylene glycol dimethyl ether (10 mL), EtOH (1 mL), H$_2$O (1 mL), Pd(PPh$_3$)$_4$ (240 mg, 0.21 mmol) and Na$_2$CO$_3$ (2.2 g, 21 mmol) was degassed with argon for 5 minutes and refluxed for 16 h under argon. The reaction mixture was cooled to room temperature, and the solid was removed by filtration. After evaporation of the volatiles, the crude product was purified by silica gel column (3.5×16 cm) chromatography with 5% CH$_3$OH/CHCl$_3$ as an eluent to give a solid. The solid was washed with chloroform to give a dark yellow solid (220 mg, 38%). $^1$H NMR DMSO-d$_6$: δ 2.22 (s, 3H), 2.54 (s, 3H), 3.77 (s, 3H), 6.89 (s, 1H), 6.90 (d, J=3 Hz, 1H), 7.24 (d, J=8 Hz, 1H), 7.66 (br s, 1H), 7.68 (s, 1H), 7.95 (d, J=1.6 Hz, 1H). MS (ESI+) m/z=281.

The product of reaction shown by scheme (CCXXIV) was further reacted as shown by scheme (CCXXXV).

(CCXXXV)

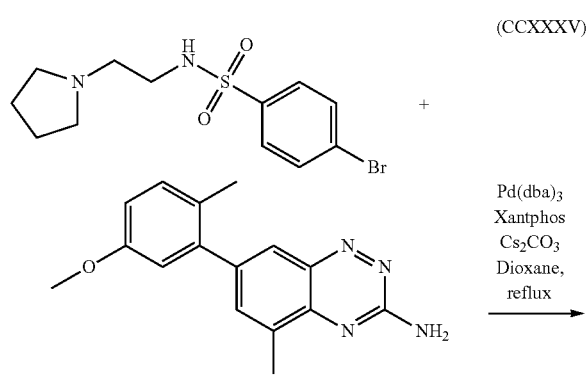

A mixture of 7-(5-methoxy-2-methylphenyl)-5-methyl-benzo[e][1,2,4]triazin-3-amine (220 mg, 0.79 mmol), 4-bromo-N-(2-pyrrolidin-1-yl-ethyl)benzenesulfonamide (340 mg, 1.0 mmol), cesium carbonate (770 mg, 2.36 mmol), Xantphos (90 mg, 0.16 mmol), Pd$_2$(dba)$_3$ (70 mg, 0.08 mmol) in anhydrous dioxane (30 mL) was degassed with argon for 5 minutes and was refluxed for 2 h. The reaction mixture was cooled to room temperature and the solvent was removed under reduced pressure. The crude product was purified by silica gel column (3.5×16 cm) chromatography with 10% CH$_3$OH in CHCl$_3$. The solid was washed with acetone/hexanes (2:1) to yield a yellow solid. (150 mg, 36%). $^1$H NMR DMSO-d$_6$: δ 1.62 (m, 4H), 2.25 (s, 3H), 2.36 (br s, 4H), 2.43 (t, J=7 Hz, 2H), 2.71 (s, 3H), 2.86 (t, J=7 Hz, 2H), 3.79 (s, 3H), 6.93 (m, 2H), 7.28 (d, J=9 Hz, 1H), 7.40 (br s, 1H), 7.83 (d, J=9 Hz, 2H), 7.89 (d, J=1.6 Hz, 1H), 8.15 (d, J=9 Hz, 2H), 11.35 (br s, 1H).

The product of reaction shown by scheme (CCXXV) was further reacted as shown by scheme (CCXXXVI).

(CCXXXVI)

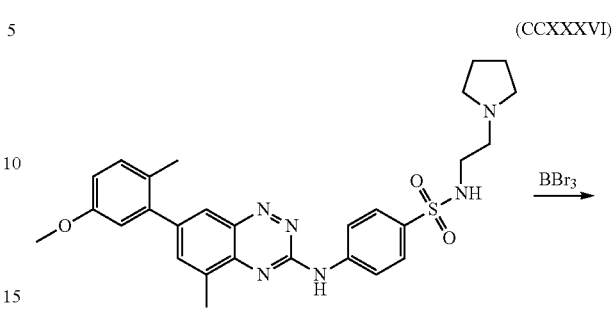

A mixture of 4-[7-(5-methoxy-2-methyl-phenyl)-5-methyl-benzo[1,2,4]triazin-3-ylamino]-N-(2-pyrrolidin-1-yl-ethyl)-benzenesulfonamide (80 mg, 0.15 mmol) in chloroform (10 mL) was stirred with 1M BBr$_3$ in dichloromethane (10 mL, 10 mmol) at room temperature for overnight. The reaction was quenched by methanol (1 mL). After removing the solvent, the crude product was neutralized with saturated sodium bicarbonate (1×25 mL). The crude product was extracted by ethyl acetate (2×50 mL). The combined ethyl acetate was dried over sodium sulfate. The salt was removed by filtration and the solvent was removed by vacuum. The crude product was purified by silica gel column chromatography with 20% CH$_3$OH/CHCl$_3$ as an eluent to afford the title product (CCXXXI), as a yellow solid (20 mg, 26%). $^1$H NMR DMSO-d$_6$: δ 1.62 (m, 4H), 2.20 (s, 3H), 2.35 (br s, 4H), 2.43 (t, J=7 Hz, 2H), 2.71 (s, 3H), 2.85 (t, J=6.6 Hz, 2H), 6.75 (m, 2H), 7.15 (d, J=9 Hz, J=1.6 Hz, 1H), 7.40 (br s, 1H), 7.84 (m, 3H), 8.09 (d, J=1.4 Hz, 1H), 8.21 (d, J=9 Hz, 2H), 9.38 (br s, 1H), 11.34 (br s, 1H). MS (ESI+) m/z=519.

Example 171

Synthesis of [7-(2'-hydroxyethyl-isopropylamino)-6-methyl-benzo[1,2,4]triazin-3-ylamino]-N-(2-pyrrolidin-1-yl-ethyl)-benzene-4-sulfonamide (CCXXXVII)

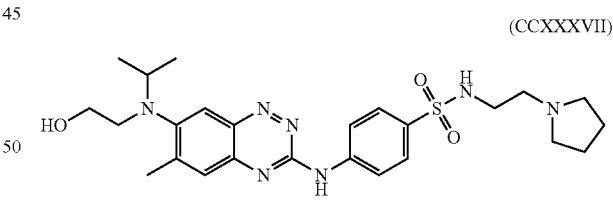

To a solution of 2-(isopropylamino)ethanol 48 μL, 0.416 mmol), 4-(7-bromo-6-methyl-benzo[1,2,4]triazin-3-ylamino)-N-(2-pyrrolidin-1-yl-ethyl)-benzenesulfonamide (245 mg, 0.5 mmol) in dioxane was added xantphos (13 mg, 0.02 mmol) and cesium carbonate (202 mg, 0.62 mmol). The solution was degassed using argon, and Pd$_2$(dba)$_3$ a (11 mg, 0.012 mmol) was added. The reaction was refluxed overnight under argon, and quenched with 2 mL of water. The crude reaction mixture was evaporated on a rotoevaporator, diluted with water (15 mL) and extracted with chloroform (2×50 mL). The chloroform extract was dried over sodium sulfate, and the chloroform was evaporated. The residue was purified using prep HPLC products were isolated to afford the title product (CCXXXVII) as a yellow solid (3 mg, % yield). $^1$H NMR DMSO-$d_6$: δ 1.05 (d, J=6.2 Hz, 6H), 1.6-1.7 (m, 4H), 2.3-2.4 (m, 4H), 2.42 (s, 3H), 2.4-2.5 (m, 2H), 2.8-2.95 (m, 3H), 3.0-3.1 (m, 2H), 4.23-4.35 (m, 2H), 7.35-7.45 (br s, 1H), 7.67 (s, 1H), 7.7 (d, J=0.9 Hz), 7.76 (d, J=8.95 Hz, 2H), 8.1 (d, J=7 Hz, 2H), 10.94 (s, 1H). MS (ESI+) m/z=514.2.

Example 172

Synthesis of 4-(7-{[2-(2-hydroxy-ethoxy)-ethyl]-isopropyl-amino}-6-methyl-benzo[1,2,4]triazin-3-ylamino)-N-(2-pyrrolidin-1-yl-ethyl)-benzene-sulfonamide (CCXXXVIII)

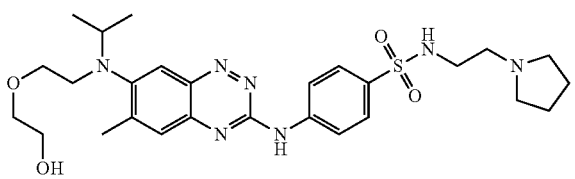

The title product was synthesized and had the following characteristics. $^1$H NMR DMSO-$d_6$: δ 1.0 (d, J=6.6 Hz, 6H), 1.53-1.65 (m, 4H), 2.33-2.39 (m, 4H), 2.35 (s, 3H), 2.42-2.47 (m, 2H), 2.58 (t, J=6.7 Hz, 2H), 2.83 (t, J=6.7 Hz, 2H), 2.90 (t, J=5.6 Hz, 2H), 2.95-3.05 (m, 1H), 3.42 (t, J=6.6 Hz, 2H), 4.03 (br s, 2H), 4.19 (t, J=5.6 Hz, 2H), 7.35-7.45 (br s, 1H), 7.69 (s, 1H), 7.7 (d, J=0.9 Hz), 7.76 (d, J=8.95 Hz, 2H), 8.1 (d, J=7.05 Hz, 2H), 10.93 (s, 1H). MS (ESI+) m/z=558.3.

Example 173

Synthesis of 4-(7-bromo-6-methyl-benzo[1,2,4]triazin-3-ylamino)-N-(2-pyrrolidin-1-yl-ethyl)-benzenesulfonamide (CCXXXIX)

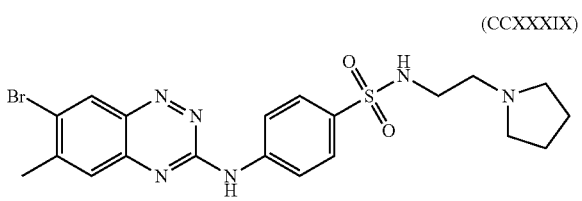 [SMILES: Cc1cc2nc(Nc3ccc(S(=O)(=O)NCCN4CCCC4)cc3)nnc2cc1Br]

A mixture of amine 1 (2.5 g, 10.45 mmol), bromide 2 (4.18 g, 12.54 mmol), $Cs_2CO_3$ (5.1 g, 15.67 mmol), Xantphos (363 mg, 0.627 mmol), $Pd_2(dba)_3$ (286 mg, 0.31 mmol), and 3 Å mol sieves in dioxane (70 mL) was purged with argon for 5 min, and was heated to reflux for 16 h under argon. Dioxane was removed in vacuo and the resulting mixture was partitioned between $CHCl_3$ and water (200 mL each). The layers were separated and the aqueous layer was extracted twice more with $CHCl_3$ (200 mL). The organic layers were combined and concentrated in vacuo. The crude product was purified by flash column chromatography (0.5% $NH_4OH$/10% MeOH/89.5% dichloromethane). Orange-yellow solid (1.5 g, 30%). $^1$H NMR DMSO-$d_6$: δ 1.82-1.92 (m, 2H), 1.95-2.05 (m, 2H), 2.59 (s, 3H), 2.96-3.08 (m, 4H), 3.2-3.28 (m, 2H), 3.53-3.61 (m, 2H), 7.83 (d, J=8.8 Hz, 2H), 7.85 (s, 1H), 7.87 (t, J=6.1 Hz, 1H), 8.18 (d, J=8.8 Hz, 1H), 8.68 (s, 1H), 9.46-9.57 (br s, 1H), 11.4 (s, 1H). MS (ESI+) m/z=493.

Example 174

Synthesis of [6-methyl-7-(3-methyl-thiophen-2-yl)-benzo[1,2,4]triazin-3-yl]-[4-(2-pyrrolidin-1-yl-ethoxy)-phenyl]-amine (CCXL)

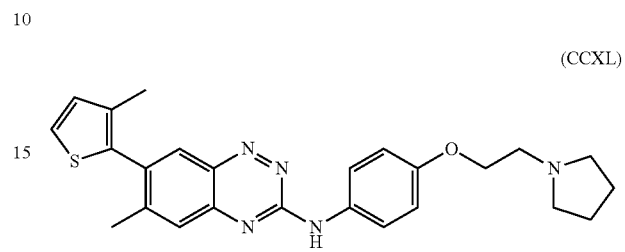

To a mixture of 3-methylthiophen-2-yl-2-boronic acid (252 mg, 2 mmol), 3-amino-7-bromo-6-methyl benzo-1,2,3-triazine (239 mg, 1 mmol) and $Pd(Ph_3)_4$ (58 mg, 0.05 mmol) in 4:1 DME/EtOH was added a 2M aqueous solution of sodium carbonate (4 mL). The mixture was flushed with argon for 5 min and was heated under reflux (ca. 100° C.) for 16 h. The volatiles were evaporated and the residue was triturated with chloroform-water (1:1, 200 mL). The chloroform layer was separated and filtered through a small silica plug. The silica plug was washed with 200 mL of 10% methanol in chloroform. On evaporation the crude product was obtained as a brown solid (255 mg).

A mixture of the crude above amine product (125 mg, 0.5 mmol), 1-(2-(4-bromophenoxy)ethyl)pyrrolidine (121 μL, 0.58 mmol), $Cs_2CO_3$ (638 mg, 1.96 mmol), Xantphos (28 mg, 0.049 mmol), $Pd_2(dba)_3$ (22 mg, 0.02 mmol), and 3 Å mol sieves in dioxane (5 mL) was purged with argon for 5 min, and was heated to reflux for 16 h under argon. The volatiles were evaporated and the residue was triturated with chloroform-water (1:1, 200 mL). The chloroform layer was separated and filtered through a small silica plug. The silica plug was washed with 200 mL of 10% methanol in chloroform. The solvent was evaporated and the crude product was purified using HPLC to afford the title product (CCXL), as a red solid (29 mg, 13%). $^1$H NMR DMSO-$d_6$: δ 1.67-1.76 (m, 4H), 2.06 (s, 3H), 2.31 (s, 3H), 2.54-2.6 (m, 4H), 2.81 (t, J=5.57 Hz, 2H), 4.07 (t, J=5.9 Hz, 2H), 6.95 (d, J=6.95 Hz, 2H), 7.07 (d, J=5.1 Hz, 1H), 7.58 (d, J=5.2 Hz, 1H), 7.66 (s, 1H), 7.85 (d, J=6.95 Hz, 2H), 8.09 (s, 1H), 10.71 (s, 1H). MS (ESI+) m/z=446.1.

Example 175

Synthesis of {4-[6-methyl-7-(4-methyl-pyridin-3-yl)-benzo[1,2,4]triazin-3-ylamino]-phenyl}-(4-methyl-piperazin-1-yl)-methanone mesylate (CCXLI)

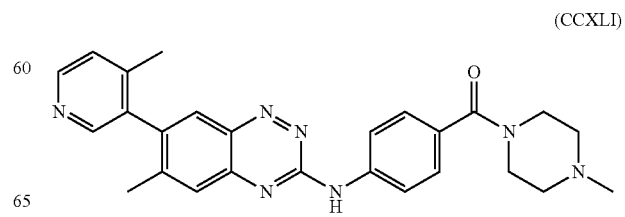

To a mixture of 4-methylpyridin-3-yl-3-boronic acid (272 mg, 2 mmol), 3-amino-7-bromo-6-methyl benzo-1,2,3-triazine (239 mg, 1 mmol) and Pd(Ph₃)₄) (58 mg, 0.05 mmol) in 4:1 DME/EtOH was added a 2M aqueous solution of sodium carbonate (4 mL). The mixture was flushed with argon for 5 min and was heated under reflux (ca. 100° C.) for 16 h. The volatiles were evaporated and the residue was triturated with chloroform-water (1:1, 200 mL). The chloroform layer was separated and filtered through a small silica plug. The silica plug was washed with 200 mL of 10% methanol in chloroform. On evaporation the crude product was obtained as a brown solid (260 mg).

A mixture of the above crude amine product (125 mg, 0.5 mmol), 1-(2-(4-bromophenoxy)ethyl)pyrrolidine (170 mg, 0.6 mmol), Cs₂CO₃ (651 mg, 2.0 mmol), Xantphos (58 mg, 0.1 mmol), Pd₂(dba)₃ (45 mg, 0.05 mmol), and 3 Å mol sieves in dioxane (5 mL) was purged with argon for 5 min, and was heated to reflux for 16 h under argon. The volatiles were evaporated and the residue was triturated with chloroform-water (1:1, 200 mL). The chloroform layer was separated and filtered through a small silica plug. The silica plug was washed with 200 mL of 10% methanol in chloroform. The solvent was evaporated and the crude product was purified using HPLC, to afford the title product (CCXXLI), as an orange solid (91 mg, 40.2%). ¹H NMR DMSO-d₆: δ 2.16, 2.22, 2.31, 2.84 (4s, 3H each), 3.05-3.18 (m, 4H), 3.45-3.55 (m, 4H), 7.53 (d, J=8.6 Hz, 2H), 7.58 (d, J=4.95 Hz, 1H), 7.81 (s, 3H), 8.10 (d, J=8.6 Hz, 2H), 8.17 (s, 1H), 8.5 (s, 1H), 8.62 (d, J=4.5 Hz, 1H), 9.67-9.76 (br s, 1H), 11.15 (s, 3H). MS (ESI+) m/z=454.3.

Example 176

Synthesis of {4-[7-(4-chloro-pyridin-3-yl)-6-methyl-benzo[1,2,4]triazin-3-ylamino]-phenyl}-(4-methyl-piperazin-1-yl)-methanone mesylate

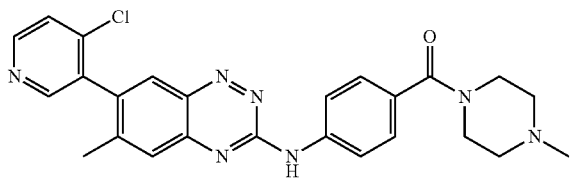

(CCXLII)

To a mixture of 4-chloropyridin-3-yl-3-boronic acid (314 mg, 2 mmol), 3-amino-7-bromo-6-methyl benzo-1,2,3-triazine (239 mg, 1 mmol) and Pd(Ph₃)₄) (58 mg, 0.05 mmol) in 4:1 DME/EtOH was added a 2M aqueous solution of sodium carbonate (4 mL). The mixture was flushed with argon for 5 min and was heated under reflux (ca. 100° C.) for 16 h. The volatiles were evaporated and the residue was triturated with chloroform-water (1:1, 200 mL). The chloroform layer was separated and filtered through a small silica plug. The silica plug was washed with 200 mL of 10% methanol in chloroform. On evaporation the crude product was obtained as a brown solid (260 mg).

A mixture of above crude amine product (125 mg, 0.46 mmol), 1-(2-(4-bromophenoxy)ethyl)pyrrolidine (156 mg, 0.55 mmol), Cs₂CO₃ (600 mg, 1.84 mmol), Xantphos (53 mg, 0.1 mmol), Pd₂(dba)₃ (45 mg, 0.05 mmol), and 3 Å mol sieves in dioxane (10 mL) was purged with argon for 5 min, and was heated to reflux for 16 h under argon. The volatiles were evaporated and the residue was triturated with chloroform-water (1:1, 200 mL). The chloroform layer was separated and filtered through a small silica plug. The silica plug was washed with 200 mL of 10% methanol in chloroform. The solvent was evaporated and the crude product was purified using HPLC. The purified product was converted to mesylate salt using methane sulfonic acid, in a form of a yellow solid (51 mg, 18% yield). ¹H NMR DMSO-d₆: δ 2.30, 2.44, 2.80 (3s, 3H each), 3.05-3.17 (m, 2H), 3.3-3.52 (m, 4H), 7.53 (d, J=6.9 Hz, 2H), 7.68 (d, J=8.5 Hz, 1H), 7.78 (s, 3H), 8.07 (d, J=2.65 Hz, 2H), 8.09 (d, J=8.65 Hz, 1H), 8.27 (s, 1H), 8.59 (d, J=2.4 Hz, 1H), 9.67-9.76 (br s, 1H), 11.17 (s, 1H). MS (ESI+) m/z=474.2.

Example 177

Synthesis of {4-[7-(2,6-dimethyl-phenyl)-5-methyl-benzo[1,2,4]triazin-3-ylamino]-phenyl}-piperazin-1-yl-methanone

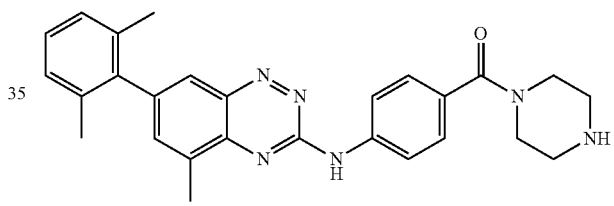

(CCXLIII)

A mixture of 7-(2,6-dimethylphenyl)-3-amino-5-methyl-1,2,3-triazine (1.66, 6.29 mmol), 4-(4-bromo-benzoyl)-piperazine-1-carboxylic acid tert-butyl ester (2.79 g, 7.55 mmol), potassium t-butoxide (1.05 g, 9.43 mmol), BINAP (235 mg, 0.377 mmol), Pd₂(dba)₃ (172 mg, 0.18 mmol), and 3 Å mol sieves in toluene (120 mL) was purged with argon for 5 min, and was heated to reflux for 16 h under argon. The volatiles were evaporated and the residue was triturated with chloroform-water (1:1, 500 mL). The chloroform layer was separated and filtered through a small silica plug. The silica plug was washed with 400 mL of 10% methanol in chloroform. The solvent was evaporated and the crude product was treated with trifluoroacetic acid (25 mL) in dichloromethane (25 mL) for 1.5 h. The solvent was evaporated and the crude product was purified by column chromatography using chloroform, methanol, ammonia (85:10:5). Some amount was converted to mesylate salt, in a form of a rusty red solid (1.51 g, 54% yield). ¹H NMR DMSO-d₆: δ 2.05 (s, 6H), 2.69 (s, 3H), 2.69-2.75 (m, 4H), 3.37-3.57 (m, 4H), 7.19 (d, J=7.6 Hz, 2H), 7.25 (dd, J=6.2 and 8.6 Hz, 1H), 7.45 (dd, J=1.75 and 6.85 Hz, 2H), 7.64 (dd, J=1 and 1.85 Hz, 1H), 7.95 (d, J=1.85 Hz, 1H), 8.09 (dd, J=1.7 and 6.85 Hz, 2H), 11.12 (s, 1H). MS (ESI+) m/z=453.3.

Example 178

Synthesis of [7-(2,6-dimethyl-phenyl)-5-methyl-benzo[1,2,4]triazin-3-yl]-[2-(2-pyrrolidin-1-yl-ethoxy)-pyridin-4-yl]-amine mesylate

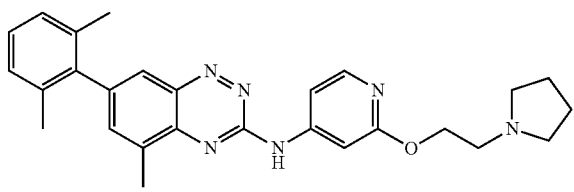

(CCXLIV)

The title product was synthesized, having the following characteristics. $^1$H NMR DMSO-d$_6$: δ 2.85-2.95 (m, 2H), 1.99-2.08 (m, 2H), 2.05 (s, 3H), 2.29 (s, 3H), 2.71 (s, 3H), 3.07-3.2 (m, 2H), 3.56-3.7 (m, 4H), 4.6 (t, J=5.2 Hz, 2H), 7.19 (d, J=7.45 Hz, 2H), 7.25 (dd, J=6.3 and 8.6 Hz, 2H), 7.61 (dd, J=1.75 and 5.8 Hz, 1H), 7.66 (d, J=1.75 Hz, 1H), 7.29 (d, J=1.0 Hz, 1H), 8.08 (d, J=1.9 Hz, 1H), 8:12 (d, J=5.8 Hz, 1H), 11.39 (s, 1H). MS (ESI+) m/z=455.3.

Example 179

Synthesis of 7-(2,6-dichloro-3-methoxyphenyl)-5-methylbenzo[e][1,2,4]triazin-3-amine

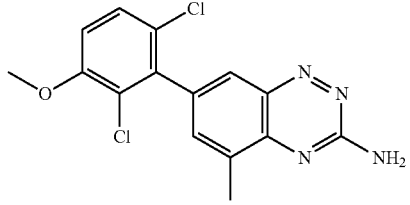

(CCXLV)

To prepare the title compound (CCXLV), an intermediate compound 96 (2,6-dichloro-3-methoxyphenylboronic acid) was synthesized first.

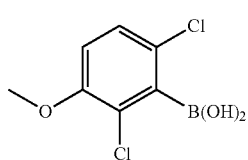

96

To synthesize compound 96, to 2,4-dichloroanisole (5 mL, 36 mmol) in THF (22 mL) at −78° C. was added 2.5 M nBuLi (17 mL, 43 mmol) keeping the temperature below −65° C. After 30 min, the reaction was poured into frozen (−78° C.) trimethylborate (14 mL, 215 mmol) followed by another portion of trimethylborate (10 mL, 90 mmol) and allowed to warm to room temperature over 16 h. The solid suspension was poured into a 1 N HCl aqueous solution and stirred for 1 h. The suspension was filtered to give 3.6 g (46%) of a white solid contaminated most likely with B(OH)$_4$. A second batch of crystals formed which were collected as an off-white solid that was compound 96 (5.8 g, 74%). $^1$H NMR DMSO-d$_6$: δ 8.53 (s, 2H), 7.29 (d, J=8.8 Hz, 1H), 7.06 (d, J=8.8 Hz, 1H), 3.83 (s, 3H).

The general Suzuki procedure was then employed using compound 32 (Example 140) (794 mg, 3.32 mmol), compound 96 (816 mg, 3.70 mmol), Pd(Ph$_3$)$_4$ (386 mg, 0.33 mmol), and 2M aqueous Na$_2$CO$_3$ (7 mL, 14.0 mmol) in 4:1 DME/EtOH (34 mL) for 16 h to afford, after filtration, the title compound (CCXLV), as a crude pale-orange solid (922 mg, 83%) which was used as is with no further purification. LC retention time: 2.98 min, MS (ESI+) m/z=334.9.

Example 180

Synthesis of 4-[7-(2,6-dichloro-3-methoxy-phenyl)-5-methyl-benzo[1,2,4]triazin-3-ylamino]-N-(2-pyrrolidin-1-yl-ethyl)-benzenesulfonamide

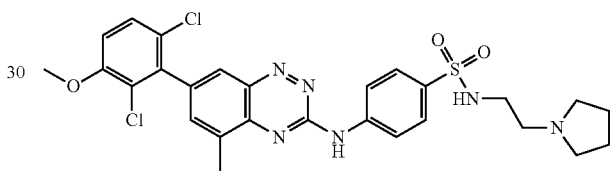

(CCXLVI)

The general Buchwald procedure was employed using crude compound (CCXLV) (Example 179) (305 mg, 0.91 mmol), compound 54 (Example 140) (304 mg, 0.91 mmol), Cs$_2$CO$_3$ (1.2 g, 3.62 mmol), Xantphos (104 mg, 0.18 mmol), Pd$_2$(dba)$_3$ (82 mg, 0.09 mmol), and 18 mL dioxane for 3 h. Chromatography was run at 0-10% gradient MeOH in CHCl$_3$ (with 0.1% NH$_{40}$H) to afford the title compound (CCXLVI), as a yellow-brown solid (373 mg, 63%). LC retention time: 2.69 min, MS (ESI+) m/z=587.1.

Example 181

Synthesis of 4-[7-(2,6-dichloro-3-hydroxy-phenyl)-5-methyl-benzo[1,2,4]triazin-3-ylamino]-N-(2-pyrrolidin-1-yl-ethyl)-benzenesulfonamide

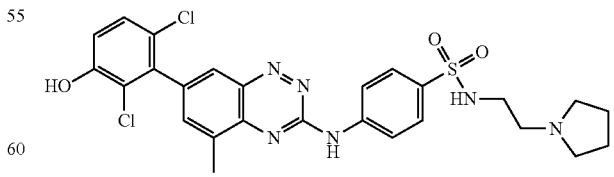

(CCXLVII)

The general aryl methoxy deprotection procedure was employed using aryl methoxy compound (CCXLVI) (Example 180) (337 mg, 0.57 mmol) and BBr$_3$ (271 μL, 2.9 mmol), in 15 mL DCM for 1 h. The reaction was quenched and the solids filtered and purified using HPLC. The aqueous HPLC fractions (100 mL) were neutralized with sat. aq. NaHCO$_3$ and extracted with EtOAc (2×150 mL). The combined organic layers were dried, filtered through celite and concentrated in vacuo. The HCl salt of the product was formed using MeOH and 4M HCl in dioxane, crashed out using Et$_2$O, and collected by filtration as a yellow solid (204 mg, 58%). LC retention time: 2.34 min, MS (ESI+) m/z=573.1 $^1$H NMR DMSO-d$_6$: δ 1.80-1.87 (m, 2H), 1.92-1.99 (m, 2H), 2.71 (s, 3H), 2.93-3.02 (m, 2H), 3.14 (q, J=6.3 Hz, 2H), 3.18-3.24 (m, 2H), 3.47-3.55 (m, 2H), 7.17 (d, J=8.9, Hz, 1H), 7.43 (d, J=8.9, Hz, 1H), 7.75 (dd, J=1.8, 1.0 Hz, 1H), 7.89 (d, J=8.9 Hz, 2H), 8.02 (t, J=5.8 Hz 1H), 8.11 (d, J=1.7 Hz, 1H), 8.26 (d, J=8.9 Hz, 2H), 10.78 (br s, 1H), 10.85 (s, 1H), 11.47 (s, 1H).

Example 182

Synthesis of 4-chloro-3-[3-(4-{[(2-hydroxy-ethyl)-isopropyl-amino]-methyl}-phenylamino)-5-methyl-benzo[1,2,4]triazin-7-yl]-phenol

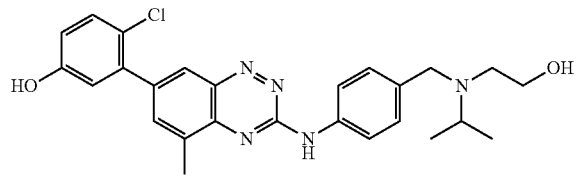

(CCXLVIII)

To synthesize the title product, intermediate compounds 97 and 98 shown below were used.

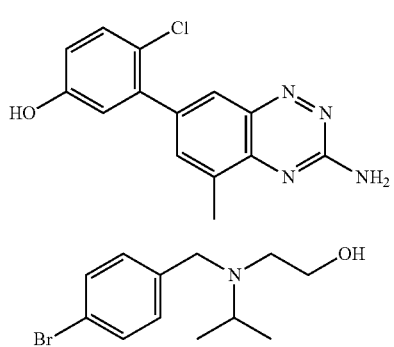

The general Buchwald procedure was employed using compounds 97 (142 mg, 0.50 mmol), 98 (104 mg, 0.38 mmol), Cs$_2$CO$_3$ (473 mg, 1.45 mmol), Xantphos (44 mg, 0.08 mmol), Pd$_2$(dba)$_3$ (34 mg, 0.04 mmol), and 7 mL dioxane for 2 h. The product was purified using HPLC to afford the TFA salt of the title compound (CCXLVIII), as a yellow-brown solid (45 mg, 21%). LC retention time: 2.32 min, MS (ESI+) m/z=478.0 $^1$H NMR DMSO-d$_6$: δ 1.31 (d, J=6.6, Hz, 3H), 1.37 (d, J=6.6, Hz, 1H), 2.69 (s, 3H), 3.01-3.11 (m, 1H), 3.22-3.28 (m, 1H), 3.47-3.54 (m, 1H), 3.62-3.72 (m, 2H), 4.29 (dd, J=13.2, 6.4, Hz, 1H), 4.36 (dd, J=13.2, 4.1, Hz, 1H), 5.31 (br s, 1H), 6.88 (dd, J=8.7, 2.9, Hz, 1H), 6.93 (d, J=2.9 Hz, 1H), 7.41 (d, J=8.7, Hz, 1H), 7.61 (d, J=8.6 Hz, 1H), 7.89 (dd, J=1.8, 1.0 Hz, 1H), 8.13 (d, J=8.7 Hz, 1H), 8.19 (d, J=1.7 Hz, 1H), 8.94 (br s, 1H), 9.95 (s, 1H), 11.17 (s, 1H).

Example 183

Synthesis of N-(4-(2-(pyrrolidin-1-yl)ethoxy)phenyl)-7-(2,6-dichloro-3-methoxyphenyl)-5-methyl-benzo[e][1,2,4]triazin-3-amine

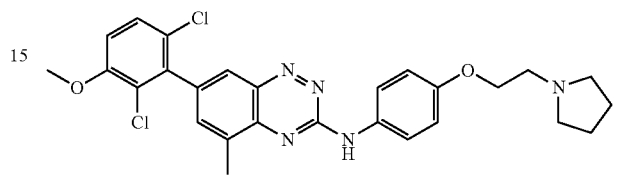

(CCXLIX)

The general Buchwald procedure was employed using crude compound (CCXLV) (Example 179) (159 mg, 0.47 mmol), compound 6 (Example 120) (134 mg, 0.50 mmol), Cs$_2$CO$_3$ (628 mg, 1.93 mmol), Xantphos (56 mg, 0.10 mmol), Pd$_2$(dba)$_3$ (46 mg, 0.05 mmol), and 10 mL dioxane for 16 h. Chromatography was run at 0-10% gradient MeOH in CHCl$_3$ (with 0.1% NH$_4$OH) followed by HPLC and NaHCO$_3$ extraction to afford the title compound (CCXLIX), as a red solid (110 mg, 44%). LC retention time: 2.74 min, MS (ESI+) m/z=524.1.

Example 184

Synthesis of 3-(3-(4-(2-(pyrrolidin-1-yl)ethoxy)phenylamino)-5-methylbenzo[e][1,2,4]triazin-7-yl)-2,4-dichlorophenol

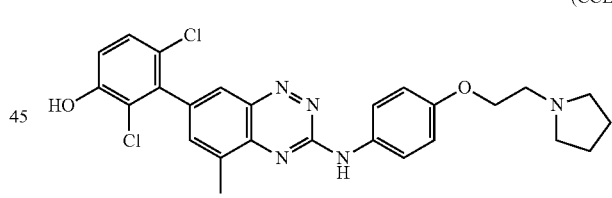

(CCL)

The general aryl methoxy deprotection procedure was employed using aryl methoxy compound (CCXLIX) (Example 183) (110 mg, 0.21 mmol) and BBr$_3$ (120 µL, 1.27 mmol), in 4 mL DCM for 20 min. The reaction was quenched and the solids filtered and purified using HPLC. The aqueous HPLC fractions (100 mL) were neutralized with sat. aq. NaHCO$_3$ and extracted with EtOAc (2×150 mL). The combined organic layers were dried, filtered through celite and concentrated in vacuo. The HCl salt of the product was formed using MeOH and 4M HCl in dioxane, crashed out using Et$_2$O, and collected the title compound (CCL) by filtration, as an orange solid (28 mg, 24%). LC retention time: 2.34 min, MS (ESI+) m/z=510.0 $^1$H NMR DMSO-d$_6$: δ 1.90 (br s, 2H), 2.03 (br s, 2H), 2.64 (s, 3H), 3.12-3.16 (m, 2H), 3.59 (br s, 4H), 4.34 (t, J=5.0, Hz, 2H), 7.10 (d, J=9.1, Hz, 2H), 7.10 (d, J=8.9, Hz, 1H), 7.42 (d, J=8.9, Hz, 1H), 7.65 (dd, J=1.8, 1.0 Hz, 1H), 7.99 (d, J=9.1 Hz, 2H), 8.02 (d, J=1.7 Hz, 1H), 10.18 (br s, 1H), 10.71 (s, 1H), 10.90 (s, 1H).

Example 185

Synthesis of benzyl 4-(4-(7-(2,6-dichloro-3-methoxyphenyl)-5-methylbenzo[e][1,2,4]triazin-3-ylamino)phenylsulfonyl)piperidine-1-carboxylate

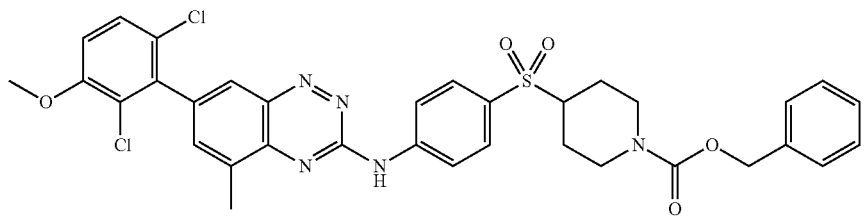

To synthesize the title product, intermediate compound 99 shown below was used.

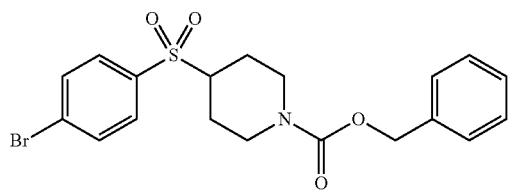

The general Buchwald procedure was employed using crude compound (CCLV) (example 179) (114 mg, 0.34 mmol), intermediate compound 99 (100 mg, 0.23 mmol), $Cs_2CO_3$ (312 mg, 0.96 mmol), Xantphos (28 mg, 0.05 mmol), $Pd_2(dba)_3$ (21 mg, 0.02 mmol), and 5 mL dioxane for 3 h. Chromatography was run at 0-50% gradient EtOAc in hexanes to afford the title compound (CCLI), as a crude yellow solid (104 mg, 65%). LC retention time: 3.37 min, MS (ESI+) m/z=692.2.

Example 186

Synthesis of 3-(3-(4-(piperidin-4-ylsulfonyl)phenylamino)-5-methylbenzo[e][1,2,4]triazin-7-yl)-2,4-dichlorophenol

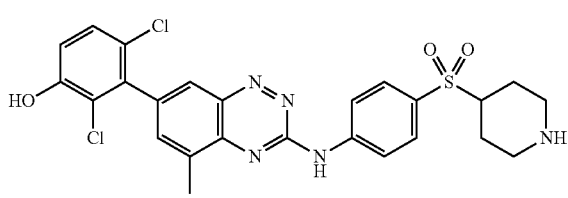

The general aryl methoxy deprotection procedure was employed using aryl methoxy compound (CCLI) (Example 185) (104 mg, 0.15 mmol) and $BBr_3$ (85 µL, 0.90 mmol), in 3 mL DCM for 5 min. The reaction was quenched and the solids filtered and purified using HPLC. The aqueous HPLC fractions (100 mL) were neutralized with sat. aq. $NaHCO_3$ and extracted with EtOAc (2×150 mL). The combined organic layers were dried, filtered through celite and concentrated in vacuo. The HCl salt of the title product was formed using MeOH and 4M HCl in dioxane, crashed out using $Et_2O$, and collected by filtration as a yellow solid (34 mg, 41%). LC retention time: 2.23 min, MS (ESI+) m/z 544.0 $^1$H NMR DMSO-$d_6$: δ 1.67-1.78 (m, 2H), 2.03-2.09 (m, 2H), 2.72 (s, 3H), 2.83-2.91 (m, 2H), 3.36 (m against $H_2O$ peak), 3.55 (tt, J=11.9, 0.8, Hz, 1H), 7.13 (d, J=8.9, Hz, 1H), 7.44 (d, J=8.8, Hz, 1H), 7.77 (s, 1H), 7.89 (d, J=9.0 Hz, 2H), 8.14 (d, J=1.3 Hz, 1H), 8.34 (d, J=8.9 Hz, 2H), 8.43 (br s, 1H), 8.96 (br s, 1H), 10.75 (s, 1H), 11.59 (s, 1H).

Example 187

Synthesis of {4-[7-(3,5-dimethyl-isoxazol-4-yl)-5-methyl-benzo[1,2,4]triazin-3-ylamino]-phenyl}-(4-methyl-piperazin-1-yl)-methanone

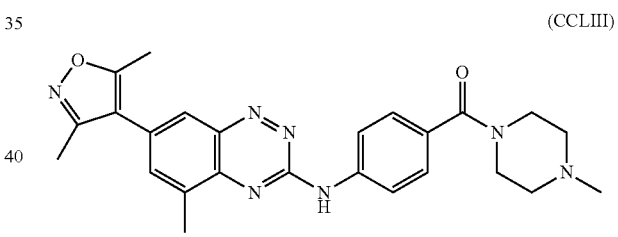

A mixture of above amine (compound (CCLII), Example 186) (125 mg, 0.46 mmol), 1-(2-(4-bromophenoxy)ethyl)pyrrolidine (156 mg, 0.55 mmol), $Cs_2CO_3$ (600 mg, 1.84 mmol), Xantphos (53 mg, 0.1 mmol), $Pd_2(dba)_3$ (45 mg, 0.05 mmol), and 3 Å mol sieves in dioxane (10 mL) was purged with argon for 5 min, and was heated to reflux for 16 h under argon. The volatiles were evaporated and the residue was triturated with chloroform-water (1:1, 200 mL). The chloroform layer was separated and filtered through a small silica plug. The silica plug was washed with 200 mL of 10% methanol in chloroform. The solvent was evaporated and the crude product was purified using HPLC. The purified product was converted to mesylate salt using methane sulfonic acid, to afford the title product (CCLIII), as an orange solid (54 mg, % yield). $^1$H NMR DMSO-$d_6$: δ 2.16, 2.22, 2.31, 2.84 (4s, 3H each), 3.05-3.18, 3.24-3.36, 3.43-3.55 (3m, 8 H), 7.55 (d, J=7 Hz, 2H), 7.89 (d, J=1.8 Hz, 1H), 8.13 (d, J=7.0 Hz, 2H), 8.22 (d, J=1.7 Hz, 1H), 9.86-9.97 (br s, 1H), 11.25 (s, 1H). MS (ESI+) m/z=458.2

The following Examples 188-192 describe the synthesis of some of the intermediate compounds 100 (7-bromo-5-methyl-benzo[1,2,4]triazin-3-ylamine), 101 (7-bromo-6-methyl-benzo[1,2,4]triazin-3-ylamine), 102 ((4-bromo-phenyl)-(4-methyl-piperazin-1-yl)-methanone), 103 (4-bromo-N-(2-pyrrolidin-1-yl-ethyl)-benzamide), 104 (4-bromo-N-(2-dimethylamino-ethyl)-benzamide), 105 (3-bromo-N-(2-pyrrolidin-1-yl-ethyl)-benzamide), 106 (3R-(3-bromo-benzoylamino)-pyrrolidine-1-carboxylic acid tert-butyl ester), 107 (1-[3-(3-bromo-benzenesulfonyl)-propyl]-pyrrolidine), and 108 (7-(2,6-dimethyl-phenyl)-5-methyl-benzo[1,2,4]triazin-3-ylamine) that were used to synthesize the title compounds of Examples 188-190, 193-205, 208, 209, and 213 that follow.

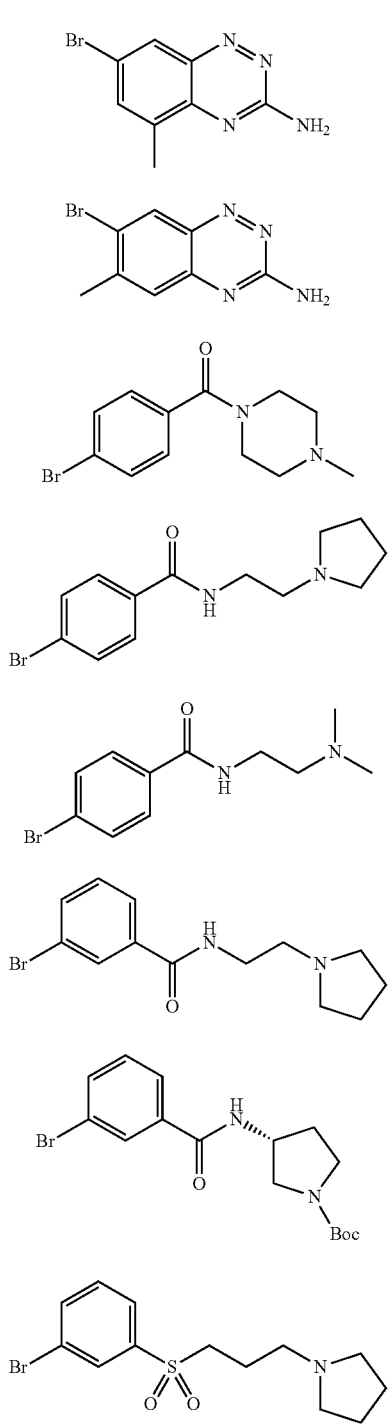

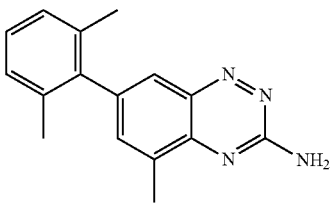

Example 188

Synthesis of (4-bromo-phenyl)-(4-methyl-piperazin-1-yl)-methanone

Intermediate Compound 102

To a solution of 4-bromo-benzoic acid (1.0 g, 5.0 mmol) in 50 mL acetonitrile and 5 mL DMF were added N-methylpiperazine (566 mmol) and EDC (980 mg, 5.1 mmol). The reaction mixture was stirred at room temperature for 16 h. The solvent was removed and the residue was dissolved in 60 mL $CH_2Cl_2$ and successively washed with water (50 mL) and aqueous saturated $NaHCO_3$ solution. The organic phase was dried ($MgSO_4$) and the solvent was removed. The crude product was purified by flash column chromatography ($R_f$=0.54, $CH_2Cl_2$/MeOH, 90:10) to yield the intermediate compound 102. $^1$H NMR CDCl$_3$: δ 2.32 (s, 3H), 2.33 (m, 2H), 2.49 (m, 2H), 3.41 (m, 2H), 3.78 (m, 2H), 7.27 (d, J=8.3 Hz, 2H), 7.53 (d, J=8.3 Hz, 2H). MS (ESI+) m/z=283/285.

Example 189

Synthesis of 4-bromo-N-(2-dimethylamino-ethyl)-benzamide

Intermediate Compound 104

To a solution of 4-bromo-benzoic acid (5.02 g, 25 mmol) in 200 mL acetonitrile were added N',N'-dimethylethylenediamine (2.8 mL, 25 mmol) and EDC (4.9 g, 25.5 mmol). The mixture was stirred at room temperature for 2 h. The white precipitate was removed by filtration and the solvent was evaporated. The residue was dissolved in 150 mL $CH_2Cl_2$, and was washed successively with water (150 mL) and aqueous saturated $NaHCO_3$ (150 mL). The organic phase was dried ($MgSO_4$) and the solvent was evaporated. The crude product was purified by flash column chromatography $R_f$=0.2, ($CH_2Cl_2$/MeOH, 90:10) to afford the title intermediate compound 104 (3.68 g, 54%). MS (ESI+) m/z=271/273.

Example 190

Synthesis of 3-bromo-N-(2-pyrrolidin-1-yl-ethyl)-benzamide

Intermediate Compound 105

The title compound was prepared according to the procedure described for the intermediate compound 104 (Example 189). The crude product was used without further purification (3.7 g, 50%). MS (ESI+) m/z=297/299.

Example 191

Synthesis of 3R-(3-bromo-benzoylamino)-pyrrolidine-1-carboxylic acid tert-butyl ester

Intermediate Compound 106

A solution of 3-bromobenzoic acid (4.0 g, 20 mmol) and EDC (3.83 g, 20 mmol) in 50 mL acetonitrile was added dropwise to a solution of (3R)-(+)-3-aminopyrrolidine (1.72 g, 20 mmol) in 100 mL acetonitrile. The reaction mixture was stirred at room temperature for 2 h and the solvent was removed. The residue was dissolved in 50 mL $CH_2Cl_2$ and washed with brine (50 mL). The organic phase was dried ($MgSO_4$) and the solvent was removed. The crude product was purified by silica gel column chromatography ($R_f$=0.22, $CH_2Cl_2$/MeOH, 75:15) to give 3-bromo-N-pyrrolidin-3-yl-benzamide as a colorless solid (2.0 g, 37%). To a solution of the above precursor (1.14 g, 4.24 mmol) in 30 mL $CH_2Cl_2$ were added di-tert-butyldicarbonate (925 mg, 4.24 mmol) and triethylamine (596 µl, 4.24 mmol). The reaction mixture was stirred at room temperature for 1 h. The solvent was removed and the crude product was purified by silica gel column chromatography ($R_f$=0.66, $CH_2Cl_2$/MeOH, 90:10) to afford the title intermediate compound 106, as a viscous, colorless oil (1.1 g, 70%). MS (ESI+) m/z=369/371.

Example 192

Synthesis of 1-[3-(3-bromo-benzenesulfonyl)-propyl]-pyrrolidine

Intermediate Compound 107

To a solution of 3-bromothiophenol (4.0 g, 21.2 mmol) in 50 mL methanol was added NaOMe (2.28 g, 42 mmol). The mixture was stirred at room temperature for 1 h and was added dropwise to 22 mL of 1,3-dibromopropane (42.5 g, 210 mmol) at room temperature. The reaction mixture was stirred at room temperature for 16 h and quenched with water (50 mL). The crude product was extracted with $CH_2Cl_2$ (100 mL) and the combined organic phase was dried ($MgSO_4$). The volatiles were removed under reduced pressure. The crude product in 150 mL $CH_2Cl_2$ was treated with 3-chloroperoxybenzoic acid (4.9 g, 20 mmol) at 0° C. for 1 h. Another batch of mCPBA (4.9 g, 20 mmol) was added and the stirring was continued for another 30 min at 0° C. before the mixture was allowed to warm to room temperature. The reaction mixture was diluted with $CH_2Cl_2$ and EtOAc (20 mL each) and washed twice with saturated aqueous $NaHCO_3$ solution. The organic phase was dried ($MgSO_4$) and the product was purified by silica gel column chromatography ($R_f$=0.53, EtOAc/hexanes 50:50) to give 1-bromo-3-(3-bromo-propane-1-sulfonyl)benzene as a colorless solid (5.47 g, 76%).

A mixture of 1-bromo-3-(3-bromo-propane-1-sulfonyl)benzene (5.47 g, 16.4 mmol $Cs_2CO_3$ (10.7 g, 32.8 mmol) and pyrrolidine (2.71 mL, 32.8 mmol)) in 100 mL anhydrous 1,4-dioxane was stirred at room temperature for 16 h. The reaction mixture was quenched with saturated aqueous sodium bicarbonate (100 mL) and was extracted with $CH_2Cl_2$ (140 mL). The combined organic phase was dried ($MgSO_4$), and the solvent was removed. The product was dried in vacuo to afford the title intermediate compound 107, as a brown oil (4.95 g, 91%).

Example 193

Synthesis of [7-(5-chloro-2-methoxy-phenyl)-5-methyl-benzo[1,2,4]triazin-3-yl]-[4-(2-pyrrolidin-1-yl-ethoxy)-phenyl]-amine trifluoroacetate

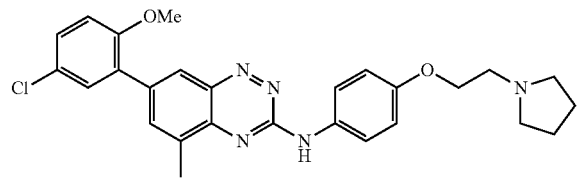

(CCLIV)

To a solution of intermediate compound 100 (24 mg, 0.1 mmol) in 2 mL DMA were added 5-chloro-2-methoxyphenylboronic acid (75 mg, 0.4 mmol) in ethanol (500 µl), $K_2CO_3$ (2.8 mg, 0.02 mmol) in water (200 µl), $PPh_3$ (3 mg, 0.01 mmol) and $Pd_2(dba)_3$ (9 mg, 0.01 mmol). The reaction mixture was stirred at 80° C. for 16 h under argon, cooled to room temperature and poured into aqueous saturated $NaHCO_3$ (50 mL). The product was extracted with $CH_2Cl_2$ (100 mL) and purified by reverse phase preparative HPLC using a gradient of acetonitrile/water containing 0.1% TFA as the eluent. The combined product fractions were washed with aqueous saturated $NaHCO_3$ solution. The product was extracted with $CH_2Cl_2$, the combined organic phase was dried ($MgSO_4$) and the solvent was evaporated to give a precursor 7-(5-chloro-2-methoxy-phenyl)-5-methyl-benzo[1,2,4]triazin-3-ylamine (25.1 mg, 83%). To a solution of the purified precursor in 4 mL anhydrous toluene were added 1-[2-(4-bromo-phenoxy)-ethyl]-pyrrolidine (41 µl, 0.2 mmol), BINAP (3.7 mg, 6 µmol), $Pd_2(dba)_3$ (2.3 mg, 2.5 µmol) and KO-$^t$Bu (9.3 mg, 0.083 mmol). Under argon, the reaction mixture was stirred at 100° C. for 18 h. It was cooled to room temperature and poured into aqueous saturated NaCl solution. The product was extracted with $CH_2Cl_2$ and purified by reverse phase preparative HPLC to afford the title compound (CCLIV) as trifluoroacetate salt, in a form of a red-solid (5 mg, 10%). $^1$H NMR DMSO-$d_6$: δ 1.90 (m, 2H), 2.05 (m, 2H), 2.64 (s, 3H), 3.15 (m, 2H), 3.61 (t, J=5.0 Hz, 2H), 3.63 (m, 2H), 4.31 (t, J=5.0 Hz, 2H), 7.09 (d, J=9.0 Hz, 2H), 7.22 (d, J=8.9 Hz, 2H), 7.47 (dd, J=8.9 Hz, J=2.6 Hz, 1H), 7.52 (d, J=2.6 Hz, 1H), 7.93 (br s, 1H), 7.99 (d, J=9.0 Hz, 2H), 8.25 (br s, 1H), 11.x (s, 1H). MS (ESI+) m/z=490.

Example 194

Synthesis of {4-[7-(2,6-dimethyl-phenyl)-5-methyl-benzo[1,2,4]triazin-3-ylamino]-phenyl}-(4-methyl-piperazin-1-yl)-methanone trifluoroacetate (CCLV)

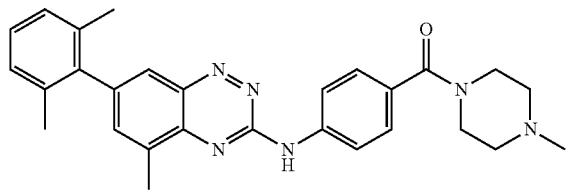

The compound was prepared from intermediate compounds 108 and 102, following the coupling procedure described above. The product was purified by reverse phase preparative HPLC to afford the title product in a form of trifluoroacetate, salt as a yellow-orange solid (yield, 56%). $^1$H NMR methanol-d$_4$: δ 2.09 (s, 6H), 2.76 (s, 3H), 2.98 (s, 3H), 3.30-3.50 (m, 8H), 7.16 (br d, J=6.9 Hz, 2H), 7.21 (dd, J=6.2 Hz, J=8.7, 1H), 7.59 (d, J=8.7 Hz, 2H), 7.60 (br s, 1H), 7.91 (br s, 1H), 8.18 (d, J=8.7 Hz), 11.12 (s, 1H). MS (ESI+) m/z=467.

Example 195

Synthesis of [7-(3,5-dimethyl-isoxazol-4-yl)-5-methyl-benzo[1,2,4]triazin-3-yl]-[4-(2-pyrrolidin-1-yl-ethoxy)-phenyl]-amine (CCLVI)

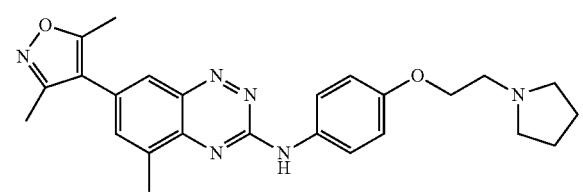

The synthesis of the title product followed the reaction scheme (CCLVII).

(CCLVII)

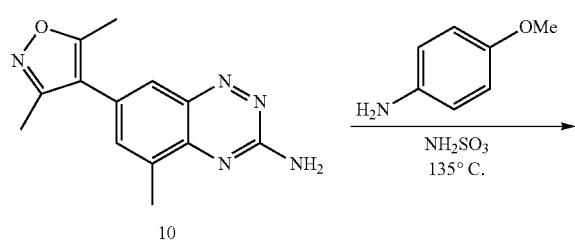

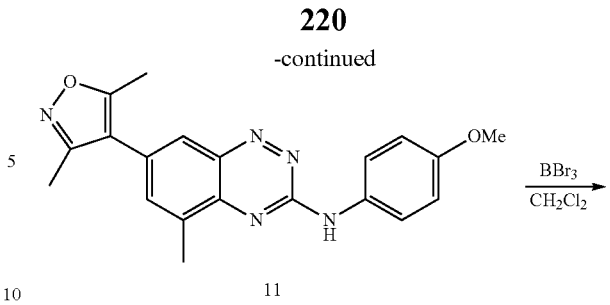

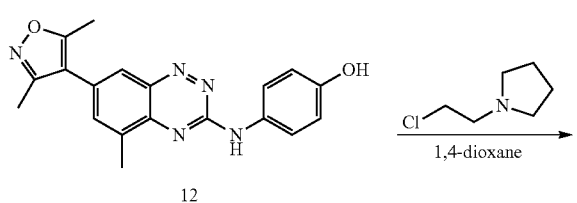

7-(3,5-dimethyl-isoxazol-4-yl)-5-methyl-benzo[1,2,4]triazin-3-ylamine (designated as compound 10 on scheme (CCLVII)) was prepared from the above described intermediate compound 100 and 3,5-dimethylisoxazole-4-boronic acid following the coupling procedure outlined above. A solution of the intermediate (160 mg, 0.627 mmol) and sulfamic acid (122 mg, 1.25 mmol) in methoxyaniline (1.2 g, 9.4 mmol) was stirred at 135° C. for 6 h to form [7-(3,5-dimethyl-isoxazol-4-yl)-5-methyl-benzo[1,2,4]triazin-3-yl]-(4-methoxy-phenyl)-amine (designated as compound 11 on scheme (CCLVII)), which was purified by silica gel column chromatography (R$_f$=0.24, hexanes/EtOAc, 70:30) (24.2 mg, 11%). The purified precursor, dissolved in 4 mL CH$_2$Cl$_2$, was treated with BBr$_3$ (32 μl, 0.34 mmol) at room temperature for 2 h. The reaction mixture was diluted with CH$_2$Cl$_2$ (20 mL) and washed with aqueous saturated sodium thiosulphate.

The organic phase was dried (Na$_2$SO$_4$) and the solvent evaporated to yield 4-[7-(3,5-dimethyl-isoxazol-4-yl)-5-methyl-benzo[1,2,4]triazin-3-ylamino]-phenol (designated as compound 12 on scheme (CCLVII)) (15 mg, 65%), to a solution of which (4.5 mg, 0.013 mmol) in 3 mL 1,4-dioxane were added Cs$_2$CO$_3$ (21 mg, 0.065 mmol) and 1-(2-chloro-ethyl)-pyrrolidine (4.4 mg, 0.026 mmol). The mixture was heated under reflux for 2 h and the solvent was removed. The crude product was purified by silica gel column chromatography using CH$_2$Cl$_2$/methanol/NEt$_3$ (90:10:0.1) as the mobile phase to afford the title product (CCLVI), as a red solid (2.6 mg, 45%). $^1$H NMR methanol-d$_4$: δ 1.89 (m, 4H), 2.34 (s, 3H), 2.50 (s, 1H), 2.70 (s, 3H), 2.79 (m, 4H), 3.02 (t, J=5.6 Hz, 2H), 4.18 (t, J=5.6 Hz, 2H), 7.01 (d, J=9.0 Hz, 2H), 7.69 (s, 1H), 7.89 (d, J=9.0 Hz, 2H), 8.02 (br s, 1H). MS (ESI+) m/z=445.

Example 196

Synthesis of 4-[7-(2,6-dimethyl-phenyl)-5-methyl-benzo[1,2,4]triazin-3-ylamino]-N-(2-pyrrolidin-1-yl-ethyl)-benzamide

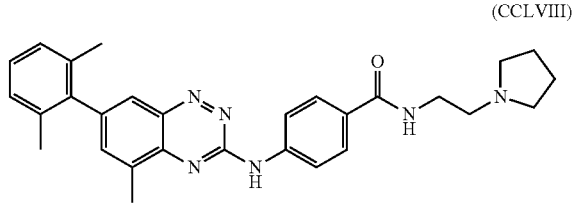 [SMILES: Cc1cccc(C)c1-c1cc(C)c2nc(Nc3ccc(C(=O)NCCN4CCCC4)cc3)nnc2c1]

(CCLVIII)

The compound was prepared from the intermediate compounds 108 and 103 following the above-described coupling procedure. The crude product was purified by reverse phase preparative HPLC to afford the title product (CCLVIII), as a yellow-orange solid. ¹H NMR methanol-d₄: δ 2.06 (m, 2H), 2.09 (s, 6H), 2.20 (m, 2H), 2.77 (s, 3H), 3.18 (m, 2H), 3.46 (t, J=5.8 Hz, 2H), 3.78 (t, J=5.8 Hz, 2H), 3.82 (m, 2H), 7.16 (br d, J=6.9 Hz, 2H), 7.21 (dd, J=6.2 Hz, J=8.7, 1H), 7.60 (br s, 1H), 7.91 (br s, 1H), 7.96 (d, J=8.9 Hz), 8.16 (d, J=8.9 Hz, 2H). MS (ESI+) m/z=481.

Example 197

Synthesis of [7-(2-chloro-5-methoxy-phenyl)-5-methyl-benzo[1,2,4]triazin-3-yl]-[4-(2-pyrrolidin-1-yl-ethoxy)-phenyl]-amine trifluoroacetate

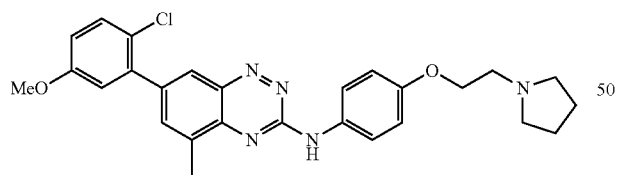

(CCLIX)

The product was prepared from the intermediate compound 100, 2-chloro-5-methoxyphenylboronic acid, and 1-[2-(4-bromo-phenoxy)-ethyl]-pyrrolidine following the above-described coupling procedures. The crude product was purified by reverse phase preparative HPLC to afford the title product (CCLIX) in a form of trifluoroacetate salt, as an orange solid (100 mg, 10%), ¹H NMR methanol-d₄: δ 2.08 (m, 2H), 2.22 (m, 2H), 2.70 (s, 3H), 3.27 (m, 2H), 3.68 (t, J=5.0 Hz, 2H), 3.75 (m, 2H), 4.37 (t, J=5.0 Hz, 2H), 7.00 (dd, J=8.8 Hz, J=3.0, 1H), 7.05 (d, J=3.0, 1H), 7.10 (d, J=9.0 Hz, 2H), 7.46 (d, J=8.8 Hz, 1H), 7.81 (br s, 1H), 7.96 (d, J=9.0 Hz, 1H), 8.11 (br s, 1H). MS (ESI+) m/z=490.

Example 198

Synthesis of N-(2-dimethylamino-ethyl)-4-[7-(2,6-dimethyl-phenyl)-5-methyl-benzo[1,2,4]triazin-3-ylamino]-benzamide dihydrate mesylate

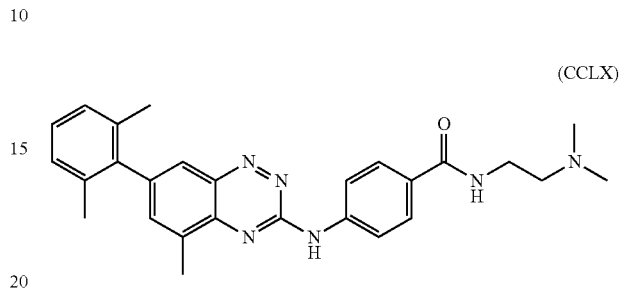

(CCLX)

The compound was prepared from the intermediate compounds 108 and 104 following the above-described coupling procedure. The crude product was purified by silica gel column chromatography using methanol/CH₂Cl₂/NEt₃ (50:50:0.1) as the mobile phase and was re-crystallized from CH₂Cl₂ to give N-(2-dimethylamino-ethyl)-4-[7-(2,6-dimethyl-phenyl)-5-methyl-benzo[1,2,4]triazin-3-ylamino]-benzamide, to a solution of 80 mg of which in 1.5 mL methanol was added methanesulfonic acid (9.5 μl, 0.146 mmol) and the mixture was stirred for 5 min until clear. The clear solution was added dropwise to 20 mL Et₂O. The yellow precipitate was isolated by filtration and dried in vacuo to afford the title product (CCLX), as a yellow solid (71 mg, 80%), ¹H NMR Methanol-d₄: δ 2.09 (s, 6H), 2.70 (s, 3H), 2.77 (s, 3H), 3.00 (s, 6H), 3.39 (t, J=5.9 Hz, 2H), 3.78 (t, J=5.9 Hz, 2H), 7.16 (br d, J=7.9 Hz, 2H), 7.21 (dd, J=6.2 Hz, J=8.8, 1H), 7.60 (br s, 1H), 7.91 (br s, 1H), 7.97 (d, J=8.8 Hz), 8.17 (d, J=8:8 Hz, 2H). Analyzed: (C₂₈H₃₈N₆O₆S), calculated: C, 57.32; H, 6.53; N, 14.32. found C, 57.00; H, 6.55; N, 14.30. MS (ESI+) m/z=455.

Example 199

Synthesis of 3-[7-(2,6-dimethyl-phenyl)-5-methyl-benzo[1,2,4]triazin-3-ylamino]-N-(2-pyrrolidin-1-yl-ethyl)-benzamide trifluoroacetate

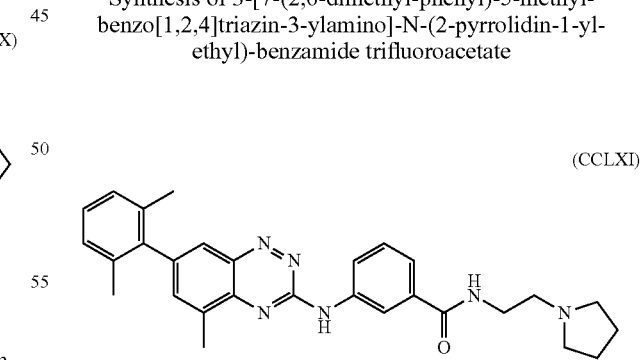

(CCLXI)

The compound was prepared from the intermediate compounds 108 and 104 following the above-described coupling procedure. The crude product was purified by reverse phase preparative HPLC to afford the title product (CCLXI), as a yellow solid (140 mg, 31%). ¹H NMR methanol-d₄: δ 2.05 (m, 2H), 2.09 (s, 6H), 2.21 (m, 2H), 2.78 (s, 3H), 3.18 (m, 2H), 3.47 (t, J=5.9 Hz, 2H), 3.80 (t, J=5.9 Hz, 2H), 3.83 (m, 2H), 7.16 (br d, J=7.5 Hz, 2H), 7.21 (dd, J=6.2 Hz, J=8.7, 1H), 7.53

(t, J=7.8 Hz, 1H), 7.56 (d, J=7.8, 1H), 7.58 (br s, 1H), 7.89 (br s, 1H), 8.15 (d, J=7.8 Hz, 1H), 8.70 (br s, 1H). MS (ESI+) m/z=481.

Example 200

Synthesis of 3-[7-(2,6-dimethyl-phenyl)-5-methyl-benzo[1,2,4]triazin-3-ylamino]-N-pyrrolidin-3-yl-benzamide trifluoroacetate (CCLXII)

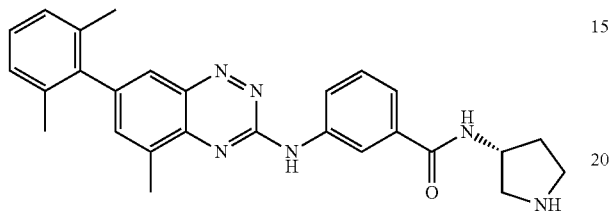

To a solution of intermediate compound 108 (66 mg, 0.25 mmol) in 4 mL anhydrous toluene were added 7 (92 mg, 0.25 mmol), BINAP (16 mg, 25 µmol), Pd$_2$(dba)$_3$ (12 mg, 12.5 µmol) and Cs$_2$CO$_3$ (122 mg, 0.375 mmol). The reaction mixture was stirred at 90° C. for 18 h under argon. The mixture was heated in the microwave at 170° C. for 10 min and poured into aqueous saturated NaCl solution. The product was extracted with CH$_2$Cl$_2$ and purified by reverse phase preparative HPLC to afford the title product (CCLXII), as a yellow solid (45 mg, 32%). $^1$H NMR DMSO-d$_6$: δ 2.01 (m, 1H), 2.06 (s, 6H), 2.24 (m, 1H), 2.67 (s, 3H), 3.53-3.95 (m, 5H), 7.19 (br d, J=7.6 Hz, 2H), 7.24 (dd, J=6.2 Hz, J=8.7, 1H), 7.50 (br t, J=7.8 Hz, 1H), 7.65 (br s, 1H), 7.96 (br s, 1H), 8.07 (br s, 1H), 8.17 (d, J=8.7 Hz, 2H), 11.07 (s, 1H). MS (ESI+) m/z=453.

Example 201

Synthesis of [7-(2,6-dimethyl-phenyl)-5-methyl-benzo[1,2,4]triazin-3-yl]-[3-(3-Pyrrolidin-1-yl-propane-1-sulfonyl)-phenyl]-amine monohydrate mesylate (CCLXIII)

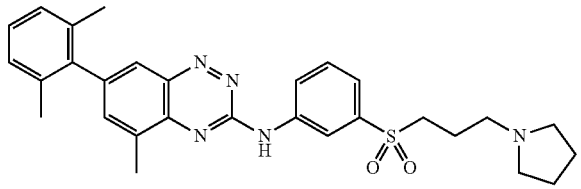

The compound was prepared from the intermediate compounds 108 and 107 following the above-described coupling procedures. The crude product was purified by reverse phase preparative HPLC to give [7-(2,6-dimethyl-phenyl)-5-methyl-benzo[1,2,4]triazin-3-yl]-[3-(3-pyrrolidin-1-yl-propane-1-sulfonyl)-phenyl]-amine trifluoroacetate salt, which was converted to the free amine by washing with saturated aqueous NaHCO$_2$ solution and extraction with CH$_2$Cl$_2$. The combined organic phases were dried (MgSO$_4$) and the solvent was removed to yield [7-(2,6-dimethyl-phenyl)-5-methyl-benzo[1,2,4]triazin-3-yl]-[3-(3-pyrrolidin-1-yl-propane-1-sulfonyl)-phenyl]-amine as a yellow solid, which (132 mg, 0.256 mmol) was combined with methanesulfonic acid (15.78 ul, 0.24 mmol) in 3 mL CH$_2$Cl$_2$ and with Et$_2$O (80 mL). The yellow precipitate was isolated by filtration and dried in vacuo to afford the title product (CCLXIII), as a yellow solid (145 mg, 93%). $^1$H NMR DMSO-d$_6$: δ 1.82 (m, 2H), 1.98 (m, 4H), 2.06 (s, 6H), 2.30 (s, 3H), 2.72 (s, 3H), 2.97 (m, 2H), 3.23 (m, 2H), 3.45 (t, J=7.8 Hz, 2H), 3.51 (m, 2H), 7.19 (d, J=7.0 Hz, 2H), 7.24 (dd, J=6.3 Hz, J=8.6, 1H), 7.60 (d, J=8.0 Hz, 1H), 7.68 (s, 1H), 7.72 (t, J=8.0 Hz, 1H), 8.00 (s, 1H), 8.13 (d, 8.0 Hz, 1H), 9.04 (s, 1H), 9.38 (br s, 1H), 11.40 (s, 1H). Analyzed: (C$_{30}$H$_{39}$N$_5$O$_6$S$_2$), calculated C, 57.21, H, 6.24; N, 11.12. found C, 56.56, H, 5.79; N, 11.04 MS (ESI+) m/z=516.

Example 202

Synthesis of {4-[7-(2-chloro-5-methoxy-phenyl)-6-methyl-benzo[1,2,4]triazin-3-ylamino]-phenyl}-(4-methyl-piperazin-1-yl)-methanone monohydrate mesylate (CCLXIV)

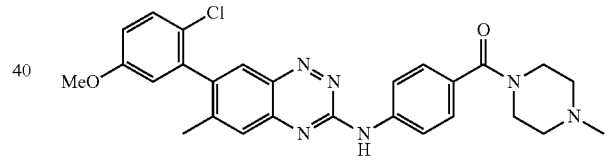

The title product was synthesized from the intermediate compounds 101, 102, and 2-chloro-5-methoxyphenylboronic acid, following the above-described coupling procedures. The crude product was purified by reverse phase preparative HPLC and the resulting trifluoroacetate salt was converted to the free amine by washing with saturated aqueous NaHCO$_3$ solution and extraction with CH$_2$Cl$_2$ to give {4-[7-(2-chloro-5-methoxy-phenyl)-6-methyl-benzo[1,2,4]triazin-3-ylamino]-phenyl}-(4-methyl-piperazin-1-yl)-methanone as a yellow solid (49.5%). The free base was converted to the title product (CCLXIV) (189 mg, 96%). $^1$H NMR DMSO-d$_6$: δ 2.29 (s, 3H), 2.31 (s, 3H, mesylate), 2.85 (br s, 3H), 3.11 (m, 2H), 3.30-3.50 (m, 6H), 3.85 (s, 3H), 7.03 (d, J=3.0 Hz, 1H), 7.09 (dd, J=8.9, J=3.0 Hz, 1H), 7.52-7.55 (m, 3H), 7.76 (s, 1H), 8.09 (d, J=8.9 Hz, 2H), 8.10 (s, 1H), 9.72 (br s, 1H), 11.13 (s, 1H). Anal. ($C_{28}H_{33}ClN_6O_6S$), Calcd C, 54.50, H, 5.39; N, 13.62. found 54.31, H, 5.64; N, 13.38 MS (ESI+) m/z=503.

Example 203

Synthesis of {4-[7-(5-chloro-2-methyl-phenyl)-6-methyl-benzo[1,2,4]triazin-3-ylamino]-phenyl}-(4-methyl-piperazin-1-yl)-methanone mono-hydrate mesylate

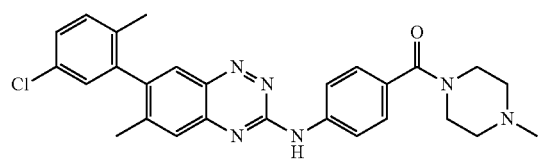
(CCLXV)

The title product was synthesized and purified as described in Example 202 for compound (CCLXIV), except 5-chloro-2-methylphenylboronic acid was used instead of 2-chloro-5-methoxyphenylboronic acid. $^1$H NMR DMSO-$d_6$: δ 2.04 (s, 3H), 2.21 (s, 3H), 2.32 (s, 3H, mesylate), 2.84 (br s, 3H), 3.11 (m, 2H), 3.30-3.50 (m, 6H), 7.31 (d, J=2.0 Hz, 1H), 7.41-7.45 (m, 2H), 7.52 (d, J=8.6 Hz, 2H), 7.78 (s, 1H), 8.08 (s, 1H), 8.09 (d, J=8.6 Hz, 2H), 9.75 (br s, 1H), 11.12 (s, 1H). Analyzed; ($C_{28}H_{33}ClN_6O_5S$), calculated: C, 55.95; H, 5.53; N, 13.98. found: C, 55.59; H, 5.57; N, 13.78. MS (ESI+) m/z=487.

Example 204

Synthesis of [7-(5-fluoro-2-methyl-phenyl)-6-methyl-benzo[1,2,4]triazin-3-yl]-[4-(2-pyrrolidin-1-yl-ethoxy)-phenyl]-amine trifluoroacetate

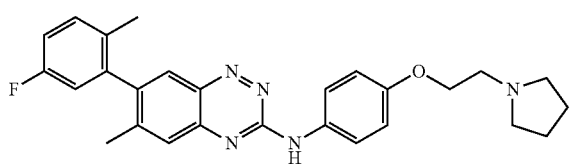
(CCLXVI)

A precursor, 7-(5-fluoro-2-methyl-phenyl)-6-methyl-benzo[1,2,4]triazin-3-ylamine, was prepared using the above-described coupling procedure. A mixture of the precursor (113 mg, 0.42 mmol), 1-[2-(4-bromo-phenoxy)-ethyl]-pyrrolidine (174 μl 0.84 mmol), Xantphos (49 mg, 0.084 mmol), $Pd_2(dba)_3$ (39 mg, 0.042 mmol) and $Cs_2CO_3$ (274 mg, 0.84 mmol) in anhydrous dioxane (4 mL) was heated under reflux for 2 h under argon. The reaction mixture was cooled to room temperature and quenched with brine. The product was extracted with $CH_2Cl_2$ and purified by reverse phase preparative HPLC to afford the title product (CCXVI), as an orange solid (10.3 mg, 4.3%). $^1$H NMR DMSO-$d_6$: δ 1.90 (m, 2H), 2.02 (s, 3H), 2.03 (m, 2H), 2.19 (s, 3H), 3.15 (m, 2H), 3.61 (m, 4H), 4.31 (t, J=5.0, 2H), 7.07 (d, J=9.0 Hz, 1H), 7.10 (dd, J=9 Hz, J=2.8 Hz, 1H), 7.21 (ddd, J=8.7 Hz, J=8.7 Hz, J=2.8 Hz, 1H), 7.41 (dd, J=6 Hz, J=8.7, 1H), 7.67 (s, 1H), 7.91 (d, J=9.0 Hz, 2H), 8.00 (s, 1H), 9.77 (br s, 1H), 10.73 (s, 1H). MS (ESI+) m/z=458.

Example 205

Synthesis of 3-{6-methyl-3-[4-(2-pyrrolidin-1-yl-ethoxy)-phenylamino]-benzo[1,2,4]triazin-7-yl}-phenol hydrochloride

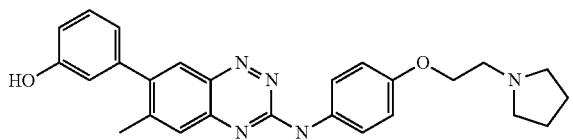
(CCLXVII)

A precursor, 3-(3-amino-6-methyl-benzo[1,2,4]triazin-7-yl)-phenol, was prepared from the intermediate compound 101 and 3-hydroxyphenylboronic acid using the above-described coupling. The final product was synthesized from the above precursor (0.73 mmol, 185 mg) and 1-[2-(4-bromo-phenoxy)-ethyl]-pyrrolidine (303 μl, 1.46 mmol) according to the procedure described above. The product was purified by reverse phase preparative HPLC and was converted to the free amine by washing with saturated aqueous $NaHCO_3$ solution and extraction with $CH_2Cl_2$ (94.6 mg, 29%). The free amine was converted to the title compound (CCLXVII), a red-orange solid (81.3 mg, 80%). $^1$H NMR DMSO-$d_6$: δ 1.90 (m, 2H); 2.04 (m, 2H), 2.40 (s, 3H), 3.13 (m, 2H), 3.59 (m, 4H), 4.34 (t, J=5.0 Hz, 2H), 6.84 (s, 1H), 6.84-6.88 (m, 2H), 7.06 (d, J=9.0 Hz, 2H), 7.30 (dd, J=7.8 Hz, J=7.8 Hz, 1H), 7.63 (s, 1H), 7.90 (d, J=9.0 Hz, 2H), 9.64 (s, OH), 10.39 (br s, 1H), 10.70 (s, 1H). MS (ESI+) m/z=442.

Example 206

Synthesis of N-{3-[4-(2-pyrrolidin-1-yl-ethylsulfamoyl)-phenylamino]-7-o-tolyl-benzo[1,2,4]triazin-6-yl}-acetamide trifluoroacetate

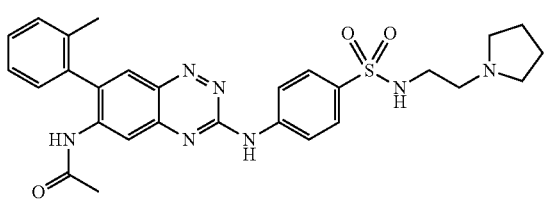
(CCLXVIII)

As a preliminary step, the synthesis of the title product included a process shown by the reaction scheme (CCLXIX).

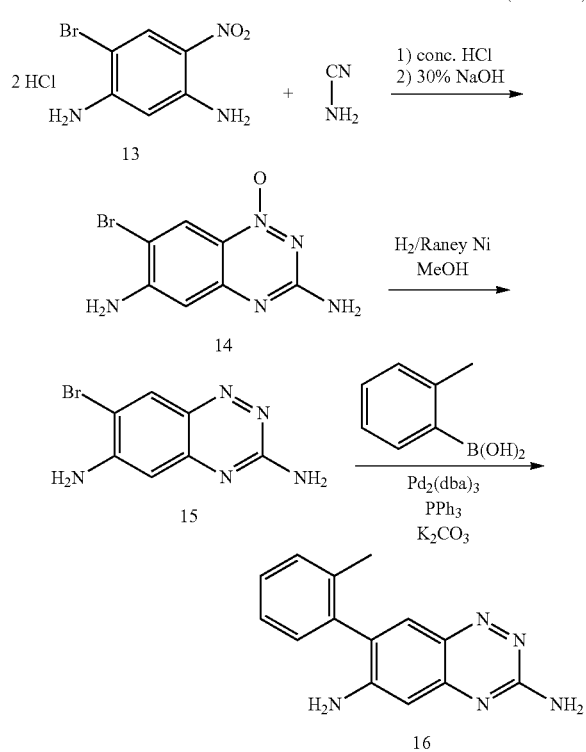

The reaction scheme (CCLXIX) illustrates a synthetic process rthat included dropwise adding of 6.4 g bromine (40 mmol) to a solution of 4-nitrobenzene-1,3-diamine (5.56 g, 36.3 mmol), in 50 mL 1,4-dioxane, followed by stirring the solution was room temperature for 16 h. The yellow precipitate was isolated by filtration, washed with 1,4-dioxane (30 mL) and dried in vacuo to give 4-bromo-6-nitro-benzene-1,3-diamine dihydrobromide salt designated on the reaction scheme (CCLXIX) as compound 13 (8 g, 95%).

A mixture of compound 13 (6.0 g, 15.3 mmol) and cyanamide (3.9 g, 92 mmol) was heated to a melt at 90° C. To the melt was cautiously added concentrated HCl (45 mL) and the reaction mixture was stirred at 95° C. for 2 h. It was cooled to room temperature and the reaction mixture was brought to pH 12 with 30% sodium hydroxide (about 65 mL). The mixture was heated to 90° C. for 2 h, cooled to room temperature and poured into water (1L). The yellow precipitate was isolated by filtration, washed with water (100 mL) and acetone (20 mL) and was dried to give 7-bromo-1-oxy-benzo[1,2,4]triazine-3,6-diamine designated on the reaction scheme (CCLXIX) as compound 14 (1.3 g, 33%). To a suspension of the crude product in 140 mL MeOH were added Raney Ni and the mixture was hydrogenated for 2 h. Solids were removed by filtration through a short silica gel column. The solvent was evaporated to give 7-bromo-benzo[1,2,4]triazine-3,6-diamine designated on the reaction scheme (CCLXIX) as compound 15 (1.0 g, 82%). To a solution of compound 15 (1.0 g, 4 mmol) in 60 mL DMA were added 2-methylphenylboronic acid (884 mg, 6.5 mmol) in 16 mL ethanol, $K_2CO_3$ (332 mg, 2.4 mmol) in 6 mL water, $PPh_3$ (262 mg, 1 mmol) and $Pd_2(dba)_3$ (184 mg, 0.2 mmol). The reaction mixture was stirred for 4 h at 100° C. under argon, cooled to room temperature and poured into aqueous saturated $NaHCO_3$ solution (100 mL). The product was extracted with $CH_2Cl_2$ (150 mL) and purified by reverse phase preparative HPLC. The product was washed with saturated aqueous $NaHCO_3$ solution and extracted with EtOAc (100 mL). The combined organic phases were dried ($Na_2SO_4$) and the solvent removed. The crude product was re-crystallized from MeOH to give 7-o-tolyl-benzo[1,2,4]triazine-3,6-diamine designated on the reaction scheme (CCLXIX) as compound 16 (133.7 mg, 13%).

To a solution of compound 16 (80 mg, 0.32 mmol) in 10 mL 1,4-dioxane was added potassium bis(trimethylsilyl)amide (127 mg, 0.64 mmol) and the mixture was stirred at room temperature under argon for 1 h. To the dark red solution was added acetylchloride (45 µl, 0.64 mmol) and stirring was continued for 30 min at room temperature. The product was poured into saturated aqueous $NaHCO_3$ solution (40 mL) and was extracted with EtOAc (100 mL). The combined organic phases were dried ($Na_2SO_4$) and the solvent was evaporated. The crude product was purified by reverse phase preparative HPLC to give a precursor, N-(3-amino-7-o-tolyl-benzo[1,2,4]triazin-6-yl)-acetamide, as trifluoroacetate salt, which was converted to the free base (511 mg, 57%) by washing with saturated aqueous $NaHCO_3$ solution. The final product was synthesized from the purified precursor and 4-bromo-N-(2-pyrrolidin-1-yl-ethyl)-benzenesulfonamide following the above-described coupling procedure. The purification using reverse phase HPLC afforded the title product (CCLXVIII), as a yellow solid (81.7 mg, 68%). $^1$H NMR DMSO-$d_6$: δ 1.87 (m, 2H); 2.01 (m, 2H), 2.02 (s, 3H), 2.11 (s, 3H), 3.04 (m, 2H), 3.07 (td, J=6.1 Hz, J=6.1 Hz, 2H), 3.25 (td, J=6.1 Hz, J=6.1 Hz, 2H), 3.57 (m, 2H), 7.30 (d, J=7.8 Hz, 1H), 7.36-7.44 (m, 3H), 7.85 (m, 1H), 7.86 (d, J=9.0 Hz, 2H), 8.06 (s, 1H), 8.20 (d, J=9.0 Hz, 2H), 8.41 (s, 1H), 8.91 (s, 1H), 9.59 (br s, 1H), 11.27 (s, 1H). MS (ESI+) m/z=546.

Example 207

Synthesis of 4-[6-(3-tert-Butyl-ureido)-7-o-tolyl-benzo[1,2,4]triazin-3-ylamino]-N-(2-pyrrolidin-1-yl-ethyl)-benzenesulfonamide trifluoroacetate

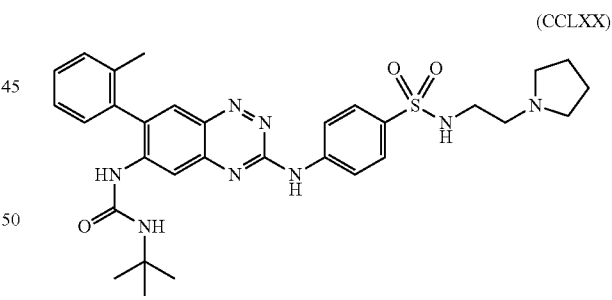

(CCLXX)

To a solution of 7-o-tolyl-benzo[1,2,4]triazine-3,6-diamine (compound 16 on scheme (CCLXIX)) (0.12 mmol, 30 mg) in 5 mL anhydrous 1,4-dioxane was added potassium bis(trimethylsilyl)amide (53 mg, 0.26 mmol) and the mixture was stirred at room temperature under argon for 1.5 h. To the red solution was added tert-butylisocyanate (28.5 µl, 0.36 mmol) and stirring was continued for 2 h at room temperature. The product was poured into saturated aqueous $NaHCO_3$ solution (40 mL) and was extracted with EtOAc (100 mL). The combined organic phases were dried ($Na_2SO_4$) and the solvent was evaporated to give 1-(3-amino-7-o-tolyl-benzo[1,2,4]triazin-6-yl)-3-tert-butyl-urea (28 mg, 67%). The title product was prepared as a red solid (27.8 mg, 48%) from the above intermediate and 4-bromo-N-(2-pyrrolidin-1-yl-ethyl)-benzenesulfonamide following the above-described coupling procedure and was purified by reverse phase preparative HPLC. ¹H NMR DMSO-d₆: δ 1.37 (s, 9H), 1.87 (m, 2H); 2.01 (m, 2H), 2.16 (s, 3H), 3.04 (m, 4H), 3.24 (td, J=6.1 Hz, J=6.1 Hz, 2H), 3.56 (m, 2H), 7.21 (s, 1H), 7.33-7.40 (m, 4H), 7.50 (d, J=9.0 Hz, 2H), 7.75 (d, J=9.0 Hz, 2H), 7.88 (t, J=6.1 Hz, 1H), 7.99 (s, 1H), 8.34 (s, 1H), 8.83 (s, 1H), 9.53 (br s, 1H), 10.21 (s, 1H). MS (ESI+) m/z=603.

Example 208

Synthesis of 4-[7-(5-hydroxymethyl-thiophen-2-yl)-6-methyl-benzo[1,2,4]triazin-3-ylamino]-N-(2-pyrrolidin-1-yl-ethyl)-benzenesulfonamide trifluoroacetate

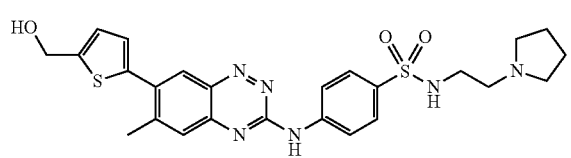

(CCLXXI)

A precursor, [5-(3-amino-6-methyl-benzo[1,2,4]triazin-7-yl)-thiophen-2-yl]-methanol, was prepared from the intermediate compound 101 and 5-hydroxymethylthiophene-2-boronic acid according to the above-described coupling procedure. The final compound was synthesized from the precursor and 4-bromo-N-(2-pyrrolidin-1-yl-ethyl)-benzenesulfonamide according to the above-described coupling procedure. The product was purified by reverse phase preparative HPLC to afford the title product (CCLXXI), as an orange solid. ¹H NMR DMSO-d₆: δ 1.86 (m, 2H); 2.00 (m, 2H), 2.63 (s, 3H), 3.00-3.07 (m, 4H), 3.24 (m, 2H), 3.56 (m, 2H), 4.71 (br s, 2H), 5.60 (m, 1H), 7.07 (d, J=3.5 Hz, 1H), 7.27 (d, 3.5 Hz, 1H), 7.80 (s, 1H), 7.84 (d, J=9.0 Hz, 2H), 7.88 (t, 6.1 Hz, 1H), 8.20 (d, J=9.0 Hz, 2H), 8.30 (s, 1H), 9.60 (br s, 1H), 11.35 (s, 1H). MS (ESI+) m/z=525.

Example 209

Synthesis of 4-[7-(5-cyano-2-methyl-phenyl)-6-methyl-benzo[1,2,4]triazin-3-ylamino]-N-(2-pyrrolidin-1-yl-ethyl)-benzenesulfonamide trifluoroacetate

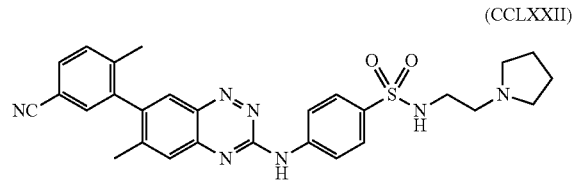 [SMILES: Cc1ccc(C#N)cc1-c1cc2nnc(Nc3ccc(S(=O)(=O)NCCN4CCCC4)cc3)nc2cc1C]

(CCLXXII)

A precursor, 3-(3-amino-6-methyl-benzo[1,2,4]triazin-7-yl)-4-methyl-benzonitrile, was prepared from the intermediate compound 101 and 2-methyl-5-cyanoboronic acid according to the above-described coupling procedure. The crude product was purified by silica gel column chromatography (R_f=0.2, EtOAc/hexanes/NEt₃, 60:40:0.5). The product was synthesized from the precursor and 4-bromo-N-(2-pyrrolidin-1-yl-ethyl)-benzenesulfonamide according to the above-described coupling procedure. The product was purified by reverse phase preparative HPLC to afford the title product (CCLXXII), as an orange solid (42 mg, 50%). ¹H NMR DMSO-d₆: δ 1.87 (m, 2H); 2.01 (m, 2H), 2.15 (s, 3H), 2.21 (s, 3H), 3.00-3.08 (m, 4H), 3.25 (td, J=6.1 Hz, J=6.1 Hz, 2H), 3.57 (m, 2H), 7.62 (d, J=8.0 Hz, 1H), 7.75 (s, 1H), 7.82-7.88 (m, 4H), 8.15 (s, 1H), 8.21 (d, J=9.0 Hz, 2H), 9.54 (br s, 1H), 11.34 (s, 1H). MS (ESI+) m/z=528

Example 210

Synthesis of 4-chloro-3-[5-methyl-3-(4-pyrrolidin-1-yl-butylamino)-benzo[1,2,4]triazin-7-yl]-phenol trifluoroacetate salt

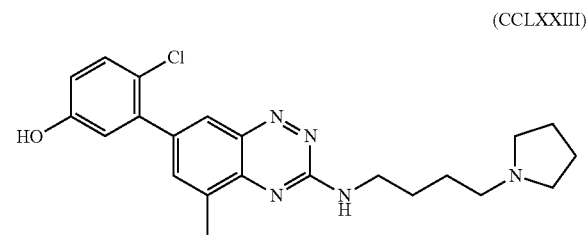 [SMILES: Cc1cc(-c2cc(O)ccc2Cl)cc2nnc(NCCCCN3CCCC3)nc12]

(CCLXXIII)

A suspension of 7-(2-chloro-5-methoxy-phenyl)-5-methyl-benzo[1,2,4]triazin-3-ylamine (80 mg, 0.27 mmol) and sulfamic acid (66 mg, 0.68 mmol) in 3 mL 4-pyrrolidinobutyl amine was stirred at 200° C. for 16 h. The mixture was diluted with EtOAc (5 mL) and purified by silica gel column chromatography (R_f=0.22, CH₂Cl₂/MeOH/NEt₃, 90:10:0.1) (40 mg, 35%). The purified intermediate (40 mg, 0.094 mmol) was treated with BBr₃ (80.3 μl, 0.47 mmol) at room temperature for 2 h and was poured into saturated aqueous sodium thiosulphate. The product was extracted with 20 mL CH₂Cl₂/methanol (90:10). The combined organic phases were dried (Na₂SO₄), and the solvent was evaporated. The crude product was purified by reverse phase preparative HPLC to afford the title product (CCLXXIII), as a red solid (43 mg, 87%). ¹H NMR DMSO-d₆: δ 1.68-1.79 (m, 4H), 1.87 (m, 2H); 2.00 (m, 1H), 2.09 (m, 1H), 2.56 (s, 3H), 2.97-3.03 (m, 2H), 3.18 (m, 2H), 3.40-3.55 (m, 4H), 6.85 (dd, J=8.6 Hz, J=2.9 Hz, 1H), 6.89 (d, J=2.9 Hz, 1H), 7:38 (d, J=8.6 Hz, 1H), 7.73 (s, 1H), 8.02 (s, 1H), 8.60 (br s, 1H), 9.50 (br s, 1H), 9.92 (br s, 1H). MS (ESI+) m/z=412.

Example 211

Synthesis of 4-[7-(3-hydroxy-piperidin-1-yl)-6-methyl-benzo[1,2,4]triazin-3-ylamino]-N-(2-pyrrolidin-1-yl-ethyl)-benzenesulfonamide trifluoroacetate

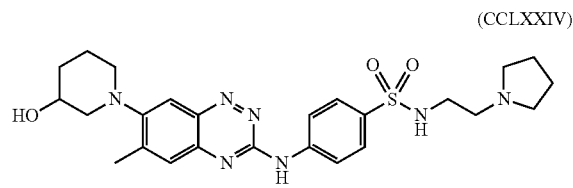 [SMILES: Cc1cc2nc(Nc3ccc(S(=O)(=O)NCCN4CCCC4)cc3)nnc2cc1N1CCCC(O)C1]

(CCLXXIV)

To a solution of 4-(7-bromo-6-methyl-benzo[1,2,4]triazin-3-ylamino)-N-(2-pyrrolidin-1-yl-ethyl)-benzenesulfonamide (71 mg, 0.145 mmol) in 2 mL anhydrous xylene were added piperidin-3-ol hydrochloride (80 mg, 0.58 mmol), xantphos (34 mg, 0.058 mmol), Pd(OAc)$_2$ (7 mg, 0.029 mmol) and KOtBu (98 mg, 0.87 mmol). The reaction mixture was heated in a microwave at 150° C. for 20 min and poured into aqueous saturated NaHCO$_3$ solution. The product was extracted with CH$_2$Cl$_2$ (50 mL) and purified by reverse phase preparative HPLC to afford the title product (CCLXIV), as a brown solid (7.5 mg, 8.3%). $^1$H NMR DMSO-d$_6$: δ 1.86 (m, 4H); 2.00 (m, 4H), 2.50 (s, 3H), 3.00-3.08 (m, 4H), 3.20-3.30 (m, 4H), 3.55 (m, 4H), 4.90 (m, 1H), 7.67 (s, 1H), 7.73 (s, 1H), 7.80 (d, J=8.9 Hz, 2H), 8.15 (d, J=8.9 Hz, 2H), 9.50 (br s, 2H), 11.06 (s, 1H). MS (ESI+) m/z=512.

Example 212

Synthesis of 4-chloro-3-{6-chloro-3-[4-(2-pyrrolidin-1-yl-ethoxy)-phenylamino]-benzo[1,2,4]triazin-7-yl}-phenol (CCLXXV)

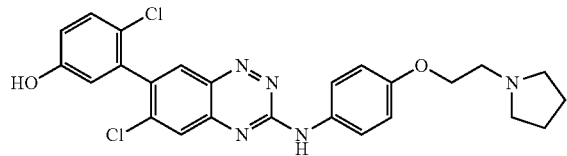

As a preliminary step, the synthesis of the title product included a process shown by the reaction scheme (CCLXXVI).

(CCLXXVI)

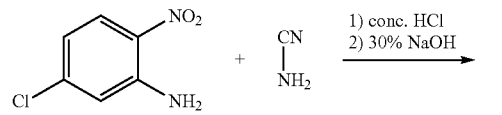

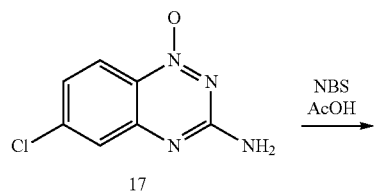

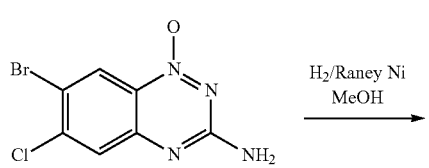

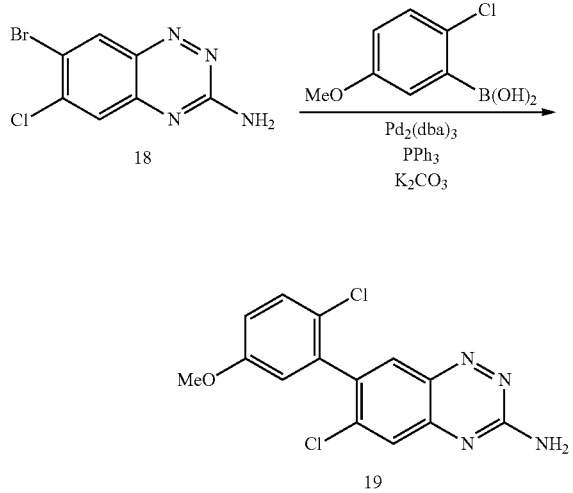

To a melt of 5-chloro-2-nitroaniline (5 g, 29 mmol) and cyanamide (9.8 g, 231 mmol) at 100° C. was cautiously added concentrated HCl (50 mL) and the mixture was stirred at 100° C. for 2.5 h. The reaction mixture was cooled to room temperature and the pH was adjusted to pH 11 using 30% aqueous NaOH. The reaction mixture was stirred at 100° C. for 2 h, cooled to room temperature and poured into water (200 mL). The yellow precipitate was isolated by filtration, washed with CH$_2$Cl$_2$ (20 mL) and dried to give 6-chloro-1-oxy-benzo[1,2,4]triazin-3-ylamine, designated on the reaction scheme (CCLXXVI) as compound 17 (3.42 g, 60%). To a solution of compound 17 (983 mg, 5 mmol) in 30 mL glacial acetic acid was added NBS (1.78 g, 10 mmol) and the mixture was heated to reflux for 4 h. It was cooled to room temperature and poured into water (700 mL). The yellow precipitate was isolated by filtration and was hydrogenated in MeOH (100 mL) for 2 h using Raney Ni (1.0 g). Solids were removed by filtration and the solvent was evaporated. The crude product was purified by silica gel column chromatography using EtOAc as the mobile phase to give 7-bromo-6-chloro-benzo[1,2,4]triazin-3-ylamine, designated on the reaction scheme (CCLXXVI) as compound 18 (95.6 mg, 7.4%).

6-chloro-7-(2-chloro-5-methoxy-phenyl)benzo[1,2,4]triazin-3-ylamine designated on the reaction scheme (CCLXXVI) as compound 19 (54 mg, 68%) was prepared from compound 18 and 2-chloro-5-methoxyphenylboronic acid according to the above-described coupling procedure. The crude product was purified by silica gel column chromatography (R$_f$=0.41, EtOAc/hexanes 50:50). The title compound (CCLXXV) was prepared from compound 19 and 1-[2-(4-bromo-phenoxy)-ethyl]-pyrrolidine following the above-described coupling procedure, followed by demethylation. The coupling product was purified by reverse phase preparative HPLC to give [6-chloro-7-(2-chloro-5-methoxy-phenyl)-benzo[1,2,4]triazin-3-yl]-[4-(2-pyrrolidin-1-yl-ethoxy)-phenyl]-amine (28.7 mg, 27%). Deprotection of the methoxy group with BBr$_3$ (22 μl, 0.23 mmol) in 2 mL CH$_2$Cl$_2$ at room temperature yielded 4-chloro-3-{6-chloro-3-[4-(2-pyrrolidin-1-yl-ethoxy)-phenylamino]-benzo[1,2,4]triazin-7-yl}-phenol, which was purified by reverse phase preparative HPLC and converted to the free amine to give a brown solid (13 mg, 57%). $^1$H NMR DMSO-d$_6$: δ 1.68 (m, 4H), 2.50-2.55 (m, 4H), 2.79 (t, J=5.9 Hz, 2H), 4.07 (t, J=5.9, 2H), 7.07 (d, J=9.0 Hz, 1H), 6.77 (d, J=2.8, 1H), 6.84 (dd, J=8.8

Hz, J=2.8 Hz, 1H), 6.98 (d, J=9.0 Hz, 2H), 7.32 (d, J=8.8, 1H), 7.85 (d, J=9.0 Hz, 2H), 7.90 (s, 1H), 8.22 (s, 1H), 10.90 (br s, 1H). MS (ESI+) m/z=496.

Example 213

Synthesis of 4-[7-(5-cyano-2-methyl-phenyl)-5-methyl-benzo[1,2,4]triazin-3-ylamino]-N-(2-pyrrolidin-1-yl-ethyl)-benzenesulfonamide trifluoroacetate (CCLXXVII)

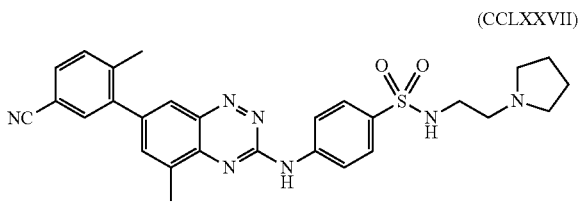 [SMILES: Cc1ccc(C#N)cc1-c1cc(C)c2nc(Nc3ccc(S(=O)(=O)NCCN4CCCC4)cc3)nnc2c1]

3-(3-amino-5-methyl-benzo[1,2,4]triazin-7-yl)-4-methyl-benzonitrile was prepared from the intermediate compound 100 and 2-methyl-3-cyanophenylboronic acid according to the above-described coupling procedure. The crude product was purified by silica gel column chromatography ($R_f$=0.35, EtOAc/hexanes, 50:50) (72.4 mg, 77%). The product was purified and reacted with 4-bromo-N-(2-pyrrolidin-1-yl-ethyl)-benzenesulfonamide following the above-described coupling procedure. The crude product was purified by reverse phase preparative HPLC to afford the title product (CCLXXVII), as a yellow solid (30 mg, 18%). $^1$H NMR DMSO-$d_6$: δ 1.87 (m, 2H); 2.01 (m, 2H), 2.41 (s, 3H), 2.72 (s, 3H), 3.04 (m, 2H), 3.07 (td, J=6.2 Hz, J=6.2 Hz, 2H), 3.25 (td, J=6.2 Hz, J=6.2 Hz, 2H), 3.57 (m, 2H), 7.61 (d, J=8.2 Hz, 1H), 7.81-7.87 (m, 2H), 7.88 (d, J=8.9 Hz, 2H), 7.94 (br s, 1H), 8.26 (d, J=8.9 Hz, 2H), 8.27 (br s, 1H), 9.63 (br s, 1H), 11.46 (s, 1H). MS (ESI+) m/z=528.

Example 214

Synthesis of {4-[7-(2-chloro-5-hydroxy-phenyl)-5-methyl-benzo[1,2,4]triazin-3-ylamino]-phenyl}-(1,1-dioxo-1l6-thiomorpholin-4-yl)-methanone (CCLXXVIII)

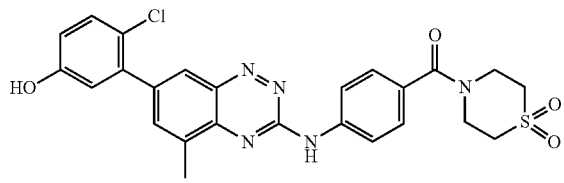

To prepare the title compound, the intermediate compound 109 ((4-bromo-phenyl)-(1,1-dioxo-1l6-thiomorpholin-4-yl)-methanone) shown below was synthesized first.

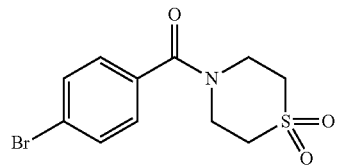

To prepare the intermediate compound 109, a solution of 4-bromo-benzoic acid (2.0 g, 10.0 mmol) in 20 mL acetonitrile were added thiomorpholine (950 μl, 10 mmol) and EDC (1.92 g, 10 mmol). The reaction mixture was stirred at room temperature for 16 h. The solvent was removed and the residue was dissolved in 60 mL CH$_2$Cl$_2$ and washed with aqueous saturated NaHCO$_3$ solution (100 mL). The organic phase was dried (Na$_2$SO$_4$) and the solvent was removed. The crude product was purified by flash column chromatography ($R_f$=0.45, EtOAc/hexanes, 50:50). To a solution of the above intermediate (100 mg, 0.35 mmol) in CH$_2$Cl$_2$ (30 mL) were added mCPBA (79 mg, 0.35 mmol) at 0° C. The mixture was stirred for 2 h before another batch of mCPBA (79 mg, 0.35 mmol) was added. The mixture was stirred at RT for 16 h and was then quenched with aqueous saturated NaHCO$_3$ solution (100 mL). The intermediate compound 109 was extracted with CH$_2$Cl$_2$ (100 mL) and used without further purification (105 mg, 94%). $^1$H NMR DMSO-$d^6$: δ 3.24 (m, 4H), 3.67 (m, 2H), 3.99 (m, 2H), 7.46 (d, J=8.2 Hz, 2H), 7.68 (d, J=8.2 Hz, 2H). MS (ESI+) m/z=182/184.

A mixture of 7-(2-chloro-5-methoxy-phenyl)-5-methyl-benzo[1,2,4]triazin-3-ylamine (50 mg, 0.17 mmol), intermediate compound 109 (80 mg, 0.25 mmol), Xantphos (20 mg, 0.0334 mmol), Pd$_2$(dba)$_3$ (16 mg, 0.0167 mmol) and Cs$_2$CO$_3$ (109 mg, 0.334 mmol) in anhydrous dioxane (4 mL) was refluxed for 4 h under argon. The reaction mixture was cooled to room temperature, diluted with CH$_2$Cl$_2$ (20 mL) and filtered. The crude product was purified by flash column chromatography to give {4-[7-(2-chloro-5-methoxy-phenyl)-5-methyl-benzo[1,2,4]triazin-3-ylamino}-phenyl]-(1,1-dioxo-1l6-thiomorpholin-4-yl)-methanone, an amount of which (54 mg, 0.1 mmol) in CH$_2$Cl$_2$ (8 mL) was treated with a 1.0 M solution of BBr$_3$ in CH$_2$Cl$_2$ (500 μl, 0.5 mmol) at 0° C. to give {4-[7-(2-chloro-5-hydroxy-phenyl)-5-methyl-benzo[1,2,4]triazin-3-ylamino]-phenyl}-(1,1-dioxo-1l6-thiomorpholin-4-yl)-methanone. The crude product was purified by reverse phase preparative HPLC to afford the title compound (CCLXXVIII), as a yellow powder (15.7 mg, 30%). $^1$H NMR DMSO-$d_6$: δ 2.70 (s, 3H), 3.26-3.30 (m, 4H), 3.90 (m, 4H), 6.88 (dd, J=8.7 Hz, J=2.9 Hz, 1H), 6.93 (d, J=2.9 Hz, 1H), 7.41 (d, J=8.7 Hz, 1H), 7.58 (d, J=8.7 Hz, 2H), 7.89 (br s, 1H), 8.12 (d, J=8.7 Hz, 2H), 8.19 (br s, 1H), 9.93 (s, 1H), 11.22 (s, 1H). MS (ESI+) m/z=524.

Example 215

Synthesis of [7-(2,6-dichloro-phenyl)-5-methyl-benzo[1,2,4]triazin-3-yl]-[4-(3-pyrrolidin-1-yl-propane-1-sulfonyl)-phenyl]-amine (CCLXXIX)

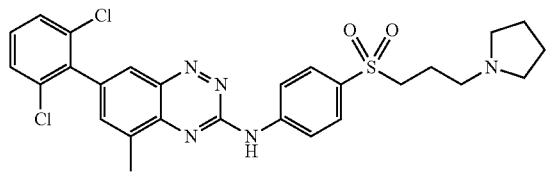

The title compound was prepared from 7-(2,6-dichlorophenyl)-5-methyl-benzo[1,2,4]triazin-3-ylamine and the intermediate compound 109 following the above-described coupling procedure, followed by purification by reverse phase preparative HPLC, to afford a yellow solid (62 mg, 31%). $^1$H NMR DMSO-$d_6$: δ 1.84 (m, 2H), 1.99 (m, 4H), 2.72 (s, 3H), 2.95 (m, 2H), 3.20 (m, 2H), 3.40-3.53 (m, 4H), 7.53 (t, J=8.2 Hz, 1H), 7.68 (d, J=8.2 Hz, 1H), 7.80 (br s, 1H), 7.95 (d, J=8.9 Hz, 2H), 8.20 (br s, 1H), 8.31 (d, J=8.9 Hz, 2H), 10.25 (br s, 1H), 11.57 (s, 1H). MS (ESI+) m/z=556.

Example 216

Synthesis of 4-[7-(2-chloro-6-fluoro-5-hydroxyphenyl)-5-methyl-benzo[1,2,4]triazin-3-ylamino]-N-methyl-N-(2-pyrrolidine-1-yl-ethyl)benzenesulfonamide (CCLXXX)

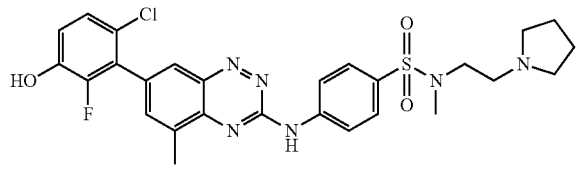

Standard Buchwald conditions were used, followed by demethylation using BBr3. Yellow solid (17 mg, 18%). $^1$H NMR (DMSO-$d_6$): δ 1.85-1.95 (m, 2H), 1.97-2.09 (m, 2H), 2.72, 2.73 (2s, 3H each), 3.05-3.15 (m, 2H), 3.25-3.3, 3.37-3.45, 3.6-3.68 (3m, 2H each), 7.08 (t, J=8.97 Hz, 1H), 7.29 (dd, J=1.5 and 9.0 Hz, 1H), 7.85 (s, 1H), 7.88 (d, J=9.0 Hz, 2H), 8.24 (d, J=1.5 Hz, 1H), 8.31 (d, J=9.0 Hz, 2H), 9.55 (br s, 1H), 10.40 (s, 1H), 11.5 (s, 1H). MS (ESI+): m/z=446.1.

Example 217

Testing of Inhibition of Kinases In Vitro

The ability of compounds of the present invention to inhibit the activity of three groups of kinases was tested. Kinases tested included the src family (primarily src and yes), some angiogenic growth factor receptors (Fgfr1, Vegfr, and Pdgfrβ) and the ephrin, EphB4. All kinase reactions were conducted in 96-well plates with a final reaction volume of 50 ul.

Src Family

Recombinant human c-Src or Yes (28 ng/well, Panvera/Invitrogen, Madison Wis.), ATP (3 μM), a tyrosine kinase substrate (PTK2, 250 μM, Promega Corp., Madison Wis.), and test agents (at concentrations ranging from about 1 nM/l to about 100 μM/l), in the presence of Src kinase reaction buffer (Upstate USA, Lake Placid N.Y.). After reacting for about 90 minutes at room temperature, residual ATP was determined using a luciferase-based assay (KinaseGlo, Promega Corp.) as a measure of kinase activity. Data from four wells were then averaged and used to determine IC$_{50}$ values for the test compounds (Prism software package, GraphPad Software, San Diego Calif.).

Growth Factor Receptors

Pdgfrβ (0.16 ug/well, Panvera/Invitrogen) 500 nM ATP and the PTK2 peptide (700 uM) were combined with compound and reaction buffer as noted above for src. The reaction was incubated for 60 minutes at 37 C, and the residual ATP concentration was determined using the luciferase-based technique also noted above.

FGFR1 and VEGFR2 kinase assays were similarly performed. FGFR1 (76 ng/well, Panvera/Invitrogen) was combined with 12.5 mg/ml poly(glu4tyr) (Sigma) and 2.5 uM ATP. VEGFR2 (14.1 U/well, Cell Signaling/ProQinase) was used with 0.3 mg/ml poly(glu4tyr) and 1.5 uM ATP. Both were incubated for 60 minutes at 37 C, and the residual ATP was measured via luminescence, per the procedure described above.

EphB4

EphB4 kinase activity was similarly measured, using the luciferase-based technique described above. 28.9 mU/well EphB4 (Upstate) was reacted with 1 mg/ml poly(glu4tyr), 6 uM ATP and test reagents. The reaction was incubated for 60 minutes at 37 C and the residual ATP concentration was measured.

The test results for inhibition of Src kinase are presented in Table 1, and the test results for inhibition of some other kinases (i.e., Yes, EphB4, and Pdgfrβ) are presented in Table 2. The abbreviation "IC$_{50}$" means that a particular compound of the invention, when present at the specified concentration, inhibited the kinase by 50%.

TABLE 1

Tests Results of Inhibition of Src Kinase by Some Compounds of the Invention

| Structure | Name | Src IC50 (nM) |
|---|---|---|
| 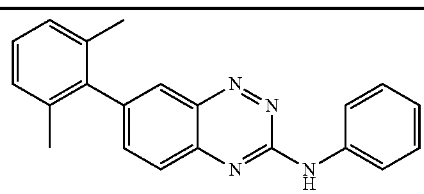 | [7-(2,6-dimethyl-phenyl)-benzo[1,2,4]triazin-3-yl]-phenyl-amine | 1520 |
| 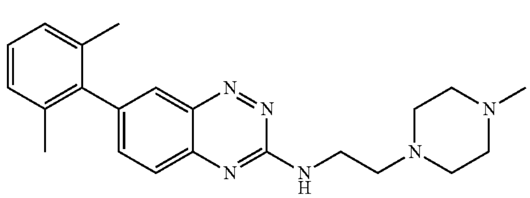 [SMILES: Cc1cccc(C)c1-c1ccc2nc(NCCN3CCN(C)CC3)nnc2c1] | [7-(2,6-dimethyl-phenyl)-benzo[1,2,4]triazin-3-yl]-[3-(4-methyl-piperazin-1-yl)-propyl]-amine | 5800 |

TABLE 1-continued

Tests Results of Inhibition of Src Kinase by Some Compounds of the Invention

| Structure | Name | Src IC50 (nM) |
|---|---|---|
| 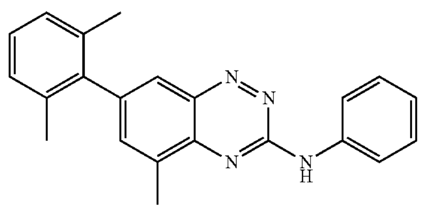 | [7-(2,6-dimethyl-phenyl)-5-methyl-benzo[1,2,4]triazin-3-yl]-phenyl-amine | 294 |
| 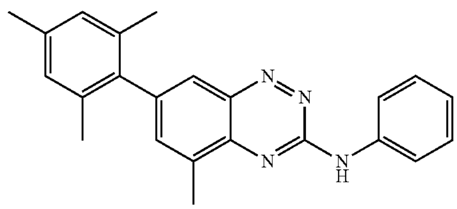 [SMILES: Cc1cc(C)c(-c2cc(C)c3nc(Nc4ccccc4)nnc3c2)c(C)c1] | [5-methyl-7-(2,4,6-trimethyl-phenyl)-benzo[1,2,4]triazin-3-yl]-phenyl-amine | >10000 |
| 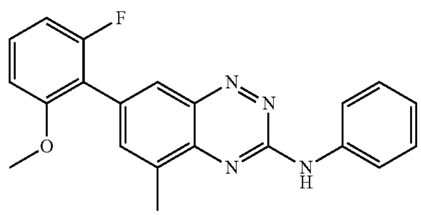 [SMILES: COc1cccc(F)c1-c1cc(C)c2nc(Nc3ccccc3)nnc2c1] | [7-(2-fluoro-6-methoxy-phenyl)-5-methyl-benzo[1,2,4]triazin-3-yl]-phenyl-amine | >10000 |
| 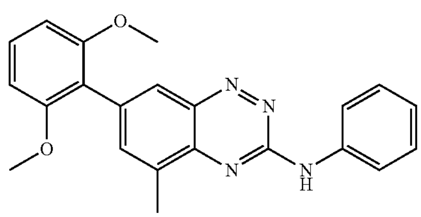 [SMILES: COc1cccc(OC)c1-c1cc(C)c2nc(Nc3ccccc3)nnc2c1] | [7-(2,6-dimethoxy-phenyl)-5-methyl-benzo[1,2,4]triazin-3-yl]-phenyl-amine | >10000 |
| 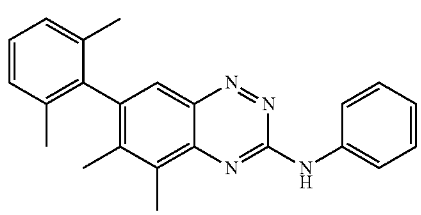 [SMILES: Cc1cccc(C)c1-c1cc2nnc(Nc3ccccc3)nc2c(C)c1C] | [7-(2,6-dimethyl-phenyl)-5,6-dimethyl-benzo[1,2,4]triazin-3-yl]-phenyl-amine | 130 |
| 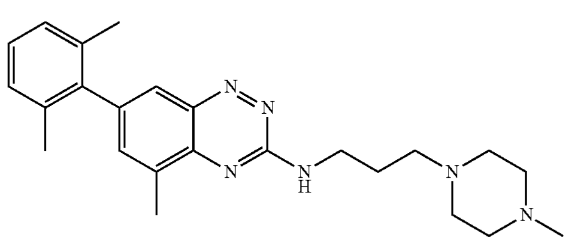 [SMILES: Cc1cccc(C)c1-c1cc(C)c2nc(NCCCN3CCN(C)CC3)nnc2c1] | [7-(2,6-dimethyl-phenyl)-5-methyl-benzo[1,2,4]triazin-3-yl]-[3-(4-methyl-piperazin-1-yl)-propyl]-amine | 9000 |

TABLE 1-continued

Tests Results of Inhibition of Src Kinase by Some Compounds of the Invention

| Structure | Name | Src IC50 (nM) |
|---|---|---|
| | [7-(2,6-dimethyl-phenyl)-5-methyl-benzo[1,2,4]triazin-3-yl]-[4-(2-pyrrolidin-1-yl-ethoxy)-phenyl]-amine | 6.8 |
| 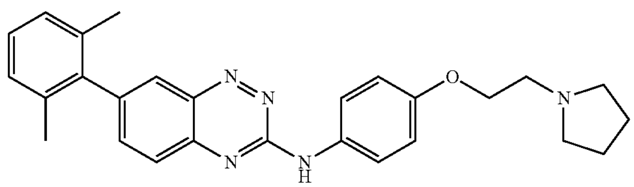 [SMILES: Cc1cccc(C)c1-c1ccc2nc(Nc3ccc(OCCN4CCCC4)cc3)nnc2c1] | [7-(2,6-dimethyl-phenyl)-benzo[1,2,4]triazin-3-yl]-[4-(2-pyrrolidin-1-yl-ethoxy)-phenyl]-amine | 15.0 |
| 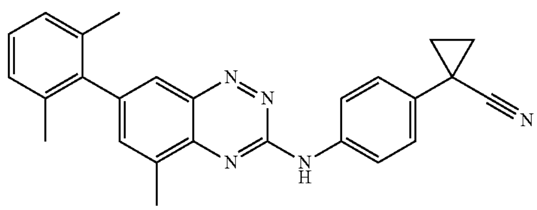 [SMILES: Cc1cccc(C)c1-c1cc(C)c2nc(Nc3ccc(C4(C#N)CC4)cc3)nnc2c1] | 1-{4-[7-(2,6-dimethyl-phenyl)-5-methyl-benzo[1,2,4]triazin-3-ylamino]-phenyl}-cyclopropanecarbonitrile | 72 |
| 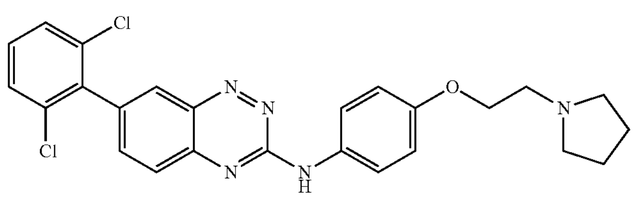 [SMILES: Clc1cccc(Cl)c1-c1ccc2nc(Nc3ccc(OCCN4CCCC4)cc3)nnc2c1] | [7-(2,6-dichloro-phenyl)-benzo[1,2,4]triazin-3-yl]-[4-(2-pyrrolidin-1-yl-ethoxy)-phenyl]-amine | 121 |
| 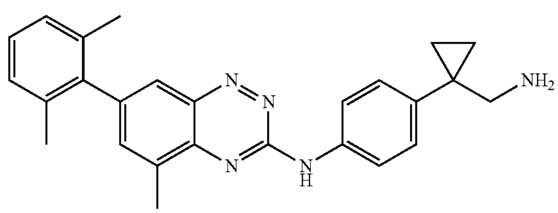 [SMILES: Cc1cccc(C)c1-c1cc(C)c2nc(Nc3ccc(C4(CN)CC4)cc3)nnc2c1] | [4-(1-aminomethyl-cyclopropyl)-phenyl]-[7-(2,6-dimethyl-phenyl)-5-methyl-benzo[1,2,4]triazin-3-yl]-amine | 76.4 |
| 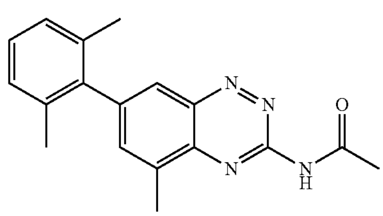 [SMILES: CC(=O)Nc1nnc2cc(-c3c(C)cccc3C)cc(C)c2n1] | N-[7-(2,6-dimethyl-phenyl)-5-methyl-benzo[1,2,4]triazin-3-yl]-acetamide | >10000 |
| 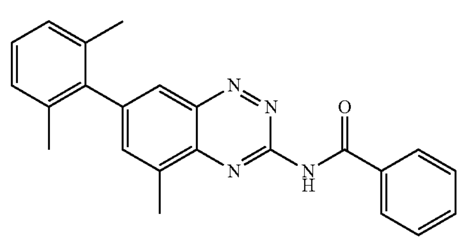 [SMILES: Cc1cccc(C)c1-c1cc(C)c2nc(NC(=O)c3ccccc3)nnc2c1] | N-[7-(2,6-dimethyl-phenyl)-5-methyl-benzo[1,2,4]triazin-3-yl]-benzamide | 1800 |

TABLE 1-continued

Tests Results of Inhibition of Src Kinase by Some Compounds of the Invention

| Structure | Name | Src IC50 (nM) |
|---|---|---|
| 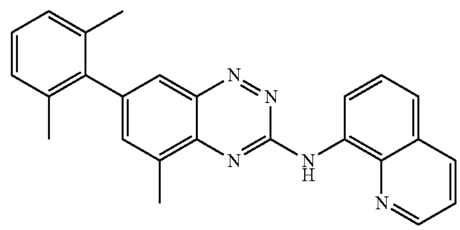 [SMILES: Cc1cccc(C)c1-c1cc(C)c2nc(Nc3cccc4cccnc34)nnc2c1] | [7-(2,6-dimethyl-phenyl)-5-methyl-benzo[1,2,4]triazin-3-yl]-quinolin-8-yl-amine | >10000 |
| 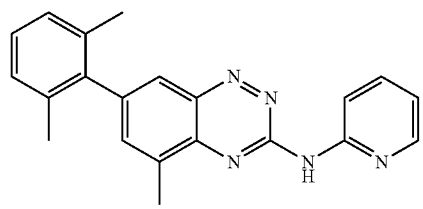 [SMILES: Cc1cccc(C)c1-c1cc(C)c2nc(Nc3ccccn3)nnc2c1] | [7-(2,6-dimethyl-phenyl)-5-methyl-benzo[1,2,4]triazin-3-yl]-pyridin-2-yl-amine | >10000 |
| 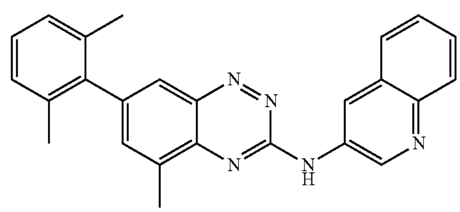 [SMILES: Cc1cccc(C)c1-c1cc(C)c2nc(Nc3cnc4ccccc4c3)nnc2c1] | [7-(2,6-dimethyl-phenyl)-5-methyl-benzo[1,2,4]triazin-3-yl]-quinolin-3-yl-amine | >10000 |
| 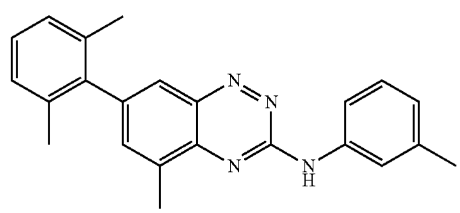 [SMILES: Cc1cccc(Nc2nnc3cc(-c4c(C)cccc4C)cc(C)c3n2)c1] | [7-(2,6-dimethyl-phenyl)-5-methyl-benzo[1,2,4]triazin-3-yl]-m-tolyl-amine | 178 |
| 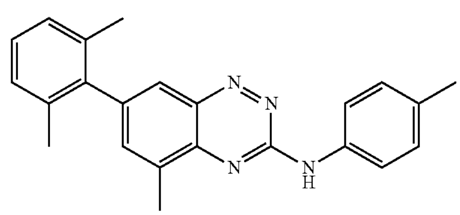 [SMILES: Cc1ccc(Nc2nnc3cc(-c4c(C)cccc4C)cc(C)c3n2)cc1] | [7-(2,6-dimethyl-phenyl)-5-methyl-benzo[1,2,4]triazin-3-yl]-p-tolyl-amine | >10000 |
| 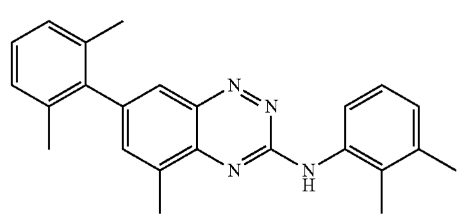 [SMILES: Cc1cccc(Nc2nnc3cc(-c4c(C)cccc4C)cc(C)c3n2)c1C] | (2,3-dimethyl-phenyl)-[7-(2,6-dimethyl-phenyl)-5-methyl-benzo[1,2,4]triazin-3-yl]-amine | >10000 |
| 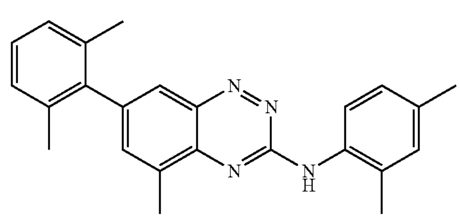 [SMILES: Cc1ccc(Nc2nnc3cc(-c4c(C)cccc4C)cc(C)c3n2)c(C)c1] | (2,4-dimethyl-phenyl)-[7-(2,6-dimethyl-phenyl)-5-methyl-benzo[1,2,4]triazin-3-yl]-amine | >10000 |

TABLE 1-continued

Tests Results of Inhibition of Src Kinase by Some Compounds of the Invention

| Structure | Name | Src IC50 (nM) |
|---|---|---|
| 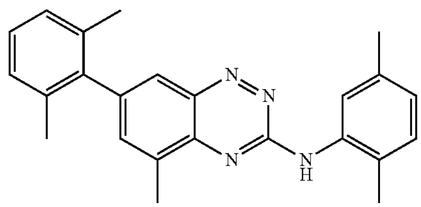 [SMILES: Cc1ccc(C)c(Nc2nnc3cc(-c4c(C)cccc4C)cc(C)c3n2)c1] | (2,5-dimethyl-phenyl)-[7-(2,6-dimethyl-phenyl)-5-methyl-benzo[1,2,4]triazin-3-yl]-amine | >10000 |
| 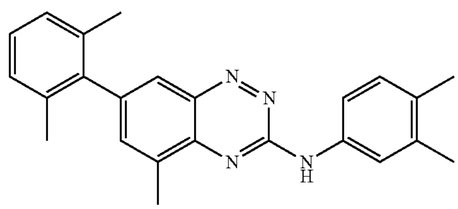 [SMILES: Cc1ccc(Nc2nnc3cc(-c4c(C)cccc4C)cc(C)c3n2)cc1C] | (3,4-dimethyl-phenyl)-[7-(2,6-dimethyl-phenyl)-5-methyl-benzo[1,2,4]triazin-3-yl]-amine | 957 |
| 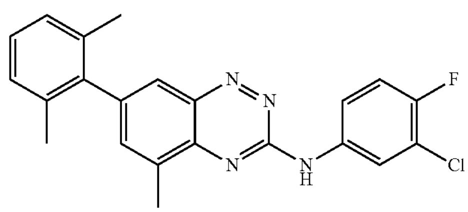 [SMILES: Cc1cccc(C)c1-c1cc(C)c2nc(Nc3ccc(F)c(Cl)c3)nnc2c1] | (3-chloro-4-fluoro-phenyl)-[7-(2,6-dimethyl-phenyl)-5-methyl-benzo[1,2,4]triazin-3-yl]-amine | >10000 |
| 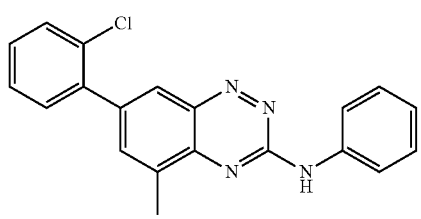 [SMILES: Cc1cc(-c2ccccc2Cl)cc2nnc(Nc3ccccc3)nc12] | [7-(2-chloro-phenyl)-5-methyl-benzo[1,2,4]triazin-3-yl]-phenyl-amine | >100000 |
| 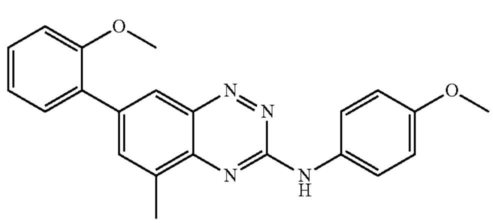 [SMILES: COc1ccc(Nc2nnc3cc(-c4ccccc4OC)cc(C)c3n2)cc1] | (4-methoxy-phenyl)-[7-(2-methoxy-phenyl)-5-methyl-benzo[1,2,4]triazin-3-yl]-amine | >100000 |
| 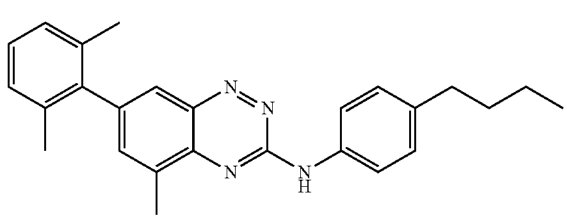 [SMILES: CCCCc1ccc(Nc2nnc3cc(-c4c(C)cccc4C)cc(C)c3n2)cc1] | (4-butyl-phenyl)-[7-(2,6-dimethyl-phenyl)-5-methyl-benzo[1,2,4]triazin-3-yl]-amine | >100000 |

TABLE 1-continued

Tests Results of Inhibition of Src Kinase by Some Compounds of the Invention

| Structure | Name | Src IC50 (nM) |
|---|---|---|
| 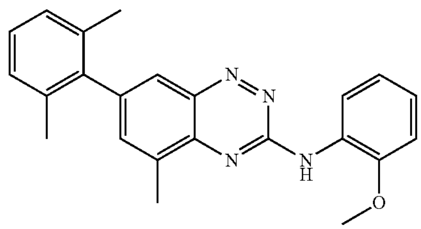 [SMILES: COc1ccccc1Nc1nnc2cc(-c3c(C)cccc3C)cc(C)c2n1] | (2-methoxy-phenyl)-[7-(2,6-dimethyl-phenyl)-5-methyl-benzo[1,2,4]triazin-3-yl]-amine | >100000 |
| 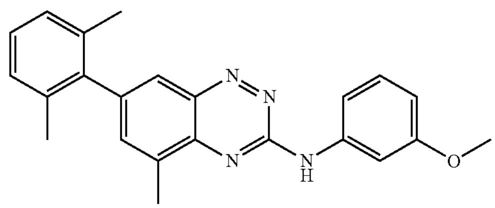 [SMILES: COc1cccc(Nc2nnc3cc(-c4c(C)cccc4C)cc(C)c3n2)c1] | (3-methoxy-phenyl)-[7-(2,6-dimethyl-phenyl)-5-methyl-benzo[1,2,4]triazin-3-yl]-amine | >100000 |
| 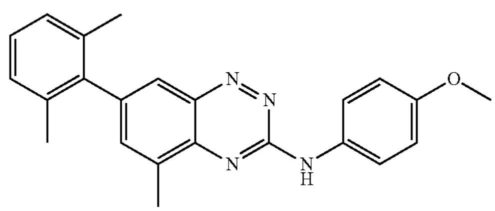 | (4-methoxy-phenyl)-[7-(2,6-dimethyl-phenyl)-5-methyl-benzo[1,2,4]triazin-3-yl]-amine | 140 |
| 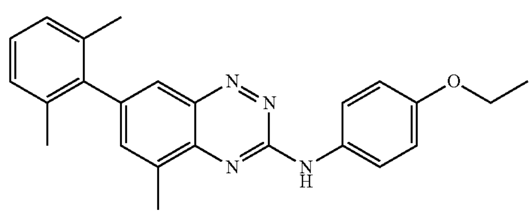 [SMILES: CCOc1ccc(Nc2nnc3cc(-c4c(C)cccc4C)cc(C)c3n2)cc1] | (4-ethoxy-phenyl)-[7-(2,6-dimethyl-phenyl)-5-methyl-benzo[1,2,4]triazin-3-yl]-amine | 108 |
| 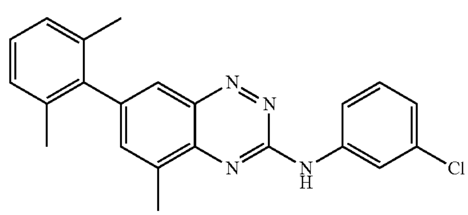 | (3-chloro-phenyl)-[7-(2,6-dimethyl-phenyl)-5-methyl-benzo[1,2,4]triazin-3-yl]-amine | 134 |
| 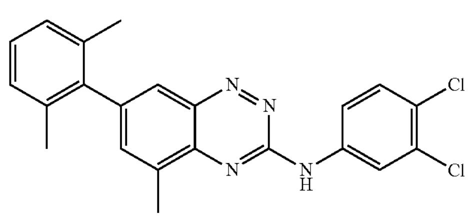 [SMILES: Cc1cccc(C)c1-c1cc(C)c2nc(Nc3ccc(Cl)c(Cl)c3)nnc2c1] | (3,4-dichloro-phenyl)-[7-(2,6-dimethyl-phenyl)-5-methyl-benzo[1,2,4]triazin-3-yl]-amine | >100000 |

TABLE 1-continued

Tests Results of Inhibition of Src Kinase by Some Compounds of the Invention

| Structure | Name | Src IC50 (nM) |
|---|---|---|
| 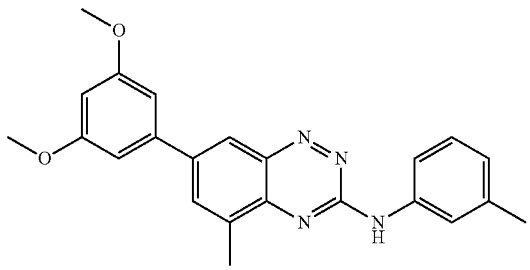 | [7-(3,5-dimethoxy-phenyl)-5-methyl-benzo[1,2,4]triazin-3-yl]-m-tolyl-amine | >100000 |
| 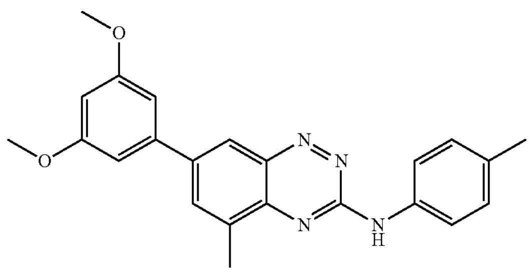 | [7-(3,5-dimethoxy-phenyl)-5-methyl-benzo[1,2,4]triazin-3-yl]-p-tolyl-amine | >100000 |
| 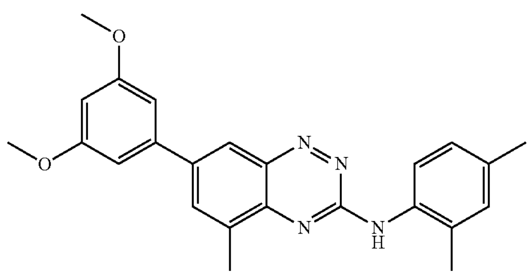 | [7-(3,5-dimethoxy-phenyl)-5-methyl-benzo[1,2,4]triazin-3-yl]-(2,4-dimethyl-phenyl)-amine | >100000 |
| 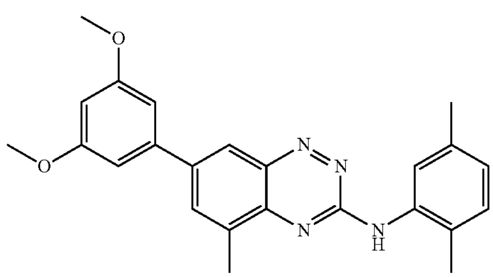 [SMILES: COc1cc(OC)cc(-c2cc(C)c3nc(Nc4cc(C)ccc4C)nnc3c2)c1] | [7-(3,5-dimethoxy-phenyl)-5-methyl-benzo[1,2,4]triazin-3-yl]-(2,5-dimethyl-phenyl)-amine | >100000 |
| 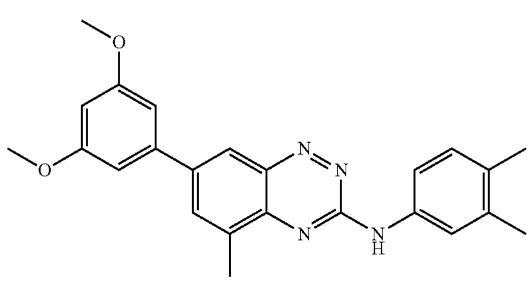 | [7-(3,5-dimethoxy-phenyl)-5-methyl-benzo[1,2,4]triazin-3-yl]-(3,4-dimethyl-phenyl)-amine | >100000 |

TABLE 1-continued

Tests Results of Inhibition of Src Kinase by Some Compounds of the Invention

| Structure | Name | Src IC50 (nM) |
|---|---|---|
| 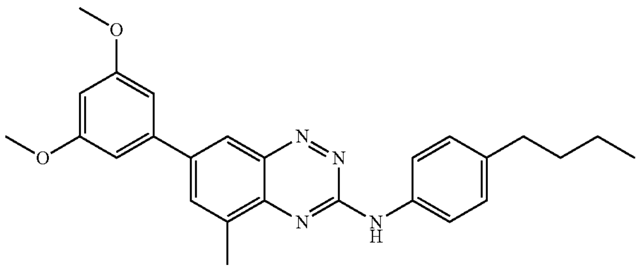 [SMILES: CCCCc1ccc(Nc2nnc3cc(-c4cc(OC)cc(OC)c4)cc(C)c3n2)cc1] | (4-butyl-phenyl)-[7-(3,5-dimethoxy-phenyl)-5-methyl-benzo[1,2,4]triazin-3-yl]-amine | >100000 |
| 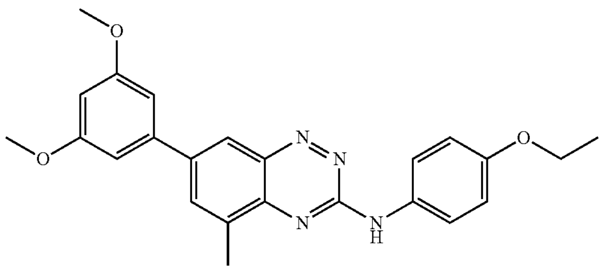 [SMILES: CCOc1ccc(Nc2nnc3cc(-c4cc(OC)cc(OC)c4)cc(C)c3n2)cc1] | (4-ethoxy-phenyl)-[7-(3,5-dimethoxy-phenyl)-5-methyl-benzo[1,2,4]triazin-3-yl]-amine | >100000 |
| 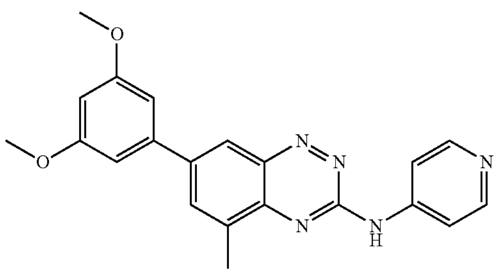 [SMILES: COc1cc(OC)cc(-c2cc(C)c3nc(Nc4ccncc4)nnc3c2)c1] | [7-(3,5-dimethoxy-phenyl)-5-methyl-benzo[1,2,4]triazin-3-yl]-pyridin-4-yl-amine | >100000 |
| 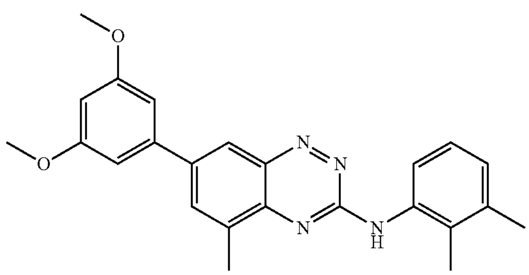 | [7-(3,5-dimethoxy-phenyl)-5-methyl-benzo[1,2,4]triazin-3-yl]-(2,3-dimethyl-phenyl)-amine | >100000 |
| 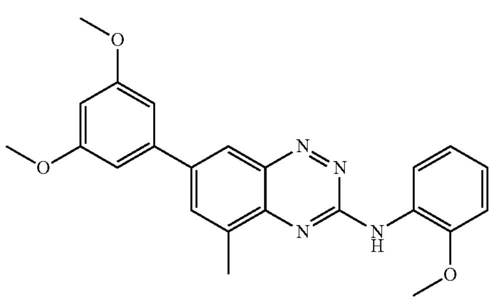 [SMILES: COc1cc(OC)cc(-c2cc(C)c3nc(Nc4ccccc4OC)nnc3c2)c1] | [7-(3,5-dimethoxy-phenyl)-5-methyl-benzo[1,2,4]triazin-3-yl]-(2-methoxy-phenyl)-amine | >100000 |

TABLE 1-continued

Tests Results of Inhibition of Src Kinase by Some Compounds of the Invention

| Structure | Name | Src IC50 (nM) |
|---|---|---|
| 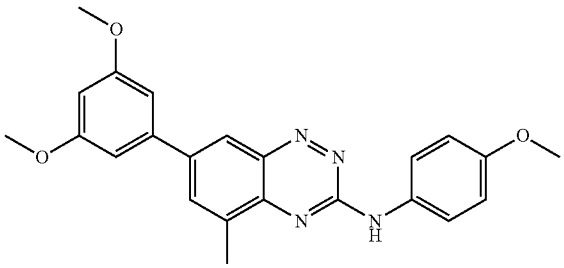 | [7-(3,5-dimethoxy-phenyl)-5-methyl-benzo[1,2,4]triazin-3-yl]-(4-methoxy-phenyl)-amine | >100000 |
| 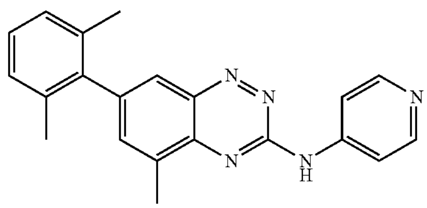 [SMILES: Cc1cccc(C)c1-c1cc(C)c2nc(Nc3ccncc3)nnc2c1] | [7-(2,6-dimethyl-phenyl)-5-methyl-benzo[1,2,4]triazin-3-yl]-pyridine-4-yl-amine | 36 |
| 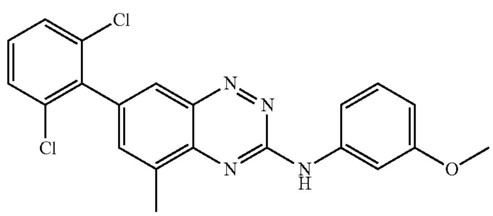 [SMILES: COc1cccc(Nc2nnc3cc(-c4c(Cl)cccc4Cl)cc(C)c3n2)c1] | [7-(2,6-dichloro-phenyl)-5-methyl-benzo[1,2,4]triazin-3-yl]-(3-methoxy-phenyl)-amine | 189 |
| 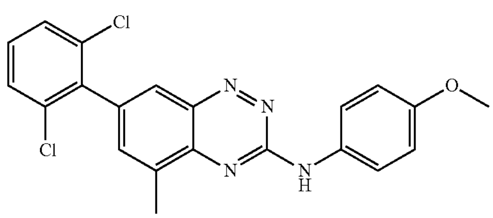 [SMILES: COc1ccc(Nc2nnc3cc(-c4c(Cl)cccc4Cl)cc(C)c3n2)cc1] | [7-(2,6-dichloro-phenyl)-5-methyl-benzo[1,2,4]triazin-3-yl]-(4-methoxy-phenyl)-amine | 137 |
| 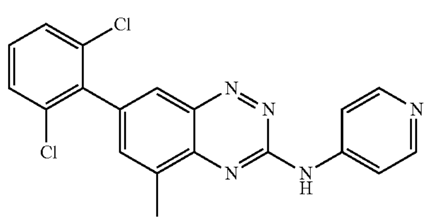 [SMILES: Cc1cc(-c2c(Cl)cccc2Cl)cc2nnc(Nc3ccncc3)nc12] | [7-(2,6-dichloro-phenyl)-5-methyl-benzo[1,2,4]triazin-3-yl]-pyridin-4-yl-amine | 42 |
| 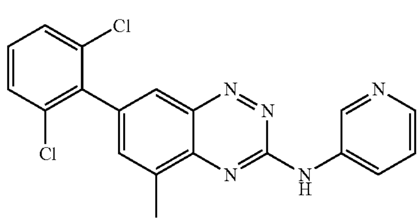 [SMILES: Cc1cc(-c2c(Cl)cccc2Cl)cc2nnc(Nc3cccnc3)nc12] | [7-(2,6-dichloro-phenyl)-5-methyl-benzo[1,2,4]triazin-3-yl]-pyridin-3-yl-amine | 27 |

TABLE 1-continued

Tests Results of Inhibition of Src Kinase by Some Compounds of the Invention

| Structure | Name | Src IC50 (nM) |
|---|---|---|
| 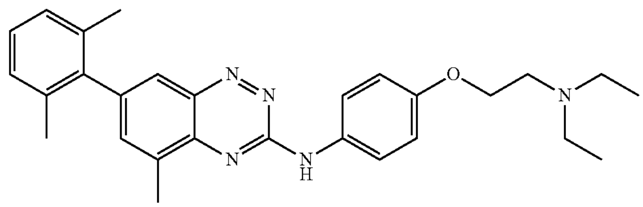 [SMILES: CCN(CC)CCOc1ccc(Nc2nnc3cc(-c4c(C)cccc4C)cc(C)c3n2)cc1] | [4-(2-diethylamino-ethoxy)-phenyl]-[7-(2,6-dimethyl-phenyl)-5-methyl-benzo[1,2,4]triazin-3-yl]-pyridin-3-yl-amine | 9.67 |
| 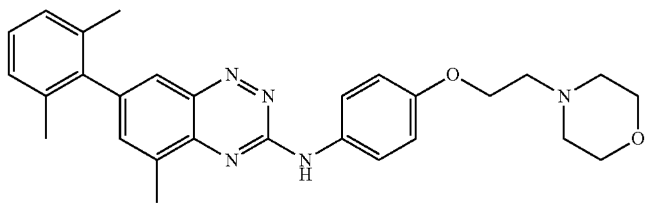 [SMILES: Cc1cccc(C)c1-c1cc(C)c2nc(Nc3ccc(OCCN4CCOCC4)cc3)nnc2c1] | [7-(2,6-dimethyl-phenyl)-5-methyl-benzo[1,2,4]triazin-3-yl]-{4-(2-morpholin-4-yl-ethoxy)-phenyl]-amine | 32.9 |
| 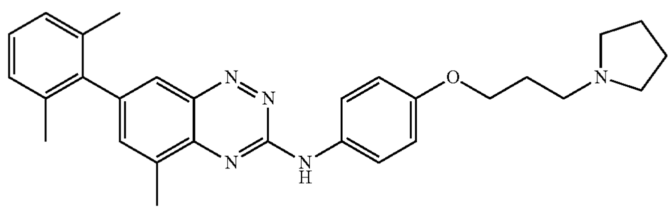 [SMILES: Cc1cccc(C)c1-c1cc(C)c2nc(Nc3ccc(OCCCN4CCCC4)cc3)nnc2c1] | [7-(2,6-dimethyl-phenyl)-5-methyl-benzo[1,2,4]triazin-3-yl]-{4-(3-pyrrolidin-1-yl-propoxy)-phenyl]-amine | 12.6 |
| 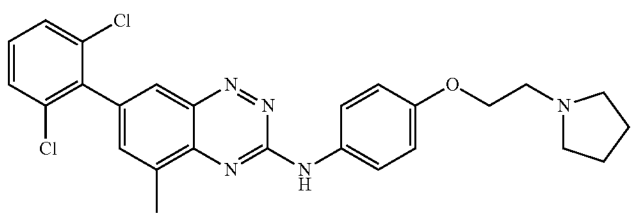 [SMILES: Cc1cc(-c2c(Cl)cccc2Cl)cc2nnc(Nc3ccc(OCCN4CCCC4)cc3)nc12] | [7-(2,6-dichloro-phenyl)-5-methyl-benzo[1,2,4]triazin-3-yl]-[4-(2-pyrrolidin-1-yl-ethoxy)-phenyl]-amine | 9.4 |
| 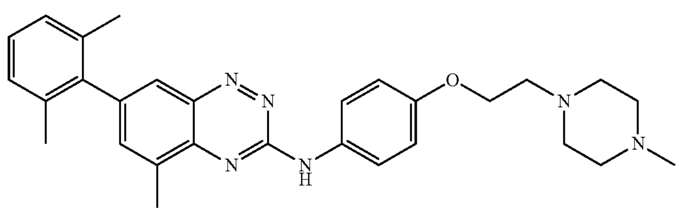 [SMILES: Cc1cccc(C)c1-c1cc(C)c2nc(Nc3ccc(OCCN4CCN(C)CC4)cc3)nnc2c1] | [7-(2,6-dimethyl-phenyl)-5-methyl-benzo[1,2,4]triazin-3-yl]-{4-[2-(4-methyl-piperazin-1-yl)-ethoxy]-phenyl}-amine | 21 |
| 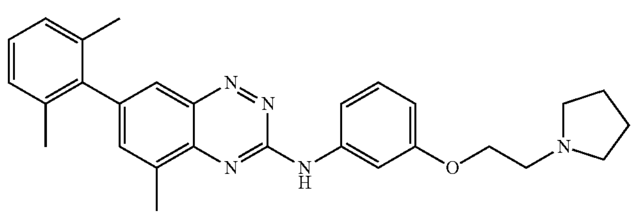 [SMILES: Cc1cccc(C)c1-c1cc(C)c2nc(Nc3cccc(OCCN4CCCC4)c3)nnc2c1] | [7-(2,6-dimethyl-phenyl)-5-methyl-benzo[1,2,4]triazin-3-yl]-[3-(2-pyrrolidin-1-yl-ethoxy]-phenyl}-amine | 6.4 |
| 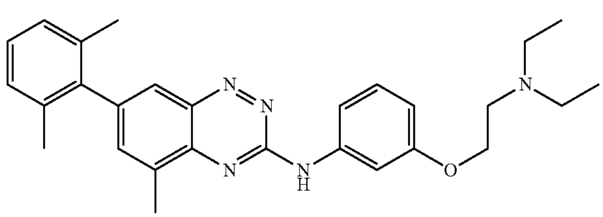 [SMILES: CCN(CC)CCOc1cccc(Nc2nnc3cc(-c4c(C)cccc4C)cc(C)c3n2)c1] | [3-(2-diethylamino-ethoxy)-phenyl]-[7-(2,6-dimethyl-phenyl)-5-methyl-benzo[1,2,4]triazin-3-yl]-amine | 10.2 |

TABLE 1-continued

Tests Results of Inhibition of Src Kinase by Some Compounds of the Invention

| Structure | Name | Src IC50 (nM) |
|---|---|---|
| 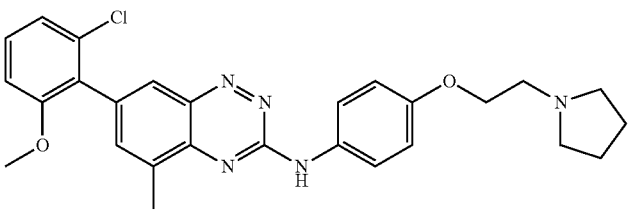 [SMILES: COc1cccc(Cl)c1-c1cc(C)c2nc(Nc3ccc(OCCN4CCCC4)cc3)nnc2c1] | [7-(2-chloro-6-methoxy-phenyl)-5-methyl-benzo[1,2,4]triazin-3-yl]-[4-(2-pyrrolidin-1-yl-ethoxy)-phenyl]-amine | 505 |
| 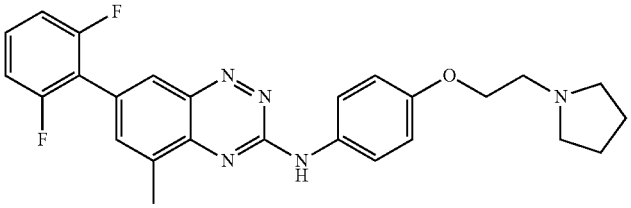 [SMILES: Cc1cc(-c2c(F)cccc2F)cc2nnc(Nc3ccc(OCCN4CCCC4)cc3)nc12] | [7-(2,6-difluoro-phenyl)-5-methyl-benzo[1,2,4]triazin-3-yl]-[4-(2-pyrrolidin-1-yl-ethoxy)-phenyl]-amine | 208 |
| 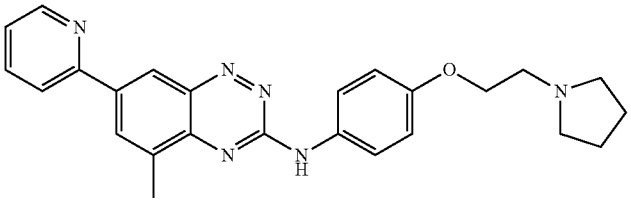 [SMILES: Cc1cc(-c2ccccn2)cc2nnc(Nc3ccc(OCCN4CCCC4)cc3)nc12] | (5-methyl-7-pyridin-2-yl-benzo[1,2,4]triazin-3-yl)-[4-(2-pyrrolidin-1-yl-ethoxy)-phenyl]-amine | 1800 |
| 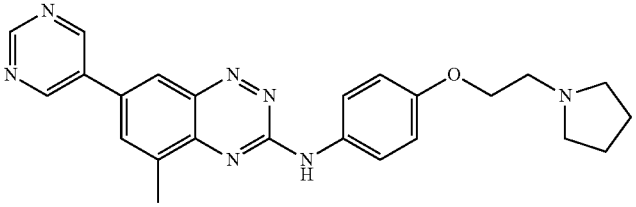 [SMILES: Cc1cc(-c2cncnc2)cc2nnc(Nc3ccc(OCCN4CCCC4)cc3)nc12] | (5-methyl-7-pyrimidin-5-yl-benzo[1,2,4]triazin-3-yl)-[4-(2-pyrrolidin-1-yl-ethoxy)-phenyl]-amine | 1500 |
| 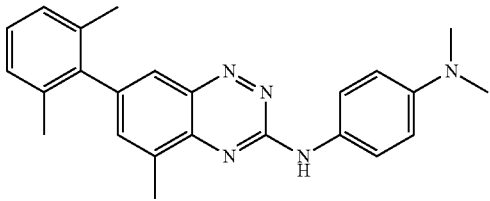 [SMILES: Cc1cccc(C)c1-c1cc(C)c2nc(Nc3ccc(N(C)C)cc3)nnc2c1] | [7-(2,6-dimethyl-phenyl)-5-methyl-benzo[1,2,4]triazin-3-yl]-4-N,N-dimethylanilinyl-amine | 244 |
| 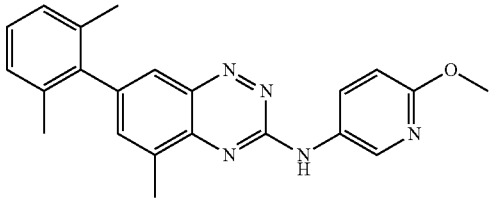 [SMILES: COc1ccc(Nc2nnc3cc(-c4c(C)cccc4C)cc(C)c3n2)cn1] | [7-(2,6-dimethyl-phenyl)-5-methyl-benzo[1,2,4]triazin-3-yl]-(6-methoxy-pyridin-3-yl)-amine | 341 |
| 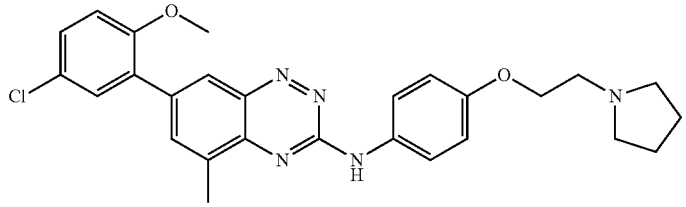 [SMILES: COc1ccc(Cl)cc1-c1cc(C)c2nc(Nc3ccc(OCCN4CCCC4)cc3)nnc2c1] | [7-(5-chloro-2-methoxy-phenyl)-5-methyl-benzo[1,2,4]triazin-3-yl]-[4-(2-pyrrolidin-1-yl-ethoxy)-phenyl]-amine | 1200 |

TABLE 1-continued

Tests Results of Inhibition of Src Kinase by Some Compounds of the Invention

| Structure | Name | Src IC50 (nM) |
|---|---|---|
| 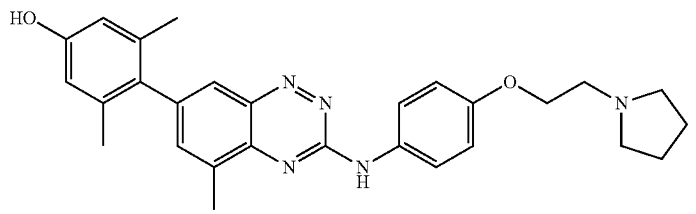 [SMILES: Cc1cc(O)cc(C)c1-c1cc(C)c2nc(Nc3ccc(OCCN4CCCC4)cc3)nnc2c1] | [7-(2,6-dimethyl-4-hydroxyphenyl)-5-methylbenzo[1,2,4]trazin-3-yl]-[4-(2-pyrrolidine-1-yl-ethoxy)-phenyl]-amine | 75 |
| 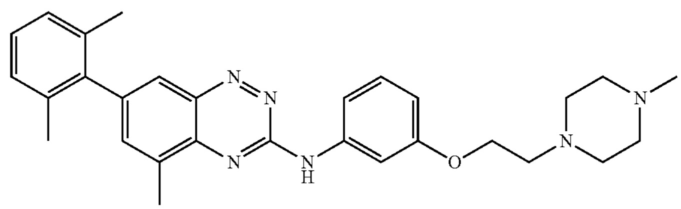 [SMILES: Cc1cccc(C)c1-c1cc(C)c2nc(Nc3cccc(OCCN4CCN(C)CC4)c3)nnc2c1] | [7-(2,6-dimethyl-phenyl)-5-methyl-benzo[1,2,4]triazin-3-yl]-{3-[2-(4-methyl-piperazin-1-yl)-ethoxy]-phenyl}-amine | 39.5 |
| 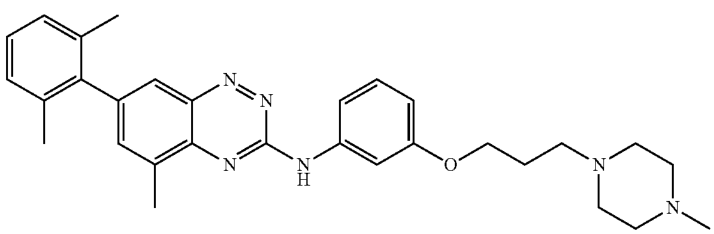 [SMILES: Cc1cccc(C)c1-c1cc(C)c2nc(Nc3cccc(OCCCN4CCN(C)CC4)c3)nnc2c1] | [7-(2,6-dimethyl-phenyl)-5-methyl-benzo[1,2,4]triazin-3-yl]-{3-[3-(4-methyl-piperazin-1-yl)-propoxy]-phenyl}-amine | 38.9 |
| 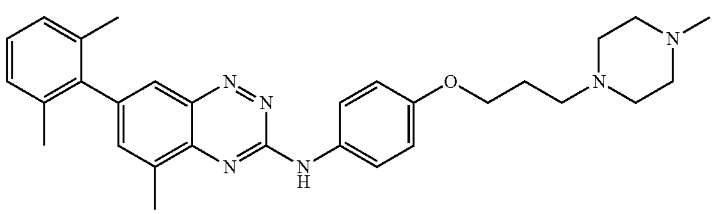 [SMILES: Cc1cccc(C)c1-c1cc(C)c2nc(Nc3ccc(OCCCN4CCN(C)CC4)cc3)nnc2c1] | [7-(2,6-dimethyl-phenyl)-5-methyl-benzo[1,2,4]triazin-3-yl]-{4-[3-(4-methyl-piperazin-1-yl)-propoxy]-phenyl}-amine | 35.8 |
| 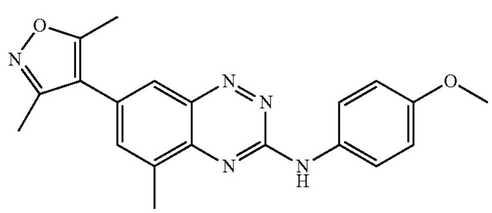 [SMILES: COc1ccc(Nc2nnc3cc(-c4c(C)noc4C)cc(C)c3n2)cc1] | [7-(3,5-dimethyl-isoxazol-4-yl)-5-methyl-benzo[1,2,4]triazin-3-yl]-(4-methoxy-phenyl)-amine | 11700 |
| 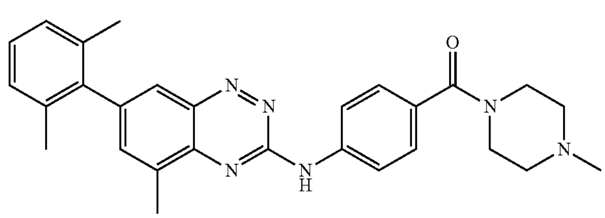 [SMILES: Cc1cccc(C)c1-c1cc(C)c2nc(Nc3ccc(C(=O)N4CCN(C)CC4)cc3)nnc2c1] | {4-[7-(2,6-dimethyl-phenyl)-5-methyl-benzo[1,2,4]triazin-3-ylamino]-phenyl}-(4-methyl-piperazin-1-yl)-methanone | 8.9 |
| 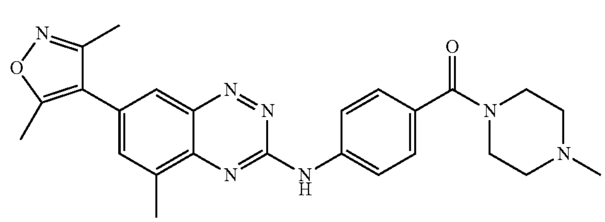 [SMILES: Cc1noc(C)c1-c1cc(C)c2nc(Nc3ccc(C(=O)N4CCN(C)CC4)cc3)nnc2c1] | {4-[7-(3,5-dimethyl-isoxazol-4-yl)-5-methyl-benzo[1,2,4]triazin-3-ylamino]-phenyl}-(4-methyl-piperazin-1-yl)-methanone | 552 |

TABLE 1-continued

Tests Results of Inhibition of Src Kinase by Some Compounds of the Invention

| Structure | Name | Src IC50 (nM) |
|---|---|---|
| 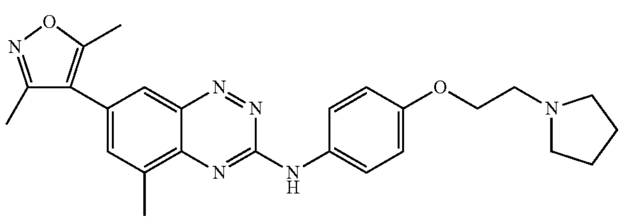 [SMILES: Cc1noc(C)c1-c1cc(C)c2nc(Nc3ccc(OCCN4CCCC4)cc3)nnc2c1] | [7-(3,5-dimethyl-isoxazol-4-yl)-5-methyl-benzo[1,2,4]triazin-3-yl]-[4-(2-pyrrolidin-1-yl-ethoxy)-phenyl]-amine | 207 |
| 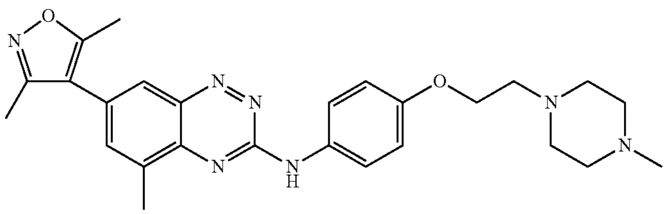 | [7-(3,5-dimethyl-isoxazol-4-yl)-5-methyl-benzo[1,2,4]triazin-3-yl]-{4-[2-(4-methyl-piperazin-1-yl)-ethoxy]-phenyl}-amine | 610 |
| 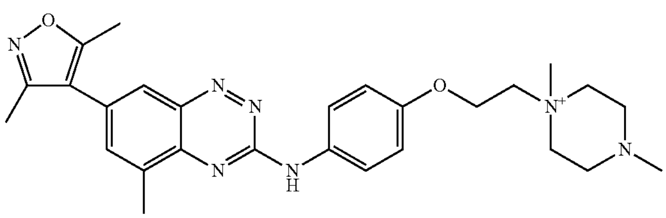 | Trifluoro-acetate1-(2-{4-[7-(3,5-dimethyl-isoxazol-4-yl)-5-methyl-benzo[1,2,4]triazin-3-ylamino]-phenoxy}-ethyl)-1,4-dimethyl-piperazin-1-ium; | 75000 |
| 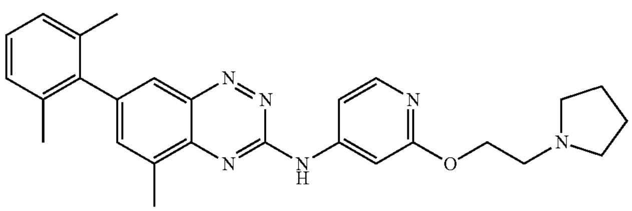 [SMILES: Cc1cccc(C)c1-c1cc(C)c2nc(Nc3ccnc(OCCN4CCCC4)c3)nnc2c1] | [7-(2,6-dimethyl-phenyl)-5-methyl-benzo[1,2,4]triazin-3-yl]-(6-methoxy-pyridin-3-yl)-amine | 5.6 |
| 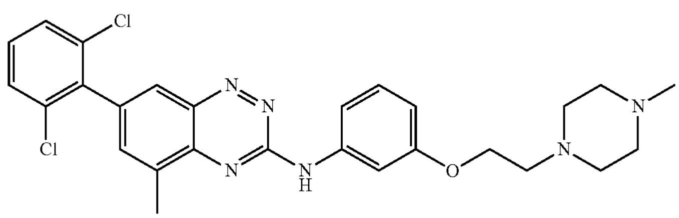 [SMILES: Cc1cc(-c2c(Cl)cccc2Cl)cc2nnc(Nc3cccc(OCCN4CCN(C)CC4)c3)nc12] | [7-(2,6-dichloro-phenyl)-5-methyl-benzo[1,2,4]triazin-3-yl]-{3-[2-(4-methyl-piperazin-1-yl)-ethoxy]-phenyl}-amine | 27.4 |
| 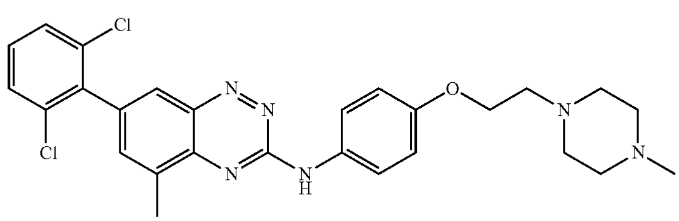 [SMILES: Cc1cc(-c2c(Cl)cccc2Cl)cc2nnc(Nc3ccc(OCCN4CCN(C)CC4)cc3)nc12] | [7-(2,6-dichloro-phenyl)-5-methyl-benzo[1,2,4]triazin-3-yl]-{4-[2-(4-methyl-piperazin-1-yl)-ethoxy]-phenyl}-amine | 23.2 |

TABLE 1-continued

Tests Results of Inhibition of Src Kinase by Some Compounds of the Invention

| Structure | Name | Src IC50 (nM) |
|---|---|---|
| 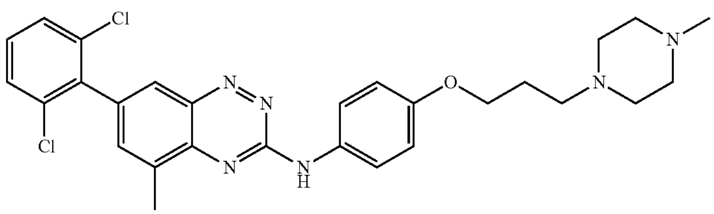 [SMILES: Cc1cc(-c2c(Cl)cccc2Cl)cc2nnc(Nc3ccc(OCCCN4CCN(C)CC4)cc3)nc12] | [7-(2,6-dichloro-phenyl)-5-methyl-benzo[1,2,4]triazin-3-yl]-{4-[3-(4-methyl-piperazin-1-yl)-propoxy]-phenyl}-amine | 25.2 |
| 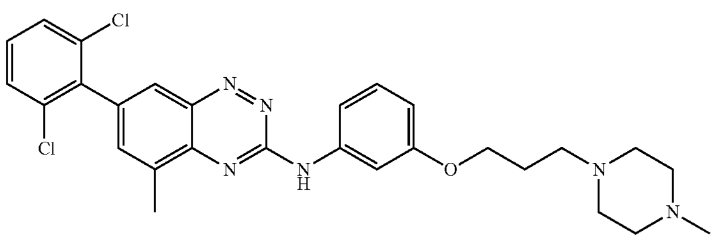 [SMILES: Cc1cc(-c2c(Cl)cccc2Cl)cc2nnc(Nc3cccc(OCCCN4CCN(C)CC4)c3)nc12] | [7-(2,6-dichloro-phenyl)-5-methyl-benzo[1,2,4]triazin-3-yl]-{3-[3-(4-methyl-piperazin-1-yl)-propoxy]-phenyl}-amine | 28.8 |
| 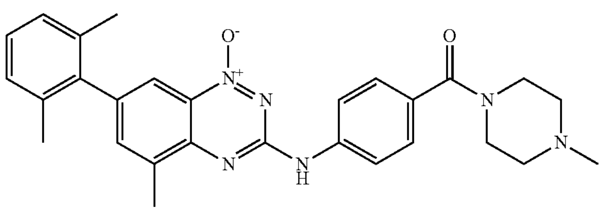 [SMILES: Cc1cccc(C)c1-c1cc(C)c2nc(Nc3ccc(C(=O)N4CCN(C)CC4)cc3)n[n+]([O-])c2c1] | {4-[7-(2,6-dimethyl-phenyl)-5-methyl-1-oxy-benzo[1,2,4]triazin-3-ylamino]-phenyl}-(4-methyl-piperazin-1-yl)-methanone | 96.1 |
| 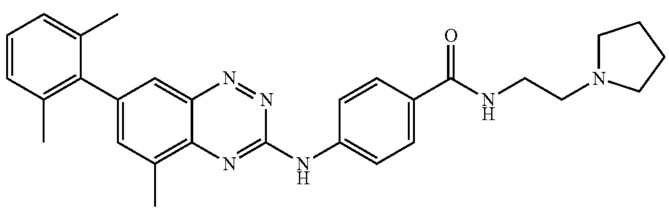 [SMILES: Cc1cccc(C)c1-c1cc(C)c2nc(Nc3ccc(C(=O)NCCN4CCCC4)cc3)nnc2c1] | 4-[7-(2,6-dimethyl-phenyl)-5-methyl-benzo[1,2,4]triazin-3-ylamino]-N-(2-pyrrolidin-1-yl-ethyl)-benzamide | 16.1 |
| 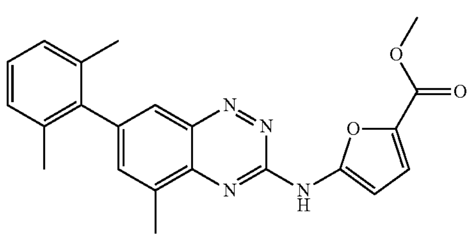 [SMILES: COC(=O)c1ccc(Nc2nnc3cc(-c4c(C)cccc4C)cc(C)c3n2)o1] | 5-[7-(2,6-dimethyl-phenyl)-5-methyl-benzo[1,2,4]triazin-3-ylamino]-furan-2-carboxylic acid methyl ester | 1000 |
| 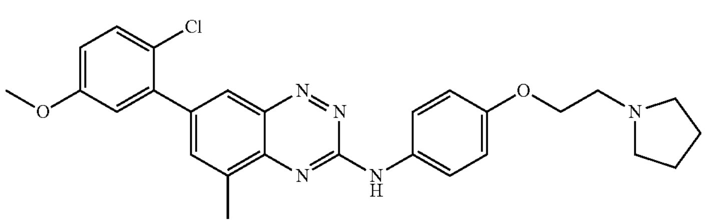 [SMILES: COc1ccc(Cl)c(-c2cc(C)c3nc(Nc4ccc(OCCN5CCCC5)cc4)nnc3c2)c1] | [7-(2-chloro-5-methoxy-phenyl)-5-methyl-benzo[1,2,4]triazin-3-yl]-[4-(2-pyrrolidin-1-yl-ethoxy)-phenyl]-amine | 788 |

TABLE 1-continued

Tests Results of Inhibition of Src Kinase by Some Compounds of the Invention

| Structure | Name | Src IC50 (nM) |
|---|---|---|
| 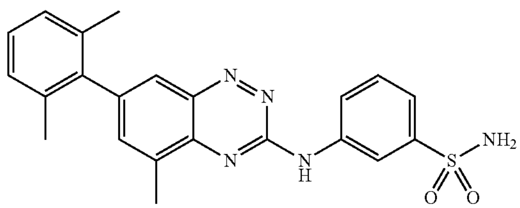 [SMILES: Cc1cccc(C)c1-c1cc(C)c2nc(Nc3cccc(S(N)(=O)=O)c3)nnc2c1] | 3-[7-(2,6-dimethyl-phenyl)-5-methyl-benzo[1,2,4]triazin-3-ylamino]-benzenesulfonamide | 143 |
| 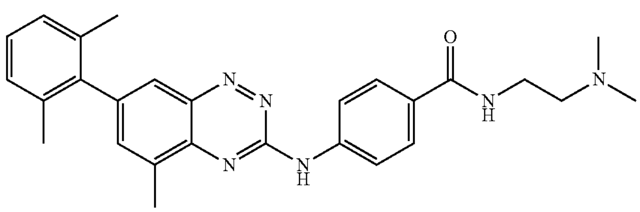 [SMILES: Cc1cccc(C)c1-c1cc(C)c2nc(Nc3ccc(C(=O)NCCN(C)C)cc3)nnc2c1] | N-(2-dimethylamino-ethyl)-4-[7-(2,6-dimethyl-phenyl)-5-methyl-benzo[1,2,4]triazin-3-ylamino]-benzamide | 4.6 |
| 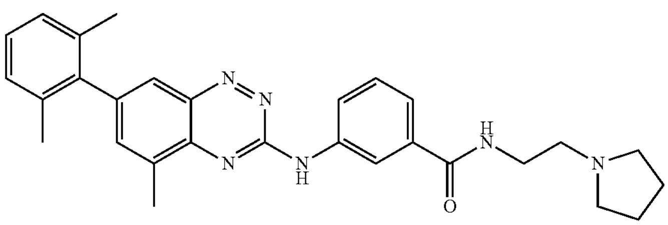 [SMILES: Cc1cccc(C)c1-c1cc(C)c2nc(Nc3cccc(C(=O)NCCN4CCCC4)c3)nnc2c1] | 3-[7-(2,6-dimethyl-phenyl)-5-methyl-benzo[1,2,4]triazin-3-ylamino]-N-(2-pyrrolidin-1-yl-ethyl)-benzamide | 17.6 |
| 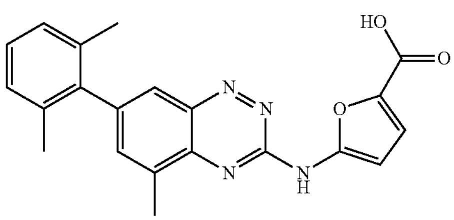 [SMILES: Cc1cccc(C)c1-c1cc(C)c2nc(Nc3ccc(C(=O)O)o3)nnc2c1] | 5-[7-(2,6-dimethyl-phenyl)-5-methyl-benzo[1,2,4]triazin-3-ylamino]-furan-2-carboxylic acid | 1500 |
| 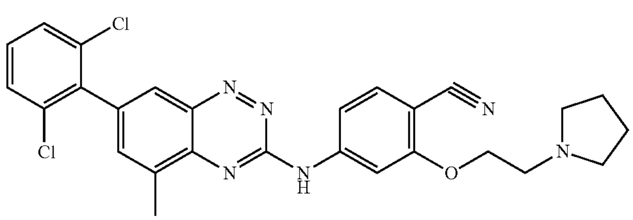 [SMILES: Cc1cc(-c2c(Cl)cccc2Cl)cc2nnc(Nc3ccc(C#N)c(OCCN4CCCC4)c3)nc12] | 4-[7-(2,6-dichloro-phenyl)-5-methyl-benzo[1,2,4]triazin-3-ylamino]-2-(2-pyrrolidin-1-yl-ethoxy)-benzonitrile | 21 |
| 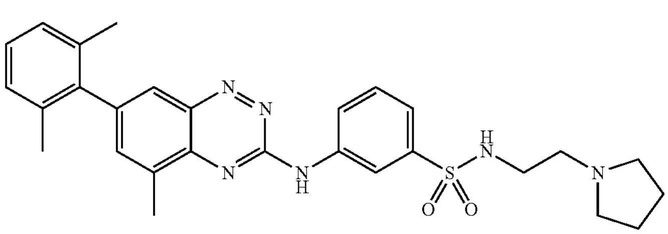 [SMILES: Cc1cccc(C)c1-c1cc(C)c2nc(Nc3cccc(S(=O)(=O)NCCN4CCCC4)c3)nnc2c1] | [7-(2,6-dimethylphenyl)-5-methylbenzo[1,2,4]trazin-3-yl]-3-(2-pyrrolidine-1-yl-ethsufomide)-phenyl]-amine | 26.4 |

TABLE 1-continued

Tests Results of Inhibition of Src Kinase by Some Compounds of the Invention

| Structure | Name | Src IC50 (nM) |
|---|---|---|
| 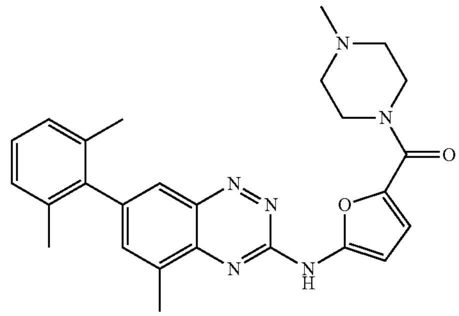 [SMILES: Cc1cccc(C)c1-c1cc(C)c2nc(Nc3ccc(C(=O)N4CCN(C)CC4)o3)nnc2c1] | {5-[7-(2,6-dimethyl-phenyl)-5-methyl-benzo[1,2,4]triazin-3-ylamino]-furan-2-yl}-(4-methyl-piperazin-1-yl)-methanone | 94 |
| 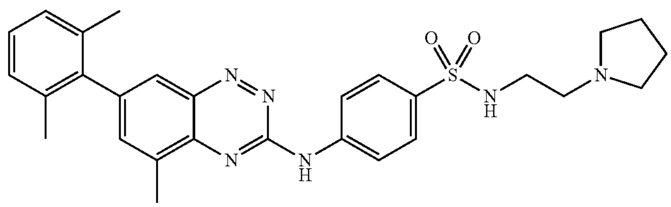 [SMILES: Cc1cccc(C)c1-c1cc(C)c2nc(Nc3ccc(S(=O)(=O)NCCN4CCCC4)cc3)nnc2c1] | 4-[7-(2,6-dimethyl-phenyl)-5-methyl-benzo[1,2,4]triazin-3-ylamino]-N-(2-pyrrolidin-1-yl-ethyl)-benzenesulfonamide | 9.1 |
| 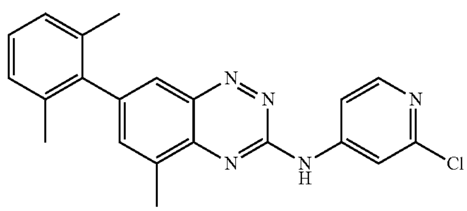 [SMILES: Cc1cccc(C)c1-c1cc(C)c2nc(Nc3ccnc(Cl)c3)nnc2c1] | (2-chloro-pyridin-4-yl)-[7-(2,6-dimethyl-phenyl)-5-methyl-benzo[1,2,4]triazin-3-yl]-amine | 118 |
| 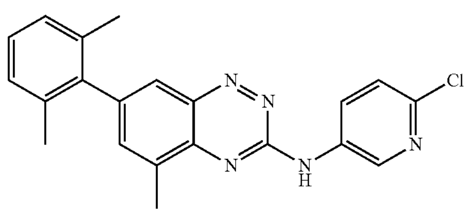 [SMILES: Cc1cccc(C)c1-c1cc(C)c2nc(Nc3ccc(Cl)nc3)nnc2c1] | (6-chloro-pyridin-3-yl)-[7-(2,6-dimethyl-phenyl)-5-methyl-benzo[1,2,4]triazin-3-yl]-amine | 232 |
| 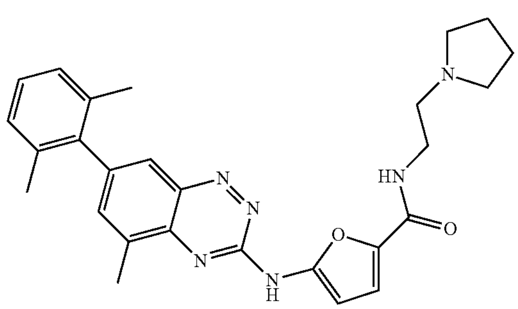 [SMILES: Cc1cccc(C)c1-c1cc(C)c2nc(Nc3ccc(C(=O)NCCN4CCCC4)o3)nnc2c1] | 5-[7-(2,6-dimethyl-phenyl)-5-methyl-benzo[1,2,4]triazin-3-ylamino]-furan-2-carboxylic acid (2-pyrrolidin-1-yl-ethyl)-amide | 17.5 |
| 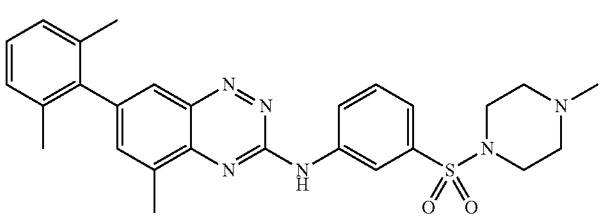 | [7-(2,6-dimethyl-phenyl)-5-methyl-benzo[1,2,4]triazin-3-yl]-[3-(4-methyl-piperazine-1-sulfonyl)-phenyl]-amine | 322 |

TABLE 1-continued

Tests Results of Inhibition of Src Kinase by Some Compounds of the Invention

| Structure | Name | Src IC50 (nM) |
|---|---|---|
| 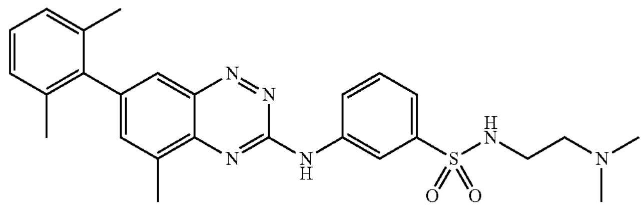 [SMILES: Cc1cccc(C)c1-c1cc(C)c2nc(Nc3cccc(S(=O)(=O)NCCN(C)C)c3)nnc2c1] | N-(2-dimethylamino-ethyl)-3-[7-(2,6-dimethyl-phenyl)-5-methyl-benzo[1,2,4]triazin-3-ylamino]-benzenesulfonamide | 41.4 |
| 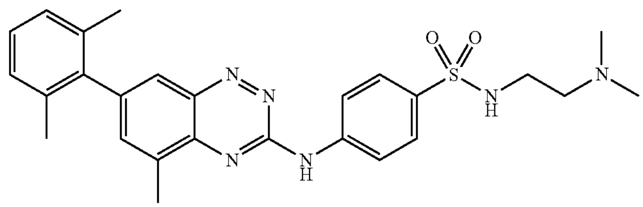 [SMILES: Cc1cccc(C)c1-c1cc(C)c2nc(Nc3ccc(S(=O)(=O)NCCN(C)C)cc3)nnc2c1] | N-(2-dimethylamino-ethyl)-4-[7-(2,6-dimethyl-phenyl)-5-methyl-benzo[1,2,4]triazin-3-ylamino]-benzenesulfonamide | 14.6 |
| 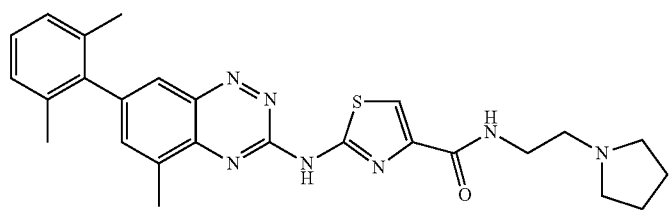 [SMILES: Cc1cccc(C)c1-c1cc(C)c2nc(Nc3nc(C(=O)NCCN4CCCC4)cs3)nnc2c1] | 2-[7-(2,6-dimethyl-phenyl)-5-methyl-benzo[1,2,4]triazin-3-ylamino]-thiazole-4-carboxylic acid (2-pyrrolidin-1-yl-ethyl)-amide | 14.6 |
| 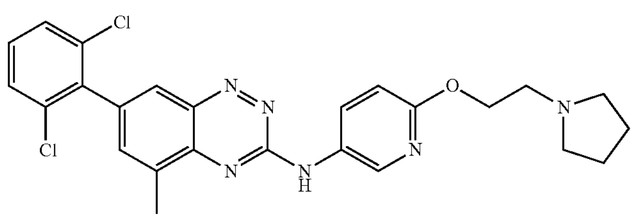 [SMILES: Cc1cc(-c2c(Cl)cccc2Cl)cc2nnc(Nc3ccc(OCCN4CCCC4)nc3)nc12] | [7-(2,6-dichloro-phenyl)-5-methyl-benzo[1,2,4]triazin-3-yl]-[6-(2-pyrrolidin-1-yl-ethoxy)-pyridin-3-yl]-amine | 15.3 |
| 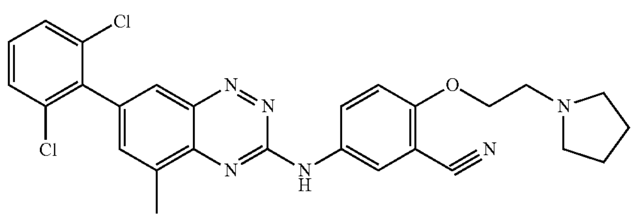 [SMILES: Cc1cc(-c2c(Cl)cccc2Cl)cc2nnc(Nc3ccc(OCCN4CCCC4)c(C#N)c3)nc12] | 5-[7-(2,6-dichloro-phenyl)-5-methyl-benzo[1,2,4]triazin-3-ylamino]-2-(2-pyrrolidin-1-yl-ethoxy)-benzonitrile | 25.2 |
| 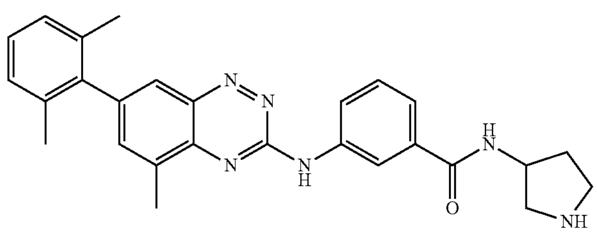 [SMILES: Cc1cccc(C)c1-c1cc(C)c2nc(Nc3cccc(C(=O)NC4CCNC4)c3)nnc2c1] | 3-[7-(2,6-dimethyl-phenyl)-5-methyl-benzo[1,2,4]triazin-3-ylamino]-N-pyrrolidin-3-yl-benzamide | 18.3 |
| 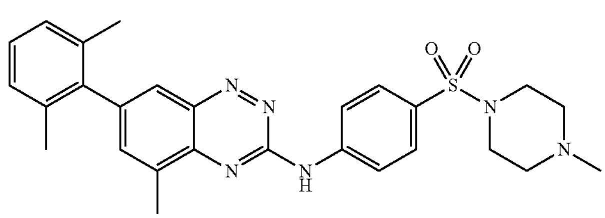 [SMILES: Cc1cccc(C)c1-c1cc(C)c2nc(Nc3ccc(S(=O)(=O)N4CCN(C)CC4)cc3)nnc2c1] | [7-(2,6-dimethyl-phenyl)-5-methyl-benzo[1,2,4]triazin-3-yl]-[4-(4-methyl-piperazine-1-sulfonyl)-phenyl]-amine | 137 |

TABLE 1-continued

Tests Results of Inhibition of Src Kinase by Some Compounds of the Invention

| Structure | Name | Src IC50 (nM) |
|---|---|---|
| 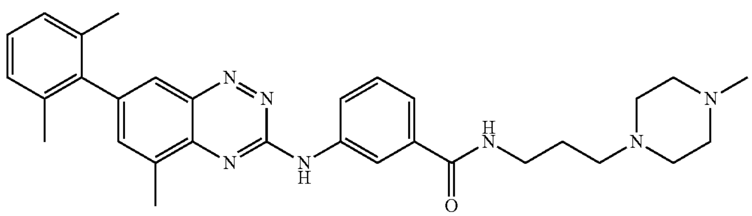 [SMILES: Cc1cccc(C)c1-c1cc(C)c2nc(Nc3cccc(C(=O)NCCCN4CCN(C)CC4)c3)nnc2c1] | 3-[7-(2,6-dimethyl-phenyl)-5-methyl-benzo[1,2,4]triazin-3-ylamino]-N-[3-(4-methyl-piperazin-1-yl)-propyl]-benzamide | 27.4 |
| 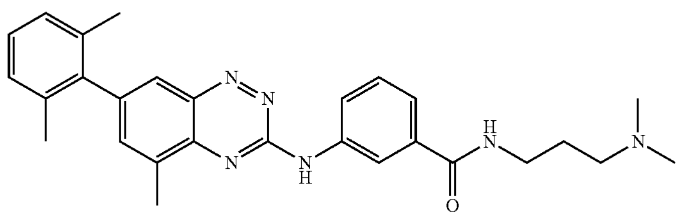 [SMILES: Cc1cccc(C)c1-c1cc(C)c2nc(Nc3cccc(C(=O)NCCCN(C)C)c3)nnc2c1] | N-(3-dimethylamino-propyl)-3-[7-(2,6-dimethyl-phenyl)-5-methyl-benzo[1,2,4]triazin-3-ylamino]-benzamide | 13.1 |
| 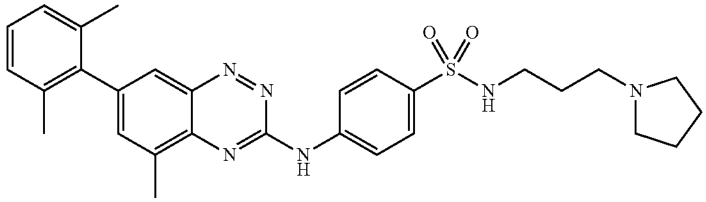 [SMILES: Cc1cccc(C)c1-c1cc(C)c2nc(Nc3ccc(S(=O)(=O)NCCCN4CCCC4)cc3)nnc2c1] | 3-[7-(2,6-dimethyl-phenyl)-5-methyl-benzo[1,2,4]triazin-3-ylamino]-N-(3-pyrrolidin-1-yl-propyl)-benzenesulfonamide | 29.2 |
| 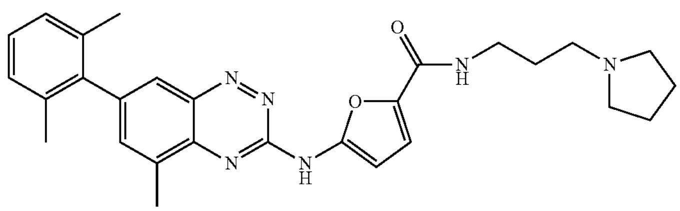 [SMILES: Cc1cccc(C)c1-c1cc(C)c2nc(Nc3ccc(C(=O)NCCCN4CCCC4)o3)nnc2c1] | 5-[7-(2,6-dimethyl-phenyl)-5-methyl-benzo[1,2,4]triazin-3-ylamino]-furan-2-carboxylic acid (3-pyrrolidin-1-yl-propyl)-amide | 18.3 |
| 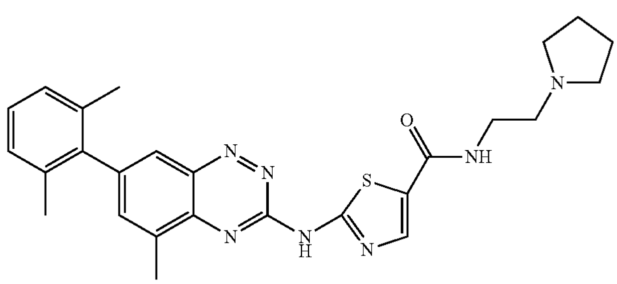 [SMILES: Cc1cccc(C)c1-c1cc(C)c2nc(Nc3ncc(C(=O)NCCN4CCCC4)s3)nnc2c1] | 2-[7-(2,6-dimethyl-phenyl)-5-methyl-benzo[1,2,4]triazin-3-ylamino]-thiazole-5-carboxylic acid (2-pyrrolidin-1-yl-ethyl)-amide | 286 |
| 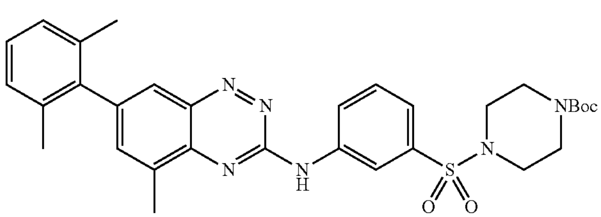 [SMILES: Cc1cccc(C)c1-c1cc(C)c2nc(Nc3cccc(S(=O)(=O)N4CCN(C(=O)OC(C)(C)C)CC4)c3)nnc2c1] | 4-{3-[7-(2,6-dimethyl-phenyl)-5-methyl-benzo[1,2,4]triazin-3-ylamino]-benzenesulfonyl}-piperazine-1-carboxylic acid tert-butyl ester | >10000 |

TABLE 1-continued

Tests Results of Inhibition of Src Kinase by Some Compounds of the Invention

| Structure | Name | Src IC50 (nM) |
|---|---|---|
| 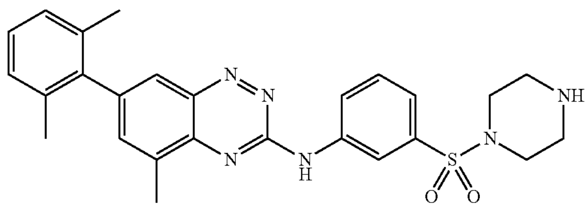 [SMILES: Cc1cccc(C)c1-c1cc(C)c2nc(Nc3cccc(S(=O)(=O)N4CCNCC4)c3)nnc2c1] | [7-(2,6-dimethyl-phenyl)-5-methyl-benzo[1,2,4]triazin-3-yl]-[3-(piperazine-1-sulfonyl)-phenyl]-amine | 48.2 |
| 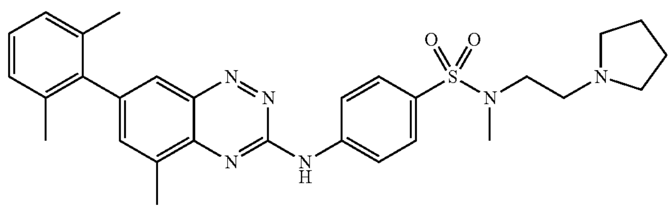 [SMILES: Cc1cccc(C)c1-c1cc(C)c2nc(Nc3ccc(S(=O)(=O)N(C)CCN4CCCC4)cc3)nnc2c1] | (2,6-dimethyl-phenyl)-5-methyl-benzo[1,2,4]triazin-3-ylamino]-N-methyl-N-(2-pyrrolidin-1-yl-ethyl)-benzenesulfonamide | 25.5 |
| 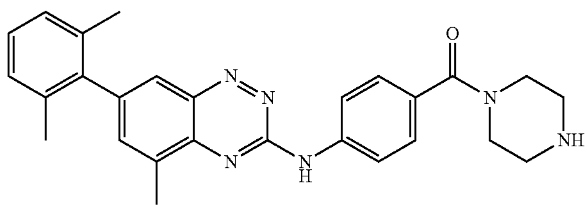 [SMILES: Cc1cccc(C)c1-c1cc(C)c2nc(Nc3ccc(C(=O)N4CCNCC4)cc3)nnc2c1] | (4-(5-methyl-7-(2,6-dimethylphenyl)benzo[e][1,2,4]triazin-3-ylamino)phenyl)(piperazin-1-yl)methanone. | 11.9 |
| 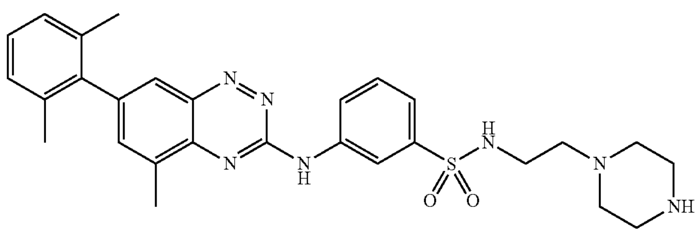 [SMILES: Cc1cccc(C)c1-c1cc(C)c2nc(Nc3cccc(S(=O)(=O)NCCN4CCNCC4)c3)nnc2c1] | 4-[7-(2,6-dimethyl-phenyl)-5-methyl-benzo[1,2,4]triazin-3-ylamino]-N-(2-piperazin-1-yl-ethyl)-benzenesulfonamide | 28.8 |
| 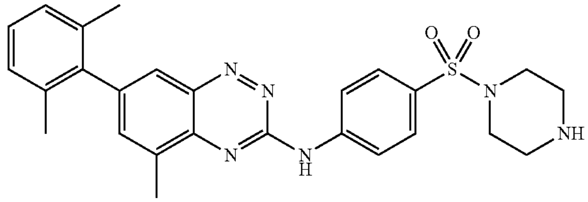 [SMILES: Cc1cccc(C)c1-c1cc(C)c2nc(Nc3ccc(S(=O)(=O)N4CCNCC4)cc3)nnc2c1] | [7-(2,6-dimethyl-phenyl)-5-methyl-benzo[1,2,4]triazin-3-yl]-[4-(piperazine-1-sulfonyl)-phenyl]-amine | 128 |
| 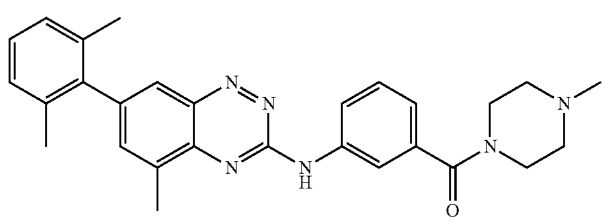 [SMILES: Cc1cccc(C)c1-c1cc(C)c2nc(Nc3cccc(C(=O)N4CCN(C)CC4)c3)nnc2c1] | {3-[7-(2,6-dimethyl-phenyl)-5-methyl-benzo[1,2,4]triazin-3-ylamino]-phenyl}-(4-methyl-piperazin-1-yl)-methanone | 88.6 |
| 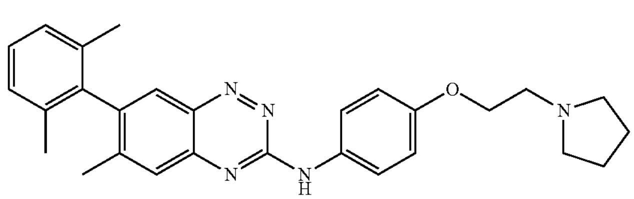 [SMILES: Cc1cc2nc(Nc3ccc(OCCN4CCCC4)cc3)nnc2cc1-c1c(C)cccc1C] | [7-(2,6-dimethyl-phenyl)-6-methyl-benzo[1,2,4]triazin-3-yl]-[4-(2-pyrrolidin-1-yl-ethoxy)-phenyl]-amine | 12.3 |

TABLE 1-continued

Tests Results of Inhibition of Src Kinase by Some Compounds of the Invention

| Structure | Name | Src IC50 (nM) |
|---|---|---|
| 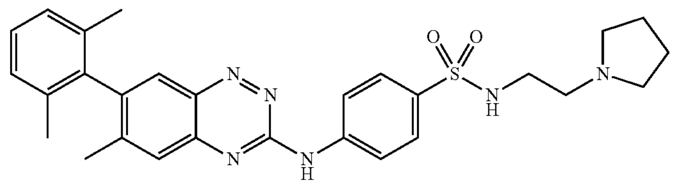 [SMILES: Cc1cc2nc(Nc3ccc(S(=O)(=O)NCCN4CCCC4)cc3)nnc2cc1-c1c(C)cccc1C] | 4-[7-(2,6-dimethyl-phenyl)-6-methyl-benzo[1,2,4]triazin-3-ylamino]-N-(2-pyrrolidin-1-yl-ethyl)-benzenesulfonamide | 10.5 |
| 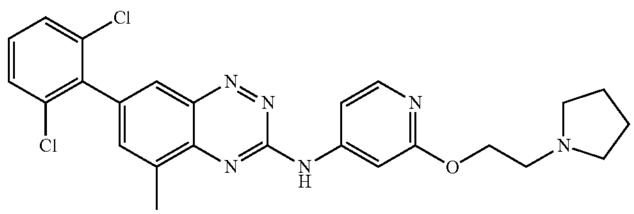 [SMILES: Cc1cc(-c2c(Cl)cccc2Cl)cc2nnc(Nc3ccnc(OCCN4CCCC4)c3)nc12] | [7-(2,6-dichloro-phenyl)-5-methyl-benzo[1,2,4]triazin-3-yl]-[2-(2-pyrrolidin-1-yl-ethoxy)-pyridin-4-yl]-amine hydrochloride | 12.2 |
| 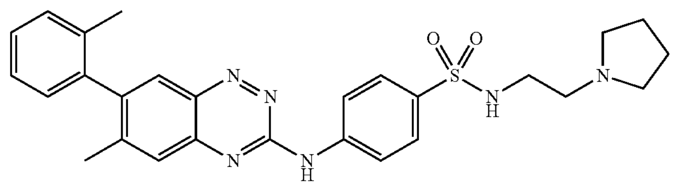 [SMILES: Cc1ccccc1-c1cc2nnc(Nc3ccc(S(=O)(=O)NCCN4CCCC4)cc3)nc2cc1C] | 4-(6-methyl-7-o-tolyl-benzo[1,2,4]triazin-3-ylamino)-N-(2-pyrrolidin-1-yl-ethyl)-benzenesulfonamide | 10.2 |
| 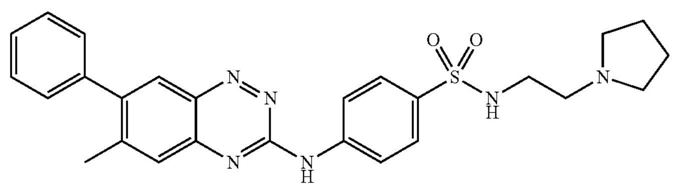 [SMILES: Cc1cc2nc(Nc3ccc(S(=O)(=O)NCCN4CCCC4)cc3)nnc2cc1-c1ccccc1] | 4-(6-methyl-7-phenyl-benzo[1,2,4]triazin-3-ylamino)-N-(2-pyrrolidin-1-yl-ethyl)-benzenesulfonamide | 315 |
| 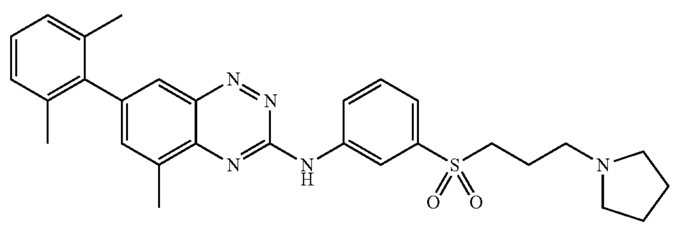 [SMILES: Cc1cccc(C)c1-c1cc(C)c2nc(Nc3cccc(S(=O)(=O)CCCN4CCCC4)c3)nnc2c1] | [7-(2,6-dimethyl-phenyl)-5-methyl-benzo[1,2,4]triazin-3-yl]-[3-(3-pyrrolidin-1-yl-propane-1-sulfonyl)-phenyl]-amine | 34.8 |
| 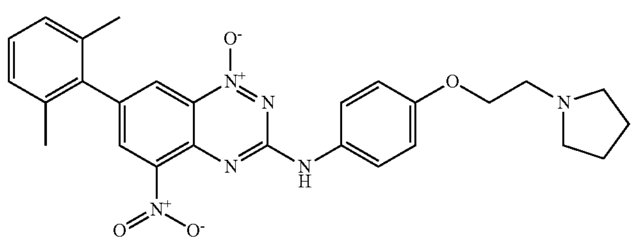 [SMILES: Cc1cccc(C)c1-c1cc([N+](=O)[O-])c2nc(Nc3ccc(OCCN4CCCC4)cc3)n[n+]([O-])c2c1] | 7-(2,6-dimethyl-phenyl)-5-nitro-3-[4-(2-pyrrolidin-1-yl-ethoxy)-phenylamino]-benzo[1,2,4]triazin-1-ol | 32 |
| 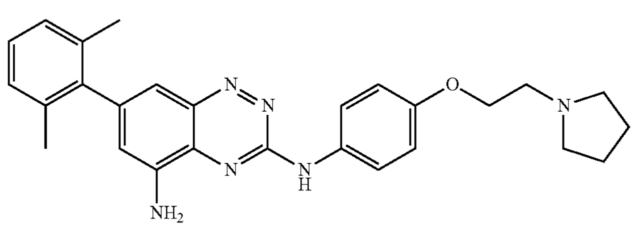 [SMILES: Cc1cccc(C)c1-c1cc(N)c2nc(Nc3ccc(OCCN4CCCC4)cc3)nnc2c1] | 7-(2,6-dimethyl-phenyl)-N3-[4-(2-pyrrolidin-1-yl-ethoxy)-phenyl]-benzo[1,2,4]triazine-3,5-diamine | 9.7 |

TABLE 1-continued

Tests Results of Inhibition of Src Kinase by Some Compounds of the Invention

| Structure | Name | Src IC50 (nM) |
|---|---|---|
| 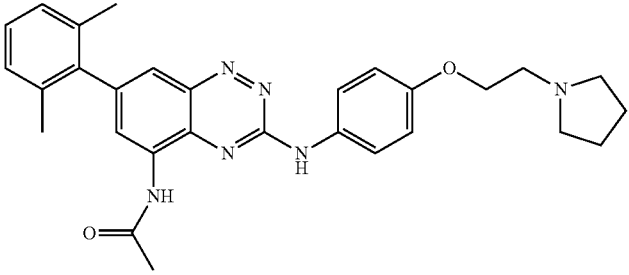 [SMILES: CC(=O)Nc1cc(-c2c(C)cccc2C)cc2nnc(Nc3ccc(OCCN4CCCC4)cc3)nc12] | N-{7-(2,6-dimethyl-phenyl)-3-[4-(2-pyrrolidin-1-yl-ethoxy)-phenylamino]-benzo[1,2,4]triazin-5-yl}-acetamide | 6.8 |
| 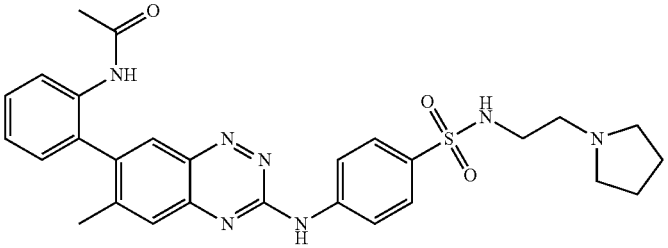 [SMILES: CC(=O)Nc1ccccc1-c1cc2nnc(Nc3ccc(S(=O)(=O)NCCN4CCCC4)cc3)nc2cc1C] | N-(2-{6-methyl-3-[4-(2-pyrrolidin-1-yl-ethylsulfamoyl)-phenylamino]-benzo[1,2,4]triazin-7-yl}-phenyl)-acetamide | 10000 |
| 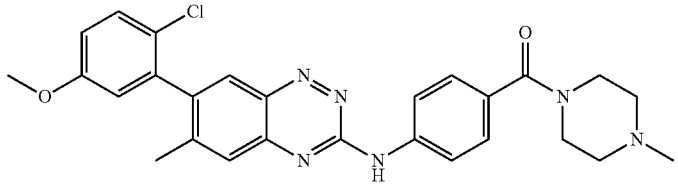 | {4-[7-(2-chloro-5-methoxy-phenyl)-6-methyl-benzo[1,2,4]triazin-3-ylamino]-phenyl}-(4-methyl-piperazin-1-yl)-methanone | 560 |
| 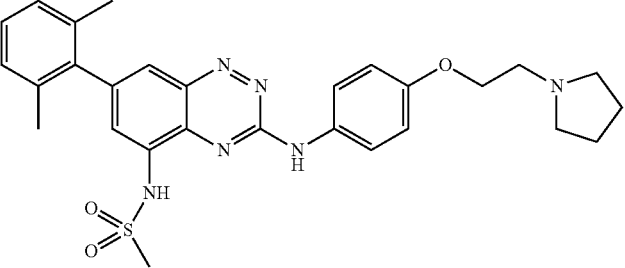 [SMILES: Cc1cccc(C)c1-c1cc(NS(C)(=O)=O)c2nc(Nc3ccc(OCCN4CCCC4)cc3)nnc2c1] | N-{7-(2,6-dimethyl-phenyl)-3-[4-(2-pyrrolidin-1-yl-ethoxy)-phenylamino]-benzo[1,2,4]triazin-5-yl}-methanesulfonamide | 20.4 |
| 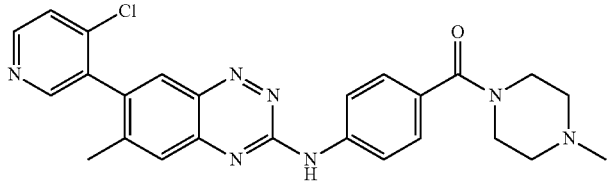 [SMILES: Cc1cc2nc(Nc3ccc(C(=O)N4CCN(C)CC4)cc3)nnc2cc1-c1cnccc1Cl] | (4-(7-(4-chloropyridin-3-yl)-6-methylbenzo[e][1,2,4]triazin-3-ylamino)phenyl)(4-methylpiperazin-1-yl)methanone | 10000 |
| 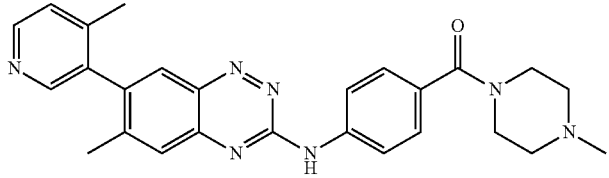 [SMILES: Cc1ccncc1-c1cc2nnc(Nc3ccc(C(=O)N4CCN(C)CC4)cc3)nc2cc1C] | (4-(6-methyl-7-(4-methylpyridin-3-yl)benzo[e][1,2,4]triazin-3-ylamino)phenyl)(4-methylpiperazin-1-yl)methanone | 47.2 |

TABLE 1-continued

Tests Results of Inhibition of Src Kinase by Some Compounds of the Invention

| Structure | Name | Src IC50 (nM) |
|---|---|---|
| 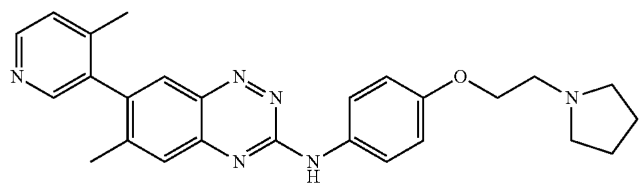 [SMILES: Cc1ccncc1-c1cc2nnc(Nc3ccc(OCCN4CCCC4)cc3)nc2cc1C] | N-(4-(2-(pyrrolidin-1-yl)ethoxy)phenyl)-6-methyl-7-(4-methylpyridin-3-yl)benzo[e][1,2,4]triazin-3-amine | 44.3 |
| 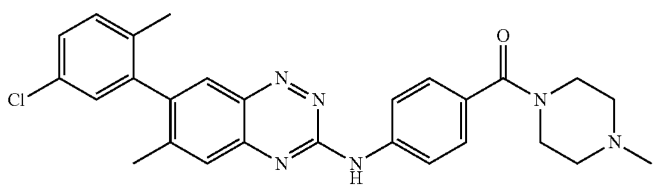 [SMILES: Cc1ccc(Cl)cc1-c1cc2nnc(Nc3ccc(C(=O)N4CCN(C)CC4)cc3)nc2cc1C] | {4-[7-(5-chloro-2-methyl-phenyl)-6-methyl-benzo[1,2,4]triazin-3-ylamino]-phenyl}-(4-methyl-piperazin-1-yl)-methanone | 7.9 |
| 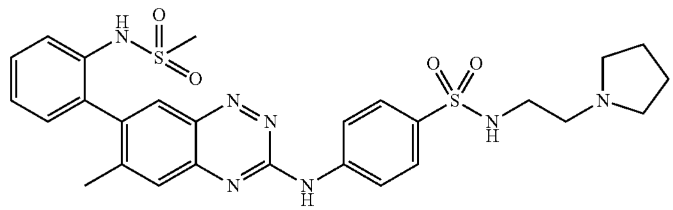 [SMILES: Cc1cc2nc(Nc3ccc(S(=O)(=O)NCCN4CCCC4)cc3)nnc2cc1-c1ccccc1NS(C)(=O)=O] | 4-[7-(2-Methanesulfonylamino-phenyl)-6-methyl-benzo[1,2,4]triazin-3-ylamino]-N-(2-pyrrolidin-1-yl-ethyl)-benzenesulfonamide | 5000 |
| 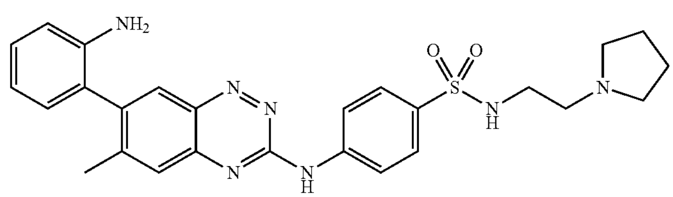 [SMILES: Cc1cc2nc(Nc3ccc(S(=O)(=O)NCCN4CCCC4)cc3)nnc2cc1-c1ccccc1N] | 4-[7-(2-amino-phenyl)-6-methyl-benzo[1,2,4]triazin-3-ylamino]-N-(2-pyrrolidin-1-yl-ethyl)-benzenesulfonamide | 91.8 |
| 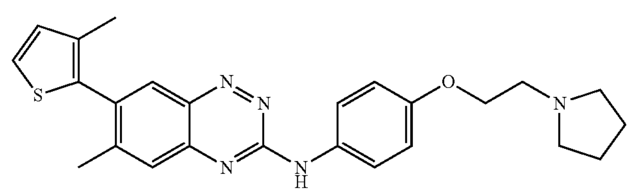 [SMILES: Cc1cc2nc(Nc3ccc(OCCN4CCCC4)cc3)nnc2cc1-c1sccc1C] | N-(4-(2-(pyrrolidin-1-yl)ethoxy)phenyl)-6-methyl-7-(3-methylthiophen-2-yl)benzo[e][1,2,4]triazin-3-amine | 60.7 |
| 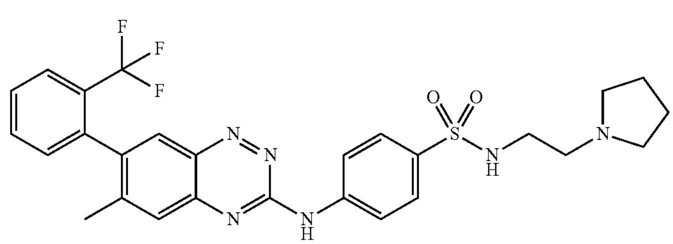 [SMILES: Cc1cc2nc(Nc3ccc(S(=O)(=O)NCCN4CCCC4)cc3)nnc2cc1-c1ccccc1C(F)(F)F] | 4-[6-methyl-7-(2-trifluoromethyl-phenyl)-benzo[1,2,4]triazin-3-ylamino]-N-(2-pyrrolidin-1-yl-ethyl)-benzenesulfonamide | 66.5 |
| 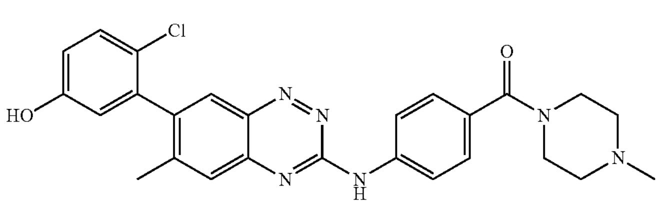 [SMILES: Cc1cc2nc(Nc3ccc(C(=O)N4CCN(C)CC4)cc3)nnc2cc1-c1cc(O)ccc1Cl] | {4-[7-(2-chloro-5-hydroxy-phenyl)-6-methyl-benzo[1,2,4]triazin-3-ylamino]-phenyl}-(4-methyl-piperazin-1-yl)-methanone | 3.4 |

TABLE 1-continued

Tests Results of Inhibition of Src Kinase by Some Compounds of the Invention

| Structure | Name | Src IC50 (nM) |
|---|---|---|
| 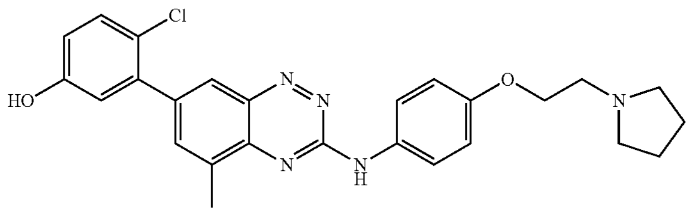 | [7-(2-chloro-5-hydroxy-phenyl)-5-methyl-benzo[1,2,4]triazin-3-yl]-[4-(2-pyrrolidine-1-yl-ethoxy)-phenyl]-amine | 1.6 |
| 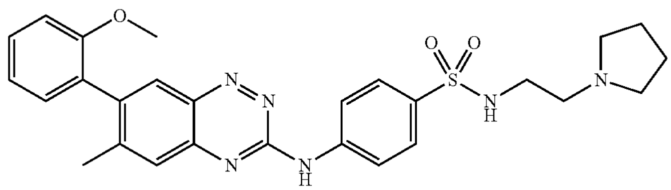 [SMILES: COc1ccccc1-c1cc2nnc(Nc3ccc(S(=O)(=O)NCCN4CCCC4)cc3)nc2cc1C] | 4-[7-(2-methoxy-phenyl)-6-methyl-benzo[1,2,4]triazin-3-ylamino]-N-(2-pyrrolidin-1-yl-ethyl)-benzenesulfonamide | 272 |
| 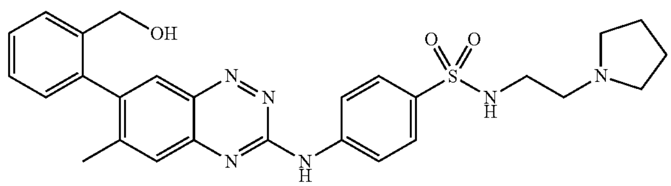 [SMILES: Cc1cc2nc(Nc3ccc(S(=O)(=O)NCCN4CCCC4)cc3)nnc2cc1-c1ccccc1CO] | 4-[7-(2-Hydroxymethyl-phenyl)-6-methyl-benzo[1,2,4]triazin-3-ylamino]-N-(2-pyrrolidin-1-yl-ethyl)-benzenesulfonamide | 72.2 |
| 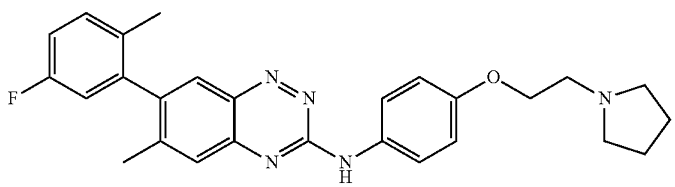 [SMILES: Cc1ccc(F)cc1-c1cc2nnc(Nc3ccc(OCCN4CCCC4)cc3)nc2cc1C] | [7-(5-fluoro-2-methyl-phenyl)-6-methyl-benzo[1,2,4]triazin-3-yl]-[4-(2-pyrrolidin-1-yl-ethoxy)-phenyl]-amine | 6.6 |
| 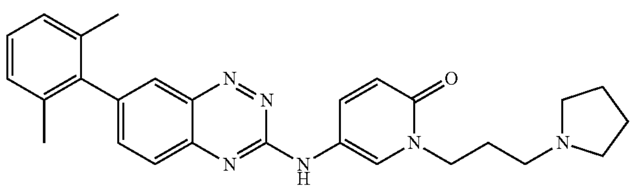 [SMILES: Cc1cccc(C)c1-c1ccc2nc(Nc3ccc(=O)n(CCCN4CCCC4)c3)nnc2c1] | 5-(5-methyl-7-(2,6-dimethylphenyl)benzo[e][1,2,4]triazin-3-ylamino)-1-(3-(pyrrolidin-1-yl)propyl)pyridin-2(1H)-one | 76 |
| 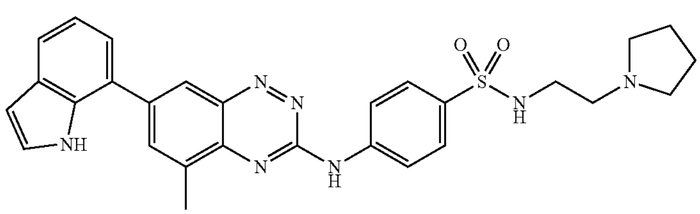 [SMILES: Cc1cc(-c2cccc3cc[nH]c23)cc2nnc(Nc3ccc(S(=O)(=O)NCCN4CCCC4)cc3)nc12] | 4-[7-(1H-indol-4-yl)-5-methyl-benzo[1,2,4]triazin-3-ylamino]-N-(2-pyrrolidin-1-yl-ethyl)-benzenesulfonamide | 339 |
| 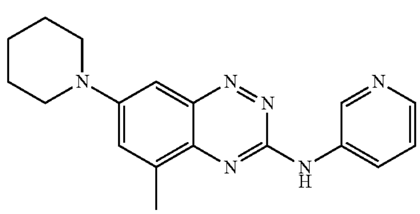 [SMILES: Cc1cc(N2CCCCC2)cc2nnc(Nc3cccnc3)nc12] | (5-methyl-7-piperidin-1-yl-benzo[1,2,4]triazin-3-yl)-pyridin-3-yl-amine | >10000 |

TABLE 1-continued

Tests Results of Inhibition of Src Kinase by Some Compounds of the Invention

| Structure | Name | Src IC50 (nM) |
|---|---|---|
| 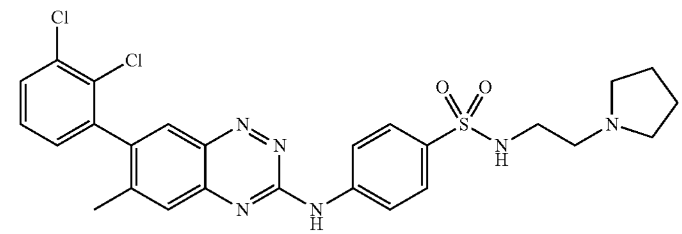 [SMILES: Cc1cc2nc(Nc3ccc(S(=O)(=O)NCCN4CCCC4)cc3)nnc2cc1-c1cccc(Cl)c1Cl] | 4-[7-(2,3-dichloro-phenyl)-6-methyl-benzo[1,2,4]triazin-3-ylamino]-N-(2-pyrrolidin-1-yl-ethyl)-benzenesulfonamide | 142 |
| 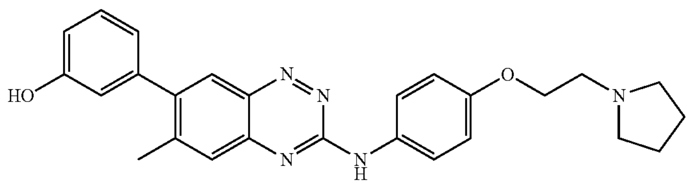 [SMILES: Cc1cc2nc(Nc3ccc(OCCN4CCCC4)cc3)nnc2cc1-c1cccc(O)c1] | 3-{6-methyl-3-[4-(2-pyrrolidin-1-yl-ethoxy)-phenylamino]-benzo[1,2,4]triazin-7-yl}-phenol | 17.7 |
| 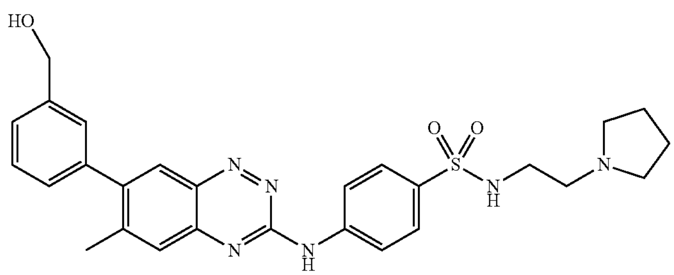 [SMILES: Cc1cc2nc(Nc3ccc(S(=O)(=O)NCCN4CCCC4)cc3)nnc2cc1-c1cccc(CO)c1] | 4-[7-(3-hydroxymethyl-phenyl)-6-methyl-benzo[1,2,4]triazin-3-ylamino]-N-(2-pyrrolidin-1-yl-ethyl)-benzenesulfonamide | 439 |
| 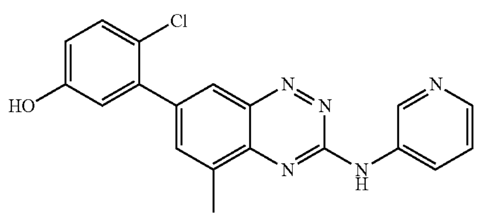 [SMILES: Cc1cc(-c2cc(O)ccc2Cl)cc2nnc(Nc3cccnc3)nc12] | 4-chloro-3-[5-methyl-3-(pyridin-3-ylamino)-benzo[1,2,4]triazin-7-yl]-phenol | 6.5 |
| 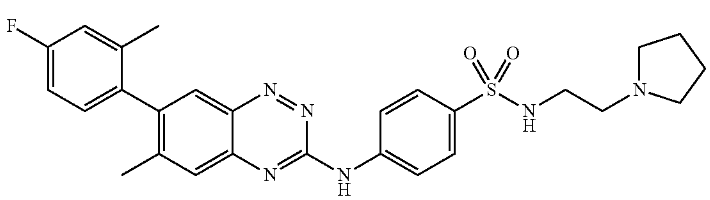 [SMILES: Cc1cc(F)ccc1-c1cc2nnc(Nc3ccc(S(=O)(=O)NCCN4CCCC4)cc3)nc2cc1C] | 4-[7-(4-fluoro-2-methyl-phenyl)-6-methyl-benzo[1,2,4]triazin-3-ylamino]-N-(2-pyrrolidin-1-yl-ethyl)-benzenesulfonamide | 20.4 |
| 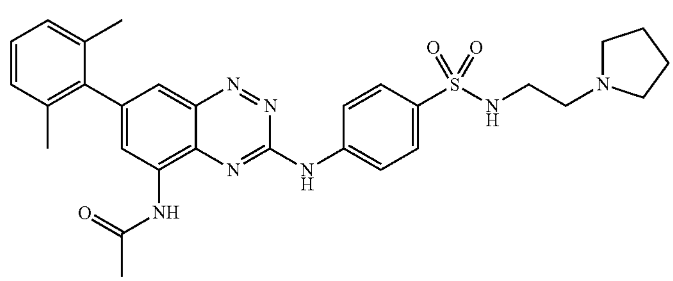 [SMILES: CC(=O)Nc1cc(-c2c(C)cccc2C)cc2nnc(Nc3ccc(S(=O)(=O)NCCN4CCCC4)cc3)nc12] | N-{7-(2,6-dimethyl-phenyl)-3-[4-(2-pyrrolidin-1-yl-ethylsulfamoyl)-phenylamino]-benzo[1,2,4]triazin-5-yl}-acetamide | 29.9 |

TABLE 1-continued

Tests Results of Inhibition of Src Kinase by Some Compounds of the Invention

| Structure | Name | Src IC50 (nM) |
|---|---|---|
| 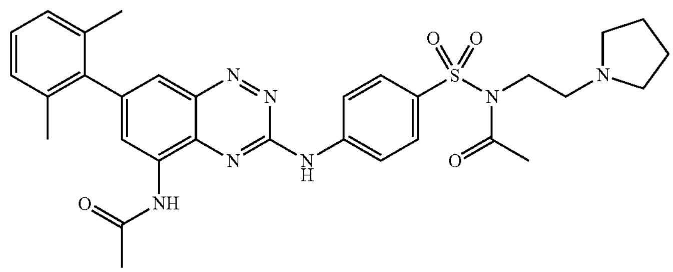 [SMILES: CC(=O)Nc1cc(-c2c(C)cccc2C)cc2nnc(Nc3ccc(S(=O)(=O)N(CCN4CCCC4)C(C)=O)cc3)nc12] | N-[3-{4-[acetyl-(2-pyrrolidin-1-yl-ethyl)-sulfamoyl]-phenylamino}-7-(2,6-dimethyl-phenyl)-benzo[1,2,4]triazin-5-yl]-acetamide | 34.2 |
| 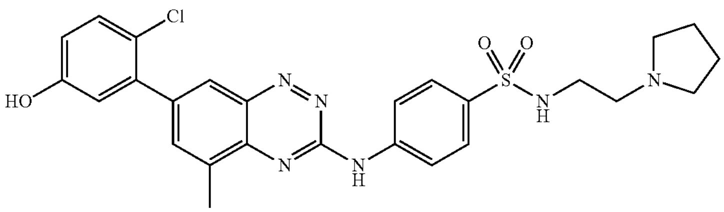 [SMILES: Cc1cc(-c2cc(O)ccc2Cl)cc2nnc(Nc3ccc(S(=O)(=O)NCCN4CCCC4)cc3)nc12] | 4-[7-(2-chloro-5-hydroxy-phenyl)-5-methyl-benzo[1,2,4]triazin-3-ylamino]-N-(2-pyrrolidin-1-yl-ethyl)-benzenesulfonamide; | 3.6 |
| 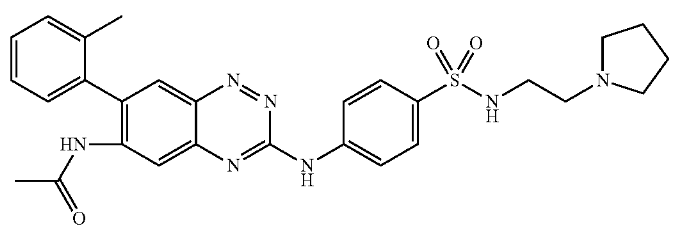 [SMILES: CC(=O)Nc1cc2nc(Nc3ccc(S(=O)(=O)NCCN4CCCC4)cc3)nnc2cc1-c1ccccc1C] | N-{3-[4-(2-pyrrolidin-1-yl-ethylsulfamoyl)-phenylamino]-7-o-tolyl-benzo[1,2,4]triazin-6-yl}-acetamide | 111 |
| 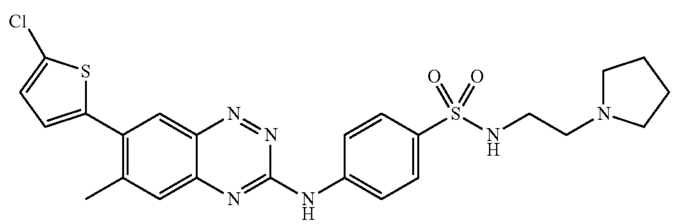 [SMILES: Cc1cc2nc(Nc3ccc(S(=O)(=O)NCCN4CCCC4)cc3)nnc2cc1-c1ccc(Cl)s1] | 4-[7-(5-chloro-thiophen-2-yl)-6-methyl-benzo[1,2,4]triazin-3-ylamino]-N-(2-pyrrolidin-1-yl-ethyl)-benzenesulfonamide | 880 |
| 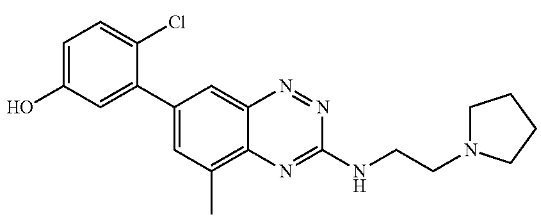 [SMILES: Cc1cc(-c2cc(O)ccc2Cl)cc2nnc(NCCN3CCCC3)nc12] | 4-chloro-3-[5-methyl-3-(2-pyrrolidin-1-yl-ethylamino)-benzo[1,2,4]triazin-7-yl]-phenol | 4510 |
| 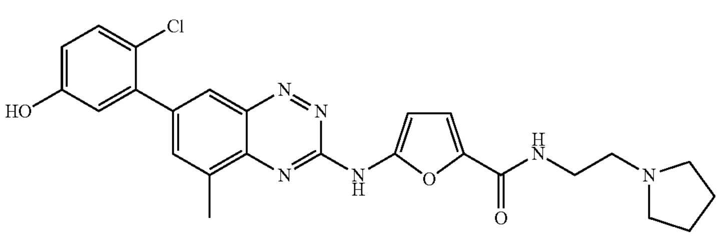 [SMILES: Cc1cc(-c2cc(O)ccc2Cl)cc2nnc(Nc3ccc(C(=O)NCCN4CCCC4)o3)nc12] | 5-[7-(2-chloro-5-hydroxy-phenyl)-5-methyl-benzo[1,2,4]triazin-3-ylamino]-furan-2-carboxylic acid (2-pyrrolidin-1-yl-ethyl)-amide | 12.2 |

TABLE 1-continued

Tests Results of Inhibition of Src Kinase by Some Compounds of the Invention

| Structure | Name | Src IC50 (nM) |
|---|---|---|
| 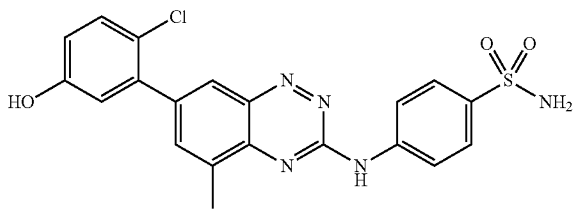 [SMILES: Cc1cc(-c2cc(O)ccc2Cl)cc2nnc(Nc3ccc(S(N)(=O)=O)cc3)nc12] | 4-[7-(2-chloro-5-hydroxy-phenyl)-5-methyl-benzo[1,2,4]triazin-3-ylamino]-benzenesulfonamide | 70.3 |
| 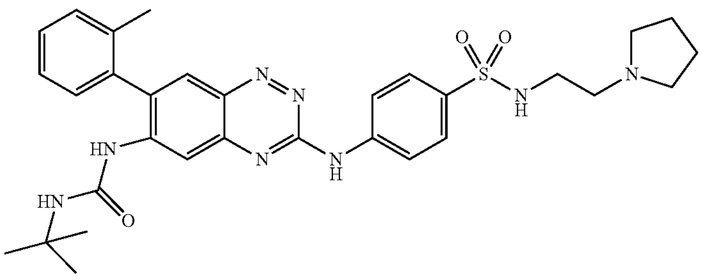 [SMILES: Cc1ccccc1-c1cc2nnc(Nc3ccc(S(=O)(=O)NCCN4CCCC4)cc3)nc2cc1NC(=O)NC(C)(C)C] | 4-[6-(3-tert-butyl-ureido)-7-o-tolyl-benzo[1,2,4]triazin-3-ylamino]-N-(2-pyrrolidin-1-yl-ethyl)-benzenesulfonamide | 8000 |
| 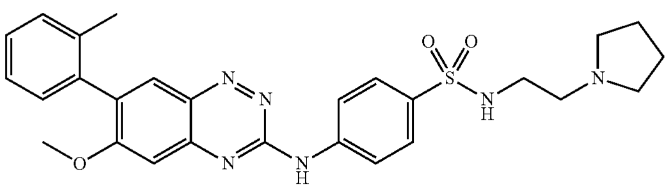 [SMILES: COc1cc2nc(Nc3ccc(S(=O)(=O)NCCN4CCCC4)cc3)nnc2cc1-c1ccccc1C] | 4-(6-methoxy-7-o-tolyl-benzo[1,2,4]triazin-3-ylamino)-N-(2-pyrrolidin-1-yl-ethyl)-benzenesulfonamide | 10 |
| 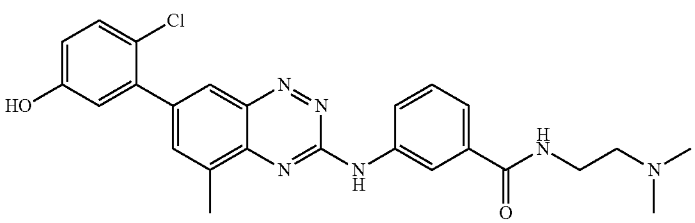 [SMILES: Cc1cc(-c2cc(O)ccc2Cl)cc2nnc(Nc3cccc(C(=O)NCCN(C)C)c3)nc12] | 3-[7-(2-chloro-5-hydroxy-phenyl)-5-methyl-benzo[1,2,4]triazin-3-ylamino]-N-(2-dimethylamino-ethyl)-benzamide | 4.8 |
| 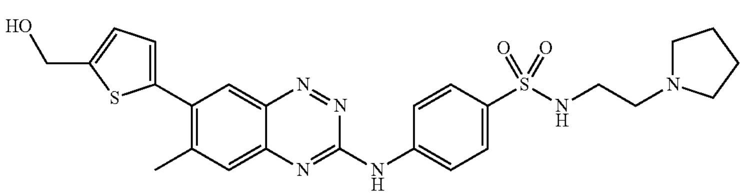 [SMILES: Cc1cc2nc(Nc3ccc(S(=O)(=O)NCCN4CCCC4)cc3)nnc2cc1-c1ccc(CO)s1] | 4-[7-(5-hydroxymethyl-thiophen-2-yl)-6-methyl-benzo[1,2,4]triazin-3-ylamino]-N-(2-pyrrolidin-1-yl-ethyl)-benzenesulfonamide | 1730 |
| 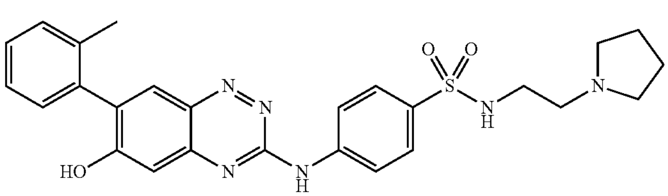 [SMILES: Cc1ccccc1-c1cc2nnc(Nc3ccc(S(=O)(=O)NCCN4CCCC4)cc3)nc2cc1O] | 4-(6-hydroxy-7-o-tolyl-benzo[1,2,4]triazin-3-ylamino)-N-(2-pyrrolidin-1-yl-ethyl)-benzenesulfonamide | 117 |
| 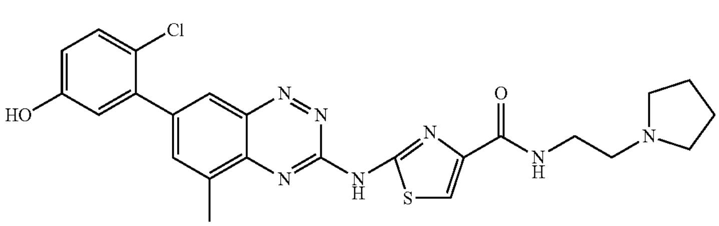 [SMILES: Cc1cc(-c2cc(O)ccc2Cl)cc2nnc(Nc3nc(C(=O)NCCN4CCCC4)cs3)nc12] | 2-(7-(2-chloro-5-hydroxyphenyl)-5-methylbenzo[e][1,2,4]triazin-3-ylamino)-N-(2-(pyrrolidin-1-yl)ethyl)thiazole-4-carboxamide | 5.7 |

TABLE 1-continued

Tests Results of Inhibition of Src Kinase by Some Compounds of the Invention

| Structure | Name | Src IC50 (nM) |
|---|---|---|
| 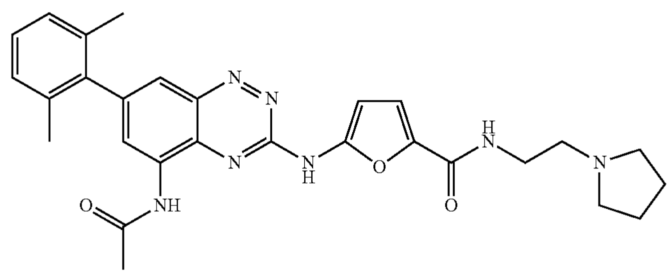 [SMILES: CC(=O)Nc1cc(-c2c(C)cccc2C)cc2nnc(Nc3ccc(C(=O)NCCN4CCCC4)o3)nc12] | 5-[5-acetylamino-7-(2,6-dimethyl-phenyl)-benzo[1,2,4]triazin-3-ylamino]-furan-2-carboxylic acid (2-pyrrolidin-1-yl-ethyl)-amide | 137 |
| 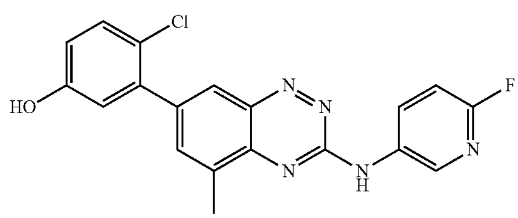 [SMILES: Cc1cc(-c2cc(O)ccc2Cl)cc2nnc(Nc3ccc(F)nc3)nc12] | 4-chloro-3-[3-(6-fluoro-pyridin-3-ylamino)-5-methyl-benzo[1,2,4]triazin-7-yl]-phenol | >10000 |
| 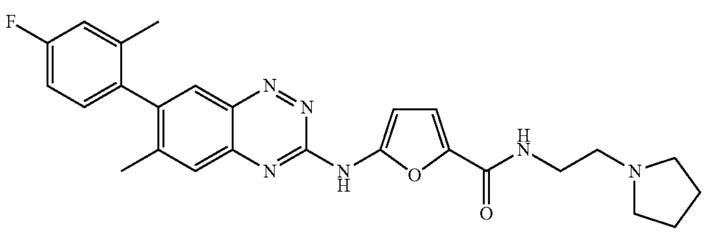 [SMILES: Cc1cc(F)ccc1-c1cc2nnc(Nc3ccc(C(=O)NCCN4CCCC4)o3)nc2cc1C] | 5-[7-(4-fluoro-2-methyl-phenyl)-6-methyl-benzo[1,2,4]triazin-3-ylamino]-furan-2-carboxylic acid (2-pyrrolidin-1-yl-ethyl)-amide | 120 |
| 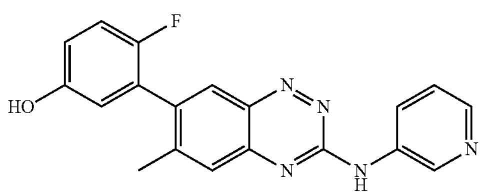 [SMILES: Cc1cc2nc(Nc3cccnc3)nnc2cc1-c1cc(O)ccc1F] | 4-fluoro-3-[6-methyl-3-(pyridin-3-ylamino)-benzo[1,2,4]triazin-7-yl]-phenol | 26.8 |
| 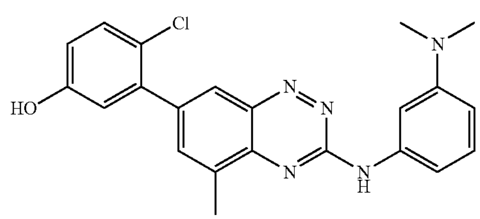 [SMILES: Cc1cc(-c2cc(O)ccc2Cl)cc2nnc(Nc3cccc(N(C)C)c3)nc12] | 4-chloro-3-[3-(3-dimethylamino-phenylamino)-5-methyl-benzo[1,2,4]triazin-7-yl]-phenol | 21.6 |
| 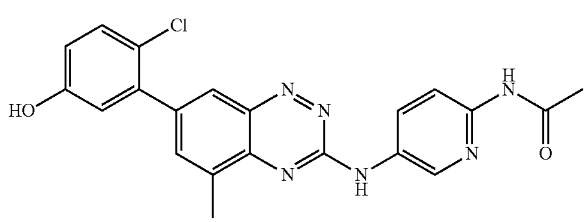 [SMILES: CC(=O)Nc1ccc(Nc2nnc3cc(-c4cc(O)ccc4Cl)cc(C)c3n2)cn1] | N-{5-[7-(2-chloro-5-hydroxy-phenyl)-5-methyl-benzo[1,2,4]triazin-3-ylamino]-pyridin-2-yl}-acetamide | 118.4 |

TABLE 1-continued

Tests Results of Inhibition of Src Kinase by Some Compounds of the Invention

| Structure | Name | Src IC50 (nM) |
|---|---|---|
| 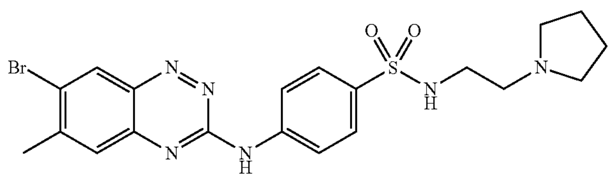 [SMILES: Cc1cc2nc(Nc3ccc(S(=O)(=O)NCCN4CCCC4)cc3)nnc2cc1Br] | [7-Bromo-6-methyl-benzo[1,2,4]triazin-3-ylamino]-N-(2-pyrrolidin-1-yl-ethyl)-benzene-4-sulfonamide. Triflate | >10000 |
| 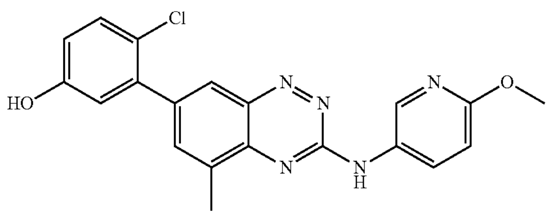 [SMILES: COc1ccc(Nc2nnc3cc(-c4cc(O)ccc4Cl)cc(C)c3n2)cn1] | 4-chloro-3-[3-(6-methoxy-pyridin-3-ylamino)-5-methyl-benzo[1,2,4]triazin-7-yl]-phenol | 11.2 |
| 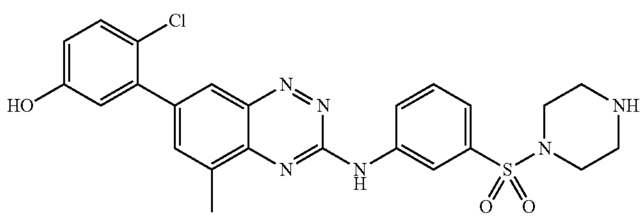 [SMILES: Cc1cc(-c2cc(O)ccc2Cl)cc2nnc(Nc3cccc(S(=O)(=O)N4CCNCC4)c3)nc12] | 4-chloro-3-{5-methyl-3-[3-(piperazine-1-sulfonyl)-phenylamino]-benzo[1,2,4]triazin-7-yl}-pheno | 52.8 |
| 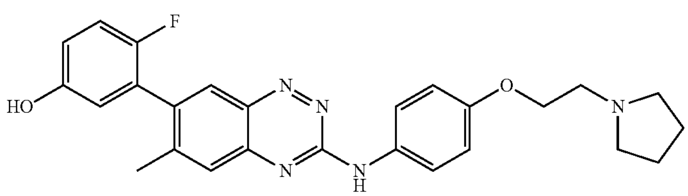 [SMILES: Cc1cc2nc(Nc3ccc(OCCN4CCCC4)cc3)nnc2cc1-c1cc(O)ccc1F] | 3-(3-(4-(2-(pyrrolidin-1-yl)ethoxy)phenylamino)-6-methylbenzo[e][1,2,4]triazin-7-yl)-4-fluorophenol | 13.7 |
| 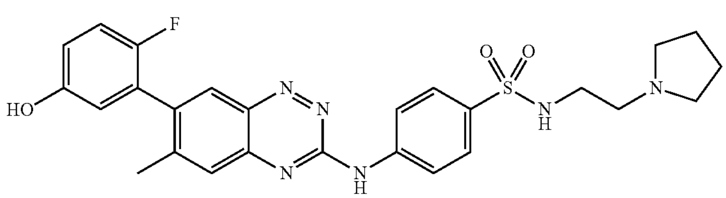 [SMILES: Cc1cc2nc(Nc3ccc(S(=O)(=O)NCCN4CCCC4)cc3)nnc2cc1-c1cc(O)ccc1F] | 4-[7-(2-fluoro-5-hydroxy-phenyl)-6-methyl-benzo[1,2,4]triazin-3-ylamino]-N-(2-pyrrolidin-1-yl-ethyl)-benzenesulfonamide | 8.5 |
| 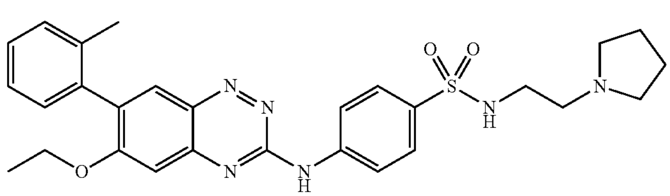 [SMILES: CCOc1cc2nc(Nc3ccc(S(=O)(=O)NCCN4CCCC4)cc3)nnc2cc1-c1ccccc1C] | 4-(6-ethoxy-7-o-tolyl-benzo[1,2,4]triazin-3-ylamino)-N-(2-pyrrolidin-1-yl-ethyl)-benzenesulfonamide | 27.2 |
| 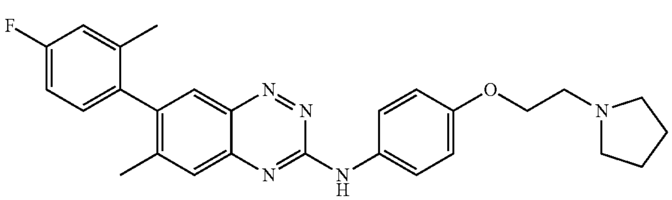 [SMILES: Cc1cc(F)ccc1-c1cc2nnc(Nc3ccc(OCCN4CCCC4)cc3)nc2cc1C] | [7-(4-fluoro-2-methyl-phenyl)-6-methyl-benzo[1,2,4]triazin-3-yl]-[4-(2-pyrrolidin-1-yl-ethoxy)-phenyl]-amine | 26.1 |

TABLE 1-continued

Tests Results of Inhibition of Src Kinase by Some Compounds of the Invention

| Structure | Name | Src IC50 (nM) |
|---|---|---|
| 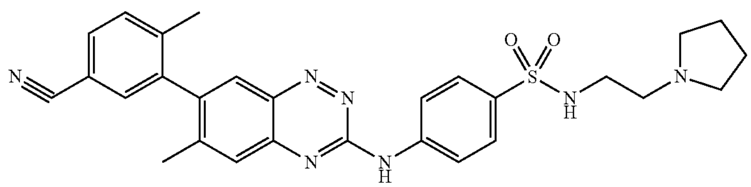 [SMILES: Cc1ccc(C#N)cc1-c1cc2nnc(Nc3ccc(S(=O)(=O)NCCN4CCCC4)cc3)nc2cc1C] | 4-[7-(5-Cyano-2-methyl-phenyl)-6-methyl-benzo[1,2,4]triazin-3-ylamino]-N-(2-pyrrolidin-1-yl-ethyl)-benzenesulfonamide | 12.3 |
| 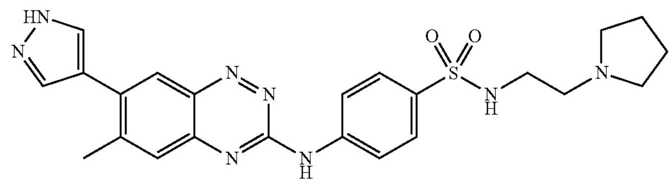 [SMILES: Cc1cc2nc(Nc3ccc(S(=O)(=O)NCCN4CCCC4)cc3)nnc2cc1-c1cn[nH]c1] | 4-[6-methyl-7-(1H-pyrazol-4-yl)-benzo[1,2,4]triazin-3-ylamino]-N-(2-pyrrolidin-1-yl-ethyl)-benzenesulfonamide | 8000 |
| 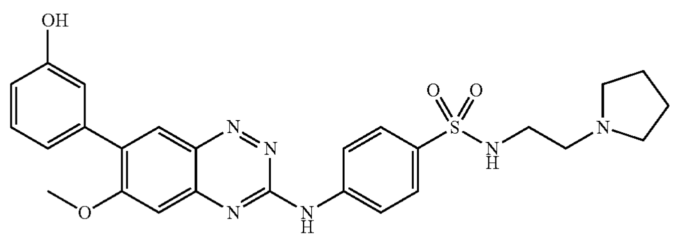 [SMILES: COc1cc2nc(Nc3ccc(S(=O)(=O)NCCN4CCCC4)cc3)nnc2cc1-c1cccc(O)c1] | 4-[7-(3-hydroxy-phenyl)-6-methoxy-benzo[1,2,4]triazin-3-ylamino]-N-(2-pyrrolidin-1-yl-ethyl)-benzenesulfonamide | 37.6 |
| 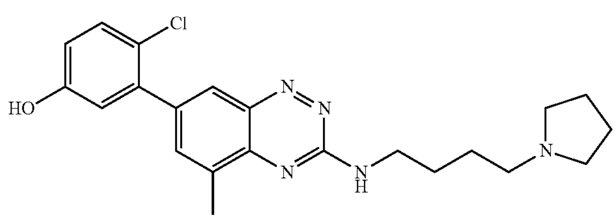 [SMILES: Cc1cc(-c2cc(O)ccc2Cl)cc2nnc(NCCCCN3CCCC3)nc12] | 4-chloro-3-[5-methyl-3-(4-pyrrolidin-1-yl-butylamino)-benzo[1,2,4]triazin-7-yl]-phenol | 1450 |
| 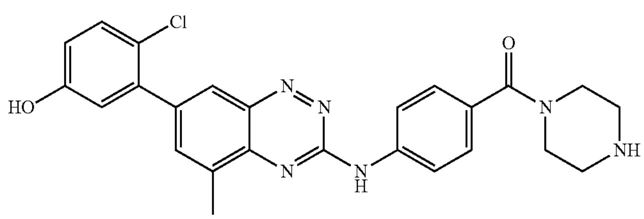 [SMILES: Cc1cc(-c2cc(O)ccc2Cl)cc2nnc(Nc3ccc(C(=O)N4CCNCC4)cc3)nc12] | {4-[7-(2-chloro-5-hydroxy-phenyl)-5-methyl-benzo[1,2,4]triazin-3-ylamino]-phenyl}-piperazin-1-yl-methanone | 3.6 |
| 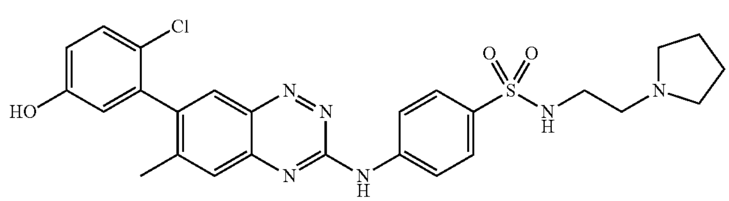 | 4-[7-(2-chloro-5-hydroxy-phenyl)-6-methyl-benzo[1,2,4]triazin-3-ylamino]-N-(2-pyrrolidin-1-yl-ethyl)-benzenesulfonamide | 1.6 |

TABLE 1-continued

Tests Results of Inhibition of Src Kinase by Some Compounds of the Invention

| Structure | Name | Src IC50 (nM) |
|---|---|---|
| 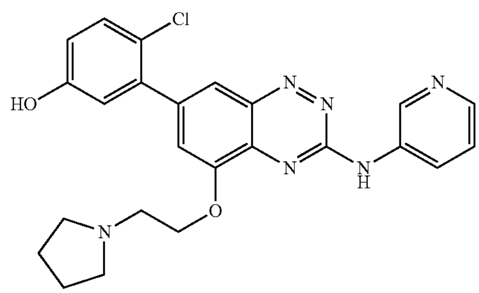 [SMILES: Oc1ccc(Cl)c(-c2cc(OCCN3CCCC3)c3nc(Nc4cccnc4)nnc3c2)c1] | 4-chloro-3-[3-(pyridin-3-ylamino)-5-(2-pyrrolidin-1-yl-ethoxy)-benzo[1,2,4]triazin-7-yl]-phenol | 46.5 |
| 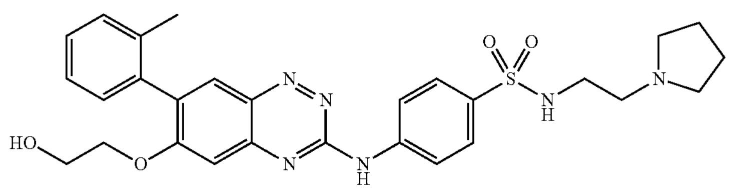 [SMILES: Cc1ccccc1-c1cc2nnc(Nc3ccc(S(=O)(=O)NCCN4CCCC4)cc3)nc2cc1OCCO] | 4-[6-(2-hydroxy-ethoxy)-7-o-tolyl-benzo[1,2,4]triazin-3-ylamino]-N-(2-pyrrolidin-1-yl-ethyl)-benzenesulfonamide | >10000 |
| 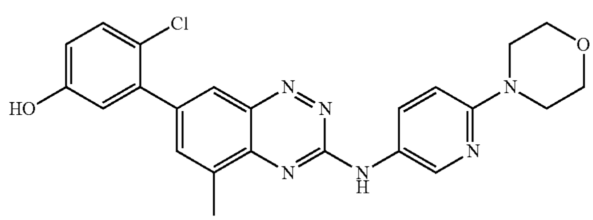 [SMILES: Cc1cc(-c2cc(O)ccc2Cl)cc2nnc(Nc3ccc(N4CCOCC4)nc3)nc12] | 4-chloro-3-[5-methyl-3-(6-morpholin-4-yl-pyridin-3-ylamino)-benzo[1,2,4]triazin-7-yl]-phenol | 6.8 |
| 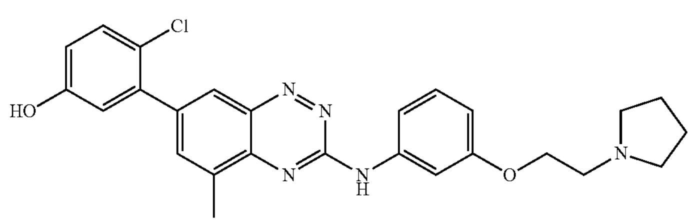 [SMILES: Cc1cc(-c2cc(O)ccc2Cl)cc2nnc(Nc3cccc(OCCN4CCCC4)c3)nc12] | 4-chloro-3-{5-methyl-3-[3-(2-pyrrolidin-1-yl-ethoxy)-phenylamino]-benzo[1,2,4]triazin-7-yl}-phenol | 1.8 |
| 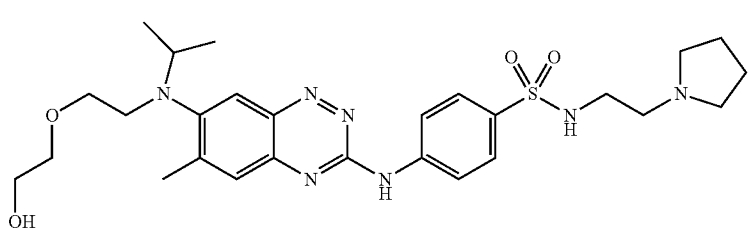 [SMILES: Cc1cc2nc(Nc3ccc(S(=O)(=O)NCCN4CCCC4)cc3)nnc2cc1N(CCOCCO)C(C)C] | 4-(7-{[2-(2-hydroxy-ethoxy)-ethyl]-isopropyl-amino}-6-methyl-benzo[1,2,4]triazin-3-ylamino)-N-(2-pyrrolidin-1-yl-ethyl)-benzenesulfonamide | 10000 |
| 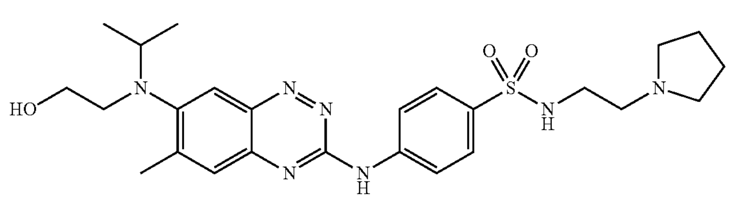 [SMILES: Cc1cc2nc(Nc3ccc(S(=O)(=O)NCCN4CCCC4)cc3)nnc2cc1N(CCO)C(C)C] | [7-(2'hydroxyethyl-isopropylamino)-6-methyl-benzo[1,2,4]triazin-3-ylamino]-N-(2-pyrrolidin-1-yl-ethyl)-benzene-4-sulfonamide | 10000 |

TABLE 1-continued

Tests Results of Inhibition of Src Kinase by Some Compounds of the Invention

| Structure | Name | Src IC50 (nM) |
|---|---|---|
| 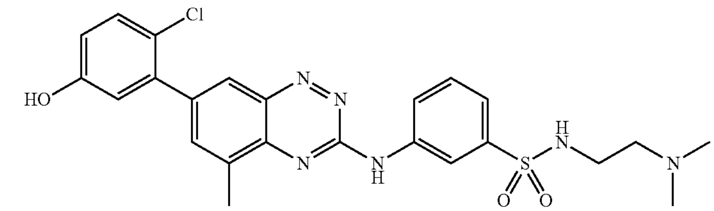 [SMILES: Cc1cc(-c2cc(O)ccc2Cl)cc2nnc(Nc3cccc(S(=O)(=O)NCCN(C)C)c3)nc12] | 3-[7-(2-chloro-5-hydroxy-phenyl)-5-methyl-benzo[1,2,4]triazin-3-ylamino]-N-(2-dimethylamino-ethyl)-benzenesulfonamide | 4.2 |
| 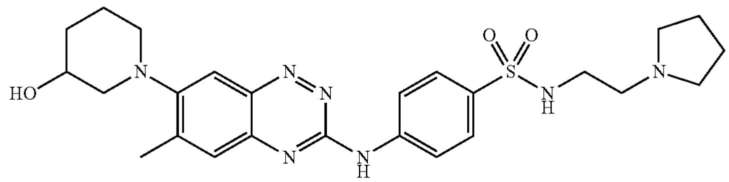 [SMILES: Cc1cc2nc(Nc3ccc(S(=O)(=O)NCCN4CCCC4)cc3)nnc2cc1N1CCCC(O)C1] | 4-[7-(3-hydroxy-piperidin-1-yl)-6-methyl-benzo[1,2,4]triazin-3-ylamino]-N-(2-pyrrolidin-1-yl-ethyl)-benzenesulfonamide | 1772 |
| 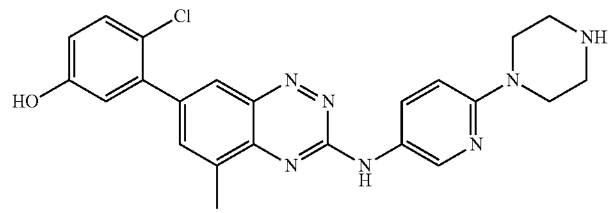 [SMILES: Cc1cc(-c2cc(O)ccc2Cl)cc2nnc(Nc3ccc(N4CCNCC4)nc3)nc12] | 4-chloro-3-[5-methyl-3-(6-piperazin-1-yl-pyridin-3-ylamino)-benzo[1,2,4]triazin-7-yl]-phenol | 3.3 |
| 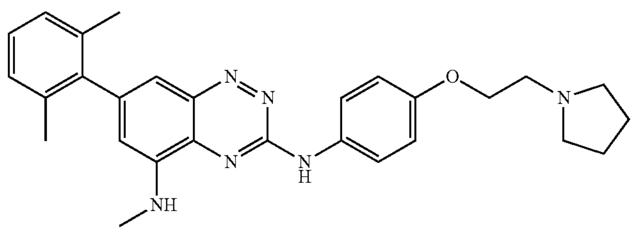 [SMILES: CNc1cc(-c2c(C)cccc2C)cc2nnc(Nc3ccc(OCCN4CCCC4)cc3)nc12] | 7-(2,6-dimethyl-phenyl)-N5-methyl-N3-[4-(2-pyrrolidin-1-yl-ethoxy)-phenyl]-benzo[1,2,4]triazine-3,5-diamine | 10.6 |
| 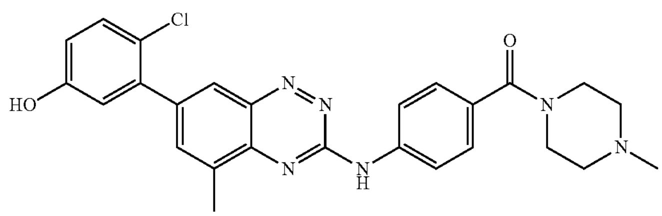 [SMILES: Cc1cc(-c2cc(O)ccc2Cl)cc2nnc(Nc3ccc(C(=O)N4CCN(C)CC4)cc3)nc12] | {4-[7-(2-chloro-5-hydroxy-phenyl)-5-methyl-benzo[1,2,4]triazin-3-ylamino]-phenyl}-(4-methyl-piperazin-1-yl)-methanone | 2.9 |
| 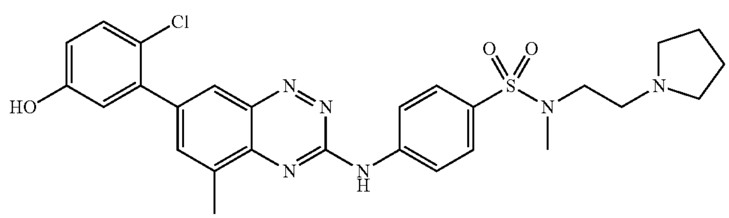 [SMILES: Cc1cc(-c2cc(O)ccc2Cl)cc2nnc(Nc3ccc(S(=O)(=O)N(C)CCN4CCCC4)cc3)nc12] | 4-[7-(2-chloro-5-hydroxy-phenyl)-5-methyl-benzo[1,2,4]triazin-3-ylamino]-N-methyl-N-(2-pyrrolidin-1-yl-ethyl)-benzenesulfonamide | 3 |
| 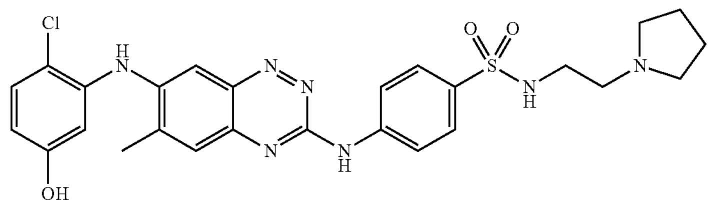 [SMILES: Cc1cc2nc(Nc3ccc(S(=O)(=O)NCCN4CCCC4)cc3)nnc2cc1Nc1cc(O)ccc1Cl] | 4-[7-(2-chloro-5-hydroxy-phenylamino)-6-methyl-benzo[1,2,4]triazin-3-ylamino]-N-(2-pyrrolidin-1-yl-ethyl)-benzenesulfonamide | 10000 |

TABLE 1-continued

Tests Results of Inhibition of Src Kinase by Some Compounds of the Invention

| Structure | Name | Src IC50 (nM) |
|---|---|---|
| 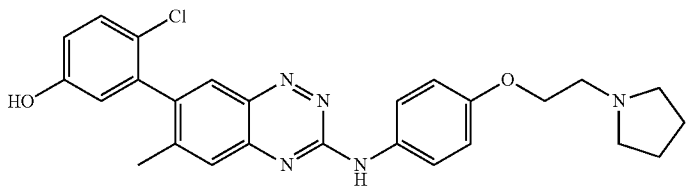 | 4-chloro-3-{6-methyl-3-[4-(2-pyrrolidin-1-yl-ethoxy)-phenylamino]-benzo[1,2,4]triazin-7-yl}-phenol | 4.2 |
| 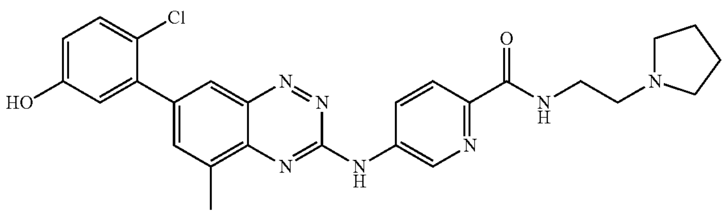 [SMILES: Cc1cc(-c2cc(O)ccc2Cl)cc2nnc(Nc3ccc(C(=O)NCCN4CCCC4)nc3)nc12] | 5-[7-(2-chloro-5-hydroxy-phenyl)-5-methyl-benzo[1,2,4]triazin-3-ylamino]-pyridine-2-carboxylic acid (2-pyrrolidin-1-yl-ethyl)-amide | 2.6 |
| 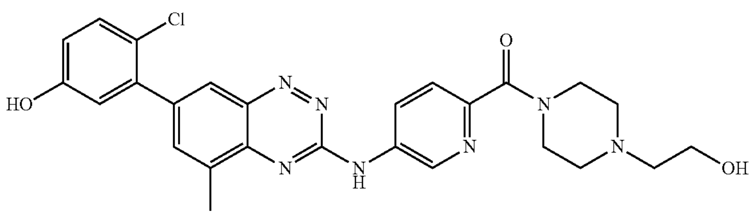 [SMILES: Cc1cc(-c2cc(O)ccc2Cl)cc2nnc(Nc3ccc(C(=O)N4CCN(CCO)CC4)nc3)nc12] | {5-[7-(2-chloro-5-hydroxy-phenyl)-5-methyl-benzo[1,2,4]triazin-3-ylamino]-pyridin-2-yl}-[4-(2-hydroxy-ethyl)-piperazin-1-yl]-methanone | 10.3 |
| 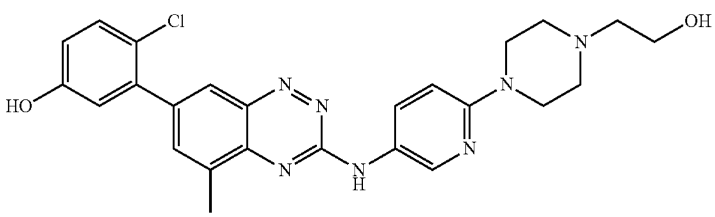 [SMILES: Cc1cc(-c2cc(O)ccc2Cl)cc2nnc(Nc3ccc(N4CCN(CCO)CC4)nc3)nc12] | 4-chloro-3-(3-{6-[4-(2-hydroxy-ethyl)-piperazin-1-yl]-pyridin-3-ylamino}-5-methyl-benzo[1,2,4]triazin-7-yl)-phenol | 1.8 |
| 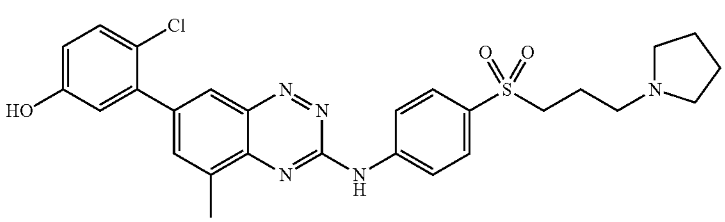 [SMILES: Cc1cc(-c2cc(O)ccc2Cl)cc2nnc(Nc3ccc(S(=O)(=O)CCCN4CCCC4)cc3)nc12] | 4-chloro-3-{5-methyl-3-[4-(3-pyrrolidin-1-yl-propane-1-sulfonyl)-phenylamino]-benzo[1,2,4]triazin-7-yl}-phenol | 5 |
| 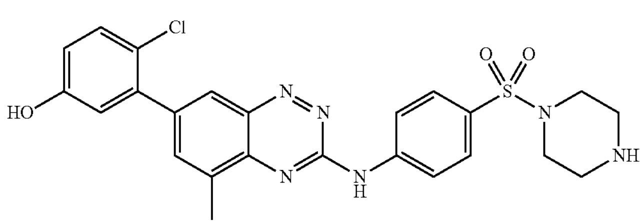 [SMILES: Cc1cc(-c2cc(O)ccc2Cl)cc2nnc(Nc3ccc(S(=O)(=O)N4CCNCC4)cc3)nc12] | 4-chloro-3-{5-methyl-3-[4-(piperazine-1-sulfonyl)-phenylamino]-benzo[1,2,4]triazin-7-yl)-phenol | 6.6 |
| 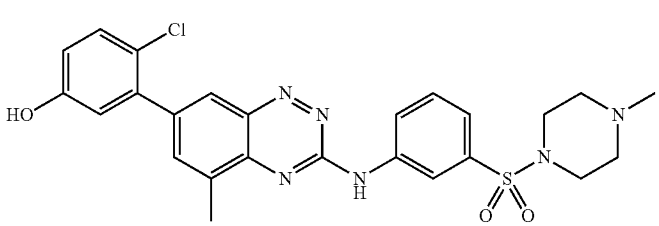 [SMILES: Cc1cc(-c2cc(O)ccc2Cl)cc2nnc(Nc3cccc(S(=O)(=O)N4CCN(C)CC4)c3)nc12] | 4-chloro-3-{5-methyl-3-[3-(4-methyl-piperazine-1-sulfonyl)-phenylamino]-benzo[1,2,4]triazin-7-yl}-phenol | 433 |

TABLE 1-continued

Tests Results of Inhibition of Src Kinase by Some Compounds of the Invention

| Structure | Name | Src IC50 (nM) |
|---|---|---|
| 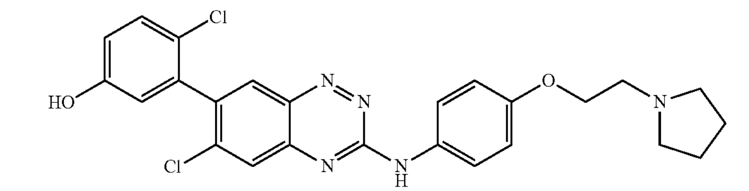 | 4-chloro-3-{6-chloro-3-[4-(2-pyrrolidin-1-yl-ethoxy)-phenylamino]-benzo[1,2,4]triazin-7-yl}-phenol | 1.2 |
| 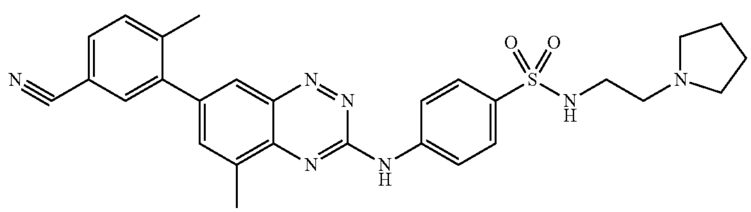 [SMILES: Cc1ccc(C#N)cc1-c1cc(C)c2nc(Nc3ccc(S(=O)(=O)NCCN4CCCC4)cc3)nnc2c1] | 4-[7-(5-cyano-2-methyl-phenyl)-5-methyl-benzo[1,2,4]triazin-3-ylamino]-N-(2-pyrrolidin-1-yl-ethyl)-benzenesulfonamide | 25.2 |
| 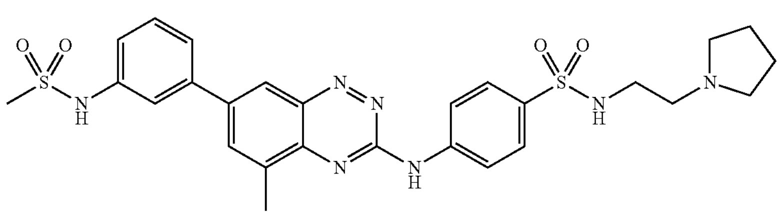 [SMILES: Cc1cc(-c2cccc(NS(C)(=O)=O)c2)cc2nnc(Nc3ccc(S(=O)(=O)NCCN4CCCC4)cc3)nc12] | 4-[7-(3-methanesulfonylamino-phenyl)-5-methyl-benzo[1,2,4]triazin-3-ylamino]-N-(2-pyrrolidin-1-yl-ethyl)-benzenesulfonamide | 2900 |
| 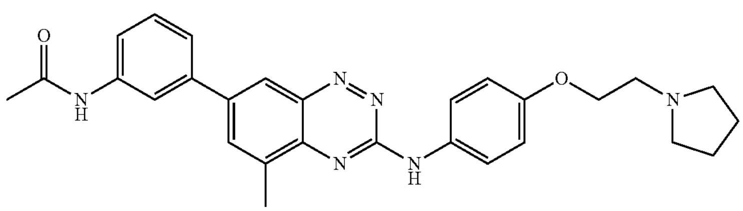 [SMILES: CC(=O)Nc1cccc(-c2cc(C)c3nc(Nc4ccc(OCCN5CCCC5)cc4)nnc3c2)c1] | N-(3-{5-methyl-3-[4-(2-pyrrolidin-1-yl-ethoxy)-phenylamino]-benzo[1,2,4]triazin-7-yl}-phenyl)-acetamide | 3977 |
| 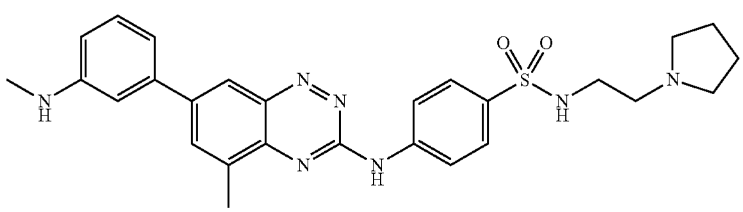 [SMILES: CNc1cccc(-c2cc(C)c3nc(Nc4ccc(S(=O)(=O)NCCN5CCCC5)cc4)nnc3c2)c1] | 4-[5-methyl-7-(3-methylamino-phenyl)-benzo[1,2,4]triazin-3-ylamino]-N-(2-pyrrolidin-1-yl-ethyl)-benzenesulfonamide | 631 |
| 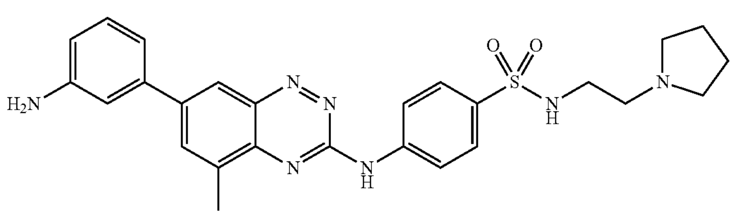 [SMILES: Cc1cc(-c2cccc(N)c2)cc2nnc(Nc3ccc(S(=O)(=O)NCCN4CCCC4)cc3)nc12] | 4-[7-(3-amino-phenyl)-5-methyl-benzo[1,2,4]triazin-3-ylamino]-N-(2-pyrrolidin-1-yl-ethyl)-benzenesulfonamide | 282 |
| 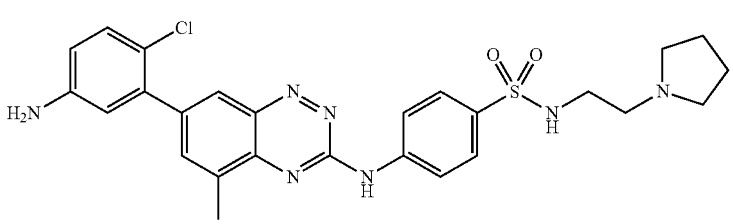 [SMILES: Cc1cc(-c2cc(N)ccc2Cl)cc2nnc(Nc3ccc(S(=O)(=O)NCCN4CCCC4)cc3)nc12] | 4-[7-(5-amino-2-chloro-phenyl)-5-methyl-benzo[1,2,4]triazin-3-ylamino]-N-(2-pyrrolidin-1-yl-ethyl)-benzenesulfonamide | 51 |

TABLE 1-continued

Tests Results of Inhibition of Src Kinase by Some Compounds of the Invention

| Structure | Name | Src IC50 (nM) |
|---|---|---|
| | [7-(2,6-dichloro-phenyl)-5-methyl-benzo[1,2,4]triazin-3-yl]-[4-(piperazine-1-sulfonyl)-phenyl]-amine | 60.5 |
| | [7-(2,6-dichloro-phenyl)-5-methyl-benzo[1,2,4]triazin-3-yl]-[4-(piperazine-1-sulfonyl)-phenyl]-amine | 22.7 |
| 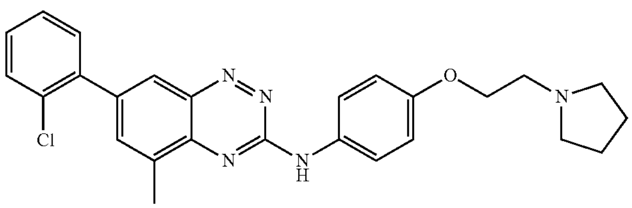 [SMILES: Cc1cc(-c2ccccc2Cl)cc2nnc(Nc3ccc(OCCN4CCCC4)cc3)nc12] | [7-(2-chloro-phenyl)-5-methyl-benzo[1,2,4]triazin-3-yl]-[4-(2-pyrrolidin-1-yl-ethoxy)-phenyl]-amine | 34.8 |
| 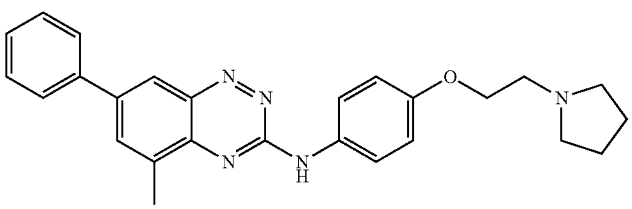 [SMILES: Cc1cc(-c2ccccc2)cc2nnc(Nc3ccc(OCCN4CCCC4)cc3)nc12] | (5-methyl-7-phenyl-benzo[1,2,4]triazin-3-yl)-[4-(2-pyrrolidin-1-yl-ethoxy)-phenyl]-amine | 341 |
| 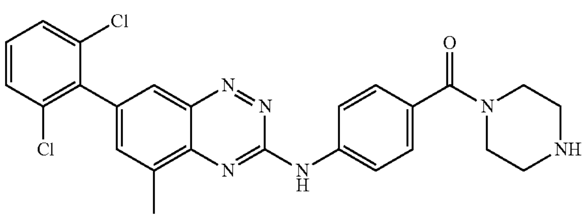 [SMILES: Cc1cc(-c2c(Cl)cccc2Cl)cc2nnc(Nc3ccc(C(=O)N4CCNCC4)cc3)nc12] | {4-[7-(2,6-dichloro-phenyl)-5-methyl-benzo[1,2,4]triazin-3-ylamino]-phenyl}-piperazin-1-yl-methanone | 10.2 |
| 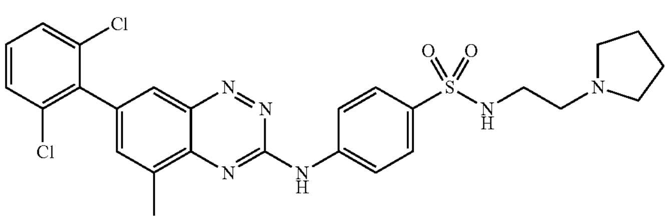 | 4-[7-(2,6-dichloro-phenyl)-5-methyl-benzo[1,2,4]triazin-3-ylamino]-N-(2-pyrrolidin-1-yl-ethyl)-benzenesulfonamide | 14 |
| 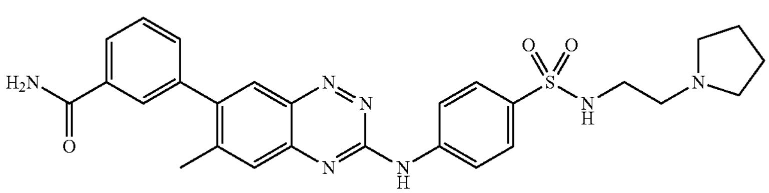 [SMILES: Cc1cc2nc(Nc3ccc(S(=O)(=O)NCCN4CCCC4)cc3)nnc2cc1-c1cccc(C(N)=O)c1] | 3-{6-methyl-3-[4-(2-pyrrolidin-1-yl-ethylsulfamoyl)-phenylamino]-benzo[1,2,4]triazin-7-yl}-benzamide | 2216 |

TABLE 1-continued

Tests Results of Inhibition of Src Kinase by Some Compounds of the Invention

| Structure | Name | Src IC50 (nM) |
|---|---|---|
| 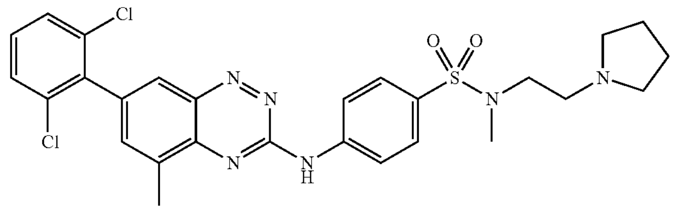 [SMILES: Cc1cc(-c2c(Cl)cccc2Cl)cc2nnc(Nc3ccc(S(=O)(=O)N(C)CCN4CCCC4)cc3)nc12] | 4-[7-(2,6-dichloro-phenyl)-5-methyl-benzo[1,2,4]triazin-3-ylamino]-N-methyl-N-(2-pyrrolidin-1-yl-ethyl)-benzenesulfonamide | 44.2 |
| 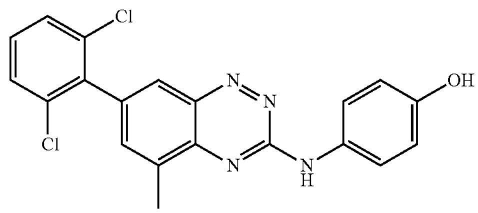 [SMILES: Cc1cc(-c2c(Cl)cccc2Cl)cc2nnc(Nc3ccc(O)cc3)nc12] | 4-[7-(2,6-dichloro-phenyl)-5-methyl-benzo[1,2,4]triazin-3-ylamino]-phenol | 281 |
| 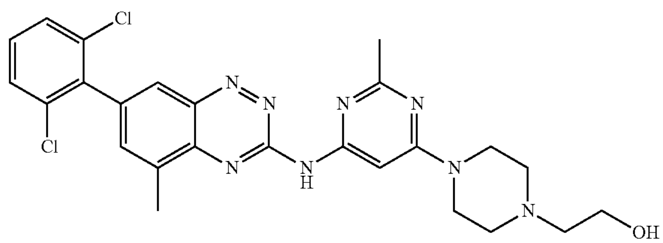 [SMILES: Cc1nc(Nc2nnc3cc(-c4c(Cl)cccc4Cl)cc(C)c3n2)cc(N2CCN(CCO)CC2)n1] | 2-(4-{6-[7-(2,6-dichloro-phenyl)-5-methyl-benzo[1,2,4]triazin-3-ylamino]-2-methyl-pyrimidin-4-yl}-piperazin-1-yl)-ethanol | 383 |
| 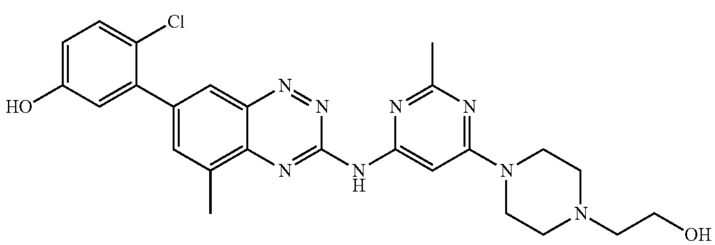 [SMILES: Cc1nc(Nc2nnc3cc(-c4cc(O)ccc4Cl)cc(C)c3n2)cc(N2CCN(CCO)CC2)n1] | 4-chloro-3-(3-{6-[4-(2-hydroxy-ethyl)-piperazin-1-yl]-2-methyl-pyrimidin-4-ylamino}-5-methyl-benzo[1,2,4]triazin-7-yl)-phenol | 68.8 |
| 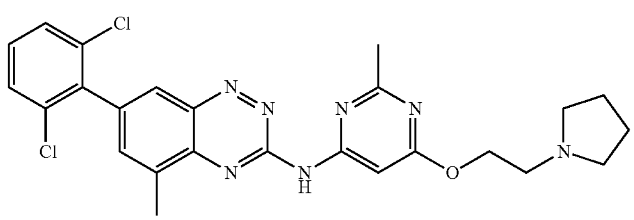 [SMILES: Cc1nc(Nc2nnc3cc(-c4c(Cl)cccc4Cl)cc(C)c3n2)cc(OCCN2CCCC2)n1] | [7-(2,6-dichloro-phenyl)-5-methyl-benzo[1,2,4]triazin-3-yl]-[2-methyl-6-(2-pyrrolidin-1-yl-ethoxy)-pyrimidin-4-yl]-amine | 365 |
| 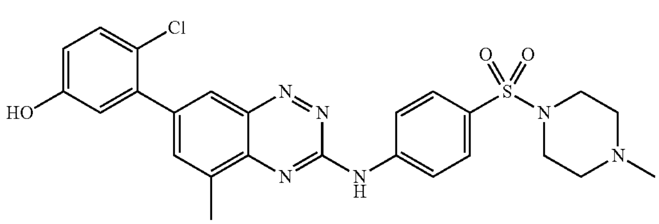 [SMILES: Cc1cc(-c2cc(O)ccc2Cl)cc2nnc(Nc3ccc(S(=O)(=O)N4CCN(C)CC4)cc3)nc12] | 4-chloro-3-{5-methyl-3-[4-(4-methyl-piperazine-1-sulfonyl)-phenylamino]-benzo[1,2,4]triazin-7-yl}-phenol | 63.4 |

TABLE 1-continued

Tests Results of Inhibition of Src Kinase by Some Compounds of the Invention

| Structure | Name | Src IC50 (nM) |
|---|---|---|
| 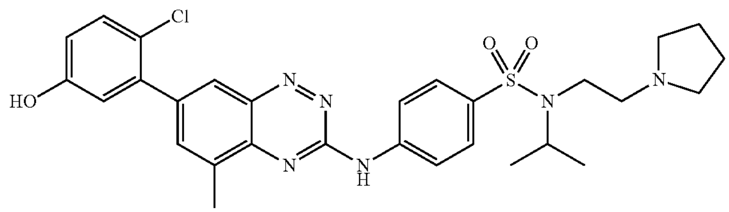 [SMILES: Cc1cc(-c2cc(O)ccc2Cl)cc2nnc(Nc3ccc(S(=O)(=O)N(CCN4CCCC4)C(C)C)cc3)nc12] | 4-[7-(2-chloro-5-hydroxy-phenyl)-5-methyl-benzo[1,2,4]triazin-3-ylamino]-N-isopropyl-N-(2-pyrrolidin-1-yl-ethyl)-benzenesulfonamide | 4.8 |
| 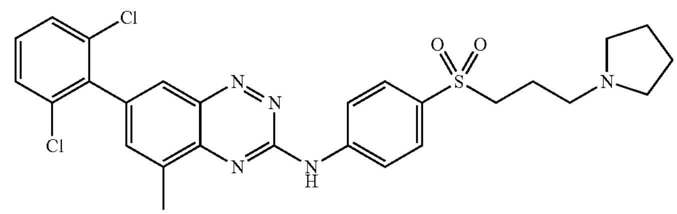 [SMILES: Cc1cc(-c2c(Cl)cccc2Cl)cc2nnc(Nc3ccc(S(=O)(=O)CCCN4CCCC4)cc3)nc12] | [7-(2,6-dichloro-phenyl)-5-methyl-benzo[1,2,4]triazin-3-yl]-[4-(3-pyrrolidine-1-yl-propane-1-sulfonyl)-phenyl]-amine | 21.6 |
| 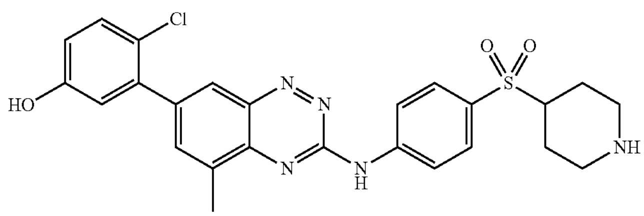 | 4-chloro-3-{5-methyl-3-[4-(piperidine-4-sulfonyl)-phenylamino]-benzo[1,2,4]triazin-7-yl}-phenol | 5.2 |
| 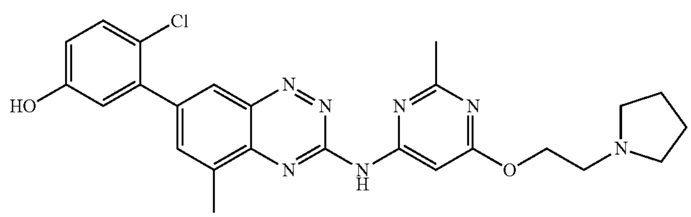 [SMILES: Cc1nc(Nc2nnc3cc(-c4cc(O)ccc4Cl)cc(C)c3n2)cc(OCCN2CCCC2)n1] | 4-chloro-3-{5-methyl-3-[2-methyl-6-(2-pyrrolidin-1-yl-ethoxy)-pyrimidin-4-ylamino]-benzo[1,2,4]triazin-7-yl}-phenol | 77.7 |
| 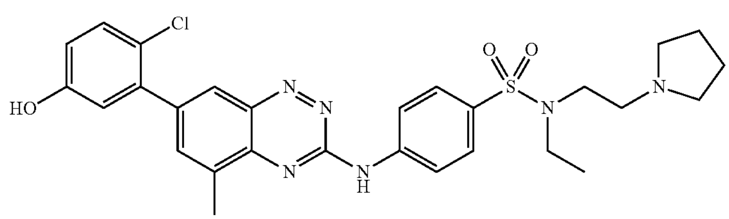 [SMILES: CCN(CCN1CCCC1)S(=O)(=O)c1ccc(Nc2nnc3cc(-c4cc(O)ccc4Cl)cc(C)c3n2)cc1] | 4-[7-(2-chloro-5-hydroxy-phenyl)-5-methyl-benzo[1,2,4]triazin-3-ylamino]-N-ethyl-N-(2-pyrrolidin-1-yl-ethyl)-benzenesulfonamide | 3.2 |
| 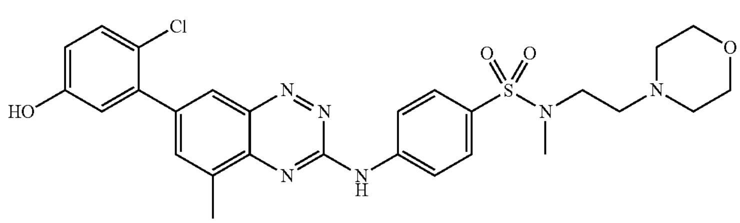 [SMILES: Cc1cc(-c2cc(O)ccc2Cl)cc2nnc(Nc3ccc(S(=O)(=O)N(C)CCN4CCOCC4)cc3)nc12] | 4-[7-(2-chloro-5-hydroxy-phenyl)-5-methyl-benzo[1,2,4]triazin-3-ylamino]-N-methyl-N-(2-morpholin-4-yl-ethyl)-benzenesulfonamide | 6.6 |
| 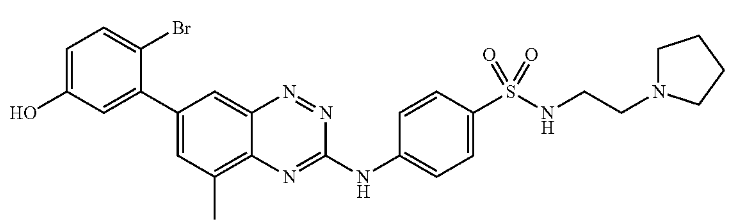 [SMILES: Cc1cc(-c2cc(O)ccc2Br)cc2nnc(Nc3ccc(S(=O)(=O)NCCN4CCCC4)cc3)nc12] | 4-[7-(2-bromo-5-hydroxy-phenyl)-5-methyl-benzo[1,2,4]triazin-3-ylamino]-N-(2-pyrrolidin-1-yl-ethyl)-benzenesulfonamide | 4.1 |

TABLE 1-continued

Tests Results of Inhibition of Src Kinase by Some Compounds of the Invention

| Structure | Name | Src IC50 (nM) |
|---|---|---|
| 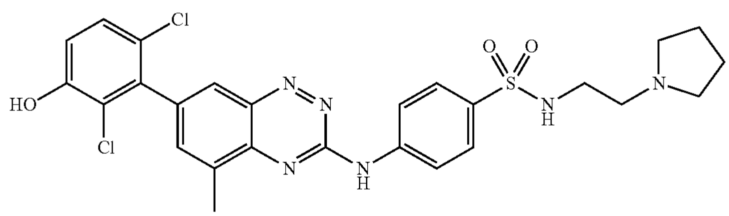 [SMILES: Cc1cc(-c2c(Cl)ccc(O)c2Cl)cc2nnc(Nc3ccc(S(=O)(=O)NCCN4CCCC4)cc3)nc12] | 4-[7-(2,6-dichloro-3-hydroxy-phenyl)-5-methyl-benzo[1,2,4]triazin-3-ylamino]-N-(2-pyrrolidin-1-yl-ethyl)-benzenesulfonamide | 1.5 |
| 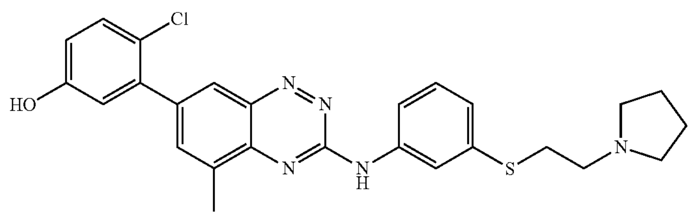 | 4-chloro-3-{5-methyl-3-[3-(2-pyrrolidin-1-yl-ethylsulfanyl)-phenylamino]-benzo[1,2,4]triazin-7-yl}-phenol | 3.4 |
| 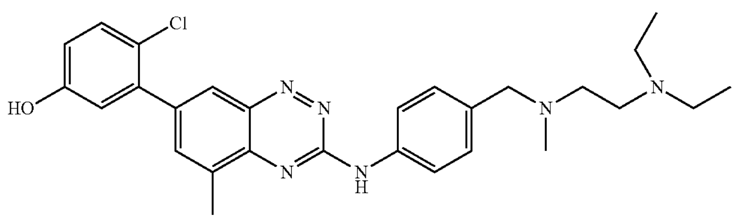 [SMILES: CCN(CC)CCN(C)Cc1ccc(Nc2nnc3cc(-c4cc(O)ccc4Cl)cc(C)c3n2)cc1] | 4-chloro-3-[3-(4-{[(2-diethylamino-ethyl)-methyl-amino]-methyl}-phenylamino)-5-methyl-benzo[1,2,4]triazin-7-yl]-phenol | 4.3 |
| 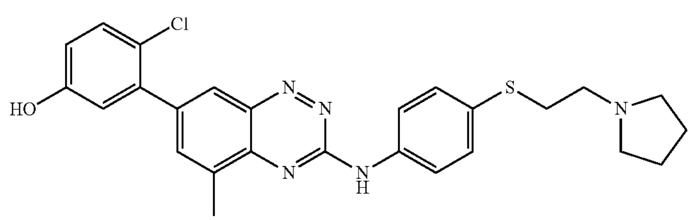 [SMILES: Cc1cc(-c2cc(O)ccc2Cl)cc2nnc(Nc3ccc(SCCN4CCCC4)cc3)nc12] | 4-chloro-3-{5-methyl-3-[4-(2-pyrrolidin-1-yl-ethylsulfanyl)-phenylamino]-benzo[1,2,4]triazin-7-yl}-phenol | 4.3 |
| | {4-[7-(2-chloro-5-hydroxy-phenyl)-5-methyl-benzo[1,2,4]triazin-3-ylamino]-phenyl}-(1,1-dioxo-1l6-thiomorpholin-4-yl)-methanone | 3.0 |
| 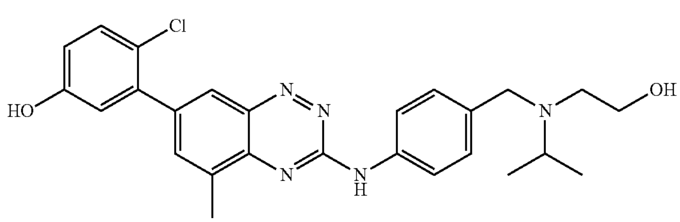 [SMILES: Cc1cc(-c2cc(O)ccc2Cl)cc2nnc(Nc3ccc(CN(CCO)C(C)C)cc3)nc12] | 4-chloro-3-[3-(4-{[(2-hydroxy-ethyl)-isopropyl-amino]-methyl}-phenylamino)-5-methyl-benzo[1,2,4]triazin-7-yl]-phenol | 1.5 |

TABLE 1-continued

Tests Results of Inhibition of Src Kinase by Some Compounds of the Invention

| Structure | Name | Src IC50 (nM) |
|---|---|---|
| 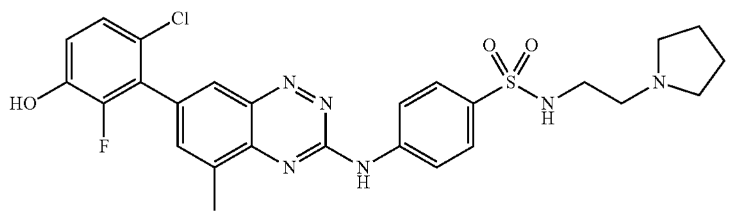 [SMILES: Cc1cc(-c2c(Cl)ccc(O)c2F)cc2nnc(Nc3ccc(S(=O)(=O)NCCN4CCCC4)cc3)nc12] | 4-[7-(6-chloro-2-fluoro-3-hydroxy-phenyl)-5-methyl-benzo[1,2,4]triazin-3-ylamino]-N-(2-pyrrolidin-1-yl-ethyl)-benzenesulfonamide | 0.700 |
| 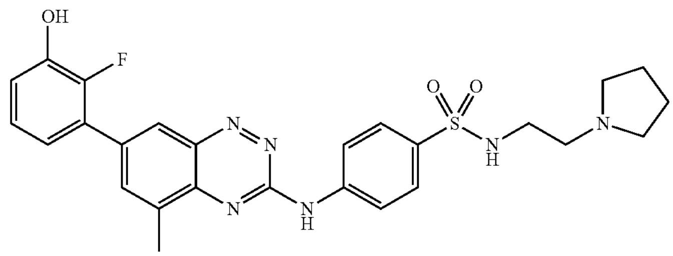 [SMILES: Cc1cc(-c2cccc(O)c2F)cc2nnc(Nc3ccc(S(=O)(=O)NCCN4CCCC4)cc3)nc12] | 4-[7-(2-fluoro-3-hydroxy-phenyl)-5-methyl-benzo[1,2,4]triazin-3-ylamino]-N-(2-pyrrolidin-1-yl-ethyl)-benzenesulfonamide | 5.2 |
| 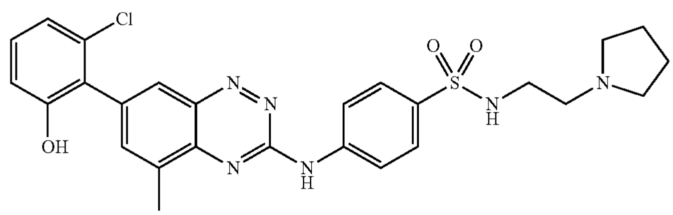 [SMILES: Cc1cc(-c2c(O)cccc2Cl)cc2nnc(Nc3ccc(S(=O)(=O)NCCN4CCCC4)cc3)nc12] | 4-(7-(2-chloro-6-hydroxyphenyl)-5-methylbenzo[e][1,2,4]triazin-3-ylamino)-N-(2-(pyrrolidin-1-yl)ethyl)benzensulfonamide | 12.6 |
| 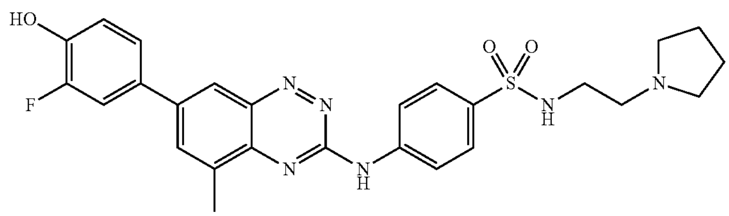 [SMILES: Cc1cc(-c2ccc(O)c(F)c2)cc2nnc(Nc3ccc(S(=O)(=O)NCCN4CCCC4)cc3)nc12] | 4-[7-(3-fluoro-4-hydroxy-phenyl)-5-methyl-benzo[1,2,4]triazin-3-ylamino]-N-(2-pyrrolidin-1-yl-ethyl)-benzenesulfonamide | 156 |
| 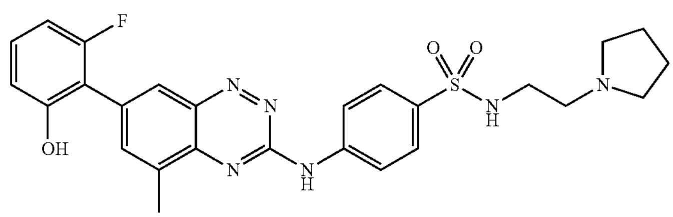 [SMILES: Cc1cc(-c2c(O)cccc2F)cc2nnc(Nc3ccc(S(=O)(=O)NCCN4CCCC4)cc3)nc12] | 4-[7-(2-fluoro-6-hydroxy-phenyl)-5-methyl-benzo[1,2,4]triazin-3-ylamino]-N-(2-pyrrolidin-1-yl-ethyl)-benzenesulfonamide | 123 |
| 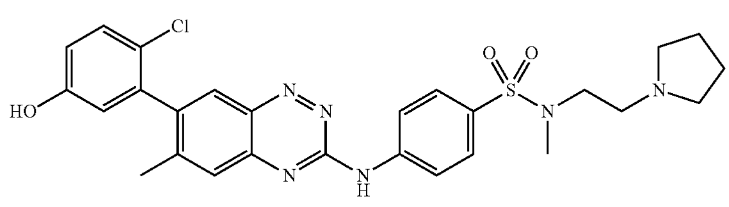 [SMILES: Cc1cc2nc(Nc3ccc(S(=O)(=O)N(C)CCN4CCCC4)cc3)nnc2cc1-c1cc(O)ccc1Cl] | 4-[7-(2-chloro-5-hydroxy-phenyl)-6-methyl-benzo[1,2,4]triazin-3-ylamino]-N-methyl-N-(2-pyrrolidin-1-yl-ethyl)-benzenesulfonamide | 3.7 |

TABLE 1-continued

Tests Results of Inhibition of Src Kinase by Some Compounds of the Invention

| Structure | Name | Src IC50 (nM) |
|---|---|---|
| 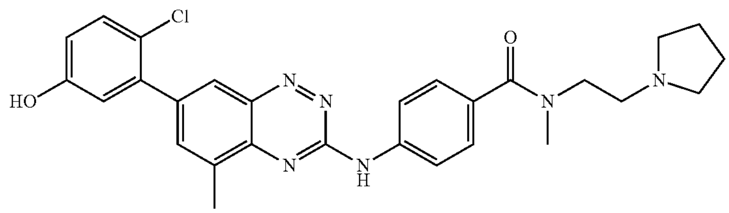 [SMILES: Cc1cc(-c2cc(O)ccc2Cl)cc2nnc(Nc3ccc(C(=O)N(C)CCN4CCCC4)cc3)nc12] | 4-[7-(2-chloro-5-hydroxy-phenyl)-5-methyl-benzo[1,2,4]triazin-3-ylamino]-N-methyl-N-(2-pyrrolidin-1-yl-ethyl)-benzamide | 1.6 |
| 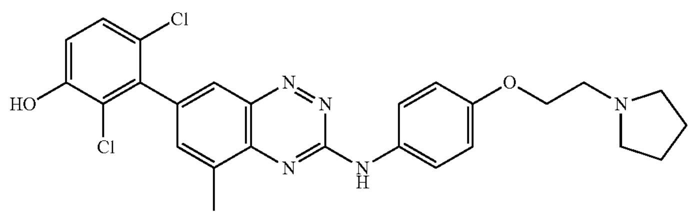 [SMILES: Cc1cc(-c2c(Cl)ccc(O)c2Cl)cc2nnc(Nc3ccc(OCCN4CCCC4)cc3)nc12] | 2,4-dichloro-3-{5-methyl-3-[4-(2-pyrrolidin-1-yl-ethoxy)-phenylamino]-benzo[1,2,4]triazin-7-yl}-phenol | 1.1 |
| 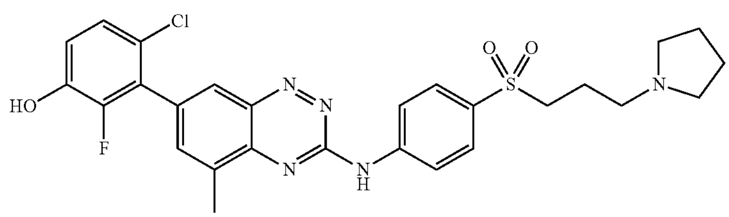 [SMILES: Cc1cc(-c2c(Cl)ccc(O)c2F)cc2nnc(Nc3ccc(S(=O)(=O)CCCN4CCCC4)cc3)nc12] | 4-chloro-2-fluoro-3-{5-methyl-3-[4-(3-pyrrolidin-1-yl-propane-1-sulfonyl)-phenylamino]-benzo[1,2,4]triazin-7-yl}-phenol | 1.0 |
| 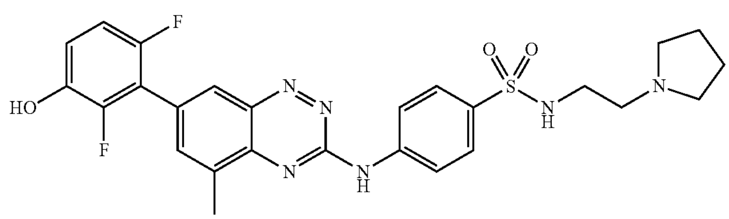 [SMILES: Cc1cc(-c2c(F)ccc(O)c2F)cc2nnc(Nc3ccc(S(=O)(=O)NCCN4CCCC4)cc3)nc12] | 4-[7-(2,6-difluoro-3-hydroxy-phenyl)-5-methyl-benzo[1,2,4]triazin-3-ylamino]-N-(2-pyrrolidin-1-yl-ethyl)-benzenesulfonamide | 3.1 |
| 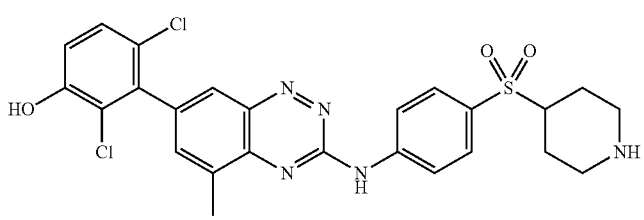 [SMILES: Cc1cc(-c2c(Cl)ccc(O)c2Cl)cc2nnc(Nc3ccc(S(=O)(=O)C4CCNCC4)cc3)nc12] | 2,4-dichloro-3-{5-methyl-3-[4-(piperidine-4-sulfonyl)-phenylamino]-benzo[1,2,4]triazin-7-yl}-phenol | 2.4 |
| 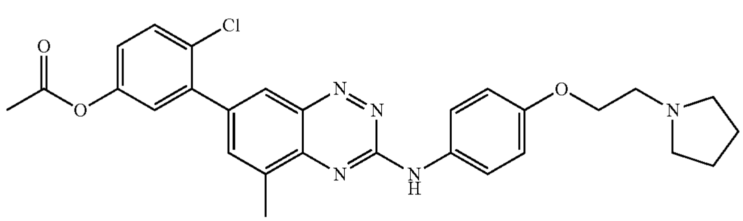 [SMILES: CC(=O)Oc1ccc(Cl)c(-c2cc(C)c3nc(Nc4ccc(OCCN5CCCC5)cc4)nnc3c2)c1] | Acetic acid 4-chloro-3-{5-methyl-3-[4-(2-pyrrolidin-1-yl-ethoxy)-phenylamino]-benzo[1,2,4]triazin-7-yl)-phenyl ester | 53.2 |
| 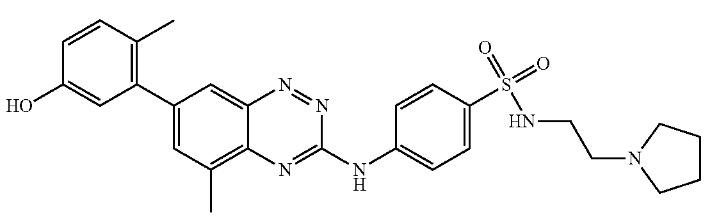 [SMILES: Cc1ccc(O)cc1-c1cc(C)c2nc(Nc3ccc(S(=O)(=O)NCCN4CCCC4)cc3)nnc2c1] | 4-[7-(5-hydroxy-2-methyl-phenyl)-5-methyl-benzo[1,2,4]triazin-3-ylamino]-N-(2-pyrrolidin-1-yl-ethyl)-benzenesulfonamide | 0.955 |

TABLE 1-continued

Tests Results of Inhibition of Src Kinase by Some Compounds of the Invention

| Structure | Name | Src IC50 (nM) |
|---|---|---|
| 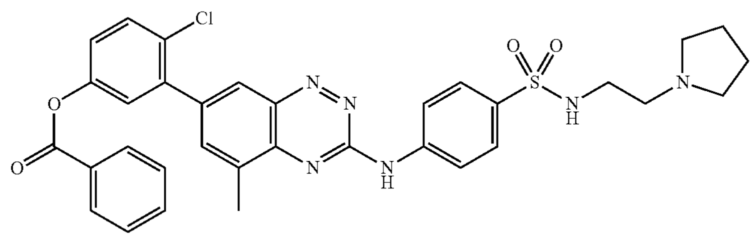 [SMILES: Cc1cc(-c2cc(OC(=O)c3ccccc3)ccc2Cl)cc2nnc(Nc3ccc(S(=O)(=O)NCCN4CCCC4)cc3)nc12] | Benzoic acid 4-chloro-3-{5-methyl-3-[4-(2-pyrrolidin-1-yl-ethylsulfamoyl)-phenylamino]-benzo[1,2,4]triazin-7-yl}-phenyl ester | 79.2 |
| 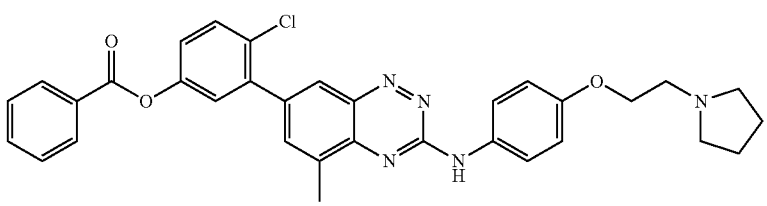 [SMILES: Cc1cc(-c2cc(OC(=O)c3ccccc3)ccc2Cl)cc2nnc(Nc3ccc(OCCN4CCCC4)cc3)nc12] | Benzoic acid 4-chloro-3-{5-methyl-3-[4-(2-pyrrolidin-1-yl-ethoxy)-phenylamino]-benzo[1,2,4]triazin-7-yl}-phenyl ester | >10000 |
| 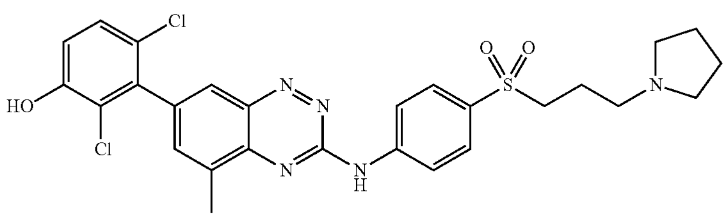 [SMILES: Cc1cc(-c2c(Cl)ccc(O)c2Cl)cc2nnc(Nc3ccc(S(=O)(=O)CCCN4CCCC4)cc3)nc12] | 2,4-dichloro-3-{5-methyl-3-[4-(3-pyrrolidin-1-yl-propane-1-sulfonyl)-phenylamino]-benzo[1,2,4]triazin-7-yl}-phenol | 2.1 |
| 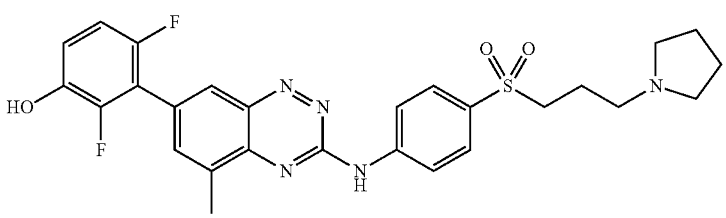 [SMILES: Cc1cc(-c2c(F)ccc(O)c2F)cc2nnc(Nc3ccc(S(=O)(=O)CCCN4CCCC4)cc3)nc12] | 2,4-difluoro-3-{5-methyl-3-[4-(3-pyrrolidin-1-yl-propane-1-sulfonyl)-phenylamino]-benzo[1,2,4]triazin-7-yl}-phenol | 3.8 |
| 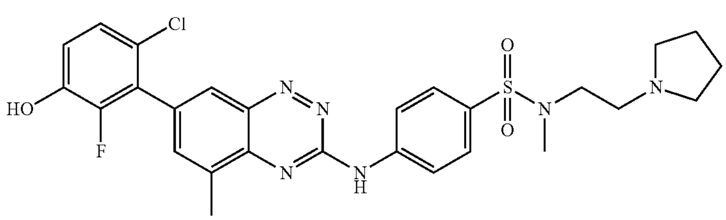 [SMILES: Cc1cc(-c2c(Cl)ccc(O)c2F)cc2nnc(Nc3ccc(S(=O)(=O)N(C)CCN4CCCC4)cc3)nc12] | 4-[7-(6-chloro-2-fluoro-3-hydroxy-phenyl)-5-methyl-benzo[1,2,4]triazin-3-ylamino]-N-methyl-N-(2-pyrrolidin-1-yl-ethyl)-benzenesulfonamide | 1.2 |
| 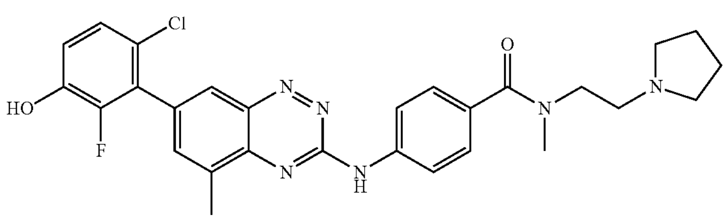 [SMILES: Cc1cc(-c2c(Cl)ccc(O)c2F)cc2nnc(Nc3ccc(C(=O)N(C)CCN4CCCC4)cc3)nc12] | 4-[7-(6-chloro-2-fluoro-3-hydroxy-phenyl)-5-methyl-benzo[1,2,4]triazin-3-ylamino]-N-methyl-N-(2-pyrrolidin-1-yl-ethyl)-benzamide | 0.542 |

TABLE 1-continued

Tests Results of Inhibition of Src Kinase by Some Compounds of the Invention

| Structure | Name | Src IC50 (nM) |
|---|---|---|
| 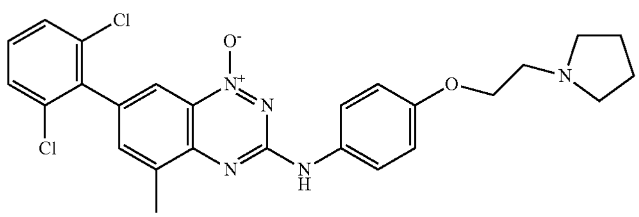 [SMILES: Cc1cc(-c2c(Cl)cccc2Cl)cc2c1nc(Nc1ccc(OCCN3CCCC3)cc1)n[n+]2[O-]] | [7-(2,6-dichloro-phenyl)-5-methyl-1-oxy-benzo[1,2,4]triazin-3-yl]-[4-(2-pyrrolidin-1-yl-ethoxy)-phenyl]-amine | 90.3 |
| 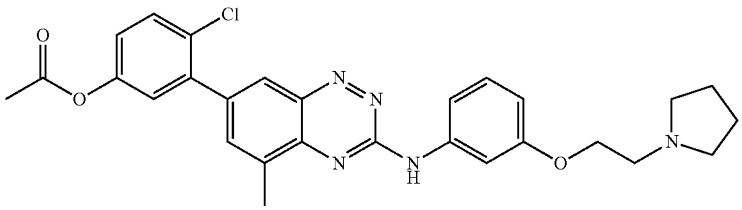 [SMILES: CC(=O)Oc1ccc(Cl)c(-c2cc(C)c3nc(Nc4cccc(OCCN5CCCC5)c4)nnc3c2)c1] | Acetic acid 4-chloro-3-{5-methyl-3-[3-(2-pyrrolidin-1-yl-ethoxy)-phenylamino]-benzo[1,2,4]triazin-7-yl}-phenyl ester | 133 |
| 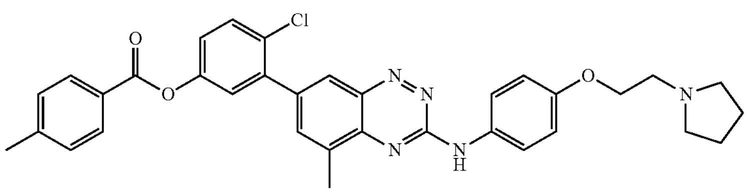 [SMILES: Cc1ccc(C(=O)Oc2ccc(Cl)c(-c3cc(C)c4nc(Nc5ccc(OCCN6CCCC6)cc5)nnc4c3)c2)cc1] | 4-methyl-benzoic acid 4-chloro-3-{5-methyl-3-[4-(2-pyrrolidin-1-yl-ethoxy)-phenylamino]-benzo[1,2,4]triazin-7-yl}-phenyl ester | 267 |
| 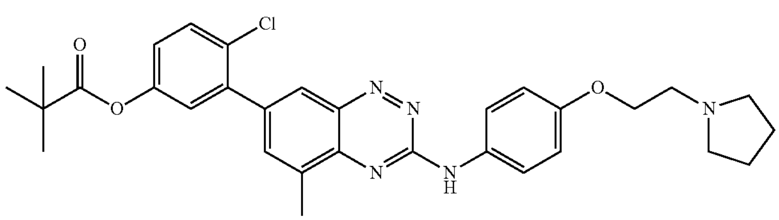 | 2,2-dimethyl-propionic acid 4-chloro-3-{5-methyl-3-[4-(2-pyrrolidin-1-yl-ethoxy)-phenylamino]-benzo[1,2,4]triazin-7-yl}-phenyl ester | >10000 |
| 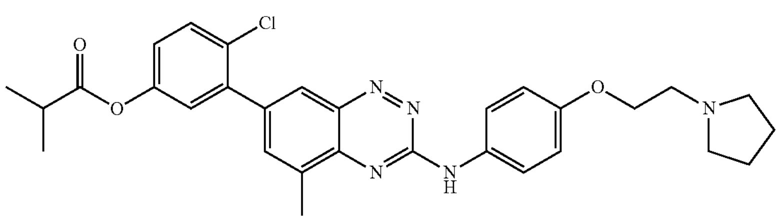 [SMILES: Cc1cc(-c2cc(OC(=O)C(C)C)ccc2Cl)cc2nnc(Nc3ccc(OCCN4CCCC4)cc3)nc12] | Isobutyric acid 4-chloro-3-{5-methyl-3-[4-(2-pyrrolidin-1-yl-ethoxy)-phenylamino]-benzo[1,2,4]triazin-7-y]}-phenyl ester | 10000 |
| 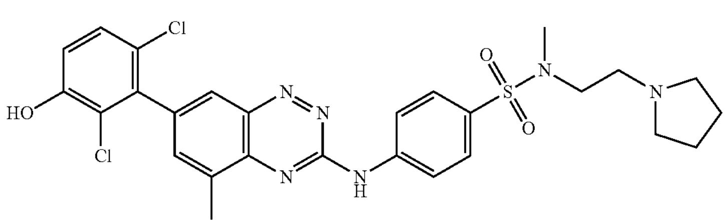 [SMILES: Cc1cc(-c2c(Cl)ccc(O)c2Cl)cc2nnc(Nc3ccc(S(=O)(=O)N(C)CCN4CCCC4)cc3)nc12] | 4-[7-(2,6-dichloro-3-hydroxy-phenyl)-5-methyl-benzo[1,2,4]triazin-3-ylamino]-N-methyl-N-(2-pyrrolidin-1-yl-ethyl)-benzenesulfonamide | 3.6 |

TABLE 2

Tests Results of Inhibition of Selected Kinases by Some Compounds of the Invention
All data represent $IC_{50}$ in nM.

| Structure | Name | Yes IC50 | PDGFR IC50 | EphB4 IC50 |
|---|---|---|---|---|
| 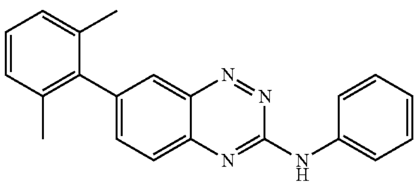 [SMILES: Cc1cccc(C)c1-c1ccc2nc(Nc3ccccc3)nnc2c1] | [7-(2,6-dimethyl-phenyl)-benzo[1,2,4]triazin-3-yl]-phenyl-amine | 822 | | |
| 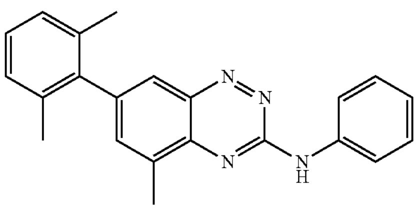 [SMILES: Cc1cccc(C)c1-c1cc(C)c2nc(Nc3ccccc3)nnc2c1] | [7-(2,6-dimethyl-phenyl)-5-methyl-benzo[1,2,4]triazin-3-yl]-phenyl-amine | | 628 | |
| 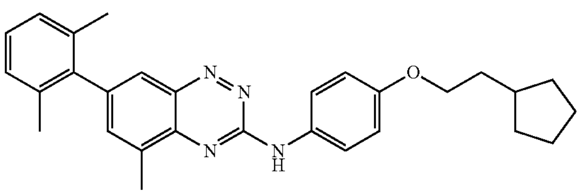 [SMILES: Cc1cccc(C)c1-c1cc(C)c2nc(Nc3ccc(OCCC4CCCC4)cc3)nnc2c1] | [7-(2,6-dimethyl-phenyl)-5-methyl-benzo[1,2,4]triazin-3-yl]-[4-(2-pyrrolidin-1-yl-ethoxy)-phenyl]-amine | 1.2 | 5.9 | 49 |
| 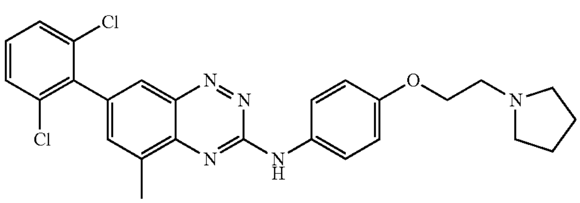 | [7-(2,6-dichloro-phenyl)-5-methyl-benzo[1,2,4]triazin-3-yl]-[4-(2-pyrrolidin-1-yl-ethoxy)-phenyl]-amine | 10.3 | 15 | 40 |
| 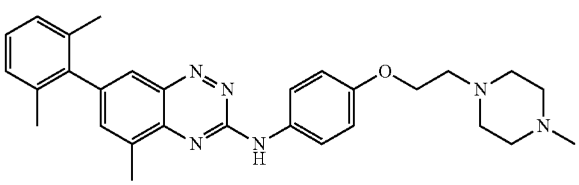 [SMILES: Cc1cccc(C)c1-c1cc(C)c2nc(Nc3ccc(OCCN4CCN(C)CC4)cc3)nnc2c1] | [7-(2,6-dimethyl-phenyl)-5-methyl-benzo[1,2,4]triazin-3-yl]-{4-[2-(4-methyl-piperazin-1-yl)-ethoxy]-phenyl}-amine | 7.7 | | |
| 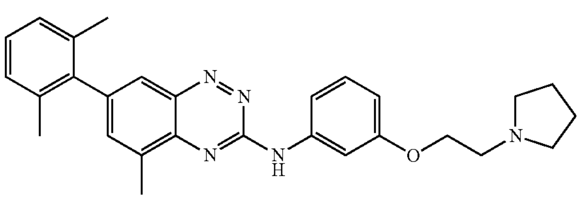 [SMILES: Cc1cccc(C)c1-c1cc(C)c2nc(Nc3cccc(OCCN4CCCC4)c3)nnc2c1] | [7-(2,6-dimethyl-phenyl)-5-methyl-benzo[1,2,4]triazin-3-yl]-[3-(2-pyrrolidin-1-yl-ethoxy]-phenyl}-amine | 3.7 | | |
| 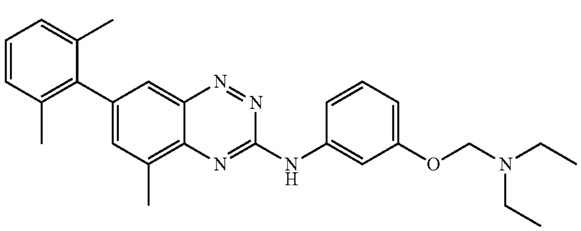 [SMILES: CCN(CC)COc1cccc(Nc2nnc3cc(-c4c(C)cccc4C)cc(C)c3n2)c1] | [3-(2-diethylamino-ethoxy)-phenyl]-[7-(2,6-dimethyl-phenyl)-5-methyl-benzo[1,2,4]triazin-3-yl]-amine | 2.6 | | |

TABLE 2-continued

Tests Results of Inhibition of Selected Kinases by Some Compounds of the Invention
All data represent $IC_{50}$ in nM.

| Structure | Name | Yes IC50 | PDGFR IC50 | EphB4 IC50 |
|---|---|---|---|---|
| 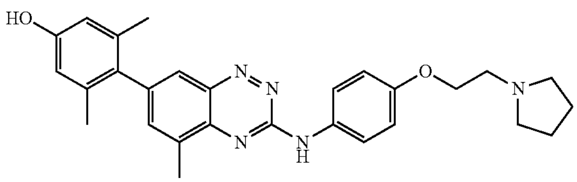 [SMILES: Cc1cc(O)cc(C)c1-c1cc(C)c2nc(Nc3ccc(OCCN4CCCC4)cc3)nnc2c1] | [7-(2,6-dimethyl-4-hydroxyphenyl)-5-methylbenzo[1,2,4]trazin-3-yl]-[4-(2-pyrrolidine-1-yl-ethoxy)-phenyl]-amine | | 41.1 | |
| 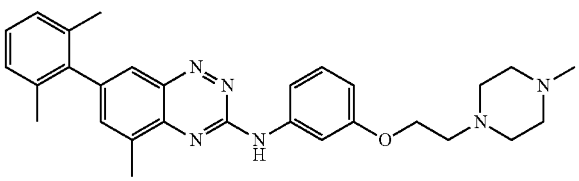 [SMILES: Cc1cccc(C)c1-c1cc(C)c2nc(Nc3cccc(OCCN4CCN(C)CC4)c3)nnc2c1] | [7-(2,6-dimethyl-phenyl)-5-methyl-benzo[1,2,4]triazin-3-yl]-{3-[2-(4-methyl-piperazin-1-yl)-ethoxy]-phenyl}-amine | | 69.1 | |
| 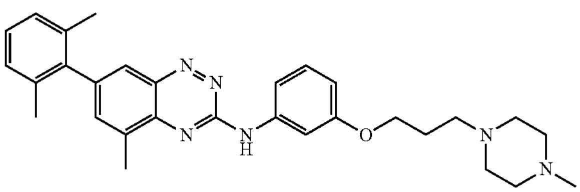 [SMILES: Cc1cccc(C)c1-c1cc(C)c2nc(Nc3cccc(OCCCN4CCN(C)CC4)c3)nnc2c1] | [7-(2,6-dimethyl-phenyl)-5-methyl-benzo[1,2,4]triazin-3-yl]-{3-[3-(4-methyl-piperazin-1-yl)-propoxy]-phenyl}-amine | | 76.3 | |
| 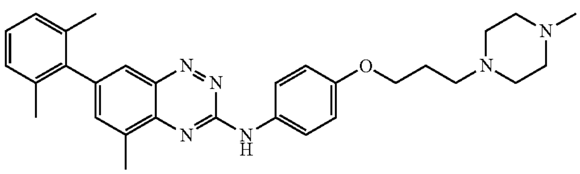 [SMILES: Cc1cccc(C)c1-c1cc(C)c2nc(Nc3ccc(OCCCN4CCN(C)CC4)cc3)nnc2c1] | [7-(2,6-dimethyl-phenyl)-5-methyl-benzo[1,2,4]triazin-3-yl]-{4-[3-(4-methyl-piperazin-1-yl)-propoxy]-phenyl}-amine | | 50.3 | |
| 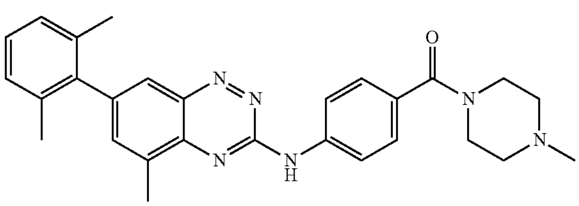 [SMILES: Cc1cccc(C)c1-c1cc(C)c2nc(Nc3ccc(C(=O)N4CCN(C)CC4)cc3)nnc2c1] | {4-[7-(2,6-dimethyl-phenyl)-5-methyl-benzo[1,2,4]triazin-3-ylaminol-phenyl}-(4-methyl-piperazin-1-yl)-methanone | | | 66 |
| 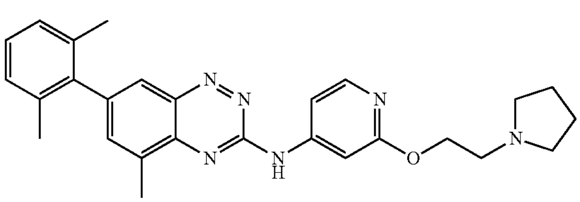 [SMILES: Cc1cccc(C)c1-c1cc(C)c2nc(Nc3ccnc(OCCN4CCCC4)c3)nnc2c1] | [7-(2,6-dimethyl-phenyl)-5-methyl-benzo[1,2,4]triazin-3-yl]-(6-methoxy-pyridin-3-yl)-amine | | | 128 |
| 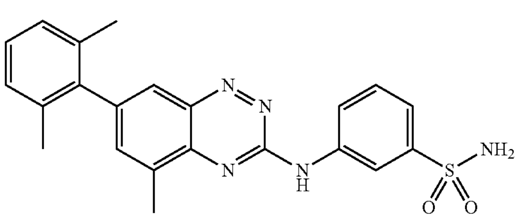 [SMILES: Cc1cccc(C)c1-c1cc(C)c2nc(Nc3cccc(S(N)(=O)=O)c3)nnc2c1] | 3-[7-(2,6-dimethyl-phenyl)-5-methyl-benzo[1,2,4]triazin-3-ylamino]-benzenesulfonamide | | | 16.3 |

US 8,481,536 B2

TABLE 2-continued

Tests Results of Inhibition of Selected Kinases by Some Compounds of the Invention
All data represent IC$_{50}$ in nM.

| Structure | Name | Yes IC50 | PDGFR IC50 | EphB4 IC50 |
|---|---|---|---|---|
| 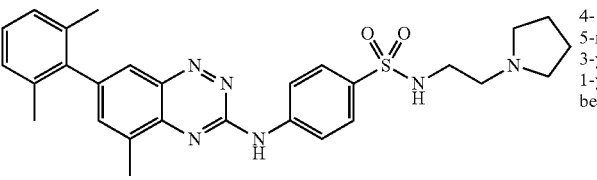 | 4-[7-(2,6-dimethyl-phenyl)-5-methyl-benzo[1,2,4]triazin-3-ylamino]-N-(2-pyrrolidin-1-yl-ethyl)-benzenesulfonamide | 3.1 | 9.3 | 73.7 |
| 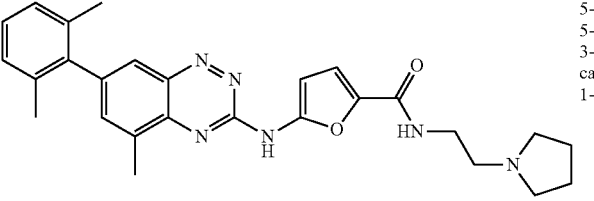 | 5-[7-(2,6-dimethyl-phenyl)-5-methyl-benzo[1,2,4]triazin-3-ylamino]-furan-2-carboxylic acid (2-pyrrolidin-1-yl-ethyl)-amide | 18.3 | 117 | 68.7 |
| 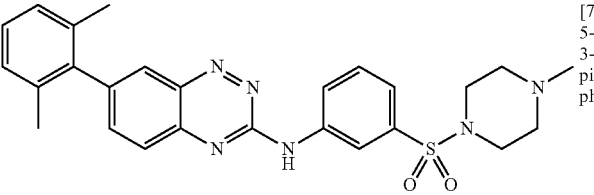 | [7-(2,6-dimethyl-phenyl)-5-methyl-benzo[1,2,4]triazin-3-yl]-[3-(4-methyl-piperazine-1-sulfonyl)-phenyl]-amine | | 81.3 | |
| 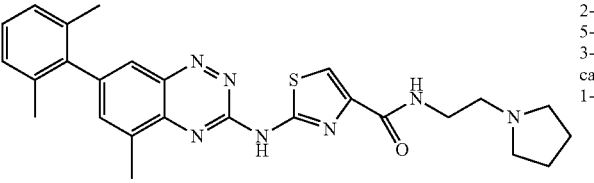 | 2-[7-(2,6-dimethyl-phenyl)-5-methyl-benzo[1,2,4]triazin-3-ylamino]-thiazole-4-carboxylic acid (2-pyrrolidin-1-yl-ethyl)-amide | 7.3 | 60 | 66.1 |
| 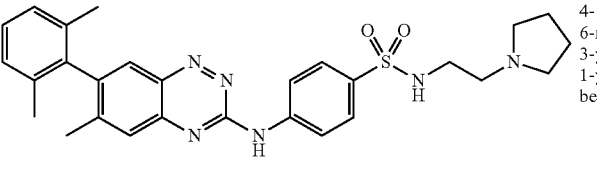 | 4-[7-(2,6-dimethyl-phenyl)-6-methyl-benzo[1,2,4]triazin-3-ylamino]-N-(2-pyrrolidin-1-yl-ethyl)-benzenesulfonamide | | 48.1 | |
| 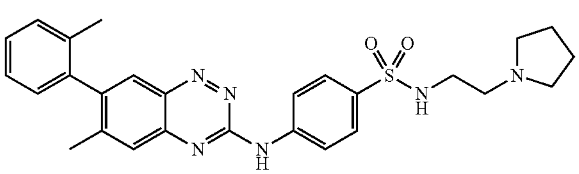 [SMILES: Cc1ccccc1-c1cc2nnc(Nc3ccc(S(=O)(=O)NCCN4CCCC4)cc3)nc2cc1C] | 4-(6-methyl-7-o-tolyl-benzo[1,2,4]triazin-3-ylamino)-N-(2-pyrrolidin-1-yl-ethyl)-benzenesulfonamide | | 24.3 | |
| 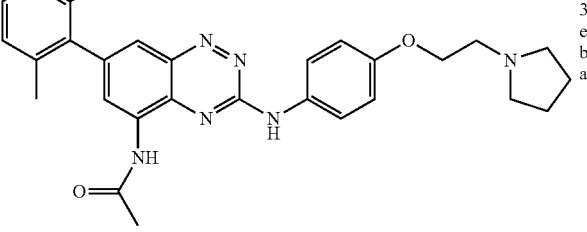 | N-{7-(2,6-dimethyl-phenyl)-3-[4-(2-pyrrolidin-1-yl-ethoxy)-phenylamino]-benzo[1,2,4]triazin-5-yl}-acetamide | | 11.5 | |

TABLE 2-continued

Tests Results of Inhibition of Selected Kinases by Some Compounds of the Invention
All data represent IC$_{50}$ in nM.

| Structure | Name | Yes IC50 | PDGFR IC50 | EphB4 IC50 |
|---|---|---|---|---|
| 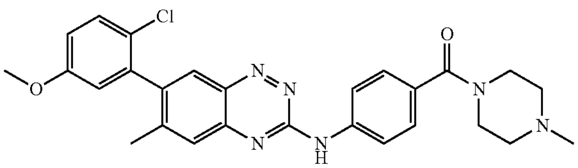 | {4-[7-(2-chloro-5-methoxy-phenyl)-6-methyl-benzo[1,2,4]triazin-3-ylamino]-phenyl}-(4-methyl-piperazin-1-yl)-methanone | | 3.5 | |
| 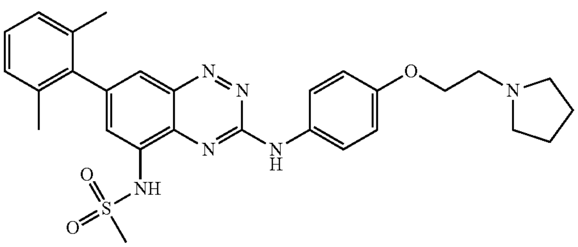 [SMILES: Cc1cccc(C)c1-c1cc(NS(C)(=O)=O)c2nc(Nc3ccc(OCCN4CCCC4)cc3)nnc2c1] | N-{7-(2,6-dimethyl-phenyl)-3-[4-(2-pyrrolidin-1-yl-ethoxy)-phenylamino]-benzo[1,2,4]triazin-5-yl}-methanesulfonamide | | 15.7 | |
| 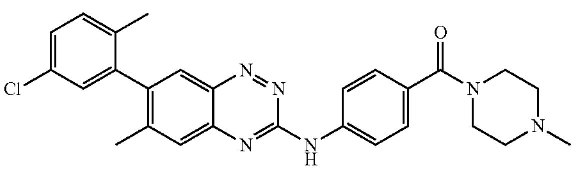 [SMILES: Cc1ccc(Cl)cc1-c1cc2nnc(Nc3ccc(C(=O)N4CCN(C)CC4)cc3)nc2cc1C] | {4-[7-(5-chloro-2-methyl-phenyl)-6-methyl-benzo[1,2,4]triazin-3-ylamino]-phenyl}-(4-methyl-piperazin-1-yl)-methanone | | 6 | |
| 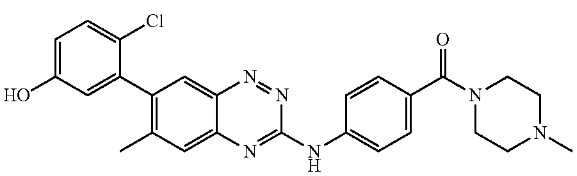 [SMILES: Cc1cc2nc(Nc3ccc(C(=O)N4CCN(C)CC4)cc3)nnc2cc1-c1cc(O)ccc1Cl] | {4-[7-(2-chloro-5-hydroxy-phenyl)-6-methyl-benzo[1,2,4]triazin-3-ylamino]-phenyl}-(4-methyl-piperazin-1-yl)-methanone | | 3.7 | |
| 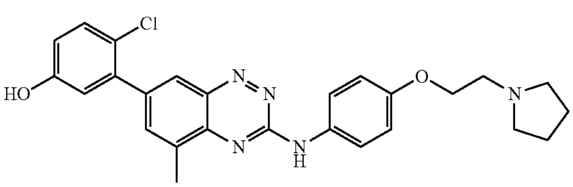 [SMILES: Cc1cc(-c2cc(O)ccc2Cl)cc2nnc(Nc3ccc(OCCN4CCCC4)cc3)nc12] | [7-(2-chloro-5-hydroxy-phenyl)-5-methyl-benzo[1,2,4]triazin-3-yl]-[4-(2-pyrrolidine-1-yl-ethoxy)-phenyl]-amine | 0.5 | 1.1 | 15.9 |
| 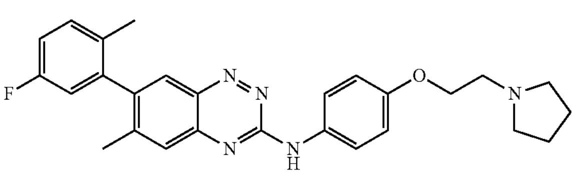 [SMILES: Cc1ccc(F)cc1-c1cc2nnc(Nc3ccc(OCCN4CCCC4)cc3)nc2cc1C] | [7-(5-fluoro-2-methyl-phenyl)-6-methyl-benzo[1,2,4]triazin-3-yl]-[4-(2-pyrrolidin-1-yl-ethoxy)-phenyl]-amine | | 26.1 | |
| 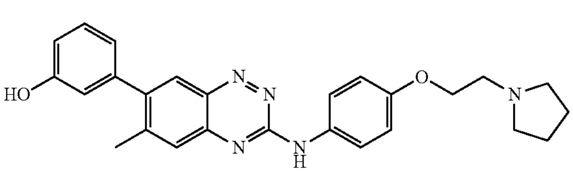 [SMILES: Cc1cc2nc(Nc3ccc(OCCN4CCCC4)cc3)nnc2cc1-c1cccc(O)c1] | 3-{6-methyl-3-[4-(2-pyrrolidin-1-yl-ethoxy)-phenylamino]-benzo[1,2,4]triazin-7-yl}-phenol | | 7.4 | |
| 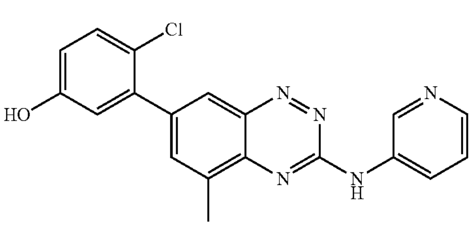 [SMILES: Cc1cc(-c2cc(O)ccc2Cl)cc2nnc(Nc3cccnc3)nc12] | 4-chloro-3-[5-methyl-3-(pyridin-3-ylamino)-benzo[1,2,4]triazin-7-yl]-phenol | | 23.5 | |

TABLE 2-continued

Tests Results of Inhibition of Selected Kinases by Some Compounds of the Invention
All data represent IC$_{50}$ in nM.

| Structure | Name | Yes IC50 | PDGFR IC50 | EphB4 IC50 |
|---|---|---|---|---|
| 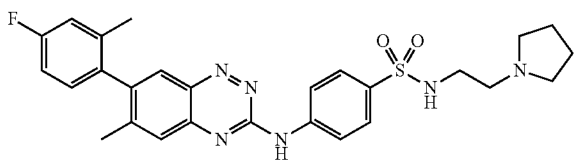 [SMILES: Cc1cc(F)ccc1-c1cc2nnc(Nc3ccc(S(=O)(=O)NCCN4CCCC4)cc3)nc2cc1C] | 4-[7-(4-fluoro-2-methyl-phenyl)-6-methyl-benzo[1,2,4]triazin-3-ylamino]-N-(2-pyrrolidin-1-yl-ethyl)-benzenesulfonamide | | 73.7 | |
| 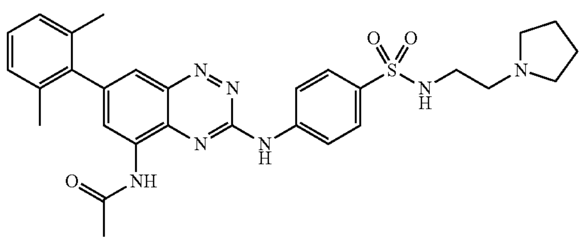 [SMILES: CC(=O)Nc1cc(-c2c(C)cccc2C)cc2nnc(Nc3ccc(S(=O)(=O)NCCN4CCCC4)cc3)nc12] | N-{7-(2,6-dimethyl-phenyl)-3-[4-(2-pyrrolidin-1-yl-ethylsulfamoyl)-phenylamino]-benzo[1,2,4]triazin-5-yl}-acetamide | | 1850 | |
| 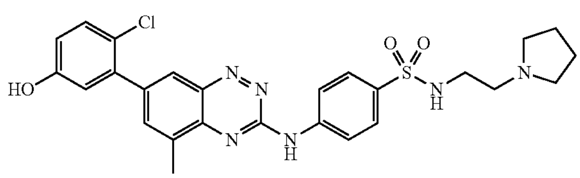 [SMILES: Cc1cc(-c2cc(O)ccc2Cl)cc2nnc(Nc3ccc(S(=O)(=O)NCCN4CCCC4)cc3)nc12] | 4-[7-(2-chloro-5-hydroxy-phenyl)-5-methyl-benzo[1,2,4]triazin-3-ylaminol-N-(2-pyrrolidin-1-yl-ethyl)-benzenesulfonamide; | 1.28 | 1.7 | 30.8 |
| 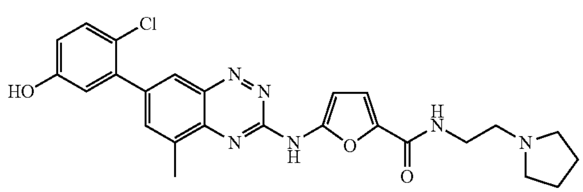 [SMILES: Cc1cc(-c2cc(O)ccc2Cl)cc2nnc(Nc3ccc(C(=O)NCCN4CCCC4)o3)nc12] | 5-[7-(2-chloro-5-hydroxy-phenyl)-5-methyl-benzo[1,2,4]triazin-3-ylamino]-furan-2-carboxylic acid (2-pyrrolidin-1-yl-ethyl)-amide | | 14.4 | |
| 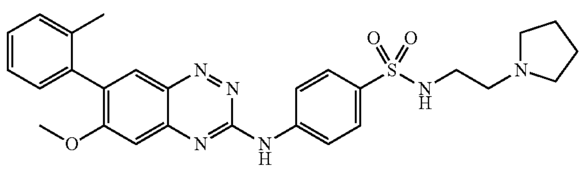 [SMILES: COc1cc2nc(Nc3ccc(S(=O)(=O)NCCN4CCCC4)cc3)nnc2cc1-c1ccccc1C] | 4-(6-methoxy-7-o-tolyl-benzo[1,2,4]triazin-3-ylamino)-N-(2-pyrrolidin-1-yl-ethyl)-benzenesulfonamide | | 39.3 | |
| 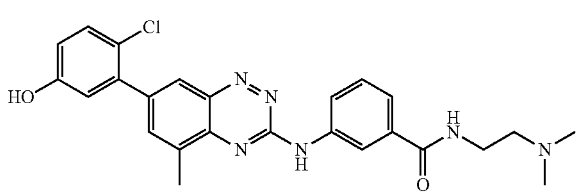 [SMILES: Cc1cc(-c2cc(O)ccc2Cl)cc2nnc(Nc3cccc(C(=O)NCCN(C)C)c3)nc12] | 3-[7-(2-chloro-5-hydroxy-phenyl)-5-methyl-benzo[1,2,4]triazin-3-ylamino]-N-(2-dimethylamino-ethyl)-benzamide | 1.24 | 5.3 | |
| 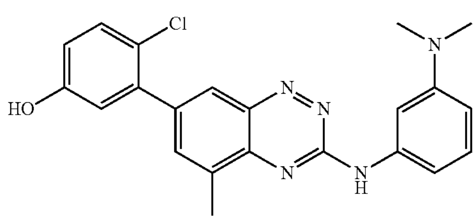 [SMILES: Cc1cc(-c2cc(O)ccc2Cl)cc2nnc(Nc3cccc(N(C)C)c3)nc12] | 4-chloro-3-[3-(3-dimethylamino-phenylamino)-5-methyl-benzo[1,2,4]triazin-7-yl]-phenol | | 20.8 | |

TABLE 2-continued

Tests Results of Inhibition of Selected Kinases by Some Compounds of the Invention
All data represent IC$_{50}$ in nM.

| Structure | Name | Yes IC50 | PDGFR IC50 | EphB4 IC50 |
|---|---|---|---|---|
| 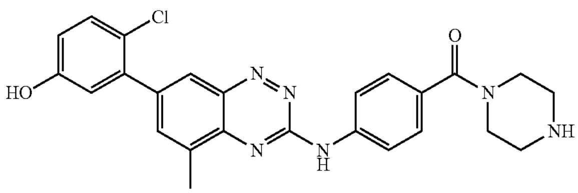 [SMILES: Cc1cc(-c2cc(O)ccc2Cl)cc2nnc(Nc3ccc(C(=O)N4CCNCC4)cc3)nc12] | {4-[7-(2-chloro-5-hydroxy-phenyl)-5-methyl-benzo[1,2,4]triazin-3-ylamino]-phenyl}-piperazin-1-yl-methanone | | 1.2 | |
| 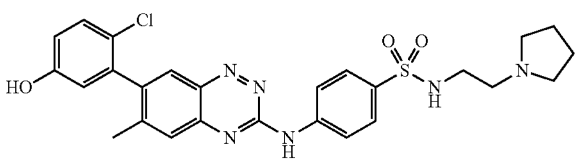 [SMILES: Cc1cc2nc(Nc3ccc(S(=O)(=O)NCCN4CCCC4)cc3)nnc2cc1-c1cc(O)ccc1Cl] | 4-[7-(2-chloro-5-hydroxy-phenyl)-6-methyl-benzo[1,2,4]triazin-3-ylamino]-N-(2-pyrrolidin-1-yl-ethyl)- | | 1.9 | |
| 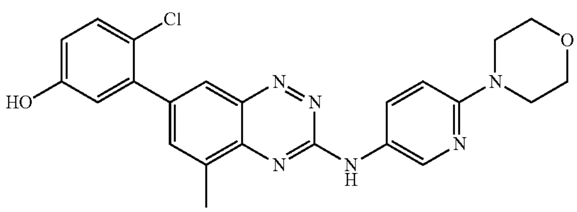 [SMILES: Cc1cc(-c2cc(O)ccc2Cl)cc2nnc(Nc3ccc(N4CCOCC4)nc3)nc12] | 4-chloro-3-[5-methyl-3-(6-morpholin-4-yl-pyridin-3-ylamino)-benzo[1,2,4]triazin-7-yl]-phenol | | 2.1 | |
| 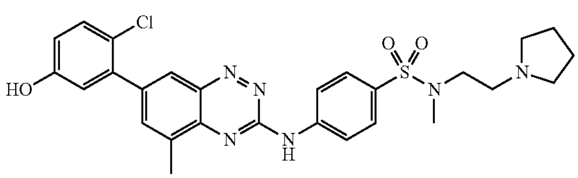 [SMILES: Cc1cc(-c2cc(O)ccc2Cl)cc2nnc(Nc3ccc(S(=O)(=O)N(C)CCN4CCCC4)cc3)nc12] | 4-[7-(2-chloro-5-hydroxy-phenyl)-5-methyl-benzo[1,2,4]triazin-3-ylamino]-N-methyl-N-(2-pyrrolidin-1-yl-ethyl)-benzenesulfonamide | | 3.1 | |
| 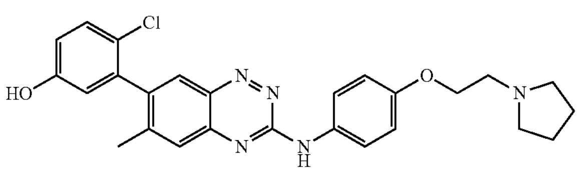 [SMILES: Cc1cc2nc(Nc3ccc(OCCN4CCCC4)cc3)nnc2cc1-c1cc(O)ccc1Cl] | 4-chloro-3-{6-methyl-3-[4-(2-pyrrolidin-1-yl-ethoxy)phenylamino]-benzo[1,2,4]triazin-7-yl}-phenol | 0.7 | 5.7 | |
| | 4-chloro-3-{5-methyl-3-[4-(3-pyrrolidin-1-yl-propane-1-sulfonyl)-phenylamino]-benzo[1,2,4]triazin-7-yl}-phenol | | 2.9 | |
| 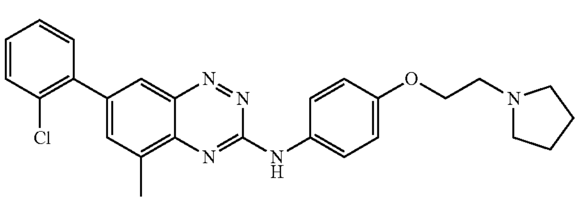 [SMILES: Cc1cc(-c2ccccc2Cl)cc2nnc(Nc3ccc(OCCN4CCCC4)cc3)nc12] | [7-(2-chloro-phenyl)-5-methyl-benzo[1,2,4]triazin-3-yl]-[4-(2-pyrrolidin-1-yl-ethoxy)-phenyl]-amine | 21.7 | | 58 |
| 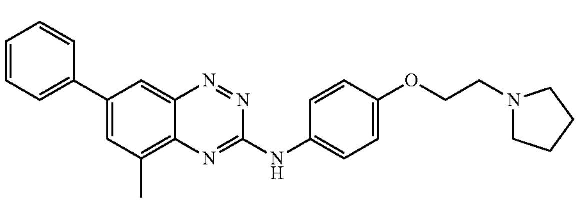 [SMILES: Cc1cc(-c2ccccc2)cc2nnc(Nc3ccc(OCCN4CCCC4)cc3)nc12] | (5-methyl-7-phenyl-benzo[1,2,4]triazin-3-yl)-[4-(2-pyrrolidin-1-yl-ethoxy)-phenyl]-amine | 111 | | 391 |

TABLE 2-continued

Tests Results of Inhibition of Selected Kinases by Some Compounds of the Invention
All data represent IC$_{50}$ in nM.

| Structure | Name | Yes IC50 | PDGFR IC50 | EphB4 IC50 |
|---|---|---|---|---|
| 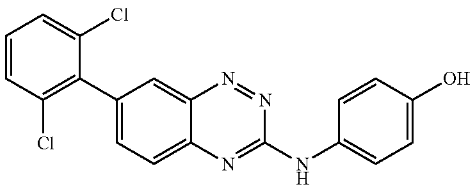 [SMILES: Oc1ccc(Nc2nnc3cc(-c4c(Cl)cccc4Cl)ccc3n2)cc1] | 4-[7-(2,6-dichloro-phenyl)-5-methyl-benzo[1,2,4]triazin-3-ylamino]-phenol | 465 | | 596 |
| 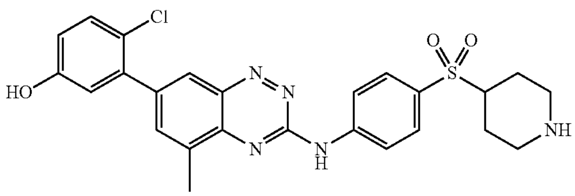 [SMILES: Cc1cc(-c2cc(O)ccc2Cl)cc2nnc(Nc3ccc(S(=O)(=O)C4CCNCC4)cc3)nc12] | 4-chloro-3-{5-methyl-3-[4-(piperidine-4-sulfonyl)-phenylamino]-benzo[1,2,4]triazin-7-yl}-phenol | | 2.8 | |
| 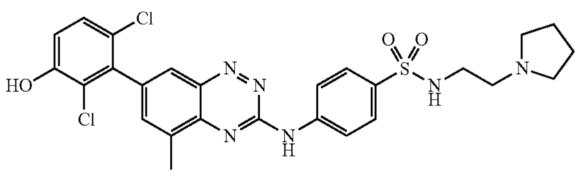 [SMILES: Cc1cc(-c2c(Cl)ccc(O)c2Cl)cc2nnc(Nc3ccc(S(=O)(=O)NCCN4CCCC4)cc3)nc12] | 4-[7-(2,6-dichloro-3-hydroxy-phenyl)-5-methyl-benzo[1,2,4]triazin-3-ylamino]-N-(2-pyrrolidin-1-yl-ethyl)-benzenesulfonamide | | 8 | |

Although the invention has been described with reference to the above examples, it will be understood that modifications and variations are encompassed within the spirit and scope of the invention. Accordingly, the invention is limited only by the following claims.

What is claimed is:

1. A method for treating breast cancer, comprising administering to a subject in need thereof a therapeutically effective amount of a compound of structure (I):

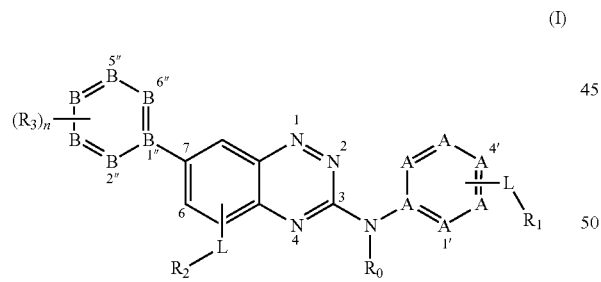

(I)

wherein each of A is independently selected from a group consisting of (CH)$_{0-1}$, N, NH, O, S, and a part of a ring fusion to form a second ring, where the second ring is an aromatic, a heteroaromatic, a bicyclic aromatic, a bicyclic aromatic heterocyclic ring, or a bicyclic with only the first ring being aromatic or heteroaromatic;

each of B is independently selected from a group consisting of (CH)$_{0-1}$, N, NH, O, S, and a part of a ring fusion to form a second ring, where the second ring is an aromatic, a heteroaromatic, a bicyclic aromatic, a bicyclic aromatic heterocyclic ring, or a bicyclic with only the first ring being aromatic or heteroaromatic, with the further proviso that if each B is (CH)$_0$, R$_3$ is bonded directly to the adjacent ring;

R$_0$ is selected from a group consisting of H and lower alkyl;

L is selected from a group consisting of a bond, and a substituted or unsubstituted alkyl, alkenyl, or alkynyl linking moiety;

R$_1$ is selected from a group consisting of C(R')$_3$, OR', N(R')$_2$, NR'C(O)R', NR'C(O)O(R'), NR'C(O)N(R')$_2$, SR', C(O)(O)R', C(O), C(O)N(R')$_2$, SO$_3$R', OSO$_2$R', SO$_2$R', SOR', S(O)N(R')$_2$, OS(O)(O)N(R')$_2$, S(O)(O)N(R')$_2$, S(O)N(R')$_2$, PO$_4$R', OPO$_2$R', PO$_3$R', PO$_2$R', and a 3-6 membered heterocycle with one or more heterocyclic atoms with each heteroatom independently being capable of carrying any R' group on it, wherein R' is selected from a group consisting of hydrogen, lower alkyl, alkyl-hydroxyl, thiol-alkyl, alkyl-thiol, aminoalkyl, alkylamino, branched alkyl, branched alkyl hydroxyl, branched thio-alkyl, branched alkyl-thiol, branched aminoalkyl, broached alkylamino, and a closed 3-6 membered carbocycle or heterocycle, with each heteroatom in the 3-6 membered heterocycle being capable of carrying any R' group on it, and wherein each R' is independent in case there is more than one R';

R$_2$ is a substituent situated at position 5, 6 or 8 of the ring, wherein R$_2$ is selected from a group consisting of methyl, ethyl, n-propyl, iso-propyl, n-butyl, iso-butyl, tert-butyl, iso-pentyl, phenyl, substituted phenyl, halogen, branched or unbranched alkylamino, branched or unbranched aminoalkyl, branched or unbranched alkyloxo, branched or unbranched oxyalkyl, branched or unbranched thioalkyl, branched or unbranched alkylthiol, CF$_3$, sulfonamido, substituted sulfonamido, sulfonate, sulfonate ester, phosphate, phosphate ester, phosphonate, phosphonate ester, carboxo, amido, ureido, substituted carboxo, substituted amido, substituted ureido, or a 3-6 membered carbocycle or heterocycle attached to positions 5, 6 or 8 directly or through group L, each heteroatom independently being capable of carrying any group R$_2$, with the further proviso that either one, two or three substituents R$_2$ are present in the ring, each of the substituents R$_2$ being the same or different;

R$_3$ is selected from a group consisting of hydrogen, alkyl, alkoxy, halogen, CF$_3$, cyano, substituted alkyl, hydroxyl, aryl, substituted aryl, heteroaryl, substituted heteroaryl, heterocycle, C(R")$_3$, OR", N(R")$_2$, NR"C(O)R", NR"C(O)NR", R", C(O)(O)R", OC(O)R", C(O)N(R")$_2$, C(O), OC(O)N(R")$_2$, SO$_3$R", OSO$_2$R", SO$_2$R", SOR", PO$_4$R", OPO$_2$R", PO$_3$R", or PO$_2$R", wherein R" is hydrogen, aryl, substituted aryl, heteroaryl, substituted heteroaryl, lower alkyl, branched lower alkyl, alkyl-hydroxyl, branched alkyl-hydroxyl, amino-alkyl, branched amino-alkyl, alkyl-amino, branched alkyl-amino, thiol-alkyl, branched thiol-alkyl, alkyl-thiol, branched thiol-alkyl, or may form a closed 3-6 membered heterocycle with one or more heterocyclic atoms, branched alkyl, or branched alkyl hydroxyl, where each R" is independent in case there is more than one R";

n is an integer having the value between 1 and 5, with the further proviso that if n >2, then each group R$_3$ is independent of the other groups R$_3$, with the further proviso that if each A is (CH)$_0$, L is a bond, with the further proviso that if each B is (CH)$_0$, R$_3$ is any substituent described above, other than hydrogen, bonded directly to the position 7 of the adjacent ring;

or a pharmaceutically acceptable salt, N-oxide, or individual diastereomer thereof.

2. The method of claim 1, wherein the breast cancer is associated with a kinase.

3. The method of claim 2, wherein the kinase is a serine kinase or a threonine kinase.

4. A method of treating breast cancer, comprising the administration of a therapeutically effective amount of a compound of structure (I):

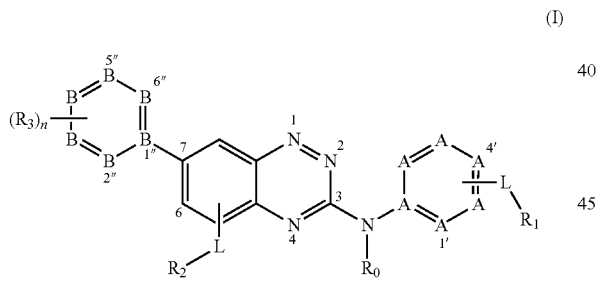

(I)

wherein each of A is independently selected from a group consisting of (CH)$_{0-1}$, N, NH, O, S, and a part of a ring fusion to form a second ring, where the second ring is an aromatic, a heteroaromatic, a bicyclic aromatic, a bicyclic aromatic heterocyclic ring, or a bicyclic with only the first ring being aromatic or heteroaromatic;

each of B is independently selected from a group consisting of (CH)$_{0-1}$, N, NH, O, S, and a part of a ring fusion to form a second ring, where the second ring is an aromatic, a heteroaromatic, a bicyclic aromatic, a bicyclic aromatic heterocyclic ring, or a bicyclic with only the first ring being aromatic or heteroaromatic, with the further proviso that if each B is (CH)$_0$, R$_3$ is bonded directly to the adjacent ring;

R$_0$ is selected from a group consisting of H and lower alkyl;

L is selected from a group consisting of a bond, and a substituted or unsubstituted alkyl, alkenyl, or alkynyl linking moiety;

R$_1$ is selected from a group consisting of C(R')$_3$, OR', N(R')$_2$, NR'C(O)R', NR'C(O)O(R'), NR'C(O)N(R')$_2$, SR', C(O)(O)R', C(O), C(O)N(R')$_2$, SO$_3$R', OSO$_2$R', SO$_2$R', SOR', S(O)N(R')$_2$, OS(O)(O)N(R')$_2$, S(O)(O)N(R')$_2$, S(O)N(R')$_2$, PO$_4$R', OPO$_2$R', PO$_3$R', PO$_2$R', and a 3-6 membered heterocycle with one or more heterocyclic atoms with each heteroatom independently being capable of carrying any R' group on it, wherein R' is selected from a group consisting of hydrogen, lower alkyl, alkyl-hydroxyl, thiol-alkyl, alkyl-thiol, aminoalkyl, alkylamino, branched alkyl, branched alkyl hydroxyl, branched thio-alkyl, branched alkyl-thiol, branched aminoalkyl, broached alkylamino, and a closed 3-6 membered carbocycle or heterocycle, with each heteroatom in the 3-6 membered heterocycle being capable of carrying any R' group on it, and wherein each R' is independent in case there is more than one R';

R$_2$ is a substituent situated at position 5, 6 or 8 of the ring, wherein R$_2$ is selected from a group consisting of methyl, ethyl, n-propyl, iso-propyl, n-butyl, iso-butyl, tert-butyl, iso-pentyl, phenyl, substituted phenyl, halogen, branched or unbranched alkylamino, branched or unbranched aminoalkyl, branched or unbranched alkyloxo, branched or unbranched oxyalkyl, branched or unbranched thioalkyl, branched or unbranched alkylthiol, CF$_3$, sulfonamido, substituted sulfonamido, sulfonate, sulfonate ester, phosphate, phosphate ester, phosphonate, phosphonate ester, carboxo, amido, ureido, substituted carboxo, substituted amido, substituted ureido, or a 3-6 membered carbocycle or heterocycle attached to positions 5, 6 or 8 directly or through group L, each heteroatom independently being capable of carrying any group R$_2$, with the further proviso that either one, two or three substituents R$_2$ are present in the ring, each of the substituents R$_2$ being the same or different;

R$_3$ is selected from a group consisting of hydrogen, alkyl, alkoxy, halogen, CF$_3$, cyano, substituted alkyl, hydroxyl, aryl, substituted aryl, heteroaryl, substituted heteroaryl, heterocycle, C(R")$_3$, OR", N(R")$_2$, NR"C(O)R", NR"C(O)NR", R", C(O)(O)R", OC(O)R", C(O)N(R")$_2$, C(O), OC(O)N(R")$_2$, SO$_3$R", OSO$_2$R", SO$_2$R", SOR", PO$_4$R", OPO$_2$R", PO$_3$R", or PO$_2$R", wherein R" is hydrogen, aryl, substituted aryl, heteroaryl, substituted heteroaryl, lower alkyl, branched lower alkyl, alkyl-hydroxyl, branched alkyl-hydroxyl, amino-alkyl, branched amino-alkyl, alkyl-amino, branched alkyl-amino, thiol-alkyl, branched thiol-alkyl, alkyl-thiol, branched thiol-alkyl, or may form a closed 3-6 membered heterocycle with one or more heterocyclic atoms, branched alkyl, or branched alkyl hydroxyl, where each R" is independent in case there is more than one R";

n is an integer having the value between 1 and 5, with the further proviso that if n >2, then each group R$_3$ is independent of the other groups R$_3$, with the further proviso that if each A is (CH)$_0$, L is a bond, with the further proviso that if each B is (CH)$_0$, R$_3$ is any substituent described above, other than hydrogen, bonded directly to the position 7 of the adjacent ring;

or a pharmaceutically acceptable salt or individual diastereomer thereof, to a subject in need of such treatment.

5. A method of treating breast cancer comprising the administration of a therapeutically effective amount of a compound of structure (I):

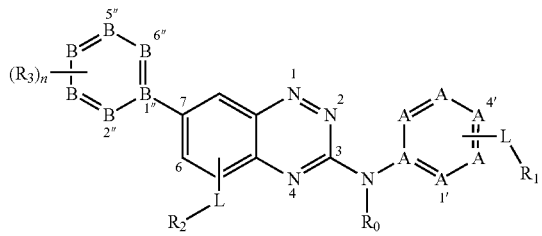

(I)

wherein each of A is independently selected from a group consisting of $(CH)_{0-1}$, N, NH, O, S, and a part of a ring fusion to form a second ring, where the second ring is an aromatic, a heteroaromatic, a bicyclic aromatic, a bicyclic aromatic heterocyclic ring, or a bicyclic with only the first ring being aromatic or heteroaromatic;

each of B is independently selected from a group consisting of $(CH)_{0-1}$, N, NH, O, S, and a part of a ring fusion to form a second ring, where the second ring is an aromatic, a heteroaromatic, a bicyclic aromatic, a bicyclic aromatic heterocyclic ring, or a bicyclic with only the first ring being aromatic or heteroaromatic, with the further proviso that if each B is $(CH)_0$, $R_3$ is bonded directly to the adjacent ring;

$R_0$ is selected from a group consisting of H and lower alkyl;

L is selected from a group consisting of a bond, and a substituted or unsubstituted alkyl, alkenyl, or alkynyl linking moiety;

$R_1$ is selected from a group consisting of $C(R')_3$, OR', $N(R')_2$, NR'C(O)R', NR'C(O)O(R'), NR'C(O)N(R')_2$, SR', C(O)(O)R', C(O), C(O)N(R')_2$, SO_3R', OSO_2R', SO_2R', SOR', S(O)N(R')_2, OS(O)(O)N(R')_2, S(O)(O)N(R')_2, S(O)N(R')_2, PO_4R', OPO_2R', PO_3R', PO_2R'$, and a 3-6 membered heterocycle with one or more heterocyclic atoms with each heteroatom independently being capable of carrying any R' group on it, wherein R' is selected from a group consisting of hydrogen, lower alkyl, alkyl-hydroxyl, thiol-alkyl, alkyl-thiol, aminoalkyl, alkylamino, branched alkyl, branched alkyl hydroxyl, branched thio-alkyl, branched alkyl-thiol, branched aminoalkyl, broached alkylamino, and a closed 3-6 membered carbocycle or heterocycle, with each heteroatom in the 3-6 membered heterocycle being capable of carrying any R' group on it, and wherein each R' is independent in case there is more than one R';

$R_2$ is a substituent situated at position 5, 6 or 8 of the ring, wherein $R_2$ is selected from a group consisting of methyl, ethyl, n-propyl, iso-propyl, n-butyl, iso-butyl, tert-butyl, iso-pentyl, phenyl, substituted phenyl, halogen, branched or unbranched alkylamino, branched or unbranched aminoalkyl, branched or unbranched alkyloxo, branched or unbranched oxyalkyl, branched or unbranched thioalkyl, branched or unbranched alkylthiol, $CF_3$, sulfonamido, substituted sulfonamido, sulfonate, sulfonate ester, phosphate, phosphate ester, phosphonate, phosphonate ester, carboxo, amido, ureido, substituted carboxo, substituted amido, substituted ureido, or a 3-6 membered carbocycle or heterocycle attached to positions 5, 6 or 8 directly or through group L, each heteroatom independently being capable of carrying any group $R_2$, with the further proviso that either one, two or three substituents $R_2$ are present in the ring, each of the substituents $R_2$ being the same or different;

$R_3$ is selected from a group consisting of hydrogen, alkyl, alkoxy, halogen, $CF_3$, cyano, substituted alkyl, hydroxyl, aryl, substituted aryl, heteroaryl, substituted heteroaryl, heterocycle, $C(R'')_3$, OR'', $N(R'')_2$, NR''C(O)R'', NR''C(O)NR'', R'', C(O)(O)R'', OC(O)R'', C(O)N(R'')_2$, C(O), OC(O)N(R'')_2, SO_3R'', OSO_2R'', SO_2R'', SOR'', PO_4R'', OPO_2R'', PO_3R''$, or $PO_2R''$, wherein R'' is hydrogen, aryl, substituted aryl, heteroaryl, substituted heteroaryl, lower alkyl, branched lower alkyl, alkyl-hydroxyl, branched alkyl-hydroxyl, amino-alkyl, branched amino-alkyl, alkyl-amino, branched alkyl-amino, thiol-alkyl, branched thiol-alkyl, alkyl-thiol, branched thiol-alkyl, or may form a closed 3-6 membered heterocycle with one or more heterocyclic atoms, branched alkyl, or branched alkyl hydroxyl, where each R'' is independent in case there is more than one R'';

n is an integer having the value between 1 and 5, with the further proviso that if n >2, then each group $R_3$ is independent of the other groups $R_3$, with the further proviso that if each A is $(CH)_0$, L is a bond, with the further proviso that if each B is $(CH)_0$, $R_3$ is any substituent described above, other than hydrogen, bonded directly to the position 7 of the adjacent ring;

or a pharmaceutically acceptable salt or individual diastereomer thereof, in combination with an anti-inflammatory agent, chemotherapeutic agent, immunomodulatory agent, therapeutic antibody, or a protein kinase inhibitor, to a subject in need of such treatment.

* * * * *